US009127085B2

(12) United States Patent
Kitajewski et al.

(10) Patent No.: US 9,127,085 B2

(45) Date of Patent: Sep. 8, 2015

(54) COMPOSITIONS OF HUMANIZED NOTCH FUSION PROTEINS AND METHODS OF TREATMENT

(75) Inventors: Jan Kitajewski, Ridgewood, NJ (US); Carrie Shawber, Township of Washington, NJ (US)

(73) Assignee: THE TRUSTEES OF COLUMBIA UNIVERSITY IN THE CITY OF NEW YORK, New York, NY (US)

(*) Notice: Subject to any disclaimer, the term of this patent is extended or adjusted under 35 U.S.C. 154(b) by 759 days.

(21) Appl. No.: 12/733,329

(22) PCT Filed: Aug. 22, 2008

(86) PCT No.: PCT/US2008/010045

§ 371 (c)(1), (2), (4) Date: Jul. 12, 2010

(87) PCT Pub. No.: WO2009/025867

PCT Pub. Date: Feb. 26, 2009

(65) Prior Publication Data

US 2011/0008342 A1 Jan. 13, 2011

Related U.S. Application Data

(60) Provisional application No. 60/966,052, filed on Aug. 23, 2007.

(51) Int. Cl.

*C07K 14/705* (2006.01)

*A61K 38/00* (2006.01)

(52) U.S. Cl.

CPC ............... *C07K 14/705* (2013.01); *A61K 38/00* (2013.01); *C07K 2319/02* (2013.01); *C07K 2319/30* (2013.01)

(58) Field of Classification Search

CPC .. C07K 14/705; C07K 2319/30; A61K 38/00; A61K 38/177

USPC .................. 530/350, 387.1, 387.3; 424/134.1

See application file for complete search history.

(56) References Cited

U.S. PATENT DOCUMENTS

| | | | | |
|---|---|---|---|---|
| 5,428,130 | A | 6/1995 | Capon et al. | |
| 6,090,922 | A | 7/2000 | Artavanis-Tsakonas et al. | |
| 6,379,925 | B1 | 4/2002 | Kitajewski et al. | |
| 6,689,744 | B2 | 2/2004 | Gao et al. | |
| 6,703,221 | B1 | 3/2004 | Chan et al. | |
| 6,716,974 | B1 | 4/2004 | Maciag et al. | |
| 7,662,919 | B2 * | 2/2010 | Kitajewski et al. | 530/350 |
| 2003/0082651 | A1 | 5/2003 | Gao et al. | |
| 2003/0186290 | A1 | 10/2003 | Tournier-Lasserue et al. | |
| 2003/0194804 | A1 | 10/2003 | Lamb et al. | |
| 2005/0261477 | A1 | 11/2005 | Champion et al. | |
| 2006/0002924 | A1 | 1/2006 | Bodmer et al. | |
| 2006/0030694 | A1 | 2/2006 | Kitajewski et al. | |
| 2006/0134121 | A1 | 6/2006 | Thurston et al. | |
| 2007/0104746 | A1 | 5/2007 | Fuji et al. | |
| 2008/0118520 | A1 | 5/2008 | Li et al. | |
| 2010/0273990 | A1 * | 10/2010 | Kitajewski et al. | 530/387.3 |
| 2011/0223183 | A1 | 9/2011 | Kitajewski et al. | |
| 2014/0271643 | A1 * | 9/2014 | Kitajewski et al. | 424/134.1 |

FOREIGN PATENT DOCUMENTS

| | | |
|---|---|---|
| WO | WO 03/042246 | 5/2003 |
| WO | WO 2003/087159 | 10/2003 |
| WO | WO 2004/024764 | 3/2004 |
| WO | WO 2005/111072 | 11/2005 |
| WO | WO 2006/047878 | 5/2006 |
| WO | WO 2008/051797 | 5/2008 |
| WO | WO 2010/021729 | 2/2010 |
| WO | WO 2013/052607 | 11/2013 |

OTHER PUBLICATIONS

International Search Report issued Feb. 20, 2009 in connection with International Application No. PCT/US2008/10045, filed Aug. 22, 2008.

Extended European Search Report and Opinion issued Dec. 23, 2011 in connection with European Application No. 08795559.7.

Written Opinion of the International Searching Authority issued Feb. 20, 2009 in connection with International Application No. PCT/US2008/10045, filed Aug. 22, 2008.

Singec et al. "The Leading Edge of Stem Cell Therapeutics" Annu. Rev. Med 58:313-328, 2007.

De La Costa, Immunol. Lett. Jan. 15, 2006;102(1):1-9 Epub. Jul. 18, 2005.

Kojika et al. Exp. Hermatol. 2001 29:1041-1052.

UniProt Protein NOTC4_Human, pp. 1-14 Mar. 27, 2002.

Varnum-Finney et al. Blood, Mar. 1, 2003: 101(5)1784-9.

Written Opinion issued Jun. 19, 2006 in connection with PCT International Application No. PCT/US05/13884.

International Search Report issued Jun. 19, 2006 in connection with PCT International Application No. PCT/US05/13884.

Written Opinion of the International Searching Authority issued Mar. 10, 2010 in connection with International Application No. PCT/US2009/04765, filed Aug. 21, 2009.

International Preliminary Report on Patentability issued Feb. 22, 2011 in connection with International Application No. PCT/US2009/004765, filed Aug. 21, 2009.

(Continued)

*Primary Examiner* — Yan Xiao

(74) *Attorney, Agent, or Firm* — John P. White; Cooper & Dunham LLP

(57) ABSTRACT

This invention provides a fusion protein comprising a single peptide, an extracellular domain of human Notch receptor protein and an Fc portion of an antibody bound thereto. This invention also provides a method for treating a subject having a tumor, a method for inhibiting angiogenesis in a subject, a method for treating a subject having ovarian cancer, and a method for treating a subject having a metabolic disorder, comprising administering to the subject an amount of the above fusion protein effective to treat the subject. This invention further provides uses of the above fusion protein for the preparation of a pharmaceutical composition for the treatment of a subject having a tumor, for inhibiting angiogenesis in a subject, for treating a subject having ovarian cancer, and for treating a subject having a metabolic disorder.

22 Claims, 143 Drawing Sheets

(56) References Cited

OTHER PUBLICATIONS

International Search Report issued Mar. 10, 2010 in connection with International Application No. PCT/US2009/04765, filed Aug. 21, 2009.
Notification of Transmittal of the international Search Report and the Written Opinion of the International Searching Authority, of the Declaration, Mar. 10, 2010.
International Search Report issued by the International Searching Authority (ISA/US) on Feb. 20, 2009 in connection with International Application No. PCT/US2008/010045.
International Preliminary Report on Patentability issued Feb. 24, 2010 in connection with International Application No. PCT/US2008/10045, filed Aug. 22, 2008.
Examination Report issued Nov. 24, 2012 in connection with New Zealand Patent Application No. 583649, filed Aug. 22, 2008.
May 23, 2012 Response to Examination Report issued Nov. 24, 2012 in connection with New Zealand Patent Application No. 583649, filed Aug. 22, 2008.
Examination Report and Notice of Acceptance of Complete Specification issued Jun. 13, 2012 in connection with New Zealand Patent Application No. 583649, filed Aug. 22, 2008.
Jul. 20, 2012 Response to Extended European Search Report and Opinion issued Dec. 23, 2011 in connection with European Application No. 08795559.7, filed Aug. 22, 2008.
Office Action issued Jan. 2, 2012 in connection with Israeli patent Application No. 204111, filed Aug. 22, 2008, including English language translation thereof.
Jul. 1, 2012 Response to Office Action issued Jan. 2, 2012 in connection with Israeli patent Application No. 204111, filed Aug. 22, 2008, and English translation thereof.
Office Action issued Jun. 20, 2012 in connection with Chinese patent Application No. 200880112057.3 filed Aug. 22, 2008, including English language translation thereof.
Official Action issued Nov. 23, 2012 in connection with Russian patent Application No. 2010110812 filed Aug. 22, 2008, including English language translation thereof.
International Search Report issued Jan. 18, 2013 in connection with PCT International Application No. PCT/US2012/058662.
Apr. 10, 2012 Office Action issued in connection with U.S. Appl. No. 12/657,573.
Oct. 4, 2012 Amendment in Response to Apr. 10, 2012 Office Action filed in connection with U.S. Appl. No. 12/657,573.
Mar. 18, 2013 Office Action issued in connection with U.S. Appl. No. 12/657,573.
Dec. 20, 2012 Office Action issued in connection with U.S. Appl. No. 13/060,254.
Jan. 22, 2013 Amendment filed in connection with U.S. Appl. No. 13/060,254.
Feb. 28, 2013 Office Action issued in connection with U.S. Appl. No. 13/060,254.
Aug. 28, 2013 Amendment filed in connection with U.S. Appl. No. 13/060,254.
Official Action issued in connection with Russian Patent Application No. 2011110741.
Jan. 31, 2013 Office Action issued in connection with Mexican Patent Application No. MX/a/2011/001805.
Jun. 7, 2013 Response to Jan. 31, 2013 Office Action filed in connection with Mexican Patent Application No. MX/a/2011/001805.
Supplementary European Search Report issued Dec. 19, 2012 in connection with European Patent Application No. EP 09 80 8518.
Dec. 25, 2012 Office Action issued in connection with Israeli Patent Application No. 211232.
Mar. 28, 2013 Response to Sep. 13, 2012 Office Action filed in connection with Chinese Patent Application No. 2009801331210.
Mar. 8, 2013 Response to Jun. 20, 2012 Office Action filed in connection with Chinese Patent Application No. 200880112057.3.
Jun. 21, 2013 Office Action issued in connection with Chinese Patent Application No. 200880112057.3.
Jan. 30, 2013 Communication issued in connection with European Patent Application No. 08 795 559.7.
Aug. 8, 2013 Response to Jan. 30, 2013 Communication filed in connection with European Patent Application No. 08 795 559.7.
May 7, 2013 Office Action issued in connection with Japanese Patent Application No. 2010-521897.
May 25, 2012 Examination Report issued in connection with New Zealand Patent Application No. 600171.
Response to Nov. 23, 2012 Office Action filed in connection with Russian Patent Application No. 2010110812.
Apr. 25, 2013 Office Action issued in connection with Russian Patent Application No. 2010110812.
Peppel et al. (1991) "A Tumor Necrosis Factor (TNF) Receptor-IgG Heavy Chain Chimeric Protein as a Bivalent Antagonist of TNF Activity" J. Exp. Med., 174:1483-1489.
Funahashi et al. (2008) "A Notch1 Ectodomain Construct Inhibits Endothelial Notch Signaling, Tumor Growth, and Angiogenesis" Cancer Res., 68:(12)4727-4735.
Ahmad et al. (2011) "Regulation of Ocular Angiogenesis by Notch Signaling . . . " Investigative Ophthalmology & Visual Science, 52:(6)2868-2878.
Bellavia et al. (2008) Notch3: from subtle structural differences to functional diversity. Oncogene 27: 5092-5098.
Peters at al. (2004) CADASIL-associated Notch3 mutations have differential effects on both ligand binding and licand-induced Notch3 receptor signaling through RBP-Jk. Exp Cell Res 299:454-464.
Rebay et al. (1991) Specific EGF repeats of Notch mediate interactions with delta and serrate: implications for Notch as a multifunctional receptor. Cell, 67:687-699.
Shimizu et al., (2000) Physical interaction of Delta1, Jagged1, and Jagged2 with Notch1 and Notch3 receptors. Biochem Biophys Res Comm. 276:385-9.
Shimizu at al. (1999) Mouse Jagged1 physically interacts with Notch2 and other notch receptors. J. Biol Chem 274(46) :32961-32969.
UniProt NOTC1_HUMAN (P46531; Apr. 1, 2004).
Xu et al., (2005) Regions of Drosophila Notch that contribute to ligand binding and the modulatory influence of Fringe. J Biol Chem. 280:30158-65.
Zlobin et al. (2000) Toward the rational design of cell fate modifiers: Notch signaling as a target for novel biopharmaceuticals. Current Pharmaceutical Technology, 1, pp. 83-106.
Apr. 19, 2006 Office Action, issued in connection with U.S. Appl. No. 11/114,962.
Aug. 21, 2006 Response, filed in connection with U.S. Appl. No. 11/114,962.
Nov. 14, 2006 Office Action, issued in connection with U.S. Appl. No. 11/114,962.
May 14, 2007 Response, filed in connection with U.S. Appl. No. 11/114,962.
Aug. 21, 2007 Final Office Action, issued in connection with U.S. Appl. No. 11/114,962.
Feb. 21, 2008 Response, filed in connection with U.S. Appl. No. 11/114,962.
Mar. 24, 2008 Office Action, issued in connection with U.S. Appl. No. 11/114,962.
Sep. 24, 2008 Response, filed in connection with U.S. Appl. No. 11/114,962.
Jun. 23, 2009 Response, filed in connection with U.S. Appl. No. 11/114,962.
Jan. 23, 2009 Final Office Action, issued in connection with U.S. Appl. No. 11/114,962.
Sep. 17, 2009 Notice of Allowance, issued in connection with U.S. Appl. No. 11/114,962.
Dec. 18, 2013 Response, filed in connection with U.S. Appl. No. 12/657,573.
Jan. 29, 2014 Office Action, issued in connection with U.S. Appl. No 12/657,573.
Apr. 29, 2014 Response, issued in connection with U.S. Appl. No. 12/657,573.
Jun. 27, 2014 Office Action, issued in connection with U.S. Appl. No. 12/657,573.

(56) References Cited

OTHER PUBLICATIONS

Oct. 22, 2014 Response, filed in connection with U.S. Appl. No. 12/657,573.
Oct. 29, 2014 Notice of Allowance, issued in connection with U.S. Appl. No. 12/657,573.
Oct. 30, 2014 Request for Continued Examination and Information Disclosure Statement, filed in connection with U.S. Appl. No. 12/657,573.
Nov. 18, 2014 Notice of Allowance, issued in connection with U.S. Appl. No. 12/657,573.
Jan. 3, 2014 Response, filed in connection with Australian Patent Application. No. 2008289462.
Jan. 14, 2014 Notice of Acceptance, issued in connection with Australian Patent Application No. 2008289462.
Dec. 3, 2012 Examination_Report_No._1, issued in connection with Australian Patent Application No. 2008289462.
Aug. 1, 2013 Examination_Report_No._2, issued in connection with Australian Patent Application No. 2008289462.
Oct. 3, 2013 Communication, issued in connection with European Patent Application No. 08 795 559.7.
Feb. 12, 2014 Response, filed in connection with European Patent Application No. 08795559.7.
Dec. 6, 2013 Examination Report, issued in connection with New Zealand Patent Application No. 600171.
Nov. 22, 2013 Response, filed in connection with New Zealand Patent Application No. 600171.
Dec. 19, 2013 Response, filed in connection with New Zealand Patent Application No. 600171.
Jan. 10, 2014 Notice of Acceptance, issued in connection with New Zealand Patent Application No. 600171.
Nov. 6, 2013 Examination Report, issued in connection with New Zealand Patent Application No. 618129.
Nov. 29, 2013 Office Action, issued in connection with Filipino Patent Application No. 1-2010-500422.
Mar. 28, 2014 Response, filed in connection with Filipino Patent Application No. 1-2010-500422.
Jan. 1, 2014 Response, filed in connection with Israeli Patent Application No. 204111, including English translation thereof.
Letter describing Jan. 19, 2014 Notification of Defects in connection with Israeli Patent Application No. 204111.
Jul. 16, 2014 Response, filed in connection with Israeli Patent Application No. 204111, including English translation thereof.
English language translation of Aug. 25, 2014 Notice issued in connection with Israeli Patent Application No. 204111.
Jan. 20, 2014 Office Action, issued in connection with Israeli Patent Application No. 220723, including English translation thereof.
Sep. 16, 2014 Response, filed in connection with Israeli Patent Application No. 220723, including English translation thereof.
Jan. 22, 2014 Office Action, issued in connection with Israeli Patent Application No. 220724, including English translation thereof.
Jun. 19, 2014 Response, filed in connection with Israeli Patent Application No. 220724, including English translation thereof.
Sep. 5, 2013 Response, filed in connection with Chinese Patent Application No. 200880112057.3, including English language version.
Nov. 21, 2013 Office Action, issued in connection with Chinese Patent Application No. 200880112057.3, including English translation thereof.
Feb. 27, 2014 Response, filed in connection with Chinese Patent Application No. 200880112057.3.
Apr. 1, 2014 Decision of Rejection, issued in connection with Chinese Patent Application No. 200880112057.3.
Nov. 7, 2013 Response, filed in connection with Japanese Patent Application No. 2010-521897.
Jul. 1, 2014 Office Action, issued in connection with corresponding Japanese Patent Application No. 2010-521897.
Oct. 1, 2014 Response, filed in connection with Japanese Patent Application No. 2010-521897.
Jan. 20, 2014 Response, filed in connection with Mexican Patent Application No. MX/a/2010/002053.
Jul. 11, 2014 Response, filed in connection with Mexican Patent Application No. MX/a/2010/002053.
Apr. 29, 2014 Office Action, issued in connection with Mexican Patent Application No. MX/a/2010/002053.
Jun. 16, 2014 Office Action, issued in connection with Indian Patent Application No. 1626/CHENP/2010.
Aug. 28, 2014 Notice of Result of Examination as to Substance, issued in connection with Vietnamese Patent Application No. 2010-521897, including English language translation thereof.
Oct. 21, 2014 Response, filed in connection with Vietnamese Patent Application No. 2010-521897, including English language translation thereof.
Nov. 5, 2013 Office Action, issued in connection with U.S. Appl. No. 13/060,254.
Apr. 2, 2014 Office Action, issued in connection with U.S. Appl. No. 13/060,254.
Sep. 2, 2014 Response, filed in connection with U.S. Appl. No. 13/060,254.
Sep. 30, 2014 Examination Report No. 1, issued in connection with Australian Patent Application No. 2009283134.
Sep. 13, 2012 Office Action, issued in connection with Chinese patent Application No. 200980133121.0 including English language translation thereof.
Response to First Office Action, filed Mar. 28, 2013 in connection with Chinese Patent Application No. 200980133121.0.
Jul. 29, 2013 Second Office Action, issued in connection with Chinese patent Application No. 200980133121.0, including English language translation thereof.
Dec. 13, 2013 Response, filed in connection with Chinese Patent Application No. 200980133121.0.
Apr. 21, 2014 Third Office Action, issued in connection with Chinese patent Application No. 200980133121.0, including English language translation thereof.
Oct. 8, 2014 Response, filed in connection with Chinese patent Application No. 200980133121.0, including English language translation of Observation Request.
May 3, 2011 Examination Report, issued in connection with New Zealand Patent Application No. 591492.
Sep. 10, 2012 Response to Examination Report issued May 3, 2011 in connection with New Zealand Patent Application No. 591492, filed Mar. 2, 2011.
Oct. 1, 2012 Examination Report and Notice of Acceptance of Complete Specification, issued in connection with New Zealand Patent Application No. 591492.
May 14, 2013 Office Action, issued in connection with Russian Patent Application No. 2011110741, including English language translation.
Feb. 18, 2014 Official Action, issued in connection with Russian Patent Application No. 2011110741, including English language translation.
Aug. 13, 2014 Response, filed in connection with Russian Patent Application No. 2011110741, including English language claims.
Oct. 13, 2014 Official Action, issued in connection with Russian Patent Application No. 2011110741, including English language translation.
Jan. 8, 2014 Response, filed in connection with Mexican Patent Application No. MX/a/2011/001805.
Nov. 20, 2013 Response, filed in connection with European Patent Application No. 09808518.6.
Jan. 8, 2014 Communication pursuant to Article 94(3) EPC, issued in connection with European Patent Application No. 09808518.6.
May 16, 2014 Response, filed in connection with European Patent Application No. 09808518.6.
Jul. 24, 2014 Communication About Intention to Grant, issued in connection with European Patent Application No. 09808518.6.
Oct. 27, 2013 Response, filed in connection with Israeli Patent Application No. 211232.
Jul. 9, 2013 Office Action, issued in connection with Israeli Patent Application No. 211232.
Letter Describing Apr. 9, 2014 Notification of Non-Substantive Defects, issued in connection with Israeli Patent Application No. 211232.

(56) References Cited

OTHER PUBLICATIONS

Aug. 10, 2014 Response, filed in connection with Israeli Patent Application No. 211232, including English language translation thereof.
Nov. 26, 2013 Response, filed in connection with Indonesian Patent Application No. W-00 2011 01013.
Jul. 22, 2013 Office Action, issued in connection with Indonesian Patent Application No. W-00 2011 01013.
Feb. 4, 2014 Office Action, issued in connection with Japanese Patent Application No. 2011-523820, including English translation thereof.
Jun. 4, 2014 Response, filed in connection with Japanese Patent Application No. 2011-523820.
Jan. 6, 2015 Office Action, issued in connection with Japanese Patent Application No. 2011-523820, including English translation thereof.
Oct. 15, 2014 Office Action, issued in connection with Malaysian Patent ApplicatiOn No. PI 2011000718.
Amended Claims filed Dec. 11, 2014 in connection with Malaysian Patent Application No. PI 2011000718.
Apr. 26, 2014 Office Action, issued in connection with Vietnamese Patent Application. No. 1-2011-00752.
Aug. 25, 2014 Response, filed in connection with Vietnamese Patent Application. No. 1-2011-00752.
First Office Action, issued in connection with Pakistani Patent Application No. 636/2012.
Feb. 2, 2015 First Examination Report, issued in connection with New Zealand Patent Application No. 624091.
Jan. 4, 2015 First Examination Report, issued in connection with Chinese Patent Application No. 201280054960.5.
Jan. 30, 2015 Office Action, issued in connection with Mexican Patent Application No. MX/a/2010/002053.
Jul. 16, 2014 Request for Re-examination, filed in connection with Chinese Patent Application No. 200880112057.3, including English language translation of Request for Re-examination Form.

* cited by examiner

*Figure 10*

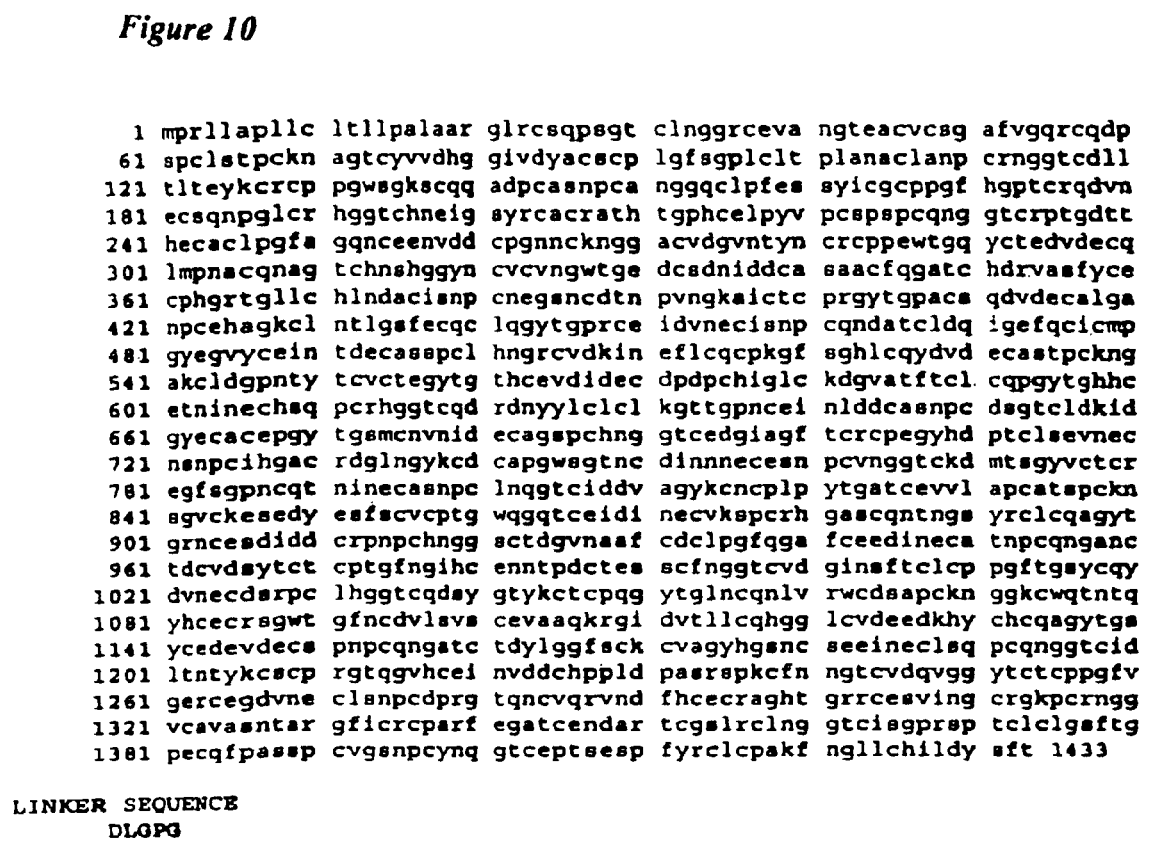

```
   1 mprllapllc ltllpalaar glrcsqpsgt clnggrceva ngteacvcsg afvgqrcqdp
  61 spclstpckn agtcyvvdhg givdyacscp lgfsgplclt planaclanp crnggtcdll
 121 tlteykcrcp pgwsgkscqq adpcasnpca nggqclpfes syicgcppgf hgptcrqdvn
 181 ecsqnpglcr hggtchneig syrcacrath tgphcelpyv pcspspcqng gtcrptgdtt
 241 hecaclpgfs gqnceenvdd cpgnnckngg acvdgvntyn crcppewtgq yctedvdecq
 301 lmpnacqnag tchnshggyn cvcvngwtge dcsdniddca sascfqgatc hdrvasfyce
 361 cphgrtgllc hlndacisnp cnegsncdtn pvngkaictc prgytgpacs qdvdecalga
 421 npcehagkcl ntlgsfecqc lqgytgprce idvnecisnp cqndatcldq igefqcicmp
 481 gyegvycein tdecasspcl hngrcvdkin eflcqcpkgf sghlcqydvd ecastpckng
 541 akcldgpnty tcvctegytg thcevdidec dpdpchiglc kdgvatftcl cqpgytghhc
 601 etninechsq pcrhggtcqd rdnyylclcl kgttgpncei nlddcasnpc dsgtcldkid
 661 gyecacepgy tgsmcnvnid ecagspchng gtcedgiagf tcrcpegyhd ptclsevnec
 721 nsnpcihgac rdglngykcd capgwsgtnc dinnnecesn pcvnggtckd mtsgyvctcr
 781 egfsgpncqt ninecasnpc lnqgtciddv agykcncplp ytgatcevvl apcatspckn
 841 sgvckesedy esfscvcptg wqgqtceidi necvkspcrh gascqntngs yrclcqagyt
 901 grncesdidd crpnpchngg sctdgvnsaf cdclpgfqga fceedineca tnpcqnganc
 961 tdcvdsytct cptgfngihc enntpdctes scfnggtcvd ginsftclcp pgftgsycqy
1021 dvnecdsrpc lhggtcqdsy gtykctcpqg ytglncqnlv rwcdsapckn ggkcwqtntq
1081 yhcecrsgwt gfncdvlsvs cevaaqkrgi dvtllcqhgg lcvdeedkhy chcqagytgs
1141 ycedevdecs pnpcqngatc tdylggfsck cvagyhgsnc seeineclsq pcqnggtcid
1201 ltntykcscp rgtqgvhcei nvddchppld pasrspkcfn ngtcvdqvgg ytctcppgfv
1261 gercegdvne clsnpcdprg tqncvqrvnd fhcecraght grrcesving crgkpcrngg
1321 vcavasntar gficrcparf egatcendar tcgslrclng gtcisgprsp tclclgsftg
1381 pecqfpassp cvgsnpcynq gtceptsesp fyrclcpakf ngllchildy sft 1433
```

LINKER SEQUENCE
DLGPG

Figure 11

```
   1 mpalrpaalr allwlwlcga gpahalqcrg gqepcvnegt cvtyhngtgy crcpegflge
  61 ycqhrdpcek nrcqnggtcv tqamlgkatc rcapgftged cqystshpcf varpcqnggt
 121 chmlswdtye ctcqvgftgk qcqvtdvcls hpcengstcs svanqfscrc pagitgqkcd
 181 adinecdipg rcqhggtcln lpgsyrcqcp qrftgqhcds pyvpcapspc vnggtcrqtg
 241 dftsechclp gfegsncern iddcpnhkcq nggvcvdgvn tyncrcppqv tgqfctedvd
 301 ecllqpnacq nggtctnrng gygcvcvngw sgddcsenid dcafasctpg stcidrvasf
 361 sclcpegkag llchlddaci snpchkgalc dtnplngqyi ctcpqaykga dctedvdeca
 421 mansnpceha gkcvntdgaf hceclkgyag prcemdinec hsdpcqndat cldkiggftc
 481 lcmpgfkgvh celevnecqs npcvnngqcv dkvnrfqclc ppgftgpvcq ididdcsstp
 541 clngakcidh pngyecqcat gftgtlcden idncdpdpch hgqcqdgids ytcicnpgym
 601 gaicsdqide cysspclndg rcidlvngyq cncqpgtsgl nceinfddca snpclhgacv
 661 dginryscvc spgftgqrcn ididecasnp crkdatcind vngfrcmcpe gphhpscysq
 721 vneclsspci hgnctgglsg ykclcdagwv gincevdkne clsnpcqngg tcnnlvngyr
 781 ctckkgfkgy ncqvnideca snpclnqgtc lddvsgytch cmlpytgknc qtvlspcspn
 841 pcenaavcke apnfesftcl capgwqgqrc tvdvdecvsk pcmnngichn tqgsymcecp
 901 pgfsgmdcee dindclanpc qnggscvdkv ntfsclclpg fvgdkcqtdm neclsepckn
 961 ggtcsdyvns ytctcpagfh gvhcennide ctesscfngg tcvdginsfs clcpvgftgp
1021 fclhdinecs snpclnsgtc vdglgtyrct cplgytgknc qtlvnlcsps pcknkgtcaq
1081 ekarprclcp pgwdgaycdv lnvsckassl qkgvpvehlc qhsgicinag nthhcqcplg
1141 ytgsyceeql decasnpcqh gatcsdfigg yrcecvpgyq gvnceyevde cqnqpcqngg
1201 tcidlvnhfk cscppgtrgl lceeniddca gaphclnggq cvdriggysc rclpgfager
1261 cegdineclk npcssegsld ciqlknnyqc vcrsaftgrh cetfldvcpq kpclnggtca
1321 vasnvpdgfi crcppgfsga rcqsscgqvk crrgeqcvht asgphcfcpn hkdcesgcas
1381 npcqhggtcy pqrqppyysc rcsppfwgsh cesytapts 1419
```

LINKER SEQUENCE
DLGPG

*Figure 12*

```
   1 mglgargrrr rrrlmalppp pppmralpll lllaglgaaa ppcldgspca nggrcthqqp
  61 sleaaclclp gwvgercqle dpchsgpcag rgvcqssvva gtarfscrcl rgfqgpdcsq
 121 pdpcvsrpcv hgapcsvgpd grfacacppg yqgqscqsdi decrsgttcr hggtclntpg
 181 sfrcqcplgy tgllcenpvv pcapspcrng gtcrqssdvt ydcaclpgfe gqncevnvdd
 241 cpghrclngg tcvdgvntyn cqcppewtgq fctedvdecq lqpnachngg tcfnllgghs
 301 cvcvngwtge scsqniddca tavcfhgatc hdrvasfyca cpmgktgllc hlddacvsnp
 361 chedaicdtn pvsgraictc ppgftggacd qdvdecsiga npcehlgrcv ntqgsflcqc
 421 grgytgprce tdvneclsgp crnqatcldr igqftcicma gftgtycevd idecqsspcv
 481 nggvckdrvn gfsctcpsgf sgsmcqldvd ecastpcrng akcvdqpdgy ecrcaegfeg
 541 tlcernvddc spdpchhgrc vdgiasfsca capgytgirc esqvdecrsq pcryggkcld
 601 lvdkylcrcp pgttgvncev niddcasnpc tfgvcrdgin rydcvcqpgf tgplcnvein
 661 ecasspcgeg gscvdgengf hclcppgslp plclpanhpc ahkpcshgvc hdapggfrcv
 721 cepgwsgprc sqslapdace sqpcqaggtc tsdgigfrct capgfqghqc evlspctpsl
 781 cehgghcesd pdrltvcscp pgwqgprcqq dvdecagasp cgphgtctnl pgnfrcichr
 841 gytgpfcdqd iddcdpnpcl hggscqdgvg sfscscldgf agprcardvd eclsspcgpg
 901 tctdhvasft cacppgyggf hceidlpdcs psscfnggtc vdgvssfscl crpgytgthc
 961 qyeadpcfsr pclhggicnp thpgfectcr egftgsqcqn pvdwcsqapc qnggrcvqtg
1021 aycicppgws grlcdiqslp cteaaaqmgv rleqlcqegg kcidkgrshy cvcpegrtgs
1081 hcehevdpct aqpcqhggtc rgymggyvce cpagyagdsc ednidecasq pcqnggscid
1141 lvarylcscp pgtlgvlcei neddcdlgps ldsgvqclhn gtcvdlvggf rcncppgytg
1201 lhceadinec rpgachsaht rdclqdpggh frcvchpgft gprcqialsp cesqpcqhgg
1261 qcrhslgrgg gltftchcvp pfwglrcerv arscrelqcp vgipcqqtar gprcacppgl
1321 sgpscrvsra spsgatnasc asapclhggs clpvqsvpff rcvcapgwgg prcetpsas 1379
```

Linker Sequence
No linker sequence

*Figure 13*

```
   1 mqpqllllll lplnfpvilt rellcggspe pcanggtclr lsrgqgicqc apgflgetcq
  61 fpdpcrdtql ckngggscqal lptppssrsp tspltphfsc tcpsgftgdr cqthleelcp
 121 psfcsngghc yvqasgrpqc scepgwtgeq cqlrdfcsan pcanggvcla typqiqcrcp
 181 pgfeghtcer dinecflepg pcpqgtschn tlgsyqclcp vgqegpqckl rkgacppgsc
 241 lnggtcqlvp eghstfhlcl cppgftgldc emnpddcvrh qcqngatcld gldtytclcp
 301 ktwkgwdcse didecargp prcrnggtcq ntagsfhcvc vsgwggagce enlddcaaat
 361 capgstcidr vgsfsclcpp grtgllchle dmclsqpchv naqcstnplt gstlcicqpg
 421 ysgstchqdl decqmaqqgp spcehggsci ntpgsfnclc lpgytgsrce adhneclsqp
 481 chpgstcldl latfhclcpp glegrlceve vnectsnpcl nqaachdlln gfqclclpgf
 541 tgarcekdmd ecsstpcang grcrdqpgaf yceclpgfeg phcekevdec lsdpcpvgas
 601 cldlpgaffc lcrpgftgql cevplctpnm cqpgqqcqgq ehrapclcpd gspgcvpaed
 661 ncpchhghcq rslcvcdegw tgpecetelg gcistpcahg gtchpqpsgy nctcpagymg
 721 ltcseevtac hsgpclnggs csirpegysc tclpshtgrh cqtavdhcvs asclnggtcv
 781 nkpgtffclc atgfqglhce ektnpscads pcrnkatcqd tprgarclcs pgytgsscqt
 841 lidlcarkpc phtarclqsg psfqclclqg wtgalcdfpl scqkaamsqg ieisglcqng
 901 glcidtgssy fcrcppgfqg klcqdnvnpc epnpchhgst cvpqpsgyvc qcapgyegqn
 961 cskvldacqs qpchnhgtct srpggfhcac ppgfvglrce gdvdecldrp chpsgtaach
1021 slanafycqc lpghtgqrce vemdlcqsqp csnggsceit tgpppgftch cpkgfegptc
1081 shkalscgih hchngglclp spkpgspplc aclsgfggpd cltppappgc gppspclhng
1141 tctetpglgn pgfqctcppd spgprcqrpg 1170
```

LINKER SEQUENCE
DLGPG

*Figure 14A*

```
   1 atgacaggct tccagggctg ccaggccctg ctgcatctgg ccaaggccgt ggttcgcttg
  61 agatgctccc agccaagtgg gacctgcctg aatggaggga ggtgcgaagt ggccaacggc
 121 actgaagcct gtgtctgcag cggagcgttc gtgggccagc gatgccagga ccccagccct
 181 tgcctcagca caccatgtaa gaatgctgga acgtgctatg ttgtggacca tggcggcatc
 241 gtggactatg cctgcagttg cccccctgggt ttctctgggc ccctctgcct gacacctctg
 301 gccaatgcct gcctggccaa cccctgccgc aacgggggga cctgtgacct gctcactctc
 361 acagaataca agtgccggtg cccgccaggg tggtcaggaa agtcatgtca gcaagccgac
 421 ccctgtgcct ccaacccctg tgccaatggt ggccagtgcc tgccctttga gtcttcatac
 481 atctgtggct gcccgcccgg cttccatggc cccacctgca gacaagatgt taacgagtgc
 541 agccagaacc ctgggttgtg ccgtcatggc ggcacgtgcc acaatgagat tggctcctat
 601 cgctgtgcct gccgtgccac ccacactggt ccccactgcg agctgcccta cgtgccctgc
 661 agcccctcac cctgccagaa cggaggcacc tgccgcccta cgggggacac caccccacgag
 721 tgtgcctgcc tgccaggctt tgctggacag aactgtgaag aaaatgtgga tgactgccca
 781 ggaaacaact gcaagaacgg gggtgcctgt gtggacggtg tgaataccta caattgccgc
 841 tgcccaccgg agtggacagg tcagtactgc acagaggatg tggacgagtg tcagctcatg
 901 cccaacgcct gccagaatgg cggaacctgc cacaactccc acggtggcta caactgcgtg
 961 tgtgtcaatg gctggactgg tgaggactgc agtgagaaca ttgatgactg tgccagtgcc
1021 gcctgttttc agggtgccac ctgccatgac cgtgtggctt ccttctactg cgagtgtcca
1081 catgggcgca caggcctgct gtgccacctg aacgatgcgt gtatcagcaa cccctgcaac
1141 gagggctcca actgcgacac caaccctgtc aacggcaagg ccatctgcac ttgcccctcg
1201 gggtacacgg ggccagcctg cagccaggac gtggatgagt gcgctctagg tgccaacccg
1261 tgtgagcacg cgggcaagtg cctcaacaca ctgggctctt tcgagtgtca gtgtctacag
1321 ggctacactg ggccccgctg tgagattgat gtcaacgagt gcatctccaa cccatgtcag
1381 aatgatgcca cgtgcctgga ccagattggg gagtttcagt gtatatgtat gccaggttat
1441 gagggtgtat actgtgagat caacacggac gagtgtgcca gcagcccctg tctacacaat
1501 ggccgctgcg tggacaagat caacgagttc ctgtgtcagt gtcccaaagg cttcagcggg
1561 cacctgtgcc agtatgacgt ggatgagtgc gccagcacac catgcaagaa cggcgccaag
1621 tgcctggatg ggcccaacac ctacacctgc gtgtgcacag aaggttacac ggggacccac
1681 tgcgaggtgg acattgacga gtgtgacccct gacccctgtc actatggttt gtgcaaggat
1741 ggtgtggcca cctttacctg cctctgccag ccaggctaca caggccatca ctgtgagacc
1801 aacattaatg agtgtcacag ccagccgtgc cgccatggcg gcacctgcca ggaccgtgac
1861 aactactacc tctgcttatg cctcaagggg accacaggac ccaactgtga gatcaatctg
1921 gatgactgtg cgagcaaccc ctgtgactct ggcacgtgtc tggacaagat cgatggctac
1981 gagtgtgcgt gcgagccagg ctacacaggg agcatgtgta atgtcaacat tgacgaatgt
2041 gcgggcagcc cctgccacaa cgggggcacc tgtgaggatg gcatcgccgg cttcacttgc
2101 cgctgccccg agggctacca cgaccctacg tgcctgtctg aggtcaacga gtgcaacagt
2161 aacccctgca tccatggagc ttgccgggat ggcctcaatg gatacaaatg tgactgtgcc
2221 cctgggtgga gtgggacaaa ctgtgacatc aacaacaatg agtgtgagtc caaccccttgt
2281 gtcaacggtg gcacctgcaa agacatgacc agtggctacg tatgcacctg ccgagaaggc
2341 ttcagtggcc ctaactgcca gaccaacatt aacgaatgtg cttccaaccc ctgcctgaac
2401 cagggcacct gcattgatga tgtcgctggg tacaaatgca actgccctct gccctataca
2461 ggagccacat gtgaggtggt gttggcccca tgtgccacca gcccctgcaa aaacagtggg
2521 gtatgcaagg agtctgagga ctatgagagc ttttcctgtg tctgtcccac aggctggcaa
2581 ggtcaaacct gcgagatcga catcaatgag tgtgtgaaaa gcccgtgtcg ccatggtgcc
2641 tcttgccaga acaccaatgg cagctaccgc tgcctctgcc aggctggcta cacgggtcgc
2701 aactgcgaga gtgacatcga tgactgccga cccaacccat gtcacaacgg gggttcctgc
2761 actgacgggg tcaacgcggc cttctgcgac tgcctgcccg gcttccaggg tgccttctgt
2821 gaggaggaca tcaacgaatg cgccagcaat ccatgccaaa atggcgccaa ctgcactgac
2881 tgcgtggaca gctacacgtg cacctgcccc acgggcttca atggcatcca ttgcgagaac
2941 aacacacctg actgtaccga gagctcctgt ttcaatggtg gcacctgtgt ggatggtatc
3001 aactccttca cctgtctgtg cccacctggc ttcacgggca gctactgcca gtatgacgtc
3061 aatgagtgtg actcacggcc ctgtctgcat ggtggcacct gccaagacag ctatggtacc
3121 tataagtgta cctgcccaca gggctacact ggtctcaact gccagaacct tgtgcgctgg
3181 tgtgactcag ctccctgcaa gaatggcggc aagtgctggc agaccaacac acagtaccac
3241 tgcgagtgcc gcagcggctg gactggcttc aactgcgacg tgctcagtgt gtcctgcgag
```

Figure 14B

```
3301 gtggctgcac agaagcgagg catcgatgtc actctcctat gccagcacgg agggctctgt
3361 gtggatgagg aagacaagca ttactgccac tgccaggcag gatacacggg cagctactgt
3421 gaggacgagg tggacgagtg ctcacctaat ccctgccaga acggagccac ctgcactgac
3481 tatctcggtg gcttttcctg caagtgtgtg gctgggtacc atggctctaa ctgctctgag
3541 gagatcaacg agtgcctatc ccaaccctgc cagaatgggg gtacctgcat tgatctgacc
3601 aacacctaca agtgctcctg ccccaggggc acacagggtg tacactgtga gatcaacgtc
3661 gatgactgcc atcctcccct agaccctgct tcccgaagcc ccaaatgctt caataatggc
3721 acctgcgtgg accaggtggg tggctatacc tgcacctgcc cgccaggctt cgtcggggag
3781 cggtgcgagg gcgatgtcaa tgagtgtctc tccaacccct gtgacccacg tggcacccag
3841 aactgcgtgc agcgtgttaa tgacttccac tgcgagtgcc gggctggcca cactggacgc
3901 cgctgtgagt cggtcattaa tggctgcagg ggcaaaccat gcaggaatgg aggtgtctgt
3961 gctgtggcct ccaacaccgc ccgtggattc atctgtaggt gccctgcggg cttcgagggt
4021 gccacttgtg aaaatgacgc ccgcacttgt ggcagtttgc gctgcctcaa cggtggtacg
4081 tgcatctcag gcccacgcag tcccacctgc ctatgcctgg gctccttcac tggccctgaa
4141 tgccagttcc cagccagcag cccctgtgtg ggtagcaacc cctgctacaa tcagggcacc
4201 tgtgagccca catccgagag ccctttctac cgctgtctat gccctgccaa attcaacggg
4261 ctgctgtgcc acatcctgga ctacagcttc aca 4293
```

*Figure 15A*

```
511 atgcccgctc tgcgtcccgc cgcgctgcgg
 541 gcgctgctgt ggctctggct gtgcggcgcg ggccccgcgc acgctttgca gtgtcgaggt
 601 ggtcaagagc cctgtgtaaa tgaggggacc tgtgttacct accacaacgg cacaggctac
 661 tgccgatgtc cagagggctt cttgggagaa tattgtcaac atcgagaccc ttgtgagaag
 721 aaccgctgtc agaatggtgg tacttgtgtg acgcaggcca tgttgggaaa agccacctgt
 781 cgatgtgctc cagggttcac aggggaggac tgccaatact cgacctctca cccctgtttt
 841 gtttcccgcc cctgtcagaa tggaggtacc tgccacatgc tcagctggga cacctatgag
 901 tgcacctgtc aagttggctt cacaggaaag cagtgtcagt ggacagatgt ctgtctgtct
 961 catccctgtg aaaatggaag cacctgtagc tctgtggcca accagttctc ctgcagatgt
1021 cctgcaggca tcacaggcca gaagtgtgac gccgacatca atgaatgtga cattccagga
1081 cgctgccaac atggtggcac ctgcctcaac cttcctgggt cctaccgatg ccaatgccct
1141 cagcggttca caggccagca ctgtgacagc ccttacgtgc cctgtgcacc ctcaccctgc
1201 gtcaatggag gcacctgccg tcagactgga gacttcactt ctgaatgcca ttgcctgcca
1261 ggctttgaag gagcaactg cgagcggaat atcgacgact gccctaacca caagtgtcag
1321 aatggagggg tgtgtgtgga tggcgtcaat acttacaact gccgctgccc ccctcagtgg
1381 actgggcagt tctgcacaga agacgtggat gagtgtctgc tgcagcccaa tgcttgtcag
1441 aatggaggca cttgcaccaa ccgcaacgga ggctacggct gcgtgtgcgt gaacggctgg
1501 agtggggatg actgcagcga gaacatcgat gactgtgcct tcgcttcctg cacgccaggc
1561 tccacctgta ttgaccgtgt ggcctccttc tcctgccttt gtccagaggg aaaggcaggg
1621 ctcctgtgtc atctggatga tgcctgtatc agcaaccctt gtcacaaggg ggcgctgtgt
1681 gataccaacc ccctgaatgg gcagtacatt tgcacctgcc cacaggcgta caagggcgct
1741 gactgcacag aagacgtgga tgagtgtgct atggccaaca gtaacccttg tgagcatgca
1801 ggaaagtgtg tgaatacaga tggcgccttc cactgcgagt gtctgaaggg ctacgcaggg
1861 cctcgctgtg agatggacat caacgagtgt cactcagacc cctgtcagaa cgacgccacc
1921 tgcctggata agattggagg cttcacctgt ctctgcatgc cgggtttcaa aggtgtgcat
1981 tgtgaactgg aggtgaatga atgccagagc aacccgtgtg taaacaatgg gcagtgtgtg
2041 gacaaagtca atcgcttcca gtgtctgtgt ccccctggtt tcacaggacc agtgtgccag
2101 atcgacattg acgactgctc cagtactccc tgcctgaatg gggccaagtg catcgatcac
2161 ccgaatggct atgaatgcca gtgtgccaca ggattcactg gcacactgtg tgatgagaac
2221 atcgacaact gtgacccgga tccttgccac catggccagt gccaggatgg gattgactcc
2281 tacacctgca tctgcaaccc cgggtacatg ggagccatct gtagtgacca gattgatgaa
2341 tgctacagca gcccctgcct gaatgatgga cgctgcatcg acctggtgaa cggctaccag
2401 tgcaactgcc aaccgggtac ctcaggcctt aattgtgaaa ttaattttga tgactgtgcc
2461 agcaacccct gtctgcacgg agcctgtgtg gacggcatca accgttacag ttgtgtgtgc
2521 tctccgggat tcacagggca gaggtgcaac atagacattg atgagtgtgc ctccaacccc
2581 tgtcgcaagg atgcgacgtg catcaatgac gtgaatggtt tccggtgtat gtgccctgag
2641 ggaccacacc atcccagctg ctactcacag gtgaacgagt gtttgagcag tccctgcatc
2701 catggaaact gtactggagg tctcagtggc tataagtgcc tctgcgatgc aggctgggtt
2761 ggtatcaact gcgaagtgga caaaaatgag tgtctttcta acccgtgcca gaatggaggg
2821 acatgtaata acctggtgaa tggctacagg tgtacatgca agaaggggtt caaaggctat
2881 aactgccagg tgaacataga tgagtgtgcc tcgaacccgt gtctgaacca agggacctgc
2941 ctcgatgacg tcagtggcta cacctgccac tgcatgctgc cttacacagg caagaattgt
3001 caaacggtgt tggcgccctg ctcccctaac ccgtgtgaga acgctgcagt ttgtaaagag
3061 gcacccaact ttgagagctt cacctgcctg tgtgcccctg gctggcaagg tcagcgctgt
3121 acagttgacg ttgatgagtg tgtctccaag ccgtgtatga acaatggcat ctgccataat
3181 actcagggca gctacatgtg cgagtgccct cccggcttca gtggtatgga ctgtgaggag
3241 gacatcaatg actgccttgc caacccctgc cagaacggag gctcctgtgt ggacaaagtg
3301 aacaccttct cctgcctgtg ccttcctggc ttcgtagggg acaagtgcca aacagacatg
3361 aatgaatgtc tgagcgagcc ctgtaagaat gggggacct gctctgacta cgtcaacagc
3421 tacacctgca cgtgccctgc gggcttccat ggagtccact gtgaaaacaa catcgatgag
3481 tgcactgaga gctcctgttt caatggcggc acgtgtgttg atgggatcaa ctctttctct
3541 tgcttatgcc ctgtgggttt cactggtccc ttctgcctcc atgatatcaa tgagtgcagc
3601 tctaacccgt gcctgaattc gggaacgtgt gttgatggcc tgggtaccta ccgatgcacc
3661 tgtcccttgg gctacactgg gaaaaactgt cagaccctgg tgaacctctg cagcccctct
3721 ccatgtaaaa acaaaggaac ttgtgctcag gaaaaggcaa ggccacgctg cctgtgtccg
3781 cctggatggg atggcgcata ctgtgatgtg ctcaatgtgt cctgtaaggc ggcagccttg
```

*Figure 15B*

```
3841 cagaaaggag tacctgttga acacttgtgc cagcactcgg gtatctgtat caatgctggc
3901 aacacgcatc actgccagtg cccccctgggc tacacgggga gctactgcga ggaacagctt
3961 gacgagtgtg cgtccaatcc atgccagcat ggtgccacct gcagtgactt catcggagga
4021 tacagatgtg agtgtgttcc agggtatcag ggtgtcaact gtgagtatga agtggacgag
4081 tgccagaacc agccctgtca gaacggaggc acctgcatcg acctcgtgaa ccatttcaag
4141 tgctcgtgcc caccaggcac ccggggcctg ctttgtgaag agaacattga tgactgtgct
4201 ggggcccccc actgccttaa tggtggccag tgtgtggacc ggattggagg ctacagttgt
4261 cgctgtttgc ctggctttgc tggggagcgg tgtgaggggg acatcaatga atgcctgtcc
4321 aatccttgca gctcagaggg cagcctggac tgcattcagc tcaaaaataa ctaccagtgt
4381 gtctgccgca gcgccttcac aggccgacac tgcgaaacct tcctagatgt gtgtccccag
4441 aagccttgcc tgaatggagg gacttgtgct gtggctagca acgtgcctga tggcttcatt
4501 tgtcgttgtc ccccagggtt ctccggggca agatgccaga gcagctgtgg acaagtgaag
4561 tgcagaagag gggagcagtg tgtgcacacc gcctcgggac cccactgctt ctgcccgaac
4621 cacaaggact gcgagtcagg ttgcgctagt aacccctgcc agcacggagg cacctgctac
4681 cctcagcgcc agcctcctta ctactcttgc cgctgctccc caccgttctg ggcagccac
4741 tgcgagagct acacagcccc caccagc 4767
```

*Figure 16A*

```
  60                                                                 a
  61 tggggctggg ggcccggggc cgccgccgcc gtcgtcgcct gatggccttg ccaccgccac
 121 caccgcccat gcgggcgctg cccctgctgc tgctgctagc ggggctgggg gctgcagcac
 181 cccccttgtct ggatggaagc ccatgtgcaa atggaggtcg gtgcacccac cagcagccct
 241 ccctggaggc tgcttgcctg tgcctgccag gctgggtggg tgagcggtgc cagctggaag
 301 acccttgcca ctcaggccct tgtgctggcc gaggcgtttg ccagagttca gtggtggcgg
 361 gcaccgcccg attctcctgt cgttgtctcc gtggcttcca aggcccagac tgctcccagc
 421 cagacccctg cgtcagcagg ccctgtgttc atggtgcccc ctgctcagtg ggccggatg
 481 gccgatttgc ctgtgcctgc ccacctggct accagggtca aagctgccaa agtgacatag
 541 atgagtgccg atctggtaca acttgccgtc atggtggtac ctgtctcaat acacctggat
 601 ccttccgctg ccagtgtcct cttggttata cagggctgct gtgtgagaac cccgtagtgc
 661 cctgtgcccc ttccccgtgt cgtaatggtg gcacctgtag gcagagcagt gatgtcacat
 721 atgactgtgc ttgccttcct ggcttcgagg gccagaactg tgaagtcaac gtggatgact
 781 gtcctggaca tcggtgtctc aatgggggaa cgtgtgtaga cggtgtcaat acttacaact
 841 gccagtgccc tccggagtgg acaggccagt tctgtacaga agatgtggat gagtgtcagc
 901 tgcagcccaa tgcctgccac aatgggggta cctgcttcaa cctactgggt ggccacagct
 961 gtgtatgtgt caatggctgg acgggtgaga gctgcagtca gaatatcgat gactgtgcta
1021 cagccgtgtg tttccatggg gccacctgcc atgaccgtgt ggcctctttc tactgtgcct
1081 gccctatggg gaagacaggc ctcttgtgtc atctggatga tgcatgtgtc agcaacccct
1141 gccatgagga tgctatctgt gacacaaacc ctgtgagtgg ccgggccatc tgcacctgcc
1201 cacctggctt cactggaggg gcatgtgacc aggatgtgga tgagtgctcg attggtgcca
1261 acccctgtga acatttgggt cggtgtgtga atacacaggg ctcattcttg tgccaatgtg
1321 gccgtggcta tactggacct cgctgtgaga ctgatgtcaa tgagtgtctc tccgggccct
1381 gccgcaacca ggccacgtgt cttgaccgaa ttggccagtt tacttgcatc tgcatggcag
1441 gcttcacagg gacctactgt gaggtggaca tcgacgaatg tcagagcagc ccatgtgtca
1501 atggtggtgt ctgcaaggac agagtcaatg gcttcagctg cacctgccca tcaggattca
1561 gtgggtccat gtgtcagctg gatgtggatg agtgtgcaag cactccctgc cggaatggtg
1621 ccaagtgtgt ggaccagcct gacggctatg agtgtcgctg tgcagagggc tttgagggca
1681 ctttgtgtga gcgaaacgtg gatgactgct ctccggatcc ctgccaccac gggcgctgtg
1741 tcgatggcat tgctagcttc tcgtgtgctt gtgccccagg ctatacgggc atacgctgtg
1801 agagccaggt ggatgagtgc cgcagccagc cctgtcgata tgggggcaaa tgtctagact
1861 tggtggacaa gtacctctgc cgttgtcctc ccggaaccac aggtgtgaac tgtgaagtca
1921 acattgatga ctgtgccagt aacccctgta cctttggagt ttgccgtgat ggcatcaacc
1981 gttatgactg tgtctgtcag cctggattca cagggcccct ctgcaacgtg gagatcaatg
2041 agtgtgcatc cagcccatgt ggagagggtg gctcctgtgt ggatggggaa aatggcttcc
2101 actgcctctg tccacctggc tccctgcctc cactttgcct acctgcgaac catccctgtg
2161 cccacaagcc ctgtagtcat ggagtctgcc atgatgcacc aggcgggttc cgctgtgttt
2221 gtgagcccgg gtggagtggc cctcgctgta gccagagcct ggctccagat gcctgtgagt
2281 cccagccctg ccaggctggt ggcacctgca ccagtgatgg aataggcttt cgctgcacct
2341 gtgcccctgg attccagggc catcagtgtg aggtgctgtc cccctgtact ccaagcctct
2401 gtgagcacgg aggccactgt gagtctgacc ctgaccggct gactgtctgt tcctgtcccc
2461 caggctggca aggcccacga tgccagcagg atgtggatga atgtgccggt gcctcacccct
2521 gcggccccca tggtacctgc accaacctgc cagggaattt caggtgcatc tgccacaggg
2581 gatacactgg cccccttctgt gatcaagaca ttgacgactg tgaccccaac ccgtgcctcc
2641 atggtggctc ctgccaggat ggcgtgggct ccttttcctg ttcttgcctc gacggctttg
2701 ctggtcctcg ctgtgcccga gatgtggacg aatgtctgag cagcccctgt ggccctggca
2761 cctgtactga tcacgtggcc tccttcacct gtgcctgtcc acctggttat ggaggcttcc
2821 actgtgagat tgacttgccg gactgcagcc ccagttcctg cttcaatgga gggacctgtg
2881 tggatggcgt gagctccttc agctgtctgt gtcgccccgg ctacacaggc acacactgcc
2941 aatacgaggc tgacccctgc ttttcccggc cctgtctgca cgggggcatc tgcaacccca
3001 cccacccagg atttgaatgc acctgccggg agggcttcac tgggagtcag tgtcagaacc
3061 cagtggactg gtgcagccag gcaccctgtc agaatggggg tcgctgtgtc cagactgggg
3121 cttactgcat ttgtccacct ggatggagtg gccgcctgtg cgacatacaa agcctgccct
3181 gcacggaggc cgcagcccag atgggggtga ggttggagca gctgtgtcag gaaggtggaa
3241 agtgcataga caagggccgc tcccactact gtgtgtgtcc agagggccgt acgggtagtc
3301 actgtgaaca cgaggtggat ccctgcacgg cccagccttg ccagcacggg ggcacttgcc
```

*Figure 16B*

```
3361 gtggttacat ggggggctat gtgtgtgagt gtccagctgg ctatgctggt gacagttgtg
3421 aggataatat agatgagtgt gcttcccagc cctgccagaa cggaggctcc tgtatcgatc
3481 ttgtggcccg ctatctctgt tcctgtcccc ctggcacact gggagttctc tgtgagatca
3541 atgaggacga ctgtgaccta ggcccatcct tggactcagg cgttcagtgc ctacacaatg
3601 gcacctgtgt ggacctggtg ggtggcttcc gctgtaactg tcccccagga tacacaggtc
3661 tgcactgtga ggcagacatc aatgagtgtc gcccgggtgc ctgccatgca gcgcatactc
3721 gggactgcct acaagatcca ggtgggcatt tccgctgcgt ctgccatcct ggcttcacag
3781 ggcctcgctg tcagattgct ctgtccccct gtgagtccca gccatgtcag catggaggcc
3841 agtgccgtca cagcctaggc cgtggaggtg ggctgacctt cacctgtcac tgtgtcccgc
3901 cattctgggg tctgcgttgt gagcgggtgg cacgctcttg ccgagagctg cagtgcccag
3961 tgggtatccc atgccagcag acagcccgtg gaccacgctg cgcttgtcct ccggggctgt
4021 ccgggccctc ctgccgggtt tctagggcgt caccctcagg agctactaac gccagctgcg
4081 cctctgcccc ttgtctgcat gggggctcat gcctacctgt acagagtgtc cctttcttcc
4141 gctgtgtgtg cgctccgggc tggggcggcc cgcgttgtga gaccccttcc gcagcc 4196
```

*Figure 17A*

```
 117                                                                     atgc
 121 agccccagtt gctgctgctg ctgctcttgc cactcaattt ccctgtcatc ctgaccagag
 181 agcttctgtg tggaggatcc ccagagccct gtgccaacgg aggcacctgc ctgaggctat
 241 ctcagggaca agggatctgc cagtgtgccc ctggatttct gggtgagact tgccagtttc
 301 ctgacccctg cagggatacc caactctgca agaatggtgg cagctgccaa gccctgctcc
 361 ccacaccccc aagctcccgt agtcctactt ctccactgac ccctcacttc tcctgcacct
 421 gcccctctgg cttcaccggt gatcgatgcc aaacccatct ggaagagctc tgtccacctt
 481 ctttctgttc caacgggggt cactgctatg ttcaggcctc aggccgccca cagtgctcct
 541 gcgagcctgg gtggacaggt gagcaatgcc agctccgaga cttctgctca gccaacccct
 601 gtgccaacgg aggcgtgtgc ctggccacat acccccagat ccagtgccgc tgtccacctg
 661 ggttcgaggg tcacacctgt gaacgcgaca tcaacgagtg cttcctggag ccgggacccc
 721 gccctcaggg cacctcctgc cataacacct tgggttccta ccagtgtctc tgccctgtgg
 781 ggcaggaagg tccccagtgc aagctcagga agggagcctg ccctcctgga agctgtctca
 841 atgggggcac ctgccagctg gtcccagagg gacactccac ctttcatctc tgcctctgtc
 901 ccccaggttt cacggggctg gactgtgaga tgaacccaga tgactgtgtc aggcaccagt
 961 gtcagaacgg ggccacctgt ctggatgggc tggataccta cacctgcctc tgccccaaga
1021 catggaaggg ctgggactgc tctgaagata tagatgaatg tgaagcccgg ggtcccccctc
1081 gctgcaggaa cggtggcacc tgccagaaca cagctggcag ctttcactgt gtgtgcgtga
1141 gtggctgggg cggtgcaggt tgtgaggaga acctggatga ctgtgcagct gccacctgtg
1201 ccccgggatc cacctgcatc gaccgtgtgg gctctttctc ctgcctctgc ccacctggac
1261 gcacaggcct cctgtgccac ctggaagaca tgtgtttgag tcagccgtgc cacgtgaatg
1321 cccagtgcag caccaaccct ctgacaggct ccaccctctg catatgccag cctggctact
1381 caggatccac ctgtcaccaa gatctggatg agtgccaaat ggcccagcaa ggacccagtc
1441 cctgcgaaca tggcggctcc tgcatcaaca cccctggctc cttcaactgc ctctgcctgc
1501 ctggttacac gggctcccgc tgtgaagctg accacaatga gtgcctgtca cagccctgcc
1561 acccaggcag cacctgcctg gacctgcttg caaccttcca ctgcctctgc ccaccaggct
1621 tggaagggag gctctgtgag gtggaggtca atgagtgcac ctctaatccc tgcctgaacc
1681 aagctgcctg ccatgacctg ctcaacggct tccagtgcct ctgccttcct ggattcaccg
1741 gcgcccgatg tgagaaagac atggacgagt gtagcagcac cccctgtgcc aatgggggc
1801 gctgccgaga ccagcctgga gccttctact gcgagtgtct cccaggcttt gaagggccac
1861 actgtgagaa agaagtggac gaatgtctga gtgacccctg ccccgtggga gccagctgcc
1921 ttgatctccc cggagcattc ttctgcctct gccgtcctgg tttcacaggt caactttgtg
1981 aggttccctt gtgcaccccc aacatgtgcc aacctggaca gcaatgccaa ggtcaggaac
2041 acagagcccc ctgcctctgc cctgacggaa gtcctggctg tgttcctgcc gaggacaact
2101 gcccctgtca ccatggccat tgccagagat ccttgtgtgt gtgtgatgag ggctggactg
2161 gaccagaatg cgagacagaa ctgggtggct gcatctccac accctgtgcc catgggggga
2221 cctgccaccc acagccgtct ggctacaact gtacctgccc tgcaggctac atggggttga
2281 cctgtagtga ggaggtgaca gcttgtcact cagggccctg tctcaatggt ggctcttgca
2341 gcatccgtcc tgagggctat tcctgcacct gccttccaag tcacacaggt cgccactgcc
2401 agactgccgt ggaccactgt gtgtctgcct cgtgcctcaa tgggggtacc tgtgtgaaca
2461 agcctggcac tttcttctgc ctctgtgcca ctggcttcca ggggctgcac tgtgaggaga
2521 agactaaccc cagctgtgca gacagcccct gcaggaacaa ggcaacctgc caagacacac
2581 ctcgaggggc ccgctgcctc tgcagccctg gctatacagg aagcagctgc cagactctga
2641 tagacttgtg tgcccggaag ccctgtccac acactgctcg atgcctccag agtgggccct
2701 cgttccagtg cctgtgcctc cagggatgga caggggctct ctgtgacttc ccactgtcct
2761 gccagatggc cgcaatgagc caaggcatag agatctctgg cctgtgccag aatggaggcc
2821 tctgtattga cacgggctcc tcctatttct gccgctgccc tcctggattc caaggcaagt
2881 tatgccagga taatatgaac ccctgcgagc ccaatccctg ccatcacggg tctacctgtg
2941 tgcctcagcc cagtggctat gtctgccagt gtgccccagg ctatgaggga cagaactgct
3001 caaaagtact tgaagcttgt cagtcccagc cctgccacaa ccacggaacc tgtacctcca
3061 ggcctggagg cttccactgt gcctgccctc caggcttcgt gggactgcgc tgtgagggag
3121 atgtggatga gtgtctggac cggccctgtc acccctcggg cactgcagct tgccactctt
3181 tagccaacgc cttctactgc cagtgtctgc ctgggcacac aggccagcgg tgtgaggtgg
3241 agatggacct ctgtcagagc caaccctgct ccaatggagg atcctgtgag atcacaacag
3301 ggccaccccc tggcttcacc tgtcactgcc ccaagggttt tgaaggcccc acctgcagcc
```

*Figure 17B*

3361 acaaagcccct ttcctgcggc atccatcact gccacaatgg aggcctatgt ctgccctccc
3421 ctaagccagg gtcaccacca ctctgtgcct gcctcagtgg ttttgggggc cctgactgtc
3481 tgacacctcc agctccaccg ggctgcggtc ccccctcacc ctgcctgcac aatggtacct
3541 gcactgagac ccctgggttg ggcaacccgg gctttcaatg cacctgcccct cctgactctc
3601 cagggccccg gtgtcaaagg ccaggg.3626

Linker sequence

GAT CTG GGC CCG GGC
D L G P G

*Figure 18A*

```
   1 atgccgccgc tcctggcgcc cctgctctgc ctggcgctgc tgcccgcgct cgccgcacga
  61 ggcccgcgat gctcccagcc cggtgagacc tgcctgaatg gcgggaagtg tgaagcggcc
 121 aatggcacgg aggcctgcgt ctgtggcggg gccttcgtgg gcccgcgatg ccaggacccc
 181 aacccgtgcc tcagcacccc ctgcaagaac gccgggacat gccacgtggt ggaccgcaga
 241 ggcgtggcag actatgcctg cagctgtgcc ctgggcttct ctgggcccct ctgcctgaca
 301 cccctggaca atgcctgcct caccaacccc tgccgcaacg gggcacctg cgacctgctc
 361 acgctgacgg agtacaagtg ccgctgcccg cccggctggt cagggaaatc gtgccagcag
 421 gctgacccgt gcgcctccaa cccctgcgcc aacggtggcc agtgcctgcc cttcgaggcc
 481 tcctacatct gccactgccc acccagcttc catggcccca cctgccggca ggatgtcaac
 541 gagtgtggcc agaagcccgg gctttgccgc cacggaggca cctgccacaa cgaggtcggc
 601 tcctaccgct gcgtctgccg cgccacccac actggcccca actgcgagcg gccctacgtg
 661 ccctgcagcc cctcgccctg ccagaacggg ggcacctgcc gccccacggg cgacgtcacc
 721 cacgagtgtg cctgcctgcc aggcttcacc ggccagaact gtgaggaaaa tatcgacgat
 781 tgtccaggaa acaactgcaa gaacgggggt gcctgtgtgg acggcgtgaa cacctacaac
 841 tgccgctgcc cgccagagtg gacaggtcag tactgtaccg aggatgtgga cgagtgccag
 901 ctgatgccaa atgcctgcca gaacggcggg acctgccaca acacccacgg tggctacaac
 961 tgcgtgtgtg tcaacggctg gactggtgag gactgcagcg agaacattga tgactgtgcc
1021 agcgccgcct gcttccacgg cgccacctgc catgaccgtg tggcctcctt ctactgcgag
1081 tgtccccatg gccgcacagg tctgctgtgc cacctcaacg acgcatgcat cagcaacccc
1141 tgtaacgagg gctccaactg cgacaccaac cctgtcaatg gcaaggccat ctgcacctgc
1201 ccctcggggt acacgggccc ggcctgcagc caggacgtgg atgagtgctc gctgggtgcc
1261 aacccctgcg agcatgcggg caagtgcatc aacacgctgg gctccttcga gtgccagtgt
1321 ctgcagggct acacgggccc ccgatgcgag atcgacgtca acgagtgcgt ctcgaacccg
1381 tgccagaacg acgccacctg cctggaccag attggggagt tccagtgcat ctgcatgccc
1441 ggctacgagg gtgtgcactg cgaggtcaac acagacgagt gtgccagcag cccctgcctg
1501 cacaatggcc gctgcctgga caagatcaat gagttccagt gcgagtgccc cacgggcttc
1561 actgggcatc tgtgccagta cgatgtggac gagtgtgcca gcacccccctg caagaatggt
1621 gccaagtgcc tggacggacc caacacttac acctgtgtgt gcacggaagg gtacacgggg
1681 acgcactgcg aggtggacat cgatgagtgc gaccccgacc cctgccacta cggctcctgc
1741 aaggacggcg tcgccacctt cacctgcctc tgccgcccag gctacacggg ccaccactgc
1801 gagaccaaca tcaacgagtg ctccagccag ccctgccgcc acgggggcac ctgccaggac
1861 cgcgacaacg cctacctctg cttctgcctg aaggggacca caggacccaa ctgcgagatc
1921 aacctggatg actgtgccag cagcccctgc gactcgggca cctgtctgga caagatcgat
1981 ggctacgagt gtgcctgtga gccgggctac acagggagca tgtgtaacat caacatcgat
2041 gagtgtgcgg gcaacccctg ccacaacggg ggcacctgcg aggacggcat caatggcttc
2101 acctgccgct gccccgaggg ctaccacgac cccacctgcc tgtctgaggt caatgagtgc
2161 aacagcaacc cctgcgtcca cggggcctgc cgggacagcc tcaacgggta caagtgcgac
2221 tgtgaccctg ggtggagtgg gaccaactgt gacatcaaca acaatgagtg tgaatccaac
2281 ccttgtgtca acggcggcac ctgcaaagac atgaccagtg gctacgtgtg cacctgccgg
2341 gagggcttca gcggtcccaa ctgccagacc aacatcaacg agtgtgcgtc caacccatgt
2401 ctgaaccagg gcacgtgtat tgacgacgtt gccgggtaca agtgcaactg cctgctgccc
2461 tacacaggtg ccacgtgtga ggtggtgctg gccccgtgtg cccccagccc ctgcagaaac
2521 ggcggggagt gcaggcaatc cgaggactat gagagcttct cctgtgtctg ccccacgggc
2581 tggcaagcag ggcagacctg tgaggtcgac atcaacgagt gcgttctgag cccgtgccgg
2641 cacggcgcat cctgccagaa cacccacggc ggctaccgct gccactgcca ggccggctac
2701 agtgggcgca actgcgagac cgacatcgac gactgccggc ccaacccgtg tcacaacggg
2761 ggctcctgca cagacggcat caacacggcc ttctgcgact gcctgcccgg cttccggggc
2821 actttctgtg aggaggacat caacgagtgt gccagtgacc cctgccgcaa cggggccaac
2881 tgcacggact gcgtggacag ctacacgtgc acctgccccg caggcttcag cgggatccac
2941 tgtgagaaca acacgcctga ctgcacagag agctcctgct tcaacggtgg cacctgcgtg
3001 gacggcatca actcgttcac ctgcctgtgt ccacccggct tcacgggcag ctactgccag
3061 cacgatgtca atgagtgcga ctcacagccc tgcctgcatg gcggcacctg tcaggacggc
3121 tgcggctcct acaggtgcac ctgcccccag ggctacactg gccccaactg ccagaacctt
3181 gtgcactggt gtgactcctc gccctgcaag aacggcggca aatgctggca gacccacacc
3241 cagtaccgct gcgagtgccc cagcggctgg accggccttt actgcgacgt gcccagcgtg
3301 tcctgtgagg tggctgcgca gcgacaaggt gttgacgttg cccgcctgtg ccagcatgga
```

*Figure 18B*

3361 gggctctgtg tggacgcggg caacacgcac cactgccgct gccaggcggg ctacacaggc
3421 agctactgtg aggacctggt ggacgagtgc tcacccagcc cctgccagaa cggggccacc
3481 tgcacggact acctgggcgg ctactcctgc aagtgcgtgg ccggctacca cggggtgaac
3541 tgctctgagg agatcgacga gtgcctctcc cacccctgcc agaacggggg cacctgcctc
3601 gacctcccca acacctacaa gtgctcctgc ccacggggca ctcagggtgt gcactgtgag
3661 atcaacgtgg acgactgcaa tcccccgtt gaccccgtgt cccggagccc caagtgcttt
3721 aacaacggca cctgcgtgga ccaggtgggc ggctacagct gcacctgccc gccgggcttc
3781 gtgggtgagc gctgtgaggg ggatgtcaac gagtgcctgt ccaatccctg cgacgcccgt
3841 ggcacccaga actgcgtgca gcgcgtcaat gacttccact gcgagtgccg tgctggtcac
3901 accgggcgcc gctgcgagtc cgtcatcaat ggctgcaaag gcaagccctg caagaatggg
3961 ggcacctgcg ccgtggcctc caacaccgcc cgcgggttca tctgcaagtg ccctgcgggc
4021 ttcgagggcg ccacgtgtga gaatgacgct cgtacctgcg gcagcctgcg ctgcctcaac
4081 ggcggcacat gcatctccgg cccgcgcagc cccacctgcc tgtgcctggg ccccttcacg
4141 ggccccgaat gccagttccc ggccagcagc ccctgcctgg gcggcaaccc ctgctacaac
4201 caggggacct gtgagcccac atccgagagc cccttctacc gttgcctgtg ccccgccaaa
4261 ttcaacgggc tcttgtgcca catcctggac tacagcttc 4299

*Figure 19A*

```
  13            atgcccgc cctgcgcccc gctctgctgt gggcgctgct ggcgctctgg
  61 ctgtgctgcg cggcccccgc gcatgcattg cagtgtcgag atggctatga accctgtgta
 121 aatgaaggaa tgtgtgttac ctaccacaat ggcacaggat actgcaaatg tccagaaggc
 181 ttcttggggg aatattgtca acatcgagac ccctgtgaga agaaccgctg ccagaatggt
 241 gggacttgtg tggcccaggc catgctgggg aaagccacgt gccgatgtgc ctcagggttt
 301 acaggagagg actgccagta ctcaacatct catccatgct ttgtgtctcg accctgcctg
 361 aatggcggca catgccatat gctcagccgg gatacctatg agtgcacctg tcaagtcggg
 421 tttacaggta aggagtgcca atggacggat gcctgcctgt ctcatccctg tgcaaatgga
 481 agtacctgta ccactgtggc caaccagttc tcctgcaaat gcctcacagg cttcacaggg
 541 cagaaatgtg agactgatgt caatgagtgt gacattccag gacactgcca gcatggtggc
 601 acctgcctca acctgcctgg ttcctaccag tgccagtgcc ctcagggctt cacaggccag
 661 tactgtgaca gcctgtatgt gccctgtgca ccctcacctt gtgtcaatgg aggcacctgt
 721 cggcagactg gtgacttcac ttttgagtgc aactgccttc caggttttga agggagcacc
 781 tgtgagagga atattgatga ctgccctaac cacaggtgtc agaatggagg ggtttgtgtg
 841 gatggggtca acacttacaa ctgccgctgt cccccacaat ggacaggaca gttctgcaca
 901 gaggatgtgg atgaatgcct gctgcagccc aatgcctgtc aaaatggggg cacctgtgcc
 961 aaccgcaatg gaggctatgg ctgtgtatgt gtcaacggct ggagtggaga tgactgcagt
1021 gagaacattg atgattgtgc cttcgcctcc tgtactccag gctccacctg catcgaccgt
1081 gtggcctcct tctcttgcat gtgcccagag gggaaggcag gtctcctgtg tcatctggat
1141 gatgcatgca tcagcaatcc ttgccacaag ggggcactgt gtgacaccaa cccccctaaat
1201 gggcaatata tttgcacctg cccacaaggc tacaaagggg ctgactgcac agaagatgtg
1261 gatgaatgtg ccatggccaa tagcaatcct tgtgagcatg caggaaaatg tgtgaacacg
1321 gatggcgcct tccactgtga gtgtctgaag ggttatgcag gacctcgttg tgagatggac
1381 atcaatgagt gccattcaga cccctgccag aatgatgcta cctgtctgga taagattgga
1441 ggcttcacat gtctgtgcat gccaggtttc aaaggtgtgc attgtgaatt agaaataaat
1501 gaatgtcaga gcaaccccttg tgtgaacaat gggcagtgtg tggataaagt caatcgtttc
1561 cagtgcctgt gtcctcctgg tttcactggg ccagtttgcc agattgatat tgatgactgt
1621 tccagtactc cgtgtctgaa tggggcaaag tgtatcgatc acccgaatgg ctatgaatgc
1681 cagtgtgcca caggtttcac tggtgtgttg tgtgaggaga acattgacaa ctgtgacccc
1741 gatccttgcc accatggtca gtgtcaggat ggtattgatt cctacacctg catctgcaat
1801 cccgggtaca tgggcgccat ctgcagtgac cagattgatg aatgttacag cagcccttgc
1861 ctgaacgatg gtcgctgcat tgacctggtc aatggctacc agtgcaactg ccagccaggc
1921 acgtcagggg ttaattgtga aattaatttt gatgactgtg caagtaaccc ttgtatccat
1981 ggaatctgta tggatggcat taatcgctac agttgtgtct gctcaccagg attcacaggg
2041 cagagatgta acattgacat tgatgagtgt gcctccaatc cctgtcgcaa gggtgcaaca
2101 tgtatcaacg gtgtgaatgg tttccgctgt atatgccccg agggaccccca tcaccccagc
2161 tgctactcac aggtgaacga atgcctgagc aatccctgca tccatggaaa ctgtactgga
2221 ggtctcagtg gatataagtg tctctgtgat gcaggctggg ttggcatcaa ctgtgaagtg
2281 gacaaaaatg aatgcctttc gaatccatgc cagaatggag gaacttgtga caatctcgtg
2341 aatggataca ggtgtacttg caagaagggc tttaaaggct ataactgcca ggtgaatatt
2401 gatgaatgtg cctcaaatcc atgcctgaac caaggaacct gctttgatga cataagtggc
2461 tacacttgcc actgtgtgct gccatacaca ggcaagaatt gtcagacagt attggctccc
2521 tgttccccaa accccttgtga gaatgctgct gtttgcaaag agtcaccaaa ttttgagagt
2581 tatacttgct tgtgtgctcc tggctggcaa ggtcagcggt gtaccattga cattgacgag
2641 tgtatctcca agccctgcat gaaccatggt ctctgccata acacccaggg cagctacatg
2701 tgtgaatgtc caccaggctt cagtggtatg gactgtgagg aggacattga tgactgcctt
2761 gccaatcctt gccagaatgg aggttcctgt atggatggag tgaatacttt ctcctgcctc
2821 tgccttccgg gtttcactgg ggataagtgc cagacagaca tgaatgagtg tctgagtgaa
2881 ccctgtaaga atggagggac ctgctctgac tacgtcaaca gttacacttg caagtgccag
2941 gcaggatttg atggagtcca ttgtgagaac aacatcaatg agtgcactga gagctcctgt
3001 ttcaatggtg gcacatgtgt tgatgggatt aactccttct cttgcttgtg ccctgtgggt
3061 ttcactggat ccttctgcct ccatgagatc aatgaatgca gctctcatcc atgcctgaat
3121 gagggaacgt gtgttgatgg cctgggtacc taccgctgca gctgccccct gggctacact
3181 gggaaaaact gtcagaccct ggtgaatctc tgcagtcggt ctccatgtaa aaacaaaggt
3241 acttgtgttc agaaaaaagc agagtcccag tgcctatgtc catctggatg ggctggtgcc
```

*Figure 19B*

```
3301 tattgtgacg tgcccaatgt ctcttgtgac atagcagcct ccaggagagg tgtgcttgtt
3361 gaacacttgt gccagcactc aggtgtctgc atcaatgctg gcaacacgca ttactgtcag
3421 tgcccccctgg gctatactgg gagctactgt gaggagcaac tcgatgagtg tgcgtccaac
3481 ccctgccagc acggggcaac atgcagtgac ttcattggtg gatacagatg cgagtgtgtc
3541 ccaggctatc agggtgtcaa ctgtgagtat gaagtggatg agtgccagaa tcagccctgc
3601 cagaatggag gcacctgtat tgaccttgtg aaccatttca agtgctcttg cccaccaggc
3661 actcggggcc tactctgtga agagaacatt gatgactgtg cccggggtcc ccattgcctt
3721 aatggtggtc agtgcatgga taggattgga ggctacagtt gtcgctgctt gcctggcttt
3781 gctggggagc gttgtgaggg agacatcaac gagtgcctct ccaacccctg cagctctgag
3841 ggcagcctgg actgtataca gctcaccaat gactacctgt gtgtttgccg tagtgccttt
3901 actggccggc actgtgaaac cttcgtcgat gtgtgtcccc agatgccctg cctgaatgga
3961 gggacttgtg ctgtggccag taacatgcct gatggtttca tttgccgttg tcccccggga
4021 ttttccgggg caaggtgcca gagcagctgt ggacaagtga aatgtaggaa gggggagcag
4081 tgtgtgcaca ccgcctctgg accccgctgc ttctgcccca gtccccggga ctgcgagtca
4141 ggctgtgcca gtagcccctg ccagcacggg ggcagctgcc accctcagcg ccagcctcct
     4201 tattactcct gcc 4213
```

*Figure 20A*

```
  77                                    atgg ggccgggggc ccgtggccgc cgccgccgcc gtcgcccgat
 121 gtcgccgcca ccgccaccgc cacccgtgcg ggcgctgccc ctgctgctgc tgctagcggg
 181 gccgggggct gcagcccccc cttgcctgga cggaagcccg tgtgcaaatg gaggtcgttg
 241 cacccagctg ccctcccggg aggctgcctg cctgtgcccg cctggctggg tgggtgagcg
 301 gtgtcagctg gaggacccct gtcactcagg cccctgtgct ggccgtggtg tctgccagag
 361 ttcagtggtg gctggcaccg cccgattctc atgccggtgc cccgtggct tccgaggccc
 421 tgactgctcc ctgccagatc cctgcctcag cagcccttgt gcccacggtg cccgctgctc
 481 agtggggccc gatggacgct tcctctgctc ctgcccacct ggctaccagg gccgcagctg
 541 ccgaagcgac gtggatgagt gccgggtggg tgagccctgc cgccatggtg gcacctgcct
 601 caacacacct ggctccttcc gctgccagtg tccagctggc tacacagggc cactatgtga
 661 gaaccccgcg gtgccctgtg caccctcacc atgccgtaac gggggcacct gcaggcagag
 721 tggcgacctc acttacgact gtgcctgtct tcctgggttt gagggtcaga attgtgaagt
 781 gaacgtggac gactgtccag gacaccgatg tctcaatggg gggacatgcg tggatggcgt
 841 caacacctat aactgccagt gccctcctga gtggacaggc cagttctgca cggaggacgt
 901 ggatgagtgt cagctgcagc ccaacgcctg ccacaatggg ggtacctgct tcaacacgct
 961 gggtggccac agctgcgtgt gtgtcaatgg ctggacaggc gagagctgca gtcagaatat
1021 cgatgactgt gccacagccg tgtgcttcca tggggccacc tgccatgacc gcgtggcttc
1081 tttctactgt gcctgcccca tgggcaagac tggcctcctg tgtcacctgg atgacgcctg
1141 tgtcagcaac ccctgccacg aggatgctat ctgtgacaca aatccggtga acggccgggc
1201 catttgcacc tgtcctcccg gcttcacggg tggggcatgt gaccaggatg tggacgagtg
1261 ctctatcggc gccaacccct gcgagcactt gggcaggtgc gtgaacacgc agggctcctt
1321 cctgtgccag tgcggtcgtg gctacactgg acctcgctgt gagaccgatg tcaacgagtg
1381 tctgtcgggg ccctgccgaa accaggccac gtgcctcgac cgcataggcc agttcacctg
1441 tatctgtatg gcaggcttca caggaaccta ttgcgaggtg gacattgacg agtgtcagag
1501 tagcccctgt gtcaacggtg ggtctgcaa ggaccgagtc aatggcttca gctgcacctg
1561 cccctcgggc ttcagcggct ccacgtgtca gctggacgtg gacgaatgcg ccagcacgcc
1621 ctgcaggaat ggcgccaaat gcgtggacca gcccgatggc tacgagtgcc gctgtgccga
1681 gggctttgag ggcacgctgt gtgatcgcaa cgtggacgac tgctcccctg acccatgcca
1741 ccatggtcgc tgcgtggatg gcatcgccag cttctcatgt gcctgtgctc ctggctacac
1801 gggcacacgc tgcgagagcc aggtggacga atgccgcagc cagccctgcc gccatggcgg
1861 caaatgccta gacctggtgg acaagtacct ctgccgctgc ccttctggga ccacaggtgt
1921 gaactgcgaa gtgaacattg acgactgtgc cagcaacccc tgcacctttg gagtctgccg
1981 tgatggcatc aaccgctacg actgtgtctg ccaacctggc ttcacagggc cccttttgtaa
2041 cgtggagatc aatgagtgtg cttccagccc atgcggcgag ggaggttcct gtgtggatgg
2101 ggaaaatggc ttccgctgcc tctgcccgcc tggctccttg cccccactct gcctcccccc
2161 gagccatccc tgtgcccatg agccctgcag tcacggcatc tgctatgatg cacctggcgg
2221 gttccgctgt gtgtgtgagc ctggctggag tggcccccgc tgcagccaga gcctggcccg
2281 agacgcctgt gagtcccagc cgtgcagggc cggtgggaca tgcagcagcg atggaatggg
2341 tttccactgc acctgcccgc ctggtgtcca gggacgtcag tgtgaactcc tctcccccctg
2401 caccccgaac ccctgtgagc atgggggccg ctgcgagtct gcccctggcc agctgcctgt
2461 ctgctcctgc ccccagggct ggcaaggccc acgatgccag caggatgtgg acgagtgtgc
2521 tggcccgca ccctgtggcc ctcatggtat ctgcaccaac ctggcaggga gtttcagctg
2581 cacctgccat ggagggtaca ctggcccttc ctgcgatcag gacatcaatg actgtgaccc
2641 caacccatgc ctgaacggtg gctcgtgcca agacggcgtg ggctcctttt cctgctcctg
2701 cctccctggt ttcgccggcc cacgatgcgc ccgcgatgtg gatgagtgcc tgagcaaccc
2761 ctgcggcccg ggcacctgta ccgaccacgt ggcctccttc acctgcacct gcccgccagg
2821 ctacggaggc ttccactgcg aacaggacct gcccgactgc agccccagct cctgcttcaa
2881 tggcgggacc tgtgtggacg gcgtgaactc gttcagctgc ctgtgccgtc ccggctacac
2941 aggagcccac tgccaacatg aggcagaccc ctgcctctcg cggccctgcc tacacggggg
3001 cgtctgcagc gccgcccacc ctggcttccg ctgcacctgc ctcgagagct tcacgggccc
3061 gcagtgccag acgctggtgg attggtgcag ccgccagcct tgtcaaaacg gggtcgctg
3121 cgtccagact ggggcctatt gcctttgtcc ccctggatgg agcggacgcc tctgtgacat
3181 ccgaagcttg ccctgcaggg aggccgcagc ccagatcggg gtgcggctgg agcagctgtg
3241 tcaggcgggt gggcagtgtg tggatgaaga cagctcccac tactgcgtgt gcccagaggg
3301 ccgtactggt agccactgtg agcaggaggt ggacccctgc ttggcccagc cctgccagca
```

*Figure 20B*

```
3361 tgggggggacc tgccgtggct atatgggggg ctacatgtgt gagtgtcttc ctggctacaa
3421 tggtgataac tgtgaggacg acgtggacga gtgtgcctcc cagccctgcc agcacggggg
3481 ttcatgcatt gacctcgtgg cccgctatct ctgctcctgt cccccaggaa cgctgggggt
3541 gctctgcgag attaatgagg atgactgcgg cccaggccca ccgctggact cagggccccg
3601 gtgcctacac aatggcacct gcgtggacct ggtgggtggt ttccgctgca cctgtccccc
3661 aggatacact ggtttgcgct gcgaggcaga catcaatgag tgtcgctcag gtgcctgcca
3721 cgcggcacac acccgggact gcctgcagga cccaggcgga ggtttccgtt gcctttgtca
3781 tgctggcttc tcaggtcctc gctgtcagac tgtcctgtct ccctgcgagt cccagccatg
3841 ccagcatgga ggccagtgcc gtcctagccc gggtcctggg ggtgggctga ccttcacctg
3901 tcactgtgcc cagccgttct ggggtccgcg ttgcgagcgg gtggcgcgct cctgccggga
3961 gctgcagtgc ccggtgggcg tcccatgcca gcagacgccc cgcgggccgc gctgcgcctg
4021 ccccccaggg ttgtcgggac cctcctgccg 4050
```

*Figure 21A*

```
  91                                                  atgcagcccc cttcactgct gctgctgctg
 121 ctgctgctgc tgctgctatg tgtctcagtg gtcagaccca gagggctgct gtgtgggagt
 181 ttcccagaac cctgtgccaa tggaggcacc tgcctgagcc tgtctctggg acaagggacc
 241 tgccagtgtg cccctggctt cctgggtgag acgtgccagt ttcctgaccc ctgccagaac
 301 gcccagctct gccaaaatgg aggcagctgc caagccctgc ttcccgctcc cctagggctc
 361 cccagctctc cctctccatt gacacccagc ttcttgtgca cttgcctccc tggcttcact
 421 ggtgagagat gccaggccaa gcttgaagac ccttgtcctc cctccttctg ttccaaaagg
 481 ggccgctgcc acatccaggc ctcgggccgc ccacagtgct cctgcatgcc tggatggaca
 541 ggtgagcagt gccagcttcg ggacttctgt tcagccaacc catgtgttaa tggaggggtg
 601 tgtctggcca catacccccca gatccagtgc cactgcccac cgggcttcga gggccatgcc
 661 tgtgaacgtg atgtcaacga gtgcttccag gacccaggac cctgccccaa aggcacctcc
 721 tgccataaca ccctgggctc cttccagtgc ctctgccctg tggggcagga gggtccacgt
 781 tgtgagctgc gggcaggacc ctgccctcct aggggctgtt cgaatggggg cacctgccag
 841 ctgatgccag agaaagactc cacctttcac ctctgcctct gtcccccagg tttcataggc
 901 ccagactgtg aggtgaatcc agacaactgt gtcagccacc agtgtcagaa tgggggcact
 961 tgccaggatg ggctggacac ctacacctgc ctctgcccag aaacctggac aggctgggac
1021 tgctccgaag atgtggatga gtgtgagacc cagggtcccc ctcactgcag aaacgggggc
1081 acctgccaga actctgctgg tagctttcac tgcgtgtgtg tgagtggctg gggcggcaca
1141 agctgtgagg agaacctgga tgactgtatt gctgccacct gtgccccggg atccacctgc
1201 attgaccggg tgggctcttt ctcctgcctc tgcccacctg gacgcacagg actcctgtgc
1261 cacttggaag acatgtgtct gagccagccg tgccatgggg atgcccaatg cagcaccaac
1321 cccctcacag gctccacact ctgcctgtgt cagcctggct attcggggcc cacctgccac
1381 caggacctgg acgagtgtct gatggcccag caaggcccaa gtccctgtga acatggcggt
1441 tcctgcctca acactcctgg ctccttcaac tgcctctgtc cacctggcta cacaggctcc
1501 cgttgtgagg ctgatcacaa tgagtgcctc tcccagccct gccacccagg aagcacctgt
1561 ctggacctac ttgccacctt ccactgcctc tgcccgccag gcttagaagg gcagctctgt
1621 gaggtggaga ccaacgagtg tgcctcagct ccctgcctga accacgcgga ttgccatgac
1681 ctgctcaacg gcttccagtg catctgcctg cctggattct ccggcacccg atgtgaggag
1741 gatatcgatg agtgcagaag ctctccctgt gccaatggtg ggcagtgcca ggaccagcct
1801 ggagccttcc actgcaagtg tctcccaggc tttgaagggc cacgctgtca aacagaggtg
1861 gatgagtgcc tgagtgaccc atgtcccgtt ggagccagct gccttgatct tccaggagcc
1921 ttcttttgcc tctgcccctc tggtttcaca ggccagctct gtgaggttcc cctgtgtgct
1981 cccaacctgt gccagcccaa gcagatatgt aaggaccaga aagacaaggc caactgcctc
2041 tgtcctgatg gaagccctgg ctgtgcccca cctgaggaca actgcacctg ccaccacggg
2101 cactgccaga gatcctcatg tgtgtgtgac gtgggttgga cggggccaga gtgtgaggca
2161 gagctagggg gctgcatctc tgcaccctgt gcccatgggg ggacctgcta cccccagccc
2221 tctggctaca actgcacctg ccctacaggc tacacaggac ccacctgtag tgaggagatg
2281 acagcttgtc actcagggcc atgtctcaat ggcggctcct gcaaccctag ccctggaggc
2341 tactactgca cctgccctcc aagccacaca gggccccagt gccaaaccag cactgactac
2401 tgtgtgtctg ccccgtgctt caatgggggt acctgtgtga acaggcctgg caccttctcc
2461 tgcctctgtg ccatgggctt ccagggcccg cgctgtgagg gaaagctccg ccccagctgt
2521 gcagacagcc cctgtaggaa tagggcaacc tgccaggaca gccctcaggg tccccgctgc
2581 ctctgcccca ctggctacac cggaggcagc tgccagactc tgatggactt atgtgcccag
2641 aagccctgcc cacgcaattc ccactgcctc cagactgggc cctccttcca ctgcttgtgc
2701 ctccagggat ggaccgggcc tctctgcaac ctttccactgt cctcctgcca gaaggctgca
2761 ctgagccaag gcatagacgt ctcttccctt tgccacaatg gaggcctctg tgtcgacagc
2821 ggcccctcct atttctgcca ctgcccccct ggattccaag gcagcctgtg ccaggatcac
2881 gtgaacccat gtgagtccag gccttgccag aacggggcca cctgcatggc ccagcccagt
2941 gggtatctct gccagtgtgc cccaggctac gatggacaga actgctcaaa ggaactcgat
3001 gcttgtcagt cccaaccctg tcacaaccat ggaacctgta ctcccaaacc tggaggattc
3061 cactgtgcct gccctccagg ctttgtgggg ctacgctgtg agggagacgt ggacgagtgt
3121 ctggaccagc cctgccaccc cacaggcact gcagcctgcc actctctggc caatgccttc
3181 tactgccagt gtctgcctgg acacacaggc cagtggtgtg aggtggagat agacccctgc
3241 cacagccaac cctgctttca tggagggacc tgtgaggcca cagcaggatc accccctgggt
3301 ttcatctgcc actgccccaa gggttttgaa ggccccacct gcagccacag ggccccttcc
```

*Figure 21B*

```
3361 tgcggcttcc atcactgcca ccacggaggc ctgtgtctgc cctcccctaa gccaggcttc
3421 ccaccacgct gtgcctgcct cagtggctat gggggtcctg actgcctgac cccaccagct
3481 cctaaaggct gtggccctcc ctccccatgc ctatacaatg gcagctgctc agagaccacg
3541 ggcttggggg gcccaggctt tcgatgctcc tgccctcaca gctctccagg gccccggtgt
3601 cagaaacccg ga
```

D2 D4 D6 D8
Ad-LacZ
Ad-VEGF
Ad-VEGF +
Ad-N1ECDFc
pro
pro
active
pro

Ad-VEGF
Ad-LacZ
Ad-N1ECDFc (moi)
20 40 60
pro
Intermediate
active

LacZ N1IC
20
25
30
GAPDH
19
22
25
MMP-2
33
36
39
MMP-9

LacZ N1IC
19
22
25
RT-PCR
α-MT1-MMP
W.B.

LacZ
VEGF
N1ECDFC
(-) (+)
GAPDH
MMP9
MT1-MMP

Adenoviral transduction efficiency

Human Notch1 Signal Peptide

Human IgG Heavy Chain (HC) Signal Peptide

Fig. 55

Human Notch1 decoy (EGF-LR 1-36)
Human Notch1 decoy (EGF-LR 9-36)
Human Notch1 decoy (EGF-LR 25-36)

Human N1

```
tac agc ttc ggg (SEQ ID NO:19)
atg tcg aag ccc (SEQ ID NO: 20)
 Y   S   F   G  (SEQ ID NO: 21)
```

Add BglII site switch last nucleotide

```
tac agc ttc gga GAT CT (SEQ ID NO:22)
atg tcg aag cct CTA GA (SEQ ID NO: 23)
 Y   S   F   G  (SEQ ID NO: 21)
```

N1/FC fusion

```
tac agc ttc gga GAT CTG GGC CCG (SEQ ID NO: 24)
atg tcg aag cct CTA GAC CCG GGC (SEQ ID NO: 25)
 Y   S   F   G   D   L   G   P  (SEQ ID NO: 26)
```

Fig. 56

Human Notch1 decoy (EGF-LR 1-13)

Human N1

```
gat gtg gac gag (SEQ ID NO: 27)
cta ctc ctg ctc (SEQ ID NO: 28)
 D   V   D   E (SEQ ID NO: 29)
```

Add a BamHI site

```
gat gtg gac gag GAT CC (SEQ ID NO: 30)
cta ctc ctg ctc CTA GG (SEQ ID NO: 31)
 D   V   D   E (SEQ ID NO: 29)
```

N1/FC fusion

```
gat gtg gac gag GAT CTG GGC CCG (SEQ ID NO: 32)
cta ctc ctg ctc CTA GAC CCG GGC (SEQ ID NO: 33)
 D   V   D   E   D   L   G   P (SEQ ID NO: 34)
```

Fig. 57

Human Notch1 decoy (EGF-LR 9-23)

Human N1 gag acc gac atc ~~gac gac~~ (SEQ ID NO: 35)
ctc tgg ctg tag ~~ctg ctg~~ (SEQ ID NO: 36)
E T D I D D (SEQ ID NO: 37)

Add a BglII site gag acc gac atA GAT CT (SEQ ID NO: 38)
ctc tgg ctg taT CTA GA (SEQ ID NO: 39)
E T D I (SEQ ID NO: 40)

N1/FC fusion gag acc gac atA GAT CTG GGC CCG (SEQ ID NO: 41)
ctc tgg ctg taT CTA GAC CCG GGC (SEQ ID NO: 42)
E T D I D L G P (SEQ ID NO: 43)

Fig. 58

Human Notch1 decoy (EGF-LR 1-24)
Human Notch1 decoy (EGF-LR 13-24)

Human N1 gac atc aac gag (SEQ ID NO: 44)
ctg tag ttg ctc (SEQ ID NO: 45)
D I N E (SEQ ID NO: 46)

Add a BamHI site gac atc aac gag GAT CC (SEQ ID NO: 47)
ctg tag ttg ctc CTA GG (SEQ ID NO: 48)
D I N E (SEQ ID NO: 46)

N1/FC fusion gac atc aac gag GAT CTG GGC CCG (SEQ ID NO: 49)
ctg tag ttg ctc CTA GAC CCG GGC (SEQ ID NO: 50)
D I N E D L G P (SEQ ID NO: 51)

*Figure 59A*

MPPLLAPLLCLALLPALAARGPRCSQPGETCLNGGKCEAANGTEACVCGGAFVGPRCQDPNPCLS
TPCKNAGTCHVVDRRGVADYACSCALGFSGPLCLTPLDNACLTNPCRNGGTCDLLTLTEYKCRCP
PGWSGKSCQQADPCASNPCANGGQCLPFEASYICHCPPSFHGPTCRQDVNECGQKPGLCRHGGTC
HNEVGSYRCVCRATHTGPNCERPYVPCSPSPCQNGGTCRPTGDVTHECACLPGFTGQNCEENIDD
CPGNNCKNGGACVDGVNTYNCRCPPEWTGQYCTEDVDECQLMPNACQNGGTCHNTHGGYNCVCVN
GWTGEDCSENIDDCASAACFHGATCHDRVASFYCECPHGRTGLLCHLNDACISNPCNEGSNCDTN
PVNGKAICTCPSGYTGPACSQDVDECSLGANPCEHAGKCINTLGSFECQCLQGYTGPRCEIDVNE
CVSNPCQNDATCLDQIGEFQCICMPGYEGVHCEVNTDECASSPCLHNGRCLDKINEFQCECPTGF
TGHLCQYDVDECASTPCKNGAKCLDGPNTYTCVCTEGYTGTHCEVDIDECDPDPCHYGSCKDGVA
TFTCLCRPGYTGHHCETNINECSSQPCRHGGTCQDRDNAYLCFCLKGTTGPNCEINLDDCASSPC
DSGTCLDKIDGYECACEPGYTGSMCNINIDECAGNPCHNGGTCEDGINGFTCRCPEGYHDPTCLS
EVNECNSNPCVHGACRDSLNGYKCDCDPGWSGTNCDINNNECESNPCVNGGTCKDMTSGYVCTCR
EGFSGPNCQTNINECASNPCLNQGTCIDDVAGYKCNCLLPYTGATCEVVLAPCAPSPCRNGGECR
QSEDYESFSCVCPTGWQGQTCEVDINECVLSPCRHGASCQNTHGGYRCHCQAGYSGRNCETDIDD
CRPNPCHNGGSCTDGINTAFCDCLPGFRGTFCEEDINECASDPCRNGANCTDCVDSYTCTCPAGF
SGIHCENNTPDCTESSCFNGGTCVDGINSFTCLCPPGFTGSYCQHDVNECDSQPCLHGGTCQDGC
GSYRCTCPQGYTGPNCQNLVHWCDSSPCKNGGKCWQTHTQYRCECPSGWTGLYCDVPSVSCEVAA
QRQGVDVARLCQHGGLCVDAGNTHHCRCQAGYTGSYCEDLVDECSPSPCQNGATCTDYLGGYSCK
CVAGYHGVNCSEEIDECLSHPCQNGGTCLDLPNTYKCSCPRGTQGVHCEINVDDCNPPVDPVSRS
PKCFNNGTCVDQVGGYSCTCPPGFVGERCEGDVNECLSNPCDARGTQNCVQRVNDFHCECRAGHT
GRRCESVINGCKGKPCKNGGTCAVASNTARGFICKCPAGFEGATCENDARTCGSLRCLNGGTCIS
GPRSPTCLCLGPFTGPECQFPASSPCLGGNPCYNQGTCEPTSESPFYRCLCPAKFNGLLCHILDY
SFGGGAGRDIPPPLIEEACELPECQEDAGNKVCSLQCNNHACGWDGGDCSLNFNDPWKNCTQSLQ
CWKYFSDGHCDSQCNSAGCLFDGFDCQRAEGQCNPLYDQYCKDHFSDGHCDQGCNSAECEWDGLD
CAEHVPERLAAGTLVVVVLMPPEQLRNSSFHFLRELSRVLHTNVVFKRDAHGQQMIFPYYGREEE
LRKHPIKRAAEGWAAPDALLGQVKASLLPGGSEGGRRRRELDPMDVRGSIVYLEIDNRQCVQASS
QCFQSATDVAAFLGALASLGSLNIPYKIEAVQSETVEPPPPAQLHFMYVAAAAFVLLFFVGCGVL
LSRKRRRQHGQLWFPEGFKVSEASKKKRREPLGEDSVGLKPLKNASDGALMDDNQNEWGDEDLET
KKFRFEEPVVLPDLDDQTDHRQWTQQHLDAADLRMSAMAPTPPQGEVDADCMDVNVRGPDGFTPL
MIASCSGGGLETGNSEEEEDAPAVISDFIYQGASLHNQTDRTGETALHLAARYSRSDAAKRLLEA
SADANIQDNMGRTPLHAAVSADAQGVFQILIRNRATDLDARMHDGTTPLILAARLAVEGMLEDLI
NSHADVNAVDDLGKS

*Figure 59B*

ALHWAAAVNNVDAAVVLLKNGANKDMQNNREETPLFLAAREGSYETAKVLLDHFANRDI
TDHMDRLPRDIAQERMHHDIVRLLDEYNLVRSPQLHGAPLGGTPTLSPPLCSPNGYLGS
LKPGVQGKKVRKPSSKGLACGSKEAKDLKARRKKSQDGKGCLLDSSGMLSPVDSLESPH
GYLSDVASPPLLPSPFQQSPSVPLNHLPGMPDTHLGIGHLNVAAKPEMAALGGGGRLAF
ETGPPRLSHLPVASGTSTVLGSSSGGALNFTVGGSTSLNGQCEWLSRLQSGMVPNQYNP
LRGSVAPGPLSTQAPSLQHGMVGPLHSSLAASALSQMMSYQGLPSTRLATQPHLVQTQQ
VQPQNLQMQQQNLQPANIQQQQSLQPPPPPPQPHLGVSSAASGHLGRSFLSGEPSQADV
QPLGPSSLAVHTILPQESPALPTSLPSSLVPPVTAAQFLTPPSQHSYSSPVDNTPSHQL
QVPEHPFLTPSPESPDQWSSSSPHSNVSDWSEGVSSPPTSMQSQIARIPEAFK

*Figure 60*

DLGPGEPKSCDKTHTCPPCPAPELLGGPSVFLFPPKPKDTLMISRTPEVTCVVVDVSHED
PEVKFNWYVDGVEVHNAKTKPREEQYNSTYRVVSVLTVLHQDWLNGKEYKCKVSNKALPA
PIEKTISKAKGQPREPQVYTLPPSRDELTKNQVSLTCLVKGFYPSDIAVEWESNGQPENN
YKTTPPVLDSDGSFFLYSKLTVDKSRWQQGNVFSCSVMHEALHNHYTQKSLSLSPGK

*Figure 61*

MPPLLAPLLCLALLPALAARGPRCSQPGETCLNGGKCEAANGTEACVCGGAFVGPRCQDP
NPCLSTPCKNAGTCHVVDRRGVADYACSCALGFSGPLCLTPLDNACLTNPCRNGGTCDLL
TLTEYKCRCPPGWSGKSCQQADPCASNPCANGGQCLPFEASYICHCPPSFHGPTCRQDVN
ECGQKPGLCRHGGTCHNEVGSYRCVCRATHTGPNCERPYVPCSPSPCQNGGTCRPTGDVT
HECACLPGFTGQNCEENIDDCPGNNCKNGGACVDGVNTYNCRCPPEWTGQYCTEDVDECQ
LMPNACQNGGTCHNTHGGYNCVCVNGWTGEDCSENIDDCASAACFHGATCHDRVASFYCE
CPHGRTGLLCHLNDACISNPCNEGSNCDTNPVNGKAICTCPSGYTGPACSQDVDECSLGA
NPCEHAGKCINTLGSFECQCLQGYTGPRCEIDVNECVSNPCQNDATCLDQIGEFQCICMP
GYEGVHCEVNTDECASSPCLHNGRCLDKINEFQCECPTGFTGHLCQYDVDECASTPCKNG
AKCLDGPNTYTCVCTEGYTGTHCEVDIDECDPDPCHYGSCKDGVATFTCLCRPGYTGHHC
ETNINECSSQPCRHGGTCQDRDNAYLCFCLKGTTGPNCEINLDDCASSPCDSGTCLDKID
GYECACEPGYTGSMCNINIDECAGNPCHNGGTCEDGINGFTCRCPEGYHDPTCLSEVNEC
NSNPCVHGACRDSLNGYKCDCDPGWSGTNCDINNNECESNPCVNGGTCKDMTSGYVCTCR
EGFSGPNCQTNINECASNPCLNQGTCIDDVAGYKCNCLLPYTGATCEVVLAPCAPSPCRN
GGECRQSEDYESFSCVCPTGWQGQTCEVDINECVLSPCRHGASCQNTHGGYRCHCQAGYS
GRNCETDIDDCRPNPCHNGGSCTDGINTAFCDCLPGFRGTFCEEDINECASDPCRNGANC
TDCVDSYTCTCPAGFSGIHCENNTPDCTESSCFNGGTCVDGINSFTCLCPPGFTGSYCQH
DVNECDSQPCLHGGTCQDGCGSYRCTCPQGYTGPNCQNLVHWCDSSPCKNGGKCWQTHTQ
YRCECPSGWTGLYCDVPSVSCEVAAQRQGVDVARLCQHGGLCVDAGNTHHCRCQAGYTGS
YCEDLVDECSPSPCQNGATCTDYLGGYSCKCVAGYHGVNCSEEIDECLSHPCQNGGTCLD
LPNTYKCSCPRGTQGVHCEINVDDCNPPVDPVSRSPKCFNNGTCVDQVGGYSCTCPPGFV
GERCEGDVNECLSNPCDARGTQNCVQRVNDFHCECRAGHTGRRCESVINGCKGKPCKNGG
TCAVASNTARGFICKCPAGFEGATCENDARTCGSLRCLNGGTCISGPRSPTCLCLGPFTG
PECQFPASSPCLGGNPCYNQGTCEPTSESPFYRCLCPAKFNGLLCHILDYSFG*DLGPGEP*
*KSCDKTHTCPPCPAPELLGGPSVFLFPPKPKDTLMISRTPEVTCVVVDVSHEDPEVKFNW*
*YVDGVEVHNAKTKPREEQYNSTYRVVSVLTVLHQDWLNGKEYKCKVSNKALPAPIEKTIS*
*KAKGQPREPQVYTLPPSRDELTKNQVSLTCLVKGFYPSDIAVEWESNGQPENNYKTTPPV*
*LDSDGSFFLYSKLTVDKSRWQQGNVFSCSVMHEALHNHYTQKSLSLSPGK*

*Figure 62*

MPPLLAPLLCLALLPALAARGPRCSQPGETCLNGGKCEAANGTEACVCGGAFVGPRCQDP
NPCLSTPCKNAGTCHVVDRRGVADYACSCALGFSGPLCLTPLDNACLTNPCRNGGTCDLL
TLTEYKCRCPPGWSGKSCQQADPCASNPCANGGQCLPFEASYICHCPPSFHGPTCRQDVN
ECGQKPGLCRHGGTCHNEVGSYRCVCRATHTGPNCERPYVPCSPSPCQNGGTCRPTGDVT
HECACLPGFTGQNCEENIDDCPGNNCKNGGACVDGVNTYNCRCPPEWTGQYCTEDVDECQ
LMPNACQNGGTCHNTHGGYNCVCVNGWTGEDCSENIDDCASAACFHGATCHDRVASFYCE
CPHGRTGLLCHLNDACISNPCNEGSNCDTNPVNGKAICTCPSGYTGPACSQDVDECSLGA
NPCEHAGKCINTLGSFECQCLQGYTGPRCEIDVNECVSNPCQNDATCLDQIGEFQCICMP
GYEGVHCEVNTDECASSPCLHNGRCLDKINEFQCECPTGFTGHLCQYDVDE*DLGPGEPKS*
*CDKTHTCPPCPAPELLGGPSVFLFPPKPKDTLMISRTPEVTCVVVDVSHEDPEVKFNWYV*
*DGVEVHNAKTKPREEQYNSTYRVVSVLTVLHQDWLNGKEYKCKVSNKALPAPIEKTISKA*
*KGQPREPQVYTLPPSRDELTKNQVSLTCLVKGFYPSDIAVEWESNGQPENNYKTTPPVLD*
*SDGSFFLYSKLTVDKSRWQQGNVFSCSVMHEALHNHYTQKSLSLSPGK*

*Figure 63*

MPPLLAPLLCLALLPALAARGPRCSQPGETCLNGGKCEAANGTEACVCGGAFVGPRCQDP
NPCLSTPCKNAGTCHVVDRRGVADYACSCALGFSGPLCLTPLDNACLTNPCRNGGTCDLL
TLTEYKCRCPPGWSGKSCQQADPCASNPCANGGQCLPFEASYICHCPPSFHGPTCRQDVN
ECGQKPGLCRHGGTCHNEVGSYRCVCRATHTGPNCERPYVPCSPSPCQNGGTCRPTGDVT
HECACLPGFTGQNCEENIDDCPGNNCKNGGACVDGVNTYNCRCPPEWTGQYCTEDVDECQ
LMPNACQNGGTCHNTHGGYNCVCVNGWTGEDCSENIDDCASAACFHGATCHDRVASFYCE
CPHGRTGLLCHLNDACISNPCNEGSNCDTNPVNGKAICTCPSGYTGPACSQDVDECSLGA
NPCEHAGKCINTLGSFECQCLQGYTGPRCEIDVNECVSNPCQNDATCLDQIGEFQCICMP
GYEGVHCEVNTDECASSPCLHNGRCLDKINEFQCECPTGFTGHLCQYDVDECASTPCKNG
AKCLDGPNTYTCVCTEGYTGTHCEVDIDECDPDPCHYGSCKDGVATFTCLCRPGYTGHHC
ETNINECSSQPCRHGGTCQDRDNAYLCFCLKGTTGPNCEINLDDCASSPCDSGTCLDKID
GYECACEPGYTGSMCNINIDECAGNPCHNGGTCEDGINGFTCRCPEGYHDPTCLSEVNEC
NSNPCVHGACRDSLNGYKCDCDPGWSGTNCDINNNECESNPCVNGGTCKDMTSGYVCTCR
EGFSGPNCQTNINECASNPCLNQGTCIDDVAGYKCNCLLPYTGATCEVVLAPCAPSPCRN
GGECRQSEDYESFSCVCPTGWQGQTCEVDINECVLSPCRHGASCQNTHGGYRCHCQAGYS
GRNCETDIDDCRPNPCHNGGSCTDGINTAFCDCLPGFRGTFCEEDINE*DLGPGEPKSCDK*
*THTCPPCPAPELLGGPSVFLFPPKPKDTLMISRTPEVTCVVVDVSHEDPEVKFNWYVDGV*
*EVHNAKTKPREEQYNSTYRVVSVLTVLHQDWLNGKEYKCKVSNKALPAPIEKTISKAKGQ*
*PREPQVYTLPPSRDELTKNQVSLTCLVKGFYPSDIAVEWESNGQPENNYKTTPPVLDSDG*
*SFFLYSKLTVDKSRWQQGNVFSCSVMHEALHNHYTQKSLSLSPGK*

*Figure 64*

MPPLLAPLLCLALLPALAARGPRCASAACFHGATCHDRVASFYCECPHGRTGLLCHLNDA
CISNPCNEGSNCDTNPVNGKAICTCPSGYTGPACSQDVDECSLGANPCEHAGKCINTLGS
FECQCLQGYTGPRCEIDVNECVSNPCQNDATCLDQIGEFQCICMPGYEGVHCEVNTDECA
SSPCLHNGRCLDKINEFQCECPTGFTGHLCQYDVDECASTPCKNGAKCLDGPNTYTCVCT
EGYTGTHCEVDIDECDPDPCHYGSCKDGVATFTCLCRPGYTGHHCETNINECSSQPCRHG
GTCQDRDNAYLCFCLKGTTGPNCEINLDDCASSPCDSGTCLDKIDGYECACEPGYTGSMC
NINIDECAGNPCHNGGTCEDGINGFTCRCPEGYHDPTCLSEVNECNSNPCVHGACRDSLN
GYKCDCDPGWSGTNCDINNNECESNPCVNGGTCKDMTSGYVCTCREGFSGPNCQTNINEC
ASNPCLNQGTCIDDVAGYKCNCLLPYTGATCEVVLAPCAPSPCRNGGECRQSEDYESFSC
VCPTGWQGQTCEVDINECVLSPCRHGASCQNTHGGYRCHCQAGYSGRNCETDI*DLGPGEP*
*KSCDKTHTCPPCPAPELLGGPSVFLFPPKPKDTLMISRTPEVTCVVVDVSHEDPEVKFNW*
*YVDGVEVHNAKTKPREEQYNSTYRVVSVLTVLHQDWLNGKEYKCKVSNKALPAPIEKTIS*
*KAKGQPREPQVYTLPPSRDELTKNQVSLTCLVKGFYPSDIAVEWESNGQPENNYKTTPPV*
*LDSDGSFFLYSKLTVDKSRWQQGNVFSCSVMHEALHNHYTQKSLSLSPGK*

*Figure 65*

MWGWKCLLFWAVLVTATLCTARCASAACFHGATCHDRVASFYCECPHGRTGLLCHLNDAC
ISNPCNEGSNCDTNPVNGKAICTCPSGYTGPACSQDVDECSLGANPCEHAGKCINTLGSF
ECQCLQGYTGPRCEIDVNECVSNPCQNDATCLDQIGEFQCICMPGYEGVHCEVNTDECAS
SPCLHNGRCLDKINEFQCECPTGFTGHLCQYDVDECASTPCKNGAKCLDGPNTYTCVCTE
GYTGTHCEVDIDECDPDPCHYGSCKDGVATFTCLCRPGYTGHHCETNINECSSQPCRHGG
TCQDRDNAYLCFCLKGTTGPNCEINLDDCASSPCDSGTCLDKIDGYECACEPGYTGSMCN
INIDECAGNPCHNGGTCEDGINGFTCRCPEGYHDPTCLSEVNECNSNPCVHGACRDSLNG
YKCDCDPGWSGTNCDINNNECESNPCVNGGTCKDMTSGYVCTCREGFSGPNCQTNINECA
SNPCLNQGTCIDDVAGYKCNCLLPYTGATCEVVLAPCAPSPCRNGGECRQSEDYESFSCV
CPTGWQGQTCEVDINECVLSPCRHGASCQNTHGGYRCHCQAGYSGRNCETDI*DLGPGEPK*
*SCDKTHTCPPCPAPELLGGPSVFLFPPKPKDTLMISRTPEVTCVVVDVSHEDPEVKFNWY*
*VDGVEVHNAKTKPREEQYNSTYRVVSVLTVLHQDWLNGKEYKCKVSNKALPAPIEKTISK*
*AKGQPREPQVYTLPPSRDELTKNQVSLTCLVKGFYPSDIAVEWESNGQPENNYKTTPPVL*
*DSDGSFFLYSKLTVDKSRWQQGNVFSCSVMHEALHNHYTQKSLSLSPGK*

*Figure 66*

MPPLLAPLLCLALLPALAARGPRCASAACFHGATCHDRVASFYCECPHGRTGLLCHLNDA
CISNPCNEGSNCDTNPVNGKAICTCPSGYTGPACSQDVDECSLGANPCEHAGKCINTLGS
FECQCLQGYTGPRCEIDVNECVSNPCQNDATCLDQIGEFQCICMPGYEGVHCEVNTDECA
SSPCLHNGRCLDKINEFQCECPTGFTGHLCQYDVDECASTPCKNGAKCLDGPNTYTCVCT
EGYTGTHCEVDIDECDPDPCHYGSCKDGVATFTCLCRPGYTGHHCETNINECSSQPCRHG
GTCQDRDNAYLCFCLKGTTGPNCEINLDDCASSPCDSGTCLDKIDGYECACEPGYTGSMC
NINIDECAGNPCHNGGTCEDGINGFTCRCPEGYHDPTCLSEVNECNSNPCVHGACRDSLN
GYKCDCDPGWSGTNCDINNNECESNPCVNGGTCKDMTSGYVCTCREGFSGPNCQTNINEC
ASNPCLNQGTCIDDVAGYKCNCLLPYTGATCEVVLAPCAPSPCRNGGECRQSEDYESFSC
VCPTGWQGQTCEVDINECVLSPCRHGASCQNTHGGYRCHCQAGYSGRNCETDIDDCRPNP
CHNGGSCTDGINTAFCDCLPGFRGTFCEEDINECASDPCRNGANCTDCVDSYTCTCPAGF
SGIHCENNTPDCTESSCFNGGTCVDGINSFTCLCPPGFTGSYCQHDVNECDSQPCLHGGT
CQDGCGSYRCTCPQGYTGPNCQNLVHWCDSSPCKNGGKCWQTHTQYRCECPSGWTGLYCD
VPSVSCEVAAQRQGVDVARLCQHGGLCVDAGNTHHCRCQAGYTGSYCEDLVDECSPSPCQ
NGATCTDYLGGYSCKCVAGYHGVNCSEEIDECLSHPCQNGGTCLDLPNTYKCSCPRGTQG
VHCEINVDDCNPPVDPVSRSPKCFNNGTCVDQVGGYSCTCPPGFVGERCEGDVNECLSNP
CDARGTQNCVQRVNDFHCECRAGHTGRRCESVINGCKGKPCKNGGTCAVASNTARGFICK
CPAGFEGATCENDARTCGSLRCLNGGTCISGPRSPTCLCLGPFTGPECQFPASSPCLGGN
PCYNQGTCEPTSESPFYRCLCPAKFNGLLCHILDYSFG*DLGPGEPKSCDKTHTCPPCPAP*
*ELLGGPSVFLFPPKPKDTLMISRTPEVTCVVVDVSHEDPEVKFNWYVDGVEVHNAKTKPR*
*EEQYNSTYRVVSVLTVLHQDWLNGKEYKCKVSNKALPAPIEKTISKAKGQPREPQVYTLP*
*PSRDELTKNQVSLTCLVKGFYPSDIAVEWESNGQPENNYKTTPPVLDSDGSFFLYSKLTV*
*DKSRWQQGNVFSCSVMHEALHNHYTQKSLSLSPGK*

*Figure 67*

MWGWKCLLFWAVLVTATLCTARCASAACFHGATCHDRVASFYCECPHGRTGLLCHLNDAC
ISNPCNEGSNCDTNPVNGKAICTCPSGYTGPACSQDVDECSLGANPCEHAGKCINTLGSF
ECQCLQGYTGPRCEIDVNECVSNPCQNDATCLDQIGEFQCICMPGYEGVHCEVNTDECAS
SPCLHNGRCLDKINEFQCECPTGFTGHLCQYDVDECASTPCKNGAKCLDGPNTYTCVCTE
GYTGTHCEVDIDECDPDPCHYGSCKDGVATFTCLCRPGYTGHHCETNINECSSQPCRHGG
TCQDRDNAYLCFCLKGTTGPNCEINLDDCASSPCDSGTCLDKIDGYECACEPGYTGSMCN
INIDECAGNPCHNGGTCEDGINGFTCRCPEGYHDPTCLSEVNECNSNPCVHGACRDSLNG
YKCDCDPGWSGTNCDINNNECESNPCVNGGTCKDMTSGYVCTCREGFSGPNCQTNINECA
SNPCLNQGTCIDDVAGYKCNCLLPYTGATCEVVLAPCAPSPCRNGGECRQSEDYESFSCV
CPTGWQGQTCEVDINECVLSPCRHGASCQNTHGGYRCHCQAGYSGRNCETDIDDCRPNPC
HNGGSCTDGINTAFCDCLPGFRGTFCEEDINECASDPCRNGANCTDCVDSYTCTCPAGFS
GIHCENNTPDCTESSCFNGGTCVDGINSFTCLCPPGFTGSYCQHDVNECDSQPCLHGGTC
QDGCGSYRCTCPQGYTGPNCQNLVHWCDSSPCKNGGKCWQTHTQYRCECPSGWTGLYCDV
PSVSCEVAAQRQGVDVARLCQHGGLCVDAGNTHHCRCQAGYTGSYCEDLVDECSPSPCQN
GATCTDYLGGYSCKCVAGYHGVNCSEEIDECLSHPCQNGGTCLDLPNTYKCSCPRGTQGV
HCEINVDDCNPPVDPVSRSPKCFNNGTCVDQVGGYSCTCPPGFVGERCEGDVNECLSNPC
DARGTQNCVQRVNDFHCECRAGHTGRRCESVINGCKGKPCKNGGTCAVASNTARGFICKC
PAGFEGATCENDARTCGSLRCLNGGTCISGPRSPTCLCLGPFTGPECQFPASSPCLGGNP
CYNQGTCEPTSESPFYRCLCPAKFNGLLCHILDYSFG*DLGPGEPKSCDKTHTCPPCPAPE*
*LLGGPSVFLFPPKPKDTLMISRTPEVTCVVVDVSHEDPEVKFNWYVDGVEVHNAKTKPRE*
*EQYNSTYRVVSVLTVLHQDWLNGKEYKCKVSNKALPAPIEKTISKAKGQPREPQVYTLPP*
*SRDELTKNQVSLTCLVKGFYPSDIAVEWESNGQPENNYKTTPPVLDSDGSFFLYSKLTVD*
*KSRWQQGNVFSCSVMHEALHNHYTQKSLSLSPGK*

*Figure 68*

MPPLLAPLLCLALLPALAARGPRCASSPCLHNGRCLDKINEFQCECPTGFTGHLCQYDVD
ECASTPCKNGAKCLDGPNTYTCVCTEGYTGTHCEVDIDECDPDPCHYGSCKDGVATFTCL
CRPGYTGHHCETNINECSSQPCRHGGTCQDRDNAYLCFCLKGTTGPNCEINLDDCASSPC
DSGTCLDKIDGYECACEPGYTGSMCNINIDECAGNPCHNGGTCEDGINGFTCRCPEGYHD
PTCLSEVNECNSNPCVHGACRDSLNGYKCDCDPGWSGTNCDINNNECESNPCVNGGTCKD
MTSGYVCTCREGFSGPNCQTNINECASNPCLNQGTCIDDVAGYKCNCLLPYTGATCEVVL
APCAPSPCRNGGECRQSEDYESFSCVCPTGWQGQTCEVDINECVLSPCRHGASCQNTHGG
YRCHCQAGYSGRNCETDIDDCRPNPCHNGGSCTDGINTAFCDCLPGFRGTFCEEDINE*DL*
*GPGEPKSCDKTHTCPPCPAPELLGGPSVFLFPPKPKDTLMISRTPEVTCVVVDVSHEDPE*
*VKFNWYVDGVEVHNAKTKPREEQYNSTYRVVSVLTVLHQDWLNGKEYKCKVSNKALPAPI*
*EKTISKAKGQPREPQVYTLPPSRDELTKNQVSLTCLVKGFYPSDIAVEWESNGQPENNYK*
*TTPPVLDSDGSFFLYSKLTVDKSRWQQGNVFSCSVMHEALHNHYTQKSLSLSPGK*

*Figure 69*

MWGWKCLLFWAVLVTATLCTARCASSPCLHNGRCLDKINEFQCECPTGFTGHLCQYDVDE
CASTPCKNGAKCLDGPNTYTCVCTEGYTGTHCEVDIDECDPDPCHYGSCKDGVATFTCLC
RPGYTGHHCETNINECSSQPCRHGGTCQDRDNAYLCFCLKGTTGPNCEINLDDCASSPCD
SGTCLDKIDGYECACEPGYTGSMCNINIDECAGNPCHNGGTCEDGINGFTCRCPEGYHDP
TCLSEVNECNSNPCVHGACRDSLNGYKCDCDPGWSGTNCDINNNECESNPCVNGGTCKDM
TSGYVCTCREGFSGPNCQTNINECASNPCLNQGTCIDDVAGYKCNCLLPYTGATCEVVLA
PCAPSPCRNGGECRQSEDYESFSCVCPTGWQGQTCEVDINECVLSPCRHGASCQNTHGGY
RCHCQAGYSGRNCETDIDDCRPNPCHNGGSCTDGINTAFCDCLPGFRGTFCEEDINE*DLG*
*PGEPKSCDKTHTCPPCPAPELLGGPSVFLFPPKPKDTLMISRTPEVTCVVVDVSHEDPEV*
*KFNWYVDGVEVHNAKTKPREEQYNSTYRVVSVLTVLHQDWLNGKEYKCKVSNKALPAPIE*
*KTISKAKGQPREPQVYTLPPSRDELTKNQVSLTCLVKGFYPSDIAVEWESNGQPENNYKT*
*TPPVLDSDGSFFLYSKLTVDKSRWQQGNVFSCSVMHEALHNHYTQKSLSLSPGK*

*Figure 70*

MPPLLAPLLCLALLPALAARGPRCASDPCRNGANCTDCVDSYTCTCPAGFSGIHCENNTP
DCTESSCFNGGTCVDGINSFTCLCPPGFTGSYCQHDVNECDSQPCLHGGTCQDGCGSYRC
TCPQGYTGPNCQNLVHWCDSSPCKNGGKCWQTHTQYRCECPSGWTGLYCDVPSVSCEVAA
QRQGVDVARLCQHGGLCVDAGNTHHCRCQAGYTGSYCEDLVDECSPSPCQNGATCTDYLG
GYSCKCVAGYHGVNCSEEIDECLSHPCQNGGTCLDLPNTYKCSCPRGTQGVHCEINVDDC
NPPVDPVSRSPKCFNNGTCVDQVGGYSCTCPPGFVGERCEGDVNECLSNPCDARGTQNCV
QRVNDFHCECRAGHTGRRCESVINGCKGKPCKNGGTCAVASNTARGFICKCPAGFEGATC
ENDARTCGSLRCLNGGTCISGPRSPTCLCLGPFTGPECQFPASSPCLGGNPCYNQGTCEP
TSESPFYRCLCPAKFNGLLCHILDYSFG*DLGPGEPKSCDKTHTCPPCPAPELLGGPSVFL*
*FPPKPKDTLMISRTPEVTCVVVDVSHEDPEVKFNWYVDGVEVHNAKTKPREEQYNSTYRV*
*VSVLTVLHQDWLNGKEYKCKVSNKALPAPIEKTISKAKGQPREPQVYTLPPSRDELTKNQ*
*VSLTCLVKGFYPSDIAVEWESNGQPENNYKTTPPVLDSDGSFFLYSKLTVDKSRWQQGNV*
*FSCSVMHEALHNHYTQKSLSLSPGK*

*Figure 71*

MWGWKCLLFWAVLVTATLCTARCASDPCRNGANCTDCVDSYTCTCPAGFSGIHCENNTPD
CTESSCFNGGTCVDGINSFTCLCPPGFTGSYCQHDVNECDSQPCLHGGTCQDGCGSYRCT
CPQGYTGPNCQNLVHWCDSSPCKNGGKCWQTHTQYRCECPSGWTGLYCDVPSVSCEVAAQ
RQGVDVARLCQHGGLCVDAGNTHHCRCQAGYTGSYCEDLVDECSPSPCQNGATCTDYLGG
YSCKCVAGYHGVNCSEEIDECLSHPCQNGGTCLDLPNTYKCSCPRGTQGVHCEINVDDCN
PPVDPVSRSPKCFNNGTCVDQVGGYSCTCPPGFVGERCEGDVNECLSNPCDARGTQNCVQ
RVNDFHCECRAGHTGRRCESVINGCKGKPCKNGGTCAVASNTARGFICKCPAGFEGATCE
NDARTCGSLRCLNGGTCISGPRSPTCLCLGPFTGPECQFPASSPCLGGNPCYNQGTCEPT
SESPFYRCLCPAKFNGLLCHILDYSFG*DLGPGEPKSCDKTHTCPPCPAPELLGGPSVFLF*
*PPKPKDTLMISRTPEVTCVVVDVSHEDPEVKFNWYVDGVEVHNAKTKPREEQYNSTYRVV*
*SVLTVLHQDWLNGKEYKCKVSNKALPAPIEKTISKAKGQPREPQVYTLPPSRDELTKNQV*
*SLTCLVKGFYPSDIAVEWESNGQPENNYKTTPPVLDSDGSFFLYSKLTVDKSRWQQGNVF*
*SCSVMHEALHNHYTQKSLSLSPGK*

*Figure 72A*

```
   1 atgccgccgc tcctggcgcc cctgctctgc ctggcgctgc tgcccgcgct cgccgcacga
  61 ggcccgcgat gctcccagcc cggtgagacc tgcctgaatg gcgggaagtg tgaagcggcc
 121 aatggcacgg aggcctgcgt ctgtggcggg gccttcgtgg gcccgcgatg ccaggacccc
 181 aacccgtgcc tcagcacccc ctgcaagaac gccgggacat gccacgtggt ggaccgcaga
 241 ggcgtggcag actatgcctg cagctgtgcc ctgggcttct ctgggcccct ctgcctgaca
 301 cccctggaca atgcctgcct caccaacccc tgccgcaacg gggcacctg cgacctgctc
 361 acgctgacgg agtacaagtg ccgctgcccg cccggctggt cagggaaatc gtgccagcag
 421 gctgacccgt gcgcctccaa cccctgcgcc aacggtggcc agtgcctgcc cttcgaggcc
 481 tcctacatct gccactgccc acccagcttc catggcccca cctgccggca ggatgtcaac
 541 gagtgtggcc agaagcccgg gctttgccgc cacggaggca cctgccacaa cgaggtcggc
 601 tcctaccgct gcgtctgccg cgccacccac actggcccca actgcgagcg gccctacgtg
 661 ccctgcagcc cctcgccctg ccagaacggg ggcacctgcc gccccacggg cgacgtcacc
 721 cacgagtgtg cctgcctgcc aggcttcacc ggccagaact gtgaggaaaa tatcgacgat
 781 tgtccaggaa acaactgcaa gaacgggggt gcctgtgtgg acggcgtgaa cacctacaac
 841 tgccgctgcc cgccagagtg gacaggtcag tactgtaccg aggatgtgga cgagtgccag
 901 ctgatgccaa atgcctgcca gaacggcggg acctgccaca acacccacgg tggctacaac
 961 tgcgtgtgtg tcaacggctg gactggtgag gactgcagcg agaacattga tgactgtgcc
1021 agcgccgcct gcttccacgg cgccacctgc catgaccgtg tggcctcctt ctactgcgag
1081 tgtccccatg gccgcacagg tctgctgtgc cacctcaacg acgcatgcat cagcaacccc
1141 tgtaacgagg gctccaactg cgacaccaac cctgtcaatg gcaaggccat ctgcacctgc
1201 ccctcggggt acacgggccc ggcctgcagc caggacgtgg atgagtgctc gctgggtgcc
1261 aacccctgcg agcatgcggg caagtgcatc aacacgctgg gctccttcga gtgccagtgt
1321 ctgcagggct acacgggccc ccgatgcgag atcgacgtca acgagtgcgt ctcgaacccg
1381 tgccagaacg acgccacctg cctggaccag attggggagt tccagtgcat ctgcatgccc
1441 ggctacgagg gtgtgcactg cgaggtcaac acagacgagt gtgccagcag cccctgcctg
1501 cacaatggcc gctgcctgga caagatcaat gagttccagt gcgagtgccc cacgggcttc
1561 actgggcatc tgtgccagta cgatgtggac gagtgtgcca gcacccccctg caagaatggt
1621 gccaagtgcc tggacggacc caacacttac acctgtgtgt gcacggaagg gtacacgggg
1681 acgcactgcg aggtggacat cgatgagtgc gaccccgacc cctgccacta cggctcctgc
1741 aaggacggcg tcgccacctt cacctgcctc tgccgcccag gctacacggg ccaccactgc
1801 gagaccaaca tcaacgagtg ctccagccag ccctgccgcc acgggggcac ctgccaggac
1861 cgcgacaacg cctacctctg cttctgcctg aaggggacca caggacccaa ctgcgagatc
1921 aacctggatg actgtgccag cagcccctgc gactcgggca cctgtctgga caagatcgat
1981 ggctacgagt gtgcctgtga gccgggctac acagggagca tgtgtaacat caacatcgat
2041 gagtgtgcgg gcaacccctg ccacaacggg ggcacctgcg aggacggcat caatggcttc
2101 acctgccgct gccccgaggg ctaccacgac cccacctgcc tgtctgaggt caatgagtgc
2161 aacagcaacc cctgcgtcca cggggcctgc cgggacagcc tcaacgggta caagtgcgac
2221 tgtgaccctg ggtggagtgg gaccaactgt gacatcaaca acaatgagtg tgaatccaac
2281 ccttgtgtca acggcggcac ctgcaaagac atgaccagtg gctacgtgtg cacctgccgg
2341 gagggcttca gcggtcccaa ctgccagacc aacatcaacg agtgtgcgtc caacccatgt
2401 ctgaaccagg gcacgtgtat tgacgacgtt gccgggtaca agtgcaactg cctgctgccc
2461 tacacaggtg ccacgtgtga ggtggtgctg gccccgtgtg cccccagccc ctgcagaaac
2521 ggcggggagt gcaggcaatc cgaggactat gagagcttct cctgtgtctg ccccacgggc
2581 tggcaagggc agacctgtga ggtcgacatc aacgagtgcg ttctgagccc gtgccggcac
2641 ggcgcatcct gccagaacac ccacggcggc taccgctgcc actgccaggc cggctacagt
2701 gggcgcaact gcgagaccga catcgacgac tgccggccca acccgtgtca caacgggggc
2761 tcctgcacag acggcatcaa cacggccttc tgcgactgcc tgcccggctt ccgggggcact
2821 ttctgtgagg aggacatcaa cgagtgtgcc agtgacccct gccgcaacgg ggccaactgc
2881 acggactgcg tggacagcta cacgtgcacc tgccccgcag gcttcagcgg gatccactgt
2941 gagaacaaca cgcctgactg cacagagagc tcctgcttca acggtggcac ctgcgtggac
3001 ggcatcaact cgttcacctg cctgtgtcca cccggcttca cgggcagcta ctgccagcac
```

*Figure 72B*

3061 gatgtcaatg agtgcgactc acagccctgc ctgcatggcg gcacctgtca ggacggctgc
3121 ggctcctaca ggtgcacctg cccccagggc tacactggcc ccaactgcca gaaccttgtg
3181 cactggtgtg actcctcgcc ctgcaagaac ggcggcaaat gctggcagac ccacacccag
3241 taccgctgcg agtgccccag cggctggacc ggcctttact gcgacgtgcc cagcgtgtcc
3301 tgtgaggtgg ctgcgcagcg acaaggtgtt gacgttgccc gcctgtgcca gcatggaggg
3361 ctctgtgtgg acgcgggcaa cacgcaccac tgccgctgcc aggcgggcta cacaggcagc
3421 tactgtgagg acctggtgga cgagtgctca cccagcccct gccagaacgg ggccacctgc
3481 acggactacc tgggcggcta ctcctgcaag tgcgtggccg gctaccacgg ggtgaactgc
3541 tctgaggaga tcgacgagtg cctctcccac ccctgccaga acgggggcac ctgcctcgac
3601 ctccccaaca cctacaagtg ctcctgccca cggggcactc agggtgtgca ctgtgagatc
3661 aacgtggacg actgcaatcc ccccgttgac cccgtgtccc ggagccccaa gtgctttaac
3721 aacggcacct gcgtggacca ggtgggcggc tacagctgca cctgcccgcc gggcttcgtg
3781 ggtgagcgct gtgaggggga tgtcaacgag tgcctgtcca atccctgcga cgcccgtggc
3841 acccagaact gcgtgcagcg cgtcaatgac ttccactgcg agtgccgtgc tggtcacacc
3901 gggcgccgct gcgagtccgt catcaatggc tgcaaaggca agccctgcaa gaatgggggc
3961 acctgcgccg tggcctccaa caccgcccgc gggttcatct gcaagtgccc tgcgggcttc
4021 gagggcgcca cgtgtgagaa tgacgctcgt acctgcggca gcctgcgctg cctcaacggc
4081 ggcacatgca tctccggccc gcgcagcccc acctgcctgt gcctgggccc cttcacgggc
4141 cccgaatgcc agttcccggc cagcagcccc tgcctgggcg gcaacccctg ctacaaccag
4201 gggacctgtg agcccacatc cgagagcccc ttctaccgtt gcctgtgccc cgccaaattc
4261 aacgggctct tgtgccacat cctggactac agcttcggag atctgggccc gggcgagccc
4321 aaatcttgtg acaaaactca cacatgccca ccgtgcccag cacctgaact cctgggggga
4381 ccgtcagtct tcctcttccc cccaaaaccc aaggacaccc tcatgatctc ccggacccct
4441 gaggtcacat gcgtggtggt ggacgtgagc cacgaagacc ctgaggtcaa gttcaactgg
4501 tacgtggacg gcgtggaggt gcataatgcc aagacaaagc cgcgggagga gcagtacaac
4561 agcacgtacc gtgtggtcag cgtcctcacc gtcctgcacc aggactggct gaatggcaag
4621 gagtacaagt gcaaggtctc caacaaagcc ctcccagccc ccatcgagaa aaccatctcc
4681 aaagccaaag ggcagccccg agaaccacag gtgtacaccc tgcccccatc ccgggatgag
4741 ctgaccaaga accaggtcag cctgacctgc ctggtcaaag gcttctatcc cagcgacatc
4801 gccgtggagt gggagagcaa tgggcagccg gagaacaact acaagaccac gcctcccgtg
4861 ctggactccg acggctcctt cttcctctac agcaagctca ccgtggacaa gagcaggtgg
4921 cagcagggga acgtcttctc atgctccgtg atgcatgagg ctctgcacaa ccactacacg
4981 cagaagagcc tctccctgtc tccgggtaaa tga

*Figure 73*

```
   1 atgccgccgc tcctggcgcc cctgctctgc ctggcgctgc tgcccgcgct cgccgcacga
  61 ggcccgcgat gctcccagcc cggtgagacc tgcctgaatg gcgggaagtg tgaagcggcc
 121 aatggcacgg aggcctgcgt ctgtggcggg gccttcgtgg gcccgcgatg ccaggacccc
 181 aacccgtgcc tcagcacccc ctgcaagaac gccgggacat gccacgtggt ggaccgcaga
 241 ggcgtggcag actatgcctg cagctgtgcc ctgggcttct ctgggcccct ctgcctgaca
 301 cccctggaca atgcctgcct caccaacccc tgccgcaacg gggcacctg cgacctgctc
 361 acgctgacgg agtacaagtg ccgctgcccg cccggctggt cagggaaatc gtgccagcag
 421 gctgacccgt gcgcctccaa cccctgcgcc aacggtggcc agtgcctgcc cttcgaggcc
 481 tcctacatct gccactgccc acccagcttc catggcccca cctgccggca ggatgtcaac
 541 gagtgtggcc agaagcccgg gctttgccgc cacggaggca cctgccacaa cgaggtcggc
 601 tcctaccgct gcgtctgccg cgccacccac actggcccca actgcgagcg gccctacgtg
 661 ccctgcagcc cctcgccctg ccagaacggg ggcacctgcc gccccacggg cgacgtcacc
 721 cacgagtgtg cctgcctgcc aggcttcacc ggccagaact gtgaggaaaa tatcgacgat
 781 tgtccaggaa acaactgcaa gaacgggggt gcctgtgtgg acggcgtgaa cacctacaac
 841 tgccgctgcc cgccagagtg gacaggtcag tactgtaccg aggatgtgga cgagtgccag
 901 ctgatgccaa atgcctgcca gaacggcggg acctgccaca acacccacgg tggctacaac
 961 tgcgtgtgtg tcaacggctg gactggtgag gactgcagcg agaacattga tgactgtgcc
1021 agcgccgcct gcttccacgg cgccacctgc catgaccgtg tggcctcctt ctactgcgag
1081 tgtccccatg gccgcacagg tctgctgtgc cacctcaacg acgcatgcat cagcaacccc
1141 tgtaacgagg gctccaactg cgacaccaac cctgtcaatg gcaaggccat ctgcacctgc
1201 ccctcggggt acacgggccc ggcctgcagc caggacgtgg atgagtgctc gctgggtgcc
1261 aacccctgcg agcatgcggg caagtgcatc aacacgctgg gctccttcga gtgccagtgt
1321 ctgcagggct acacgggccc ccgatgcgag atcgacgtca acgagtgcgt ctcgaacccg
1381 tgccagaacg acgccacctg cctggaccag attggggagt tccagtgcat ctgcatgccc
1441 ggctacgagg gtgtgcactg cgaggtcaac acagacgagt gtgccagcag cccctgcctg
1501 cacaatggcc gctgcctgga caagatcaat gagttccagt gcgagtgccc cacgggcttc
1561 actgggcatc tgtgccagta cgatgtggac gaggatctgg gcccgggcga gcccaaatct
1621 tgtgacaaaa ctcacacatg cccaccgtgc ccagcacctg aactcctggg gggaccgtca
1681 gtcttcctct tccccccaaa acccaaggac accctcatga tctcccggac ccctgaggtc
1741 acatgcgtgg tggtggacgt gagccacgaa gaccctgagg tcaagttcaa ctggtacgtg
1801 gacggcgtgg aggtgcataa tgccaagaca aagccgcggg aggagcagta caacagcacg
1861 taccgtgtgg tcagcgtcct caccgtcctg caccaggact ggctgaatgg caaggagtac
1921 aagtgcaagg tctccaacaa agccctccca gcccccatcg agaaaaccat ctccaaagcc
1981 aaagggcagc cccgagaacc acaggtgtac accctgcccc catcccggga tgagctgacc
2041 aagaaccagg tcagcctgac ctgcctggtc aaaggcttct atcccagcga catcgccgtg
2101 gagtgggaga gcaatgggca gccggagaac aactacaaga ccacgcctcc cgtgctggac
2161 tccgacggct ccttcttcct ctacagcaag ctcaccgtgg acaagagcag gtggcagcag
2221 gggaacgtct tctcatgctc cgtgatgcat gaggctctgc acaaccacta cacgcagaag
2281 agcctctccc tgtctccggg taaatga
```

*Figure 74A*

```
   1 atgccgccgc tcctggcgcc cctgctctgc ctggcgctgc tgcccgcgct cgccgcacga
  61 ggcccgcgat gctcccagcc cggtgagacc tgcctgaatg gcgggaagtg tgaagcggcc
 121 aatggcacgg aggcctgcgt ctgtggcggg gccttcgtgg gcccgcgatg ccaggacccc
 181 aacccgtgcc tcagcacccc ctgcaagaac gccgggacat gccacgtggt ggaccgcaga
 241 ggcgtggcag actatgcctg cagctgtgcc ctgggcttct ctgggcccct ctgcctgaca
 301 cccctggaca atgcctgcct caccaacccc tgccgcaacg gggcacctg cgacctgctc
 361 acgctgacgg agtacaagtg ccgctgcccg cccggctggt cagggaaatc gtgccagcag
 421 gctgacccgt gcgcctccaa cccctgcgcc aacggtggcc agtgcctgcc cttcgaggcc
 481 tcctacatct gccactgccc acccagcttc catggcccca cctgccggca ggatgtcaac
 541 gagtgtggcc agaagcccgg gctttgccgc cacggaggca cctgccacaa cgaggtcggc
 601 tcctaccgct gcgtctgccg cgccacccac actggcccca actgcgagcg gccctacgtg
 661 ccctgcagcc cctcgccctg ccagaacggg ggcacctgcc gccccacggg cgacgtcacc
 721 cacgagtgtg cctgcctgcc aggcttcacc ggccagaact gtgaggaaaa tatcgacgat
 781 tgtccaggaa acaactgcaa gaacgggggt gcctgtgtgg acggcgtgaa cacctacaac
 841 tgccgctgcc cgccagagtg gacaggtcag tactgtaccg aggatgtgga cgagtgccag
 901 ctgatgccaa atgcctgcca gaacggcggg acctgccaca acacccacgg tggctacaac
 961 tgcgtgtgtg tcaacggctg gactggtgag gactgcagcg agaacattga tgactgtgcc
1021 agcgccgcct gcttccacgg cgccacctgc catgaccgtg tggcctcctt ctactgcgag
1081 tgtccccatg gccgcacagg tctgctgtgc cacctcaacg acgcatgcat cagcaacccc
1141 tgtaacgagg gctccaactg cgacaccaac cctgtcaatg gcaaggccat ctgcacctgc
1201 ccctcggggt acacgggccc ggcctgcagc caggacgtgg atgagtgctc gctgggtgcc
1261 aacccctgcg agcatgcggg caagtgcatc aacacgctgg gctccttcga gtgccagtgt
1321 ctgcagggct acacgggccc ccgatgcgag atcgacgtca acgagtgcgt ctcgaacccg
1381 tgccagaacg acgccacctg cctggaccag attggggagt tccagtgcat ctgcatgccc
1441 ggctacgagg gtgtgcactg cgaggtcaac acagacgagt gtgccagcag cccctgcctg
1501 cacaatggcc gctgcctgga caagatcaat gagttccagt gcgagtgccc cacgggcttc
1561 actgggcatc tgtgccagta cgatgtggac gagtgtgcca gcacccccctg caagaatggt
1621 gccaagtgcc tggacggacc caacacttac acctgtgtgt gcacggaagg gtacacgggg
1681 acgcactgcg aggtggacat cgatgagtgc gaccccgacc cctgccacta cggctcctgc
1741 aaggacggcg tcgccacctt cacctgcctc tgccgcccag gctacacggg ccaccactgc
1801 gagaccaaca tcaacgagtg ctccagccag ccctgccgcc acgggggcac ctgccaggac
1861 cgcgacaacg cctacctctg cttctgcctg aaggggacca caggacccaa ctgcgagatc
1921 aacctggatg actgtgccag cagcccctgc gactcgggca cctgtctgga caagatcgat
1981 ggctacgagt gtgcctgtga gccgggctac acagggagca tgtgtaacat caacatcgat
2041 gagtgtgcgg gcaacccctg ccacaacggg ggcacctgcg aggacggcat caatggcttc
2101 acctgccgct gccccgaggg ctaccacgac cccacctgcc tgtctgaggt caatgagtgc
2161 aacagcaacc cctgcgtcca cggggcctgc cgggacagcc tcaacgggta caagtgcgac
2221 tgtgaccctg ggtggagtgg gaccaactgt gacatcaaca acaatgagtg tgaatccaac
2281 ccttgtgtca acggcggcac ctgcaaagac atgaccagtg gctacgtgtg cacctgccgg
2341 gagggcttca gcggtcccaa ctgccagacc aacatcaacg agtgtgcgtc caacccatgt
2401 ctgaaccagg gcacgtgtat tgacgacgtt gccgggtaca agtgcaactg cctgctgccc
2461 tacacaggtg ccacgtgtga ggtggtgctg gccccgtgtg cccccagccc ctgcagaaac
2521 ggcggggagt gcaggcaatc cgaggactat gagagcttct cctgtgtctg ccccacgggc
2581 tggcaagggc agacctgtga ggtcgacatc aacgagtgcg ttctgagccc gtgccggcac
2641 ggcgcatcct gccagaacac ccacggcggc taccgctgcc actgccaggc cggctacagt
2701 gggcgcaact gcgagaccga catcgacgac tgccggccca acccgtgtca caacgggggc
2761 tcctgcacag acggcatcaa cacggccttc tgcgactgcc tgcccggctt ccggggcact
2821 ttctgtgagg aggacatcaa cgaggatctg ggcccgggcg agcccaaatc ttgtgacaaa
2881 actcacacat gcccaccgtg cccagcacct gaactcctgg ggggaccgtc agtcttcctc
2941 ttccccccaa aacccaagga caccctcatg atctcccgga cccctgaggt cacatgcgtg
3001 gtggtggacg tgagccacga agaccctgag gtcaagttca actggtacgt ggacggcgtg
```

*Figure 74B*

```
3061 gaggtgcata atgccaagac aaagccgcgg gaggagcagt acaacagcac gtaccgtgtg
3121 gtcagcgtcc tcaccgtcct gcaccaggac tggctgaatg gcaaggagta caagtgcaag
3181 gtctccaaca aagccctccc agcccccatc gagaaaacca tctccaaagc caaagggcag
3241 ccccgagaac cacaggtgta caccctgccc ccatcccggg atgagctgac caagaaccag
3301 gtcagcctga cctgcctggt caaaggcttc tatcccagcg acatcgccgt ggagtgggag
3361 agcaatgggc agccggagaa caactacaag accacgcctc ccgtgctgga ctccgacggc
3421 tccttcttcc tctacagcaa gctcaccgtg gacaagagca ggtggcagca ggggaacgtc
3481 ttctcatgct ccgtgatgca tgaggctctg cacaaccact acacgcagaa gagcctctcc
3541 ctgtctccgg gtaaatga
```

*Figure 75*

```
   1 atgccgccgc tcctggcgcc cctgctctgc ctggcgctgc tgcccgcgct cgccgcacga
  61 ggcccgcgat gtgccagcgc cgcctgcttc cacggcgcca cctgccatga ccgtgtggcc
 121 tccttctact gcgagtgtcc ccatggccgc acaggtctgc tgtgccacct caacgacgca
 181 tgcatcagca acccctgtaa cgagggctcc aactgcgaca ccaaccctgt caatggcaag
 241 gccatctgca cctgcccctc ggggtacacg ggcccggcct gcagccagga cgtggatgag
 301 tgctcgctgg gtgccaaccc ctgcgagcat gcgggcaagt gcatcaacac gctgggctcc
 361 ttcgagtgcc agtgtctgca gggctacacg ggcccccgat gcgagatcga cgtcaacgag
 421 tgcgtctcga acccgtgcca gaacgacgcc acctgcctgg accagattgg ggagttccag
 481 tgcatctgca tgcccggcta cgagggtgtg cactgcgagg tcaacacaga cgagtgtgcc
 541 agcagcccct gcctgcacaa tggccgctgc ctggacaaga tcaatgagtt ccagtgcgag
 601 tgccccacgg gcttcactgg gcatctgtgc cagtacgatg tggacgagtg tgccagcacc
 661 ccctgcaaga atggtgccaa gtgcctggac ggacccaaca cttacacctg tgtgtgcacg
 721 gaagggtaca cggggacgca ctgcgaggtg gacatcgatg agtgcgaccc cgacccctgc
 781 cactacggct cctgcaagga cggcgtcgcc accttcacct gcctctgccg cccaggctac
 841 acgggccacc actgcgagac caacatcaac gagtgctcca gccagccctg ccgccacggg
 901 ggcacctgcc aggaccgcga caacgcctac ctctgcttct gcctgaaggg gaccacagga
 961 cccaactgcg agatcaacct ggatgactgt gccagcagcc cctgcgactc gggcacctgt
1021 ctggacaaga tcgatggcta cgagtgtgcc tgtgagccgg gctacacagg gagcatgtgt
1081 aacatcaaca tcgatgagtg tgcgggcaac ccctgccaca acgggggcac ctgcgaggac
1141 ggcatcaatg gcttcacctg ccgctgcccc gagggctacc acgaccccac ctgcctgtct
1201 gaggtcaatg agtgcaacag caacccctgc gtccacgggg cctgccggga cagcctcaac
1261 gggtacaagt gcgactgtga ccctgggtgg agtgggacca actgtgacat caacaacaat
1321 gagtgtgaat ccaacccttg tgtcaacggc ggcacctgca aagacatgac cagtggctac
1381 gtgtgcacct gccgggaggg cttcagcggt cccaactgcc agaccaacat caacgagtgt
1441 gcgtccaacc catgtctgaa ccagggcacg tgtattgacg acgttgccgg gtacaagtgc
1501 aactgcctgc tgccctacac aggtgccacg tgtgaggtgg tgctggcccc gtgtgccccc
1561 agcccctgca gaaacggcgg ggagtgcagg caatccgagg actatgagag cttctcctgt
1611 gtctgcccca cgggctggca agggcagacc tgtgaggtcg acatcaacga gtgcgttctg
1681 agcccgtgcc ggcacggcgc atcctgccag aacacccacg gcggctaccg ctgccactgc
1741 caggccggct acagtgggcg caactgcgag accgacatag atctgggccc gggcgagccc
1801 aaatcttgtg acaaaactca cacatgccca ccgtgcccag cacctgaact cctgggggga
1861 ccgtcagtct tcctcttccc cccaaaaccc aaggacaccc tcatgatctc ccggacccct
1921 gaggtcacat gcgtggtggt ggacgtgagc cacgaagacc ctgaggtcaa gttcaactgg
1981 tacgtggacg gcgtggaggt gcataatgcc aagacaaagc cgcgggagga gcagtacaac
2041 agcacgtacc gtgtggtcag cgtcctcacc gtcctgcacc aggactggct gaatggcaag
2101 gagtacaagt gcaaggtctc caacaaagcc ctcccagccc ccatcgagaa aaccatctcc
2161 aaagccaaag ggcagccccg agaaccacag gtgtacaccc tgcccccatc ccgggatgag
2221 ctgaccaaga accaggtcag cctgacctgc ctggtcaaag gcttctatcc cagcgacatc
2281 gccgtggagt gggagagcaa tgggcagccg gagaacaact acaagaccac gcctcccgtg
2341 ctggactccg acggctcctt cttcctctac agcaagctca ccgtggacaa gagcaggtgg
2401 cagcagggga acgtcttctc atgctccgtg atgcatgagg ctctgcacaa ccactacacg
2461 cagaagagcc tctccctgtc tccgggtaaa tga
```

*Figure 76*

```
   1 atgtggggct ggaagtgcct cctcttctgg gctgtgctgg tcacagccac tctctgcact
  61 gccaggtgtg ccagcgccgc ctgcttccac ggcgccacct gccatgaccg tgtggcctcc
 121 ttctactgcg agtgtcccca tggccgcaca ggtctgctgt gccacctcaa cgacgcatgc
 181 atcagcaacc cctgtaacga gggctccaac tgcgacacca accctgtcaa tggcaaggcc
 241 atctgcacct gcccctcggg gtacacgggc ccggcctgca gccaggacgt ggatgagtgc
 301 tcgctgggtg ccaacccctg cgagcatgcg ggcaagtgca tcaacacgct gggctccttc
 361 gagtgccagt gtctgcaggg ctacacgggc ccccgatgcg agatcgacgt caacgagtgc
 421 gtctcgaacc cgtgccagaa cgacgccacc tgcctggacc agattgggga gttccagtgc
 481 atctgcatgc ccggctacga gggtgtgcac tgcgaggtca acacagacga gtgtgccagc
 541 agcccctgcc tgcacaatgg ccgctgcctg gacaagatca atgagttcca gtgcgagtgc
 601 cccacgggct tcactgggca tctgtgccag tacgatgtgg acgagtgtgc cagcaccccc
 661 tgcaagaatg gtgccaagtg cctggacgga cccaacactt acacctgtgt gtgcacggaa
 721 gggtacacgg ggacgcactg cgaggtggac atcgatgagt gcgaccccga cccctgccac
 781 tacggctcct gcaaggacgg cgtcgccacc ttcacctgcc tctgccgccc aggctacacg
 841 ggccaccact gcgagaccaa catcaacgag tgctccagcc agccctgccg ccacgggggc
 901 acctgccagg accgcgacaa cgcctacctc tgcttctgcc tgaaggggac cacaggaccc
 961 aactgcgaga tcaacctgga tgactgtgcc agcagcccct gcgactcggg cacctgtctg
1021 gacaagatcg atggctacga gtgtgcctgt gagccgggct acacagggag catgtgtaac
1081 atcaacatcg atgagtgtgc gggcaacccc tgccacaacg gggcacctg cgaggacggc
1141 atcaatggct tcacctgccg ctgccccgag ggctaccacg accccacctg cctgtctgag
1201 gtcaatgagt gcaacagcaa cccctgcgtc cacggggcct gccgggacag cctcaacggg
1261 tacaagtgcg actgtgaccc tgggtggagt gggaccaact gtgacatcaa caacaatgag
1321 tgtgaatcca acccttgtgt caacggcggc acctgcaaag acatgaccag tggctacgtg
1381 tgcacctgcc gggagggctt cagcggtccc aactgccaga ccaacatcaa cgagtgtgcg
1441 tccaacccat gtctgaacca gggcacgtgt attgacgacg ttgccgggta caagtgcaac
1501 tgcctgctgc cctacacagg tgccacgtgt gaggtggtgc tggccccgtg tgcccccagc
1561 ccctgcagaa acggcgggga gtgcaggcaa tccgaggact atgagagctt ctcctgtgtc
1621 tgccccacgg gctggcaagg gcagacctgt gaggtcgaca tcaacgagtg cgttctgagc
1681 ccgtgccggc acggcgcatc ctgccagaac acccacggcg gctaccgctg ccactgccag
1741 gccggctaca gtgggcgcaa ctgcgagacc gacatagatc tgggcccggg cgagcccaaa
1801 tcttgtgaca aaactcacac atgcccaccg tgcccagcac ctgaactcct ggggggaccg
1861 tcagtcttcc tcttcccccc aaaacccaag gacaccctca tgatctcccg gacccctgag
1921 gtcacatgcg tggtggtgga cgtgagccac gaagaccctg aggtcaagtt caactggtac
1981 gtggacggcg tggaggtgca taatgccaag acaaagccgc gggaggagca gtacaacagc
2041 acgtaccgtg tggtcagcgt cctcaccgtc ctgcaccagg actggctgaa tggcaaggag
2101 tacaagtgca aggtctccaa caaagccctc ccagccccca tcgagaaaac catctccaaa
2161 gccaaagggc agccccgaga accacaggtg tacaccctgc ccccatcccg ggatgagctg
2221 accaagaacc aggtcagcct gacctgcctg gtcaaaggct tctatcccag cgacatcgcc
2281 gtggagtggg agagcaatgg gcagccggag aacaactaca agaccacgcc tcccgtgctg
2341 gactccgacg gctccttctt cctctacagc aagctcaccg tggacaagag caggtggcag
2401 caggggaacg tcttctcatg ctccgtgatg catgaggctc tgcacaacca ctacacgcag
2461 aagagcctct ccctgtctcc gggtaaatga
```

*Figure 77A*

```
   1 atgccgccgc tcctggcgcc cctgctctgc ctggcgctgc tgcccgcgct cgccgcacga
  61 ggcccgcgat gtgccagcgc cgcctgcttc cacggcgcca cctgccatga ccgtgtggcc
 121 tccttctact gcgagtgtcc ccatggccgc acaggtctgc tgtgccacct caacgacgca
 181 tgcatcagca accccctgtaa cgagggctcc aactgcgaca ccaaccctgt caatggcaag
 241 gccatctgca cctgcccctc ggggtacacg ggcccggcct gcagccagga cgtggatgag
 301 tgctcgctgg gtgccaaccc ctgcgagcat gcgggcaagt gcatcaacac gctgggctcc
 361 ttcgagtgcc agtgtctgca gggctacacg ggcccccgat gcgagatcga cgtcaacgag
 421 tgcgtctcga acccgtgcca gaacgacgcc acctgcctgg accagattgg ggagttccag
 481 tgcatctgca tgcccggcta cgagggtgtg cactgcgagg tcaacacaga cgagtgtgcc
 541 agcagcccct gcctgcacaa tggccgctgc ctggacaaga tcaatgagtt ccagtgcgag
 601 tgccccacgg gcttcactgg gcatctgtgc cagtacgatg tggacgagtg tgccagcacc
 661 ccctgcaaga atggtgccaa gtgcctggac ggacccaaca cttacacctg tgtgtgcacg
 721 gaagggtaca cggggacgca ctgcgaggtg gacatcgatg agtgcgaccc cgacccctgc
 781 cactacggct cctgcaagga cggcgtcgcc accttcacct gcctctgccg cccaggctac
 841 acgggccacc actgcgagac caacatcaac gagtgctcca gccagccctg ccgccacggg
 901 ggcacctgcc aggaccgcga caacgcctac ctctgcttct gcctgaaggg gaccacagga
 961 cccaactgcg agatcaacct ggatgactgt gccagcagcc cctgcgactc gggcacctgt
1021 ctggacaaga tcgatggcta cgagtgtgcc tgtgagccgg gctacacagg gagcatgtgt
1081 aacatcaaca tcgatgagtg tgcgggcaac ccctgccaca acgggggcac ctgcgaggac
1141 ggcatcaatg gcttcacctg ccgctgcccc gagggctacc acgaccccac ctgcctgtct
1201 gaggtcaatg agtgcaacag caacccctgc gtccacgggg cctgccggga cagcctcaac
1261 gggtacaagt gcgactgtga ccctgggtgg agtgggacca actgtgacat caacaacaat
1321 gagtgtgaat ccaacccttg tgtcaacggc ggcacctgca aagacatgac cagtggctac
1381 gtgtgcacct gccgggaggg cttcagcggt cccaactgcc agaccaacat caacgagtgt
1441 gcgtccaacc catgtctgaa ccagggcacg tgtattgacg acgttgccgg gtacaagtgc
1501 aactgcctgc tgccctacac aggtgccacg tgtgaggtgg tgctggcccc gtgtgccccc
1561 agcccctgca gaaacggcgg ggagtgcagg caatccgagg actatgagag cttctcctgt
1621 gtctgcccca cgggctggca agggcagacc tgtgaggtcg acatcaacga gtgcgttctg
1681 agcccgtgcc ggcacggcgc atcctgccag aacacccacg gcggctaccg ctgccactgc
1741 caggccggct acagtgggcg caactgcgag accgacatcg acgactgccg gcccaacccg
1801 tgtcacaacg gggggctcctg cacagacggc atcaacacgg ccttctgcga ctgcctgccc
1861 ggcttccggg gcactttctg tgaggaggac atcaacgagt gtgccagtga ccccctgccgc
1921 aacggggcca actgcacgga ctgcgtggac agctacacgt gcacctgccc cgcaggcttc
1981 agcgggatcc actgtgagaa caacacgcct gactgcacag agagctcctg cttcaacggt
2041 ggcacctgcg tggacggcat caactcgttc acctgcctgt gtccacccgg cttcacgggc
2101 agctactgcc agcacgatgt caatgagtgc gactcacagc cctgcctgca tggcggcacc
2161 tgtcaggacg gctgcggctc ctacaggtgc acctgccccc agggctacac tggccccaac
2221 tgccagaacc ttgtgcactg gtgtgactcc tcgccctgca agaacggcgg caaatgctgg
2281 cagacccaca cccagtaccg ctgcgagtgc cccagcggct ggaccggcct ttactgcgac
2341 gtgcccagcg tgtcctgtga ggtggctgcg cagcgacaag gtgttgacgt tgcccgcctg
2401 tgccagcatg gagggctctg tgtggacgcg ggcaacacgc accactgccg ctgccaggcg
2461 ggctacacag gcagctactg tgaggacctg gtggacgagt gctcacccag cccctgccag
2521 aacggggcca cctgcacgga ctacctgggc ggctactcct gcaagtgcgt ggccggctac
2581 cacggggtga actgctctga ggagatcgac gagtgcctct cccacccctg ccagaacggg
2641 ggcacctgcc tcgacctccc caacacctac aagtgctcct gcccacgggg cactcagggt
2701 gtgcactgtg agatcaacgt ggacgactgc aatcccccg ttgaccccgt gtcccggagc
2761 cccaagtgct ttaacaacgg cacctgcgtg gaccaggtgg gcggctacag ctgcacctgc
2821 ccgccgggct tcgtgggtga gcgctgtgag gggggatgtca acgagtgcct gtccaatccc
```

*Figure 77B*

```
2881 tgcgacgccc gtggcaccca gaactgcgtg cagcgcgtca atgacttcca ctgcgagtgc
2941 cgtgctggtc acaccgggcg ccgctgcgag tccgtcatca atggctgcaa aggcaagccc
3001 tgcaagaatg gggcacctg cgccgtggcc tccaacaccg cccgcgggtt catctgcaag
3061 tgccctgcgg gcttcgaggg cgccacgtgt gagaatgacg ctcgtacctg cggcagcctg
3121 cgctgcctca acggcggcac atgcatctcc ggcccgcgca gccccacctg cctgtgcctg
3181 ggccccttca cgggccccga atgccagttc ccggccagca gcccctgcct gggcggcaac
3241 ccctgctaca accaggggac ctgtgagccc acatccgaga gccccttcta ccgttgcctg
3301 tgccccgcca aattcaacgg gctcttgtgc cacatcctgg actacagctt cggagatctg
3361 ggcccgggcg agcccaaatc ttgtgacaaa actcacacat gcccaccgtg cccagcacct
3421 gaactcctgg ggggaccgtc agtcttcctc ttccccccaa aacccaagga caccctcatg
3481 atctcccgga cccctgaggt cacatgcgtg gtggtggacg tgagccacga agaccctgag
3541 gtcaagttca actggtacgt ggacggcgtg gaggtgcata atgccaagac aaagccgcgg
3601 gaggagcagt acaacagcac gtaccgtgtg gtcagcgtcc tcaccgtcct gcaccaggac
3661 tggctgaatg gcaaggagta caagtgcaag gtctccaaca aagccctccc agcccccatc
3721 gagaaaacca tctccaaagc caaagggcag ccccgagaac cacaggtgta caccctgccc
3781 ccatcccggg atgagctgac caagaaccag gtcagcctga cctgcctggt caaaggcttc
3841 tatcccagcg acatcgccgt ggagtgggag agcaatgggc agccggagaa caactacaag
3901 accacgcctc ccgtgctgga ctccgacggc tccttcttcc tctacagcaa gctcaccgtg
3961 gacaagagca ggtggcagca ggggaacgtc ttctcatgct ccgtgatgca tgaggctctg
4021 cacaaccact acacgcagaa gagcctctcc ctgtctccgg gtaaatga
```

*Figure 78A*

```
   1 atgtggggct ggaagtgcct cctcttctgg gctgtgctgg tcacagccac tctctgcact
  61 gccaggtgtg ccagcgccgc ctgcttccac ggcgccacct gccatgaccg tgtggcctcc
 121 ttctactgcg agtgtcccca tggccgcaca ggtctgctgt gccacctcaa cgacgcatgc
 181 atcagcaacc cctgtaacga gggctccaac tgcgacacca accctgtcaa tggcaaggcc
 241 atctgcacct gcccctcggg gtacacgggc ccggcctgca gccaggacgt ggatgagtgc
 301 tcgctgggtg ccaacccctg cgagcatgcg ggcaagtgca tcaacacgct gggctccttc
 361 gagtgccagt gtctgcaggg ctacacgggc ccccgatgcg agatcgacgt caacgagtgc
 421 gtctcgaacc cgtgccagaa cgacgccacc tgcctggacc agattgggga gttccagtgc
 481 atctgcatgc ccggctacga gggtgtgcac tgcgaggtca acacagacga gtgtgccagc
 541 agcccctgcc tgcacaatgg ccgctgcctg gacaagatca atgagttcca gtgcgagtgc
 601 cccacgggct tcactgggca tctgtgccag tacgatgtgg acgagtgtgc cagcaccccc
 661 tgcaagaatg gtgccaagtg cctggacgga cccaacactt acacctgtgt gtgcacggaa
 721 gggtacacgg ggacgcactg cgaggtggac atcgatgagt gcgacccccga cccctgccac
 781 tacggctcct gcaaggacgg cgtcgccacc ttcacctgcc tctgccgccc aggctacacg
 841 ggccaccact gcgagaccaa catcaacgag tgctccagcc agccctgccg ccacgggggc
 901 acctgccagg accgcgacaa cgcctacctc tgcttctgcc tgaaggggac cacaggaccc
 961 aactgcgaga tcaacctgga tgactgtgcc agcagcccct gcgactcggg cacctgtctg
1021 gacaagatcg atggctacga gtgtgcctgt gagccgggct acacagggag catgtgtaac
1081 atcaacatcg atgagtgtgc gggcaacccc tgccacaacg gggcacctg cgaggacggc
1141 atcaatggct tcacctgccg ctgccccgag ggctaccacg accccacctg cctgtctgag
1201 gtcaatgagt gcaacagcaa cccctgcgtc cacggggcct gccgggacag cctcaacggg
1261 tacaagtgcg actgtgaccc tgggtggagt gggaccaact gtgacatcaa caacaatgag
1321 tgtgaatcca acccttgtgt caacggcggc acctgcaaag acatgaccag tggctacgtg
1381 tgcacctgcc gggagggctt cagcggtccc aactgccaga ccaacatcaa cgagtgtgcg
1441 tccaacccat gtctgaacca gggcacgtgt attgacgacg ttgccgggta caagtgcaac
1501 tgcctgctgc cctacacagg tgccacgtgt gaggtggtgc tggccccgtg tgcccccagc
1561 ccctgcagaa acggcgggga gtgcaggcaa tccgaggact atgagagctt ctcctgtgtc
1621 tgccccacgg gctggcaagg gcagacctgt gaggtcgaca tcaacgagtg cgttctgagc
1681 ccgtgccggc acggcgcatc ctgccagaac acccacggcg gctaccgctg ccactgccag
1741 gccggctaca gtgggcgcaa ctgcgagacc gacatcgacg actgccggcc caacccgtgt
1801 cacaacgggg gctcctgcac agacggcatc aacacggcct tctgcgactg cctgcccggc
1861 ttccggggca ctttctgtga ggaggacatc aacgagtgtg ccagtgaccc ctgccgcaac
1921 ggggccaact gcacggactg cgtggacagc tacacgtgca cctgccccgc aggcttcagc
1981 gggatccact gtgagaacaa cacgcctgac tgcacagaga gctcctgctt caacggtggc
2041 acctgcgtgg acggcatcaa ctcgttcacc tgcctgtgtc cacccggctt cacgggcagc
2101 tactgccagc acgatgtcaa tgagtgcgac tcacagccct gcctgcatgg cggcacctgt
2161 caggacggct gcggctccta caggtgcacc tgccccccagg gctacactgg ccccaactgc
2221 cagaaccttg tgcactggtg tgactcctcg ccctgcaaga acggcggcaa atgctggcag
2281 acccacaccc agtaccgctg cgagtgcccc agcggctgga ccggccttta ctgcgacgtg
2341 cccagcgtgt cctgtgaggt ggctgcgcag cgacaaggtg ttgacgttgc ccgcctgtgc
2401 cagcatggag ggctctgtgt ggacgcgggc aacacgcacc actgccgctg ccaggcgggc
2461 tacacaggca gctactgtga ggacctggtg gacgagtgct cacccagccc ctgccagaac
2521 ggggccacct gcacggacta cctgggcggc tactcctgca agtgcgtggc cggctaccac
2581 ggggtgaact gctctgagga gatcgacgag tgcctctccc accccctgcca gaacgggggc
2641 acctgcctcg acctccccaa cacctacaag tgctcctgcc cacggggcac tcagggtgtg
2701 cactgtgaga tcaacgtgga cgactgcaat cccccccgttg accccgtgtc ccggagcccc
2761 aagtgcttta acaacggcac ctgcgtggac caggtgggcg gctacagctg cacctgcccg
2821 ccgggcttcg tgggtgagcg ctgtgagggg gatgtcaacg agtgcctgtc caatccctgc
2881 gacgcccgtg gcacccagaa ctgcgtgcag cgcgtcaatg acttccactg cgagtgccgt
2941 gctggtcaca ccgggcgccg ctgcgagtcc gtcatcaatg gctgcaaagg caagccctgc
```

*Figure 78B*

```
3001 aagaatgggg gcacctgcgc cgtggcctcc aacaccgccc gcgggttcat ctgcaagtgc
3061 cctgcgggct tcgagggcgc cacgtgtgag aatgacgctc gtacctgcgg cagcctgcgc
3121 tgcctcaacg gcggcacatg catctccggc ccgcgcagcc ccacctgcct gtgcctgggc
3181 cccttcacgg gccccgaatg ccagttcccg gccagcagcc cctgcctggg cggcaacccc
3241 tgctacaacc aggggacctg tgagcccaca tccgagagcc ccttctaccg ttgcctgtgc
3301 cccgccaaat tcaacgggct cttgtgccac atcctggact acagcttcgg agatctgggc
3361 ccgggcgagc ccaaatcttg tgacaaaact cacacatgcc caccgtgccc agcacctgaa
3421 ctcctggggg gaccgtcagt cttcctcttc cccccaaaac ccaaggacac cctcatgatc
3481 tcccggaccc ctgaggtcac atgcgtggtg gtggacgtga gccacgaaga ccctgaggtc
3541 aagttcaact ggtacgtgga cggcgtggag gtgcataatg ccaagacaaa gccgcgggag
3601 gagcagtaca acagcacgta ccgtgtggtc agcgtcctca ccgtcctgca ccaggactgg
3661 ctgaatggca aggagtacaa gtgcaaggtc tccaacaaag ccctcccagc ccccatcgag
3721 aaaaccatct ccaaagccaa agggcagccc cgagaaccac aggtgtacac cctgccccca
3781 tcccgggatg agctgaccaa gaaccaggtc agcctgacct gcctggtcaa aggcttctat
3841 cccagcgaca tcgccgtgga gtgggagagc aatgggcagc cggagaacaa ctacaagacc
3901 acgcctcccg tgctggactc cgacggctcc ttcttcctct acagcaagct caccgtggac
3961 aagagcaggt ggcagcaggg gaacgtcttc tcatgctccg tgatgcatga ggctctgcac
4021 aaccactaca cgcagaagag cctctccctg tctccgggta aatga
```

*Figure 79*

```
   1 atgccgccgc tcctggcgcc cctgctctgc ctggcgctgc tgcccgcgct cgccgcacga
  61 ggcccgcgat gtgccagcag cccctgcctg cacaatggcc gctgcctgga caagatcaat
 121 gagttccagt gcgagtgccc cacgggcttc actgggcatc tgtgccagta cgatgtggac
 181 gagtgtgcca gcacccccctg caagaatggt gccaagtgcc tggacggacc caacacttac
 241 acctgtgtgt gcacggaagg gtacacgggg acgcactgcg aggtggacat cgatgagtgc
 301 gaccccgacc cctgccacta cggctcctgc aaggacggcg tcgccacctt cacctgcctc
 361 tgccgcccag gctacacggg ccaccactgc gagaccaaca tcaacgagtg ctccagccag
 421 ccctgccgcc acgggggcac ctgccaggac cgcgacaacg cctacctctg cttctgcctg
 481 aaggggacca caggacccaa ctgcgagatc aacctggatg actgtgccag cagcccctgc
 541 gactcgggca cctgtctgga caagatcgat ggctacgagt gtgcctgtga gccgggctac
 601 acagggagca tgtgtaacat caacatcgat gagtgtgcgg gcaacccctg ccacaacggg
 661 ggcacctgcg aggacggcat caatggcttc acctgccgct gccccgaggg ctaccacgac
 721 cccacctgcc tgtctgaggt caatgagtgc aacagcaacc cctgcgtcca cggggcctgc
 781 cgggacagcc tcaacgggta caagtgcgac tgtgaccctg ggtggagtgg gaccaactgt
 841 gacatcaaca acaatgagtg tgaatccaac ccttgtgtca acggcggcac ctgcaaagac
 901 atgaccagtg gctacgtgtg cacctgccgg gagggcttca gcggtcccaa ctgccagacc
 961 aacatcaacg agtgtgcgtc caacccatgt ctgaaccagg gcacgtgtat tgacgacgtt
1021 gccgggtaca agtgcaactg cctgctgccc tacacaggtg ccacgtgtga ggtggtgctg
1081 gccccgtgtg cccccagccc ctgcagaaac ggcggggagt gcaggcaatc cgaggactat
1141 gagagcttct cctgtgtctg ccccacgggc tggcaagggc agacctgtga ggtcgacatc
1201 aacgagtgcg ttctgagccc gtgccggcac ggcgcatcct gccagaacac ccacggcggc
1261 taccgctgcc actgccaggc cggctacagt gggcgcaact gcgagaccga catcgacgac
1321 tgccggccca acccgtgtca caacgggggc tcctgcacag acggcatcaa cacggccttc
1381 tgcgactgcc tgcccggctt ccggggcact ttctgtgagg aggacatcaa cgaggatctg
1441 ggcccgggcg agcccaaatc ttgtgacaaa actcacacat gcccaccgtg cccagcacct
1501 gaactcctgg ggggaccgtc agtcttcctc ttccccccaa aacccaagga caccctcatg
1561 atctcccgga cccctgaggt cacatgcgtg gtggtggacg tgagccacga agaccctgag
1621 gtcaagttca actggtacgt ggacggcgtg gaggtgcata atgccaagac aaagccgcgg
1681 gaggagcagt acaacagcac gtaccgtgtg gtcagcgtcc tcaccgtcct gcaccaggac
1741 tggctgaatg gcaaggagta caagtgcaag gtctccaaca aagccctccc agcccccatc
1801 gagaaaacca tctccaaagc caaagggcag ccccgagaac cacaggtgta caccctgccc
1861 ccatcccggg atgagctgac caagaaccag gtcagcctga cctgcctggt caaaggcttc
1921 tatcccagcg acatcgccgt ggagtgggag agcaatgggc agccggagaa caactacaag
1981 accacgcctc ccgtgctgga ctccgacggc tccttcttcc tctacagcaa gctcaccgtg
2041 gacaagagca ggtggcagca ggggaacgtc ttctcatgct ccgtgatgca tgaggctctg
2101 cacaaccact acacgcagaa gagcctctcc ctgtctccgg gtaaatga
```

*Figure 80*

```
   1 atgtggggct ggaagtgcct cctcttctgg gctgtgctgg tcacagccac tctctgcact
  61 gccaggtgtg ccagcagccc ctgcctgcac aatggccgct gcctggacaa gatcaatgag
 121 ttccagtgcg agtgccccac gggcttcact gggcatctgt gccagtacga tgtggacgag
 181 tgtgccagca ccccctgcaa gaatggtgcc aagtgcctgg acggacccaa cacttacacc
 241 tgtgtgtgca cggaagggta cacggggacg cactgcgagg tggacatcga tgagtgcgac
 301 cccgacccct gccactacgg ctcctgcaag gacggcgtcg ccaccttcac ctgcctctgc
 361 cgcccaggct acacgggcca ccactgcgag accaacatca acgagtgctc cagccagccc
 421 tgccgccacg gggcacctg ccaggaccgc gacaacgcct acctctgctt ctgcctgaag
 481 gggaccacag gacccaactg cgagatcaac ctggatgact gtgccagcag cccctgcgac
 541 tcgggcacct gtctggacaa gatcgatggc tacgagtgtg cctgtgagcc gggctacaca
 601 gggagcatgt gtaacatcaa catcgatgag tgtgcgggca accccctgcca caacgggggc
 661 acctgcgagg acggcatcaa tggcttcacc tgccgctgcc ccgagggcta ccacgacccc
 721 acctgcctgt ctgaggtcaa tgagtgcaac agcaacccct gcgtccacgg ggcctgccgg
 781 gacagcctca acgggtacaa gtgcgactgt gaccctgggt ggagtgggac caactgtgac
 841 atcaacaaca atgagtgtga atccaacccct tgtgtcaacg gcggcacctg caaagacatg
 901 accagtggct acgtgtgcac ctgccgggag ggcttcagcg gtcccaactg ccagaccaac
 961 atcaacgagt gtgcgtccaa cccatgtctg aaccagggca cgtgtattga cgacgttgcc
1021 gggtacaagt gcaactgcct gctgccctac acaggtgcca cgtgtgaggt ggtgctggcc
1081 ccgtgtgccc ccagcccctg cagaaacggc ggggagtgca ggcaatccga ggactatgag
1141 agcttctcct gtgtctgccc cacgggctgg caagggcaga cctgtgaggt cgacatcaac
1201 gagtgcgttc tgagcccgtg ccggcacggc gcatcctgcc agaacaccca cggcggctac
1261 cgctgccact gccaggccgg ctacagtggg cgcaactgcg agaccgacat cgacgactgc
1321 cggcccaacc cgtgtcacaa cgggggctcc tgcacagacg gcatcaacac ggccttctgc
1381 gactgcctgc ccggcttccg gggcactttc tgtgaggagg acatcaacga ggatctgggc
1441 ccgggcgagc ccaaatcttg tgacaaaact cacacatgcc caccgtgccc agcacctgaa
1501 ctcctggggg gaccgtcagt cttcctcttc cccccaaaac ccaaggacac cctcatgatc
1561 tcccggaccc ctgaggtcac atgcgtggtg gtggacgtga gccacgaaga ccctgaggtc
1621 aagttcaact ggtacgtgga cggcgtggag gtgcataatg ccaagacaaa gccgcgggag
1681 gagcagtaca acagcacgta ccgtgtggtc agcgtcctca ccgtcctgca ccaggactgg
1741 ctgaatggca aggagtacaa gtgcaaggtc tccaacaaag ccctcccagc ccccatcgag
1801 aaaaccatct ccaaagccaa agggcagccc cgagaaccac aggtgtacac cctgccccca
1861 tcccgggatg agctgaccaa gaaccaggtc agcctgacct gcctggtcaa aggcttctat
1921 cccagcgaca tcgccgtgga gtgggagagc aatgggcagc cggagaacaa ctacaagacc
1981 acgcctcccg tgctggactc cgacggctcc ttcttcctct acagcaagct caccgtggac
2041 aagagcaggt ggcagcaggg gaacgtcttc tcatgctccg tgatgcatga ggctctgcac
2101 aaccactaca cgcagaagag cctctccctg tctccgggta aatga
```

*Figure 81*

```
   1 atgccgccgc tcctggcgcc cctgctctgc ctggcgctgc tgcccgcgct cgccgcacga
  61 ggcccgcgat gtgccagtga cccctgccgc aacggggcca actgcacgga ctgcgtggac
 121 agctacacgt gcacctgccc cgcaggcttc agcgggatcc actgtgagaa caacacgcct
 181 gactgcacag agagctcctg cttcaacggt ggcacctgcg tggacggcat caactcgttc
 241 acctgcctgt gtccacccgg cttcacgggc agctactgcc agcacgatgt caatgagtgc
 301 gactcacagc cctgcctgca tggcggcacc tgtcaggacg gctgcggctc ctacaggtgc
 361 acctgccccc agggctacac tggccccaac tgccagaacc ttgtgcactg gtgtgactcc
 421 tcgccctgca agaacggcgg caaatgctgg cagacccaca cccagtaccg ctgcgagtgc
 481 cccagcggct ggaccggcct ttactgcgac gtgcccagcg tgtcctgtga ggtggctgcg
 541 cagcgacaag gtgttgacgt tgcccgcctg tgccagcatg gagggctctg tgtggacgcg
 601 ggcaacacgc accactgccg ctgccaggcg ggctacacag gcagctactg tgaggacctg
 661 gtggacgagt gctcacccag cccctgccag aacggggcca cctgcacgga ctacctgggc
 721 ggctactcct gcaagtgcgt ggccggctac cacggggtga actgctctga ggagatcgac
 781 gagtgcctct cccacccctg ccagaacggg ggcacctgcc tcgacctccc caacacctac
 841 aagtgctcct gcccacgggg cactcagggt gtgcactgtg agatcaacgt ggacgactgc
 901 aatcccccccg ttgaccccgt gtcccggagc cccaagtgct ttaacaacgg cacctgcgtg
 961 gaccaggtgg gcggctacag ctgcacctgc ccgccgggct tcgtgggtga gcgctgtgag
1021 ggggatgtca acgagtgcct gtccaatccc tgcgacgccc gtggcaccca gaactgcgtg
1081 cagcgcgtca atgacttcca ctgcgagtgc cgtgctggtc acaccgggcg ccgctgcgag
1141 tccgtcatca atggctgcaa aggcaagccc tgcaagaatg gggcacctg cgccgtggcc
1201 tccaacaccg cccgcgggtt catctgcaag tgccctgcgg gcttcgaggg cgccacgtgt
1261 gagaatgacg ctcgtacctg cggcagcctg cgctgcctca acggcggcac atgcatctcc
1321 ggcccgcgca gccccacctg cctgtgcctg ggccccttca cgggccccga atgccagttc
1381 ccggccagca gcccctgcct gggcggcaac ccctgctaca accaggggac ctgtgagccc
1441 acatccgaga gccccttcta ccgttgcctg tgccccgcca aattcaacgg gctcttgtgc
1501 cacatcctgg actacagctt cggagatctg ggcccgggcg agcccaaatc ttgtgacaaa
1561 actcacacat gcccaccgtg cccagcacct gaactcctgg ggggaccgtc agtcttcctc
1621 ttccccccaa aacccaagga caccctcatg atctcccgga cccctgaggt cacatgcgtg
1681 gtggtggacg tgagccacga agaccctgag gtcaagttca actggtacgt ggacggcgtg
1741 gaggtgcata atgccaagac aaagccgcgg gaggagcagt acaacagcac gtaccgtgtg
1801 gtcagcgtcc tcaccgtcct gcaccaggac tggctgaatg gcaaggagta caagtgcaag
1861 gtctccaaca aagccctccc agcccccatc gagaaaacca tctccaaagc caaagggcag
1921 ccccgagaac cacaggtgta caccctgccc ccatcccggg atgagctgac caagaaccag
1981 gtcagcctga cctgcctggt caaaggcttc tatcccagcg acatcgccgt ggagtgggag
2041 agcaatgggc agccggagaa caactacaag accacgcctc ccgtgctgga ctccgacggc
2101 tccttcttcc tctacagcaa gctcaccgtg gacaagagca ggtggcagca ggggaacgtc
2161 ttctcatgct ccgtgatgca tgaggctctg cacaaccact acacgcagaa gagcctctcc
2221 ctgtctccgg gtaaatga
```

*Figure 82*

```
   1 atgtggggct ggaagtgcct cctcttctgg gctgtgctgg tcacagccac tctctgcact
  61 gccaggtgtg ccagtgaccc ctgccgcaac ggggccaact gcacggactg cgtggacagc
 121 tacacgtgca cctgccccgc aggcttcagc gggatccact gtgagaacaa cacgcctgac
 181 tgcacagaga gctcctgctt caacggtggc acctgcgtgg acggcatcaa ctcgttcacc
 241 tgcctgtgtc cacccggctt cacgggcagc tactgccagc acgatgtcaa tgagtgcgac
 301 tcacagccct gcctgcatgg cggcacctgt caggacggct gcggctccta caggtgcacc
 361 tgcccccagg gctacactgg ccccaactgc cagaaccttg tgcactggtg tgactcctcg
 421 ccctgcaaga acggcggcaa atgctggcag acccacaccc agtaccgctg cgagtgcccc
 481 agcggctgga ccggccttta ctgcgacgtg cccagcgtgt cctgtgaggt ggctgcgcag
 541 cgacaaggtg ttgacgttgc ccgcctgtgc cagcatggag ggctctgtgt ggacgcgggc
 601 aacacgcacc actgccgctg ccaggcgggc tacacaggca gctactgtga ggacctggtg
 661 gacgagtgct cacccagccc ctgccagaac ggggccacct gcacggacta cctgggcggc
 721 tactcctgca agtgcgtggc cggctaccac ggggtgaact gctctgagga gatcgacgag
 781 tgcctctccc accccctgcca gaacgggggc acctgcctcg acctccccaa cacctacaag
 841 tgctcctgcc cacggggcac tcagggtgtg cactgtgaga tcaacgtgga cgactgcaat
 901 ccccccgttg accccgtgtc ccggagcccc aagtgcttta acaacggcac ctgcgtggac
 961 caggtgggcg gctacagctg cacctgcccg ccgggcttcg tgggtgagcg ctgtgagggg
1021 gatgtcaacg agtgcctgtc caatccctgc gacgcccgtg gcacccagaa ctgcgtgcag
1081 cgcgtcaatg acttccactg cgagtgccgt gctggtcaca ccgggcgccg ctgcgagtcc
1141 gtcatcaatg gctgcaaagg caagccctgc aagaatgggg gcacctgcgc cgtggcctcc
1201 aacaccgccc gcgggttcat ctgcaagtgc cctgcgggct tcgagggcgc cacgtgtgag
1261 aatgacgctc gtacctgcgg cagcctgcgc tgcctcaacg gcggcacatg catctccggc
1321 ccgcgcagcc ccacctgcct gtgcctgggc cccttcacgg gccccgaatg ccagttcccg
1381 gccagcagcc cctgcctggg cggcaacccc tgctacaacc aggggacctg tgagcccaca
1441 tccgagagcc ccttctaccg ttgcctgtgc cccgccaaat tcaacgggct cttgtgccac
1501 atcctggact acagcttcgg agatctgggc ccgggcgagc ccaaatcttg tgacaaaact
1561 cacacatgcc caccgtgccc agcacctgaa ctcctggggg gaccgtcagt cttcctcttc
1621 cccccaaaac ccaaggacac cctcatgatc tcccggaccc ctgaggtcac atgcgtggtg
1681 gtggacgtga gccacgaaga ccctgaggtc aagttcaact ggtacgtgga cggcgtggag
1741 gtgcataatg ccaagacaaa gccgcgggag gagcagtaca acagcacgta ccgtgtggtc
1801 agcgtcctca ccgtcctgca ccaggactgg ctgaatggca aggagtacaa gtgcaaggtc
1861 tccaacaaag ccctcccagc ccccatcgag aaaaccatct ccaaagccaa agggcagccc
1921 cgagaaccac aggtgtacac cctgccccca tcccgggatg agctgaccaa gaaccaggtc
1981 agcctgacct gcctggtcaa aggcttctat cccagcgaca tcgccgtgga gtgggagagc
2041 aatgggcagc cggagaacaa ctacaagacc acgcctcccg tgctggactc cgacggctcc
2101 ttcttcctct acagcaagct caccgtggac aagagcaggt ggcagcaggg gaacgtcttc
2161 tcatgctccg tgatgcatga ggctctgcac aaccactaca cgcagaagag cctctccctg
2221 tctccgggta aatga
```

*Figure 83*

MQPPSLLLLLLLLLLLCVSVVRPRGLLCGSFPEPCANGGTCLSLSLGQGTCQCAPGFLGE
TCQFPDPCQNAQLCQNGGSCQALLPAPLGLPSSPSPLTPSFLCTCLPGFTGERCQAKLED
PCPPSFCSKRGRCHIQASGRPQCSCMPGWTGEQCQLRDFCSANPCVNGGVCLATYPQIQC
HCPPGFEGHACERDVNECFQDPGPCPKGTSCHNTLGSFQCLCPVGQEGPRCELRAGPCPP
RGCSNGGTCQLMPEKDSTFHLCLCPPGFIGPDCEVNPDNCVSHQCQNGGTCQDGLDTYTC
LCPETWTGWDCSEDVDECETQGPPHCRNGGTCQNSAGSFHCVCVSGWGGTSCEENLDDCI
AATCAPGSTCIDRVGSFSCLCPPGRTGLLCHLEDMCLSQPCHGDAQCSTNPLTGSTLCLC
QPGYSGPTCHQDLDECLMAQQGPSPCEHGGSCLNTPGSFNCLCPPGYTGSRCEADHNECL
SQPCHPGSTCLDLLATFHCLCPPGLEGQLCEVETNECASAPCLNHADCHDLLNGFQCICL
PGFSGTRCEEDIDECRSSPCANGGQCQDQPGAFHCKCLPGFEGPRCQTEVDECLSDPCPV
GASCLDLPGAFFCLCPSGFTGQLCEVPLCAPNLCQPKQICKDQKDKANCLCPDGSPGCAP
PEDNCTCHHGHCQRSSCVCDVGWTGPECEAELGGCISAPCAHGGTCYPQPSGYNCTCPTG
YTGPTCSEEMTACHSGPCLNGGSCNPSPGGYYCTCPPSHTGPQCQTSTDYCVSAPCFNGG
TCVNRPGTFSCLCAMGFQGPRCEGKLRPSCADSPCRNRATCQDSPQGPRCLCPTGYTGGS
CQTLMDLCAQKPCPRNSHCLQTGPSFHCLCLQGWTGPLCNLPLSSCQKAALSQGIDVSSL
CHNGGLCVDSGPSYFCHCPPGFQGSLCQDHVNPCESRPCQNGATCMAQPSGYLCQCAPGY
DGQNCSKELDACQSQPCHNHGTCTPKPGGFHCACPPGFVGLRCEGDVDECLDQPCHPTGT
AACHSLANAFYCQCLPGHTGQWCEVEIDPCHSQPCFHGGTCEATAGSPLGFICHCPKGFE
GPTCSHRAPSCGFHHCHHGGLCLPSPKPGFPPRCACLSGYGGPDCLTPPAPKGCGPPSPC
LYNGSCSETTGLGGPGFRCSCPHSSPGPRCQKPGAKGCEGRSGDGACDAGCSGPGGNWDG
GDCSLGVPDPWKGCPSHSRCWLLFRDGQCHPQCDSEECLFDGYDCETPPACTPAYDQYCH
DHFHNGHCEKGCNTAECGWDGGDCRPEDGDPEWGPSLALLVVLSPPALDQQLFALARVLS
LTLRVGLWVRKDRDGRDMVYPYPGARAEEKLGGTRDPTYQERAAPQTQPLGKETDSLSAG
FVVVMGVDLSRCGPDHPASRCPWDPGLLLRFLAAMAAVGALEPLLPGPLLAVHPHAGTAP
PANQLPWPVLCSPVAGVILLALGALLVLQLIRRRRREHGALWLPPGFTRRPRTQSAPHRR
RPPLGEDSIGLKALKPKAEVDEDGVVMCSGPEEGEEVGQAEETGPPSTCQLWSLSGGCGA
LPQAAMLTPPQESEMEAPDLDTRGPDGVTPLMSAVCCGEVQSGTFQGAWLGCPEPWEPLL
DGGACPQAHTVGTGETPLHLAARFSRPTAARRLLEAGANPNQPDRAGRTPLHAAVAADAR
EVCQLLLRSRQTAVDARTEDGTTPLMLAARLAVEDLVEELIAAQADVGARDKWGKTALHW
AAAVNNARAARSLLQAGADKDAQDNREQTPLFLAAREGAVEVAQLLLGLGAARELRDQAG
LAPADVAHQRNHWDLLTLLEGAGPPEARHKATPGREAGPFPRARTVSVSVPPHGGALPR
CRTLSAGAGPRGGGACLQARTWSVDLAARGGGAYSHCRSLSGVGAGGGPTPRGRRFSAGM
RGPRPNPAIMRGRYGVAAGRGGRVSTDDWPCDWVALGACGSASNIPIPPPCLTPSPERGS
PQLDCGPPALQEMPINQGGEGKK

*Figure 84*

DLGPGEPKSCDKTHTCPPCPAPELLGGPSVFLFPPKPKDTLMISRTPEVTCVVVDVSHED
PEVKFNWYVDGVEVHNAKTKPREEQYNSTYRVVSVLTVLHQDWLNGKEYKCKVSNKALPA
PIEKTISKAKGQPREPQVYTLPPSRDELTKNQVSLTCLVKGFYPSDIAVEWESNGQPENN
YKTTPPVLDSDGSFFLYSKLTVDKSRWQQGNVFSCSVMHEALHNHYTQKSLSLSPGK

*Figure 85*

QPPSLLLLLLLLLLLCVSVVRPRGLLCGSFPEPCANGGTCLSLSLGQGTCQCAPGFLGET
CQFPDPCQNAQLCQNGGSCQALLPAPLGLPSSPSPLTPSFLCTCLPGFTGERCQAKLEDP
CPPSFCSKRGRCHIQASGRPQCSCMPGWTGEQCQLRDFCSANPCVNGGVCLATYPQIQCH
CPPGFEGHACERDVNECFQDPGPCPKGTSCHNTLGSFQCLCPVGQEGPRCELRAGPCPPR
GCSNGGTCQLMPEKDSTFHLCLCPPGFIGPDCEVNPDNCVSHQCQNGGTCQDGLDTYTCL
CPETWTGWDCSEDVDECETQGPPHCRNGGTCQNSAGSFHCVCVSGWGGTSCEENLDDCIA
ATCAPGSTCIDRVGSFSCLCPPGRTGLLCHLEDMCLSQPCHGDAQCSTNPLTGSTLCLCQ
PGYSGPTCHQDLDECLMAQQGPSPCEHGGSCLNTPGSFNCLCPPGYTGSRCEADHNECLS
QPCHPGSTCLDLLATFHCLCPPGLEGQLCEVETNECASAPCLNHADCHDLLNGFQCICLP
GFSGTRCEEDIDECRSSPCANGGQCQDQPGAFHCKCLPGFEGPRCQTEVDECLSDPCPVG
ASCLDLPGAFFCLCPSGFTGQLCEVPLCAPNLCQPKQICKDQKDKANCLCPDGSPGCAPP
EDNCTCHHGHCQRSSCVCDVGWTGPECEAELGGCISAPCAHGGTCYPQPSGYNCTCPTGY
TGPTCSEEMTACHSGPCLNGGSCNPSPGGYYCTCPPSHTGPQCQTSTDYCVSAPCFNGGT
CVNRPGTFSCLCAMGFQGPRCEGKLRPSCADSPCRNRATCQDSPQGPRCLCPTGYTGGSC
QTLMDLCAQKPCPRNSHCLQTGPSFHCLCLQGWTGPLCNLPLSSCQKAALSQGIDVSSLC
HNGGLCVDSGPSYFCHCPPGFQGSLCQDHVNPCESRPCQNGATCMAQPSGYLCQCAPGYD
GQNCSKELDACQSQPCHNHGTCTPKPGGFHCACPPGFVGLRCEGDVDECLDQPCHPTGTA
ACHSLANAFYCQCLPGHTGQWCEVEIDPCHSQPCFHGGTCEATAGSPLGFICHCPKGFEG
PTCSHRAPSCGFHHCHHGGLCLPSPKPGFPPRCACLSGYGGPDCLTPPAPKGCGPPSPCL
YNGSCSETTGLGGPGFRCSCPHSSPGPRCQKPG*DLGPGEPKSCDKTHTCPPCPAPELLGG*
*PSVFLFPPKPKDTLMISRTPEVTCVVVDVSHEDPEVKFNWYVDGVEVHNAKTKPREEQYN*
*STYRVVSVLTVLHQDWLNGKEYKCKVSNKALPAPIEKTISKAKGQPREPQVYTLPPSRDE*
*LTKNQVSLTCLVKGFYPSDIAVEWESNGQPENNYKTTPPVLDSDGSFFLYSKLTVDKSRW*
*QQGNVFSCSVMHEALHNHYTQKSLSLSPGK*

*Figure 86*

MQPPSLLLLLLLLLLLCVSVVRPRGLLCGSFPEPCANGGTCLSLSLGQGTCQCAPGFLGE
TCQFPDPCQNAQLCQNGGSCQALLPAPLGLPSSPSPLTPSFLCTCLPGFTGERCQAKLED
PCPPSFCSKRGRCHIQASGRPQCSCMPGWTGEQCQLRDFCSANPCVNGGVCLATYPQIQC
HCPPGFEGHACERDVNECFQDPGPCPKGTSCHNTLGSFQCLCPVGQEGPRCELRAGPCPP
RGCSNGGTCQLMPEKDSTFHLCLCPPGFIGPDCEVNPDNCVSHQCQNGGTCQDGLDTYTC
LCPETWTGWDCSEDVDECETQGPPHCRNGGTCQNSAGSFHCVCVSGWGGTSCEENLDDCI
AATCAPGSTCIDRVGSFSCLCPPGRTGLLCHLEDMCLSQPCHGDAQCSTNPLTGSTLCLC
QPGYSGPTCHQDLDECLMAQQGPSPCEHGGSCLNTPGSFNCLCPPGYTGSRCEADHNECL
SQPCHPGSTCLDLLATFHCLCPPGLEGQLCEVETNECASAPCLNHADCHDLLNGFQCICL
PGFSGTRCEEDIDE*DLGPGEPKSCDKTHTCPPCPAPELLGGPSVFLFPPKPKDTLMISRT*
*PEVTCVVVDVSHEDPEVKFNWYVDGVEVHNAKTKPREEQYNSTYRVVSVLTVLHQDWLNG*
*KEYKCKVSNKALPAPIEKTISKAKGQPREPQVYTLPPSRDELTKNQVSLTCLVKGFYPSD*
*IAVEWESNGQPENNYKTTPPVLDSDGSFFLYSKLTVDKSRWQQGNVFSCSVMHEALHNHY*
*TQKSLSLSPGK*

*Figure 87*

MQPPSLLLLLLLLLLLCVSVVRPRGLLCGSFPEPCANGGTCLSLSLGQGTCQCAPGFLGE
TCQFPDPCQNAQLCQNGGSCQALLPAPLGLPSSPSPLTPSFLCTCLPGFTGERCQAKLED
PCPPSFCSKRGRCHIQASGRPQCSCMPGWTGEQCQLRDFCSANPCVNGGVCLATYPQIQC
HCPPGFEGHACERDVNECFQDPGPCPKGTSCHNTLGSFQCLCPVGQEGPRCELRAGPCPP
RGCSNGGTCQLMPEKDSTFHLCLCPPGFIGPDCEVNPDNCVSHQCQNGGTCQDGLDTYTC
LCPETWTGWDCSEDVDECETQGPPHCRNGGTCQNSAGSFHCVCVSGWGGTSCEENLDDCI
AATCAPGSTCIDRVGSFSCLCPPGRTGLLCHLEDMCLSQPCHGDAQCSTNPLTGSTLCLC
QPGYSGPTCHQDLDECLMAQQGPSPCEHGGSCLNTPGSFNCLCPPGYTGSRCEADHNECL
SQPCHPGSTCLDLLATFHCLCPPGLEGQLCEVETNECASAPCLNHADCHDLLNGFQCICL
PGFSGTRCEEDIDECRSSPCANGGQCQDQPGAFHCKCLPGFEGPRCQTEVDECLSDPCPV
GASCLDLPGAFFCLCPSGFTGQLCEVPLCAPNLCQPKQICKDQKDKANCLCPDGSPGCAP
PEDNCTCHHGHCQRSSCVCDVGWTGPECEAELGGCISAPCAHGGTCYPQPSGYNCTCPTG
YTGPTCSEEMTACHSGPCLNGGSCNPSPGGYYCTCPPSHTGPQCQTSTDYCVSAPCFNGG
TCVNRPGTFSCLCAMGFQGPRCEGKLRPSCADSPCRNRATCQDSPQGPRCLCPTGYTGGS
CQTLMDLCAQKPCPRNSHCLQTGPSFHCLCLQGWTGPLCNLPLSSCQKAALSQGIDVSSL
CHNGGLCVDSGPSYFCHCPPGFQGSLCQDHVNP*DLGPGEPKSCDKTHTCPPCPAPELLGG*
*PSVFLFPPKPKDTLMISRTPEVTCVVVDVSHEDPEVKFNWYVDGVEVHNAKTKPREEQYN*
*STYRVVSVLTVLHQDWLNGKEYKCKVSNKALPAPIEKTISKAKGQPREPQVYTLPPSRDE*
*LTKNQVSLTCLVKGFYPSDIAVEWESNGQPENNYKTTPPVLDSDGSFFLYSKLTVDKSRW*
*QQGNVFSCSVMHEALHNHYTQKSLSLSPGK*

*Figure 88*

MQPPSLLLLLLLLLLLCVSVVRPRGLLCIAATCAPGSTCIDRVGSFSCLCPPGRTGLLCH
LEDMCLSQPCHGDAQCSTNPLTGSTLCLCQPGYSGPTCHQDLDECLMAQQGPSPCEHGGS
CLNTPGSFNCLCPPGYTGSRCEADHNECLSQPCHPGSTCLDLLATFHCLCPPGLEGQLCE
VETNECASAPCLNHADCHDLLNGFQCICLPGFSGTRCEEDIDECRSSPCANGGQCQDQPG
AFHCKCLPGFEGPRCQTEVDECLSDPCPVGASCLDLPGAFFCLCPSGFTGQLCEVPLCAP
NLCQPKQICKDQKDKANCLCPDGSPGCAPPEDNCTCHHGHCQRSSCVCDVGWTGPECEAE
LGGCISAPCAHGGTCYPQPSGYNCTCPTGYTGPTCSEEMTACHSGPCLNGGSCNPSPGGY
YCTCPPSHTGPQCQTSTDYCVSAPCFNGGTCVNRPGTFSCLCAMGFQGPRCEGKLRPSCA
DSPCRNRATCQDSPQGPRCLCPTGYTGGSCQTLMDLCAQKPCPRNSHCLQTGPSFHCLCL
QGWTGPLCNLPLSSCQKAALSQGIDVSSLCHNGGLCVDSGPSYFCHCPPGFQGSLCQDHV
NP*DLGPGEPKSCDKTHTCPPCPAPELLGGPSVFLFPPKPKDTLMISRTPEVTCVVVDVSH*
*EDPEVKFNWYVDGVEVHNAKTKPREEQYNSTYRVVSVLTVLHQDWLNGKEYKCKVSNKAL*
*PAPIEKTISKAKGQPREPQVYTLPPSRDELTKNQVSLTCLVKGFYPSDIAVEWESNGQPE*
*NNYKTTPPVLDSDGSFFLYSKLTVDKSRWQQGNVFSCSVMHEALHNHYTQKSLSLSPGK*

*Figure 89*

MWGWKCLLFWAVLVTATLCTARCIAATCAPGSTCIDRVGSFSCLCPPGRTGLLCHLEDMC
LSQPCHGDAQCSTNPLTGSTLCLCQPGYSGPTCHQDLDECLMAQQGPSPCEHGGSCLNTP
GSFNCLCPPGYTGSRCEADHNECLSQPCHPGSTCLDLLATFHCLCPPGLEGQLCEVETNE
CASAPCLNHADCHDLLNGFQCICLPGFSGTRCEEDIDECRSSPCANGGQCQDQPGAFHCK
CLPGFEGPRCQTEVDECLSDPCPVGASCLDLPGAFFCLCPSGFTGQLCEVPLCAPNLCQP
KQICKDQKDKANCLCPDGSPGCAPPEDNCTCHHGHCQRSSCVCDVGWTGPECEAELGGCI
SAPCAHGGTCYPQPSGYNCTCPTGYTGPTCSEEMTACHSGPCLNGGSCNPSPGGYYCTCP
PSHTGPQCQTSTDYCVSAPCFNGGTCVNRPGTFSCLCAMGFQGPRCEGKLRPSCADSPCR
NRATCQDSPQGPRCLCPTGYTGGSCQTLMDLCAQKPCPRNSHCLQTGPSFHCLCLQGWTG
PLCNLPLSSCQKAALSQGIDVSSLCHNGGLCVDSGPSYFCHCPPGFQGSLCQDHVNP*DLG*
*PGEPKSCDKTHTCPPCPAPELLGGPSVFLFPPKPKDTLMISRTPEVTCVVVDVSHEDPEV*
*KFNWYVDGVEVHNAKTKPREEQYNSTYRVVSVLTVLHQDWLNGKEYKCKVSNKALPAPIE*
*KTISKAKGQPREPQVYTLPPSRDELTKNQVSLTCLVKGFYPSDIAVEWESNGQPENNYKT*
*TPPVLDSDGSFFLYSKLTVDKSRWQQGNVFSCSVMHEALHNHYTQKSLSLSPGK*

*Figure 90*

MQPPSLLLLLLLLLLLCVSVVRPRGLLCIAATCAPGSTCIDRVGSFSCLCPPGRTGLLCH
LEDMCLSQPCHGDAQCSTNPLTGSTLCLCQPGYSGPTCHQDLDECLMAQQGPSPCEHGGS
CLNTPGSFNCLCPPGYTGSRCEADHNECLSQPCHPGSTCLDLLATFHCLCPPGLEGQLCE
VETNECASAPCLNHADCHDLLNGFQCICLPGFSGTRCEEDIDECRSSPCANGGQCQDQPG
AFHCKCLPGFEGPRCQTEVDECLSDPCPVGASCLDLPGAFFCLCPSGFTGQLCEVPLCAP
NLCQPKQICKDQKDKANCLCPDGSPGCAPPEDNCTCHHGHCQRSSCVCDVGWTGPECEAE
LGGCISAPCAHGGTCYPQPSGYNCTCPTGYTGPTCSEEMTACHSGPCLNGGSCNPSPGGY
YCTCPPSHTGPQCQTSTDYCVSAPCFNGGTCVNRPGTFSCLCAMGFQGPRCEGKLRPSCA
DSPCRNRATCQDSPQGPRCLCPTGYTGGSCQTLMDLCAQKPCPRNSHCLQTGPSFHCLCL
QGWTGPLCNLPLSSCQKAALSQGIDVSSLCHNGGLCVDSGPSYFCHCPPGFQGSLCQDHV
NPCESRPCQNGATCMAQPSGYLCQCAPGYDGQNCSKELDACQSQPCHNHGTCTPKPGGFH
CACPPGFVGLRCEGDVDECLDQPCHPTGTAACHSLANAFYCQCLPGHTGQWCEVEIDPCH
SQPCFHGGTCEATAGSPLGFICHCPKGFEGPTCSHRAPSCGFHHCHHGGLCLPSPKPGFP
PRCACLSGYGGPDCLTPPAPKGCGPPSPCLYNGSCSETTGLGGPGFRCSCPHSSPGPRCQ
KPG*DLGPGEPKSCDKTHTCPPCPAPELLGGPSVFLFPPKPKDTLMISRTPEVTCVVVDVS*
*HEDPEVKFNWYVDGVEVHNAKTKPREEQYNSTYRVVSVLTVLHQDWLNGKEYKCKVSNKA*
*LPAPIEKTISKAKGQPREPQVYTLPPSRDELTKNQVSLTCLVKGFYPSDIAVEWESNGQP*
*ENNYKTTPPVLDSDGSFFLYSKLTVDKSRWQQGNVFSCSVMHEALHNHYTQKSLSLSPGK*

*Figure 91*

MWGWKCLLFWAVLVTATLCTARCIAATCAPGSTCIDRVGSFSCLCPPGRTGLLCHLEDMC
LSQPCHGDAQCSTNPLTGSTLCLCQPGYSGPTCHQDLDECLMAQQGPSPCEHGGSCLNTP
GSFNCLCPPGYTGSRCEADHNECLSQPCHPGSTCLDLLATFHCLCPPGLEGQLCEVETNE
CASAPCLNHADCHDLLNGFQCICLPGFSGTRCEEDIDECRSSPCANGGQCQDQPGAFHCK
CLPGFEGPRCQTEVDECLSDPCPVGASCLDLPGAFFCLCPSGFTGQLCEVPLCAPNLCQP
KQICKDQKDKANCLCPDGSPGCAPPEDNCTCHHGHCQRSSCVCDVGWTGPECEAELGGCI
SAPCAHGGTCYPQPSGYNCTCPTGYTGPTCSEEMTACHSGPCLNGGSCNPSPGGYYCTCP
PSHTGPQCQTSTDYCVSAPCFNGGTCVNRPGTFSCLCAMGFQGPRCEGKLRPSCADSPCR
NRATCQDSPQGPRCLCPTGYTGGSCQTLMDLCAQKPCPRNSHCLQTGPSFHCLCLQGWTG
PLCNLPLSSCQKAALSQGIDVSSLCHNGGLCVDSGPSYFCHCPPGFQGSLCQDHVNPCES
RPCQNGATCMAQPSGYLCQCAPGYDGQNCSKELDACQSQPCHNHGTCTPKPGGFHCACPP
GFVGLRCEGDVDECLDQPCHPTGTAACHSLANAFYCQCLPGHTGQWCEVEIDPCHSQPCF
HGGTCEATAGSPLGFICHCPKGFEGPTCSHRAPSCGFHHCHHGGLCLPSPKPGFPPRCAC
LSGYGGPDCLTPPAPKGCGPPSPCLYNGSCSETTGLGGPGFRCSCPHSSPGPRCQKPG*DL*
*GPGEPKSCDKTHTCPPCPAPELLGGPSVFLFPPKPKDTLMISRTPEVTCVVVDVSHEDPE*
*VKFNWYVDGVEVHNAKTKPREEQYNSTYRVVSVLTVLHQDWLNGKEYKCKVSNKALPAPI*
*EKTISKAKGQPREPQVYTLPPSRDELTKNQVSLTCLVKGFYPSDIAVEWESNGQPENNYK*
*TTPPVLDSDGSFFLYSKLTVDKSRWQQGNVFSCSVMHEALHNHYTQKSLSLSPGK*

*Figure 92*

MQPPSLLLLLLLLLLLCVSVVRPRGLLCASAPCLNHADCHDLLNGFQCICLPGFSGTRCE
EDIDECRSSPCANGGQCQDQPGAFHCKCLPGFEGPRCQTEVDECLSDPCPVGASCLDLPG
AFFCLCPSGFTGQLCEVPLCAPNLCQPKQICKDQKDKANCLCPDGSPGCAPPEDNCTCHH
GHCQRSSCVCDVGWTGPECEAELGGCISAPCAHGGTCYPQPSGYNCTCPTGYTGPTCSEE
MTACHSGPCLNGGSCNPSPGGYYCTCPPSHTGPQCQTSTDYCVSAPCFNGGTCVNRPGTF
SCLCAMGFQGPRCEGKLRPSCADSPCRNRATCQDSPQGPRCLCPTGYTGGSCQTLMDLCA
QKPCPRNSHCLQTGPSFHCLCLQGWTGPLCNLPLSSCQKAALSQGIDVSSLCHNGGLCVD
SGPSYFCHCPPGFQGSLCQDHVNP*DLGPGEPKSCDKTHTCPPCPAPELLGGPSVFLFPPK*
*PKDTLMISRTPEVTCVVVDVSHEDPEVKFNWYVDGVEVHNAKTKPREEQYNSTYRVVSVL*
*TVLHQDWLNGKEYKCKVSNKALPAPIEKTISKAKGQPREPQVYTLPPSRDELTKNQVSLT*
*CLVKGFYPSDIAVEWESNGQPENNYKTTPPVLDSDGSFFLYSKLTVDKSRWQQGNVFSCS*
*VMHEALHNHYTQKSLSLSPGK*

*Figure 93*

MWGWKCLLFWAVLVTATLCTARCASAPCLNHADCHDLLNGFQCICLPGFSGTRCEEDIDE
CRSSPCANGGQCQDQPGAFHCKCLPGFEGPRCQTEVDECLSDPCPVGASCLDLPGAFFCL
CPSGFTGQLCEVPLCAPNLCQPKQICKDQKDKANCLCPDGSPGCAPPEDNCTCHHGHCQR
SSCVCDVGWTGPECEAELGGCISAPCAHGGTCYPQPSGYNCTCPTGYTGPTCSEEMTACH
SGPCLNGGSCNPSPGGYYCTCPPSHTGPQCQTSTDYCVSAPCFNGGTCVNRPGTFSCLCA
MGFQGPRCEGKLRPSCADSPCRNRATCQDSPQGPRCLCPTGYTGGSCQTLMDLCAQKPCP
RNSHCLQTGPSFHCLCLQGWTGPLCNLPLSSCQKAALSQGIDVSSLCHNGGLCVDSGPSY
FCHCPPGFQGSLCQDHVNP*DLGPGEPKSCDKTHTCPPCPAPELLGGPSVFLFPPKPKDTL*
*MISRTPEVTCVVVDVSHEDPEVKFNWYVDGVEVHNAKTKPREEQYNSTYRVVSVLTVLHQ*
*DWLNGKEYKCKVSNKALPAPIEKTISKAKGQPREPQVYTLPPSRDELTKNQVSLTCLVKG*
*FYPSDIAVEWESNGQPENNYKTTPPVLDSDGSFFLYSKLTVDKSRWQQGNVFSCSVMHEA*
*LHNHYTQKSLSLSPGK*

*Figure 94*

MQPPSLLLLLLLLLLLCVSVVRPRGLLCADSPCRNRATCQDSPQGPRCLCPTGYTGGSCQ
TLMDLCAQKPCPRNSHCLQTGPSFHCLCLQGWTGPLCNLPLSSCQKAALSQGIDVSSLCH
NGGLCVDSGPSYFCHCPPGFQGSLCQDHVNPCESRPCQNGATCMAQPSGYLCQCAPGYDG
QNCSKELDACQSQPCHNHGTCTPKPGGFHCACPPGFVGLRCEGDVDECLDQPCHPTGTAA
CHSLANAFYCQCLPGHTGQWCEVEIDPCHSQPCFHGGTCEATAGSPLGFICHCPKGFEGP
TCSHRAPSCGFHHCHHGGLCLPSPKPGFPPRCACLSGYGGPDCLTPPAPKGCGPPSPCLY
NGSCSETTGLGGPGFRCSCPHSSPGPRCQKPG*DLGPGEPKSCDKTHTCPPCPAPELLGGP*
*SVFLFPPKPKDTLMISRTPEVTCVVVDVSHEDPEVKFNWYVDGVEVHNAKTKPREEQYNS*
*TYRVVSVLTVLHQDWLNGKEYKCKVSNKALPAPIEKTISKAKGQPREPQVYTLPPSRDEL*
*TKNQVSLTCLVKGFYPSDIAVEWESNGQPENNYKTTPPVLDSDGSFFLYSKLTVDKSRWQ*
*QGNVFSCSVMHEALHNHYTQKSLSLSPGK*

*Figure 95*

MWGWKCLLFWAVLVTATLCTARCADSPCRNRATCQDSPQGPRCLCPTGYTGGSCQTLMDL
CAQKPCPRNSHCLQTGPSFHCLCLQGWTGPLCNLPLSSCQKAALSQGIDVSSLCHNGGLC
VDSGPSYFCHCPPGFQGSLCQDHVNPCESRPCQNGATCMAQPSGYLCQCAPGYDGQNCSK
ELDACQSQPCHNHGTCTPKPGGFHCACPPGFVGLRCEGDVDECLDQPCHPTGTAACHSLA
NAFYCQCLPGHTGQWCEVEIDPCHSQPCFHGGTCEATAGSPLGFICHCPKGFEGPTCSHR
APSCGFHHCHHGGLCLPSPKPGFPPRCACLSGYGGPDCLTPPAPKGCGPPSPCLYNGSCS
ETTGLGGPGFRCSCPHSSPGPRCQKPG*DLGPGEPKSCDKTHTCPPCPAPELLGGPSVFLF*
*PPKPKDTLMISRTPEVTCVVVDVSHEDPEVKFNWYVDGVEVHNAKTKPREEQYNSTYRVV*
*SVLTVLHQDWLNGKEYKCKVSNKALPAPIEKTISKAKGQPREPQVYTLPPSRDELTKNQV*
*SLTCLVKGFYPSDIAVEWESNGQPENNYKTTPPVLDSDGSFFLYSKLTVDKSRWQQGNVF*
*SCSVMHEALHNHYTQKSLSLSPGK*

*Figure 96A*

```
   1 atgcagcccc cttcactgct gctgctgctg ctgctgctgc tgctgctatg tgtctcagtg
  61 gtcagaccca gagggctgct gtgtgggagt ttcccagaac cctgtgccaa tggaggcacc
 121 tgcctgagcc tgtctctggg acaagggacc tgccagtgtg cccctggctt cctgggtgag
 181 acgtgccagt ttcctgaccc ctgccagaac gcccagctct gccaaaatgg aggcagctgc
 241 caagccctgc ttcccgctcc cctagggctc cccagctctc cctctccatt gacacccagc
 301 ttcttgtgca cttgcctccc tggcttcact ggtgagagat gccaggccaa gcttgaagac
 361 ccttgtcctc cctccttctg ttccaaaagg ggccgctgcc acatccaggc ctcgggccgc
 421 ccacagtgct cctgcatgcc tggatggaca ggtgagcagt gccagcttcg ggacttctgt
 481 tcagccaacc catgtgttaa tggaggggtg tgtctggcca cataccccca gatccagtgc
 541 cactgcccac cgggcttcga gggccatgcc tgtgaacgtg atgtcaacga gtgcttccag
 601 gacccaggac cctgccccaa aggcacctcc tgccataaca ccctgggctc cttccagtgc
 661 ctctgccctg tggggcagga gggtccacgt tgtgagctgc gggcaggacc ctgccctcct
 721 aggggctgtt cgaatggggg cacctgccag ctgatgccag agaaagactc cacctttcac
 781 ctctgcctct gtcccccagg tttcataggc ccagactgtg aggtgaatcc agacaactgt
 841 gtcagccacc agtgtcagaa tggggggcact tgccaggatg ggctggacac ctacacctgc
 901 ctctgcccag aaacctggac aggctgggac tgctccgaag atgtggatga gtgtgagacc
 961 cagggtcccc ctcactgcag aaacgggggc acctgccaga actctgctgg tagctttcac
1021 tgcgtgtgtg tgagtggctg gggcggcaca agctgtgagg agaacctgga tgactgtatt
1081 gctgccacct gtgccccggg atccacctgc attgaccggg tgggctcttt ctcctgcctc
1141 tgcccacctg gacgcacagg actcctgtgc cacttggaag acatgtgtct gagccagccg
1201 tgccatgggg atgcccaatg cagcaccaac cccctcacag gctccacact ctgcctgtgt
1261 cagcctggct attcggggcc cacctgccac caggacctgg acgagtgtct gatggcccag
1321 caaggcccaa gtccctgtga acatggcggt tcctgcctca acactcctgg ctccttcaac
1381 tgcctctgtc cacctggcta cacaggctcc cgttgtgagg ctgatcacaa tgagtgcctc
1441 tcccagccct gccacccagg aagcacctgt ctggacctac ttgccacctt ccactgcctc
1501 tgcccgccag gcttagaagg gcagctctgt gaggtggaga ccaacgagtg tgcctcagct
1561 ccctgcctga accacgcgga ttgccatgac ctgctcaacg gcttccagtg catctgcctg
1621 cctggattct ccggcacccg atgtgaggag gatatcgatg agtgcagaag ctctccctgt
1681 gccaatggtg ggcagtgcca ggaccagcct ggagccttcc actgcaagtg tctcccaggc
1741 tttgaagggc cacgctgtca aacagaggtg gatgagtgcc tgagtgaccc atgtcccgtt
1801 ggagccagct gccttgatct tccaggagcc ttcttttgcc tctgcccctc tggtttcaca
1861 ggccagctct gtgaggttcc cctgtgtgct cccaacctgt gccagcccaa gcagatatgt
1921 aaggaccaga aagacaaggc caactgcctc tgtcctgatg gaagccctgg ctgtgcccca
1981 cctgaggaca actgcacctg ccaccacggg cactgccaga gatcctcatg tgtgtgtgac
2041 gtgggttgga cggggccaga gtgtgaggca gagctagggg gctgcatctc tgcaccctgt
2101 gcccatgggg ggacctgcta cccccagccc tctggctaca actgcacctg ccctacaggc
2161 tacacaggac ccacctgtag tgaggagatg acagcttgtc actcagggcc atgtctcaat
2221 ggcggctcct gcaaccctag ccctggaggc tactactgca cctgccctcc aagccacaca
2281 gggccccagt gccaaaccag cactgactac tgtgtgtctg ccccgtgctt caatgggggt
2341 acctgtgtga acaggcctgg caccttctcc tgcctctgtg ccatgggctt ccagggcccg
2401 cgctgtgagg gaaagctccg ccccagctgt gcagacagcc cctgtaggaa tagggcaacc
2461 tgccaggaca gccctcaggg tccccgctgc ctctgcccca ctggctacac cggaggcagc
2521 tgccagactc tgatggactt atgtgcccag aagccctgcc cacgcaattc ccactgcctc
2581 cagactgggc cctccttcca ctgcttgtgc ctccagggat ggaccgggcc tctctgcaac
2641 cttccactgt cctcctgcca gaaggctgca ctgagccaag gcatagacgt ctcttccctt
2701 tgccacaatg gaggcctctg tgtcgacagc ggcccctcct atttctgcca ctgccccccct
2761 ggattccaag gcagcctgtg ccaggatcac gtgaacccat gtgagtccag gccttgccag
2821 aacgggggcca cctgcatggc ccagcccagt gggtatctct gccagtgtgc cccaggctac
2881 gatggacaga actgctcaaa ggaactcgat gcttgtcagt cccaaccctg tcacaaccat
2941 ggaacctgta ctcccaaacc tggaggattc cactgtgcct gccctccagg ctttgtgggg
```

*Figure 96B*

```
3001 ctacgctgtg agggagacgt ggacgagtgt ctggaccagc cctgccaccc cacaggcact
3061 gcagcctgcc actctctggc caatgccttc tactgccagt gtctgcctgg acacacaggc
3121 cagtggtgtg aggtggagat agacccctgc cacagccaac cctgctttca tggagggacc
3181 tgtgaggcca cagcaggatc accccctgggt ttcatctgcc actgccccaa gggttttgaa
3241 ggccccacct gcagccacag ggccccttcc tgcggcttcc atcactgcca ccacggaggc
3301 ctgtgtctgc cctcccctaa gccaggcttc ccaccacgct gtgcctgcct cagtggctat
3361 gggggtcctg actgcctgac cccaccagct cctaaaggct gtggccctcc ctccccatgc
3421 ctatacaatg gcagctgctc agagaccacg ggcttggggg gcccaggctt tcgatgctcc
3481 tgccctcaca gctctccagg gccccggtgt cagaaacccg gagccaaggg gtgtgagggc
3541 agaagtggag atggggcctg cgatgctggc tgcagtggcc cgggaggaaa ctgggatgga
3601 ggggactgct ctctgggagt cccagacccc tggaagggct gcccctccca ctctcggtgc
3661 tggcttctct tccgggacgg gcagtgccac ccacagtgtg actctgaaga gtgtctgttt
3721 gatggctacg actgtgagac ccctccagcc tgcactccag cctatgacca gtactgccat
3781 gatcacttcc acaacgggca ctgtgagaaa ggctgcaaca ctgcagagtg tggctgggat
3841 ggaggtgact gcaggcctga agatggggac ccagagtggg ggccctccct ggccctgctg
3901 gtggtactga gcccccccagc cctagaccag cagctgtttg ccctggcccg ggtgctgtcc
3961 ctgactctga gggtaggact ctgggtaagg aaggatcgtg atggcaggga catggtgtac
4021 ccctatcctg ggcccgggc tgaagaaaag ctaggaggaa ctcgggaccc cacctatcag
4081 gagagagcag cccctcaaac gcagcccctg ggcaaggaga ccgactccct cagtgctggg
4141 tttgtggtgg tcatgggtgt ggatttgtcc cgctgtggcc ctgaccaccc ggcatcccgc
4201 tgtccctggg accctgggct tctactccgc ttccttgctg cgatggctgc agtgggagcc
4261 ctggagcccc tgctgcctgg accactgctg gctgtccacc ctcatgcagg gaccgcaccc
4321 cctgccaacc agcttccctg gcctgtgctg tgctccccag tggccggggt gattctcctg
4381 gccctagggg ctcttctcgt cctccagctc atccggcgtc gacgccgaga gcatggagct
4441 ctctggctgc cccctggttt cactcgacgg cctcggactc agtcagctcc ccaccgacgc
4501 cggcccccac taggcgagga cagcattggt ctcaaggcac tgaagccaaa ggcagaagtt
4561 gatgaggatg gagttgtgat gtgctcaggc cctgaggagg gagaggaggt gggccaggct
4621 gaagaaacag gcccaccctc cacgtgccag ctctggtctc tgagtggtgg ctgtggggcg
4681 ctccctcagg cagccatgct aactcctccc caggaatctg agatggaagc ccctgacctg
4741 gacacccgtg gacctgatgg ggtgacaccc ctgatgtcag cagtttgctg tggggaagta
4801 cagtccggga ccttccaagg ggcatggttg ggatgtcctg agccctggga acctctgctg
4861 gatggagggg cctgtcccca ggctcacacc gtgggcactg gggagacccc cctgcacctg
4921 gctgcccgat tctcccggcc aaccgctgcc cgccgcctcc ttgaggctgg agccaacccc
4981 aaccagccag accgggcagg gcgcacaccc cttcatgctg ctgtggctgc tgatgctcgg
5041 gaggtctgcc agcttctgct ccgtagcaga caaactgcag tggacgctcg cacagaggac
5101 gggaccacac ccttgatgct ggctgccagg ctggcggtgg aagacctggt tgaagaactg
5161 attgcagccc aagcagacgt gggggccaga gataaatggg ggaaaactgc gctgcactgg
5221 gctgctgccg tgaacaacgc ccgagccgcc cgctcgcttc tccaggccgg agccgataaa
5281 gatgcccagg acaacaggga gcagacgccg ctattcctgg cggcgcggga aggagcggtg
5341 gaagtagccc agctactgct ggggctgggg gcagcccgag agctgcggga ccaggctggg
5401 ctagcgccgg cggacgtcgc tcaccaacgt aaccactggg atctgctgac gctgctggaa
5461 ggggctgggc caccagaggc ccgtcacaaa gccacgccgg gccgcgaggc tgggcccttc
5521 ccgcgcgcac ggacggtgtc agtaagcgtg cccccgcatg gggcggggc tctgccgcgc
5581 tgccggacgc tgtcagccgg agcaggccct cgtgggggcg gagcttgtct gcaggctcgg
5641 acttggtccg tagacttggc tgcgcggggg ggcggggcct attctcattg ccggagcctc
5701 tcgggagtag gagcaggagg aggcccgacc cctcgcggcc gtaggttttc tgcaggcatg
5761 cgcgggcctc ggcccaaccc tgcgataatg cgaggaagat acggagtggc tgccgggcgc
5821 ggaggcaggg tctcaacgga tgactggccc tgtgattggg tggccctggg agcttgcggt
5881 tctgcctcca acattccgat cccgcctcct tgccttactc cgtccccgga gcggggatca
5941 cctcaacttg actgtggtcc cccagccctc caagaaatgc ccataaacca aggaggagag
6001 ggtaaaaaat ag
```

*Figure 97*

```
 1 atgcagcccc cttcactgct gctgctgctg ctgctgctgc tgctgctatg tgtctcagtg
61 gtcagaccca gagggctgct g  81
```

*Figure 98*

```
 1 atgtggggct ggaagtgcct cctcttctgg gctgtgctgg tcacagccac tctctgcact
61 gccagg
```

*Figure 99*

```
                                                        gatct gggcccgggc
 781 gagcccaaat cttgtgacaa aactcacaca tgcccaccgt gcccagcacc tgaactcctg
 841 gggggaccgt cagtcttcct cttcccccca aaacccaagg acaccctcat gatctcccgg
 901 acccctgagg tcacatgcgt ggtggtggac gtgagccacg aagaccctga ggtcaagttc
 961 aactggtacg tggacggcgt ggaggtgcat aatgccaaga caaagccgcg ggaggagcag
1021 tacaacagca cgtaccgtgt ggtcagcgtc ctcaccgtcc tgcaccagga ctggctgaat
1081 ggcaaggagt acaagtgcaa ggtctccaac aaagccctcc cagcccccat cgagaaaacc
1141 atctccaaag ccaaagggca gccccgagaa ccacaggtgt acaccctgcc cccatcccgg
1201 gatgagctga ccaagaacca ggtcagcctg acctgcctgg tcaaaggctt ctatcccagc
1261 gacatcgccg tggagtggga gagcaatggg cagccggaga acaactacaa gaccacgcct
1321 cccgtgctgg actccgacgg ctccttcttc ctctacagca agctcaccgt ggacaagagc
1381 aggtggcagc aggggaacgt cttctcatgc tccgtgatgc atgaggctct gcacaaccac
1441 tacacgcaga agagcctctc cctgtctccg ggtaaatga
```

*Figure 100A*

```
   1 atgcagcccc cttcactgct gctgctgctg ctgctgctgc tgctgctatg tgtctcagtg
  61 gtcagaccca gagggctgct gtgtgggagt ttcccagaac cctgtgccaa tggaggcacc
 121 tgcctgagcc tgtctctggg acaagggacc tgccagtgtg cccctggctt cctgggtgag
 181 acgtgccagt ttcctgaccc ctgccagaac gcccagctct gccaaaatgg aggcagctgc
 241 caagccctgc ttcccgctcc cctagggctc cccagctctc cctctccatt gacacccagc
 301 ttcttgtgca cttgcctccc tggcttcact ggtgagagat gccaggccaa gcttgaagac
 361 ccttgtcctc cctccttctg ttccaaaagg ggccgctgcc acatccaggc ctcgggccgc
 421 ccacagtgct cctgcatgcc tggatggaca ggtgagcagt gccagcttcg ggacttctgt
 481 tcagccaacc catgtgttaa tggagggggtg tgtctggcca catacccccca gatccagtgc
 541 cactgcccac cgggcttcga gggccatgcc tgtgaacgtg atgtcaacga gtgcttccag
 601 gacccaggac cctgccccaa aggcacctcc tgccataaca ccctgggctc cttccagtgc
 661 ctctgccctg tggggcagga gggtccacgt tgtgagctgc gggcaggacc ctgccctcct
 721 aggggctgtt cgaatggggg cacctgccag ctgatgccag agaaagactc cacctttcac
 781 ctctgcctct gtcccccagg tttcataggc ccagactgtg aggtgaatcc agacaactgt
 841 gtcagccacc agtgtcagaa tgggggcact tgccaggatg ggctggacac ctacacctgc
 901 ctctgcccag aaacctggac aggctgggac tgctccgaag atgtggatga gtgtgagacc
 961 cagggtcccc ctcactgcag aaacgggggc acctgccaga actctgctgg tagctttcac
1021 tgcgtgtgtg tgagtggctg gggcggcaca agctgtgagg agaacctgga tgactgtatt
1081 gctgccacct gtgccccggg atccacctgc attgaccggg tgggctcttt ctcctgcctc
1141 tgcccacctg gacgcacagg actcctgtgc cacttggaag acatgtgtct gagccagccg
1201 tgccatgggg atgcccaatg cagcaccaac cccctcacag gctccacact ctgcctgtgt
1261 cagcctggct attcggggcc cacctgccac caggacctgg acgagtgtct gatggcccag
1321 caaggcccaa gtccctgtga acatggcggt tcctgcctca acactcctgg ctccttcaac
1381 tgcctctgtc cacctggcta cacaggctcc cgttgtgagg ctgatcacaa tgagtgcctc
1441 tcccagccct gccacccagg aagcacctgt ctggacctac ttgccacctt ccactgcctc
1501 tgcccgccag gcttagaagg gcagctctgt gaggtggaga ccaacgagtg tgcctcagct
1561 ccctgcctga accacgcgga ttgccatgac ctgctcaacg gcttccagtg catctgcctg
1621 cctggattct ccggcacccg atgtgaggag gatatcgatg agtgcagaag ctctccctgt
1681 gccaatggtg ggcagtgcca ggaccagcct ggagccttcc actgcaagtg tctcccaggc
1741 tttgaagggc cacgctgtca aacagaggtg gatgagtgcc tgagtgaccc atgtcccgtt
1801 ggagccagct gccttgatct tccaggagcc ttcttttgcc tctgcccctc tggtttcaca
1861 ggccagctct gtgaggttcc cctgtgtgct cccaacctgt gccagcccaa gcagatatgt
1921 aaggaccaga aagacaaggc caactgcctc tgtcctgatg gaagccctgg ctgtgcccca
1981 cctgaggaca actgcacctg ccaccacggg cactgccaga gatcctcatg tgtgtgtgac
2041 gtgggttgga cggggccaga gtgtgaggca gagctagggg gctgcatctc tgcaccctgt
2101 gcccatgggg ggacctgcta cccccagccc tctggctaca actgcacctg ccctacaggc
2161 tacacaggac ccacctgtag tgaggagatg acagcttgtc actcagggcc atgtctcaat
2221 ggcggctcct gcaaccctag ccctggaggc tactactgca cctgccctcc aagccacaca
2281 gggccccagt gccaaaccag cactgactac tgtgtgtctg ccccgtgctt caatgggggt
2341 acctgtgtga acaggcctgg caccttctcc tgcctctgtg ccatgggctt ccagggcccg
2401 cgctgtgagg gaaagctccg ccccagctgt gcagacagcc cctgtaggaa tagggcaacc
2461 tgccaggaca gccctcaggg tccccgctgc ctctgcccca ctggctacac cggaggcagc
2521 tgccagactc tgatggactt atgtgcccag aagccctgcc cacgcaattc ccactgcctc
2581 cagactgggc cctccttcca ctgcttgtgc ctccagggat ggaccgggcc tctctgcaac
2641 cttccactgt cctcctgcca gaaggctgca ctgagccaag gcatagacgt ctcttccctt
2701 tgccacaatg gaggcctctg tgtcgacagc ggcccctcct atttctgcca ctgcccccct
2761 ggattccaag gcagcctgtg ccaggatcac gtgaacccat gtgagtccag gccttgccag
2821 aacggggcca cctgcatggc ccagcccagt gggtatctct gccagtgtgc cccaggctac
2881 gatggacaga actgctcaaa ggaactcgat gcttgtcagt cccaaccctg tcacaaccat
2941 ggaacctgta ctcccaaacc tggaggattc cactgtgcct gccctccagg ctttgtgggg
3001 ctacgctgtg agggagacgt ggacgagtgt ctggaccagc cctgccaccc cacaggcact
```

*Figure 100B*

```
3061 gcagcctgcc actctctggc caatgccttc tactgccagt gtctgcctgg acacacaggc
3121 cagtggtgtg aggtggagat agacccctgc cacagccaac cctgctttca tggagggacc
3181 tgtgaggcca cagcaggatc accccctgggt ttcatctgcc actgccccaa gggttttgaa
3241 ggccccacct gcagccacag ggccccttcc tgcggcttcc atcactgcca ccacggaggc
3301 ctgtgtctgc cctcccctaa gccaggcttc ccaccacgct gtgcctgcct cagtggctat
3361 gggggtcctg actgcctgac cccaccagct cctaaaggct gtggccctcc ctccccatgc
3421 ctatacaatg gcagctgctc agagaccacg ggcttggggg gcccaggctt tcgatgctcc
3481 tgccctcaca gctctccagg gccccggtgt cagaaacccg gagatctggg cccgggcgag
3541 cccaaatctt gtgacaaaac tcacacatgc ccaccgtgcc cagcacctga actcctgggg
3601 ggaccgtcag tcttcctctt ccccccaaaa cccaaggaca ccctcatgat ctcccggacc
3661 cctgaggtca catgcgtggt ggtggacgtg agccacgaag accctgaggt caagttcaac
3721 tggtacgtgg acggcgtgga ggtgcataat gccaagacaa agccgcggga ggagcagtac
3781 aacagcacgt accgtgtggt cagcgtcctc accgtcctgc accaggactg gctgaatggc
3841 aaggagtaca agtgcaaggt ctccaacaaa gccctcccag cccccatcga gaaaaccatc
3901 tccaaagcca aagggcagcc ccgagaacca caggtgtaca ccctgccccc atcccgggat
3961 gagctgacca agaaccaggt cagcctgacc tgcctggtca aaggcttcta tcccagcgac
4021 atcgccgtgg agtgggagag caatgggcag ccggagaaca actacaagac cacgcctccc
4081 gtgctggact ccgacggctc cttcttcctc tacagcaagc tcaccgtgga caagagcagg
4141 tggcagcagg ggaacgtctt ctcatgctcc gtgatgcatg aggctctgca caaccactac
4201 acgcagaaga gcctctccct gtctccgggt aaatga
```

*Figure 101*

```
   1 atgcagcccc cttcactgct gctgctgctg ctgctgctgc tgctgctatg tgtctcagtg
  61 gtcagaccca gagggctgct gtgtgggagt ttcccagaac cctgtgccaa tggaggcacc
 121 tgcctgagcc tgtctctggg acaagggacc tgccagtgtg cccctggctt cctgggtgag
 181 acgtgccagt ttcctgaccc ctgccagaac gcccagctct gccaaaatgg aggcagctgc
 241 caagccctgc ttcccgctcc cctagggctc cccagctctc cctctccatt gacacccagc
 301 ttcttgtgca cttgcctccc tggcttcact ggtgagagat gccaggccaa gcttgaagac
 361 ccttgtcctc cctccttctg ttccaaaagg ggccgctgcc acatccaggc ctcgggccgc
 421 ccacagtgct cctgcatgcc tggatggaca ggtgagcagt gccagcttcg ggacttctgt
 481 tcagccaacc catgtgttaa tggaggggtg tgtctggcca cataccccca gatccagtgc
 541 cactgcccac cgggcttcga gggccatgcc tgtgaacgtg atgtcaacga gtgcttccag
 601 gacccaggac cctgccccaa aggcacctcc tgccataaca ccctgggctc cttccagtgc
 661 ctctgccctg tggggcagga gggtccacgt tgtgagctgc gggcaggacc ctgccctcct
 721 aggggctgtt cgaatggggg cacctgccag ctgatgccag agaaagactc cacctttcac
 781 ctctgcctct gtcccccagg tttcataggc ccagactgtg aggtgaatcc agacaactgt
 841 gtcagccacc agtgtcagaa tgggggcact tgccaggatg ggctggacac ctacacctgc
 901 ctctgcccag aaacctggac aggctgggac tgctccgaag atgtggatga gtgtgagacc
 961 cagggtcccc ctcactgcag aaacgggggc acctgccaga actctgctgg tagctttcac
1021 tgcgtgtgtg tgagtggctg ggcggcaca agctgtgagg agaacctgga tgactgtatt
1081 gctgccacct gtgccccggg atccacctgc attgaccggg tgggctcttt ctcctgcctc
1141 tgcccacctg gacgcacagg actcctgtgc cacttggaag acatgtgtct gagccagccg
1201 tgccatgggg atgcccaatg cagcaccaac cccctcacag gctccacact ctgcctgtgt
1261 cagcctggct attcggggcc cacctgccac caggacctgg acgagtgtct gatggcccag
1321 caaggcccaa gtccctgtga acatggcggt tcctgcctca acactcctgg ctccttcaac
1381 tgcctctgtc cacctggcta cacaggctcc cgttgtgagg ctgatcacaa tgagtgcctc
1441 tcccagccct gccacccagg aagcacctgt ctggacctac ttgccacctt ccactgcctc
1501 tgcccgccag gcttagaagg gcagctctgt gaggtggaga ccaacgagtg tgcctcagct
1561 ccctgcctga accacgcgga ttgccatgac ctgctcaacg gcttccagtg catctgcctg
1621 cctggattct ccggcacccg atgtgaggag gatatcgatg aggatctggg cccgggcgag
1681 cccaaatctt gtgacaaaac tcacacatgc ccaccgtgcc cagcacctga actcctgggg
1741 ggaccgtcag tcttcctctt ccccccaaaa cccaaggaca ccctcatgat ctcccggacc
1801 cctgaggtca catgcgtggt ggtggacgtg agccacgaag accctgaggt caagttcaac
1861 tggtacgtgg acggcgtgga ggtgcataat gccaagacaa agccgcggga ggagcagtac
1921 aacagcacgt accgtgtggt cagcgtcctc accgtcctgc accaggactg gctgaatggc
1981 aaggagtaca agtgcaaggt ctccaacaaa gccctcccag cccccatcga gaaaaccatc
2041 tccaaagcca aagggcagcc ccgagaacca caggtgtaca ccctgccccc atcccgggat
2101 gagctgacca agaaccaggt cagcctgacc tgcctggtca aaggcttcta tcccagcgac
2161 atcgccgtgg agtgggagag caatgggcag ccggagaaca actacaagac cacgcctccc
2221 gtgctggact ccgacggctc cttcttcctc tacagcaagc tcaccgtgga caagagcagg
2281 tggcagcagg ggaacgtctt ctcatgctcc gtgatgcatg aggctctgca caaccactac
2341 acgcagaaga gcctctccct gtctccgggt aaatga
```

*Figure 102A*

```
   1 atgcagcccc cttcactgct gctgctgctg ctgctgctgc tgctgctatg tgtctcagtg
  61 gtcagaccca gagggctgct gtgtgggagt ttcccagaac cctgtgccaa tggaggcacc
 121 tgcctgagcc tgtctctggg acaaggacc tgccagtgtg cccctggctt cctgggtgag
 181 acgtgccagt ttcctgaccc ctgccagaac gcccagctct gccaaaatgg aggcagctgc
 241 caagccctgc ttcccgctcc cctagggctc cccagctctc cctctccatt gacacccagc
 301 ttcttgtgca cttgcctccc tggcttcact ggtgagagat gccaggccaa gcttgaagac
 361 ccttgtcctc cctccttctg ttccaaaagg ggccgctgcc acatccaggc ctcgggccgc
 421 ccacagtgct cctgcatgcc tggatggaca ggtgagcagt gccagcttcg ggacttctgt
 481 tcagccaacc catgtgttaa tggaggggtg tgtctggcca catacccca gatccagtgc
 541 cactgcccac cgggcttcga gggccatgcc tgtgaacgtg atgtcaacga gtgcttccag
 601 gacccaggac cctgccccaa aggcacctcc tgccataaca ccctgggctc cttccagtgc
 661 ctctgccctg tggggcagga gggtccacgt tgtgagctgc gggcaggacc ctgccctcct
 721 aggggctgtt cgaatggggg cacctgccag ctgatgccag agaaagactc cacctttcac
 781 ctctgcctct gtcccccagg tttcataggc ccagactgtg aggtgaatcc agacaactgt
 841 gtcagccacc agtgtcagaa tgggggcact tgccaggatg ggctggacac ctacacctgc
 901 ctctgcccag aaacctggac aggctgggac tgctccgaag atgtggatga gtgtgagacc
 961 cagggtcccc ctcactgcag aaacgggggc acctgccaga actctgctgg tagctttcac
1021 tgcgtgtgtg tgagtggctg ggcggcaca agctgtgagg agaacctgga tgactgtatt
1081 gctgccacct gtgccccggg atccacctgc attgaccggg tgggctcttt ctcctgcctc
1141 tgcccacctg gacgcacagg actcctgtgc cacttggaag acatgtgtct gagccagccg
1201 tgccatgggg atgcccaatg cagcaccaac cccctcacag gctccacact ctgcctgtgt
1261 cagcctggct attcggggcc cacctgccac caggacctgg acgagtgtct gatggcccag
1321 caaggcccaa gtccctgtga acatggcggt tcctgcctca acactcctgg ctccttcaac
1381 tgcctctgtc cacctggcta cacaggctcc cgttgtgagg ctgatcacaa tgagtgcctc
1441 tcccagccct gccacccagg aagcacctgt ctggacctac ttgccacctt ccactgcctc
1501 tgcccgccag gcttagaagg gcagctctgt gaggtggaga ccaacgagtg tgcctcagct
1561 ccctgcctga accacgcgga ttgccatgac ctgctcaacg gcttccagtg catctgcctg
1621 cctggattct ccggcacccg atgtgaggag gatatcgatg agtgcagaag ctctccctgt
1681 gccaatggtg ggcagtgcca ggaccagcct ggagccttcc actgcaagtg tctcccaggc
1741 tttgaagggc cacgctgtca aacagaggtg gatgagtgcc tgagtgaccc atgtcccgtt
1801 ggagccagct gccttgatct tccaggagcc ttcttttgcc tctgcccctc tggtttcaca
1861 ggccagctct gtgaggttcc cctgtgtgct cccaacctgt gccagcccaa gcagatatgt
1921 aaggaccaga aagacaaggc caactgcctc tgtcctgatg gaagccctgg ctgtgcccca
1981 cctgaggaca actgcacctg ccaccacggg cactgccaga gatcctcatg tgtgtgtgac
2041 gtgggttgga cggggccaga gtgtgaggca gagctagggg gctgcatctc tgcaccctgt
2101 gcccatgggg ggacctgcta cccccagccc tctggctaca actgcacctg ccctacaggc
2161 tacacaggac ccacctgtag tgaggagatg acagcttgtc actcagggcc atgtctcaat
2221 ggcggctcct gcaaccctag ccctggaggc tactactgca cctgccctcc aagccacaca
2281 gggccccagt gccaaaccag cactgactac tgtgtgtctg ccccgtgctt caatgggggt
2341 acctgtgtga acaggcctgg caccttctcc tgcctctgtg ccatgggctt ccagggcccg
2401 cgctgtgagg gaaagctccg ccccagctgt gcagacagcc cctgtaggaa tagggcaacc
2461 tgccaggaca gccctcaggg tccccgctgc ctctgcccca ctggctacac cggaggcagc
2521 tgccagactc tgatggactt atgtgcccag aagccctgcc cacgcaattc ccactgcctc
2581 cagactgggc cctccttcca ctgcttgtgc ctccagggat ggaccgggcc tctctgcaac
2641 cttccactgt cctcctgcca gaaggctgca ctgagccaag gcatagacgt ctcttccctt
2701 tgccacaatg gaggcctctg tgtcgacagc ggcccctcct atttctgcca ctgccccct
2761 ggattccaag gcagcctgtg ccaggatcac gtgaacccag atctgggccc gggcgagccc
2821 aaatcttgtg acaaaactca cacatgccca ccgtgcccag cacctgaact cctgggggga
2881 ccgtcagtct tcctcttccc cccaaaaccc aaggacaccc tcatgatctc ccggacccct
2941 gaggtcacat gcgtggtggt ggacgtgagc cacgaagacc ctgaggtcaa gttcaactgg
3001 tacgtggacg gcgtggaggt gcataatgcc aagacaaagc cgcgggagga gcagtacaac
3061 agcacgtacc gtgtggtcag cgtcctcacc gtcctgcacc aggactggct gaatggcaag
```

*Figure 102B*

```
3121 gagtacaagt gcaaggtctc caacaaagcc ctcccagccc ccatcgagaa aaccatctcc
3181 aaagccaaag ggcagccccg agaaccacag gtgtacaccc tgcccccatc ccgggatgag
3241 ctgaccaaga accaggtcag cctgacctgc ctggtcaaag gcttctatcc cagcgacatc
3301 gccgtggagt gggagagcaa tgggcagccg gagaacaact acaagaccac gcctcccgtg
3361 ctggactccg acggctcctt cttcctctac agcaagctca ccgtggacaa gagcaggtgg
3421 cagcagggga acgtcttctc atgctccgtg atgcatgagg ctctgcacaa ccactacacg
3481 cagaagagcc tctccctgtc tccgggtaaa tga
```

Figure 103

```
   1 atgcagcccc cttcactgct gctgctgctg ctgctgctgc tgctgctatg tgtctcagtg
  61 gtcagaccca gagggctgct gtgtattgct gccacctgtg ccccgggatc cacctgcatt
 121 gaccgggtgg gctctttctc ctgcctctgc ccacctggac gcacaggact cctgtgccac
 181 ttggaagaca tgtgtctgag ccagccgtgc catggggatg cccaatgcag caccaacccc
 241 ctcacaggct ccacactctg cctgtgtcag cctggctatt cggggcccac ctgccaccag
 301 gacctggacg agtgtctgat ggcccagcaa ggcccaagtc cctgtgaaca tggcggttcc
 361 tgcctcaaca ctcctggctc cttcaactgc ctctgtccac ctggctacac aggctcccgt
 421 tgtgaggctg atcacaatga gtgcctctcc cagccctgcc acccaggaag cacctgtctg
 481 gacctacttg ccaccttcca ctgcctctgc ccgccaggct tagaagggca gctctgtgag
 541 gtggagacca acgagtgtgc ctcagctccc tgcctgaacc acgcggattg ccatgacctg
 601 ctcaacggct tccagtgcat ctgcctgcct ggattctccg gcacccgatg tgaggaggat
 661 atcgatgagt gcagaagctc tccctgtgcc aatggtgggc agtgccagga ccagcctgga
 721 gccttccact gcaagtgtct cccaggcttt gaagggccac gctgtcaaac agaggtggat
 781 gagtgcctga gtgacccatg tcccgttgga gccagctgcc ttgatcttcc aggagccttc
 841 ttttgcctct gcccctctgg tttcacaggc cagctctgtg aggttcccct gtgtgctccc
 901 aacctgtgcc agcccaagca gatatgtaag gaccagaaag acaaggccaa ctgcctctgt
 961 cctgatggaa gccctggctg tgccccacct gaggacaact gcacctgcca ccacgggcac
1021 tgccagagat cctcatgtgt gtgtgacgtg ggttggacgg ggccagagtg tgaggcagag
1081 ctagggggct gcatctctgc accctgtgcc catgggggga cctgctaccc ccagccctct
1141 ggctacaact gcacctgccc tacaggctac acaggaccca cctgtagtga ggagatgaca
1201 gcttgtcact cagggccatg tctcaatggc ggctcctgca accctagccc tggaggctac
1261 tactgcacct gccctccaag ccacacaggg ccccagtgcc aaaccagcac tgactactgt
1321 gtgtctgccc cgtgcttcaa tgggggtacc tgtgtgaaca ggcctggcac cttctcctgc
1381 ctctgtgcca tgggcttcca gggcccgcgc tgtgagggaa agctccgccc cagctgtgca
1441 gacagcccct gtaggaatag ggcaacctgc caggacagcc ctcagggtcc ccgctgcctc
1501 tgccccactg gctacaccgg aggcagctgc cagactctga tggacttatg tgcccagaag
1561 ccctgcccac gcaattccca ctgcctccag actgggccct ccttccactg cttgtgcctc
1621 cagggatgga ccgggcctct ctgcaacctt ccactgtcct cctgccagaa ggctgcactg
1681 agccaaggca tagacgtctc ttccctttgc cacaatggag gcctctgtgt cgacagcggc
1741 ccctcctatt tctgccactg ccccccctgga ttccaaggca gcctgtgcca ggatcacgtg
1801 aacccatgtg agtccaggcc ttgccagaac ggggccacct gcatggccca gcccagtggg
1861 tatctctgcc agtgtgcccc aggctacgat ggacagaact gctcaaagga actcgatgct
1921 tgtcagtccc aaccctgtca caaccatgga acctgtactc ccaaacctgg aggattccac
1981 tgtgcctgcc ctccaggctt tgtggggcta cgctgtgagg gagacgtgga cgagtgtctg
2041 gaccagccct gccaccccac aggcactgca gcctgccact ctctggccaa tgccttctac
2100 tgccagtgtc tgcctggaca cacaggccag tggtgtgagg tggagataga cccctgccac
2161 agccaaccct gctttcatgg agggacctgt gaggccacag caggatcacc cctgggtttc
2221 atctgccact gccccaaggg ttttgaaggc cccacctgca gccacagggc cccttcctgc
2281 ggcttccatc actgccacca cggaggcctg tgtctgccct cccctaagcc aggcttccca
2341 ccacgctgtg cctgcctcag tggctatggg ggtcctgact gcctgacccc accagctcct
2401 aaaggctgtg gccctccctc cccatgccta tacaatggca gctgctcaga gaccacgggc
2461 ttgggggggcc caggctttcg atgctcctgc cctcacagct ctccagggcc ccggtgtcag
2521 aaacccggag atctgggccc gggcgagccc aaatcttgtg acaaaactca cacatgccca
2581 ccgtgcccag cacctgaact cctgggggga ccgtcagtct tcctcttccc cccaaaaccc
2641 aaggacaccc tcatgatctc ccggacccct gaggtcacat gcgtggtggt ggacgtgagc
2701 cacgaagacc ctgaggtcaa gttcaactgg tacgtggacg gcgtggaggt gcataatgcc
2761 aagacaaagc cgcgggagga gcagtacaac agcacgtacc gtgtggtcag cgtcctcacc
2821 gtcctgcacc aggactggct gaatggcaag gagtacaagt gcaaggtctc caacaaagcc
2881 ctcccagccc ccatcgagaa aaccatctcc aaagccaaag ggcagccccg agaaccacag
2941 gtgtacaccc tgcccccatc ccgggatgag ctgaccaaga accaggtcag cctgacctgc
3001 ctggtcaaag gcttctatcc cagcgacatc gccgtggagt gggagagcaa tgggcagccg
3061 gagaacaact acaagaccac gcctcccgtg ctggactccg acggctcctt cttcctctac
3121 agcaagctca ccgtggacaa gagcaggtgg cagcagggga acgtcttctc atgctccgtg
3181 ttgcatgagg ctctgcacaa ccactacacg cagaagagcc tctccctgtc tccgggtaaa
3241 tga
```

*Figure 104*

```
   1 atgtggggct ggaagtgcct cctcttctgg gctgtgctgg tcacagccac tctctgcact
  61 gccaggtgta ttgctgccac ctgtgccccg ggatccacct gcattgaccg ggtgggctct
 121 ttctcctgcc tctgcccacc tggacgcaca ggactcctgt gccacttgga agacatgtgt
 181 ctgagccagc cgtgccatgg ggatgcccaa tgcagcacca accccctcac aggctccaca
 241 ctctgcctgt gtcagcctgg ctattcgggg cccacctgcc accaggacct ggacgagtgt
 301 ctgatggccc agcaaggccc aagtccctgt gaacatggcg gttcctgcct caacactcct
 361 ggctccttca actgcctctg tccacctggc tacacaggct cccgttgtga ggctgatcac
 421 aatgagtgcc tctcccagcc ctgccaccca ggaagcacct gtctggacct acttgccacc
 481 ttccactgcc tctgcccgcc aggcttagaa gggcagctct gtgaggtgga gaccaacgag
 541 tgtgcctcag ctccctgcct gaaccacgcg gattgccatg acctgctcaa cggcttccag
 601 tgcatctgcc tgcctggatt ctccggcacc cgatgtgagg aggatatcga tgagtgcaga
 661 agctctccct gtgccaatgg tgggcagtgc caggaccagc ctggagcctt ccactgcaag
 721 tgtctcccag gctttgaagg gccacgctgt caaacagagg tggatgagtg cctgagtgac
 781 ccatgtcccg ttggagccag ctgccttgat cttccaggag ccttcttttg cctctgcccc
 841 tctggtttca caggccagct ctgtgaggtt cccctgtgtg ctcccaacct gtgccagccc
 901 aagcagatat gtaaggacca gaaagacaag gccaactgcc tctgtcctga tggaagccct
 961 ggctgtgccc cacctgagga caactgcacc tgccaccacg ggcactgcca gagatcctca
1021 tgtgtgtgtg acgtgggttg gacggggcca gagtgtgagg cagagctagg gggctgcatc
1081 tctgcaccct gtgcccatgg ggggacctgc tacccccagc cctctggcta caactgcacc
1141 tgccctacag gctacacagg acccacctgt agtgaggaga tgacagcttg tcactcaggg
1201 ccatgtctca atggcggctc ctgcaaccct agccctggag gctactactg cacctgccct
1261 ccaagccaca cagggcccca gtgccaaacc agcactgact actgtgtgtc tgccccgtgc
1321 ttcaatgggg gtacctgtgt gaacaggcct ggcaccttct cctgcctctg tgccatgggc
1381 ttccagggcc cgcgctgtga gggaaagctc cgccccagct gtgcagacag cccctgtagg
1441 aatagggcaa cctgccagga cagccctcag ggtccccgct gcctctgccc cactggctac
1501 accggaggca gctgccagac tctgatggac ttatgtgccc agaagccctg cccacgcaat
1561 tcccactgcc tccagactgg gccctccttc cactgcttgt gcctccaggg atggaccggg
1621 cctctctgca accttccact gtcctcctgc cagaaggctg cactgagcca aggcatagac
1681 gtctcttccc tttgccacaa tggaggcctc tgtgtcgaca gcggcccctc ctatttctgc
1741 cactgccccc ctggattcca aggcagcctg tgccaggatc acgtgaaccc atgtgagtcc
1801 aggccttgcc agaacggggc cacctgcatg gcccagccca gtgggtatct ctgccagtgt
1861 gccccaggct acgatggaca gaactgctca aaggaactcg atgcttgtca gtcccaaccc
1921 tgtcacaacc atggaacctg tactcccaaa cctggaggat tccactgtgc ctgccctcca
1981 ggctttgtgg ggctacgctg tgagggagac gtggacgagt gtctggacca gccctgccac
2041 cccacaggca ctgcagcctg ccactctctg gccaatgcct tctactgcca gtgtctgcct
2101 ggacacacag gccagtggtg tgaggtggag atagacccct gccacagcca accctgcttt
2161 catggaggga cctgtgaggc cacagcagga tcacccctgg gtttcatctg ccactgcccc
2221 aagggttttg aaggccccac ctgcagccac agggcccctt cctgcggctt ccatcactgc
2281 caccacggag gcctgtgtct gccctcccct aagccaggct tcccaccacg ctgtgcctgc
2341 ctcagtggct atgggggtcc tgactgcctg accccaccag ctcctaaagg ctgtggccct
2401 ccctccccat gcctatacaa tggcagctgc tcagagacca cgggcttggg gggcccaggc
2461 tttcgatgct cctgccctca cagctctcca gggccccggt gtcagaaacc cggagatctg
2521 ggcccgggcg agcccaaatc ttgtgacaaa actcacacat gcccaccgtg cccagcacct
2581 gaactcctgg ggggaccgtc agtcttcctc ttccccccaa aacccaagga caccctcatg
2641 atctcccgga cccctgaggt cacatgcgtg gtggtggacg tgagccacga agaccctgag
2701 gtcaagttca actggtacgt ggacggcgtg gaggtgcata atgccaagac aaagccgcgg
2761 gaggagcagt acaacagcac gtaccgtgtg gtcagcgtcc tcaccgtcct gcaccaggac
2821 tggctgaatg gcaaggagta caagtgcaag gtctccaaca aagccctccc agcccccatc
2881 gagaaaacca tctccaaagc caaagggcag ccccgagaac cacaggtgta caccctgccc
2941 ccatcccggg atgagctgac caagaaccag gtcagcctga cctgcctggt caaaggcttc
3001 tatcccagcg acatcgccgt ggagtgggag agcaatgggc agccggagaa caactacaag
3061 accacgcctc ccgtgctgga ctccgacggc tccttcttcc tctacagcaa gctcaccgtg
3121 gacaagagca ggtggcagca ggggaacgtc ttctcatgct ccgtgatgca tgaggctctg
3181 cacaaccact acacgcagaa gagcctctcc ctgtctccgg gtaaatga
```

*Figure 105*

```
   1 atgcagcccc cttcactgct gctgctgctg ctgctgctgc tgctgctatg tgtctcagtg
  61 gtcagaccca gagggctgct gtgtattgct gccacctgtg ccccgggatc cacctgcatt
 121 gaccgggtgg gctctttctc ctgcctctgc ccacctggac gcacaggact cctgtgccac
 181 ttggaagaca tgtgtctgag ccagccgtgc catggggatg cccaatgcag caccaacccc
 241 ctcacaggct ccacactctg cctgtgtcag cctggctatt cggggcccac ctgccaccag
 301 gacctggacg agtgtctgat ggcccagcaa ggcccaagtc cctgtgaaca tggcggttcc
 361 tgcctcaaca ctcctggctc cttcaactgc ctctgtccac ctggctacac aggctcccgt
 421 tgtgaggctg atcacaatga gtgcctctcc cagccctgcc acccaggaag cacctgtctg
 481 gacctacttg ccaccttcca ctgcctctgc ccgccaggct tagaagggca gctctgtgag
 541 gtggagacca acgagtgtgc ctcagctccc tgcctgaacc acgcggattg ccatgacctg
 601 ctcaacggct tccagtgcat ctgcctgcct ggattctccg gcacccgatg tgaggaggat
 661 atcgatgagt gcagaagctc tccctgtgcc aatggtgggc agtgccagga ccagcctgga
 721 gccttccact gcaagtgtct cccaggcttt gaagggccac gctgtcaaac agaggtggat
 781 gagtgcctga gtgacccatg tcccgttgga gccagctgcc ttgatcttcc aggagccttc
 841 ttttgcctct gcccctctgg tttcacaggc cagctctgtg aggttcccct gtgtgctccc
 901 aacctgtgcc agcccaagca gatatgtaag gaccagaaag acaaggccaa ctgcctctgt
 961 cctgatggaa gccctggctg tgccccacct gaggacaact gcacctgcca ccacgggcac
1021 tgccagagat cctcatgtgt gtgtgacgtg ggttggacgg ggccagagtg tgaggcagag
1081 ctaggggggct gcatctctgc accctgtgcc catgggggga cctgctaccc ccagccctct
1141 ggctacaact gcacctgccc tacaggctac acaggaccca cctgtagtga ggagatgaca
1201 gcttgtcact cagggccatg tctcaatggc ggctcctgca accctagccc tggaggctac
1261 tactgcacct gccctccaag ccacacaggg ccccagtgcc aaaccagcac tgactactgt
1321 gtgtctgccc cgtgcttcaa tgggggtacc tgtgtgaaca ggcctggcac cttctcctgc
1381 ctctgtgcca tgggcttcca gggcccgcgc tgtgagggaa agctccgccc cagctgtgca
1441 gacagcccct gtaggaatag ggcaacctgc caggacagcc ctcagggtcc ccgctgcctc
1501 tgccccactg gctacaccgg aggcagctgc cagactctga tggacttatg tgcccagaag
1561 ccctgcccac gcaattccca ctgcctccag actgggccct ccttccactg cttgtgcctc
1621 cagggatgga ccgggcctct ctgcaacctt ccactgtcct cctgccagaa ggctgcactg
1681 agccaaggca tagacgtctc ttccctttgc cacaatggag gcctctgtgt cgacagcggc
1741 ccctcctatt tctgccactg ccccccctgga ttccaaggca gcctgtgcca ggatcacgtg
1801 aacccagatc tgggcccggg cgagcccaaa tcttgtgaca aaactcacac atgcccaccg
1861 tgcccagcac ctgaactcct ggggggaccg tcagtcttcc tcttcccccc aaaacccaag
1901 gacaccctca tgatctcccg gacccctgag gtcacatgcg tggtggtgga cgtgagccac
1961 gaagaccctg aggtcaagtt caactggtac gtggacggcg tggaggtgca taatgccaag
2021 acaaagccgc gggaggagca gtacaacagc acgtaccgtg tggtcagcgt cctcaccgtc
2081 ctgcaccagg actggctgaa tggcaaggag tacaagtgca aggtctccaa caaagccctc
2041 ccagccccca tcgagaaaac catctccaaa gccaaagggc agccccgaga accacaggtg
2101 tacaccctgc ccccatcccg ggatgagctg accaagaacc aggtcagcct gacctgcctg
2161 gtcaaaggct tctatcccag cgacatcgcc gtggagtggg agagcaatgg gcagccggag
2221 aacaactaca agaccacgcc tcccgtgctg gactccgacg gctccttctt cctctacagc
2281 aagctcaccg tggacaagag caggtggcag caggggaacg tcttctcatg ctccgtgatg
2341 catgaggctc tgcacaacca ctacacgcag aagagcctct ccctgtctcc gggtaaatga
```

*Figure 106*

```
   1 atgtggggct ggaagtgcct cctcttctgg gctgtgctgg tcacagccac tctctgcact
  61 gccaggtgta ttgctgccac ctgtgccccg ggatccacct gcattgaccg ggtgggctct
 121 ttctcctgcc tctgcccacc tggacgcaca ggactcctgt gccacttgga agacatgtgt
 181 ctgagccagc cgtgccatgg ggatgcccaa tgcagcacca accccctcac aggctccaca
 241 ctctgcctgt gtcagcctgg ctattcgggg cccacctgcc accaggacct ggacgagtgt
 301 ctgatggccc agcaaggccc aagtccctgt gaacatggcg gttcctgcct caacactcct
 361 ggctccttca actgcctctg tccacctggc tacacaggct cccgttgtga ggctgatcac
 421 aatgagtgcc tctcccagcc ctgccaccca ggaagcacct gtctggacct acttgccacc
 481 ttccactgcc tctgcccgcc aggcttagaa gggcagctct gtgaggtgga gaccaacgag
 541 tgtgcctcag ctccctgcct gaaccacgcg gattgccatg acctgctcaa cggcttccag
 601 tgcatctgcc tgcctggatt ctccggcacc cgatgtgagg aggatatcga tgagtgcaga
 661 agctctccct gtgccaatgg tgggcagtgc caggaccagc ctggagcctt ccactgcaag
 721 tgtctcccag gctttgaagg gccacgctgt caaacagagg tggatgagtg cctgagtgac
 781 ccatgtcccg ttggagccag ctgccttgat cttccaggag ccttcttttg cctctgcccc
 841 tctggtttca caggccagct ctgtgaggtt cccctgtgtg ctcccaacct gtgccagccc
 901 aagcagatat gtaaggacca gaaagacaag gccaactgcc tctgtcctga tggaagccct
 961 ggctgtgccc cacctgagga caactgcacc tgccaccacg ggcactgcca gagatcctca
1021 tgtgtgtgtg acgtgggttg gacgggggca gagtgtgagg cagagctagg gggctgcatc
1081 tctgcaccct gtgcccatgg ggggacctgc taccccccagc cctctggcta caactgcacc
1141 tgccctacag gctacacagg acccacctgt agtgaggaga tgacagcttg tcactcaggg
1201 ccatgtctca atggcggctc ctgcaaccct agccctggag gctactactg cacctgccct
1261 ccaagccaca cagggcccca gtgccaaacc agcactgact actgtgtgtc tgccccgtgc
1321 ttcaatgggg gtacctgtgt gaacaggcct ggcaccttct cctgcctctg tgccatgggc
1381 ttccagggcc cgcgctgtga gggaaagctc cgccccagct gtgcagacag cccctgtagg
1441 aatagggcaa cctgccagga cagccctcag ggtccccgct gcctctgccc cactggctac
1501 accggaggca gctgccagac tctgatggac ttatgtgccc agaagccctg cccacgcaat
1561 tcccactgcc tccagactgg gccctccttc cactgcttgt gcctccaggg atggaccggg
1621 cctctctgca accttccact gtcctcctgc cagaaggctg cactgagcca aggcatagac
1681 gtctcttccc tttgccacaa tggaggcctc tgtgtcgaca gcggcccctc ctatttctgc
1741 cactgccccc ctggattcca aggcagcctg tgccaggatc acgtgaaccc agatctgggc
1801 ccgggcgagc ccaaatcttg tgacaaaact cacacatgcc caccgtgccc agcacctgaa
1861 ctcctggggg gaccgtcagt cttcctcttc cccccaaaac ccaaggacac cctcatgatc
1921 tcccggaccc ctgaggtcac atgcgtggtg gtggacgtga gccacgaaga ccctgaggtc
1981 aagttcaact ggtacgtgga cggcgtggag gtgcataatg ccaagacaaa gccgcgggag
2041 gagcagtaca acagcacgta ccgtgtggtc agcgtcctca ccgtcctgca ccaggactgg
2101 ctgaatggca aggagtacaa gtgcaaggtc tccaacaaag ccctcccagc ccccatcgag
2161 aaaaccatct ccaaagccaa agggcagccc cgagaaccac aggtgtacac cctgccccca
2221 tcccgggatg agctgaccaa gaaccaggtc agcctgacct gcctggtcaa aggcttctat
2281 cccagcgaca tcgccgtgga gtgggagagc aatgggcagc cggagaacaa ctacaagacc
2341 acgcctcccg tgctggactc cgacggctcc ttcttcctct acagcaagct caccgtggac
2401 aagagcaggt ggcagcaggg gaacgtcttc tcatgctccg tgatgcatga ggctctgcac
2461 aaccactaca cgcagaagag cctctccctg tctccgggta aatga
```

*Figure 107*

```
   1 atgcagcccc cttcactgct gctgctgctg ctgctgctgc tgctgctatg tgtctcagtg
  61 gtcagaccca gagggctgct gtgtgcctca gctccctgcc tgaaccacgc ggattgccat
 121 gacctgctca acggcttcca gtgcatctgc ctgcctggat tctccggcac ccgatgtgag
 181 gaggatatcg atgagtgcag aagctctccc tgtgccaatg gtgggcagtg ccaggaccag
 241 cctggagcct tccactgcaa gtgtctccca ggctttgaag ggccacgctg tcaaacagag
 301 gtggatgagt gcctgagtga cccatgtccc gttggagcca gctgccttga tcttccagga
 361 gccttctttt gcctctgccc ctctggtttc acaggccagc tctgtgaggt tcccctgtgt
 421 gctcccaacc tgtgccagcc caagcagata tgtaaggacc agaaagacaa ggccaactgc
 481 ctctgtcctg atggaagccc tggctgtgcc ccacctgagg acaactgcac ctgccaccac
 541 gggcactgcc agagatcctc atgtgtgtgt gacgtgggtt ggacggggcc agagtgtgag
 601 gcagagctag gggctgcat ctctgcaccc tgtgcccatg gggggacctg ctacccccag
 661 ccctctggct acaactgcac ctgccctaca ggctacacag gacccacctg tagtgaggag
 721 atgacagctt gtcactcagg gccatgtctc aatggcggct cctgcaaccc tagccctgga
 781 ggctactact gcacctgccc tccaagccac acagggcccc agtgccaaac cagcactgac
 841 tactgtgtgt ctgccccgtg cttcaatggg ggtacctgtg tgaacaggcc tggcaccttc
 901 tcctgcctct gtgccatggg cttccagggc ccgcgctgtg agggaaagct ccgccccagc
 961 tgtgcagaca gcccctgtag gaatagggca acctgccagg acagccctca gggtccccgc
1021 tgcctctgcc ccactggcta caccggaggc agctgccaga ctctgatgga cttatgtgcc
1081 cagaagccct gcccacgcaa ttcccactgc ctccagactg ggccctcctt ccactgcttg
1141 tgcctccagg gatggaccgg gcctctctgc aaccttccac tgtcctcctg ccagaaggct
1201 gcactgagcc aaggcataga cgtctcttcc ctttgccaca atggaggcct ctgtgtcgac
1261 agcggcccct cctatttctg ccactgcccc cctggattcc aaggcagcct gtgccaggat
1321 cacgtgaacc cagatctggg cccgggcgag cccaaatctt gtgacaaaac tcacacatgc
1381 ccaccgtgcc cagcacctga actcctgggg ggaccgtcag tcttcctctt ccccccaaaa
1441 cccaaggaca ccctcatgat ctcccggacc cctgaggtca catgcgtggt ggtggacgtg
1501 agccacgaag accctgaggt caagttcaac tggtacgtgg acggcgtgga ggtgcataat
1561 gccaagacaa agccgcggga ggagcagtac aacagcacgt accgtgtggt cagcgtcctc
1621 accgtcctgc accaggactg gctgaatggc aaggagtaca agtgcaaggt ctccaacaaa
1681 gccctcccag cccccatcga gaaaaccatc tccaaagcca aagggcagcc ccgagaacca
1741 caggtgtaca ccctgccccc atcccgggat gagctgacca agaaccaggt cagcctgacc
1801 tgcctggtca aaggcttcta tcccagcgac atcgccgtgg agtgggagag caatgggcag
1861 ccggagaaca actacaagac cacgcctccc gtgctggact ccgacggctc cttcttcctc
1921 tacagcaagc tcaccgtgga caagagcagg tggcagcagg ggaacgtctt ctcatgctcc
1981 gtgatgcatg aggctctgca caaccactac acgcagaaga gcctctccct gtctccgggt
2041 aaatga
```

*Figure 108*

```
   1 atgtggggct ggaagtgcct cctcttctgg gctgtgctgg tcacagccac tctctgcact
  61 gccaggtgtg cctcagctcc ctgcctgaac cacgcggatt gccatgacct gctcaacggc
 121 ttccagtgca tctgcctgcc tggattctcc ggcacccgat gtgaggagga tatcgatgag
 181 tgcagaagct ctccctgtgc caatggtggg cagtgccagg accagcctgg agccttccac
 241 tgcaagtgtc tcccaggctt tgaagggcca cgctgtcaaa cagaggtgga tgagtgcctg
 301 agtgacccat gtcccgttgg agccagctgc cttgatcttc caggagcctt cttttgcctc
 361 tgcccctctg gtttcacagg ccagctctgt gaggttcccc tgtgtgctcc caacctgtgc
 421 cagcccaagc agatatgtaa ggaccagaaa gacaaggcca actgcctctg tcctgatgga
 481 agccctggct gtgccccacc tgaggacaac tgcacctgcc accacgggca ctgccagaga
 541 tcctcatgtg tgtgtgacgt gggttggacg gggccagagt gtgaggcaga gctagggggc
 601 tgcatctctg caccctgtgc ccatgggggg acctgctacc cccagccctc tggctacaac
 661 tgcacctgcc ctacaggcta cacaggaccc acctgtagtg aggagatgac agcttgtcac
 721 tcagggccat gtctcaatgg cggctcctgc aaccctagcc ctggaggcta ctactgcacc
 781 tgccctccaa gccacacagg gccccagtgc caaaccagca ctgactactg tgtgtctgcc
 841 ccgtgcttca atgggggtac ctgtgtgaac aggcctggca ccttctcctg cctctgtgcc
 901 atgggcttcc agggcccgcg ctgtgaggga aagctccgcc ccagctgtgc agacagcccc
 961 tgtaggaata gggcaacctg ccaggacagc cctcagggtc cccgctgcct ctgccccact
1021 ggctacaccg gaggcagctg ccagactctg atggacttat gtgcccagaa gccctgccca
1081 cgcaattccc actgcctcca gactgggccc tccttccact gcttgtgcct ccagggatgg
1141 accgggcctc tctgcaacct tccactgtcc tcctgccaga aggctgcact gagccaaggc
1201 atagacgtct cttccctttg ccacaatgga ggcctctgtg tcgacagcgg cccctcctat
1261 ttctgccact gccccccctgg attccaaggc agcctgtgcc aggatcacgt gaacccagat
1321 ctgggcccgg gcgagcccaa atcttgtgac aaaactcaca catgcccacc gtgcccagca
1381 cctgaactcc tgggggggacc gtcagtcttc ctcttccccc caaaacccaa ggacaccctc
1441 atgatctccc ggacccctga ggtcacatgc gtggtggtgg acgtgagcca cgaagaccct
1501 gaggtcaagt tcaactggta cgtggacggc gtggaggtgc ataatgccaa gacaaagccg
1561 cgggaggagc agtacaacag cacgtaccgt gtggtcagcg tcctcaccgt cctgcaccag
1621 gactggctga atggcaagga gtacaagtgc aaggtctcca acaaagccct cccagccccc
1681 atcgagaaaa ccatctccaa agccaaaggg cagccccgag aaccacaggt gtacaccctg
1741 cccccatccc gggatgagct gaccaagaac caggtcagcc tgacctgcct ggtcaaaggc
1801 ttctatccca gcgacatcgc cgtggagtgg gagagcaatg ggcagccgga gaacaactac
1861 aagaccacgc ctcccgtgct ggactccgac ggctccttct tcctctacag caagctcacc
1921 gtggacaaga gcaggtggca gcaggggaac gtcttctcat gctccgtgat gcatgaggct
1981 ctgcacaacc actacacgca gaagagcctc tccctgtctc cgggtaaatg a
```

*Figure 109*

```
   1 atgcagcccc cttcactgct gctgctgctg ctgctgctgc tgctgctatg tgtctcagtg
  61 gtcagaccca gagggctgct gtgtgcagac agcccctgta ggaatagggc aacctgccag
 121 gacagccctc agggtccccg ctgcctctgc ccccactggct acaccggagg cagctgccag
 181 actctgatgg acttatgtgc ccagaagccc tgcccacgca attcccactg cctccagact
 241 gggccctcct tccactgctt gtgcctccag ggatggaccg ggcctctctg caaccttcca
 301 ctgtcctcct gccagaaggc tgcactgagc caaggcatag acgtctcttc cctttgccac
 361 aatggaggcc tctgtgtcga cagcggcccc tcctatttct gccactgccc ccctggattc
 421 caaggcagcc tgtgccagga tcacgtgaac ccatgtgagt ccaggccttg ccagaacggg
 481 gccacctgca tggcccagcc cagtgggtat ctctgccagt gtgccccagg ctacgatgga
 541 cagaactgct caaaggaact cgatgcttgt cagtcccaac cctgtcacaa ccatggaacc
 601 tgtactccca aacctggagg attccactgt gcctgccctc caggctttgt ggggctacgc
 661 tgtgagggag acgtggacga gtgtctggac cagccctgcc accccacagg cactgcagcc
 721 tgccactctc tggccaatgc cttctactgc cagtgtctgc ctggacacac aggccagtgg
 781 tgtgaggtgg agatagaccc ctgccacagc caaccctgct ttcatggagg gacctgtgag
 841 gccacagcag gatcacccct gggtttcatc tgccactgcc ccaagggttt tgaaggcccc
 901 acctgcagcc acagggcccc ttcctgcggc ttccatcact gccaccacgg aggcctgtgt
 961 ctgccctccc ctaagccagg cttcccacca cgctgtgcct gcctcagtgg ctatgggggt
1021 cctgactgcc tgaccccacc agctcctaaa ggctgtggcc ctccctcccc atgcctatac
1081 aatggcagct gctcagagac cacgggcttg gggggcccag gctttcgatg ctcctgccct
1141 cacagctctc cagggccccg gtgtcagaaa cccggagatc tgggcccggg cgagcccaaa
1201 tcttgtgaca aaactcacac atgcccaccg tgcccagcac ctgaactcct ggggggaccg
1261 tcagtcttcc tcttcccccc aaaacccaag gacaccctca tgatctcccg gacccctgag
1321 gtcacatgcg tggtggtgga cgtgagccac gaagaccctg aggtcaagtt caactggtac
1381 gtggacggcg tggaggtgca taatgccaag acaaagccgc gggaggagca gtacaacagc
1441 acgtaccgtg tggtcagcgt cctcaccgtc ctgcaccagg actggctgaa tggcaaggag
1501 tacaagtgca aggtctccaa caaagccctc ccagccccca tcgagaaaac catctccaaa
1561 gccaaagggc agccccgaga accacaggtg tacaccctgc ccccatcccg ggatgagctg
1621 accaagaacc aggtcagcct gacctgcctg gtcaaaggct tctatcccag cgacatcgcc
1681 gtggagtggg agagcaatgg gcagccggag aacaactaca agaccacgcc tcccgtgctg
1741 gactccgacg gctccttctt cctctacagc aagctcaccg tggacaagag caggtggcag
1801 caggggaacg tcttctcatg ctccgtgatg catgaggctc tgcacaacca ctacacgcag
1861 aagagcctct ccctgtctcc gggtaaatga
```

*Figure 110*

```
   1 atgtggggct ggaagtgcct cctcttctgg gctgtgctgg tcacagccac tctctgcact
  61 gccaggtgtg cagacagccc ctgtaggaat agggcaacct gccaggacag ccctcagggt
 121 ccccgctgcc tctgccccac tggctacacc ggaggcagct gccagactct gatggactta
 181 tgtgcccaga agccctgccc acgcaattcc cactgcctcc agactgggcc ctccttccac
 241 tgcttgtgcc tccagggatg gaccgggcct ctctgcaacc ttccactgtc ctcctgccag
 301 aaggctgcac tgagccaagg catagacgtc tcttcccttt gccacaatgg aggcctctgt
 361 gtcgacagcg gcccctccta tttctgccac tgcccccctg gattccaagg cagcctgtgc
 421 caggatcacg tgaacccatg tgagtccagg ccttgccaga acggggccac ctgcatggcc
 481 cagcccagtg ggtatctctg ccagtgtgcc ccaggctacg atggacagaa ctgctcaaag
 541 gaactcgatg cttgtcagtc ccaaccctgt cacaaccatg gaacctgtac tcccaaacct
 601 ggaggattcc actgtgcctg ccctccaggc tttgtggggc tacgctgtga gggagacgtg
 661 gacgagtgtc tggaccagcc ctgccacccc acaggcactg cagcctgcca ctctctggcc
 721 aatgccttct actgccagtg tctgcctgga cacacaggcc agtggtgtga ggtggagata
 781 gacccctgcc acagccaacc ctgctttcat ggagggacct gtgaggccac agcaggatca
 841 cccctgggtt tcatctgcca ctgccccaag ggttttgaag gccccacctg cagccacagg
 901 gccccttcct gcggcttcca tcactgccac cacggaggcc tgtgtctgcc ctcccctaag
 961 ccaggcttcc caccacgctg tgcctgcctc agtggctatg gggtcctga ctgcctgacc
1021 ccaccagctc ctaaaggctg tggccctccc tccccatgcc tatacaatgg cagctgctca
1081 gagaccacgg gcttgggggg cccaggcttt cgatgctcct gccctcacag ctctccaggg
1141 ccccggtgtc agaaacccgg agatctgggc ccgggcgagc ccaaatcttg tgacaaaact
1201 cacacatgcc caccgtgccc agcacctgaa ctcctggggg gaccgtcagt cttcctcttc
1261 cccccaaaac ccaaggacac cctcatgatc tcccggaccc ctgaggtcac atgcgtggtg
1321 gtggacgtga gccacgaaga ccctgaggtc aagttcaact ggtacgtgga cggcgtggag
1381 gtgcataatg ccaagacaaa gccgcgggag gagcagtaca acagcacgta ccgtgtggtc
1441 agcgtcctca ccgtcctgca ccaggactgg ctgaatggca aggagtacaa gtgcaaggtc
1501 tccaacaaag ccctcccagc ccccatcgag aaaaccatct ccaaagccaa agggcagccc
1561 cgagaaccac aggtgtacac cctgccccca tcccgggatg agctgaccaa gaaccaggtc
1621 agcctgacct gcctggtcaa aggcttctat cccagcgaca tcgccgtgga gtgggagagc
1681 aatgggcagc cggagaacaa ctacaagacc acgcctcccg tgctggactc cgacggctcc
1741 ttcttcctct acagcaagct caccgtggac aagagcaggt ggcagcaggg gaacgtcttc
1801 tcatgctccg tgatgcatga ggctctgcac aaccactaca cgcagaagag cctctccctg
1861 tctccgggta aatga
```

Human Notch4 Signal Peptide

Fig. 113

Human Notch4 decoy (EGF-LR 1-29)
Human Notch4 decoy (EGF-LR 9-29)
Human Notch4 decoy (EGF-LR 21-29)

```
Human N4

cag aaa ccc gga (SEQ ID NO:106)
gtc ttt ggg cct (SEQ ID NO:107)
 Q   K   P   G  (SEQ ID NO:108)

Add BglII site

cag aaa ccc gga GAT CT (SEQ ID NO:109)
gtc ttt ggg cct CTA GA (SEQ ID NO:110)
 Q   K   P   G (SEQ ID NO:108)

N4/FC fusion

cag aaa ccc gga GAT CTG GGC CCG (SEQ ID NO:111)
gtc ttt ggg cct CTA GAC CCG GGC (SEQ ID NO:112)
 Q   K   P   G   D   L   G   P  (SEQ ID NO 113)
```

Fig. 114

Human Notch4 decoy (EGF-LR 1-13)

Human N4 gat atc gat gag (SEQ ID NO:114)
cta tag cta ctc (SEQ ID NO:115)
D I D E (SEQ ID NO:116)

Add a BamHI site gat atc gat gag GAT CC (SEQ ID NO:117)
cta tag cta ctc CTA GG (SEQ ID NO:118)
D I D E (SEQ ID NO:116)

N4/FC fusion gat atc gat gag GAT CTG GGC CCG (SEQ ID NO:119)
cta tag cta ctc CTA GAC CCG GGC (SEQ ID NO:120)
D I D E D L G P (SEQ ID NO:121)

Fig. 115

Human Notch4 decoy (EGF-LR 1-23)
Human Notch4 decoy (EGF-LR 9-23)
Human Notch4 decoy (EGF-LR 13-23)

Human N4

```
cac gtg aac cca (SEQ ID NO:122)
gtg cac ttg ggt (SEQ ID NO:123)
 H   V   N   P (SEQ ID NO:124)
```

Add a BglII site

```
cac gtg aac cca GAT CT (SEQ ID NO:125)
gtg cac ttg ggt CTA GA (SEQ ID NO:126)
 H   V   N   P (SEQ ID NO:124)
```

N4/FC fusion

```
cac gtg aac cca GAT CTG GGC CCG (SEQ ID NO:127)
gtg cac ttg ggt CTA GAC CCG GGC (SEQ ID NO:128)
 H   V   N   P   D   L   G   P  (SEQ ID NO:129)
```

Loss of Notch4 expression suppressed weight gain in mice fed a high fat diet

- Control:
  - 8 out of 12 positive
- Rat Notch1 decoy s2:
  - 5 out of 13 positive
- Rat Notch1 decoy s4:
  - 4 out of 10 positive

```
                        SEQUENCE LISTING

<160> NUMBER OF SEQ ID NOS: 131

<210> SEQ ID NO 1
<211> LENGTH: 1433
<212> TYPE: PRT
<213> ORGANISM: Rattus norvegicus

<400> SEQUENCE: 1

Met Pro Arg Leu Leu Ala Pro Leu Leu Cys Leu Thr Leu Leu Pro Ala
1               5                   10                  15

Leu Ala Ala Arg Gly Leu Arg Cys Ser Gln Pro Ser Gly Thr Cys Leu
            20                  25                  30

Asn Gly Gly Arg Cys Glu Val Ala Asn Gly Thr Glu Ala Cys Val Cys
        35                  40                  45

Ser Gly Ala Phe Val Gly Gln Arg Cys Gln Asp Pro Ser Pro Cys Leu
    50                  55                  60

Ser Thr Pro Cys Lys Asn Ala Gly Thr Cys Tyr Val Val Asp His Gly
65                  70                  75                  80

Gly Ile Val Asp Tyr Ala Cys Ser Cys Pro Leu Gly Phe Ser Gly Pro
                85                  90                  95

Leu Cys Leu Thr Pro Leu Ala Asn Ala Cys Leu Ala Asn Pro Cys Arg
            100                 105                 110

Asn Gly Gly Thr Cys Asp Leu Leu Thr Leu Thr Glu Tyr Lys Cys Arg
        115                 120                 125

Cys Pro Pro Gly Trp Ser Gly Lys Ser Cys Gln Gln Ala Asp Pro Cys
    130                 135                 140

Ala Ser Asn Pro Cys Ala Asn Gly Gly Gln Cys Leu Pro Phe Glu Ser
145                 150                 155                 160

Ser Tyr Ile Cys Gly Cys Pro Pro Gly Phe His Gly Pro Thr Cys Arg
                165                 170                 175

Gln Asp Val Asn Glu Cys Ser Gln Asn Pro Gly Leu Cys Arg His Gly
            180                 185                 190

Gly Thr Cys His Asn Glu Ile Gly Ser Tyr Arg Cys Ala Cys Arg Ala
        195                 200                 205

Thr His Thr Gly Pro His Cys Glu Leu Pro Tyr Val Pro Cys Ser Pro
    210                 215                 220

Ser Pro Cys Gln Asn Gly Gly Thr Cys Arg Pro Thr Gly Asp Thr Thr
225                 230                 235                 240

His Glu Cys Ala Cys Leu Pro Gly Phe Ala Gly Gln Asn Cys Glu Glu
                245                 250                 255

Asn Val Asp Asp Cys Pro Gly Asn Asn Cys Lys Asn Gly Gly Ala Cys
            260                 265                 270

Val Asp Gly Val Asn Thr Tyr Asn Cys Arg Cys Pro Pro Glu Trp Thr
        275                 280                 285

Gly Gln Tyr Cys Thr Glu Asp Val Asp Glu Cys Gln Leu Met Pro Asn
    290                 295                 300
```

-continued

```
Ala Cys Gln Asn Ala Gly Thr Cys His Asn Ser His Gly Gly Tyr Asn
305                 310                 315                 320

Cys Val Cys Val Asn Gly Trp Thr Gly Glu Asp Cys Ser Asp Asn Ile
                325                 330                 335

Asp Asp Cys Ala Ser Ala Ala Cys Phe Gln Gly Ala Thr Cys His Asp
            340                 345                 350

Arg Val Ala Ser Phe Tyr Cys Glu Cys Pro His Gly Arg Thr Gly Leu
        355                 360                 365

Leu Cys His Leu Asn Asp Ala Cys Ile Ser Asn Pro Cys Asn Glu Gly
    370                 375                 380

Ser Asn Cys Asp Thr Asn Pro Val Asn Gly Lys Ala Ile Cys Thr Cys
385                 390                 395                 400

Pro Arg Gly Tyr Thr Gly Pro Ala Cys Ser Gln Asp Val Asp Glu Cys
                405                 410                 415

Ala Leu Gly Ala Asn Pro Cys Glu His Ala Gly Lys Cys Leu Asn Thr
            420                 425                 430

Leu Gly Ser Phe Glu Cys Gln Cys Leu Gln Gly Tyr Thr Gly Pro Arg
        435                 440                 445

Cys Glu Ile Asp Val Asn Glu Cys Ile Ser Asn Pro Cys Gln Asn Asp
    450                 455                 460

Ala Thr Cys Leu Asp Gln Ile Gly Glu Phe Gln Cys Ile Cys Met Pro
465                 470                 475                 480

Gly Tyr Glu Gly Val Tyr Cys Glu Ile Asn Thr Asp Glu Cys Ala Ser
                485                 490                 495

Ser Pro Cys Leu His Asn Gly Arg Cys Val Asp Lys Ile Asn Glu Phe
            500                 505                 510

Leu Cys Gln Cys Pro Lys Gly Phe Ser Gly His Leu Cys Gln Tyr Asp
        515                 520                 525

Val Asp Glu Cys Ala Ser Thr Pro Cys Lys Asn Gly Ala Lys Cys Leu
    530                 535                 540

Asp Gly Pro Asn Thr Tyr Thr Cys Val Cys Thr Glu Gly Tyr Thr Gly
545                 550                 555                 560

Thr His Cys Glu Val Asp Ile Asp Glu Cys Asp Pro Asp Pro Cys His
                565                 570                 575

Ile Gly Leu Cys Lys Asp Gly Val Ala Thr Phe Thr Cys Leu Cys Gln
            580                 585                 590

Pro Gly Tyr Thr Gly His His Cys Glu Thr Asn Ile Asn Glu Cys His
        595                 600                 605

Ser Gln Pro Cys Arg His Gly Gly Thr Cys Gln Asp Arg Asp Asn Tyr
    610                 615                 620

Tyr Leu Cys Leu Cys Leu Lys Gly Thr Thr Gly Pro Asn Cys Glu Ile
625                 630                 635                 640

Asn Leu Asp Asp Cys Ala Ser Asn Pro Cys Asp Ser Gly Thr Cys Leu
                645                 650                 655

Asp Lys Ile Asp Gly Tyr Glu Cys Ala Cys Glu Pro Gly Tyr Thr Gly
            660                 665                 670

Ser Met Cys Asn Val Asn Ile Asp Glu Cys Ala Gly Ser Pro Cys His
        675                 680                 685

Asn Gly Gly Thr Cys Glu Asp Gly Ile Ala Gly Phe Thr Cys Arg Cys
    690                 695                 700

Pro Glu Gly Tyr His Asp Pro Thr Cys Leu Ser Glu Val Asn Glu Cys
705                 710                 715                 720
```

-continued

```
Asn Ser Asn Pro Cys Ile His Gly Ala Cys Arg Asp Gly Leu Asn Gly
                725                 730                 735

Tyr Lys Cys Asp Cys Ala Pro Gly Trp Ser Gly Thr Asn Cys Asp Ile
            740                 745                 750

Asn Asn Asn Glu Cys Glu Ser Asn Pro Cys Val Asn Gly Gly Thr Cys
        755                 760                 765

Lys Asp Met Thr Ser Gly Tyr Val Cys Thr Cys Arg Glu Gly Phe Ser
    770                 775                 780

Gly Pro Asn Cys Gln Thr Asn Ile Asn Glu Cys Ala Ser Asn Pro Cys
785                 790                 795                 800

Leu Asn Gln Gly Thr Cys Ile Asp Asp Val Ala Gly Tyr Lys Cys Asn
                805                 810                 815

Cys Pro Leu Pro Tyr Thr Gly Ala Thr Cys Glu Val Val Leu Ala Pro
            820                 825                 830

Cys Ala Thr Ser Pro Cys Lys Asn Ser Gly Val Cys Lys Glu Ser Glu
        835                 840                 845

Asp Tyr Glu Ser Phe Ser Cys Val Cys Pro Thr Gly Trp Gln Gly Gln
    850                 855                 860

Thr Cys Glu Ile Asp Ile Asn Glu Cys Val Lys Ser Pro Cys Arg His
865                 870                 875                 880

Gly Ala Ser Cys Gln Asn Thr Asn Gly Ser Tyr Arg Cys Leu Cys Gln
                885                 890                 895

Ala Gly Tyr Thr Gly Arg Asn Cys Glu Ser Asp Ile Asp Asp Cys Arg
            900                 905                 910

Pro Asn Pro Cys His Asn Gly Gly Ser Cys Thr Asp Gly Val Asn Ala
        915                 920                 925

Ala Phe Cys Asp Cys Leu Pro Gly Phe Gln Gly Ala Phe Cys Glu Glu
    930                 935                 940

Asp Ile Asn Glu Cys Ala Thr Asn Pro Cys Gln Asn Gly Ala Asn Cys
945                 950                 955                 960

Thr Asp Cys Val Asp Ser Tyr Thr Cys Thr Cys Pro Thr Gly Phe Asn
                965                 970                 975

Gly Ile His Cys Glu Asn Asn Thr Pro Asp Cys Thr Glu Ser Ser Cys
            980                 985                 990

Phe Asn Gly Gly Thr Cys Val Asp  Gly Ile Asn Ser Phe  Thr Cys Leu
        995                 1000                1005

Cys Pro  Pro Gly Phe Thr Gly  Ser Tyr Cys Gln Tyr  Asp Val Asn
    1010                1015                1020

Glu Cys  Asp Ser Arg Pro Cys  Leu His Gly Gly Thr  Cys Gln Asp
    1025                1030                1035

Ser Tyr  Gly Thr Tyr Lys Cys  Thr Cys Pro Gln Gly  Tyr Thr Gly
    1040                1045                1050

Leu Asn  Cys Gln Asn Leu Val  Arg Trp Cys Asp Ser  Ala Pro Cys
    1055                1060                1065

Lys Asn  Gly Gly Lys Cys Trp  Gln Thr Asn Thr Gln  Tyr His Cys
    1070                1075                1080

Glu Cys  Arg Ser Gly Trp Thr  Gly Phe Asn Cys Asp  Val Leu Ser
    1085                1090                1095

Val Ser  Cys Glu Val Ala Ala  Gln Lys Arg Gly Ile  Asp Val Thr
    1100                1105                1110

Leu Leu  Cys Gln His Gly Gly  Leu Cys Val Asp Glu  Glu Asp Lys
    1115                1120                1125

His Tyr  Cys His Cys Gln Ala  Gly Tyr Thr Gly Ser  Tyr Cys Glu
```

```
    1130                1135                1140

Asp Glu  Val Asp Glu Cys Ser  Pro Asn Pro Cys Gln  Asn Gly Ala
    1145                1150                1155

Thr Cys  Thr Asp Tyr Leu Gly  Gly Phe Ser Cys Lys  Cys Val Ala
    1160                1165                1170

Gly Tyr  His Gly Ser Asn Cys  Ser Glu Glu Ile Asn  Glu Cys Leu
    1175                1180                1185

Ser Gln  Pro Cys Gln Asn Gly  Gly Thr Cys Ile Asp  Leu Thr Asn
    1190                1195                1200

Thr Tyr  Lys Cys Ser Cys Pro  Arg Gly Thr Gln Gly  Val His Cys
    1205                1210                1215

Glu Ile  Asn Val Asp Asp Cys  His Pro Pro Leu Asp  Pro Ala Ser
    1220                1225                1230

Arg Ser  Pro Lys Cys Phe Asn  Asn Gly Thr Cys Val  Asp Gln Val
    1235                1240                1245

Gly Gly  Tyr Thr Cys Thr Cys  Pro Pro Gly Phe Val  Gly Glu Arg
    1250                1255                1260

Cys Glu  Gly Asp Val Asn Glu  Cys Leu Ser Asn Pro  Cys Asp Pro
    1265                1270                1275

Arg Gly  Thr Gln Asn Cys Val  Gln Arg Val Asn Asp  Phe His Cys
    1280                1285                1290

Glu Cys  Arg Ala Gly His Thr  Gly Arg Arg Cys Glu  Ser Val Ile
    1295                1300                1305

Asn Gly  Cys Arg Gly Lys Pro  Cys Arg Asn Gly Gly  Val Cys Ala
    1310                1315                1320

Val Ala  Ser Asn Thr Ala Arg  Gly Phe Ile Cys Arg  Cys Pro Ala
    1325                1330                1335

Arg Phe  Glu Gly Ala Thr Cys  Glu Asn Asp Ala Arg  Thr Cys Gly
    1340                1345                1350

Ser Leu  Arg Cys Leu Asn Gly  Gly Thr Cys Ile Ser  Gly Pro Arg
    1355                1360                1365

Ser Pro  Thr Cys Leu Cys Leu  Gly Ser Phe Thr Gly  Pro Glu Cys
    1370                1375                1380

Gln Phe  Pro Ala Ser Ser Pro  Cys Val Gly Ser Asn  Pro Cys Tyr
    1385                1390                1395

Asn Gln  Gly Thr Cys Glu Pro  Thr Ser Glu Ser Pro  Phe Tyr Arg
    1400                1405                1410

Cys Leu  Cys Pro Ala Lys Phe  Asn Gly Leu Leu Cys  His Ile Leu
    1415                1420                1425

Asp Tyr  Ser Phe Thr
    1430

<210> SEQ ID NO 2
<211> LENGTH: 5
<212> TYPE: PRT
<213> ORGANISM: Rattus norvegius

<400> SEQUENCE: 2

Asp Leu Gly Pro Gly
1               5


<210> SEQ ID NO 3
<211> LENGTH: 1419
<212> TYPE: PRT
<213> ORGANISM: Rattus norvegicus
```

-continued

<400> SEQUENCE: 3

```
Met Pro Ala Leu Arg Pro Ala Ala Leu Arg Ala Leu Leu Trp Leu Trp
1               5                   10                  15

Leu Cys Gly Ala Gly Pro Ala His Ala Leu Gln Cys Arg Gly Gly Gln
            20                  25                  30

Glu Pro Cys Val Asn Glu Gly Thr Cys Val Thr Tyr His Asn Gly Thr
        35                  40                  45

Gly Tyr Cys Arg Cys Pro Glu Gly Phe Leu Gly Glu Tyr Cys Gln His
    50                  55                  60

Arg Asp Pro Cys Glu Lys Asn Arg Cys Gln Asn Gly Gly Thr Cys Val
65                  70                  75                  80

Thr Gln Ala Met Leu Gly Lys Ala Thr Cys Arg Cys Ala Pro Gly Phe
                85                  90                  95

Thr Gly Glu Asp Cys Gln Tyr Ser Thr Ser His Pro Cys Phe Val Ser
            100                 105                 110

Arg Pro Cys Gln Asn Gly Gly Thr Cys His Met Leu Ser Trp Asp Thr
        115                 120                 125

Tyr Glu Cys Thr Cys Gln Val Gly Phe Thr Gly Lys Gln Cys Gln Trp
    130                 135                 140

Thr Asp Val Cys Leu Ser His Pro Cys Glu Asn Gly Ser Thr Cys Ser
145                 150                 155                 160

Ser Val Ala Asn Gln Phe Ser Cys Arg Cys Pro Ala Gly Ile Thr Gly
                165                 170                 175

Gln Lys Cys Asp Ala Asp Ile Asn Glu Cys Asp Ile Pro Gly Arg Cys
            180                 185                 190

Gln His Gly Gly Thr Cys Leu Asn Leu Pro Gly Ser Tyr Arg Cys Gln
        195                 200                 205

Cys Pro Gln Arg Phe Thr Gly Gln His Cys Asp Ser Pro Tyr Val Pro
    210                 215                 220

Cys Ala Pro Ser Pro Cys Val Asn Gly Gly Thr Cys Arg Gln Thr Gly
225                 230                 235                 240

Asp Phe Thr Ser Glu Cys His Cys Leu Pro Gly Phe Glu Gly Ser Asn
                245                 250                 255

Cys Glu Arg Asn Ile Asp Asp Cys Pro Asn His Lys Cys Gln Asn Gly
            260                 265                 270

Gly Val Cys Val Asp Gly Val Asn Thr Tyr Asn Cys Arg Cys Pro Pro
        275                 280                 285

Gln Trp Thr Gly Gln Phe Cys Thr Glu Asp Val Asp Glu Cys Leu Leu
    290                 295                 300

Gln Pro Asn Ala Cys Gln Asn Gly Gly Thr Cys Thr Asn Arg Asn Gly
305                 310                 315                 320

Gly Tyr Gly Cys Val Cys Val Asn Gly Trp Ser Gly Asp Asp Cys Ser
                325                 330                 335

Glu Asn Ile Asp Asp Cys Ala Phe Ala Ser Cys Thr Pro Gly Ser Thr
            340                 345                 350

Cys Ile Asp Arg Val Ala Ser Phe Ser Cys Leu Cys Pro Glu Gly Lys
        355                 360                 365

Ala Gly Leu Leu Cys His Leu Asp Asp Ala Cys Ile Ser Asn Pro Cys
    370                 375                 380

His Lys Gly Ala Leu Cys Asp Thr Asn Pro Leu Asn Gly Gln Tyr Ile
385                 390                 395                 400

Cys Thr Cys Pro Gln Ala Tyr Lys Gly Ala Asp Cys Thr Glu Asp Val
                405                 410                 415
```

-continued

```
Asp Glu Cys Ala Met Ala Asn Ser Asn Pro Cys Glu His Ala Gly Lys
            420                 425                 430

Cys Val Asn Thr Asp Gly Ala Phe His Cys Glu Cys Leu Lys Gly Tyr
        435                 440                 445

Ala Gly Pro Arg Cys Glu Met Asp Ile Asn Glu Cys His Ser Asp Pro
    450                 455                 460

Cys Gln Asn Asp Ala Thr Cys Leu Asp Lys Ile Gly Gly Phe Thr Cys
465                 470                 475                 480

Leu Cys Met Pro Gly Phe Lys Gly Val His Cys Glu Leu Glu Val Asn
                485                 490                 495

Glu Cys Gln Ser Asn Pro Cys Val Asn Asn Gly Gln Cys Val Asp Lys
            500                 505                 510

Val Asn Arg Phe Gln Cys Leu Cys Pro Pro Gly Phe Thr Gly Pro Val
        515                 520                 525

Cys Gln Ile Asp Ile Asp Asp Cys Ser Ser Thr Pro Cys Leu Asn Gly
    530                 535                 540

Ala Lys Cys Ile Asp His Pro Asn Gly Tyr Glu Cys Gln Cys Ala Thr
545                 550                 555                 560

Gly Phe Thr Gly Thr Leu Cys Asp Glu Asn Ile Asp Asn Cys Asp Pro
                565                 570                 575

Asp Pro Cys His His Gly Gln Cys Gln Asp Gly Ile Asp Ser Tyr Thr
            580                 585                 590

Cys Ile Cys Asn Pro Gly Tyr Met Gly Ala Ile Cys Ser Asp Gln Ile
        595                 600                 605

Asp Glu Cys Tyr Ser Ser Pro Cys Leu Asn Asp Gly Arg Cys Ile Asp
    610                 615                 620

Leu Val Asn Gly Tyr Gln Cys Asn Cys Gln Pro Gly Thr Ser Gly Leu
625                 630                 635                 640

Asn Cys Glu Ile Asn Phe Asp Asp Cys Ala Ser Asn Pro Cys Leu His
                645                 650                 655

Gly Ala Cys Val Asp Gly Ile Asn Arg Tyr Ser Cys Val Cys Ser Pro
            660                 665                 670

Gly Phe Thr Gly Gln Arg Cys Asn Ile Asp Ile Asp Glu Cys Ala Ser
        675                 680                 685

Asn Pro Cys Arg Lys Asp Ala Thr Cys Ile Asn Asp Val Asn Gly Phe
    690                 695                 700

Arg Cys Met Cys Pro Glu Gly Pro His His Pro Ser Cys Tyr Ser Gln
705                 710                 715                 720

Val Asn Glu Cys Leu Ser Ser Pro Cys Ile His Gly Asn Cys Thr Gly
                725                 730                 735

Gly Leu Ser Gly Tyr Lys Cys Leu Cys Asp Ala Gly Trp Val Gly Ile
            740                 745                 750

Asn Cys Glu Val Asp Lys Asn Glu Cys Leu Ser Asn Pro Cys Gln Asn
        755                 760                 765

Gly Gly Thr Cys Asn Asn Leu Val Asn Gly Tyr Arg Cys Thr Cys Lys
    770                 775                 780

Lys Gly Phe Lys Gly Tyr Asn Cys Gln Val Asn Ile Asp Glu Cys Ala
785                 790                 795                 800

Ser Asn Pro Cys Leu Asn Gln Gly Thr Cys Leu Asp Asp Val Ser Gly
                805                 810                 815

Tyr Thr Cys His Cys Met Leu Pro Tyr Thr Gly Lys Asn Cys Gln Thr
            820                 825                 830
```

-continued

```
Val Leu Ala Pro Cys Ser Pro Asn Pro Cys Glu Asn Ala Ala Val Cys
      835                 840                 845

Lys Glu Ala Pro Asn Phe Glu Ser Phe Thr Cys Leu Cys Ala Pro Gly
   850                 855                 860

Trp Gln Gly Gln Arg Cys Thr Val Asp Val Asp Glu Cys Val Ser Lys
865                 870                 875                 880

Pro Cys Met Asn Asn Gly Ile Cys His Asn Thr Gln Gly Ser Tyr Met
                885                 890                 895

Cys Glu Cys Pro Pro Gly Phe Ser Gly Met Asp Cys Glu Glu Asp Ile
            900                 905                 910

Asn Asp Cys Leu Ala Asn Pro Cys Gln Asn Gly Gly Ser Cys Val Asp
        915                 920                 925

Lys Val Asn Thr Phe Ser Cys Leu Cys Leu Pro Gly Phe Val Gly Asp
    930                 935                 940

Lys Cys Gln Thr Asp Met Asn Glu Cys Leu Ser Glu Pro Cys Lys Asn
945                 950                 955                 960

Gly Gly Thr Cys Ser Asp Tyr Val Asn Ser Tyr Thr Cys Thr Cys Pro
                965                 970                 975

Ala Gly Phe His Gly Val His Cys Glu Asn Asn Ile Asp Glu Cys Thr
            980                 985                 990

Glu Ser Ser Cys Phe Asn Gly Gly  Thr Cys Val Asp Gly  Ile Asn Ser
        995                 1000                1005

Phe Ser  Cys Leu Cys Pro Val  Gly Phe Thr Gly Pro  Phe Cys Leu
    1010                1015                1020

His Asp  Ile Asn Glu Cys Ser  Ser Asn Pro Cys Leu  Asn Ser Gly
    1025                1030                1035

Thr Cys  Val Asp Gly Leu Gly  Thr Tyr Arg Cys Thr  Cys Pro Leu
    1040                1045                1050

Gly Tyr  Thr Gly Lys Asn Cys  Gln Thr Leu Val Asn  Leu Cys Ser
    1055                1060                1065

Pro Ser  Pro Cys Lys Asn Lys  Gly Thr Cys Ala Gln  Glu Lys Ala
    1070                1075                1080

Arg Pro  Arg Cys Leu Cys Pro  Pro Gly Trp Asp Gly  Ala Tyr Cys
    1085                1090                1095

Asp Val  Leu Asn Val Ser Cys  Lys Ala Ala Ala Leu  Gln Lys Gly
    1100                1105                1110

Val Pro  Val Glu His Leu Cys  Gln His Ser Gly Ile  Cys Ile Asn
    1115                1120                1125

Ala Gly  Asn Thr His His Cys  Gln Cys Pro Leu Gly  Tyr Thr Gly
    1130                1135                1140

Ser Tyr  Cys Glu Glu Gln Leu  Asp Glu Cys Ala Ser  Asn Pro Cys
    1145                1150                1155

Gln His  Gly Ala Thr Cys Ser  Asp Phe Ile Gly Gly  Tyr Arg Cys
    1160                1165                1170

Glu Cys  Val Pro Gly Tyr Gln  Gly Val Asn Cys Glu  Tyr Glu Val
    1175                1180                1185

Asp Glu  Cys Gln Asn Gln Pro  Cys Gln Asn Gly Gly  Thr Cys Ile
    1190                1195                1200

Asp Leu  Val Asn His Phe Lys  Cys Ser Cys Pro Pro  Gly Thr Arg
    1205                1210                1215

Gly Leu  Leu Cys Glu Glu Asn  Ile Asp Asp Cys Ala  Gly Ala Pro
    1220                1225                1230

His Cys  Leu Asn Gly Gly Gln  Cys Val Asp Arg Ile  Gly Gly Tyr
```

```
    1235                1240                1245

Ser Cys  Arg Cys Leu Pro Gly  Phe Ala Gly Glu Arg  Cys Glu Gly
    1250                1255                1260

Asp Ile  Asn Glu Cys Leu Ser  Asn Pro Cys Ser Ser  Glu Gly Ser
    1265                1270                1275

Leu Asp  Cys Ile Gln Leu Lys  Asn Asn Tyr Gln Cys  Val Cys Arg
    1280                1285                1290

Ser Ala  Phe Thr Gly Arg His  Cys Glu Thr Phe Leu  Asp Val Cys
    1295                1300                1305

Pro Gln  Lys Pro Cys Leu Asn  Gly Gly Thr Cys Ala  Val Ala Ser
    1310                1315                1320

Asn Val  Pro Asp Gly Phe Ile  Cys Arg Cys Pro Pro  Gly Phe Ser
    1325                1330                1335

Gly Ala  Arg Cys Gln Ser Ser  Cys Gly Gln Val Lys  Cys Arg Arg
    1340                1345                1350

Gly Glu  Gln Cys Val His Thr  Ala Ser Gly Pro His  Cys Phe Cys
    1355                1360                1365

Pro Asn  His Lys Asp Cys Glu  Ser Gly Cys Ala Ser  Asn Pro Cys
    1370                1375                1380

Gln His  Gly Gly Thr Cys Tyr  Pro Gln Arg Gln Pro  Pro Tyr Tyr
    1385                1390                1395

Ser Cys  Arg Cys Ser Pro Pro  Phe Trp Gly Ser His  Cys Glu Ser
    1400                1405                1410

Tyr Thr  Ala Pro Thr Ser
    1415


<210> SEQ ID NO 4
<211> LENGTH: 1379
<212> TYPE: PRT
<213> ORGANISM: Mus musculus

<400> SEQUENCE: 4

Met Gly Leu Gly Ala Arg Gly Arg Arg Arg Arg Arg Arg Leu Met Ala
1               5                   10                  15

Leu Pro Pro Pro Pro Pro Pro Met Arg Ala Leu Pro Leu Leu Leu Leu
            20                  25                  30

Leu Ala Gly Leu Gly Ala Ala Ala Pro Pro Cys Leu Asp Gly Ser Pro
        35                  40                  45

Cys Ala Asn Gly Gly Arg Cys Thr His Gln Gln Pro Ser Leu Glu Ala
    50                  55                  60

Ala Cys Leu Cys Leu Pro Gly Trp Val Gly Glu Arg Cys Gln Leu Glu
65                  70                  75                  80

Asp Pro Cys His Ser Gly Pro Cys Ala Gly Arg Gly Val Cys Gln Ser
                85                  90                  95

Ser Val Val Ala Gly Thr Ala Arg Phe Ser Cys Arg Cys Leu Arg Gly
            100                 105                 110

Phe Gln Gly Pro Asp Cys Ser Gln Pro Asp Pro Cys Val Ser Arg Pro
        115                 120                 125

Cys Val His Gly Ala Pro Cys Ser Val Gly Pro Asp Gly Arg Phe Ala
    130                 135                 140

Cys Ala Cys Pro Pro Gly Tyr Gln Gly Gln Ser Cys Gln Ser Asp Ile
145                 150                 155                 160

Asp Glu Cys Arg Ser Gly Thr Thr Cys Arg His Gly Gly Thr Cys Leu
                165                 170                 175
```

-continued

```
Asn Thr Pro Gly Ser Phe Arg Cys Gln Cys Pro Leu Gly Tyr Thr Gly
            180                 185                 190

Leu Leu Cys Glu Asn Pro Val Val Pro Cys Ala Pro Ser Pro Cys Arg
        195                 200                 205

Asn Gly Gly Thr Cys Arg Gln Ser Ser Asp Val Thr Tyr Asp Cys Ala
    210                 215                 220

Cys Leu Pro Gly Phe Glu Gly Gln Asn Cys Glu Val Asn Val Asp Asp
225                 230                 235                 240

Cys Pro Gly His Arg Cys Leu Asn Gly Gly Thr Cys Val Asp Gly Val
                245                 250                 255

Asn Thr Tyr Asn Cys Gln Cys Pro Pro Glu Trp Thr Gly Gln Phe Cys
            260                 265                 270

Thr Glu Asp Val Asp Glu Cys Gln Leu Gln Pro Asn Ala Cys His Asn
        275                 280                 285

Gly Gly Thr Cys Phe Asn Leu Leu Gly Gly His Ser Cys Val Cys Val
    290                 295                 300

Asn Gly Trp Thr Gly Glu Ser Cys Ser Gln Asn Ile Asp Asp Cys Ala
305                 310                 315                 320

Thr Ala Val Cys Phe His Gly Ala Thr Cys His Asp Arg Val Ala Ser
                325                 330                 335

Phe Tyr Cys Ala Cys Pro Met Gly Lys Thr Gly Leu Leu Cys His Leu
            340                 345                 350

Asp Asp Ala Cys Val Ser Asn Pro Cys His Glu Asp Ala Ile Cys Asp
        355                 360                 365

Thr Asn Pro Val Ser Gly Arg Ala Ile Cys Thr Cys Pro Pro Gly Phe
    370                 375                 380

Thr Gly Gly Ala Cys Asp Gln Asp Val Asp Glu Cys Ser Ile Gly Ala
385                 390                 395                 400

Asn Pro Cys Glu His Leu Gly Arg Cys Val Asn Thr Gln Gly Ser Phe
                405                 410                 415

Leu Cys Gln Cys Gly Arg Gly Tyr Thr Gly Pro Arg Cys Glu Thr Asp
            420                 425                 430

Val Asn Glu Cys Leu Ser Gly Pro Cys Arg Asn Gln Ala Thr Cys Leu
        435                 440                 445

Asp Arg Ile Gly Gln Phe Thr Cys Ile Cys Met Ala Gly Phe Thr Gly
    450                 455                 460

Thr Tyr Cys Glu Val Asp Ile Asp Glu Cys Gln Ser Ser Pro Cys Val
465                 470                 475                 480

Asn Gly Gly Val Cys Lys Asp Arg Val Asn Gly Phe Ser Cys Thr Cys
                485                 490                 495

Pro Ser Gly Phe Ser Gly Ser Met Cys Gln Leu Asp Val Asp Glu Cys
            500                 505                 510

Ala Ser Thr Pro Cys Arg Asn Gly Ala Lys Cys Val Asp Gln Pro Asp
        515                 520                 525

Gly Tyr Glu Cys Arg Cys Ala Glu Gly Phe Glu Gly Thr Leu Cys Glu
    530                 535                 540

Arg Asn Val Asp Asp Cys Ser Pro Asp Pro Cys His His Gly Arg Cys
545                 550                 555                 560

Val Asp Gly Ile Ala Ser Phe Ser Cys Ala Cys Ala Pro Gly Tyr Thr
                565                 570                 575

Gly Ile Arg Cys Glu Ser Gln Val Asp Glu Cys Arg Ser Gln Pro Cys
            580                 585                 590

Arg Tyr Gly Gly Lys Cys Leu Asp Leu Val Asp Lys Tyr Leu Cys Arg
```

```
        595                 600                 605

Cys Pro Pro Gly Thr Thr Gly Val Asn Cys Glu Val Asn Ile Asp Asp
    610                 615                 620

Cys Ala Ser Asn Pro Cys Thr Phe Gly Val Cys Arg Asp Gly Ile Asn
625                 630                 635                 640

Arg Tyr Asp Cys Val Cys Gln Pro Gly Phe Thr Gly Pro Leu Cys Asn
                645                 650                 655

Val Glu Ile Asn Glu Cys Ala Ser Ser Pro Cys Gly Glu Gly Gly Ser
            660                 665                 670

Cys Val Asp Gly Glu Asn Gly Phe His Cys Leu Cys Pro Pro Gly Ser
        675                 680                 685

Leu Pro Pro Leu Cys Leu Pro Ala Asn His Pro Cys Ala His Lys Pro
    690                 695                 700

Cys Ser His Gly Val Cys His Asp Ala Pro Gly Gly Phe Arg Cys Val
705                 710                 715                 720

Cys Glu Pro Gly Trp Ser Gly Pro Arg Cys Ser Gln Ser Leu Ala Pro
                725                 730                 735

Asp Ala Cys Glu Ser Gln Pro Cys Gln Ala Gly Gly Thr Cys Thr Ser
            740                 745                 750

Asp Gly Ile Gly Phe Arg Cys Thr Cys Ala Pro Gly Phe Gln Gly His
        755                 760                 765

Gln Cys Glu Val Leu Ser Pro Cys Thr Pro Ser Leu Cys Glu His Gly
    770                 775                 780

Gly His Cys Glu Ser Asp Pro Asp Arg Leu Thr Val Cys Ser Cys Pro
785                 790                 795                 800

Pro Gly Trp Gln Gly Pro Arg Cys Gln Gln Asp Val Asp Glu Cys Ala
                805                 810                 815

Gly Ala Ser Pro Cys Gly Pro His Gly Thr Cys Thr Asn Leu Pro Gly
            820                 825                 830

Asn Phe Arg Cys Ile Cys His Arg Gly Tyr Thr Gly Pro Phe Cys Asp
        835                 840                 845

Gln Asp Ile Asp Asp Cys Asp Pro Asn Pro Cys Leu His Gly Gly Ser
    850                 855                 860

Cys Gln Asp Gly Val Gly Ser Phe Ser Cys Ser Cys Leu Asp Gly Phe
865                 870                 875                 880

Ala Gly Pro Arg Cys Ala Arg Asp Val Asp Glu Cys Leu Ser Ser Pro
                885                 890                 895

Cys Gly Pro Gly Thr Cys Thr Asp His Val Ala Ser Phe Thr Cys Ala
            900                 905                 910

Cys Pro Pro Gly Tyr Gly Gly Phe His Cys Glu Ile Asp Leu Pro Asp
        915                 920                 925

Cys Ser Pro Ser Ser Cys Phe Asn Gly Gly Thr Cys Val Asp Gly Val
    930                 935                 940

Ser Ser Phe Ser Cys Leu Cys Arg Pro Gly Tyr Thr Gly Thr His Cys
945                 950                 955                 960

Gln Tyr Glu Ala Asp Pro Cys Phe Ser Arg Pro Cys Leu His Gly Gly
                965                 970                 975

Ile Cys Asn Pro Thr His Pro Gly Phe Glu Cys Thr Cys Arg Glu Gly
            980                 985                 990

Phe Thr Gly Ser Gln Cys Gln Asn  Pro Val Asp Trp Cys  Ser Gln Ala
        995                 1000                1005

Pro Cys  Gln Asn Gly Gly Arg  Cys Val Gln Thr Gly  Ala Tyr Cys
    1010                1015                1020
```

```
Ile Cys  Pro Pro Gly Trp Ser  Gly Arg Leu Cys Asp  Ile Gln Ser
    1025                 1030                 1035

Leu Pro  Cys Thr Glu Ala Ala  Ala Gln Met Gly Val  Arg Leu Glu
    1040                 1045                 1050

Gln Leu  Cys Gln Glu Gly Gly  Lys Cys Ile Asp Lys  Gly Arg Ser
    1055                 1060                 1065

His Tyr  Cys Val Cys Pro Glu  Gly Arg Thr Gly Ser  His Cys Glu
    1070                 1075                 1080

His Glu  Val Asp Pro Cys Thr  Ala Gln Pro Cys Gln  His Gly Gly
    1085                 1090                 1095

Thr Cys  Arg Gly Tyr Met Gly  Gly Tyr Val Cys Glu  Cys Pro Ala
    1100                 1105                 1110

Gly Tyr  Ala Gly Asp Ser Cys  Glu Asp Asn Ile Asp  Glu Cys Ala
    1115                 1120                 1125

Ser Gln  Pro Cys Gln Asn Gly  Gly Ser Cys Ile Asp  Leu Val Ala
    1130                 1135                 1140

Arg Tyr  Leu Cys Ser Cys Pro  Pro Gly Thr Leu Gly  Val Leu Cys
    1145                 1150                 1155

Glu Ile  Asn Glu Asp Asp Cys  Asp Leu Gly Pro Ser  Leu Asp Ser
    1160                 1165                 1170

Gly Val  Gln Cys Leu His Asn  Gly Thr Cys Val Asp  Leu Val Gly
    1175                 1180                 1185

Gly Phe  Arg Cys Asn Cys Pro  Pro Gly Tyr Thr Gly  Leu His Cys
    1190                 1195                 1200

Glu Ala  Asp Ile Asn Glu Cys  Arg Pro Gly Ala Cys  His Ala Ala
    1205                 1210                 1215

His Thr  Arg Asp Cys Leu Gln  Asp Pro Gly Gly His  Phe Arg Cys
    1220                 1225                 1230

Val Cys  His Pro Gly Phe Thr  Gly Pro Arg Cys Gln  Ile Ala Leu
    1235                 1240                 1245

Ser Pro  Cys Glu Ser Gln Pro  Cys Gln His Gly Gly  Gln Cys Arg
    1250                 1255                 1260

His Ser  Leu Gly Arg Gly Gly  Gly Leu Thr Phe Thr  Cys His Cys
    1265                 1270                 1275

Val Pro  Pro Phe Trp Gly Leu  Arg Cys Glu Arg Val  Ala Arg Ser
    1280                 1285                 1290

Cys Arg  Glu Leu Gln Cys Pro  Val Gly Ile Pro Cys  Gln Gln Thr
    1295                 1300                 1305

Ala Arg  Gly Pro Arg Cys Ala  Cys Pro Pro Gly Leu  Ser Gly Pro
    1310                 1315                 1320

Ser Cys  Arg Val Ser Arg Ala  Ser Pro Ser Gly Ala  Thr Asn Ala
    1325                 1330                 1335

Ser Cys  Ala Ser Ala Pro Cys  Leu His Gly Gly Ser  Cys Leu Pro
    1340                 1345                 1350

Val Gln  Ser Val Pro Phe Phe  Arg Cys Val Cys Ala  Pro Gly Trp
    1355                 1360                 1365

Gly Gly  Pro Arg Cys Glu Thr  Pro Ser Ala Ala
    1370                 1375
```

<210> SEQ ID NO 5
<211> LENGTH: 1170
<212> TYPE: PRT
<213> ORGANISM: Mus musculus

<400> SEQUENCE: 5

```
Met Gln Pro Gln Leu Leu Leu Leu Leu Leu Leu Pro Leu Asn Phe Pro
1               5                   10                  15

Val Ile Leu Thr Arg Glu Leu Leu Cys Gly Gly Ser Pro Glu Pro Cys
            20                  25                  30

Ala Asn Gly Gly Thr Cys Leu Arg Leu Ser Arg Gly Gln Gly Ile Cys
        35                  40                  45

Gln Cys Ala Pro Gly Phe Leu Gly Glu Thr Cys Gln Phe Pro Asp Pro
    50                  55                  60

Cys Arg Asp Thr Gln Leu Cys Lys Asn Gly Gly Ser Cys Gln Ala Leu
65                  70                  75                  80

Leu Pro Thr Pro Pro Ser Ser Arg Ser Pro Thr Ser Pro Leu Thr Pro
                85                  90                  95

His Phe Ser Cys Thr Cys Pro Ser Gly Phe Thr Gly Asp Arg Cys Gln
            100                 105                 110

Thr His Leu Glu Glu Leu Cys Pro Pro Ser Phe Cys Ser Asn Gly Gly
        115                 120                 125

His Cys Tyr Val Gln Ala Ser Gly Arg Pro Gln Cys Ser Cys Glu Pro
    130                 135                 140

Gly Trp Thr Gly Glu Gln Cys Gln Leu Arg Asp Phe Cys Ser Ala Asn
145                 150                 155                 160

Pro Cys Ala Asn Gly Gly Val Cys Leu Ala Thr Tyr Pro Gln Ile Gln
                165                 170                 175

Cys Arg Cys Pro Pro Gly Phe Glu Gly His Thr Cys Glu Arg Asp Ile
            180                 185                 190

Asn Glu Cys Phe Leu Glu Pro Gly Pro Cys Pro Gln Gly Thr Ser Cys
        195                 200                 205

His Asn Thr Leu Gly Ser Tyr Gln Cys Leu Cys Pro Val Gly Gln Glu
    210                 215                 220

Gly Pro Gln Cys Lys Leu Arg Lys Gly Ala Cys Pro Pro Gly Ser Cys
225                 230                 235                 240

Leu Asn Gly Gly Thr Cys Gln Leu Val Pro Glu Gly His Ser Thr Phe
                245                 250                 255

His Leu Cys Leu Cys Pro Pro Gly Phe Thr Gly Leu Asp Cys Glu Met
            260                 265                 270

Asn Pro Asp Asp Cys Val Arg His Gln Cys Gln Asn Gly Ala Thr Cys
        275                 280                 285

Leu Asp Gly Leu Asp Thr Tyr Thr Cys Leu Cys Pro Lys Thr Trp Lys
    290                 295                 300

Gly Trp Asp Cys Ser Glu Asp Ile Asp Glu Cys Glu Ala Arg Gly Pro
305                 310                 315                 320

Pro Arg Cys Arg Asn Gly Gly Thr Cys Gln Asn Thr Ala Gly Ser Phe
                325                 330                 335

His Cys Val Cys Val Ser Gly Trp Gly Gly Ala Gly Cys Glu Glu Asn
            340                 345                 350

Leu Asp Asp Cys Ala Ala Ala Thr Cys Ala Pro Gly Ser Thr Cys Ile
        355                 360                 365

Asp Arg Val Gly Ser Phe Ser Cys Leu Cys Pro Pro Gly Arg Thr Gly
    370                 375                 380

Leu Leu Cys His Leu Glu Asp Met Cys Leu Ser Gln Pro Cys His Val
385                 390                 395                 400

Asn Ala Gln Cys Ser Thr Asn Pro Leu Thr Gly Ser Thr Leu Cys Ile
                405                 410                 415
```

```
Cys Gln Pro Gly Tyr Ser Gly Ser Thr Cys His Gln Asp Leu Asp Glu
            420                 425                 430

Cys Gln Met Ala Gln Gln Gly Pro Ser Pro Cys Glu His Gly Gly Ser
        435                 440                 445

Cys Ile Asn Thr Pro Gly Ser Phe Asn Cys Leu Cys Leu Pro Gly Tyr
    450                 455                 460

Thr Gly Ser Arg Cys Glu Ala Asp His Asn Glu Cys Leu Ser Gln Pro
465                 470                 475                 480

Cys His Pro Gly Ser Thr Cys Leu Asp Leu Leu Ala Thr Phe His Cys
                485                 490                 495

Leu Cys Pro Pro Gly Leu Glu Gly Arg Leu Cys Glu Val Glu Val Asn
            500                 505                 510

Glu Cys Thr Ser Asn Pro Cys Leu Asn Gln Ala Ala Cys His Asp Leu
        515                 520                 525

Leu Asn Gly Phe Gln Cys Leu Cys Leu Pro Gly Phe Thr Gly Ala Arg
    530                 535                 540

Cys Glu Lys Asp Met Asp Glu Cys Ser Ser Thr Pro Cys Ala Asn Gly
545                 550                 555                 560

Gly Arg Cys Arg Asp Gln Pro Gly Ala Phe Tyr Cys Glu Cys Leu Pro
                565                 570                 575

Gly Phe Glu Gly Pro His Cys Glu Lys Glu Val Asp Glu Cys Leu Ser
            580                 585                 590

Asp Pro Cys Pro Val Gly Ala Ser Cys Leu Asp Leu Pro Gly Ala Phe
        595                 600                 605

Phe Cys Leu Cys Arg Pro Gly Phe Thr Gly Gln Leu Cys Glu Val Pro
    610                 615                 620

Leu Cys Thr Pro Asn Met Cys Gln Pro Gly Gln Gln Cys Gln Gly Gln
625                 630                 635                 640

Glu His Arg Ala Pro Cys Leu Cys Pro Asp Gly Ser Pro Gly Cys Val
                645                 650                 655

Pro Ala Glu Asp Asn Cys Pro Cys His His Gly His Cys Gln Arg Ser
            660                 665                 670

Leu Cys Val Cys Asp Glu Gly Trp Thr Gly Pro Glu Cys Glu Thr Glu
        675                 680                 685

Leu Gly Gly Cys Ile Ser Thr Pro Cys Ala His Gly Gly Thr Cys His
    690                 695                 700

Pro Gln Pro Ser Gly Tyr Asn Cys Thr Cys Pro Ala Gly Tyr Met Gly
705                 710                 715                 720

Leu Thr Cys Ser Glu Glu Val Thr Ala Cys His Ser Gly Pro Cys Leu
                725                 730                 735

Asn Gly Gly Ser Cys Ser Ile Arg Pro Glu Gly Tyr Ser Cys Thr Cys
            740                 745                 750

Leu Pro Ser His Thr Gly Arg His Cys Gln Thr Ala Val Asp His Cys
        755                 760                 765

Val Ser Ala Ser Cys Leu Asn Gly Gly Thr Cys Val Asn Lys Pro Gly
    770                 775                 780

Thr Phe Phe Cys Leu Cys Ala Thr Gly Phe Gln Gly Leu His Cys Glu
785                 790                 795                 800

Glu Lys Thr Asn Pro Ser Cys Ala Asp Ser Pro Cys Arg Asn Lys Ala
                805                 810                 815

Thr Cys Gln Asp Thr Pro Arg Gly Ala Arg Cys Leu Cys Ser Pro Gly
            820                 825                 830
```

Tyr Thr Gly Ser Ser Cys Gln Thr Leu Ile Asp Leu Cys Ala Arg Lys
835 840 845

Pro Cys Pro His Thr Ala Arg Cys Leu Gln Ser Gly Pro Ser Phe Gln
850 855 860

Cys Leu Cys Leu Gln Gly Trp Thr Gly Ala Leu Cys Asp Phe Pro Leu
865 870 875 880

Ser Cys Gln Lys Ala Ala Met Ser Gln Gly Ile Glu Ile Ser Gly Leu
885 890 895

Cys Gln Asn Gly Gly Leu Cys Ile Asp Thr Gly Ser Ser Tyr Phe Cys
900 905 910

Arg Cys Pro Pro Gly Phe Gln Gly Lys Leu Cys Gln Asp Asn Val Asn
915 920 925

Pro Cys Glu Pro Asn Pro Cys His His Gly Ser Thr Cys Val Pro Gln
930 935 940

Pro Ser Gly Tyr Val Cys Gln Cys Ala Pro Gly Tyr Glu Gly Gln Asn
945 950 955 960

Cys Ser Lys Val Leu Asp Ala Cys Gln Ser Gln Pro Cys His Asn His
965 970 975

Gly Thr Cys Thr Ser Arg Pro Gly Gly Phe His Cys Ala Cys Pro Pro
980 985 990

Gly Phe Val Gly Leu Arg Cys Glu Gly Asp Val Asp Glu Cys Leu Asp
995 1000 1005

Arg Pro Cys His Pro Ser Gly Thr Ala Ala Cys His Ser Leu Ala
1010 1015 1020

Asn Ala Phe Tyr Cys Gln Cys Leu Pro Gly His Thr Gly Gln Arg
1025 1030 1035

Cys Glu Val Glu Met Asp Leu Cys Gln Ser Gln Pro Cys Ser Asn
1040 1045 1050

Gly Gly Ser Cys Glu Ile Thr Thr Gly Pro Pro Pro Gly Phe Thr
1055 1060 1065

Cys His Cys Pro Lys Gly Phe Glu Gly Pro Thr Cys Ser His Lys
1070 1075 1080

Ala Leu Ser Cys Gly Ile His His Cys His Asn Gly Gly Leu Cys
1085 1090 1095

Leu Pro Ser Pro Lys Pro Gly Ser Pro Pro Leu Cys Ala Cys Leu
1100 1105 1110

Ser Gly Phe Gly Gly Pro Asp Cys Leu Thr Pro Pro Ala Pro Pro
1115 1120 1125

Gly Cys Gly Pro Pro Ser Pro Cys Leu His Asn Gly Thr Cys Thr
1130 1135 1140

Glu Thr Pro Gly Leu Gly Asn Pro Gly Phe Gln Cys Thr Cys Pro
1145 1150 1155

Pro Asp Ser Pro Gly Pro Arg Cys Gln Arg Pro Gly
1160 1165 1170

<210> SEQ ID NO 6
<211> LENGTH: 4293
<212> TYPE: DNA
<213> ORGANISM: Rattus norvegicus

<400> SEQUENCE: 6
atgacaggct tccagggctg ccaggccctg ctgcatctgg ccaaggccgt ggttcgcttg 60
agatgctccc agccaagtgg gacctgcctg aatggaggga ggtgcgaagt ggccaacggc 120
actgaagcct gtgtctgcag cggagcgttc gtgggccagc gatgccagga ccccagccct 180

-continued

```
tgcctcagca caccatgtaa gaatgctgga acgtgctatg ttgtggacca tggcggcatc    240
gtggactatg cctgcagttg ccccctgggt ttctctgggc ccctctgcct gacacctctg    300
gccaatgcct gcctggccaa cccctgccgc aacgggggga cctgtgacct gctcactctc    360
acagaataca agtgccggtg cccgccaggg tggtcaggaa agtcatgtca gcaagccgac    420
ccctgtgcct ccaacccctg tgccaatggt ggccagtgcc tgccctttga gtcttcatac    480
atctgtggct gcccgcccgg cttccatggc cccacctgca gacaagatgt taacgagtgc    540
agccagaacc ctgggttgtg ccgtcatggc ggcacgtgcc acaatgagat tggctcctat    600
cgctgtgcct gccgtgccac ccacactggt ccccactgcg agctgcccta cgtgccctgc    660
agcccctcac cctgccagaa cggaggcacc tgccgcccta cgggggacac cacccacgag    720
tgtgcctgcc tgccaggctt tgctggacag aactgtgaag aaaatgtgga tgactgccca    780
ggaaacaact gcaagaacgg gggtgcctgt gtggacggtg tgaataccta caattgccgc    840
tgcccaccgg agtggacagg tcagtactgc acagaggatg tggacgagtg tcagctcatg    900
cccaacgcct gccagaatgg cggaacctgc cacaactccc acggtggcta caactgcgtg    960
tgtgtcaatg gctggactgg tgaggactgc agtgagaaca ttgatgactg tgccagtgcc   1020
gcctgttttc agggtgccac ctgccatgac cgtgtggctt ccttctactg cgagtgtcca   1080
catgggcgca caggcctgct gtgccacctg aacgatgcgt gtatcagcaa cccctgcaac   1140
gagggctcca actgcgacac caaccctgtc aacggcaagg ccatctgcac ttgcccctcg   1200
gggtacacgg ggccagcctg cagccaggac gtggatgagt gcgctctagg tgccaacccg   1260
tgtgagcacg cgggcaagtg cctcaacaca ctgggctctt tcgagtgtca gtgtctacag   1320
ggctacactg ggccccgctg tgagattgat gtcaacgagt gcatctccaa cccatgtcag   1380
aatgatgcca cgtgcctgga ccagattggg gagtttcagt gtatatgtat gccaggttat   1440
gagggtgtat actgtgagat caacacggac gagtgtgcca gcagcccctg tctacacaat   1500
ggccgctgcg tggacaagat caacgagttc ctgtgtcagt gtcccaaagg cttcagcggg   1560
cacctgtgcc agtatgacgt ggatgagtgc gccagcacac catgcaagaa cggcgccaag   1620
tgcctggatg ggcccaacac ctacacctgc gtgtgcacag aaggttacac ggggacccac   1680
tgcgaggtgg acattgacga gtgtgaccct gacccctgtc actatggttt gtgcaaggat   1740
ggtgtggcca cctttacctg cctctgccag ccaggctaca caggccatca ctgtgagacc   1800
aacattaatg agtgtcacag ccagccgtgc cgccatggcg gcacctgcca ggaccgtgac   1860
aactactacc tctgcttatg cctcaagggg accacaggac ccaactgtga gatcaatctg   1920
gatgactgtg cgagcaaccc ctgtgactct ggcacgtgtc tggacaagat cgatggctac   1980
gagtgtgcgt gcgagccagg ctacacaggg agcatgtgta atgtcaacat tgacgaatgt   2040
gcgggcagcc cctgccacaa cgggggcacc tgtgaggatg gcatcgccgg cttcacttgc   2100
cgctgccccg agggctacca cgaccctacg tgcctgtctg aggtcaacga gtgcaacagt   2160
aacccctgca tccatggagc ttgccgggat ggcctcaatg gatacaaatg tgactgtgcc   2220
cctgggtgga gtgggacaaa ctgtgacatc aacaacaatg agtgtgagtc caacccttgt   2280
gtcaacggtg gcacctgcaa agacatgacc agtggctacg tatgcacctg ccgagaaggc   2340
ttcagtggcc ctaactgcca gaccaacatt aacgaatgtg cttccaaccc ctgcctgaac   2400
cagggcacct gcattgatga tgtcgctggg tacaaatgca actgccctct gccctataca   2460
ggagccacat gtgaggtggt gttggcccca tgtgccacca gcccctgcaa aaacagtggg   2520
```

-continued

```
gtatgcaagg agtctgagga ctatgagagc ttttcctgtg tctgtcccac aggctggcaa   2580
ggtcaaacct gcgagatcga catcaatgag tgtgtgaaaa gcccgtgtcg ccatggtgcc   2640
tcttgccaga acaccaatgg cagctaccgc tgcctctgcc aggctggcta cacgggtcgc   2700
aactgcgaga gtgacatcga tgactgccga cccaacccat gtcacaacgg gggttcctgc   2760
actgacgggg tcaacgcggc cttctgcgac tgcctgcccg gcttccaggg tgccttctgt   2820
gaggaggaca tcaacgaatg cgccagcaat ccatgccaaa atggcgccaa ctgcactgac   2880
tgcgtggaca gctacacgtg cacctgcccc acgggcttca atggcatcca ttgcgagaac   2940
aacacacctg actgtaccga gagctcctgt ttcaatggtg gcacctgtgt ggatggtatc   3000
aactccttca cctgtctgtg cccacctggc ttcacgggca gctactgcca gtatgacgtc   3060
aatgagtgtg actcacggcc ctgtctgcat ggtggcacct gccaagacag ctatggtacc   3120
tataagtgta cctgcccaca gggctacact ggtctcaact gccagaacct tgtgcgctgg   3180
tgtgactcag ctccctgcaa gaatggcggc aagtgctggc agaccaacac acagtaccac   3240
tgcgagtgcc gcagcggctg gactggcttc aactgcgacg tgctcagtgt gtcctgcgag   3300
gtggctgcac agaagcgagg catcgatgtc actctcctat gccagcacgg agggctctgt   3360
gtggatgagg aagacaagca ttactgccac tgccaggcag gatacacggg cagctactgt   3420
gaggacgagg tggacgagtg ctcacctaat ccctgccaga acggagccac ctgcactgac   3480
tatctcggtg gcttttcctg caagtgtgtg gctgggtacc atggctctaa ctgctctgag   3540
gagatcaacg agtgcctatc ccaaccctgc cagaatgggg gtacctgcat tgatctgacc   3600
aacacctaca agtgctcctg ccccaggggc acacagggtg tacactgtga gatcaacgtc   3660
gatgactgcc atcctcccct agaccctgct tcccgaagcc ccaaatgctt caataatggc   3720
acctgcgtgg accaggtggg tggctatacc tgcacctgcc cgccaggctt cgtcggggag   3780
cggtgcgagg gcgatgtcaa tgagtgtctc tccaacccct gtgacccacg tggcacccag   3840
aactgcgtgc agcgtgttaa tgacttccac tgcgagtgcc gggctggcca cactggacgc   3900
cgctgtgagt cggtcattaa tggctgcagg ggcaaaccat gcaggaatgg aggtgtctgt   3960
gctgtggcct ccaacaccgc ccgtggattc atctgtaggt gccctgcggg cttcgagggt   4020
gccacttgtg aaaatgacgc ccgcacttgt ggcagtttgc gctgcctcaa cggtggtacg   4080
tgcatctcag gcccacgcag tcccacctgc ctatgcctgg gctccttcac tggccctgaa   4140
tgccagttcc cagccagcag cccctgtgtg ggtagcaacc cctgctacaa tcagggcacc   4200
tgtgagccca catccgagag ccctttctac cgctgtctat gccctgccaa attcaacggg   4260
ctgctgtgcc acatcctgga ctacagcttc aca                                4293
```

<210> SEQ ID NO 7
<211> LENGTH: 4257
<212> TYPE: DNA
<213> ORGANISM: Rattus norvegicus

<400> SEQUENCE: 7

```
atgcccgctc tgcgtcccgc cgcgctgcgg gcgctgctgt ggctctggct gtgcggcgcg     60
ggccccgcgc acgctttgca gtgtcgaggt ggtcaagagc cctgtgtaaa tgaggggacc    120
tgtgttacct accacaacgg cacaggctac tgccgatgtc cagagggctt cttgggagaa    180
tattgtcaac atcgagaccc ttgtgagaag aaccgctgtc agaatggtgg tacttgtgtg    240
acgcaggcca tgttgggaaa agccacctgt cgatgtgctc cagggttcac aggggaggac    300
tgccaatact cgacctctca cccctgtttt gtttcccgcc cctgtcagaa tggaggtacc    360
```

-continued

```
tgccacatgc tcagctggga cacctatgag tgcacctgtc aagttggctt cacaggaaag    420
cagtgtcagt ggacagatgt ctgtctgtct catccctgtg aaaatggaag cacctgtagc    480
tctgtggcca accagttctc ctgcagatgt cctgcaggca tcacaggcca gaagtgtgac    540
gccgacatca atgaatgtga cattccagga cgctgccaac atggtggcac ctgcctcaac    600
cttcctgggt cctaccgatg ccaatgccct cagcggttca caggccagca ctgtgacagc    660
ccttacgtgc cctgtgcacc ctcaccctgc gtcaatggag gcacctgccg tcagactgga    720
gacttcactt ctgaatgcca ttgcctgcca ggctttgaag ggagcaactg cgagcggaat    780
atcgacgact gccctaacca caagtgtcag aatggagggg tgtgtgtgga tggcgtcaat    840
acttacaact gccgctgccc ccctcagtgg actgggcagt tctgcacaga agacgtggat    900
gagtgtctgc tgcagcccaa tgcttgtcag aatggaggca cttgcaccaa ccgcaacgga    960
ggctacggct gcgtgtgcgt gaacggctgg agtggggatg actgcagcga gaacatcgat   1020
gactgtgcct tcgcttcctg cacgccaggc tccacctgta ttgaccgtgt ggcctccttc   1080
tcctgccttt gtccagaggg aaaggcaggg ctcctgtgtc atctggatga tgcctgtatc   1140
agcaaccctt gtcacaaggg ggcgctgtgt gataccaacc ccctgaatgg gcagtacatt   1200
tgcacctgcc cacaggcgta caagggcgct gactgcacag aagacgtgga tgagtgtgct   1260
atggccaaca gtaacccttg tgagcatgca ggaaagtgtg tgaatacaga tggcgccttc   1320
cactgcgagt gtctgaaggg ctacgcaggg cctcgctgtg agatggacat caacgagtgt   1380
cactcagacc cctgtcagaa cgacgccacc tgcctggata agattggagg cttcacctgt   1440
ctctgcatgc cgggtttcaa aggtgtgcat tgtgaactgg aggtgaatga atgccagagc   1500
aacccgtgtg taaacaatgg gcagtgtgtg gacaaagtca atcgcttcca gtgtctgtgt   1560
ccccctggtt tcacaggacc agtgtgccag atcgacattg acgactgctc cagtactccc   1620
tgcctgaatg gggccaagtg catcgatcac ccgaatggct atgaatgcca gtgtgccaca   1680
ggattcactg gcacactgtg tgatgagaac atcgacaact gtgacccgga tccttgccac   1740
catggccagt gccaggatgg gattgactcc tacacctgca tctgcaaccc cgggtacatg   1800
ggagccatct gtagtgacca gattgatgaa tgctacagca gcccctgcct gaatgatgga   1860
cgctgcatcg acctggtgaa cggctaccag tgcaactgcc aaccgggtac ctcaggcctt   1920
aattgtgaaa ttaattttga tgactgtgcc agcaaccctt gtctgcacgg agcctgtgtg   1980
gacggcatca accgttacag ttgtgtgtgc tctccgggat tcacagggca gaggtgcaac   2040
atagacattg atgagtgtgc ctccaacccc tgtcgcaagg atgcgacgtg catcaatgac   2100
gtgaatggtt tccggtgtat gtgccctgag ggaccacacc atcccagctg ctactcacag   2160
gtgaacgagt gtttgagcag tccctgcatc catggaaact gtactggagg tctcagtggc   2220
tataagtgcc tctgcgatgc aggctgggtt ggtatcaact gcgaagtgga caaaaatgag   2280
tgtctttcta acccgtgcca gaatggaggg acatgtaata acctggtgaa tggctacagg   2340
tgtacatgca agaaggggtt caaaggctat aactgccagg tgaacataga tgagtgtgcc   2400
tcgaacccgt gtctgaacca agggacctgc ctcgatgacg tcagtggcta cacctgccac   2460
tgcatgctgc cttacacagg caagaattgt caaacggtgt tggcgccctg ctcccctaac   2520
ccgtgtgaga acgctgcagt ttgtaaagag gcacccaact ttgagagctt cacctgcctg   2580
tgtgcccctg gctggcaagg tcagcgctgt acagttgacg ttgatgagtg tgtctccaag   2640
ccgtgtatga acaatggcat ctgccataat actcagggca gctacatgtg cgagtgccct   2700
```

-continued

```
cccggcttca gtggtatgga ctgtgaggag gacatcaatg actgccttgc caacccctgc   2760

cagaacggag gctcctgtgt ggacaaagtg aacaccttct cctgcctgtg ccttcctggc   2820

ttcgtagggg acaagtgcca aacagacatg aatgaatgtc tgagcgagcc ctgtaagaat   2880

ggggggacct gctctgacta cgtcaacagc tacacctgca cgtgccctgc gggcttccat   2940

ggagtccact gtgaaaacaa catcgatgag tgcactgaga gctcctgttt caatggcggc   3000

acgtgtgttg atgggatcaa ctctttctct tgcttatgcc ctgtgggttt cactggtccc   3060

ttctgcctcc atgatatcaa tgagtgcagc tctaacccgt gcctgaattc gggaacgtgt   3120

gttgatggcc tgggtaccta ccgatgcacc tgtcccttgg gctacactgg gaaaaactgt   3180

cagaccctgg tgaacctctg cagcccctct ccatgtaaaa acaaaggaac ttgtgctcag   3240

gaaaaggcaa ggccacgctg cctgtgtccg cctggatggg atggcgcata ctgtgatgtg   3300

ctcaatgtgt cctgtaaggc ggcagccttg cagaaaggag tacctgttga acacttgtgc   3360

cagcactcgg gtatctgtat caatgctggc aacacgcatc actgccagtg cccccctgggc  3420

tacacgggga gctactgcga ggaacagctt gacgagtgtg cgtccaatcc atgccagcat   3480

ggtgccacct gcagtgactt catcggagga tacagatgtg agtgtgttcc agggtatcag   3540

ggtgtcaact gtgagtatga agtggacgag tgccagaacc agccctgtca gaacggaggc   3600

acctgcatcg acctcgtgaa ccatttcaag tgctcgtgcc caccaggcac ccggggcctg   3660

ctttgtgaag agaacattga tgactgtgct ggggcccccc actgccttaa tggtggccag   3720

tgtgtggacc ggattggagg ctacagttgt cgctgtttgc ctggctttgc tggggagcgg   3780

tgtgaggggg acatcaatga atgcctgtcc aatccttgca gctcagaggg cagcctggac   3840

tgcattcagc tcaaaaataa ctaccagtgt gtctgccgca gcgccttcac aggccgacac   3900

tgcgaaacct tcctagatgt gtgtccccag aagccttgcc tgaatggagg gacttgtgct   3960

gtggctagca acgtgcctga tggcttcatt tgtcgttgtc cccagggtt ctccggggca    4020

agatgccaga gcagctgtgg acaagtgaag tgcagaagag gggagcagtg tgtgcacacc   4080

gcctcgggac cccactgctt ctgcccgaac cacaaggact gcgagtcagg ttgcgctagt   4140

aacccctgcc agcacggagg cacctgctac cctcagcgcc agcctcctta ctactcttgc   4200

cgctgctccc caccgttctg ggcagccac tgcgagagct acacagcccc caccagc       4257
```

<210> SEQ ID NO 8
<211> LENGTH: 4137
<212> TYPE: DNA
<213> ORGANISM: Mus musculus

<400> SEQUENCE: 8

```
atggggctgg gggcccgggg ccgccgccgc cgtcgtcgcc tgatggcctt gccaccgcca     60

ccaccgccca tgcgggcgct gcccctgctg ctgctgctag cggggctggg ggctgcagca    120

ccccccttgtc tggatggaag cccatgtgca aatggaggtc ggtgcaccca ccagcagccc   180

tccctggagg ctgcttgcct gtgcctgcca ggctgggtgg gtgagcggtg ccagctggaa    240

gacccttgcc actcaggccc ttgtgctggc cgaggcgttt gccagagttc agtggtggcg    300

ggcaccgccc gattctcctg tcgttgtctc cgtggcttcc aaggcccaga ctgctcccag    360

ccagacccct gcgtcagcag gccctgtgtt catggtgccc cctgctcagt ggggccggat    420

ggccgatttg cctgtgcctg cccacctggc taccagggtc aaagctgcca aagtgacata    480

gatgagtgcc gatctggtac aacttgccgt catggtggta cctgtctcaa tacacctgga    540

tccttccgct gccagtgtcc tcttggttat acagggctgc tgtgtgagaa ccccgtagtg    600
```

-continued

```
ccctgtgccc cttccccgtg tcgtaatggt ggcacctgta ggcagagcag tgatgtcaca    660
tatgactgtg cttgccttcc tggcttcgag ggccagaact gtgaagtcaa cgtggatgac    720
tgtcctggac atcggtgtct caatgggggga acgtgtgtag acggtgtcaa tacttacaac    780
tgccagtgcc ctccggagtg gacaggccag ttctgtacag aagatgtgga tgagtgtcag    840
ctgcagccca atgcctgcca caatgggggt acctgcttca acctactggg tggccacagc    900
tgtgtatgtg tcaatggctg gacgggtgag agctgcagtc agaatatcga tgactgtgct    960
acagccgtgt gtttccatgg ggccacctgc catgaccgtg tggcctcttt ctactgtgcc   1020
tgccctatgg ggaagacagg cctcttgtgt catctggatg atgcatgtgt cagcaacccc   1080
tgccatgagg atgctatctg tgacacaaac cctgtgagtg gccgggccat ctgcacctgc   1140
ccacctggct tcactggagg ggcatgtgac caggatgtgg atgagtgctc gattggtgcc   1200
aacccctgtg aacatttggg tcggtgtgtg aatacacagg gctcattctt gtgccaatgt   1260
ggccgtggct atactggacc tcgctgtgag actgatgtca atgagtgtct ctccgggccc   1320
tgccgcaacc aggccacgtg tcttgaccga attggccagt ttacttgcat ctgcatggca   1380
ggcttcacag ggacctactg tgaggtggac atcgacgaat gtcagagcag cccatgtgtc   1440
aatggtggtg tctgcaagga cagagtcaat ggcttcagct gcacctgccc atcaggattc   1500
agtgggtcca tgtgtcagct ggatgtggat gagtgtgcaa gcactccctg ccggaatggt   1560
gccaagtgtg tggaccagcc tgacggctat gagtgtcgct gtgcagaggg ctttgagggc   1620
actttgtgtg agcgaaacgt ggatgactgc tctccggatc cctgccacca cgggcgctgt   1680
gtcgatggca ttgctagctt ctcgtgtgct tgtgccccag gctatacggg catacgctgt   1740
gagagccagg tggatgagtg ccgcagccag ccctgtcgat atgggggcaa atgtctagac   1800
ttggtggaca agtacctctg ccgttgtcct cccggaacca caggtgtgaa ctgtgaagtc   1860
aacattgatg actgtgccag taacccctgt acctttggag tttgccgtga tggcatcaac   1920
cgttatgact gtgtctgtca gcctggattc acagggcccc tctgcaacgt ggagatcaat   1980
gagtgtgcat ccagcccatg tggagagggt ggctcctgtg tggatgggga aaatggcttc   2040
cactgcctct gtccacctgg ctccctgcct ccactttgcc tacctgcgaa ccatccctgt   2100
gcccacaagc cctgtagtca tggagtctgc catgatgcac caggcgggtt ccgctgtgtt   2160
tgtgagcccg ggtggagtgg ccctcgctgt agccagagcc tggctccaga tgcctgtgag   2220
tcccagccct gccaggctgg tggcacctgc accagtgatg gaataggctt tcgctgcacc   2280
tgtgccccctg gattccaggg ccatcagtgt gaggtgctgt ccccctgtac tccaagcctc   2340
tgtgagcacg gaggccactg tgagtctgac cctgaccggc tgactgtctg ttcctgtccc   2400
ccaggctggc aaggcccacg atgccagcag gatgtggatg aatgtgccgg tgcctcaccc   2460
tgcggccccc atggtacctg caccaacctg ccagggaatt tcaggtgcat ctgccacagg   2520
ggatacactg gccccttctg tgatcaagac attgacgact gtgaccccaa cccgtgcctc   2580
catggtggct cctgccagga tggcgtgggc tccttttcct gttcttgcct cgacggcttt   2640
gctggtcctc gctgtgcccg agatgtggac gaatgtctga gcagcccctg tggccctggc   2700
acctgtactg atcacgtggc ctccttcacc tgtgcctgtc cacctggtta tggaggcttc   2760
cactgtgaga ttgacttgcc ggactgcagc cccagttcct gcttcaatgg agggacctgt   2820
gtggatggcg tgagctcctt cagctgtctg tgtcgccccg gctacacagg cacacactgc   2880
caatacgagg ctgaccccctg cttttcccgg ccctgtctgc acgggggcat ctgcaacccc   2940
```

-continued

```
acccacccag gatttgaatg cacctgccgg gagggcttca ctgggagtca gtgtcagaac   3000

ccagtggact ggtgcagcca ggcaccctgt cagaatgggg gtcgctgtgt ccagactggg   3060

gcttactgca tttgtccacc tggatggagt ggccgcctgt gcgacataca aagcctgccc   3120

tgcacggagg ccgcagccca gatgggggtg aggttggagc agctgtgtca ggaaggtgga   3180

aagtgcatag acaagggccg ctcccactac tgtgtgtgtc cagagggccg tacgggtagt   3240

cactgtgaac acgaggtgga tccctgcacg gcccagcctt gccagcacgg gggcacttgc   3300

cgtggttaca tgggggggcta tgtgtgtgag tgtccagctg gctatgctgg tgacagttgt   3360

gaggataata tagatgagtg tgcttcccag ccctgccaga acggaggctc ctgtatcgat   3420

cttgtggccc gctatctctg ttcctgtccc cctggcacac tgggagttct ctgtgagatc   3480

aatgaggacg actgtgacct aggcccatcc ttggactcag gcgttcagtg cctacacaat   3540

ggcacctgtg tggacctggt gggtggcttc cgctgtaact gtcccccagg atacacaggt   3600

ctgcactgtg aggcagacat caatgagtgt cgcccgggtg cctgccatgc agcgcatact   3660

cgggactgcc tacaagatcc aggtgggcat ttccgctgcg tctgccatcc tggcttcaca   3720

gggcctcgct gtcagattgc tctgtccccc tgtgagtccc agccatgtca gcatggaggc   3780

cagtgccgtc acagcctagg ccgtggaggt gggctgacct tcacctgtca ctgtgtcccg   3840

ccattctggg gtctgcgttg tgagcgggtg gcacgctctt gccgagagct gcagtgccca   3900

gtgggtatcc catgccagca gacagcccgt ggaccacgct gcgcttgtcc tccggggctg   3960

tccgggccct cctgccgggt ttctagggcg tcaccctcag gagctactaa cgccagctgc   4020

gcctctgccc cttgtctgca tggggggctca tgcctacctg tacagagtgt ccctttcttc   4080

cgctgtgtgt gcgctccggg ctggggcggc ccgcgttgtg agacccccttc cgcagcc      4137
```

```
<210> SEQ ID NO 9
<211> LENGTH: 3510
<212> TYPE: DNA
<213> ORGANISM: Mus musculus

<400> SEQUENCE: 9
```

```
atgcagcccc agttgctgct gctgctgctc ttgccactca atttccctgt catcctgacc     60

agagagcttc tgtgtggagg atccccagag ccctgtgcca acggaggcac ctgcctgagg    120

ctatctcagg gacaagggat ctgccagtgt gcccctggat ttctgggtga gacttgccag    180

tttcctgacc cctgcaggga tacccaactc tgcaagaatg gtggcagctg ccaagccctg    240

ctccccacac ccccaagctc ccgtagtcct acttctccac tgacccctca cttctcctgc    300

acctgcccct ctggcttcac cggtgatcga tgccaaaccc atctggaaga gctctgtcca    360

ccttctttct gttccaacgg gggtcactgc tatgttcagg cctcaggccg cccacagtgc    420

tcctgcgagc ctgggtggac aggtgagcaa tgccagctcc gagacttctg ctcagccaac    480

ccctgtgcca acggaggcgt gtgcctggcc acatacccccc agatccagtg ccgctgtcca    540

cctgggttcg agggtcacac ctgtgaacgc gacatcaacg agtgcttcct ggagccggga    600

ccctgccctc agggcacctc ctgccataac accttgggtt cctaccagtg tctctgccct    660

gtggggcagg aaggtcccca gtgcaagctc aggaagggag cctgccctcc tggaagctgt    720

ctcaatgggg gcacctgcca gctggtccca gagggacact ccacctttca tctctgcctc    780

tgtcccccag gtttcacggg gctggactgt gagatgaacc cagatgactg tgtcaggcac    840

cagtgtcaga acggggccac ctgtctggat gggctggata cctacacctg cctctgcccc    900

aagacatgga agggctggga ctgctctgaa gatatagatg aatgtgaagc ccggggtccc    960
```

-continued

```
cctcgctgca ggaacggtgg cacctgccag aacacagctg gcagctttca ctgtgtgtgc   1020
gtgagtggct ggggcggtgc aggttgtgag gagaacctgg atgactgtgc agctgccacc   1080
tgtgccccgg gatccacctg catcgaccgt gtgggctctt tctcctgcct ctgcccacct   1140
ggacgcacag gcctcctgtg ccacctggaa gacatgtgtt tgagtcagcc gtgccacgtg   1200
aatgcccagt gcagcaccaa ccctctgaca ggctccaccc tctgcatatg ccagcctggc   1260
tactcaggat ccacctgtca ccaagatctg gatgagtgcc aaatggccca gcaaggaccc   1320
agtccctgcg aacatggcgg ctcctgcatc aacacccctg gctccttcaa ctgcctctgc   1380
ctgcctggtt acacgggctc ccgctgtgaa gctgaccaca atgagtgcct gtcacagccc   1440
tgccacccag gcagcacctg cctggacctg cttgcaacct tccactgcct ctgcccacca   1500
ggcttggaag ggaggctctg tgaggtggag gtcaatgagt gcacctctaa tccctgcctg   1560
aaccaagctg cctgccatga cctgctcaac ggcttccagt gcctctgcct tcctggattc   1620
accggcgccc gatgtgagaa agacatggac gagtgtagca gcacccccctg tgccaatggg   1680
gggcgctgcc gagaccagcc tggagccttc tactgcgagt gtctcccagg ctttgaaggg   1740
ccacactgtg agaaagaagt ggacgaatgt ctgagtgacc cctgccccgt gggagccagc   1800
tgccttgatc tccccggagc attcttctgc ctctgccgtc ctggtttcac aggtcaactt   1860
tgtgaggttc ccttgtgcac ccccaacatg tgccaacctg gacagcaatg ccaaggtcag   1920
gaacacagag cccccctgcct ctgccctgac ggaagtcctg gctgtgttcc tgccgaggac   1980
aactgcccct gtcaccatgg ccattgccag agatccttgt gtgtgtgtga tgagggctgg   2040
actggaccag aatgcgagac agaactgggt ggctgcatct ccacaccctg tgcccatggg   2100
gggacctgcc acccacagcc gtctggctac aactgtacct gccctgcagg ctacatgggg   2160
ttgacctgta gtgaggaggt gacagcttgt cactcagggc cctgtctcaa tggtggctct   2220
tgcagcatcc gtcctgaggg ctattcctgc acctgccttc caagtcacac aggtcgccac   2280
tgccagactg ccgtggacca ctgtgtgtct gcctcgtgcc tcaatggggg tacctgtgtg   2340
aacaagcctg gcactttctt ctgcctctgt gccactggct tccaggggct gcactgtgag   2400
gagaagacta accccagctg tgcagacagc cccctgcagga acaaggcaac ctgccaagac   2460
acacctcgag ggcccgctg cctctgcagc cctggctata caggaagcag ctgccagact   2520
ctgatagact tgtgtgcccg gaagccctgt ccacacactg ctcgatgcct ccagagtggg   2580
ccctcgttcc agtgcctgtg cctccaggga tggacagggg ctctctgtga cttcccactg   2640
tcctgccaga tggccgcaat gagccaaggc atagagatct ctggcctgtg ccagaatgga   2700
ggcctctgta ttgacacggg ctcctcctat ttctgccgct gccctcctgg attccaaggc   2760
aagttatgcc aggataaatat gaacccctgc gagcccaatc cctgccatca cgggtctacc   2820
tgtgtgcctc agcccagtgg ctatgtctgc cagtgtgccc caggctatga gggacagaac   2880
tgctcaaaag tacttgaagc ttgtcagtcc cagccctgcc acaaccacgg aacctgtacc   2940
tccaggcctg gaggcttcca ctgtgcctgc cctccaggct tcgtgggact gcgctgtgag   3000
ggagatgtgg atgagtgtct ggaccggccc tgtcacccct cgggcactgc agcttgccac   3060
tctttagcca acgccttcta ctgccagtgt ctgcctgggc acacaggcca gcggtgtgag   3120
gtggagatgg acctctgtca gagccaaccc tgctccaatg gaggatcctg tgagatcaca   3180
acagggccac cccctggctt cacctgtcac tgccccaagg gttttgaagg ccccacctgc   3240
agccacaaag ccctttcctg cggcatccat cactgccaca atggaggcct atgtctgccc   3300
```

```
tcccctaagc cagggtcacc accactctgt gcctgcctca gtggttttgg gggccctgac   3360

tgtctgacac ctccagctcc accgggctgc ggtcccccct caccctgcct gcacaatggt   3420

acctgcactg agacccctgg gttgggcaac ccgggctttc aatgcacctg ccctcctgac   3480

tctccagggc cccggtgtca aaggccaggg                                    3510
```

<210> SEQ ID NO 10
<211> LENGTH: 15
<212> TYPE: DNA
<213> ORGANISM: Mus musculus

<400> SEQUENCE: 10

```
gatctgggcc cgggc                                                      15
```

<210> SEQ ID NO 11
<211> LENGTH: 4299
<212> TYPE: DNA
<213> ORGANISM: Homo sapiens

<400> SEQUENCE: 11

```
atgccgccgc tcctggcgcc cctgctctgc ctggcgctgc tgcccgcgct cgccgcacga     60

ggcccgcgat gctcccagcc cggtgagacc tgcctgaatg gcgggaagtg tgaagcggcc    120

aatggcacgg aggcctgcgt ctgtggcggg gccttcgtgg gcccgcgatg ccaggacccc    180

aacccgtgcc tcagcacccc ctgcaagaac gccgggacat gccacgtggt ggaccgcaga    240

ggcgtggcag actatgcctg cagctgtgcc ctgggcttct ctgggcccct ctgcctgaca    300

cccctggaca atgcctgcct caccaacccc tgccgcaacg gggcacctg cgacctgctc    360

acgctgacgg agtacaagtg ccgctgcccg cccggctggt cagggaaatc gtgccagcag    420

gctgacccgt gcgcctccaa cccctgcgcc aacggtggcc agtgcctgcc cttcgaggcc    480

tcctacatct gccactgccc acccagcttc catggcccca cctgccggca ggatgtcaac    540

gagtgtggcc agaagcccgg gctttgccgc cacggaggca cctgccacaa cgaggtcggc    600

tcctaccgct gcgtctgccg cgccacccac actggcccca actgcgagcg gccctacgtg    660

ccctgcagcc cctcgccctg ccagaacggg ggcacctgcc gccccacggg cgacgtcacc    720

cacgagtgtg cctgcctgcc aggcttcacc ggccagaact gtgaggaaaa tatcgacgat    780

tgtccaggaa acaactgcaa gaacgggggt gcctgtgtgg acggcgtgaa cacctacaac    840

tgccgctgcc cgccagagtg gacaggtcag tactgtaccg aggatgtgga cgagtgccag    900

ctgatgccaa atgcctgcca gaacggcggg acctgccaca acacccacgg tggctacaac    960

tgcgtgtgtg tcaacggctg gactggtgag gactgcagcg agaacattga tgactgtgcc   1020

agcgccgcct gcttccacgg cgccacctgc catgaccgtg tggcctcctt ctactgcgag   1080

tgtccccatg gccgcacagg tctgctgtgc cacctcaacg acgcatgcat cagcaacccc   1140

tgtaacgagg gctccaactg cgacaccaac cctgtcaatg gcaaggccat ctgcacctgc   1200

ccctcggggt acacgggccc ggcctgcagc caggacgtgg atgagtgctc gctgggtgcc   1260

aacccctgcg agcatgcggg caagtgcatc aacacgctgg gctccttcga gtgccagtgt   1320

ctgcagggct acacgggccc ccgatgcgag atcgacgtca acgagtgcgt ctcgaacccg   1380

tgccagaacg acgccacctg cctggaccag attggggagt tccagtgcat ctgcatgccc   1440

ggctacgagg gtgtgcactg cgaggtcaac acagacgagt gtgccagcag cccctgcctg   1500

cacaatggcc gctgcctgga caagatcaat gagttccagt gcgagtgccc cacgggcttc   1560

actgggcatc tgtgccagta cgatgtggac gagtgtgcca gcacccccctg caagaatggt   1620
```

-continued

```
gccaagtgcc tggacggacc caacacttac acctgtgtgt gcacggaagg gtacacgggg   1680
acgcactgcg aggtggacat cgatgagtgc gaccccgacc cctgccacta cggctcctgc   1740
aaggacggcg tcgccacctt cacctgcctc tgccgcccag gctacacggg ccaccactgc   1800
gagaccaaca tcaacgagtg ctccagccag ccctgccgcc acgggggcac ctgccaggac   1860
cgcgacaacg cctacctctg cttctgcctg aaggggacca caggacccaa ctgcgagatc   1920
aacctggatg actgtgccag cagcccctgc gactcgggca cctgtctgga caagatcgat   1980
ggctacgagt gtgcctgtga gccgggctac acagggagca tgtgtaacat caacatcgat   2040
gagtgtgcgg gcaacccctg ccacaacggg ggcacctgcg aggacggcat caatggcttc   2100
acctgccgct gccccgaggg ctaccacgac cccacctgcc tgtctgaggt caatgagtgc   2160
aacagcaacc cctgcgtcca cggggcctgc cgggacagcc tcaacgggta caagtgcgac   2220
tgtgaccctg ggtggagtgg gaccaactgt gacatcaaca acaatgagtg tgaatccaac   2280
ccttgtgtca acggcggcac ctgcaaagac atgaccagtg gctacgtgtg cacctgccgg   2340
gagggcttca gcggtcccaa ctgccagacc aacatcaacg agtgtgcgtc caacccatgt   2400
ctgaaccagg gcacgtgtat tgacgacgtt gccgggtaca agtgcaactg cctgctgccc   2460
tacacaggtg ccacgtgtga ggtggtgctg gccccgtgtg cccccagccc ctgcagaaac   2520
ggcggggagt gcaggcaatc cgaggactat gagagcttct cctgtgtctg ccccacgggc   2580
tggcaagcag ggcagacctg tgaggtcgac atcaacgagt gcgttctgag cccgtgccgg   2640
cacggcgcat cctgccagaa cacccacggc ggctaccgct gccactgcca ggccggctac   2700
agtgggcgca actgcgagac cgacatcgac gactgccggc ccaacccgtg tcacaacggg   2760
ggctcctgca cagacggcat caacacggcc ttctgcgact gcctgcccgg cttccggggc   2820
actttctgtg aggaggacat caacgagtgt gccagtgacc cctgccgcaa cggggccaac   2880
tgcacggact gcgtggacag ctacacgtgc acctgccccg caggcttcag cgggatccac   2940
tgtgagaaca acacgcctga ctgcacagag agctcctgct tcaacggtgg cacctgcgtg   3000
gacggcatca actcgttcac ctgcctgtgt ccacccggct tcacgggcag ctactgccag   3060
cacgatgtca atgagtgcga ctcacagccc tgcctgcatg gcggcacctg tcaggacggc   3120
tgcggctcct acaggtgcac ctgcccccag ggctacactg gccccaactg ccagaacctt   3180
gtgcactggt gtgactcctc gccctgcaag aacggcggca aatgctggca gacccacacc   3240
cagtaccgct gcgagtgccc cagcggctgg accggccttt actgcgacgt gcccagcgtg   3300
tcctgtgagg tggctgcgca gcgacaaggt gttgacgttg cccgcctgtg ccagcatgga   3360
gggctctgtg tggacgcggg caacacgcac cactgccgct gccaggcggg ctacacaggc   3420
agctactgtg aggacctggt ggacgagtgc tcacccagcc cctgccagaa cggggccacc   3480
tgcacggact acctgggcgg ctactcctgc aagtgcgtgg ccggctacca cggggtgaac   3540
tgctctgagg agatcgacga gtgcctctcc cacccctgcc agaacggggg cacctgcctc   3600
gacctcccca acacctacaa gtgctcctgc ccacggggca ctcagggtgt gcactgtgag   3660
atcaacgtgg acgactgcaa tcccccgtt gaccccgtgt cccggagccc caagtgcttt   3720
aacaacggca cctgcgtgga ccaggtgggc ggctacagct gcacctgccc gccgggcttc   3780
gtgggtgagc gctgtgaggg ggatgtcaac gagtgcctgt ccaatccctg cgacgcccgt   3840
ggcacccaga actgcgtgca gcgcgtcaat gacttccact gcgagtgccg tgctggtcac   3900
accgggcgcc gctgcgagtc cgtcatcaat ggctgcaaag gcaagccctg caagaatggg   3960
```

-continued

```
ggcacctgcg ccgtggcctc caacaccgcc cgcgggttca tctgcaagtg ccctgcgggc   4020

ttcgagggcg ccacgtgtga gaatgacgct cgtacctgcg gcagcctgcg ctgcctcaac   4080

ggcggcacat gcatctccgg cccgcgcagc cccacctgcc tgtgcctggg ccccttcacg   4140

ggccccgaat gccagttccc ggccagcagc ccctgcctgg gcggcaaccc ctgctacaac   4200

caggggacct gtgagcccac atccgagagc cccttctacc gttgcctgtg ccccgccaaa   4260

ttcaacgggc tcttgtgcca catcctggac tacagcttc                          4299
```

<210> SEQ ID NO 12
<211> LENGTH: 4213
<212> TYPE: DNA
<213> ORGANISM: Homo sapiens

<400> SEQUENCE: 12

```
tcatctggaa ttatgcccgc cctgcgcccc gctctgctgt gggcgctgct ggcgctctgg     60

ctgtgctgcg cggcccccgc gcatgcattg cagtgtcgag atggctatga accctgtgta    120

aatgaaggaa tgtgtgttac ctaccacaat ggcacaggat actgcaaatg tccagaaggc    180

ttcttggggg aatattgtca acatcgagac ccctgtgaga agaaccgctg ccagaatggt    240

gggacttgtg tggcccaggc catgctgggg aaagccacgt gccgatgtgc ctcagggttt    300

acaggagagg actgccagta ctcaacatct catccatgct ttgtgtctcg accctgcctg    360

aatggcggca catgccatat gctcagccgg gatacctatg agtgcacctg tcaagtcggg    420

tttacaggta aggagtgcca atggacggat gcctgcctgt ctcatccctg tgcaaatgga    480

agtacctgta ccactgtggc caaccagttc tcctgcaaat gcctcacagg cttcacaggg    540

cagaaatgtg agactgatgt caatgagtgt gacattccag gacactgcca gcatggtggc    600

acctgcctca acctgcctgg ttcctaccag tgccagtgcc ctcagggctt cacaggccag    660

tactgtgaca gcctgtatgt gccctgtgca ccctcacctt gtgtcaatgg aggcacctgt    720

cggcagactg gtgacttcac ttttgagtgc aactgccttc caggttttga agggagcacc    780

tgtgagagga atattgatga ctgccctaac cacaggtgtc agaatggagg ggtttgtgtg    840

gatggggtca acacttacaa ctgccgctgt cccccacaat ggacaggaca gttctgcaca    900

gaggatgtgg atgaatgcct gctgcagccc aatgcctgtc aaaatggggg cacctgtgcc    960

aaccgcaatg gaggctatgg ctgtgtatgt gtcaacggct ggagtggaga tgactgcagt   1020

gagaacattg atgattgtgc cttcgcctcc tgtactccag gctccacctg catcgaccgt   1080

gtggcctcct tctcttgcat gtgcccagag gggaaggcag gtctcctgtg tcatctggat   1140

gatgcatgca tcagcaatcc ttgccacaag ggggcactgt gtgacaccaa ccccctaaat   1200

gggcaatata tttgcacctg cccacaaggc tacaaagggg ctgactgcac agaagatgtg   1260

gatgaatgtg ccatggccaa tagcaatcct tgtgagcatg caggaaaatg tgtgaacacg   1320

gatggcgcct tccactgtga gtgtctgaag ggttatgcag gacctcgttg tgagatggac   1380

atcaatgagt gccattcaga cccctgccag aatgatgcta cctgtctgga taagattgga   1440

ggcttcacat gtctgtgcat gccaggtttc aaaggtgtgc attgtgaatt agaaataaat   1500

gaatgtcaga gcaacccttg tgtgaacaat gggcagtgtg tggataaagt caatcgtttc   1560

cagtgcctgt gtcctcctgg tttcactggg ccagtttgcc agattgatat tgatgactgt   1620

tccagtactc cgtgtctgaa tggggcaaag tgtatcgatc acccgaatgg ctatgaatgc   1680

cagtgtgcca caggtttcac tggtgtgttg tgtgaggaga acattgacaa ctgtgacccc   1740

gatccttgcc accatggtca gtgtcaggat ggtattgatt cctacacctg catctgcaat   1800
```

-continued

```
cccgggtaca tgggcgccat ctgcagtgac cagattgatg aatgttacag cagcccttgc   1860
ctgaacgatg gtcgctgcat tgacctggtc aatggctacc agtgcaactg ccagccaggc   1920
acgtcagggg ttaattgtga aattaatttt gatgactgtg caagtaaccc ttgtatccat   1980
ggaatctgta tggatggcat taatcgctac agttgtgtct gctcaccagg attcacaggg   2040
cagagatgta acattgacat tgatgagtgt gcctccaatc cctgtcgcaa gggtgcaaca   2100
tgtatcaacg gtgtgaatgg tttccgctgt atatgccccg agggacccca tcaccccagc   2160
tgctactcac aggtgaacga atgcctgagc aatccctgca tccatggaaa ctgtactgga   2220
ggtctcagtg gatataagtg tctctgtgat gcaggctggg ttggcatcaa ctgtgaagtg   2280
gacaaaaatg aatgcctttc gaatccatgc cagaatggag gaacttgtga caatctggtg   2340
aatggataca ggtgtacttg caagaagggc tttaaaggct ataactgcca ggtgaatatt   2400
gatgaatgtg cctcaaatcc atgcctgaac caaggaacct gctttgatga cataagtggc   2460
tacacttgcc actgtgtgct gccatacaca ggcaagaatt gtcagacagt attggctccc   2520
tgttccccaa acccttgtga gaatgctgct gtttgcaaag agtcaccaaa ttttgagagt   2580
tatacttgct tgtgtgctcc tggctggcaa ggtcagcggt gtaccattga cattgacgag   2640
tgtatctcca agccctgcat gaaccatggt ctctgccata acacccaggg cagctacatg   2700
tgtgaatgtc caccaggctt cagtggtatg gactgtgagg aggacattga tgactgcctt   2760
gccaatcctt gccagaatgg aggttcctgt atggatggag tgaatacttt ctcctgcctc   2820
tgccttccgg gtttcactgg ggataagtgc cagacagaca tgaatgagtg tctgagtgaa   2880
ccctgtaaga atggagggac ctgctctgac tacgtcaaca gttacacttg caagtgccag   2940
gcaggatttg atggagtcca ttgtgagaac aacatcaatg agtgcactga gagctcctgt   3000
ttcaatggtg gcacatgtgt tgatgggatt aactccttct cttgcttgtg ccctgtgggt   3060
ttcactggat ccttctgcct ccatgagatc aatgaatgca gctctcatcc atgcctgaat   3120
gagggaacgt gtgttgatgg cctgggtacc taccgctgca gctgccccct gggctacact   3180
gggaaaaact gtcagaccct ggtgaatctc tgcagtcggt ctccatgtaa aaacaaaggt   3240
acttgtgttc agaaaaaagc agagtcccag tgcctatgtc catctggatg ggctggtgcc   3300
tattgtgacg tgcccaatgt ctcttgtgac atagcagcct ccaggagagg tgtgcttgtt   3360
gaacacttgt gccagcactc aggtgtctgc atcaatgctg gcaacacgca ttactgtcag   3420
tgccccctgg gctatactgg gagctactgt gaggagcaac tcgatgagtg tgcgtccaac   3480
ccctgccagc acggggcaac atgcagtgac ttcattggtg gatacagatg cgagtgtgtc   3540
ccaggctatc agggtgtcaa ctgtgagtat gaagtggatg agtgccagaa tcagccctgc   3600
cagaatggag gcacctgtat tgaccttgtg aaccatttca agtgctcttg cccaccaggc   3660
actcggggcc tactctgtga agagaacatt gatgactgtg cccggggtcc ccattgcctt   3720
aatggtggtc agtgcatgga taggattgga ggctacagtt gtcgctgctt gcctggcttt   3780
gctggggagc gttgtgaggg agacatcaac gagtgcctct ccaacccctg cagctctgag   3840
ggcagcctgg actgtataca gctcaccaat gactacctgt gtgtttgccg tagtgccttt   3900
actggccggc actgtgaaac cttcgtcgat gtgtgtcccc agatgccctg cctgaatgga   3960
gggacttgtg ctgtggccag taacatgcct gatggtttca tttgccgttg tcccccggga   4020
ttttccgggg caaggtgcca gagcagctgt ggacaagtga aatgtaggaa gggggagcag   4080
tgtgtgcaca ccgcctctgg accccgctgc ttctgcccca gtccccggga ctgcgagtca   4140
```

-continued

```
ggctgtgcca gtagcccctg ccagcacggg ggcagctgcc accctcagcg ccagcctcct   4200

tattactcct gcc                                                      4213


<210> SEQ ID NO 13
<211> LENGTH: 3974
<212> TYPE: DNA
<213> ORGANISM: Homo sapiens

<400> SEQUENCE: 13

atggggccgg gggcccgtgg ccgccgccgc cgccgtcgcc cgatgtcgcc gccaccgcca     60

ccgccacccg tgcgggcgct gcccctgctg ctgctgctag cggggccggg ggctgcagcc    120

ccccccttgcc tggacggaag cccgtgtgca aatggaggtc gttgcaccca gctgccctcc   180

cgggaggctg cctgcctgtg cccgcctggc tgggtgggtg agcggtgtca gctggaggac    240

ccctgtcact caggcccctg tgctggccgt ggtgtctgcc agagttcagt ggtggctggc    300

accgcccgat tctcatgccg gtgcccccgt ggcttccgag gccctgactg ctccctgcca    360

gatccctgcc tcagcagccc ttgtgcccac ggtgcccgct gctcagtggg gcccgatgga    420

cgcttcctct gctcctgccc acctggctac cagggccgca gctgccgaag cgacgtggat    480

gagtgccggg tgggtgagcc ctgccgccat ggtggcacct gcctcaacac acctggctcc    540

ttccgctgcc agtgtccagc tggctacaca gggccactat gtgagaaccc cgcggtgccc    600

tgtgcaccct caccatgccg taacgggggc acctgcaggc agagtggcga cctcacttac    660

gactgtgcct gtcttcctgg gtttgagggt cagaattgtg aagtgaacgt ggacgactgt    720

ccaggacacc gatgtctcaa tgggggggaca tgcgtggatg gcgtcaacac ctataactgc   780

cagtgccctc ctgagtggac aggccagttc tgcacggagg acgtggatga gtgtcagctg    840

cagcccaacg cctgccacaa tgggggtacc tgcttcaaca cgctgggtgg ccacagctgc    900

gtgtgtgtca atggctggac aggcgagagc tgcagtcaga atatcgatga ctgtgccaca    960

gccgtgtgct tccatggggc cacctgccat gaccgcgtgg cttctttcta ctgtgcctgc   1020

cccatgggca agactggcct cctgtgtcac ctggatgacg cctgtgtcag caacccctgc   1080

cacgaggatg ctatctgtga cacaaatccg gtgaacggcc gggccatttg cacctgtcct   1140

cccggcttca cgggtggggc atgtgaccag gatgtggacg agtgctctat cggcgccaac   1200

ccctgcgagc acttgggcag gtgcgtgaac acgcagggct ccttcctgtg ccagtgcggt   1260

cgtggctaca ctggacctcg ctgtgagacc gatgtcaacg agtgtctgtc ggggccctgc   1320

cgaaaccagg ccacgtgcct cgaccgcata ggccagttca cctgtatctg tatggcaggc   1380

ttcacaggaa cctattgcga ggtggacatt gacgagtgtc agagtagccc ctgtgtcaac   1440

ggtggggtct gcaaggaccg agtcaatggc ttcagctgca cctgcccctc gggcttcagc   1500

ggctccacgt gtcagctgga cgtggacgaa tgcgccagca cgccctgcag gaatggcgcc   1560

aaatgcgtgg accagcccga tggctacgag tgccgctgtg ccgagggctt tgagggcacg   1620

ctgtgtgatc gcaacgtgga cgactgctcc cctgacccat gccaccatgg tcgctgcgtg   1680

gatggcatcg ccagcttctc atgtgcctgt gctcctggct acacgggcac acgctgcgag   1740

agccaggtgg acgaatgccg cagccagccc tgccgccatg gcggcaaatg cctagacctg   1800

gtggacaagt acctctgccg ctgcccttct gggaccacag gtgtgaactg cgaagtgaac   1860

attgacgact gtgccagcaa cccctgcacc tttggagtct gccgtgatgg catcaaccgc   1920

tacgactgtg tctgccaacc tggcttcaca gggccccttt gtaacgtgga gatcaatgag   1980

tgtgcttcca gcccatgcgg cgagggaggt tcctgtgtgg atggggaaaa tggcttccgc   2040
```

-continued

```
tgcctctgcc cgcctggctc cttgccccca ctctgcctcc ccccgagcca tccctgtgcc   2100
catgagccct gcagtcacgg catctgctat gatgcacctg gcgggttccg ctgtgtgtgt   2160
gagcctggct ggagtggccc ccgctgcagc cagagcctgg cccgagacgc ctgtgagtcc   2220
cagccgtgca gggccggtgg gacatgcagc agcgatggaa tgggtttcca ctgcacctgc   2280
ccgcctggtg tccagggacg tcagtgtgaa ctcctctccc cctgcacccc gaacccctgt   2340
gagcatgggg gccgctgcga gtctgcccct ggccagctgc ctgtctgctc ctgcccccag   2400
ggctggcaag gcccacgatg ccagcaggat gtggacgagt gtgctggccc cgcaccctgt   2460
ggccctcatg gtatctgcac caacctggca gggagtttca gctgcacctg ccatggaggg   2520
tacactggcc cttcctgcga tcaggacatc aatgactgtg accccaaccc atgcctgaac   2580
ggtggctcgt gccaagacgg cgtgggctcc ttttcctgct cctgcctccc tggtttcgcc   2640
ggcccacgat gcgcccgcga tgtggatgag tgcctgagca acccctgcgg cccgggcacc   2700
tgtaccgacc acgtggcctc cttcacctgc acctgcccgc caggctacgg aggcttccac   2760
tgcgaacagg acctgcccga ctgcagcccc agctcctgct tcaatggcgg gacctgtgtg   2820
gacggcgtga actcgttcag ctgcctgtgc cgtcccggct acacaggagc ccactgccaa   2880
catgaggcag acccctgcct ctcgcggccc tgcctacacg gggcgtctg cagcgccgcc    2940
caccctggct tccgctgcac ctgcctcgag agcttcacgg gcccgcagtg ccagacgctg   3000
gtggattggt gcagccgcca gccttgtcaa aacgggggtc gctgcgtcca gactggggcc   3060
tattgccttt gtccccctgg atggagcgga cgcctctgtg acatccgaag cttgccctgc   3120
agggaggccg cagcccagat cggggtgcgg ctggagcagc tgtgtcaggc gggtgggcag   3180
tgtgtggatg aagacagctc ccactactgc gtgtgcccag agggccgtac tggtagccac   3240
tgtgagcagg aggtggaccc ctgcttggcc cagccctgcc agcatggggg gacctgccgt   3300
ggctatatgg ggggctacat gtgtgagtgt cttcctggct acaatggtga taactgtgag   3360
gacgacgtgg acgagtgtgc ctcccagccc tgccagcacg gggggttcatg cattgacctc  3420
gtggcccgct atctctgctc ctgtccccca ggaacgctgg gggtgctctg cgagattaat   3480
gaggatgact gcggcccagg cccaccgctg gactcagggc cccggtgcct acacaatggc   3540
acctgcgtgg acctggtggg tggtttccgc tgcacctgtc ccccaggata cactggtttg   3600
cgctgcgagg cagacatcaa tgagtgtcgc tcaggtgcct gccacgcggc acacacccgg   3660
gactgcctgc aggacccagg cggaggtttc cgttgccttt gtcatgctgg cttctcaggt   3720
cctcgctgtc agactgtcct gtctccctgc gagtcccagc catgccagca tggaggccag   3780
tgccgtccta gcccgggtcc tgggggtggg ctgaccttca cctgtcactg tgcccagccg   3840
ttctggggtc cgcgttgcga gcgggtggcg cgctcctgcc gggagctgca gtgcccggtg   3900
ggcgtcccat gccagcagac gccccgcggg ccgcgctgcg cctgcccccc agggttgtcg   3960
ggaccctcct gccg                                                      3974
```

<210> SEQ ID NO 14
<211> LENGTH: 3522
<212> TYPE: DNA
<213> ORGANISM: Homo sapiens

<400> SEQUENCE: 14

```
atgcagcccc cttcactgct gctgctgctg ctgctgctgc tgctgctatg tgtctcagtg     60
gtcagaccca gagggctgct gtgtgggagt ttcccagaac cctgtgccaa tggaggcacc    120
```

-continued

```
tgcctgagcc tgtctctggg acaagggacc tgccagtgtg cccctggctt cctgggtgag    180
acgtgccagt ttcctgaccc ctgccagaac gcccagctct gccaaaatgg aggcagctgc    240
caagccctgc ttcccgctcc cctagggctc cccagctctc cctctccatt gacacccagc    300
ttcttgtgca cttgcctccc tggcttcact ggtgagagat gccaggccaa gcttgaagac    360
ccttgtcctc cctccttctg ttccaaaagg ggccgctgcc acatccaggc ctcgggccgc    420
ccacagtgct cctgcatgcc tggatggaca ggtgagcagt gccagcttcg ggacttctgt    480
tcagccaacc catgtgttaa tggaggggtg tgtctggcca catacccccca gatccagtgc   540
cactgcccac cgggcttcga gggccatgcc tgtgaacgtg atgtcaacga gtgcttccag    600
gacccaggac cctgccccaa aggcacctcc tgccataaca ccctgggctc cttccagtgc    660
ctctgccctg tggggcagga gggtccacgt tgtgagctgc gggcaggacc ctgccctcct    720
aggggctgtt cgaatggggg cacctgccag ctgatgccag agaaagactc cacctttcac    780
ctctgcctct gtcccccagg tttcataggc ccagactgtg aggtgaatcc agacaactgt    840
gtcagccacc agtgtcagaa tgggggcact tgccaggatg ggctggacac ctacacctgc    900
ctctgcccag aaacctggac aggctgggac tgctccgaag atgtggatga gtgtgagacc    960
cagggtcccc ctcactgcag aaacgggggc acctgccaga actctgctgg tagctttcac   1020
tgcgtgtgtg tgagtggctg gggcggcaca agctgtgagg agaacctgga tgactgtatt   1080
gctgccacct gtgccccggg atccacctgc attgaccggg tgggctcttt ctcctgcctc   1140
tgcccacctg gacgcacagg actcctgtgc cacttggaag acatgtgtct gagccagccg   1200
tgccatgggg atgcccaatg cagcaccaac cccctcacag gctccacact ctgcctgtgt   1260
cagcctggct attcggggcc cacctgccac caggacctgg acgagtgtct gatggcccag   1320
caaggcccaa gtccctgtga acatggcggt tcctgcctca acactcctgg ctccttcaac   1380
tgcctctgtc cacctggcta cacaggctcc cgttgtgagg ctgatcacaa tgagtgcctc   1440
tcccagccct gccacccagg aagcacctgt ctggacctac ttgccacctt ccactgcctc   1500
tgcccgccag gcttagaagg gcagctctgt gaggtggaga ccaacgagtg tgcctcagct   1560
ccctgcctga accacgcgga ttgccatgac ctgctcaacg gcttccagtg catctgcctg   1620
cctggattct ccggcacccg atgtgaggag gatatcgatg agtgcagaag ctctccctgt   1680
gccaatggtg ggcagtgcca ggaccagcct ggagccttcc actgcaagtg tctcccaggc   1740
tttgaagggc cacgctgtca aacagaggtg gatgagtgcc tgagtgaccc atgtcccgtt   1800
ggagccagct gccttgatct tccaggagcc ttcttttgcc tctgcccctc tggtttcaca   1860
ggccagctct gtgaggttcc cctgtgtgct cccaacctgt gccagcccaa gcagatatgt   1920
aaggaccaga aagacaaggc caactgcctc tgtcctgatg gaagccctgg ctgtgcccca   1980
cctgaggaca actgcacctg ccaccacggg cactgccaga gatcctcatg tgtgtgtgac   2040
gtgggttgga cggggccaga gtgtgaggca gagctagggg gctgcatctc tgcaccctgt   2100
gcccatgggg ggacctgcta cccccagccc tctggctaca actgcacctg ccctacaggc   2160
tacacaggac ccacctgtag tgaggagatg acagcttgtc actcagggcc atgtctcaat   2220
ggcggctcct gcaaccctag ccctggaggc tactactgca cctgccctcc aagccacaca   2280
gggccccagt gccaaaccag cactgactac tgtgtgtctg ccccgtgctt caatgggggt   2340
acctgtgtga acaggcctgg caccttctcc tgcctctgtg ccatgggctt ccagggcccg   2400
cgctgtgagg gaaagctccg ccccagctgt gcagacagcc cctgtaggaa tagggcaacc   2460
tgccaggaca gccctcaggg tccccgctgc ctctgcccca ctggctacac cggaggcagc   2520
```

-continued

```
tgccagactc tgatggactt atgtgcccag aagccctgcc cacgcaattc ccactgcctc   2580

cagactgggc cctccttcca ctgcttgtgc ctccagggat ggaccgggcc tctctgcaac   2640

cttccactgt cctcctgcca gaaggctgca ctgagccaag gcatagacgt ctcttccctt   2700

tgccacaatg gaggcctctg tgtcgacagc ggcccctcct atttctgcca ctgccccccct   2760

ggattccaag gcagcctgtg ccaggatcac gtgaacccat gtgagtccag gccttgccag   2820

aacggggcca cctgcatggc ccagcccagt gggtatctct gccagtgtgc cccaggctac   2880

gatggacaga actgctcaaa ggaactcgat gcttgtcagt cccaaccctg tcacaaccat   2940

ggaacctgta ctcccaaacc tggaggattc cactgtgcct gccctccagg ctttgtgggg   3000

ctacgctgtg agggagacgt ggacgagtgt ctggaccagc cctgccaccc cacaggcact   3060

gcagcctgcc actctctggc caatgccttc tactgccagt gtctgcctgg acacacaggc   3120

cagtggtgtg aggtggagat agacccctgc cacagccaac cctgctttca tggagggacc   3180

tgtgaggcca cagcaggatc accccctgggt ttcatctgcc actgccccaa gggttttgaa   3240

ggccccacct gcagccacag ggccccttcc tgcggcttcc atcactgcca ccacggaggc   3300

ctgtgtctgc cctcccctaa gccaggcttc ccaccacgct gtgcctgcct cagtggctat   3360

gggggtcctg actgcctgac cccaccagct cctaaaggct gtggccctcc ctccccatgc   3420

ctatacaatg gcagctgctc agagaccacg ggcttggggg gcccaggctt tcgatgctcc   3480

tgccctcaca gctctccagg gccccggtgt cagaaacccg ga                      3522
```

<210> SEQ ID NO 15
<211> LENGTH: 20
<212> TYPE: PRT
<213> ORGANISM: Homo sapiens

<400> SEQUENCE: 15

```
Met Pro Pro Leu Leu Ala Pro Leu Leu Cys Leu Ala Leu Leu Pro Ala
1               5                   10                  15

Leu Ala Ala Arg
            20
```

<210> SEQ ID NO 16
<211> LENGTH: 69
<212> TYPE: DNA
<213> ORGANISM: Homo sapiens

<400> SEQUENCE: 16

```
atgccgccgc tcctggcgcc cctgctctgc ctggcgctgc tgcccgcgct cgccgcacga     60

ggcccgcga                                                             69
```

<210> SEQ ID NO 17
<211> LENGTH: 22
<212> TYPE: PRT
<213> ORGANISM: Homo sapiens

<400> SEQUENCE: 17

```
Met Trp Gly Trp Lys Cys Leu Leu Phe Trp Ala Val Leu Val Thr Ala
1               5                   10                  15

Thr Leu Cys Thr Ala Arg
            20
```

<210> SEQ ID NO 18
<211> LENGTH: 66
<212> TYPE: DNA

<213> ORGANISM: Homo sapiens

<400> SEQUENCE: 18
atgtggggct ggaagtgcct cctcttctgg gctgtgctgg tcacagccac tctctgcact 60
gccagg 66

<210> SEQ ID NO 19
<211> LENGTH: 12
<212> TYPE: DNA
<213> ORGANISM: Homo sapiens

<400> SEQUENCE: 19
tacagcttcg gg 12

<210> SEQ ID NO 20
<211> LENGTH: 12
<212> TYPE: DNA
<213> ORGANISM: Homo sapiens

<400> SEQUENCE: 20
cccgaagctg ta 12

<210> SEQ ID NO 21
<211> LENGTH: 4
<212> TYPE: PRT
<213> ORGANISM: Homo sapiens

<400> SEQUENCE: 21

Tyr Ser Phe Gly
1

<210> SEQ ID NO 22
<211> LENGTH: 17
<212> TYPE: DNA
<213> ORGANISM: Homo sapiens

<400> SEQUENCE: 22
tacagcttcg gagatct 17

<210> SEQ ID NO 23
<211> LENGTH: 17
<212> TYPE: DNA
<213> ORGANISM: Homo sapiens

<400> SEQUENCE: 23
agatctccga agctgta 17

<210> SEQ ID NO 24
<211> LENGTH: 24
<212> TYPE: DNA
<213> ORGANISM: Homo sapiens

<400> SEQUENCE: 24
tacagcttcg gagatctggg cccg 24

<210> SEQ ID NO 25
<211> LENGTH: 24
<212> TYPE: DNA
<213> ORGANISM: Homo sapiens

<400> SEQUENCE: 25
cgggcccaga tctccgaagc tgta 24

<210> SEQ ID NO 26
<211> LENGTH: 8
<212> TYPE: PRT
<213> ORGANISM: Homo sapiens

<400> SEQUENCE: 26

Tyr Ser Phe Gly Asp Leu Gly Pro
1               5

<210> SEQ ID NO 27
<211> LENGTH: 12
<212> TYPE: DNA
<213> ORGANISM: Homo sapiens

<400> SEQUENCE: 27
gatgtggacg ag 12

<210> SEQ ID NO 28
<211> LENGTH: 12
<212> TYPE: DNA
<213> ORGANISM: Homo sapiens

<400> SEQUENCE: 28
ctcgtcctca tc 12

<210> SEQ ID NO 29
<211> LENGTH: 4
<212> TYPE: PRT
<213> ORGANISM: Homo sapiens

<400> SEQUENCE: 29

Asp Val Asp Glu
1

<210> SEQ ID NO 30
<211> LENGTH: 17
<212> TYPE: DNA
<213> ORGANISM: Homo sapiens

<400> SEQUENCE: 30
gatgtggacg aggatcc 17

<210> SEQ ID NO 31
<211> LENGTH: 17
<212> TYPE: DNA
<213> ORGANISM: Homo sapiens

<400> SEQUENCE: 31
ggatcctcgt cctcatc 17

<210> SEQ ID NO 32
<211> LENGTH: 24
<212> TYPE: DNA
<213> ORGANISM: Homo sapiens

<400> SEQUENCE: 32
gatgtggacg aggatctggg cccg 24

<210> SEQ ID NO 33
<211> LENGTH: 24
<212> TYPE: DNA
<213> ORGANISM: Homo sapiens

<400> SEQUENCE: 33
cgggcccaga tcctcgtcct catc 24

<210> SEQ ID NO 34
<211> LENGTH: 8
<212> TYPE: PRT
<213> ORGANISM: Homo sapiens

<400> SEQUENCE: 34

Asp Val Asp Glu Asp Leu Gly Pro
1 5

<210> SEQ ID NO 35
<211> LENGTH: 18
<212> TYPE: DNA
<213> ORGANISM: Homo sapiens

<400> SEQUENCE: 35
gagaccgaca tcgacgac 18

<210> SEQ ID NO 36
<211> LENGTH: 18
<212> TYPE: DNA
<213> ORGANISM: Homo sapiens

<400> SEQUENCE: 36
gtcgtcgatg tcggtctc 18

<210> SEQ ID NO 37
<211> LENGTH: 6
<212> TYPE: PRT
<213> ORGANISM: Homo sapiens

<400> SEQUENCE: 37

Glu Thr Asp Ile Asp Asp
1 5

<210> SEQ ID NO 38
<211> LENGTH: 17
<212> TYPE: DNA
<213> ORGANISM: Homo sapiens

<400> SEQUENCE: 38
gagaccgaca tagatct 17

<210> SEQ ID NO 39
<211> LENGTH: 17
<212> TYPE: DNA
<213> ORGANISM: Homo sapiens

<400> SEQUENCE: 39
agatctatgt cggtctc 17

<210> SEQ ID NO 40
<211> LENGTH: 4
<212> TYPE: PRT
<213> ORGANISM: Homo sapiens

<400> SEQUENCE: 40

Glu Thr Asp Ile
1

<210> SEQ ID NO 41
<211> LENGTH: 24

<212> TYPE: DNA
<213> ORGANISM: Homo sapiens

<400> SEQUENCE: 41
gagaccgaca tagatctggg cccg 24

<210> SEQ ID NO 42
<211> LENGTH: 24
<212> TYPE: DNA
<213> ORGANISM: Homo sapiens

<400> SEQUENCE: 42
cgggcccaga tctatgtcgg tctc 24

<210> SEQ ID NO 43
<211> LENGTH: 8
<212> TYPE: PRT
<213> ORGANISM: Homo sapiens

<400> SEQUENCE: 43

Glu Thr Asp Ile Asp Leu Gly Pro
1 5

<210> SEQ ID NO 44
<211> LENGTH: 12
<212> TYPE: DNA
<213> ORGANISM: Homo sapiens

<400> SEQUENCE: 44
gacatcaacg ag 12

<210> SEQ ID NO 45
<211> LENGTH: 12
<212> TYPE: DNA
<213> ORGANISM: Homo sapiens

<400> SEQUENCE: 45
ctcgttgatg tc 12

<210> SEQ ID NO 46
<211> LENGTH: 4
<212> TYPE: PRT
<213> ORGANISM: Homo sapiens

<400> SEQUENCE: 46

Asp Ile Asn Glu
1

<210> SEQ ID NO 47
<211> LENGTH: 17
<212> TYPE: DNA
<213> ORGANISM: Homo sapiens

<400> SEQUENCE: 47
gacatcaacg aggatcc 17

<210> SEQ ID NO 48
<211> LENGTH: 17
<212> TYPE: DNA
<213> ORGANISM: Homo sapiens

<400> SEQUENCE: 48
ggatcctcgt tgatgtc 17

<210> SEQ ID NO 49
<211> LENGTH: 24
<212> TYPE: DNA
<213> ORGANISM: Homo sapiens

<400> SEQUENCE: 49
gacatcaacg aggatctggg cccg 24

<210> SEQ ID NO 50
<211> LENGTH: 24
<212> TYPE: DNA
<213> ORGANISM: Homo sapiens

<400> SEQUENCE: 50
cgggcccaga tcctcgttga tgtc 24

<210> SEQ ID NO 51
<211> LENGTH: 8
<212> TYPE: PRT
<213> ORGANISM: Homo sapiens

<400> SEQUENCE: 51

Asp Ile Asn Glu Asp Leu Gly Pro
1 5

<210> SEQ ID NO 52
<211> LENGTH: 2555
<212> TYPE: PRT
<213> ORGANISM: Homo sapiens

<400> SEQUENCE: 52

Met Pro Pro Leu Leu Ala Pro Leu Leu Cys Leu Ala Leu Leu Pro Ala
1 5 10 15

Leu Ala Ala Arg Gly Pro Arg Cys Ser Gln Pro Gly Glu Thr Cys Leu
20 25 30

Asn Gly Gly Lys Cys Glu Ala Ala Asn Gly Thr Glu Ala Cys Val Cys
35 40 45

Gly Gly Ala Phe Val Gly Pro Arg Cys Gln Asp Pro Asn Pro Cys Leu
50 55 60

Ser Thr Pro Cys Lys Asn Ala Gly Thr Cys His Val Val Asp Arg Arg
65 70 75 80

Gly Val Ala Asp Tyr Ala Cys Ser Cys Ala Leu Gly Phe Ser Gly Pro
85 90 95

Leu Cys Leu Thr Pro Leu Asp Asn Ala Cys Leu Thr Asn Pro Cys Arg
100 105 110

Asn Gly Gly Thr Cys Asp Leu Leu Thr Leu Thr Glu Tyr Lys Cys Arg
115 120 125

Cys Pro Pro Gly Trp Ser Gly Lys Ser Cys Gln Gln Ala Asp Pro Cys
130 135 140

Ala Ser Asn Pro Cys Ala Asn Gly Gly Gln Cys Leu Pro Phe Glu Ala
145 150 155 160

Ser Tyr Ile Cys His Cys Pro Pro Ser Phe His Gly Pro Thr Cys Arg
165 170 175

Gln Asp Val Asn Glu Cys Gly Gln Lys Pro Gly Leu Cys Arg His Gly
180 185 190

Gly Thr Cys His Asn Glu Val Gly Ser Tyr Arg Cys Val Cys Arg Ala
195 200 205

Thr His Thr Gly Pro Asn Cys Glu Arg Pro Tyr Val Pro Cys Ser Pro

-continued

```
    210                 215                 220

Ser Pro Cys Gln Asn Gly Gly Thr Cys Arg Pro Thr Gly Asp Val Thr
225                 230                 235                 240

His Glu Cys Ala Cys Leu Pro Gly Phe Thr Gly Gln Asn Cys Glu Glu
                245                 250                 255

Asn Ile Asp Asp Cys Pro Gly Asn Asn Cys Lys Asn Gly Gly Ala Cys
            260                 265                 270

Val Asp Gly Val Asn Thr Tyr Asn Cys Arg Cys Pro Pro Glu Trp Thr
        275                 280                 285

Gly Gln Tyr Cys Thr Glu Asp Val Asp Glu Cys Gln Leu Met Pro Asn
    290                 295                 300

Ala Cys Gln Asn Gly Gly Thr Cys His Asn Thr His Gly Gly Tyr Asn
305                 310                 315                 320

Cys Val Cys Val Asn Gly Trp Thr Gly Glu Asp Cys Ser Glu Asn Ile
                325                 330                 335

Asp Asp Cys Ala Ser Ala Ala Cys Phe His Gly Ala Thr Cys His Asp
            340                 345                 350

Arg Val Ala Ser Phe Tyr Cys Glu Cys Pro His Gly Arg Thr Gly Leu
        355                 360                 365

Leu Cys His Leu Asn Asp Ala Cys Ile Ser Asn Pro Cys Asn Glu Gly
    370                 375                 380

Ser Asn Cys Asp Thr Asn Pro Val Asn Gly Lys Ala Ile Cys Thr Cys
385                 390                 395                 400

Pro Ser Gly Tyr Thr Gly Pro Ala Cys Ser Gln Asp Val Asp Glu Cys
                405                 410                 415

Ser Leu Gly Ala Asn Pro Cys Glu His Ala Gly Lys Cys Ile Asn Thr
            420                 425                 430

Leu Gly Ser Phe Glu Cys Gln Cys Leu Gln Gly Tyr Thr Gly Pro Arg
        435                 440                 445

Cys Glu Ile Asp Val Asn Glu Cys Val Ser Asn Pro Cys Gln Asn Asp
    450                 455                 460

Ala Thr Cys Leu Asp Gln Ile Gly Glu Phe Gln Cys Ile Cys Met Pro
465                 470                 475                 480

Gly Tyr Glu Gly Val His Cys Glu Val Asn Thr Asp Glu Cys Ala Ser
                485                 490                 495

Ser Pro Cys Leu His Asn Gly Arg Cys Leu Asp Lys Ile Asn Glu Phe
            500                 505                 510

Gln Cys Glu Cys Pro Thr Gly Phe Thr Gly His Leu Cys Gln Tyr Asp
        515                 520                 525

Val Asp Glu Cys Ala Ser Thr Pro Cys Lys Asn Gly Ala Lys Cys Leu
    530                 535                 540

Asp Gly Pro Asn Thr Tyr Thr Cys Val Cys Thr Glu Gly Tyr Thr Gly
545                 550                 555                 560

Thr His Cys Glu Val Asp Ile Asp Glu Cys Asp Pro Asp Pro Cys His
                565                 570                 575

Tyr Gly Ser Cys Lys Asp Gly Val Ala Thr Phe Thr Cys Leu Cys Arg
            580                 585                 590

Pro Gly Tyr Thr Gly His His Cys Glu Thr Asn Ile Asn Glu Cys Ser
        595                 600                 605

Ser Gln Pro Cys Arg His Gly Gly Thr Cys Gln Asp Arg Asp Asn Ala
    610                 615                 620

Tyr Leu Cys Phe Cys Leu Lys Gly Thr Thr Gly Pro Asn Cys Glu Ile
625                 630                 635                 640
```

-continued

```
Asn Leu Asp Asp Cys Ala Ser Ser Pro Cys Asp Ser Gly Thr Cys Leu
                645                 650                 655

Asp Lys Ile Asp Gly Tyr Glu Cys Ala Cys Glu Pro Gly Tyr Thr Gly
            660                 665                 670

Ser Met Cys Asn Ile Asn Ile Asp Glu Cys Ala Gly Asn Pro Cys His
        675                 680                 685

Asn Gly Gly Thr Cys Glu Asp Gly Ile Asn Gly Phe Thr Cys Arg Cys
    690                 695                 700

Pro Glu Gly Tyr His Asp Pro Thr Cys Leu Ser Glu Val Asn Glu Cys
705                 710                 715                 720

Asn Ser Asn Pro Cys Val His Gly Ala Cys Arg Asp Ser Leu Asn Gly
                725                 730                 735

Tyr Lys Cys Asp Cys Asp Pro Gly Trp Ser Gly Thr Asn Cys Asp Ile
            740                 745                 750

Asn Asn Asn Glu Cys Glu Ser Asn Pro Cys Val Asn Gly Gly Thr Cys
        755                 760                 765

Lys Asp Met Thr Ser Gly Tyr Val Cys Thr Cys Arg Glu Gly Phe Ser
    770                 775                 780

Gly Pro Asn Cys Gln Thr Asn Ile Asn Glu Cys Ala Ser Asn Pro Cys
785                 790                 795                 800

Leu Asn Gln Gly Thr Cys Ile Asp Asp Val Ala Gly Tyr Lys Cys Asn
                805                 810                 815

Cys Leu Leu Pro Tyr Thr Gly Ala Thr Cys Glu Val Val Leu Ala Pro
            820                 825                 830

Cys Ala Pro Ser Pro Cys Arg Asn Gly Gly Glu Cys Arg Gln Ser Glu
        835                 840                 845

Asp Tyr Glu Ser Phe Ser Cys Val Cys Pro Thr Gly Trp Gln Gly Gln
    850                 855                 860

Thr Cys Glu Val Asp Ile Asn Glu Cys Val Leu Ser Pro Cys Arg His
865                 870                 875                 880

Gly Ala Ser Cys Gln Asn Thr His Gly Gly Tyr Arg Cys His Cys Gln
                885                 890                 895

Ala Gly Tyr Ser Gly Arg Asn Cys Glu Thr Asp Ile Asp Asp Cys Arg
            900                 905                 910

Pro Asn Pro Cys His Asn Gly Gly Ser Cys Thr Asp Gly Ile Asn Thr
        915                 920                 925

Ala Phe Cys Asp Cys Leu Pro Gly Phe Arg Gly Thr Phe Cys Glu Glu
    930                 935                 940

Asp Ile Asn Glu Cys Ala Ser Asp Pro Cys Arg Asn Gly Ala Asn Cys
945                 950                 955                 960

Thr Asp Cys Val Asp Ser Tyr Thr Cys Thr Cys Pro Ala Gly Phe Ser
                965                 970                 975

Gly Ile His Cys Glu Asn Asn Thr Pro Asp Cys Thr Glu Ser Ser Cys
            980                 985                 990

Phe Asn Gly Gly Thr Cys Val Asp  Gly Ile Asn Ser Phe  Thr Cys Leu
        995                 1000                1005

Cys Pro  Pro Gly Phe Thr Gly  Ser Tyr Cys Gln His  Asp Val Asn
    1010                1015                1020

Glu Cys  Asp Ser Gln Pro Cys  Leu His Gly Gly Thr  Cys Gln Asp
    1025                1030                1035

Gly Cys  Gly Ser Tyr Arg Cys  Thr Cys Pro Gln Gly  Tyr Thr Gly
    1040                1045                1050
```

-continued

Pro Asn Cys Gln Asn Leu Val His Trp Cys Asp Ser Ser Pro Cys
1055 1060 1065

Lys Asn Gly Gly Lys Cys Trp Gln Thr His Thr Gln Tyr Arg Cys
1070 1075 1080

Glu Cys Pro Ser Gly Trp Thr Gly Leu Tyr Cys Asp Val Pro Ser
1085 1090 1095

Val Ser Cys Glu Val Ala Ala Gln Arg Gln Gly Val Asp Val Ala
1100 1105 1110

Arg Leu Cys Gln His Gly Gly Leu Cys Val Asp Ala Gly Asn Thr
1115 1120 1125

His His Cys Arg Cys Gln Ala Gly Tyr Thr Gly Ser Tyr Cys Glu
1130 1135 1140

Asp Leu Val Asp Glu Cys Ser Pro Ser Pro Cys Gln Asn Gly Ala
1145 1150 1155

Thr Cys Thr Asp Tyr Leu Gly Gly Tyr Ser Cys Lys Cys Val Ala
1160 1165 1170

Gly Tyr His Gly Val Asn Cys Ser Glu Glu Ile Asp Glu Cys Leu
1175 1180 1185

Ser His Pro Cys Gln Asn Gly Gly Thr Cys Leu Asp Leu Pro Asn
1190 1195 1200

Thr Tyr Lys Cys Ser Cys Pro Arg Gly Thr Gln Gly Val His Cys
1205 1210 1215

Glu Ile Asn Val Asp Asp Cys Asn Pro Pro Val Asp Pro Val Ser
1220 1225 1230

Arg Ser Pro Lys Cys Phe Asn Asn Gly Thr Cys Val Asp Gln Val
1235 1240 1245

Gly Gly Tyr Ser Cys Thr Cys Pro Pro Gly Phe Val Gly Glu Arg
1250 1255 1260

Cys Glu Gly Asp Val Asn Glu Cys Leu Ser Asn Pro Cys Asp Ala
1265 1270 1275

Arg Gly Thr Gln Asn Cys Val Gln Arg Val Asn Asp Phe His Cys
1280 1285 1290

Glu Cys Arg Ala Gly His Thr Gly Arg Arg Cys Glu Ser Val Ile
1295 1300 1305

Asn Gly Cys Lys Gly Lys Pro Cys Lys Asn Gly Gly Thr Cys Ala
1310 1315 1320

Val Ala Ser Asn Thr Ala Arg Gly Phe Ile Cys Lys Cys Pro Ala
1325 1330 1335

Gly Phe Glu Gly Ala Thr Cys Glu Asn Asp Ala Arg Thr Cys Gly
1340 1345 1350

Ser Leu Arg Cys Leu Asn Gly Gly Thr Cys Ile Ser Gly Pro Arg
1355 1360 1365

Ser Pro Thr Cys Leu Cys Leu Gly Pro Phe Thr Gly Pro Glu Cys
1370 1375 1380

Gln Phe Pro Ala Ser Ser Pro Cys Leu Gly Gly Asn Pro Cys Tyr
1385 1390 1395

Asn Gln Gly Thr Cys Glu Pro Thr Ser Glu Ser Pro Phe Tyr Arg
1400 1405 1410

Cys Leu Cys Pro Ala Lys Phe Asn Gly Leu Leu Cys His Ile Leu
1415 1420 1425

Asp Tyr Ser Phe Gly Gly Gly Ala Gly Arg Asp Ile Pro Pro Pro
1430 1435 1440

Leu Ile Glu Glu Ala Cys Glu Leu Pro Glu Cys Gln Glu Asp Ala

```
    1445                1450                1455

Gly Asn  Lys Val Cys Ser Leu  Gln Cys Asn Asn His  Ala Cys Gly
    1460                1465                1470

Trp Asp  Gly Gly Asp Cys Ser  Leu Asn Phe Asn Asp  Pro Trp Lys
    1475                1480                1485

Asn Cys  Thr Gln Ser Leu Gln  Cys Trp Lys Tyr Phe  Ser Asp Gly
    1490                1495                1500

His Cys  Asp Ser Gln Cys Asn  Ser Ala Gly Cys Leu  Phe Asp Gly
    1505                1510                1515

Phe Asp  Cys Gln Arg Ala Glu  Gly Gln Cys Asn Pro  Leu Tyr Asp
    1520                1525                1530

Gln Tyr  Cys Lys Asp His Phe  Ser Asp Gly His Cys  Asp Gln Gly
    1535                1540                1545

Cys Asn  Ser Ala Glu Cys Glu  Trp Asp Gly Leu Asp  Cys Ala Glu
    1550                1555                1560

His Val  Pro Glu Arg Leu Ala  Ala Gly Thr Leu Val  Val Val Val
    1565                1570                1575

Leu Met  Pro Pro Glu Gln Leu  Arg Asn Ser Ser Phe  His Phe Leu
    1580                1585                1590

Arg Glu  Leu Ser Arg Val Leu  His Thr Asn Val Val  Phe Lys Arg
    1595                1600                1605

Asp Ala  His Gly Gln Gln Met  Ile Phe Pro Tyr Tyr  Gly Arg Glu
    1610                1615                1620

Glu Glu  Leu Arg Lys His Pro  Ile Lys Arg Ala Ala  Glu Gly Trp
    1625                1630                1635

Ala Ala  Pro Asp Ala Leu Leu  Gly Gln Val Lys Ala  Ser Leu Leu
    1640                1645                1650

Pro Gly  Gly Ser Glu Gly Gly  Arg Arg Arg Arg Glu  Leu Asp Pro
    1655                1660                1665

Met Asp  Val Arg Gly Ser Ile  Val Tyr Leu Glu Ile  Asp Asn Arg
    1670                1675                1680

Gln Cys  Val Gln Ala Ser Ser  Gln Cys Phe Gln Ser  Ala Thr Asp
    1685                1690                1695

Val Ala  Ala Phe Leu Gly Ala  Leu Ala Ser Leu Gly  Ser Leu Asn
    1700                1705                1710

Ile Pro  Tyr Lys Ile Glu Ala  Val Gln Ser Glu Thr  Val Glu Pro
    1715                1720                1725

Pro Pro  Pro Ala Gln Leu His  Phe Met Tyr Val Ala  Ala Ala Ala
    1730                1735                1740

Phe Val  Leu Leu Phe Phe Val  Gly Cys Gly Val Leu  Leu Ser Arg
    1745                1750                1755

Lys Arg  Arg Arg Gln His Gly  Gln Leu Trp Phe Pro  Glu Gly Phe
    1760                1765                1770

Lys Val  Ser Glu Ala Ser Lys  Lys Lys Arg Arg Glu  Pro Leu Gly
    1775                1780                1785

Glu Asp  Ser Val Gly Leu Lys  Pro Leu Lys Asn Ala  Ser Asp Gly
    1790                1795                1800

Ala Leu  Met Asp Asp Asn Gln  Asn Glu Trp Gly Asp  Glu Asp Leu
    1805                1810                1815

Glu Thr  Lys Lys Phe Arg Phe  Glu Glu Pro Val Val  Leu Pro Asp
    1820                1825                1830

Leu Asp  Asp Gln Thr Asp His  Arg Gln Trp Thr Gln  Gln His Leu
    1835                1840                1845
```

```
Asp Ala  Ala Asp Leu Arg Met  Ser Ala Met Ala Pro  Thr Pro Pro
    1850                 1855                 1860

Gln Gly  Glu Val Asp Ala Asp  Cys Met Asp Val Asn  Val Arg Gly
    1865                 1870                 1875

Pro Asp  Gly Phe Thr Pro Leu  Met Ile Ala Ser Cys  Ser Gly Gly
    1880                 1885                 1890

Gly Leu  Glu Thr Gly Asn Ser  Glu Glu Glu Glu Asp  Ala Pro Ala
    1895                 1900                 1905

Val Ile  Ser Asp Phe Ile Tyr  Gln Gly Ala Ser Leu  His Asn Gln
    1910                 1915                 1920

Thr Asp  Arg Thr Gly Glu Thr  Ala Leu His Leu Ala  Ala Arg Tyr
    1925                 1930                 1935

Ser Arg  Ser Asp Ala Ala Lys  Arg Leu Leu Glu Ala  Ser Ala Asp
    1940                 1945                 1950

Ala Asn  Ile Gln Asp Asn Met  Gly Arg Thr Pro Leu  His Ala Ala
    1955                 1960                 1965

Val Ser  Ala Asp Ala Gln Gly  Val Phe Gln Ile Leu  Ile Arg Asn
    1970                 1975                 1980

Arg Ala  Thr Asp Leu Asp Ala  Arg Met His Asp Gly  Thr Thr Pro
    1985                 1990                 1995

Leu Ile  Leu Ala Ala Arg Leu  Ala Val Glu Gly Met  Leu Glu Asp
    2000                 2005                 2010

Leu Ile  Asn Ser His Ala Asp  Val Asn Ala Val Asp  Asp Leu Gly
    2015                 2020                 2025

Lys Ser  Ala Leu His Trp Ala  Ala Ala Val Asn Asn  Val Asp Ala
    2030                 2035                 2040

Ala Val  Val Leu Leu Lys Asn  Gly Ala Asn Lys Asp  Met Gln Asn
    2045                 2050                 2055

Asn Arg  Glu Glu Thr Pro Leu  Phe Leu Ala Ala Arg  Glu Gly Ser
    2060                 2065                 2070

Tyr Glu  Thr Ala Lys Val Leu  Leu Asp His Phe Ala  Asn Arg Asp
    2075                 2080                 2085

Ile Thr  Asp His Met Asp Arg  Leu Pro Arg Asp Ile  Ala Gln Glu
    2090                 2095                 2100

Arg Met  His His Asp Ile Val  Arg Leu Leu Asp Glu  Tyr Asn Leu
    2105                 2110                 2115

Val Arg  Ser Pro Gln Leu His  Gly Ala Pro Leu Gly  Gly Thr Pro
    2120                 2125                 2130

Thr Leu  Ser Pro Pro Leu Cys  Ser Pro Asn Gly Tyr  Leu Gly Ser
    2135                 2140                 2145

Leu Lys  Pro Gly Val Gln Gly  Lys Lys Val Arg Lys  Pro Ser Ser
    2150                 2155                 2160

Lys Gly  Leu Ala Cys Gly Ser  Lys Glu Ala Lys Asp  Leu Lys Ala
    2165                 2170                 2175

Arg Arg  Lys Lys Ser Gln Asp  Gly Lys Gly Cys Leu  Leu Asp Ser
    2180                 2185                 2190

Ser Gly  Met Leu Ser Pro Val  Asp Ser Leu Glu Ser  Pro His Gly
    2195                 2200                 2205

Tyr Leu  Ser Asp Val Ala Ser  Pro Pro Leu Leu Pro  Ser Pro Phe
    2210                 2215                 2220

Gln Gln  Ser Pro Ser Val Pro  Leu Asn His Leu Pro  Gly Met Pro
    2225                 2230                 2235
```

-continued

Asp Thr His Leu Gly Ile Gly His Leu Asn Val Ala Ala Lys Pro
    2240 2245 2250

Glu Met Ala Ala Leu Gly Gly Gly Gly Arg Leu Ala Phe Glu Thr
    2255 2260 2265

Gly Pro Pro Arg Leu Ser His Leu Pro Val Ala Ser Gly Thr Ser
    2270 2275 2280

Thr Val Leu Gly Ser Ser Ser Gly Gly Ala Leu Asn Phe Thr Val
    2285 2290 2295

Gly Gly Ser Thr Ser Leu Asn Gly Gln Cys Glu Trp Leu Ser Arg
    2300 2305 2310

Leu Gln Ser Gly Met Val Pro Asn Gln Tyr Asn Pro Leu Arg Gly
    2315 2320 2325

Ser Val Ala Pro Gly Pro Leu Ser Thr Gln Ala Pro Ser Leu Gln
    2330 2335 2340

His Gly Met Val Gly Pro Leu His Ser Ser Leu Ala Ala Ser Ala
    2345 2350 2355

Leu Ser Gln Met Met Ser Tyr Gln Gly Leu Pro Ser Thr Arg Leu
    2360 2365 2370

Ala Thr Gln Pro His Leu Val Gln Thr Gln Gln Val Gln Pro Gln
    2375 2380 2385

Asn Leu Gln Met Gln Gln Gln Asn Leu Gln Pro Ala Asn Ile Gln
    2390 2395 2400

Gln Gln Gln Ser Leu Gln Pro Pro Pro Pro Pro Pro Gln Pro His
    2405 2410 2415

Leu Gly Val Ser Ser Ala Ala Ser Gly His Leu Gly Arg Ser Phe
    2420 2425 2430

Leu Ser Gly Glu Pro Ser Gln Ala Asp Val Gln Pro Leu Gly Pro
    2435 2440 2445

Ser Ser Leu Ala Val His Thr Ile Leu Pro Gln Glu Ser Pro Ala
    2450 2455 2460

Leu Pro Thr Ser Leu Pro Ser Ser Leu Val Pro Pro Val Thr Ala
    2465 2470 2475

Ala Gln Phe Leu Thr Pro Pro Ser Gln His Ser Tyr Ser Ser Pro
    2480 2485 2490

Val Asp Asn Thr Pro Ser His Gln Leu Gln Val Pro Glu His Pro
    2495 2500 2505

Phe Leu Thr Pro Ser Pro Glu Ser Pro Asp Gln Trp Ser Ser Ser
    2510 2515 2520

Ser Pro His Ser Asn Val Ser Asp Trp Ser Glu Gly Val Ser Ser
    2525 2530 2535

Pro Pro Thr Ser Met Gln Ser Gln Ile Ala Arg Ile Pro Glu Ala
    2540 2545 2550

Phe Lys
    2555

<210> SEQ ID NO 53
<211> LENGTH: 237
<212> TYPE: PRT
<213> ORGANISM: Homo sapiens

<400> SEQUENCE: 53

Asp Leu Gly Pro Gly Glu Pro Lys Ser Cys Asp Lys Thr His Thr Cys
1 5 10 15

Pro Pro Cys Pro Ala Pro Glu Leu Leu Gly Gly Pro Ser Val Phe Leu
    20 25 30

-continued

```
Phe Pro Pro Lys Pro Lys Asp Thr Leu Met Ile Ser Arg Thr Pro Glu
        35                  40                  45

Val Thr Cys Val Val Val Asp Val Ser His Glu Asp Pro Glu Val Lys
    50                  55                  60

Phe Asn Trp Tyr Val Asp Gly Val Glu Val His Asn Ala Lys Thr Lys
65                  70                  75                  80

Pro Arg Glu Glu Gln Tyr Asn Ser Thr Tyr Arg Val Val Ser Val Leu
                85                  90                  95

Thr Val Leu His Gln Asp Trp Leu Asn Gly Lys Glu Tyr Lys Cys Lys
            100                 105                 110

Val Ser Asn Lys Ala Leu Pro Ala Pro Ile Glu Lys Thr Ile Ser Lys
        115                 120                 125

Ala Lys Gly Gln Pro Arg Glu Pro Gln Val Tyr Thr Leu Pro Pro Ser
    130                 135                 140

Arg Asp Glu Leu Thr Lys Asn Gln Val Ser Leu Thr Cys Leu Val Lys
145                 150                 155                 160

Gly Phe Tyr Pro Ser Asp Ile Ala Val Glu Trp Glu Ser Asn Gly Gln
                165                 170                 175

Pro Glu Asn Asn Tyr Lys Thr Thr Pro Pro Val Leu Asp Ser Asp Gly
            180                 185                 190

Ser Phe Phe Leu Tyr Ser Lys Leu Thr Val Asp Lys Ser Arg Trp Gln
        195                 200                 205

Gln Gly Asn Val Phe Ser Cys Ser Val Met His Glu Ala Leu His Asn
    210                 215                 220

His Tyr Thr Gln Lys Ser Leu Ser Leu Ser Pro Gly Lys
225                 230                 235


<210> SEQ ID NO 54
<211> LENGTH: 1670
<212> TYPE: PRT
<213> ORGANISM: Homo sapiens

<400> SEQUENCE: 54

Met Pro Pro Leu Leu Ala Pro Leu Leu Cys Leu Ala Leu Leu Pro Ala
1               5                   10                  15

Leu Ala Ala Arg Gly Pro Arg Cys Ser Gln Pro Gly Glu Thr Cys Leu
            20                  25                  30

Asn Gly Gly Lys Cys Glu Ala Ala Asn Gly Thr Glu Ala Cys Val Cys
        35                  40                  45

Gly Gly Ala Phe Val Gly Pro Arg Cys Gln Asp Pro Asn Pro Cys Leu
    50                  55                  60

Ser Thr Pro Cys Lys Asn Ala Gly Thr Cys His Val Val Asp Arg Arg
65                  70                  75                  80

Gly Val Ala Asp Tyr Ala Cys Ser Cys Ala Leu Gly Phe Ser Gly Pro
                85                  90                  95

Leu Cys Leu Thr Pro Leu Asp Asn Ala Cys Leu Thr Asn Pro Cys Arg
            100                 105                 110

Asn Gly Gly Thr Cys Asp Leu Leu Thr Leu Thr Glu Tyr Lys Cys Arg
        115                 120                 125

Cys Pro Pro Gly Trp Ser Gly Lys Ser Cys Gln Gln Ala Asp Pro Cys
    130                 135                 140

Ala Ser Asn Pro Cys Ala Asn Gly Gly Gln Cys Leu Pro Phe Glu Ala
145                 150                 155                 160

Ser Tyr Ile Cys His Cys Pro Pro Ser Phe His Gly Pro Thr Cys Arg
```

-continued

```
            165                 170                 175

Gln Asp Val Asn Glu Cys Gly Gln Lys Pro Gly Leu Cys Arg His Gly
            180                 185                 190

Gly Thr Cys His Asn Glu Val Gly Ser Tyr Arg Cys Val Cys Arg Ala
        195                 200                 205

Thr His Thr Gly Pro Asn Cys Glu Arg Pro Tyr Val Pro Cys Ser Pro
    210                 215                 220

Ser Pro Cys Gln Asn Gly Gly Thr Cys Arg Pro Thr Gly Asp Val Thr
225                 230                 235                 240

His Glu Cys Ala Cys Leu Pro Gly Phe Thr Gly Gln Asn Cys Glu Glu
                245                 250                 255

Asn Ile Asp Asp Cys Pro Gly Asn Asn Cys Lys Asn Gly Gly Ala Cys
            260                 265                 270

Val Asp Gly Val Asn Thr Tyr Asn Cys Arg Cys Pro Pro Glu Trp Thr
        275                 280                 285

Gly Gln Tyr Cys Thr Glu Asp Val Asp Glu Cys Gln Leu Met Pro Asn
    290                 295                 300

Ala Cys Gln Asn Gly Gly Thr Cys His Asn Thr His Gly Gly Tyr Asn
305                 310                 315                 320

Cys Val Cys Val Asn Gly Trp Thr Gly Glu Asp Cys Ser Glu Asn Ile
                325                 330                 335

Asp Asp Cys Ala Ser Ala Ala Cys Phe His Gly Ala Thr Cys His Asp
            340                 345                 350

Arg Val Ala Ser Phe Tyr Cys Glu Cys Pro His Gly Arg Thr Gly Leu
        355                 360                 365

Leu Cys His Leu Asn Asp Ala Cys Ile Ser Asn Pro Cys Asn Glu Gly
    370                 375                 380

Ser Asn Cys Asp Thr Asn Pro Val Asn Gly Lys Ala Ile Cys Thr Cys
385                 390                 395                 400

Pro Ser Gly Tyr Thr Gly Pro Ala Cys Ser Gln Asp Val Asp Glu Cys
                405                 410                 415

Ser Leu Gly Ala Asn Pro Cys Glu His Ala Gly Lys Cys Ile Asn Thr
            420                 425                 430

Leu Gly Ser Phe Glu Cys Gln Cys Leu Gln Gly Tyr Thr Gly Pro Arg
        435                 440                 445

Cys Glu Ile Asp Val Asn Glu Cys Val Ser Asn Pro Cys Gln Asn Asp
    450                 455                 460

Ala Thr Cys Leu Asp Gln Ile Gly Glu Phe Gln Cys Ile Cys Met Pro
465                 470                 475                 480

Gly Tyr Glu Gly Val His Cys Glu Val Asn Thr Asp Glu Cys Ala Ser
                485                 490                 495

Ser Pro Cys Leu His Asn Gly Arg Cys Leu Asp Lys Ile Asn Glu Phe
            500                 505                 510

Gln Cys Glu Cys Pro Thr Gly Phe Thr Gly His Leu Cys Gln Tyr Asp
        515                 520                 525

Val Asp Glu Cys Ala Ser Thr Pro Cys Lys Asn Gly Ala Lys Cys Leu
    530                 535                 540

Asp Gly Pro Asn Thr Tyr Thr Cys Val Cys Thr Glu Gly Tyr Thr Gly
545                 550                 555                 560

Thr His Cys Glu Val Asp Ile Asp Glu Cys Asp Pro Asp Pro Cys His
                565                 570                 575

Tyr Gly Ser Cys Lys Asp Gly Val Ala Thr Phe Thr Cys Leu Cys Arg
            580                 585                 590
```

-continued

```
Pro Gly Tyr Thr Gly His His Cys Glu Thr Asn Ile Asn Glu Cys Ser
        595                 600                 605

Ser Gln Pro Cys Arg His Gly Gly Thr Cys Gln Asp Arg Asp Asn Ala
    610                 615                 620

Tyr Leu Cys Phe Cys Leu Lys Gly Thr Thr Gly Pro Asn Cys Glu Ile
625                 630                 635                 640

Asn Leu Asp Asp Cys Ala Ser Ser Pro Cys Asp Ser Gly Thr Cys Leu
                645                 650                 655

Asp Lys Ile Asp Gly Tyr Glu Cys Ala Cys Glu Pro Gly Tyr Thr Gly
            660                 665                 670

Ser Met Cys Asn Ile Asn Ile Asp Glu Cys Ala Gly Asn Pro Cys His
        675                 680                 685

Asn Gly Gly Thr Cys Glu Asp Gly Ile Asn Gly Phe Thr Cys Arg Cys
    690                 695                 700

Pro Glu Gly Tyr His Asp Pro Thr Cys Leu Ser Glu Val Asn Glu Cys
705                 710                 715                 720

Asn Ser Asn Pro Cys Val His Gly Ala Cys Arg Asp Ser Leu Asn Gly
                725                 730                 735

Tyr Lys Cys Asp Cys Asp Pro Gly Trp Ser Gly Thr Asn Cys Asp Ile
            740                 745                 750

Asn Asn Asn Glu Cys Glu Ser Asn Pro Cys Val Asn Gly Gly Thr Cys
        755                 760                 765

Lys Asp Met Thr Ser Gly Tyr Val Cys Thr Cys Arg Glu Gly Phe Ser
    770                 775                 780

Gly Pro Asn Cys Gln Thr Asn Ile Asn Glu Cys Ala Ser Asn Pro Cys
785                 790                 795                 800

Leu Asn Gln Gly Thr Cys Ile Asp Asp Val Ala Gly Tyr Lys Cys Asn
                805                 810                 815

Cys Leu Leu Pro Tyr Thr Gly Ala Thr Cys Glu Val Val Leu Ala Pro
            820                 825                 830

Cys Ala Pro Ser Pro Cys Arg Asn Gly Gly Glu Cys Arg Gln Ser Glu
        835                 840                 845

Asp Tyr Glu Ser Phe Ser Cys Val Cys Pro Thr Gly Trp Gln Gly Gln
    850                 855                 860

Thr Cys Glu Val Asp Ile Asn Glu Cys Val Leu Ser Pro Cys Arg His
865                 870                 875                 880

Gly Ala Ser Cys Gln Asn Thr His Gly Gly Tyr Arg Cys His Cys Gln
                885                 890                 895

Ala Gly Tyr Ser Gly Arg Asn Cys Glu Thr Asp Ile Asp Asp Cys Arg
            900                 905                 910

Pro Asn Pro Cys His Asn Gly Gly Ser Cys Thr Asp Gly Ile Asn Thr
        915                 920                 925

Ala Phe Cys Asp Cys Leu Pro Gly Phe Arg Gly Thr Phe Cys Glu Glu
    930                 935                 940

Asp Ile Asn Glu Cys Ala Ser Asp Pro Cys Arg Asn Gly Ala Asn Cys
945                 950                 955                 960

Thr Asp Cys Val Asp Ser Tyr Thr Cys Thr Cys Pro Ala Gly Phe Ser
                965                 970                 975

Gly Ile His Cys Glu Asn Asn Thr Pro Asp Cys Thr Glu Ser Ser Cys
            980                 985                 990

Phe Asn Gly Gly Thr Cys Val Asp  Gly Ile Asn Ser Phe  Thr Cys Leu
        995                 1000                1005
```

```
Cys Pro  Pro Gly Phe Thr Gly  Ser Tyr Cys Gln His  Asp Val Asn
    1010                 1015                 1020

Glu Cys  Asp Ser Gln Pro Cys  Leu His Gly Gly Thr  Cys Gln Asp
    1025                 1030                 1035

Gly Cys  Gly Ser Tyr Arg Cys  Thr Cys Pro Gln Gly  Tyr Thr Gly
    1040                 1045                 1050

Pro Asn  Cys Gln Asn Leu Val  His Trp Cys Asp Ser  Ser Pro Cys
    1055                 1060                 1065

Lys Asn  Gly Gly Lys Cys Trp  Gln Thr His Thr Gln  Tyr Arg Cys
    1070                 1075                 1080

Glu Cys  Pro Ser Gly Trp Thr  Gly Leu Tyr Cys Asp  Val Pro Ser
    1085                 1090                 1095

Val Ser  Cys Glu Val Ala Ala  Gln Arg Gln Gly Val  Asp Val Ala
    1100                 1105                 1110

Arg Leu  Cys Gln His Gly Gly  Leu Cys Val Asp Ala  Gly Asn Thr
    1115                 1120                 1125

His His  Cys Arg Cys Gln Ala  Gly Tyr Thr Gly Ser  Tyr Cys Glu
    1130                 1135                 1140

Asp Leu  Val Asp Glu Cys Ser  Pro Ser Pro Cys Gln  Asn Gly Ala
    1145                 1150                 1155

Thr Cys  Thr Asp Tyr Leu Gly  Gly Tyr Ser Cys Lys  Cys Val Ala
    1160                 1165                 1170

Gly Tyr  His Gly Val Asn Cys  Ser Glu Glu Ile Asp  Glu Cys Leu
    1175                 1180                 1185

Ser His  Pro Cys Gln Asn Gly  Gly Thr Cys Leu Asp  Leu Pro Asn
    1190                 1195                 1200

Thr Tyr  Lys Cys Ser Cys Pro  Arg Gly Thr Gln Gly  Val His Cys
    1205                 1210                 1215

Glu Ile  Asn Val Asp Asp Cys  Asn Pro Pro Val Asp  Pro Val Ser
    1220                 1225                 1230

Arg Ser  Pro Lys Cys Phe Asn  Asn Gly Thr Cys Val  Asp Gln Val
    1235                 1240                 1245

Gly Gly  Tyr Ser Cys Thr Cys  Pro Pro Gly Phe Val  Gly Glu Arg
    1250                 1255                 1260

Cys Glu  Gly Asp Val Asn Glu  Cys Leu Ser Asn Pro  Cys Asp Ala
    1265                 1270                 1275

Arg Gly  Thr Gln Asn Cys Val  Gln Arg Val Asn Asp  Phe His Cys
    1280                 1285                 1290

Glu Cys  Arg Ala Gly His Thr  Gly Arg Arg Cys Glu  Ser Val Ile
    1295                 1300                 1305

Asn Gly  Cys Lys Gly Lys Pro  Cys Lys Asn Gly Gly  Thr Cys Ala
    1310                 1315                 1320

Val Ala  Ser Asn Thr Ala Arg  Gly Phe Ile Cys Lys  Cys Pro Ala
    1325                 1330                 1335

Gly Phe  Glu Gly Ala Thr Cys  Glu Asn Asp Ala Arg  Thr Cys Gly
    1340                 1345                 1350

Ser Leu  Arg Cys Leu Asn Gly  Gly Thr Cys Ile Ser  Gly Pro Arg
    1355                 1360                 1365

Ser Pro  Thr Cys Leu Cys Leu  Gly Pro Phe Thr Gly  Pro Glu Cys
    1370                 1375                 1380

Gln Phe  Pro Ala Ser Ser Pro  Cys Leu Gly Gly Asn  Pro Cys Tyr
    1385                 1390                 1395

Asn Gln  Gly Thr Cys Glu Pro  Thr Ser Glu Ser Pro  Phe Tyr Arg
```

```
    1400                1405                1410

Cys Leu  Cys Pro Ala Lys Phe  Asn Gly Leu Leu Cys  His Ile Leu
    1415                1420                1425

Asp Tyr  Ser Phe Gly Asp Leu  Gly Pro Gly Glu Pro  Lys Ser Cys
    1430                1435                1440

Asp Lys  Thr His Thr Cys Pro  Pro Cys Pro Ala Pro  Glu Leu Leu
    1445                1450                1455

Gly Gly  Pro Ser Val Phe Leu  Phe Pro Pro Lys Pro  Lys Asp Thr
    1460                1465                1470

Leu Met  Ile Ser Arg Thr Pro  Glu Val Thr Cys Val  Val Val Asp
    1475                1480                1485

Val Ser  His Glu Asp Pro Glu  Val Lys Phe Asn Trp  Tyr Val Asp
    1490                1495                1500

Gly Val  Glu Val His Asn Ala  Lys Thr Lys Pro Arg  Glu Glu Gln
    1505                1510                1515

Tyr Asn  Ser Thr Tyr Arg Val  Val Ser Val Leu Thr  Val Leu His
    1520                1525                1530

Gln Asp  Trp Leu Asn Gly Lys  Glu Tyr Lys Cys Lys  Val Ser Asn
    1535                1540                1545

Lys Ala  Leu Pro Ala Pro Ile  Glu Lys Thr Ile Ser  Lys Ala Lys
    1550                1555                1560

Gly Gln  Pro Arg Glu Pro Gln  Val Tyr Thr Leu Pro  Pro Ser Arg
    1565                1570                1575

Asp Glu  Leu Thr Lys Asn Gln  Val Ser Leu Thr Cys  Leu Val Lys
    1580                1585                1590

Gly Phe  Tyr Pro Ser Asp Ile  Ala Val Glu Trp Glu  Ser Asn Gly
    1595                1600                1605

Gln Pro  Glu Asn Asn Tyr Lys  Thr Thr Pro Pro Val  Leu Asp Ser
    1610                1615                1620

Asp Gly  Ser Phe Phe Leu Tyr  Ser Lys Leu Thr Val  Asp Lys Ser
    1625                1630                1635

Arg Trp  Gln Gln Gly Asn Val  Phe Ser Cys Ser Val  Met His Glu
    1640                1645                1650

Ala Leu  His Asn His Tyr Thr  Gln Lys Ser Leu Ser  Leu Ser Pro
    1655                1660                1665

Gly Lys
    1670


<210> SEQ ID NO 55
<211> LENGTH: 768
<212> TYPE: PRT
<213> ORGANISM: Homo sapiens

<400> SEQUENCE: 55

Met Pro Pro Leu Leu Ala Pro Leu Leu Cys Leu Ala Leu Leu Pro Ala
1               5                   10                  15

Leu Ala Ala Arg Gly Pro Arg Cys Ser Gln Pro Gly Glu Thr Cys Leu
            20                  25                  30

Asn Gly Gly Lys Cys Glu Ala Ala Asn Gly Thr Glu Ala Cys Val Cys
        35                  40                  45

Gly Gly Ala Phe Val Gly Pro Arg Cys Gln Asp Pro Asn Pro Cys Leu
    50                  55                  60

Ser Thr Pro Cys Lys Asn Ala Gly Thr Cys His Val Val Asp Arg Arg
65                  70                  75                  80
```

-continued

```
Gly Val Ala Asp Tyr Ala Cys Ser Cys Ala Leu Gly Phe Ser Gly Pro
                85                  90                  95

Leu Cys Leu Thr Pro Leu Asp Asn Ala Cys Leu Thr Asn Pro Cys Arg
            100                 105                 110

Asn Gly Gly Thr Cys Asp Leu Leu Thr Leu Thr Glu Tyr Lys Cys Arg
        115                 120                 125

Cys Pro Pro Gly Trp Ser Gly Lys Ser Cys Gln Gln Ala Asp Pro Cys
    130                 135                 140

Ala Ser Asn Pro Cys Ala Asn Gly Gly Gln Cys Leu Pro Phe Glu Ala
145                 150                 155                 160

Ser Tyr Ile Cys His Cys Pro Pro Ser Phe His Gly Pro Thr Cys Arg
                165                 170                 175

Gln Asp Val Asn Glu Cys Gly Gln Lys Pro Gly Leu Cys Arg His Gly
            180                 185                 190

Gly Thr Cys His Asn Glu Val Gly Ser Tyr Arg Cys Val Cys Arg Ala
        195                 200                 205

Thr His Thr Gly Pro Asn Cys Glu Arg Pro Tyr Val Pro Cys Ser Pro
    210                 215                 220

Ser Pro Cys Gln Asn Gly Gly Thr Cys Arg Pro Thr Gly Asp Val Thr
225                 230                 235                 240

His Glu Cys Ala Cys Leu Pro Gly Phe Thr Gly Gln Asn Cys Glu Glu
                245                 250                 255

Asn Ile Asp Asp Cys Pro Gly Asn Asn Cys Lys Asn Gly Gly Ala Cys
            260                 265                 270

Val Asp Gly Val Asn Thr Tyr Asn Cys Arg Cys Pro Pro Glu Trp Thr
        275                 280                 285

Gly Gln Tyr Cys Thr Glu Asp Val Asp Glu Cys Gln Leu Met Pro Asn
    290                 295                 300

Ala Cys Gln Asn Gly Gly Thr Cys His Asn Thr His Gly Gly Tyr Asn
305                 310                 315                 320

Cys Val Cys Val Asn Gly Trp Thr Gly Glu Asp Cys Ser Glu Asn Ile
                325                 330                 335

Asp Asp Cys Ala Ser Ala Ala Cys Phe His Gly Ala Thr Cys His Asp
            340                 345                 350

Arg Val Ala Ser Phe Tyr Cys Glu Cys Pro His Gly Arg Thr Gly Leu
        355                 360                 365

Leu Cys His Leu Asn Asp Ala Cys Ile Ser Asn Pro Cys Asn Glu Gly
    370                 375                 380

Ser Asn Cys Asp Thr Asn Pro Val Asn Gly Lys Ala Ile Cys Thr Cys
385                 390                 395                 400

Pro Ser Gly Tyr Thr Gly Pro Ala Cys Ser Gln Asp Val Asp Glu Cys
                405                 410                 415

Ser Leu Gly Ala Asn Pro Cys Glu His Ala Gly Lys Cys Ile Asn Thr
            420                 425                 430

Leu Gly Ser Phe Glu Cys Gln Cys Leu Gln Gly Tyr Thr Gly Pro Arg
        435                 440                 445

Cys Glu Ile Asp Val Asn Glu Cys Val Ser Asn Pro Cys Gln Asn Asp
    450                 455                 460

Ala Thr Cys Leu Asp Gln Ile Gly Glu Phe Gln Cys Ile Cys Met Pro
465                 470                 475                 480

Gly Tyr Glu Gly Val His Cys Glu Val Asn Thr Asp Glu Cys Ala Ser
                485                 490                 495

Ser Pro Cys Leu His Asn Gly Arg Cys Leu Asp Lys Ile Asn Glu Phe
```

```
            500                 505                 510

Gln Cys Glu Cys Pro Thr Gly Phe Thr Gly His Leu Cys Gln Tyr Asp
        515                 520                 525

Val Asp Glu Asp Leu Gly Pro Gly Glu Pro Lys Ser Cys Asp Lys Thr
    530                 535                 540

His Thr Cys Pro Pro Cys Pro Ala Pro Glu Leu Leu Gly Gly Pro Ser
545                 550                 555                 560

Val Phe Leu Phe Pro Pro Lys Pro Lys Asp Thr Leu Met Ile Ser Arg
                565                 570                 575

Thr Pro Glu Val Thr Cys Val Val Val Asp Val Ser His Glu Asp Pro
            580                 585                 590

Glu Val Lys Phe Asn Trp Tyr Val Asp Gly Val Glu Val His Asn Ala
        595                 600                 605

Lys Thr Lys Pro Arg Glu Glu Gln Tyr Asn Ser Thr Tyr Arg Val Val
    610                 615                 620

Ser Val Leu Thr Val Leu His Gln Asp Trp Leu Asn Gly Lys Glu Tyr
625                 630                 635                 640

Lys Cys Lys Val Ser Asn Lys Ala Leu Pro Ala Pro Ile Glu Lys Thr
                645                 650                 655

Ile Ser Lys Ala Lys Gly Gln Pro Arg Glu Pro Gln Val Tyr Thr Leu
            660                 665                 670

Pro Pro Ser Arg Asp Glu Leu Thr Lys Asn Gln Val Ser Leu Thr Cys
        675                 680                 685

Leu Val Lys Gly Phe Tyr Pro Ser Asp Ile Ala Val Glu Trp Glu Ser
    690                 695                 700

Asn Gly Gln Pro Glu Asn Asn Tyr Lys Thr Thr Pro Pro Val Leu Asp
705                 710                 715                 720

Ser Asp Gly Ser Phe Phe Leu Tyr Ser Lys Leu Thr Val Asp Lys Ser
                725                 730                 735

Arg Trp Gln Gln Gly Asn Val Phe Ser Cys Ser Val Met His Glu Ala
            740                 745                 750

Leu His Asn His Tyr Thr Gln Lys Ser Leu Ser Leu Ser Pro Gly Lys
        755                 760                 765


<210> SEQ ID NO 56
<211> LENGTH: 1185
<212> TYPE: PRT
<213> ORGANISM: Homo sapiens

<400> SEQUENCE: 56

Met Pro Pro Leu Leu Ala Pro Leu Leu Cys Leu Ala Leu Leu Pro Ala
1               5                   10                  15

Leu Ala Ala Arg Gly Pro Arg Cys Ser Gln Pro Gly Glu Thr Cys Leu
            20                  25                  30

Asn Gly Gly Lys Cys Glu Ala Ala Asn Gly Thr Glu Ala Cys Val Cys
        35                  40                  45

Gly Gly Ala Phe Val Gly Pro Arg Cys Gln Asp Pro Asn Pro Cys Leu
    50                  55                  60

Ser Thr Pro Cys Lys Asn Ala Gly Thr Cys His Val Val Asp Arg Arg
65                  70                  75                  80

Gly Val Ala Asp Tyr Ala Cys Ser Cys Ala Leu Gly Phe Ser Gly Pro
                85                  90                  95

Leu Cys Leu Thr Pro Leu Asp Asn Ala Cys Leu Thr Asn Pro Cys Arg
            100                 105                 110
```

-continued

```
Asn Gly Gly Thr Cys Asp Leu Leu Thr Leu Thr Glu Tyr Lys Cys Arg
        115                 120                 125

Cys Pro Pro Gly Trp Ser Gly Lys Ser Cys Gln Gln Ala Asp Pro Cys
    130                 135                 140

Ala Ser Asn Pro Cys Ala Asn Gly Gly Gln Cys Leu Pro Phe Glu Ala
145                 150                 155                 160

Ser Tyr Ile Cys His Cys Pro Pro Ser Phe His Gly Pro Thr Cys Arg
                165                 170                 175

Gln Asp Val Asn Glu Cys Gly Gln Lys Pro Gly Leu Cys Arg His Gly
            180                 185                 190

Gly Thr Cys His Asn Glu Val Gly Ser Tyr Arg Cys Val Cys Arg Ala
        195                 200                 205

Thr His Thr Gly Pro Asn Cys Glu Arg Pro Tyr Val Pro Cys Ser Pro
    210                 215                 220

Ser Pro Cys Gln Asn Gly Gly Thr Cys Arg Pro Thr Gly Asp Val Thr
225                 230                 235                 240

His Glu Cys Ala Cys Leu Pro Gly Phe Thr Gly Gln Asn Cys Glu Glu
                245                 250                 255

Asn Ile Asp Asp Cys Pro Gly Asn Asn Cys Lys Asn Gly Gly Ala Cys
            260                 265                 270

Val Asp Gly Val Asn Thr Tyr Asn Cys Arg Cys Pro Pro Glu Trp Thr
        275                 280                 285

Gly Gln Tyr Cys Thr Glu Asp Val Asp Glu Cys Gln Leu Met Pro Asn
    290                 295                 300

Ala Cys Gln Asn Gly Gly Thr Cys His Asn Thr His Gly Gly Tyr Asn
305                 310                 315                 320

Cys Val Cys Val Asn Gly Trp Thr Gly Glu Asp Cys Ser Glu Asn Ile
                325                 330                 335

Asp Asp Cys Ala Ser Ala Ala Cys Phe His Gly Ala Thr Cys His Asp
            340                 345                 350

Arg Val Ala Ser Phe Tyr Cys Glu Cys Pro His Gly Arg Thr Gly Leu
        355                 360                 365

Leu Cys His Leu Asn Asp Ala Cys Ile Ser Asn Pro Cys Asn Glu Gly
    370                 375                 380

Ser Asn Cys Asp Thr Asn Pro Val Asn Gly Lys Ala Ile Cys Thr Cys
385                 390                 395                 400

Pro Ser Gly Tyr Thr Gly Pro Ala Cys Ser Gln Asp Val Asp Glu Cys
                405                 410                 415

Ser Leu Gly Ala Asn Pro Cys Glu His Ala Gly Lys Cys Ile Asn Thr
            420                 425                 430

Leu Gly Ser Phe Glu Cys Gln Cys Leu Gln Gly Tyr Thr Gly Pro Arg
        435                 440                 445

Cys Glu Ile Asp Val Asn Glu Cys Val Ser Asn Pro Cys Gln Asn Asp
    450                 455                 460

Ala Thr Cys Leu Asp Gln Ile Gly Glu Phe Gln Cys Ile Cys Met Pro
465                 470                 475                 480

Gly Tyr Glu Gly Val His Cys Glu Val Asn Thr Asp Glu Cys Ala Ser
                485                 490                 495

Ser Pro Cys Leu His Asn Gly Arg Cys Leu Asp Lys Ile Asn Glu Phe
            500                 505                 510

Gln Cys Glu Cys Pro Thr Gly Phe Thr Gly His Leu Cys Gln Tyr Asp
        515                 520                 525

Val Asp Glu Cys Ala Ser Thr Pro Cys Lys Asn Gly Ala Lys Cys Leu
```

-continued

```
    530                 535                 540

Asp Gly Pro Asn Thr Tyr Thr Cys Val Cys Thr Glu Gly Tyr Thr Gly
545                 550                 555                 560

Thr His Cys Glu Val Asp Ile Asp Glu Cys Asp Pro Asp Pro Cys His
                565                 570                 575

Tyr Gly Ser Cys Lys Asp Gly Val Ala Thr Phe Thr Cys Leu Cys Arg
            580                 585                 590

Pro Gly Tyr Thr Gly His His Cys Glu Thr Asn Ile Asn Glu Cys Ser
        595                 600                 605

Ser Gln Pro Cys Arg His Gly Gly Thr Cys Gln Asp Arg Asp Asn Ala
    610                 615                 620

Tyr Leu Cys Phe Cys Leu Lys Gly Thr Thr Gly Pro Asn Cys Glu Ile
625                 630                 635                 640

Asn Leu Asp Asp Cys Ala Ser Ser Pro Cys Asp Ser Gly Thr Cys Leu
                645                 650                 655

Asp Lys Ile Asp Gly Tyr Glu Cys Ala Cys Glu Pro Gly Tyr Thr Gly
            660                 665                 670

Ser Met Cys Asn Ile Asn Ile Asp Glu Cys Ala Gly Asn Pro Cys His
        675                 680                 685

Asn Gly Gly Thr Cys Glu Asp Gly Ile Asn Gly Phe Thr Cys Arg Cys
    690                 695                 700

Pro Glu Gly Tyr His Asp Pro Thr Cys Leu Ser Glu Val Asn Glu Cys
705                 710                 715                 720

Asn Ser Asn Pro Cys Val His Gly Ala Cys Arg Asp Ser Leu Asn Gly
                725                 730                 735

Tyr Lys Cys Asp Cys Asp Pro Gly Trp Ser Gly Thr Asn Cys Asp Ile
            740                 745                 750

Asn Asn Asn Glu Cys Glu Ser Asn Pro Cys Val Asn Gly Gly Thr Cys
        755                 760                 765

Lys Asp Met Thr Ser Gly Tyr Val Cys Thr Cys Arg Glu Gly Phe Ser
    770                 775                 780

Gly Pro Asn Cys Gln Thr Asn Ile Asn Glu Cys Ala Ser Asn Pro Cys
785                 790                 795                 800

Leu Asn Gln Gly Thr Cys Ile Asp Asp Val Ala Gly Tyr Lys Cys Asn
                805                 810                 815

Cys Leu Leu Pro Tyr Thr Gly Ala Thr Cys Glu Val Val Leu Ala Pro
            820                 825                 830

Cys Ala Pro Ser Pro Cys Arg Asn Gly Gly Glu Cys Arg Gln Ser Glu
        835                 840                 845

Asp Tyr Glu Ser Phe Ser Cys Val Cys Pro Thr Gly Trp Gln Gly Gln
    850                 855                 860

Thr Cys Glu Val Asp Ile Asn Glu Cys Val Leu Ser Pro Cys Arg His
865                 870                 875                 880

Gly Ala Ser Cys Gln Asn Thr His Gly Gly Tyr Arg Cys His Cys Gln
                885                 890                 895

Ala Gly Tyr Ser Gly Arg Asn Cys Glu Thr Asp Ile Asp Asp Cys Arg
            900                 905                 910

Pro Asn Pro Cys His Asn Gly Gly Ser Cys Thr Asp Gly Ile Asn Thr
        915                 920                 925

Ala Phe Cys Asp Cys Leu Pro Gly Phe Arg Gly Thr Phe Cys Glu Glu
    930                 935                 940

Asp Ile Asn Glu Asp Leu Gly Pro Gly Glu Pro Lys Ser Cys Asp Lys
945                 950                 955                 960
```

Thr His Thr Cys Pro Pro Cys Pro Ala Pro Glu Leu Leu Gly Gly Pro
965 970 975

Ser Val Phe Leu Phe Pro Pro Lys Pro Lys Asp Thr Leu Met Ile Ser
980 985 990

Arg Thr Pro Glu Val Thr Cys Val Val Val Asp Val Ser His Glu Asp
995 1000 1005

Pro Glu Val Lys Phe Asn Trp Tyr Val Asp Gly Val Glu Val His
1010 1015 1020

Asn Ala Lys Thr Lys Pro Arg Glu Glu Gln Tyr Asn Ser Thr Tyr
1025 1030 1035

Arg Val Val Ser Val Leu Thr Val Leu His Gln Asp Trp Leu Asn
1040 1045 1050

Gly Lys Glu Tyr Lys Cys Lys Val Ser Asn Lys Ala Leu Pro Ala
1055 1060 1065

Pro Ile Glu Lys Thr Ile Ser Lys Ala Lys Gly Gln Pro Arg Glu
1070 1075 1080

Pro Gln Val Tyr Thr Leu Pro Pro Ser Arg Asp Glu Leu Thr Lys
1085 1090 1095

Asn Gln Val Ser Leu Thr Cys Leu Val Lys Gly Phe Tyr Pro Ser
1100 1105 1110

Asp Ile Ala Val Glu Trp Glu Ser Asn Gly Gln Pro Glu Asn Asn
1115 1120 1125

Tyr Lys Thr Thr Pro Pro Val Leu Asp Ser Asp Gly Ser Phe Phe
1130 1135 1140

Leu Tyr Ser Lys Leu Thr Val Asp Lys Ser Arg Trp Gln Gln Gly
1145 1150 1155

Asn Val Phe Ser Cys Ser Val Met His Glu Ala Leu His Asn His
1160 1165 1170

Tyr Thr Gln Lys Ser Leu Ser Leu Ser Pro Gly Lys
1175 1180 1185

<210> SEQ ID NO 57
<211> LENGTH: 830
<212> TYPE: PRT
<213> ORGANISM: Homo sapiens

<400> SEQUENCE: 57

Met Pro Pro Leu Leu Ala Pro Leu Leu Cys Leu Ala Leu Leu Pro Ala
1 5 10 15

Leu Ala Ala Arg Gly Pro Arg Cys Ala Ser Ala Ala Cys Phe His Gly
20 25 30

Ala Thr Cys His Asp Arg Val Ala Ser Phe Tyr Cys Glu Cys Pro His
35 40 45

Gly Arg Thr Gly Leu Leu Cys His Leu Asn Asp Ala Cys Ile Ser Asn
50 55 60

Pro Cys Asn Glu Gly Ser Asn Cys Asp Thr Asn Pro Val Asn Gly Lys
65 70 75 80

Ala Ile Cys Thr Cys Pro Ser Gly Tyr Thr Gly Pro Ala Cys Ser Gln
85 90 95

Asp Val Asp Glu Cys Ser Leu Gly Ala Asn Pro Cys Glu His Ala Gly
100 105 110

Lys Cys Ile Asn Thr Leu Gly Ser Phe Glu Cys Gln Cys Leu Gln Gly
115 120 125

Tyr Thr Gly Pro Arg Cys Glu Ile Asp Val Asn Glu Cys Val Ser Asn

-continued

```
    130                 135                 140

Pro Cys Gln Asn Asp Ala Thr Cys Leu Asp Gln Ile Gly Glu Phe Gln
145                 150                 155                 160

Cys Ile Cys Met Pro Gly Tyr Glu Gly Val His Cys Glu Val Asn Thr
                165                 170                 175

Asp Glu Cys Ala Ser Ser Pro Cys Leu His Asn Gly Arg Cys Leu Asp
            180                 185                 190

Lys Ile Asn Glu Phe Gln Cys Glu Cys Pro Thr Gly Phe Thr Gly His
        195                 200                 205

Leu Cys Gln Tyr Asp Val Asp Glu Cys Ala Ser Thr Pro Cys Lys Asn
    210                 215                 220

Gly Ala Lys Cys Leu Asp Gly Pro Asn Thr Tyr Thr Cys Val Cys Thr
225                 230                 235                 240

Glu Gly Tyr Thr Gly Thr His Cys Glu Val Asp Ile Asp Glu Cys Asp
                245                 250                 255

Pro Asp Pro Cys His Tyr Gly Ser Cys Lys Asp Gly Val Ala Thr Phe
            260                 265                 270

Thr Cys Leu Cys Arg Pro Gly Tyr Thr Gly His His Cys Glu Thr Asn
        275                 280                 285

Ile Asn Glu Cys Ser Ser Gln Pro Cys Arg His Gly Gly Thr Cys Gln
    290                 295                 300

Asp Arg Asp Asn Ala Tyr Leu Cys Phe Cys Leu Lys Gly Thr Thr Gly
305                 310                 315                 320

Pro Asn Cys Glu Ile Asn Leu Asp Asp Cys Ala Ser Ser Pro Cys Asp
                325                 330                 335

Ser Gly Thr Cys Leu Asp Lys Ile Asp Gly Tyr Glu Cys Ala Cys Glu
            340                 345                 350

Pro Gly Tyr Thr Gly Ser Met Cys Asn Ile Asn Ile Asp Glu Cys Ala
        355                 360                 365

Gly Asn Pro Cys His Asn Gly Gly Thr Cys Glu Asp Gly Ile Asn Gly
    370                 375                 380

Phe Thr Cys Arg Cys Pro Glu Gly Tyr His Asp Pro Thr Cys Leu Ser
385                 390                 395                 400

Glu Val Asn Glu Cys Asn Ser Asn Pro Cys Val His Gly Ala Cys Arg
                405                 410                 415

Asp Ser Leu Asn Gly Tyr Lys Cys Asp Cys Asp Pro Gly Trp Ser Gly
            420                 425                 430

Thr Asn Cys Asp Ile Asn Asn Asn Glu Cys Glu Ser Asn Pro Cys Val
        435                 440                 445

Asn Gly Gly Thr Cys Lys Asp Met Thr Ser Gly Tyr Val Cys Thr Cys
    450                 455                 460

Arg Glu Gly Phe Ser Gly Pro Asn Cys Gln Thr Asn Ile Asn Glu Cys
465                 470                 475                 480

Ala Ser Asn Pro Cys Leu Asn Gln Gly Thr Cys Ile Asp Asp Val Ala
                485                 490                 495

Gly Tyr Lys Cys Asn Cys Leu Leu Pro Tyr Thr Gly Ala Thr Cys Glu
            500                 505                 510

Val Val Leu Ala Pro Cys Ala Pro Ser Pro Cys Arg Asn Gly Gly Glu
        515                 520                 525

Cys Arg Gln Ser Glu Asp Tyr Glu Ser Phe Ser Cys Val Cys Pro Thr
    530                 535                 540

Gly Trp Gln Gly Gln Thr Cys Glu Val Asp Ile Asn Glu Cys Val Leu
545                 550                 555                 560
```

Ser Pro Cys Arg His Gly Ala Ser Cys Gln Asn Thr His Gly Gly Tyr
565 570 575

Arg Cys His Cys Gln Ala Gly Tyr Ser Gly Arg Asn Cys Glu Thr Asp
580 585 590

Ile Asp Leu Gly Pro Gly Glu Pro Lys Ser Cys Asp Lys Thr His Thr
595 600 605

Cys Pro Pro Cys Pro Ala Pro Glu Leu Leu Gly Gly Pro Ser Val Phe
610 615 620

Leu Phe Pro Pro Lys Pro Lys Asp Thr Leu Met Ile Ser Arg Thr Pro
625 630 635 640

Glu Val Thr Cys Val Val Val Asp Val Ser His Glu Asp Pro Glu Val
645 650 655

Lys Phe Asn Trp Tyr Val Asp Gly Val Glu Val His Asn Ala Lys Thr
660 665 670

Lys Pro Arg Glu Glu Gln Tyr Asn Ser Thr Tyr Arg Val Val Ser Val
675 680 685

Leu Thr Val Leu His Gln Asp Trp Leu Asn Gly Lys Glu Tyr Lys Cys
690 695 700

Lys Val Ser Asn Lys Ala Leu Pro Ala Pro Ile Glu Lys Thr Ile Ser
705 710 715 720

Lys Ala Lys Gly Gln Pro Arg Glu Pro Gln Val Tyr Thr Leu Pro Pro
725 730 735

Ser Arg Asp Glu Leu Thr Lys Asn Gln Val Ser Leu Thr Cys Leu Val
740 745 750

Lys Gly Phe Tyr Pro Ser Asp Ile Ala Val Glu Trp Glu Ser Asn Gly
755 760 765

Gln Pro Glu Asn Asn Tyr Lys Thr Thr Pro Pro Val Leu Asp Ser Asp
770 775 780

Gly Ser Phe Phe Leu Tyr Ser Lys Leu Thr Val Asp Lys Ser Arg Trp
785 790 795 800

Gln Gln Gly Asn Val Phe Ser Cys Ser Val Met His Glu Ala Leu His
805 810 815

Asn His Tyr Thr Gln Lys Ser Leu Ser Leu Ser Pro Gly Lys
820 825 830

<210> SEQ ID NO 58
<211> LENGTH: 829
<212> TYPE: PRT
<213> ORGANISM: Homo sapiens

<400> SEQUENCE: 58

Met Trp Gly Trp Lys Cys Leu Leu Phe Trp Ala Val Leu Val Thr Ala
1 5 10 15

Thr Leu Cys Thr Ala Arg Cys Ala Ser Ala Ala Cys Phe His Gly Ala
20 25 30

Thr Cys His Asp Arg Val Ala Ser Phe Tyr Cys Glu Cys Pro His Gly
35 40 45

Arg Thr Gly Leu Leu Cys His Leu Asn Asp Ala Cys Ile Ser Asn Pro
50 55 60

Cys Asn Glu Gly Ser Asn Cys Asp Thr Asn Pro Val Asn Gly Lys Ala
65 70 75 80

Ile Cys Thr Cys Pro Ser Gly Tyr Thr Gly Pro Ala Cys Ser Gln Asp
85 90 95

Val Asp Glu Cys Ser Leu Gly Ala Asn Pro Cys Glu His Ala Gly Lys

```
            100                 105                 110

Cys Ile Asn Thr Leu Gly Ser Phe Glu Cys Gln Cys Leu Gln Gly Tyr
        115                 120                 125

Thr Gly Pro Arg Cys Glu Ile Asp Val Asn Glu Cys Val Ser Asn Pro
    130                 135                 140

Cys Gln Asn Asp Ala Thr Cys Leu Asp Gln Ile Gly Glu Phe Gln Cys
145                 150                 155                 160

Ile Cys Met Pro Gly Tyr Glu Gly Val His Cys Glu Val Asn Thr Asp
                165                 170                 175

Glu Cys Ala Ser Ser Pro Cys Leu His Asn Gly Arg Cys Leu Asp Lys
            180                 185                 190

Ile Asn Glu Phe Gln Cys Glu Cys Pro Thr Gly Phe Thr Gly His Leu
        195                 200                 205

Cys Gln Tyr Asp Val Asp Glu Cys Ala Ser Thr Pro Cys Lys Asn Gly
    210                 215                 220

Ala Lys Cys Leu Asp Gly Pro Asn Thr Tyr Thr Cys Val Cys Thr Glu
225                 230                 235                 240

Gly Tyr Thr Gly Thr His Cys Glu Val Asp Ile Asp Glu Cys Asp Pro
                245                 250                 255

Asp Pro Cys His Tyr Gly Ser Cys Lys Asp Gly Val Ala Thr Phe Thr
            260                 265                 270

Cys Leu Cys Arg Pro Gly Tyr Thr Gly His His Cys Glu Thr Asn Ile
        275                 280                 285

Asn Glu Cys Ser Ser Gln Pro Cys Arg His Gly Gly Thr Cys Gln Asp
    290                 295                 300

Arg Asp Asn Ala Tyr Leu Cys Phe Cys Leu Lys Gly Thr Thr Gly Pro
305                 310                 315                 320

Asn Cys Glu Ile Asn Leu Asp Asp Cys Ala Ser Ser Pro Cys Asp Ser
                325                 330                 335

Gly Thr Cys Leu Asp Lys Ile Asp Gly Tyr Glu Cys Ala Cys Glu Pro
            340                 345                 350

Gly Tyr Thr Gly Ser Met Cys Asn Ile Asn Ile Asp Glu Cys Ala Gly
        355                 360                 365

Asn Pro Cys His Asn Gly Gly Thr Cys Glu Asp Gly Ile Asn Gly Phe
    370                 375                 380

Thr Cys Arg Cys Pro Glu Gly Tyr His Asp Pro Thr Cys Leu Ser Glu
385                 390                 395                 400

Val Asn Glu Cys Asn Ser Asn Pro Cys Val His Gly Ala Cys Arg Asp
                405                 410                 415

Ser Leu Asn Gly Tyr Lys Cys Asp Cys Asp Pro Gly Trp Ser Gly Thr
            420                 425                 430

Asn Cys Asp Ile Asn Asn Asn Glu Cys Glu Ser Asn Pro Cys Val Asn
        435                 440                 445

Gly Gly Thr Cys Lys Asp Met Thr Ser Gly Tyr Val Cys Thr Cys Arg
    450                 455                 460

Glu Gly Phe Ser Gly Pro Asn Cys Gln Thr Asn Ile Asn Glu Cys Ala
465                 470                 475                 480

Ser Asn Pro Cys Leu Asn Gln Gly Thr Cys Ile Asp Asp Val Ala Gly
                485                 490                 495

Tyr Lys Cys Asn Cys Leu Leu Pro Tyr Thr Gly Ala Thr Cys Glu Val
            500                 505                 510

Val Leu Ala Pro Cys Ala Pro Ser Pro Cys Arg Asn Gly Gly Glu Cys
        515                 520                 525
```

```
Arg Gln Ser Glu Asp Tyr Glu Ser Phe Ser Cys Val Cys Pro Thr Gly
    530                 535                 540

Trp Gln Gly Gln Thr Cys Glu Val Asp Ile Asn Glu Cys Val Leu Ser
545                 550                 555                 560

Pro Cys Arg His Gly Ala Ser Cys Gln Asn Thr His Gly Gly Tyr Arg
                565                 570                 575

Cys His Cys Gln Ala Gly Tyr Ser Gly Arg Asn Cys Glu Thr Asp Ile
            580                 585                 590

Asp Leu Gly Pro Gly Glu Pro Lys Ser Cys Asp Lys Thr His Thr Cys
        595                 600                 605

Pro Pro Cys Pro Ala Pro Glu Leu Leu Gly Gly Pro Ser Val Phe Leu
    610                 615                 620

Phe Pro Pro Lys Pro Lys Asp Thr Leu Met Ile Ser Arg Thr Pro Glu
625                 630                 635                 640

Val Thr Cys Val Val Val Asp Val Ser His Glu Asp Pro Glu Val Lys
                645                 650                 655

Phe Asn Trp Tyr Val Asp Gly Val Glu Val His Asn Ala Lys Thr Lys
            660                 665                 670

Pro Arg Glu Glu Gln Tyr Asn Ser Thr Tyr Arg Val Val Ser Val Leu
        675                 680                 685

Thr Val Leu His Gln Asp Trp Leu Asn Gly Lys Glu Tyr Lys Cys Lys
    690                 695                 700

Val Ser Asn Lys Ala Leu Pro Ala Pro Ile Glu Lys Thr Ile Ser Lys
705                 710                 715                 720

Ala Lys Gly Gln Pro Arg Glu Pro Gln Val Tyr Thr Leu Pro Pro Ser
                725                 730                 735

Arg Asp Glu Leu Thr Lys Asn Gln Val Ser Leu Thr Cys Leu Val Lys
            740                 745                 750

Gly Phe Tyr Pro Ser Asp Ile Ala Val Glu Trp Glu Ser Asn Gly Gln
        755                 760                 765

Pro Glu Asn Asn Tyr Lys Thr Thr Pro Pro Val Leu Asp Ser Asp Gly
    770                 775                 780

Ser Phe Phe Leu Tyr Ser Lys Leu Thr Val Asp Lys Ser Arg Trp Gln
785                 790                 795                 800

Gln Gly Asn Val Phe Ser Cys Ser Val Met His Glu Ala Leu His Asn
                805                 810                 815

His Tyr Thr Gln Lys Ser Leu Ser Leu Ser Pro Gly Lys
            820                 825


<210> SEQ ID NO 59
<211> LENGTH: 1355
<212> TYPE: PRT
<213> ORGANISM: Homo sapiens

<400> SEQUENCE: 59

Met Pro Pro Leu Leu Ala Pro Leu Leu Cys Leu Ala Leu Leu Pro Ala
1               5                   10                  15

Leu Ala Ala Arg Gly Pro Arg Cys Ala Ser Ala Ala Cys Phe His Gly
            20                  25                  30

Ala Thr Cys His Asp Arg Val Ala Ser Phe Tyr Cys Glu Cys Pro His
        35                  40                  45

Gly Arg Thr Gly Leu Leu Cys His Leu Asn Asp Ala Cys Ile Ser Asn
    50                  55                  60

Pro Cys Asn Glu Gly Ser Asn Cys Asp Thr Asn Pro Val Asn Gly Lys
```

-continued

```
65                  70                  75                  80

Ala Ile Cys Thr Cys Pro Ser Gly Tyr Thr Gly Pro Ala Cys Ser Gln
                85                  90                  95

Asp Val Asp Glu Cys Ser Leu Gly Ala Asn Pro Cys Glu His Ala Gly
            100                 105                 110

Lys Cys Ile Asn Thr Leu Gly Ser Phe Glu Cys Gln Cys Leu Gln Gly
        115                 120                 125

Tyr Thr Gly Pro Arg Cys Glu Ile Asp Val Asn Glu Cys Val Ser Asn
    130                 135                 140

Pro Cys Gln Asn Asp Ala Thr Cys Leu Asp Gln Ile Gly Glu Phe Gln
145                 150                 155                 160

Cys Ile Cys Met Pro Gly Tyr Glu Gly Val His Cys Glu Val Asn Thr
                165                 170                 175

Asp Glu Cys Ala Ser Ser Pro Cys Leu His Asn Gly Arg Cys Leu Asp
            180                 185                 190

Lys Ile Asn Glu Phe Gln Cys Glu Cys Pro Thr Gly Phe Thr Gly His
        195                 200                 205

Leu Cys Gln Tyr Asp Val Asp Glu Cys Ala Ser Thr Pro Cys Lys Asn
    210                 215                 220

Gly Ala Lys Cys Leu Asp Gly Pro Asn Thr Tyr Thr Cys Val Cys Thr
225                 230                 235                 240

Glu Gly Tyr Thr Gly Thr His Cys Glu Val Asp Ile Asp Glu Cys Asp
                245                 250                 255

Pro Asp Pro Cys His Tyr Gly Ser Cys Lys Asp Gly Val Ala Thr Phe
            260                 265                 270

Thr Cys Leu Cys Arg Pro Gly Tyr Thr Gly His His Cys Glu Thr Asn
        275                 280                 285

Ile Asn Glu Cys Ser Ser Gln Pro Cys Arg His Gly Gly Thr Cys Gln
    290                 295                 300

Asp Arg Asp Asn Ala Tyr Leu Cys Phe Cys Leu Lys Gly Thr Thr Gly
305                 310                 315                 320

Pro Asn Cys Glu Ile Asn Leu Asp Asp Cys Ala Ser Ser Pro Cys Asp
                325                 330                 335

Ser Gly Thr Cys Leu Asp Lys Ile Asp Gly Tyr Glu Cys Ala Cys Glu
            340                 345                 350

Pro Gly Tyr Thr Gly Ser Met Cys Asn Ile Asn Ile Asp Glu Cys Ala
        355                 360                 365

Gly Asn Pro Cys His Asn Gly Gly Thr Cys Glu Asp Gly Ile Asn Gly
    370                 375                 380

Phe Thr Cys Arg Cys Pro Glu Gly Tyr His Asp Pro Thr Cys Leu Ser
385                 390                 395                 400

Glu Val Asn Glu Cys Asn Ser Asn Pro Cys Val His Gly Ala Cys Arg
                405                 410                 415

Asp Ser Leu Asn Gly Tyr Lys Cys Asp Cys Asp Pro Gly Trp Ser Gly
            420                 425                 430

Thr Asn Cys Asp Ile Asn Asn Asn Glu Cys Glu Ser Asn Pro Cys Val
        435                 440                 445

Asn Gly Gly Thr Cys Lys Asp Met Thr Ser Gly Tyr Val Cys Thr Cys
    450                 455                 460

Arg Glu Gly Phe Ser Gly Pro Asn Cys Gln Thr Asn Ile Asn Glu Cys
465                 470                 475                 480

Ala Ser Asn Pro Cys Leu Asn Gln Gly Thr Cys Ile Asp Asp Val Ala
                485                 490                 495
```

```
Gly Tyr Lys Cys Asn Cys Leu Leu Pro Tyr Thr Gly Ala Thr Cys Glu
            500                 505                 510

Val Val Leu Ala Pro Cys Ala Pro Ser Pro Cys Arg Asn Gly Gly Glu
        515                 520                 525

Cys Arg Gln Ser Glu Asp Tyr Glu Ser Phe Ser Cys Val Cys Pro Thr
    530                 535                 540

Gly Trp Gln Gly Gln Thr Cys Glu Val Asp Ile Asn Glu Cys Val Leu
545                 550                 555                 560

Ser Pro Cys Arg His Gly Ala Ser Cys Gln Asn Thr His Gly Gly Tyr
                565                 570                 575

Arg Cys His Cys Gln Ala Gly Tyr Ser Gly Arg Asn Cys Glu Thr Asp
            580                 585                 590

Ile Asp Asp Cys Arg Pro Asn Pro Cys His Asn Gly Gly Ser Cys Thr
        595                 600                 605

Asp Gly Ile Asn Thr Ala Phe Cys Asp Cys Leu Pro Gly Phe Arg Gly
    610                 615                 620

Thr Phe Cys Glu Glu Asp Ile Asn Glu Cys Ala Ser Asp Pro Cys Arg
625                 630                 635                 640

Asn Gly Ala Asn Cys Thr Asp Cys Val Asp Ser Tyr Thr Cys Thr Cys
                645                 650                 655

Pro Ala Gly Phe Ser Gly Ile His Cys Glu Asn Asn Thr Pro Asp Cys
            660                 665                 670

Thr Glu Ser Ser Cys Phe Asn Gly Gly Thr Cys Val Asp Gly Ile Asn
        675                 680                 685

Ser Phe Thr Cys Leu Cys Pro Pro Gly Phe Thr Gly Ser Tyr Cys Gln
    690                 695                 700

His Asp Val Asn Glu Cys Asp Ser Gln Pro Cys Leu His Gly Gly Thr
705                 710                 715                 720

Cys Gln Asp Gly Cys Gly Ser Tyr Arg Cys Thr Cys Pro Gln Gly Tyr
                725                 730                 735

Thr Gly Pro Asn Cys Gln Asn Leu Val His Trp Cys Asp Ser Ser Pro
            740                 745                 750

Cys Lys Asn Gly Gly Lys Cys Trp Gln Thr His Thr Gln Tyr Arg Cys
        755                 760                 765

Glu Cys Pro Ser Gly Trp Thr Gly Leu Tyr Cys Asp Val Pro Ser Val
    770                 775                 780

Ser Cys Glu Val Ala Ala Gln Arg Gln Gly Val Asp Val Ala Arg Leu
785                 790                 795                 800

Cys Gln His Gly Gly Leu Cys Val Asp Ala Gly Asn Thr His His Cys
                805                 810                 815

Arg Cys Gln Ala Gly Tyr Thr Gly Ser Tyr Cys Glu Asp Leu Val Asp
            820                 825                 830

Glu Cys Ser Pro Ser Pro Cys Gln Asn Gly Ala Thr Cys Thr Asp Tyr
        835                 840                 845

Leu Gly Gly Tyr Ser Cys Lys Cys Val Ala Gly Tyr His Gly Val Asn
    850                 855                 860

Cys Ser Glu Glu Ile Asp Glu Cys Leu Ser His Pro Cys Gln Asn Gly
865                 870                 875                 880

Gly Thr Cys Leu Asp Leu Pro Asn Thr Tyr Lys Cys Ser Cys Pro Arg
                885                 890                 895

Gly Thr Gln Gly Val His Cys Glu Ile Asn Val Asp Asp Cys Asn Pro
            900                 905                 910
```

-continued

```
Pro Val Asp Pro Val Ser Arg Ser Pro Lys Cys Phe Asn Asn Gly Thr
        915                 920                 925

Cys Val Asp Gln Val Gly Gly Tyr Ser Cys Thr Cys Pro Pro Gly Phe
    930                 935                 940

Val Gly Glu Arg Cys Glu Gly Asp Val Asn Glu Cys Leu Ser Asn Pro
945                 950                 955                 960

Cys Asp Ala Arg Gly Thr Gln Asn Cys Val Gln Arg Val Asn Asp Phe
                965                 970                 975

His Cys Glu Cys Arg Ala Gly His Thr Gly Arg Arg Cys Glu Ser Val
            980                 985                 990

Ile Asn Gly Cys Lys Gly Lys Pro  Cys Lys Asn Gly Gly  Thr Cys Ala
        995                 1000                 1005

Val Ala  Ser Asn Thr Ala Arg  Gly Phe Ile Cys Lys  Cys Pro Ala
    1010                 1015                 1020

Gly Phe  Glu Gly Ala Thr Cys  Glu Asn Asp Ala Arg  Thr Cys Gly
    1025                 1030                 1035

Ser Leu  Arg Cys Leu Asn Gly  Gly Thr Cys Ile Ser  Gly Pro Arg
    1040                 1045                 1050

Ser Pro  Thr Cys Leu Cys Leu  Gly Pro Phe Thr Gly  Pro Glu Cys
    1055                 1060                 1065

Gln Phe  Pro Ala Ser Ser Pro  Cys Leu Gly Gly Asn  Pro Cys Tyr
    1070                 1075                 1080

Asn Gln  Gly Thr Cys Glu Pro  Thr Ser Glu Ser Pro  Phe Tyr Arg
    1085                 1090                 1095

Cys Leu  Cys Pro Ala Lys Phe  Asn Gly Leu Leu Cys  His Ile Leu
    1100                 1105                 1110

Asp Tyr  Ser Phe Gly Asp Leu  Gly Pro Gly Glu Pro  Lys Ser Cys
    1115                 1120                 1125

Asp Lys  Thr His Thr Cys Pro  Pro Cys Pro Ala Pro  Glu Leu Leu
    1130                 1135                 1140

Gly Gly  Pro Ser Val Phe Leu  Phe Pro Pro Lys Pro  Lys Asp Thr
    1145                 1150                 1155

Leu Met  Ile Ser Arg Thr Pro  Glu Val Thr Cys Val  Val Val Asp
    1160                 1165                 1170

Val Ser  His Glu Asp Pro Glu  Val Lys Phe Asn Trp  Tyr Val Asp
    1175                 1180                 1185

Gly Val  Glu Val His Asn Ala  Lys Thr Lys Pro Arg  Glu Glu Gln
    1190                 1195                 1200

Tyr Asn  Ser Thr Tyr Arg Val  Val Ser Val Leu Thr  Val Leu His
    1205                 1210                 1215

Gln Asp  Trp Leu Asn Gly Lys  Glu Tyr Lys Cys Lys  Val Ser Asn
    1220                 1225                 1230

Lys Ala  Leu Pro Ala Pro Ile  Glu Lys Thr Ile Ser  Lys Ala Lys
    1235                 1240                 1245

Gly Gln  Pro Arg Glu Pro Gln  Val Tyr Thr Leu Pro  Pro Ser Arg
    1250                 1255                 1260

Asp Glu  Leu Thr Lys Asn Gln  Val Ser Leu Thr Cys  Leu Val Lys
    1265                 1270                 1275

Gly Phe  Tyr Pro Ser Asp Ile  Ala Val Glu Trp Glu  Ser Asn Gly
    1280                 1285                 1290

Gln Pro  Glu Asn Asn Tyr Lys  Thr Thr Pro Pro Val  Leu Asp Ser
    1295                 1300                 1305

Asp Gly  Ser Phe Phe Leu Tyr  Ser Lys Leu Thr Val  Asp Lys Ser
```

```
    1310                1315                1320

Arg Trp  Gln Gln Gly Asn Val  Phe Ser Cys Ser Val  Met His Glu
    1325                1330                1335

Ala Leu  His Asn His Tyr Thr  Gln Lys Ser Leu Ser  Leu Ser Pro
    1340                1345                1350

Gly Lys
    1355


<210> SEQ ID NO 60
<211> LENGTH: 1354
<212> TYPE: PRT
<213> ORGANISM: Homo sapiens

<400> SEQUENCE: 60

Met Trp Gly Trp Lys Cys Leu Leu Phe Trp Ala Val Leu Val Thr Ala
1               5                   10                  15

Thr Leu Cys Thr Ala Arg Cys Ala Ser Ala Ala Cys Phe His Gly Ala
            20                  25                  30

Thr Cys His Asp Arg Val Ala Ser Phe Tyr Cys Glu Cys Pro His Gly
        35                  40                  45

Arg Thr Gly Leu Leu Cys His Leu Asn Asp Ala Cys Ile Ser Asn Pro
    50                  55                  60

Cys Asn Glu Gly Ser Asn Cys Asp Thr Asn Pro Val Asn Gly Lys Ala
65                  70                  75                  80

Ile Cys Thr Cys Pro Ser Gly Tyr Thr Gly Pro Ala Cys Ser Gln Asp
                85                  90                  95

Val Asp Glu Cys Ser Leu Gly Ala Asn Pro Cys Glu His Ala Gly Lys
            100                 105                 110

Cys Ile Asn Thr Leu Gly Ser Phe Glu Cys Gln Cys Leu Gln Gly Tyr
        115                 120                 125

Thr Gly Pro Arg Cys Glu Ile Asp Val Asn Glu Cys Val Ser Asn Pro
    130                 135                 140

Cys Gln Asn Asp Ala Thr Cys Leu Asp Gln Ile Gly Glu Phe Gln Cys
145                 150                 155                 160

Ile Cys Met Pro Gly Tyr Glu Gly Val His Cys Glu Val Asn Thr Asp
                165                 170                 175

Glu Cys Ala Ser Ser Pro Cys Leu His Asn Gly Arg Cys Leu Asp Lys
            180                 185                 190

Ile Asn Glu Phe Gln Cys Glu Cys Pro Thr Gly Phe Thr Gly His Leu
        195                 200                 205

Cys Gln Tyr Asp Val Asp Glu Cys Ala Ser Thr Pro Cys Lys Asn Gly
    210                 215                 220

Ala Lys Cys Leu Asp Gly Pro Asn Thr Tyr Thr Cys Val Cys Thr Glu
225                 230                 235                 240

Gly Tyr Thr Gly Thr His Cys Glu Val Asp Ile Asp Glu Cys Asp Pro
                245                 250                 255

Asp Pro Cys His Tyr Gly Ser Cys Lys Asp Gly Val Ala Thr Phe Thr
            260                 265                 270

Cys Leu Cys Arg Pro Gly Tyr Thr Gly His His Cys Glu Thr Asn Ile
        275                 280                 285

Asn Glu Cys Ser Ser Gln Pro Cys Arg His Gly Gly Thr Cys Gln Asp
    290                 295                 300

Arg Asp Asn Ala Tyr Leu Cys Phe Cys Leu Lys Gly Thr Thr Gly Pro
305                 310                 315                 320
```

-continued

```
Asn Cys Glu Ile Asn Leu Asp Asp Cys Ala Ser Ser Pro Cys Asp Ser
                325                 330                 335

Gly Thr Cys Leu Asp Lys Ile Asp Gly Tyr Glu Cys Ala Cys Glu Pro
            340                 345                 350

Gly Tyr Thr Gly Ser Met Cys Asn Ile Asn Ile Asp Glu Cys Ala Gly
        355                 360                 365

Asn Pro Cys His Asn Gly Gly Thr Cys Glu Asp Gly Ile Asn Gly Phe
    370                 375                 380

Thr Cys Arg Cys Pro Glu Gly Tyr His Asp Pro Thr Cys Leu Ser Glu
385                 390                 395                 400

Val Asn Glu Cys Asn Ser Asn Pro Cys Val His Gly Ala Cys Arg Asp
                405                 410                 415

Ser Leu Asn Gly Tyr Lys Cys Asp Cys Asp Pro Gly Trp Ser Gly Thr
            420                 425                 430

Asn Cys Asp Ile Asn Asn Asn Glu Cys Glu Ser Asn Pro Cys Val Asn
        435                 440                 445

Gly Gly Thr Cys Lys Asp Met Thr Ser Gly Tyr Val Cys Thr Cys Arg
    450                 455                 460

Glu Gly Phe Ser Gly Pro Asn Cys Gln Thr Asn Ile Asn Glu Cys Ala
465                 470                 475                 480

Ser Asn Pro Cys Leu Asn Gln Gly Thr Cys Ile Asp Asp Val Ala Gly
                485                 490                 495

Tyr Lys Cys Asn Cys Leu Leu Pro Tyr Thr Gly Ala Thr Cys Glu Val
            500                 505                 510

Val Leu Ala Pro Cys Ala Pro Ser Pro Cys Arg Asn Gly Gly Glu Cys
        515                 520                 525

Arg Gln Ser Glu Asp Tyr Glu Ser Phe Ser Cys Val Cys Pro Thr Gly
    530                 535                 540

Trp Gln Gly Gln Thr Cys Glu Val Asp Ile Asn Glu Cys Val Leu Ser
545                 550                 555                 560

Pro Cys Arg His Gly Ala Ser Cys Gln Asn Thr His Gly Gly Tyr Arg
                565                 570                 575

Cys His Cys Gln Ala Gly Tyr Ser Gly Arg Asn Cys Glu Thr Asp Ile
            580                 585                 590

Asp Asp Cys Arg Pro Asn Pro Cys His Asn Gly Gly Ser Cys Thr Asp
        595                 600                 605

Gly Ile Asn Thr Ala Phe Cys Asp Cys Leu Pro Gly Phe Arg Gly Thr
    610                 615                 620

Phe Cys Glu Glu Asp Ile Asn Glu Cys Ala Ser Asp Pro Cys Arg Asn
625                 630                 635                 640

Gly Ala Asn Cys Thr Asp Cys Val Asp Ser Tyr Thr Cys Thr Cys Pro
                645                 650                 655

Ala Gly Phe Ser Gly Ile His Cys Glu Asn Asn Thr Pro Asp Cys Thr
            660                 665                 670

Glu Ser Ser Cys Phe Asn Gly Gly Thr Cys Val Asp Gly Ile Asn Ser
        675                 680                 685

Phe Thr Cys Leu Cys Pro Pro Gly Phe Thr Gly Ser Tyr Cys Gln His
    690                 695                 700

Asp Val Asn Glu Cys Asp Ser Gln Pro Cys Leu His Gly Gly Thr Cys
705                 710                 715                 720

Gln Asp Gly Cys Gly Ser Tyr Arg Cys Thr Cys Pro Gln Gly Tyr Thr
                725                 730                 735

Gly Pro Asn Cys Gln Asn Leu Val His Trp Cys Asp Ser Ser Pro Cys
```

-continued

```
            740                 745                 750

Lys Asn Gly Gly Lys Cys Trp Gln Thr His Thr Gln Tyr Arg Cys Glu
        755                 760                 765

Cys Pro Ser Gly Trp Thr Gly Leu Tyr Cys Asp Val Pro Ser Val Ser
    770                 775                 780

Cys Glu Val Ala Ala Gln Arg Gln Gly Val Asp Val Ala Arg Leu Cys
785                 790                 795                 800

Gln His Gly Gly Leu Cys Val Asp Ala Gly Asn Thr His His Cys Arg
                805                 810                 815

Cys Gln Ala Gly Tyr Thr Gly Ser Tyr Cys Glu Asp Leu Val Asp Glu
            820                 825                 830

Cys Ser Pro Ser Pro Cys Gln Asn Gly Ala Thr Cys Thr Asp Tyr Leu
        835                 840                 845

Gly Gly Tyr Ser Cys Lys Cys Val Ala Gly Tyr His Gly Val Asn Cys
    850                 855                 860

Ser Glu Glu Ile Asp Glu Cys Leu Ser His Pro Cys Gln Asn Gly Gly
865                 870                 875                 880

Thr Cys Leu Asp Leu Pro Asn Thr Tyr Lys Cys Ser Cys Pro Arg Gly
                885                 890                 895

Thr Gln Gly Val His Cys Glu Ile Asn Val Asp Asp Cys Asn Pro Pro
            900                 905                 910

Val Asp Pro Val Ser Arg Ser Pro Lys Cys Phe Asn Asn Gly Thr Cys
        915                 920                 925

Val Asp Gln Val Gly Gly Tyr Ser Cys Thr Cys Pro Pro Gly Phe Val
    930                 935                 940

Gly Glu Arg Cys Glu Gly Asp Val Asn Glu Cys Leu Ser Asn Pro Cys
945                 950                 955                 960

Asp Ala Arg Gly Thr Gln Asn Cys Val Gln Arg Val Asn Asp Phe His
                965                 970                 975

Cys Glu Cys Arg Ala Gly His Thr Gly Arg Arg Cys Glu Ser Val Ile
            980                 985                 990

Asn Gly Cys Lys Gly Lys Pro Cys  Lys Asn Gly Gly Thr  Cys Ala Val
        995                 1000                1005

Ala Ser  Asn Thr Ala Arg Gly  Phe Ile Cys Lys Cys  Pro Ala Gly
    1010                1015                1020

Phe Glu  Gly Ala Thr Cys Glu  Asn Asp Ala Arg Thr  Cys Gly Ser
    1025                1030                1035

Leu Arg  Cys Leu Asn Gly Gly  Thr Cys Ile Ser Gly  Pro Arg Ser
    1040                1045                1050

Pro Thr  Cys Leu Cys Leu Gly  Pro Phe Thr Gly Pro  Glu Cys Gln
    1055                1060                1065

Phe Pro  Ala Ser Ser Pro Cys  Leu Gly Gly Asn Pro  Cys Tyr Asn
    1070                1075                1080

Gln Gly  Thr Cys Glu Pro Thr  Ser Glu Ser Pro Phe  Tyr Arg Cys
    1085                1090                1095

Leu Cys  Pro Ala Lys Phe Asn  Gly Leu Leu Cys His  Ile Leu Asp
    1100                1105                1110

Tyr Ser  Phe Gly Asp Leu Gly  Pro Gly Glu Pro Lys  Ser Cys Asp
    1115                1120                1125

Lys Thr  His Thr Cys Pro Pro  Cys Pro Ala Pro Glu  Leu Leu Gly
    1130                1135                1140

Gly Pro  Ser Val Phe Leu Phe  Pro Pro Lys Pro Lys  Asp Thr Leu
    1145                1150                1155
```

```
Met Ile  Ser Arg Thr Pro Glu  Val Thr Cys Val Val  Val Asp Val
    1160                 1165                 1170

Ser His  Glu Asp Pro Glu Val  Lys Phe Asn Trp Tyr  Val Asp Gly
    1175                 1180                 1185

Val Glu  Val His Asn Ala Lys  Thr Lys Pro Arg Glu  Glu Gln Tyr
    1190                 1195                 1200

Asn Ser  Thr Tyr Arg Val Val  Ser Val Leu Thr Val  Leu His Gln
    1205                 1210                 1215

Asp Trp  Leu Asn Gly Lys Glu  Tyr Lys Cys Lys Val  Ser Asn Lys
    1220                 1225                 1230

Ala Leu  Pro Ala Pro Ile Glu  Lys Thr Ile Ser Lys  Ala Lys Gly
    1235                 1240                 1245

Gln Pro  Arg Glu Pro Gln Val  Tyr Thr Leu Pro Pro  Ser Arg Asp
    1250                 1255                 1260

Glu Leu  Thr Lys Asn Gln Val  Ser Leu Thr Cys Leu  Val Lys Gly
    1265                 1270                 1275

Phe Tyr  Pro Ser Asp Ile Ala  Val Glu Trp Glu Ser  Asn Gly Gln
    1280                 1285                 1290

Pro Glu  Asn Asn Tyr Lys Thr  Thr Pro Pro Val Leu  Asp Ser Asp
    1295                 1300                 1305

Gly Ser  Phe Phe Leu Tyr Ser  Lys Leu Thr Val Asp  Lys Ser Arg
    1310                 1315                 1320

Trp Gln  Gln Gly Asn Val Phe  Ser Cys Ser Val Met  His Glu Ala
    1325                 1330                 1335

Leu His  Asn His Tyr Thr Gln  Lys Ser Leu Ser Leu  Ser Pro Gly
    1340                 1345                 1350

Lys


<210> SEQ ID NO 61
<211> LENGTH: 715
<212> TYPE: PRT
<213> ORGANISM: Homo sapiens

<400> SEQUENCE: 61

Met Pro Pro Leu Leu Ala Pro Leu Leu Cys Leu Ala Leu Leu Pro Ala
1               5                   10                  15

Leu Ala Ala Arg Gly Pro Arg Cys Ala Ser Ser Pro Cys Leu His Asn
            20                  25                  30

Gly Arg Cys Leu Asp Lys Ile Asn Glu Phe Gln Cys Glu Cys Pro Thr
        35                  40                  45

Gly Phe Thr Gly His Leu Cys Gln Tyr Asp Val Asp Glu Cys Ala Ser
    50                  55                  60

Thr Pro Cys Lys Asn Gly Ala Lys Cys Leu Asp Gly Pro Asn Thr Tyr
65                  70                  75                  80

Thr Cys Val Cys Thr Glu Gly Tyr Thr Gly Thr His Cys Glu Val Asp
                85                  90                  95

Ile Asp Glu Cys Asp Pro Asp Pro Cys His Tyr Gly Ser Cys Lys Asp
            100                 105                 110

Gly Val Ala Thr Phe Thr Cys Leu Cys Arg Pro Gly Tyr Thr Gly His
        115                 120                 125

His Cys Glu Thr Asn Ile Asn Glu Cys Ser Ser Gln Pro Cys Arg His
    130                 135                 140

Gly Gly Thr Cys Gln Asp Arg Asp Asn Ala Tyr Leu Cys Phe Cys Leu
145                 150                 155                 160
```

-continued

```
Lys Gly Thr Thr Gly Pro Asn Cys Glu Ile Asn Leu Asp Asp Cys Ala
                165                 170                 175

Ser Ser Pro Cys Asp Ser Gly Thr Cys Leu Asp Lys Ile Asp Gly Tyr
            180                 185                 190

Glu Cys Ala Cys Glu Pro Gly Tyr Thr Gly Ser Met Cys Asn Ile Asn
        195                 200                 205

Ile Asp Glu Cys Ala Gly Asn Pro Cys His Asn Gly Gly Thr Cys Glu
    210                 215                 220

Asp Gly Ile Asn Gly Phe Thr Cys Arg Cys Pro Glu Gly Tyr His Asp
225                 230                 235                 240

Pro Thr Cys Leu Ser Glu Val Asn Glu Cys Asn Ser Asn Pro Cys Val
                245                 250                 255

His Gly Ala Cys Arg Asp Ser Leu Asn Gly Tyr Lys Cys Asp Cys Asp
            260                 265                 270

Pro Gly Trp Ser Gly Thr Asn Cys Asp Ile Asn Asn Asn Glu Cys Glu
        275                 280                 285

Ser Asn Pro Cys Val Asn Gly Gly Thr Cys Lys Asp Met Thr Ser Gly
    290                 295                 300

Tyr Val Cys Thr Cys Arg Glu Gly Phe Ser Gly Pro Asn Cys Gln Thr
305                 310                 315                 320

Asn Ile Asn Glu Cys Ala Ser Asn Pro Cys Leu Asn Gln Gly Thr Cys
                325                 330                 335

Ile Asp Asp Val Ala Gly Tyr Lys Cys Asn Cys Leu Leu Pro Tyr Thr
            340                 345                 350

Gly Ala Thr Cys Glu Val Val Leu Ala Pro Cys Ala Pro Ser Pro Cys
        355                 360                 365

Arg Asn Gly Gly Glu Cys Arg Gln Ser Glu Asp Tyr Glu Ser Phe Ser
    370                 375                 380

Cys Val Cys Pro Thr Gly Trp Gln Gly Gln Thr Cys Glu Val Asp Ile
385                 390                 395                 400

Asn Glu Cys Val Leu Ser Pro Cys Arg His Gly Ala Ser Cys Gln Asn
                405                 410                 415

Thr His Gly Gly Tyr Arg Cys His Cys Gln Ala Gly Tyr Ser Gly Arg
            420                 425                 430

Asn Cys Glu Thr Asp Ile Asp Asp Cys Arg Pro Asn Pro Cys His Asn
        435                 440                 445

Gly Gly Ser Cys Thr Asp Gly Ile Asn Thr Ala Phe Cys Asp Cys Leu
    450                 455                 460

Pro Gly Phe Arg Gly Thr Phe Cys Glu Glu Asp Ile Asn Glu Asp Leu
465                 470                 475                 480

Gly Pro Gly Glu Pro Lys Ser Cys Asp Lys Thr His Thr Cys Pro Pro
                485                 490                 495

Cys Pro Ala Pro Glu Leu Leu Gly Gly Pro Ser Val Phe Leu Phe Pro
            500                 505                 510

Pro Lys Pro Lys Asp Thr Leu Met Ile Ser Arg Thr Pro Glu Val Thr
        515                 520                 525

Cys Val Val Val Asp Val Ser His Glu Asp Pro Glu Val Lys Phe Asn
    530                 535                 540

Trp Tyr Val Asp Gly Val Glu Val His Asn Ala Lys Thr Lys Pro Arg
545                 550                 555                 560

Glu Glu Gln Tyr Asn Ser Thr Tyr Arg Val Val Ser Val Leu Thr Val
                565                 570                 575
```

```
Leu His Gln Asp Trp Leu Asn Gly Lys Glu Tyr Lys Cys Lys Val Ser
            580                 585                 590

Asn Lys Ala Leu Pro Ala Pro Ile Glu Lys Thr Ile Ser Lys Ala Lys
        595                 600                 605

Gly Gln Pro Arg Glu Pro Gln Val Tyr Thr Leu Pro Pro Ser Arg Asp
    610                 615                 620

Glu Leu Thr Lys Asn Gln Val Ser Leu Thr Cys Leu Val Lys Gly Phe
625                 630                 635                 640

Tyr Pro Ser Asp Ile Ala Val Glu Trp Glu Ser Asn Gly Gln Pro Glu
                645                 650                 655

Asn Asn Tyr Lys Thr Thr Pro Pro Val Leu Asp Ser Asp Gly Ser Phe
            660                 665                 670

Phe Leu Tyr Ser Lys Leu Thr Val Asp Lys Ser Arg Trp Gln Gln Gly
        675                 680                 685

Asn Val Phe Ser Cys Ser Val Met His Glu Ala Leu His Asn His Tyr
    690                 695                 700

Thr Gln Lys Ser Leu Ser Leu Ser Pro Gly Lys
705                 710                 715


<210> SEQ ID NO 62
<211> LENGTH: 714
<212> TYPE: PRT
<213> ORGANISM: Homo sapiens

<400> SEQUENCE: 62

Met Trp Gly Trp Lys Cys Leu Leu Phe Trp Ala Val Leu Val Thr Ala
1               5                   10                  15

Thr Leu Cys Thr Ala Arg Cys Ala Ser Ser Pro Cys Leu His Asn Gly
            20                  25                  30

Arg Cys Leu Asp Lys Ile Asn Glu Phe Gln Cys Glu Cys Pro Thr Gly
        35                  40                  45

Phe Thr Gly His Leu Cys Gln Tyr Asp Val Asp Glu Cys Ala Ser Thr
    50                  55                  60

Pro Cys Lys Asn Gly Ala Lys Cys Leu Asp Gly Pro Asn Thr Tyr Thr
65                  70                  75                  80

Cys Val Cys Thr Glu Gly Tyr Thr Gly Thr His Cys Glu Val Asp Ile
                85                  90                  95

Asp Glu Cys Asp Pro Asp Pro Cys His Tyr Gly Ser Cys Lys Asp Gly
            100                 105                 110

Val Ala Thr Phe Thr Cys Leu Cys Arg Pro Gly Tyr Thr Gly His His
        115                 120                 125

Cys Glu Thr Asn Ile Asn Glu Cys Ser Ser Gln Pro Cys Arg His Gly
    130                 135                 140

Gly Thr Cys Gln Asp Arg Asp Asn Ala Tyr Leu Cys Phe Cys Leu Lys
145                 150                 155                 160

Gly Thr Thr Gly Pro Asn Cys Glu Ile Asn Leu Asp Asp Cys Ala Ser
                165                 170                 175

Ser Pro Cys Asp Ser Gly Thr Cys Leu Asp Lys Ile Asp Gly Tyr Glu
            180                 185                 190

Cys Ala Cys Glu Pro Gly Tyr Thr Gly Ser Met Cys Asn Ile Asn Ile
        195                 200                 205

Asp Glu Cys Ala Gly Asn Pro Cys His Asn Gly Gly Thr Cys Glu Asp
    210                 215                 220

Gly Ile Asn Gly Phe Thr Cys Arg Cys Pro Glu Gly Tyr His Asp Pro
225                 230                 235                 240
```

```
Thr Cys Leu Ser Glu Val Asn Glu Cys Asn Ser Asn Pro Cys Val His
                245                 250                 255

Gly Ala Cys Arg Asp Ser Leu Asn Gly Tyr Lys Cys Asp Cys Asp Pro
            260                 265                 270

Gly Trp Ser Gly Thr Asn Cys Asp Ile Asn Asn Asn Glu Cys Glu Ser
        275                 280                 285

Asn Pro Cys Val Asn Gly Gly Thr Cys Lys Asp Met Thr Ser Gly Tyr
    290                 295                 300

Val Cys Thr Cys Arg Glu Gly Phe Ser Gly Pro Asn Cys Gln Thr Asn
305                 310                 315                 320

Ile Asn Glu Cys Ala Ser Asn Pro Cys Leu Asn Gln Gly Thr Cys Ile
                325                 330                 335

Asp Asp Val Ala Gly Tyr Lys Cys Asn Cys Leu Leu Pro Tyr Thr Gly
            340                 345                 350

Ala Thr Cys Glu Val Val Leu Ala Pro Cys Ala Pro Ser Pro Cys Arg
        355                 360                 365

Asn Gly Gly Glu Cys Arg Gln Ser Glu Asp Tyr Glu Ser Phe Ser Cys
    370                 375                 380

Val Cys Pro Thr Gly Trp Gln Gly Gln Thr Cys Glu Val Asp Ile Asn
385                 390                 395                 400

Glu Cys Val Leu Ser Pro Cys Arg His Gly Ala Ser Cys Gln Asn Thr
                405                 410                 415

His Gly Gly Tyr Arg Cys His Cys Gln Ala Gly Tyr Ser Gly Arg Asn
            420                 425                 430

Cys Glu Thr Asp Ile Asp Asp Cys Arg Pro Asn Pro Cys His Asn Gly
        435                 440                 445

Gly Ser Cys Thr Asp Gly Ile Asn Thr Ala Phe Cys Asp Cys Leu Pro
    450                 455                 460

Gly Phe Arg Gly Thr Phe Cys Glu Glu Asp Ile Asn Glu Asp Leu Gly
465                 470                 475                 480

Pro Gly Glu Pro Lys Ser Cys Asp Lys Thr His Thr Cys Pro Pro Cys
                485                 490                 495

Pro Ala Pro Glu Leu Leu Gly Gly Pro Ser Val Phe Leu Phe Pro Pro
            500                 505                 510

Lys Pro Lys Asp Thr Leu Met Ile Ser Arg Thr Pro Glu Val Thr Cys
        515                 520                 525

Val Val Val Asp Val Ser His Glu Asp Pro Glu Val Lys Phe Asn Trp
    530                 535                 540

Tyr Val Asp Gly Val Glu Val His Asn Ala Lys Thr Lys Pro Arg Glu
545                 550                 555                 560

Glu Gln Tyr Asn Ser Thr Tyr Arg Val Val Ser Val Leu Thr Val Leu
                565                 570                 575

His Gln Asp Trp Leu Asn Gly Lys Glu Tyr Lys Cys Lys Val Ser Asn
            580                 585                 590

Lys Ala Leu Pro Ala Pro Ile Glu Lys Thr Ile Ser Lys Ala Lys Gly
        595                 600                 605

Gln Pro Arg Glu Pro Gln Val Tyr Thr Leu Pro Pro Ser Arg Asp Glu
    610                 615                 620

Leu Thr Lys Asn Gln Val Ser Leu Thr Cys Leu Val Lys Gly Phe Tyr
625                 630                 635                 640

Pro Ser Asp Ile Ala Val Glu Trp Glu Ser Asn Gly Gln Pro Glu Asn
                645                 650                 655
```

```
Asn Tyr Lys Thr Thr Pro Pro Val Leu Asp Ser Asp Gly Ser Phe Phe
            660                 665                 670

Leu Tyr Ser Lys Leu Thr Val Asp Lys Ser Arg Trp Gln Gln Gly Asn
        675                 680                 685

Val Phe Ser Cys Ser Val Met His Glu Ala Leu His Asn His Tyr Thr
    690                 695                 700

Gln Lys Ser Leu Ser Leu Ser Pro Gly Lys
705                 710


<210> SEQ ID NO 63
<211> LENGTH: 745
<212> TYPE: PRT
<213> ORGANISM: Homo sapiens

<400> SEQUENCE: 63

Met Pro Pro Leu Leu Ala Pro Leu Leu Cys Leu Ala Leu Leu Pro Ala
1               5                   10                  15

Leu Ala Ala Arg Gly Pro Arg Cys Ala Ser Asp Pro Cys Arg Asn Gly
            20                  25                  30

Ala Asn Cys Thr Asp Cys Val Asp Ser Tyr Thr Cys Thr Cys Pro Ala
        35                  40                  45

Gly Phe Ser Gly Ile His Cys Glu Asn Asn Thr Pro Asp Cys Thr Glu
    50                  55                  60

Ser Ser Cys Phe Asn Gly Gly Thr Cys Val Asp Gly Ile Asn Ser Phe
65                  70                  75                  80

Thr Cys Leu Cys Pro Pro Gly Phe Thr Gly Ser Tyr Cys Gln His Asp
                85                  90                  95

Val Asn Glu Cys Asp Ser Gln Pro Cys Leu His Gly Gly Thr Cys Gln
            100                 105                 110

Asp Gly Cys Gly Ser Tyr Arg Cys Thr Cys Pro Gln Gly Tyr Thr Gly
        115                 120                 125

Pro Asn Cys Gln Asn Leu Val His Trp Cys Asp Ser Ser Pro Cys Lys
    130                 135                 140

Asn Gly Gly Lys Cys Trp Gln Thr His Thr Gln Tyr Arg Cys Glu Cys
145                 150                 155                 160

Pro Ser Gly Trp Thr Gly Leu Tyr Cys Asp Val Pro Ser Val Ser Cys
                165                 170                 175

Glu Val Ala Ala Gln Arg Gln Gly Val Asp Val Ala Arg Leu Cys Gln
            180                 185                 190

His Gly Gly Leu Cys Val Asp Ala Gly Asn Thr His His Cys Arg Cys
        195                 200                 205

Gln Ala Gly Tyr Thr Gly Ser Tyr Cys Glu Asp Leu Val Asp Glu Cys
    210                 215                 220

Ser Pro Ser Pro Cys Gln Asn Gly Ala Thr Cys Thr Asp Tyr Leu Gly
225                 230                 235                 240

Gly Tyr Ser Cys Lys Cys Val Ala Gly Tyr His Gly Val Asn Cys Ser
                245                 250                 255

Glu Glu Ile Asp Glu Cys Leu Ser His Pro Cys Gln Asn Gly Gly Thr
            260                 265                 270

Cys Leu Asp Leu Pro Asn Thr Tyr Lys Cys Ser Cys Pro Arg Gly Thr
        275                 280                 285

Gln Gly Val His Cys Glu Ile Asn Val Asp Asp Cys Asn Pro Pro Val
    290                 295                 300

Asp Pro Val Ser Arg Ser Pro Lys Cys Phe Asn Asn Gly Thr Cys Val
305                 310                 315                 320
```

-continued

```
Asp Gln Val Gly Gly Tyr Ser Cys Thr Cys Pro Pro Gly Phe Val Gly
                325                 330                 335

Glu Arg Cys Glu Gly Asp Val Asn Glu Cys Leu Ser Asn Pro Cys Asp
            340                 345                 350

Ala Arg Gly Thr Gln Asn Cys Val Gln Arg Val Asn Asp Phe His Cys
        355                 360                 365

Glu Cys Arg Ala Gly His Thr Gly Arg Arg Cys Glu Ser Val Ile Asn
    370                 375                 380

Gly Cys Lys Gly Lys Pro Cys Lys Asn Gly Gly Thr Cys Ala Val Ala
385                 390                 395                 400

Ser Asn Thr Ala Arg Gly Phe Ile Cys Lys Cys Pro Ala Gly Phe Glu
                405                 410                 415

Gly Ala Thr Cys Glu Asn Asp Ala Arg Thr Cys Gly Ser Leu Arg Cys
            420                 425                 430

Leu Asn Gly Gly Thr Cys Ile Ser Gly Pro Arg Ser Pro Thr Cys Leu
        435                 440                 445

Cys Leu Gly Pro Phe Thr Gly Pro Glu Cys Gln Phe Pro Ala Ser Ser
    450                 455                 460

Pro Cys Leu Gly Gly Asn Pro Cys Tyr Asn Gln Gly Thr Cys Glu Pro
465                 470                 475                 480

Thr Ser Glu Ser Pro Phe Tyr Arg Cys Leu Cys Pro Ala Lys Phe Asn
                485                 490                 495

Gly Leu Leu Cys His Ile Leu Asp Tyr Ser Phe Gly Asp Leu Gly Pro
            500                 505                 510

Gly Glu Pro Lys Ser Cys Asp Lys Thr His Thr Cys Pro Pro Cys Pro
        515                 520                 525

Ala Pro Glu Leu Leu Gly Gly Pro Ser Val Phe Leu Phe Pro Pro Lys
    530                 535                 540

Pro Lys Asp Thr Leu Met Ile Ser Arg Thr Pro Glu Val Thr Cys Val
545                 550                 555                 560

Val Val Asp Val Ser His Glu Asp Pro Glu Val Lys Phe Asn Trp Tyr
                565                 570                 575

Val Asp Gly Val Glu Val His Asn Ala Lys Thr Lys Pro Arg Glu Glu
            580                 585                 590

Gln Tyr Asn Ser Thr Tyr Arg Val Val Ser Val Leu Thr Val Leu His
        595                 600                 605

Gln Asp Trp Leu Asn Gly Lys Glu Tyr Lys Cys Lys Val Ser Asn Lys
    610                 615                 620

Ala Leu Pro Ala Pro Ile Glu Lys Thr Ile Ser Lys Ala Lys Gly Gln
625                 630                 635                 640

Pro Arg Glu Pro Gln Val Tyr Thr Leu Pro Pro Ser Arg Asp Glu Leu
                645                 650                 655

Thr Lys Asn Gln Val Ser Leu Thr Cys Leu Val Lys Gly Phe Tyr Pro
            660                 665                 670

Ser Asp Ile Ala Val Glu Trp Glu Ser Asn Gly Gln Pro Glu Asn Asn
        675                 680                 685

Tyr Lys Thr Thr Pro Pro Val Leu Asp Ser Asp Gly Ser Phe Phe Leu
    690                 695                 700

Tyr Ser Lys Leu Thr Val Asp Lys Ser Arg Trp Gln Gln Gly Asn Val
705                 710                 715                 720

Phe Ser Cys Ser Val Met His Glu Ala Leu His Asn His Tyr Thr Gln
                725                 730                 735
```

```
Lys Ser Leu Ser Leu Ser Pro Gly Lys
            740                 745


<210> SEQ ID NO 64
<211> LENGTH: 744
<212> TYPE: PRT
<213> ORGANISM: Homo sapiens

<400> SEQUENCE: 64

Met Trp Gly Trp Lys Cys Leu Leu Phe Trp Ala Val Leu Val Thr Ala
1               5                   10                  15

Thr Leu Cys Thr Ala Arg Cys Ala Ser Asp Pro Cys Arg Asn Gly Ala
            20                  25                  30

Asn Cys Thr Asp Cys Val Asp Ser Tyr Thr Cys Thr Cys Pro Ala Gly
        35                  40                  45

Phe Ser Gly Ile His Cys Glu Asn Asn Thr Pro Asp Cys Thr Glu Ser
    50                  55                  60

Ser Cys Phe Asn Gly Gly Thr Cys Val Asp Gly Ile Asn Ser Phe Thr
65                  70                  75                  80

Cys Leu Cys Pro Pro Gly Phe Thr Gly Ser Tyr Cys Gln His Asp Val
                85                  90                  95

Asn Glu Cys Asp Ser Gln Pro Cys Leu His Gly Gly Thr Cys Gln Asp
            100                 105                 110

Gly Cys Gly Ser Tyr Arg Cys Thr Cys Pro Gln Gly Tyr Thr Gly Pro
        115                 120                 125

Asn Cys Gln Asn Leu Val His Trp Cys Asp Ser Ser Pro Cys Lys Asn
    130                 135                 140

Gly Gly Lys Cys Trp Gln Thr His Thr Gln Tyr Arg Cys Glu Cys Pro
145                 150                 155                 160

Ser Gly Trp Thr Gly Leu Tyr Cys Asp Val Pro Ser Val Ser Cys Glu
                165                 170                 175

Val Ala Ala Gln Arg Gln Gly Val Asp Val Ala Arg Leu Cys Gln His
            180                 185                 190

Gly Gly Leu Cys Val Asp Ala Gly Asn Thr His His Cys Arg Cys Gln
        195                 200                 205

Ala Gly Tyr Thr Gly Ser Tyr Cys Glu Asp Leu Val Asp Glu Cys Ser
    210                 215                 220

Pro Ser Pro Cys Gln Asn Gly Ala Thr Cys Thr Asp Tyr Leu Gly Gly
225                 230                 235                 240

Tyr Ser Cys Lys Cys Val Ala Gly Tyr His Gly Val Asn Cys Ser Glu
                245                 250                 255

Glu Ile Asp Glu Cys Leu Ser His Pro Cys Gln Asn Gly Gly Thr Cys
            260                 265                 270

Leu Asp Leu Pro Asn Thr Tyr Lys Cys Ser Cys Pro Arg Gly Thr Gln
        275                 280                 285

Gly Val His Cys Glu Ile Asn Val Asp Asp Cys Asn Pro Pro Val Asp
    290                 295                 300

Pro Val Ser Arg Ser Pro Lys Cys Phe Asn Asn Gly Thr Cys Val Asp
305                 310                 315                 320

Gln Val Gly Gly Tyr Ser Cys Thr Cys Pro Pro Gly Phe Val Gly Glu
                325                 330                 335

Arg Cys Glu Gly Asp Val Asn Glu Cys Leu Ser Asn Pro Cys Asp Ala
            340                 345                 350

Arg Gly Thr Gln Asn Cys Val Gln Arg Val Asn Asp Phe His Cys Glu
        355                 360                 365
```

```
Cys Arg Ala Gly His Thr Gly Arg Arg Cys Glu Ser Val Ile Asn Gly
    370                 375                 380

Cys Lys Gly Lys Pro Cys Lys Asn Gly Gly Thr Cys Ala Val Ala Ser
385                 390                 395                 400

Asn Thr Ala Arg Gly Phe Ile Cys Lys Cys Pro Ala Gly Phe Glu Gly
                405                 410                 415

Ala Thr Cys Glu Asn Asp Ala Arg Thr Cys Gly Ser Leu Arg Cys Leu
            420                 425                 430

Asn Gly Gly Thr Cys Ile Ser Gly Pro Arg Ser Pro Thr Cys Leu Cys
        435                 440                 445

Leu Gly Pro Phe Thr Gly Pro Glu Cys Gln Phe Pro Ala Ser Ser Pro
    450                 455                 460

Cys Leu Gly Gly Asn Pro Cys Tyr Asn Gln Gly Thr Cys Glu Pro Thr
465                 470                 475                 480

Ser Glu Ser Pro Phe Tyr Arg Cys Leu Cys Pro Ala Lys Phe Asn Gly
                485                 490                 495

Leu Leu Cys His Ile Leu Asp Tyr Ser Phe Gly Asp Leu Gly Pro Gly
            500                 505                 510

Glu Pro Lys Ser Cys Asp Lys Thr His Thr Cys Pro Pro Cys Pro Ala
        515                 520                 525

Pro Glu Leu Leu Gly Gly Pro Ser Val Phe Leu Phe Pro Pro Lys Pro
    530                 535                 540

Lys Asp Thr Leu Met Ile Ser Arg Thr Pro Glu Val Thr Cys Val Val
545                 550                 555                 560

Val Asp Val Ser His Glu Asp Pro Glu Val Lys Phe Asn Trp Tyr Val
                565                 570                 575

Asp Gly Val Glu Val His Asn Ala Lys Thr Lys Pro Arg Glu Glu Gln
            580                 585                 590

Tyr Asn Ser Thr Tyr Arg Val Val Ser Val Leu Thr Val Leu His Gln
        595                 600                 605

Asp Trp Leu Asn Gly Lys Glu Tyr Lys Cys Lys Val Ser Asn Lys Ala
    610                 615                 620

Leu Pro Ala Pro Ile Glu Lys Thr Ile Ser Lys Ala Lys Gly Gln Pro
625                 630                 635                 640

Arg Glu Pro Gln Val Tyr Thr Leu Pro Pro Ser Arg Asp Glu Leu Thr
                645                 650                 655

Lys Asn Gln Val Ser Leu Thr Cys Leu Val Lys Gly Phe Tyr Pro Ser
            660                 665                 670

Asp Ile Ala Val Glu Trp Glu Ser Asn Gly Gln Pro Glu Asn Asn Tyr
        675                 680                 685

Lys Thr Thr Pro Pro Val Leu Asp Ser Asp Gly Ser Phe Phe Leu Tyr
    690                 695                 700

Ser Lys Leu Thr Val Asp Lys Ser Arg Trp Gln Gln Gly Asn Val Phe
705                 710                 715                 720

Ser Cys Ser Val Met His Glu Ala Leu His Asn His Tyr Thr Gln Lys
                725                 730                 735

Ser Leu Ser Leu Ser Pro Gly Lys
            740
```

<210> SEQ ID NO 65
<211> LENGTH: 5013
<212> TYPE: DNA
<213> ORGANISM: Homo sapiens

<400> SEQUENCE: 65
atgccgccgc tcctggcgcc cctgctctgc ctggcgctgc tgcccgcgct cgccgcacga 60
ggcccgcgat gctcccagcc cggtgagacc tgcctgaatg gcgggaagtg tgaagcggcc 120
aatggcacgg aggcctgcgt ctgtggcggg gccttcgtgg gcccgcgatg ccaggacccc 180
aacccgtgcc tcagcacccc ctgcaagaac gccgggacat gccacgtggt ggaccgcaga 240
ggcgtggcag actatgcctg cagctgtgcc ctgggcttct ctgggcccct ctgcctgaca 300
cccctggaca atgcctgcct caccaacccc tgccgcaacg gggcacctg cgacctgctc 360
acgctgacgg agtacaagtg ccgctgcccg cccggctggt cagggaaatc gtgccagcag 420
gctgacccgt gcgcctccaa cccctgcgcc aacggtggcc agtgcctgcc cttcgaggcc 480
tcctacatct gccactgccc acccagcttc catggcccca cctgccggca ggatgtcaac 540
gagtgtggcc agaagcccgg gctttgccgc cacggaggca cctgccacaa cgaggtcggc 600
tcctaccgct gcgtctgccg cgccacccac actggcccca actgcgagcg gccctacgtg 660
ccctgcagcc cctcgccctg ccagaacggg ggcacctgcc gccccacggg cgacgtcacc 720
cacgagtgtg cctgcctgcc aggcttcacc ggccagaact gtgaggaaaa tatcgacgat 780
tgtccaggaa acaactgcaa gaacgggggt gcctgtgtgg acggcgtgaa cacctacaac 840
tgccgctgcc cgccagagtg gacaggtcag tactgtaccg aggatgtgga cgagtgccag 900
ctgatgccaa atgcctgcca gaacggcggg acctgccaca acacccacgg tggctacaac 960
tgcgtgtgtg tcaacggctg gactggtgag gactgcagcg agaacattga tgactgtgcc 1020
agcgccgcct gcttccacgg cgccacctgc catgaccgtg tggcctcctt ctactgcgag 1080
tgtccccatg gccgcacagg tctgctgtgc cacctcaacg acgcatgcat cagcaacccc 1140
tgtaacgagg gctccaactg cgacaccaac cctgtcaatg gcaaggccat ctgcacctgc 1200
ccctcggggt acacgggccc ggcctgcagc caggacgtgg atgagtgctc gctgggtgcc 1260
aacccctgcg agcatgcggg caagtgcatc aacacgctgg gctccttcga gtgccagtgt 1320
ctgcagggct acacgggccc ccgatgcgag atcgacgtca acgagtgcgt ctcgaacccg 1380
tgccagaacg acgccacctg cctggaccag attggggagt tccagtgcat ctgcatgccc 1440
ggctacgagg gtgtgcactg cgaggtcaac acagacgagt gtgccagcag cccctgcctg 1500
cacaatggcc gctgcctgga caagatcaat gagttccagt gcgagtgccc cacgggcttc 1560
actgggcatc tgtgccagta cgatgtggac gagtgtgcca gcacccccctg caagaatggt 1620
gccaagtgcc tggacggacc caacacttac acctgtgtgt gcacggaagg gtacacgggg 1680
acgcactgcg aggtggacat cgatgagtgc gaccccgacc cctgccacta cggctcctgc 1740
aaggacggcg tcgccacctt cacctgcctc tgccgcccag gctacacggg ccaccactgc 1800
gagaccaaca tcaacgagtg ctccagccag ccctgccgcc acgggggcac ctgccaggac 1860
cgcgacaacg cctacctctg cttctgcctg aaggggacca caggacccaa ctgcgagatc 1920
aacctggatg actgtgccag cagcccctgc gactcgggca cctgtctgga caagatcgat 1980
ggctacgagt gtgcctgtga gccgggctac acagggagca tgtgtaacat caacatcgat 2040
gagtgtgcgg gcaacccctg ccacaacggg ggcacctgcg aggacggcat caatggcttc 2100
acctgccgct gccccgaggg ctaccacgac cccacctgcc tgtctgaggt caatgagtgc 2160
aacagcaacc cctgcgtcca cggggcctgc cgggacagcc tcaacgggta caagtgcgac 2220
tgtgaccctg ggtggagtgg gaccaactgt gacatcaaca acaatgagtg tgaatccaac 2280
ccttgtgtca acggcggcac ctgcaaagac atgaccagtg gctacgtgtg cacctgccgg 2340

-continued gagggcttca gcggtcccaa ctgccagacc aacatcaacg agtgtgcgtc caacccatgt 2400
ctgaaccagg gcacgtgtat tgacgacgtt gccgggtaca agtgcaactg cctgctgccc 2460
tacacaggtg ccacgtgtga ggtggtgctg gccccgtgtg cccccagccc ctgcagaaac 2520
ggcggggagt gcaggcaatc cgaggactat gagagcttct cctgtgtctg ccccacgggc 2580
tggcaagggc agacctgtga ggtcgacatc aacgagtgcg ttctgagccc gtgccggcac 2640
ggcgcatcct gccagaacac ccacggcggc taccgctgcc actgccaggc cggctacagt 2700
gggcgcaact gcgagaccga catcgacgac tgccggccca acccgtgtca caacgggggc 2760
tcctgcacag acggcatcaa cacggccttc tgcgactgcc tgcccggctt ccggggcact 2820
ttctgtgagg aggacatcaa cgagtgtgcc agtgacccct gccgcaacgg ggccaactgc 2880
acggactgcg tggacagcta cacgtgcacc tgccccgcag gcttcagcgg gatccactgt 2940
gagaacaaca cgcctgactg cacagagagc tcctgcttca acggtggcac ctgcgtggac 3000
ggcatcaact cgttcacctg cctgtgtcca cccggcttca cgggcagcta ctgccagcac 3060
gatgtcaatg agtgcgactc acagccctgc ctgcatggcg gcacctgtca ggacggctgc 3120
ggctcctaca ggtgcacctg cccccagggc tacactggcc ccaactgcca gaaccttgtg 3180
cactggtgtg actcctcgcc ctgcaagaac ggcggcaaat gctggcagac ccacacccag 3240
taccgctgcg agtgccccag cggctggacc ggcctttact gcgacgtgcc cagcgtgtcc 3300
tgtgaggtgg ctgcgcagcg acaaggtgtt gacgttgccc gcctgtgcca gcatggaggg 3360
ctctgtgtgg acgcgggcaa cacgcaccac tgccgctgcc aggcgggcta cacaggcagc 3420
tactgtgagg acctggtgga cgagtgctca cccagcccct gccagaacgg ggccacctgc 3480
acggactacc tgggcggcta ctcctgcaag tgcgtggccg gctaccacgg ggtgaactgc 3540
tctgaggaga tcgacgagtg cctctcccac ccctgccaga acgggggcac ctgcctcgac 3600
ctccccaaca cctacaagtg ctcctgccca cggggcactc agggtgtgca ctgtgagatc 3660
aacgtggacg actgcaatcc ccccgttgac cccgtgtccc ggagccccaa gtgctttaac 3720
aacggcacct gcgtggacca ggtgggcggc tacagctgca cctgcccgcc gggcttcgtg 3780
ggtgagcgct gtgaggggga tgtcaacgag tgcctgtcca atccctgcga cgcccgtggc 3840
acccagaact gcgtgcagcg cgtcaatgac ttccactgcg agtgccgtgc tggtcacacc 3900
gggcgccgct gcgagtccgt catcaatggc tgcaaaggca agccctgcaa gaatgggggc 3960
acctgcgccg tggcctccaa caccgcccgc gggttcatct gcaagtgccc tgcgggcttc 4020
gagggcgcca cgtgtgagaa tgacgctcgt acctgcggca gcctgcgctg cctcaacggc 4080
ggcacatgca tctccggccc gcgcagcccc acctgcctgt gcctgggccc cttcacgggc 4140
cccgaatgcc agttcccggc cagcagcccc tgcctgggcg gcaacccctg ctacaaccag 4200
gggacctgtg agcccacatc cgagagcccc ttctaccgtt gcctgtgccc cgccaaattc 4260
aacgggctct tgtgccacat cctggactac agcttcggag atctgggccc gggcgagccc 4320
aaatcttgtg acaaaactca cacatgccca ccgtgcccag cacctgaact cctgggggga 4380
ccgtcagtct tcctcttccc cccaaaaccc aaggacaccc tcatgatctc ccggacccct 4440
gaggtcacat gcgtggtggt ggacgtgagc cacgaagacc ctgaggtcaa gttcaactgg 4500
tacgtggacg gcgtggaggt gcataatgcc aagacaaagc cgcgggagga gcagtacaac 4560
agcacgtacc gtgtggtcag cgtcctcacc gtcctgcacc aggactggct gaatggcaag 4620
gagtacaagt gcaaggtctc caacaaagcc ctcccagccc ccatcgagaa aaccatctcc 4680

```
aaagccaaag ggcagccccg agaaccacag gtgtacaccc tgcccccatc ccgggatgag   4740

ctgaccaaga accaggtcag cctgacctgc ctggtcaaag gcttctatcc cagcgacatc   4800

gccgtggagt gggagagcaa tgggcagccg gagaacaact acaagaccac gcctcccgtg   4860

ctggactccg acggctcctt cttcctctac agcaagctca ccgtggacaa gagcaggtgg   4920

cagcagggga acgtcttctc atgctccgtg atgcatgagg ctctgcacaa ccactacacg   4980

cagaagagcc tctccctgtc tccgggtaaa tga                                5013
```

<210> SEQ ID NO 66
<211> LENGTH: 2307
<212> TYPE: DNA
<213> ORGANISM: Homo sapiens

<400> SEQUENCE: 66

```
atgccgccgc tcctggcgcc cctgctctgc ctggcgctgc tgcccgcgct cgccgcacga     60

ggcccgcgat gctcccagcc cggtgagacc tgcctgaatg gcgggaagtg tgaagcggcc    120

aatggcacgg aggcctgcgt ctgtggcggg gccttcgtgg gcccgcgatg ccaggacccc    180

aacccgtgcc tcagcacccc ctgcaagaac gccgggacat gccacgtggt ggaccgcaga    240

ggcgtggcag actatgcctg cagctgtgcc ctgggcttct ctgggcccct ctgcctgaca    300

cccctggaca atgcctgcct caccaacccc tgccgcaacg gggcacctg cgacctgctc    360

acgctgacgg agtacaagtg ccgctgcccg cccggctggt cagggaaatc gtgccagcag    420

gctgacccgt gcgcctccaa cccctgcgcc aacggtggcc agtgcctgcc cttcgaggcc    480

tcctacatct gccactgccc acccagcttc catggcccca cctgccggca ggatgtcaac    540

gagtgtggcc agaagcccgg gctttgccgc cacggaggca cctgccacaa cgaggtcggc    600

tcctaccgct gcgtctgccg cgccacccac actggcccca actgcgagcg gccctacgtg    660

ccctgcagcc cctcgccctg ccagaacggg ggcacctgcc gccccacggg cgacgtcacc    720

cacgagtgtg cctgcctgcc aggcttcacc ggccagaact gtgaggaaaa tatcgacgat    780

tgtccaggaa acaactgcaa gaacgggggt gcctgtgtgg acggcgtgaa cacctacaac    840

tgccgctgcc cgccagagtg gacaggtcag tactgtaccg aggatgtgga cgagtgccag    900

ctgatgccaa atgcctgcca gaacggcggg acctgccaca acacccacgg tggctacaac    960

tgcgtgtgtg tcaacggctg gactggtgag gactgcagcg agaacattga tgactgtgcc   1020

agcgccgcct gcttccacgg cgccacctgc catgaccgtg tggcctcctt ctactgcgag   1080

tgtccccatg gccgcacagg tctgctgtgc cacctcaacg acgcatgcat cagcaacccc   1140

tgtaacgagg gctccaactg cgacaccaac cctgtcaatg gcaaggccat ctgcacctgc   1200

ccctcggggt acacgggccc ggcctgcagc caggacgtgg atgagtgctc gctgggtgcc   1260

aacccctgcg agcatgcggg caagtgcatc aacacgctgg gctccttcga gtgccagtgt   1320

ctgcagggct acacgggccc ccgatgcgag atcgacgtca acgagtgcgt ctcgaacccg   1380

tgccagaacg acgccacctg cctggaccag attggggagt tccagtgcat ctgcatgccc   1440

ggctacgagg gtgtgcactg cgaggtcaac acagacgagt gtgccagcag cccctgcctg   1500

cacaatggcc gctgcctgga caagatcaat gagttccagt gcgagtgccc cacgggcttc   1560

actgggcatc tgtgccagta cgatgtggac gaggatctgg gcccgggcga gcccaaatct   1620

tgtgacaaaa ctcacacatg cccaccgtgc ccagcacctg aactcctggg gggaccgtca   1680

gtcttcctct tccccccaaa acccaaggac accctcatga tctcccggac ccctgaggtc   1740

acatgcgtgg tggtggacgt gagccacgaa gaccctgagg tcaagttcaa ctggtacgtg   1800
```

-continued

```
gacggcgtgg aggtgcataa tgccaagaca aagccgcggg aggagcagta caacagcacg   1860

taccgtgtgg tcagcgtcct caccgtcctg caccaggact ggctgaatgg caaggagtac   1920

aagtgcaagg tctccaacaa agccctccca gcccccatcg agaaaaccat ctccaaagcc   1980

aaagggcagc cccgagaacc acaggtgtac accctgcccc catcccggga tgagctgacc   2040

aagaaccagg tcagcctgac ctgcctggtc aaaggcttct atcccagcga catcgccgtg   2100

gagtgggaga gcaatgggca gccggagaac aactacaaga ccacgcctcc cgtgctggac   2160

tccgacggct ccttcttcct ctacagcaag ctcaccgtgg acaagagcag gtggcagcag   2220

gggaacgtct tctcatgctc cgtgatgcat gaggctctgc acaaccacta cacgcagaag   2280

agcctctccc tgtctccggg taaatga                                       2307
```

<210> SEQ ID NO 67
<211> LENGTH: 3558
<212> TYPE: DNA
<213> ORGANISM: Homo sapiens

<400> SEQUENCE: 67

```
atgccgccgc tcctggcgcc cctgctctgc ctggcgctgc tgcccgcgct cgccgcacga     60

ggcccgcgat gctcccagcc cggtgagacc tgcctgaatg gcgggaagtg tgaagcggcc    120

aatggcacgg aggcctgcgt ctgtggcggg gccttcgtgg gcccgcgatg ccaggacccc    180

aacccgtgcc tcagcacccc ctgcaagaac gccgggacat gccacgtggt ggaccgcaga    240

ggcgtggcag actatgcctg cagctgtgcc ctgggcttct ctgggcccct ctgcctgaca    300

cccctggaca atgcctgcct caccaacccc tgccgcaacg gggggcacctg cgacctgctc   360

acgctgacgg agtacaagtg ccgctgcccg cccggctggt cagggaaatc gtgccagcag    420

gctgacccgt gcgcctccaa cccctgcgcc aacggtggcc agtgcctgcc cttcgaggcc    480

tcctacatct gccactgccc acccagcttc catggcccca cctgccggca ggatgtcaac    540

gagtgtggcc agaagcccgg gctttgccgc cacggaggca cctgccacaa cgaggtcggc    600

tcctaccgct gcgtctgccg cgccacccac actggcccca actgcgagcg gccctacgtg    660

ccctgcagcc cctcgccctg ccagaacggg ggcacctgcc gccccacggg cgacgtcacc    720

cacgagtgtg cctgcctgcc aggcttcacc ggccagaact gtgaggaaaa tatcgacgat    780

tgtccaggaa acaactgcaa gaacgggggt gcctgtgtgg acggcgtgaa cacctacaac    840

tgccgctgcc cgccagagtg gacaggtcag tactgtaccg aggatgtgga cgagtgccag    900

ctgatgccaa atgcctgcca gaacggcggg acctgccaca acacccacgg tggctacaac    960

tgcgtgtgtg tcaacggctg gactggtgag gactgcagcg agaacattga tgactgtgcc   1020

agcgccgcct gcttccacgg cgccacctgc catgaccgtg tggcctcctt ctactgcgag   1080

tgtccccatg gccgcacagg tctgctgtgc cacctcaacg acgcatgcat cagcaacccc   1140

tgtaacgagg gctccaactg cgacaccaac cctgtcaatg gcaaggccat ctgcacctgc   1200

ccctcggggt acacgggccc ggcctgcagc caggacgtgg atgagtgctc gctgggtgcc   1260

aacccctgcg agcatgcggg caagtgcatc aacacgctgg gctccttcga gtgccagtgt   1320

ctgcagggct acacgggccc ccgatgcgag atcgacgtca acgagtgcgt ctcgaacccg   1380

tgccagaacg acgccacctg cctggaccag attggggagt tccagtgcat ctgcatgccc   1440

ggctacgagg gtgtgcactg cgaggtcaac acagacgagt gtgccagcag cccctgcctg   1500

cacaatggcc gctgcctgga caagatcaat gagttccagt gcgagtgccc cacgggcttc   1560
```

-continued actgggcatc tgtgccagta cgatgtggac gagtgtgcca gcacccccctg caagaatggt 1620 gccaagtgcc tggacggacc caacacttac acctgtgtgt gcacggaagg gtacacgggg 1680
acgcactgcg aggtggacat cgatgagtgc gaccccgacc cctgccacta cggctcctgc 1740
aaggacggcg tcgccacctt cacctgcctc tgccgcccag gctacacggg ccaccactgc 1800
gagaccaaca tcaacgagtg ctccagccag ccctgccgcc acgggggcac ctgccaggac 1860
cgcgacaacg cctacctctg cttctgcctg aaggggacca caggacccaa ctgcgagatc 1920
aacctggatg actgtgccag cagcccctgc gactcgggca cctgtctgga caagatcgat 1980
ggctacgagt gtgcctgtga gccgggctac acagggagca tgtgtaacat caacatcgat 2040
gagtgtgcgg gcaacccctg ccacaacggg ggcacctgcg aggacggcat caatggcttc 2100
acctgccgct gccccgaggg ctaccacgac cccacctgcc tgtctgaggt caatgagtgc 2160
aacagcaacc cctgcgtcca cggggcctgc cgggacagcc tcaacgggta caagtgcgac 2220
tgtgaccctg ggtggagtgg gaccaactgt gacatcaaca acaatgagtg tgaatccaac 2280
ccttgtgtca acggcggcac ctgcaaagac atgaccagtg gctacgtgtg cacctgccgg 2340
gagggcttca gcggtcccaa ctgccagacc aacatcaacg agtgtgcgtc caacccatgt 2400
ctgaaccagg gcacgtgtat tgacgacgtt gccgggtaca agtgcaactg cctgctgccc 2460
tacacaggtg ccacgtgtga ggtggtgctg gccccgtgtg cccccagccc ctgcagaaac 2520
ggcggggagt gcaggcaatc cgaggactat gagagcttct cctgtgtctg ccccacgggc 2580
tggcaagggc agacctgtga ggtcgacatc aacgagtgcg ttctgagccc gtgccggcac 2640
ggcgcatcct gccagaacac ccacggcggc taccgctgcc actgccaggc cggctacagt 2700
gggcgcaact gcgagaccga catcgacgac tgccggccca acccgtgtca caacgggggc 2760
tcctgcacag acggcatcaa cacggccttc tgcgactgcc tgcccggctt ccggggcact 2820
ttctgtgagg aggacatcaa cgaggatctg ggcccgggcg agcccaaatc ttgtgacaaa 2880
actcacacat gcccaccgtg cccagcacct gaactcctgg ggggaccgtc agtcttcctc 2940
ttccccccaa aacccaagga caccctcatg atctcccgga cccctgaggt cacatgcgtg 3000
gtggtggacg tgagccacga agaccctgag gtcaagttca actggtacgt ggacggcgtg 3060
gaggtgcata atgccaagac aaagccgcgg gaggagcagt acaacagcac gtaccgtgtg 3120
gtcagcgtcc tcaccgtcct gcaccaggac tggctgaatg gcaaggagta caagtgcaag 3180
gtctccaaca aagccctccc agcccccatc gagaaaacca tctccaaagc caaagggcag 3240
ccccgagaac cacaggtgta caccctgccc ccatcccggg atgagctgac caagaaccag 3300
gtcagcctga cctgcctggt caaaggcttc tatcccagcg acatcgccgt ggagtgggag 3360
agcaatgggc agccggagaa caactacaag accacgcctc ccgtgctgga ctccgacggc 3420
tccttcttcc tctacagcaa gctcaccgtg gacaagagca ggtggcagca ggggaacgtc 3480
ttctcatgct ccgtgatgca tgaggctctg cacaaccact acacgcagaa gagcctctcc 3540
ctgtctccgg gtaaatga 3558

<210> SEQ ID NO 68
<211> LENGTH: 2493
<212> TYPE: DNA
<213> ORGANISM: Homo sapiens

<400> SEQUENCE: 68
atgccgccgc tcctggcgcc cctgctctgc ctggcgctgc tgcccgcgct cgccgcacga 60
ggcccgcgat gtgccagcgc cgcctgcttc cacggcgcca cctgccatga ccgtgtggcc 120

-continued

```
tccttctact gcgagtgtcc ccatggccgc acaggtctgc tgtgccacct caacgacgca    180
tgcatcagca acccctgtaa cgagggctcc aactgcgaca ccaaccctgt caatggcaag    240
gccatctgca cctgcccctc ggggtacacg ggcccggcct gcagccagga cgtggatgag    300
tgctcgctgg gtgccaaccc ctgcgagcat gcgggcaagt gcatcaacac gctgggctcc    360
ttcgagtgcc agtgtctgca gggctacacg ggcccccgat gcgagatcga cgtcaacgag    420
tgcgtctcga acccgtgcca gaacgacgcc acctgcctgg accagattgg ggagttccag    480
tgcatctgca tgcccggcta cgagggtgtg cactgcgagg tcaacacaga cgagtgtgcc    540
agcagcccct gcctgcacaa tggccgctgc ctggacaaga tcaatgagtt ccagtgcgag    600
tgccccacgg gcttcactgg gcatctgtgc cagtacgatg tggacgagtg tgccagcacc    660
ccctgcaaga atggtgccaa gtgcctggac ggacccaaca cttacacctg tgtgtgcacg    720
gaagggtaca cggggacgca ctgcgaggtg gacatcgatg agtgcgaccc cgacccctgc    780
cactacggct cctgcaagga cggcgtcgcc accttcacct gcctctgccg cccaggctac    840
acgggccacc actgcgagac caacatcaac gagtgctcca gccagccctg ccgccacggg    900
ggcacctgcc aggaccgcga caacgcctac ctctgcttct gcctgaaggg gaccacagga    960
cccaactgcg agatcaacct ggatgactgt gccagcagcc cctgcgactc gggcacctgt   1020
ctggacaaga tcgatggcta cgagtgtgcc tgtgagccgg gctacacagg gagcatgtgt   1080
aacatcaaca tcgatgagtg tgcgggcaac ccctgccaca acgggggcac ctgcgaggac   1140
ggcatcaatg gcttcacctg ccgctgcccc gagggctacc acgaccccac ctgcctgtct   1200
gaggtcaatg agtgcaacag caacccctgc gtccacgggg cctgccggga cagcctcaac   1260
gggtacaagt gcgactgtga ccctgggtgg agtgggacca actgtgacat caacaacaat   1320
gagtgtgaat ccaacccttg tgtcaacggc ggcacctgca aagacatgac cagtggctac   1380
gtgtgcacct gccgggaggg cttcagcggt cccaactgcc agaccaacat caacgagtgt   1440
gcgtccaacc catgtctgaa ccagggcacg tgtattgacg acgttgccgg gtacaagtgc   1500
aactgcctgc tgccctacac aggtgccacg tgtgaggtgg tgctggcccc gtgtgccccc   1560
agcccctgca gaaacggcgg ggagtgcagg caatccgagg actatgagag cttctcctgt   1620
gtctgcccca cgggctggca agggcagacc tgtgaggtcg acatcaacga gtgcgttctg   1680
agcccgtgcc ggcacggcgc atcctgccag aacacccacg gcggctaccg ctgccactgc   1740
caggccggct acagtgggcg caactgcgag accgacatag atctgggccc gggcgagccc   1800
aaatcttgtg acaaaactca cacatgccca ccgtgcccag cacctgaact cctgggggga   1860
ccgtcagtct tcctcttccc cccaaaaccc aaggacaccc tcatgatctc ccggacccct   1920
gaggtcacat gcgtggtggt ggacgtgagc cacgaagacc ctgaggtcaa gttcaactgg   1980
tacgtggacg gcgtggaggt gcataatgcc aagacaaagc cgcgggagga gcagtacaac   2040
agcacgtacc gtgtggtcag cgtcctcacc gtcctgcacc aggactggct gaatggcaag   2100
gagtacaagt gcaaggtctc caacaaagcc ctcccagccc ccatcgagaa aaccatctcc   2160
aaagccaaag ggcagccccg agaaccacag gtgtacaccc tgcccccatc ccgggatgag   2220
ctgaccaaga accaggtcag cctgacctgc ctggtcaaag gcttctatcc cagcgacatc   2280
gccgtggagt gggagagcaa tgggcagccg gagaacaact acaagaccac gcctcccgtg   2340
ctggactccg acggctcctt cttcctctac agcaagctca ccgtggacaa gagcaggtgg   2400
cagcagggga acgtcttctc atgctccgtg atgcatgagg ctctgcacaa ccactacacg   2460
```

cagaagagcc tctccctgtc tccgggtaaa tga 2493

<210> SEQ ID NO 69
<211> LENGTH: 2490
<212> TYPE: DNA
<213> ORGANISM: Homo sapiens

<400> SEQUENCE: 69
atgtggggct ggaagtgcct cctcttctgg gctgtgctgg tcacagccac tctctgcact 60
gccaggtgtg ccagcgccgc ctgcttccac ggcgccacct gccatgaccg tgtggcctcc 120
ttctactgcg agtgtcccca tggccgcaca ggtctgctgt gccacctcaa cgacgcatgc 180
atcagcaacc cctgtaacga gggctccaac tgcgacacca accctgtcaa tggcaaggcc 240
atctgcacct gcccctcggg gtacacgggc ccggcctgca gccaggacgt ggatgagtgc 300
tcgctgggtg ccaaccccctg cgagcatgcg ggcaagtgca tcaacacgct gggctccttc 360
gagtgccagt gtctgcaggg ctacacgggc ccccgatgcg agatcgacgt caacgagtgc 420
gtctcgaacc cgtgccagaa cgacgccacc tgcctggacc agattgggga gttccagtgc 480
atctgcatgc ccggctacga gggtgtgcac tgcgaggtca acacagacga gtgtgccagc 540
agcccctgcc tgcacaatgg ccgctgcctg gacaagatca atgagttcca gtgcgagtgc 600
cccacgggct tcactgggca tctgtgccag tacgatgtgg acgagtgtgc cagcaccccc 660
tgcaagaatg gtgccaagtg cctggacgga cccaacactt acacctgtgt gtgcacggaa 720
gggtacacgg ggacgcactg cgaggtggac atcgatgagt gcgacccccga cccctgccac 780 tacggctcct gcaaggacgg cgtcgccacc ttcacctgcc tctgccgccc aggctacacg 840
ggccaccact gcgagaccaa catcaacgag tgctccagcc agccctgccg ccacgggggc 900
acctgccagg accgcgacaa cgcctacctc tgcttctgcc tgaaggggac cacaggaccc 960
aactgcgaga tcaacctgga tgactgtgcc agcagcccct gcgactcggg cacctgtctg 1020
gacaagatcg atggctacga gtgtgcctgt gagccgggct acacagggag catgtgtaac 1080
atcaacatcg atgagtgtgc gggcaacccc tgccacaacg gggggcacctg cgaggacggc 1140 atcaatggct tcacctgccg ctgccccgag ggctaccacg accccacctg cctgtctgag 1200
gtcaatgagt gcaacagcaa cccctgcgtc cacggggcct gccgggacag cctcaacggg 1260
tacaagtgcg actgtgaccc tgggtggagt gggaccaact gtgacatcaa caacaatgag 1320
tgtgaatcca acccttgtgt caacggcggc acctgcaaag acatgaccag tggctacgtg 1380
tgcacctgcc gggagggctt cagcggtccc aactgccaga ccaacatcaa cgagtgtgcg 1440
tccaacccat gtctgaacca gggcacgtgt attgacgacg ttgccgggta caagtgcaac 1500
tgcctgctgc cctacacagg tgccacgtgt gaggtggtgc tggccccgtg tgcccccagc 1560
ccctgcagaa acggcgggga gtgcaggcaa tccgaggact atgagagctt ctcctgtgtc 1620
tgccccacgg gctggcaagg gcagacctgt gaggtcgaca tcaacgagtg cgttctgagc 1680
ccgtgccggc acggcgcatc ctgccagaac acccacggcg gctaccgctg ccactgccag 1740
gccggctaca gtgggcgcaa ctgcgagacc gacatagatc tgggcccggg cgagcccaaa 1800
tcttgtgaca aaactcacac atgcccaccg tgcccagcac ctgaactcct ggggggaccg 1860
tcagtcttcc tcttcccccc aaaacccaag gacaccctca tgatctcccg gacccctgag 1920
gtcacatgcg tggtggtgga cgtgagccac gaagaccctg aggtcaagtt caactggtac 1980
gtggacggcg tggaggtgca taatgccaag acaaagccgc gggaggagca gtacaacagc 2040
acgtaccgtg tggtcagcgt cctcaccgtc ctgcaccagg actggctgaa tggcaaggag 2100

```
tacaagtgca aggtctccaa caaagccctc ccagccccca tcgagaaaac catctccaaa   2160

gccaaagggc agccccgaga accacaggtg tacaccctgc ccccatcccg ggatgagctg   2220

accaagaacc aggtcagcct gacctgcctg gtcaaaggct tctatcccag cgacatcgcc   2280

gtggagtggg agagcaatgg gcagccggag aacaactaca agaccacgcc tcccgtgctg   2340

gactccgacg gctccttctt cctctacagc aagctcaccg tggacaagag caggtggcag   2400

caggggaacg tcttctcatg ctccgtgatg catgaggctc tgcacaacca ctacacgcag   2460

aagagcctct ccctgtctcc gggtaaatga                                   2490
```

<210> SEQ ID NO 70
<211> LENGTH: 4068
<212> TYPE: DNA
<213> ORGANISM: Homo sapiens

<400> SEQUENCE: 70

```
atgccgccgc tcctggcgcc cctgctctgc ctggcgctgc tgcccgcgct cgccgcacga     60

ggcccgcgat gtgccagcgc cgcctgcttc cacggcgcca cctgccatga ccgtgtggcc    120

tccttctact gcgagtgtcc ccatggccgc acaggtctgc tgtgccacct caacgacgca    180

tgcatcagca accccctgtaa cgagggctcc aactgcgaca ccaaccctgt caatggcaag    240

gccatctgca cctgcccctc ggggtacacg ggcccggcct gcagccagga cgtggatgag    300

tgctcgctgg gtgccaaccc ctgcgagcat gcgggcaagt gcatcaacac gctgggctcc    360

ttcgagtgcc agtgtctgca gggctacacg ggcccccgat gcgagatcga cgtcaacgag    420

tgcgtctcga acccgtgcca gaacgacgcc acctgcctgg accagattgg ggagttccag    480

tgcatctgca tgcccggcta cgagggtgtg cactgcgagg tcaacacaga cgagtgtgcc    540

agcagcccct gcctgcacaa tggccgctgc ctggacaaga tcaatgagtt ccagtgcgag    600

tgccccacgg gcttcactgg gcatctgtgc cagtacgatg tggacgagtg tgccagcacc    660

ccctgcaaga atggtgccaa gtgcctggac ggacccaaca cttacacctg tgtgtgcacg    720

gaagggtaca cggggacgca ctgcgaggtg gacatcgatg agtgcgaccc cgacccctgc    780

cactacggct cctgcaagga cggcgtcgcc accttcacct gcctctgccg cccaggctac    840

acgggccacc actgcgagac caacatcaac gagtgctcca gccagccctg ccgccacggg    900

ggcacctgcc aggaccgcga caacgcctac ctctgcttct gcctgaaggg gaccacagga    960

cccaactgcg agatcaacct ggatgactgt gccagcagcc cctgcgactc gggcacctgt   1020

ctggacaaga tcgatggcta cgagtgtgcc tgtgagccgg gctacacagg gagcatgtgt   1080

aacatcaaca tcgatgagtg tgcgggcaac ccctgccaca acgggggcac ctgcgaggac   1140

ggcatcaatg gcttcacctg ccgctgcccc gagggctacc acgaccccac ctgcctgtct   1200

gaggtcaatg agtgcaacag caacccctgc gtccacgggg cctgccggga cagcctcaac   1260

gggtacaagt gcgactgtga ccctgggtgg agtgggacca actgtgacat caacaacaat   1320

gagtgtgaat ccaacccttg tgtcaacggc ggcacctgca aagacatgac cagtggctac   1380

gtgtgcacct gccgggaggg cttcagcggt cccaactgcc agaccaacat caacgagtgt   1440

gcgtccaacc catgtctgaa ccagggcacg tgtattgacg acgttgccgg gtacaagtgc   1500

aactgcctgc tgccctacac aggtgccacg tgtgaggtgg tgctggcccc gtgtgccccc   1560

agcccctgca gaaacggcgg ggagtgcagg caatccgagg actatgagag cttctcctgt   1620

gtctgcccca cgggctggca agggcagacc tgtgaggtcg acatcaacga gtgcgttctg   1680
```

-continued

```
agcccgtgcc ggcacggcgc atcctgccag aacacccacg gcggctaccg ctgccactgc   1740
caggccggct acagtgggcg caactgcgag accgacatcg acgactgccg gcccaacccg   1800
tgtcacaacg gggctcctg cacagacggc atcaacacgg ccttctgcga ctgcctgccc   1860
ggcttccggg gcactttctg tgaggaggac atcaacgagt gtgccagtga cccctgccgc   1920
aacggggcca actgcacgga ctgcgtggac agctacacgt gcacctgccc cgcaggcttc   1980
agcgggatcc actgtgagaa caacacgcct gactgcacag agagctcctg cttcaacggt   2040
ggcacctgcg tggacggcat caactcgttc acctgcctgt gtccacccgg cttcacgggc   2100
agctactgcc agcacgatgt caatgagtgc gactcacagc cctgcctgca tggcggcacc   2160
tgtcaggacg gctgcggctc ctacaggtgc acctgccccc agggctacac tggccccaac   2220
tgccagaacc ttgtgcactg gtgtgactcc tcgccctgca agaacggcgg caaatgctgg   2280
cagacccaca cccagtaccg ctgcgagtgc cccagcggct ggaccggcct ttactgcgac   2340
gtgcccagcg tgtcctgtga ggtggctgcg cagcgacaag gtgttgacgt tgcccgcctg   2400
tgccagcatg gagggctctg tgtggacgcg ggcaacacgc accactgccg ctgccaggcg   2460
ggctacacag gcagctactg tgaggacctg gtggacgagt gctcacccag cccctgccag   2520
aacggggcca cctgcacgga ctacctgggc ggctactcct gcaagtgcgt ggccggctac   2580
cacggggtga actgctctga ggagatcgac gagtgcctct cccacccctg ccagaacggg   2640
ggcacctgcc tcgacctccc caacacctac aagtgctcct gcccacgggg cactcagggt   2700
gtgcactgtg agatcaacgt ggacgactgc aatcccccg ttgaccccgt gtcccggagc   2760
cccaagtgct ttaacaacgg cacctgcgtg gaccaggtgg gcggctacag ctgcacctgc   2820
ccgccgggct tcgtgggtga gcgctgtgag gggatgtca acgagtgcct gtccaatccc   2880
tgcgacgccc gtggcaccca gaactgcgtg cagcgcgtca atgacttcca ctgcgagtgc   2940
cgtgctggtc acaccgggcg ccgctgcgag tccgtcatca atggctgcaa aggcaagccc   3000
tgcaagaatg gggcacctg cgccgtggcc tccaacaccg cccgcgggtt catctgcaag   3060
tgccctgcgg gcttcgaggg cgccacgtgt gagaatgacg ctcgtacctg cggcagcctg   3120
cgctgcctca acggcggcac atgcatctcc ggcccgcgca gccccacctg cctgtgcctg   3180
ggcccttca cgggccccga atgccagttc ccggccagca gcccctgcct gggcggcaac   3240
ccctgctaca accaggggac ctgtgagccc acatccgaga gccccttcta ccgttgcctg   3300
tgccccgcca aattcaacgg gctcttgtgc cacatcctgg actacagctt cggagatctg   3360
ggcccgggcg agcccaaatc ttgtgacaaa actcacacat gcccaccgtg cccagcacct   3420
gaactcctgg ggggaccgtc agtcttcctc ttcccccaa aacccaagga caccctcatg   3480
atctcccgga cccctgaggt cacatgcgtg gtggtggacg tgagccacga agaccctgag   3540
gtcaagttca actggtacgt ggacggcgtg gaggtgcata atgccaagac aaagccgcgg   3600
gaggagcagt acaacagcac gtaccgtgtg gtcagcgtcc tcaccgtcct gcaccaggac   3660
tggctgaatg gcaaggagta caagtgcaag gtctccaaca aagccctccc agcccccatc   3720
gagaaaacca tctccaaagc caaagggcag ccccgagaac cacaggtgta caccctgccc   3780
ccatcccggg atgagctgac caagaaccag gtcagcctga cctgcctggt caaaggcttc   3840
tatcccagcg acatcgccgt ggagtgggag agcaatgggc agccggagaa caactacaag   3900
accacgcctc ccgtgctgga ctccgacggc tccttcttcc tctacagcaa gctcaccgtg   3960
gacaagagca ggtggcagca ggggaacgtc ttctcatgct ccgtgatgca tgaggctctg   4020
cacaaccact acacgcagaa gagcctctcc ctgtctccgg gtaaatga                 4068
```

<210> SEQ ID NO 71
<211> LENGTH: 4065
<212> TYPE: DNA
<213> ORGANISM: Homo sapiens

<400> SEQUENCE: 71
atgtggggct ggaagtgcct cctcttctgg gctgtgctgg tcacagccac tctctgcact 60
gccaggtgtg ccagcgccgc ctgcttccac ggcgccacct gccatgaccg tgtggcctcc 120
ttctactgcg agtgtcccca tggccgcaca ggtctgctgt gccacctcaa cgacgcatgc 180
atcagcaacc cctgtaacga gggctccaac tgcgacacca accctgtcaa tggcaaggcc 240
atctgcacct gcccctcggg gtacacgggc ccggcctgca gccaggacgt ggatgagtgc 300
tcgctgggtg ccaacccctg cgagcatgcg ggcaagtgca tcaacacgct gggctccttc 360
gagtgccagt gtctgcaggg ctacacgggc ccccgatgcg agatcgacgt caacgagtgc 420
gtctcgaacc cgtgccagaa cgacgccacc tgcctggacc agattgggga gttccagtgc 480
atctgcatgc ccggctacga gggtgtgcac tgcgaggtca acacagacga gtgtgccagc 540
agcccctgcc tgcacaatgg ccgctgcctg gacaagatca atgagttcca gtgcgagtgc 600
cccacgggct tcactgggca tctgtgccag tacgatgtgg acgagtgtgc cagcaccccc 660
tgcaagaatg gtgccaagtg cctggacgga cccaacactt acacctgtgt gtgcacggaa 720
gggtacacgg ggacgcactg cgaggtggac atcgatgagt gcgaccccga cccctgccac 780
tacggctcct gcaaggacgg cgtcgccacc ttcacctgcc tctgccgccc aggctacacg 840
ggccaccact gcgagaccaa catcaacgag tgctccagcc agccctgccg ccacgggggc 900
acctgccagg accgcgacaa cgcctacctc tgcttctgcc tgaaggggac cacaggaccc 960
aactgcgaga tcaacctgga tgactgtgcc agcagcccct gcgactcggg cacctgtctg 1020
gacaagatcg atggctacga gtgtgcctgt gagccgggct acacagggag catgtgtaac 1080
atcaacatcg atgagtgtgc gggcaacccc tgccacaacg gggggcacctg cgaggacggc 1140 atcaatggct tcacctgccg ctgccccgag ggctaccacg accccacctg cctgtctgag 1200
gtcaatgagt gcaacagcaa cccctgcgtc cacggggcct gccgggacag cctcaacggg 1260
tacaagtgcg actgtgaccc tgggtggagt gggaccaact gtgacatcaa caacaatgag 1320
tgtgaatcca acccttgtgt caacggcggc acctgcaaag acatgaccag tggctacgtg 1380
tgcacctgcc gggagggctt cagcggtccc aactgccaga ccaacatcaa cgagtgtgcg 1440
tccaacccat gtctgaacca gggcacgtgt attgacgacg ttgccgggta caagtgcaac 1500
tgcctgctgc cctacacagg tgccacgtgt gaggtggtgc tggccccgtg tgcccccagc 1560
ccctgcagaa acggcgggga gtgcaggcaa tccgaggact atgagagctt ctcctgtgtc 1620
tgccccacgg gctggcaagg gcagacctgt gaggtcgaca tcaacgagtg cgttctgagc 1680
ccgtgccggc acggcgcatc ctgccagaac acccacggcg gctaccgctg ccactgccag 1740
gccggctaca gtgggcgcaa ctgcgagacc gacatcgacg actgccggcc caacccgtgt 1800
cacaacgggg gctcctgcac agacggcatc aacacggcct tctgcgactg cctgcccggc 1860
ttccggggca ctttctgtga ggaggacatc aacgagtgtg ccagtgaccc ctgccgcaac 1920
ggggccaact gcacggactg cgtggacagc tacacgtgca cctgccccgc aggcttcagc 1980
gggatccact gtgagaacaa cacgcctgac tgcacagaga gctcctgctt caacggtggc 2040
acctgcgtgg acggcatcaa ctcgttcacc tgcctgtgtc cacccggctt cacgggcagc 2100

-continued

```
tactgccagc acgatgtcaa tgagtgcgac tcacagccct gcctgcatgg cggcacctgt   2160

caggacggct gcggctccta caggtgcacc tgcccccagg gctacactgg ccccaactgc   2220

cagaaccttg tgcactggtg tgactcctcg ccctgcaaga acggcggcaa atgctggcag   2280

acccacaccc agtaccgctg cgagtgcccc agcggctgga ccggccttta ctgcgacgtg   2340

cccagcgtgt cctgtgaggt ggctgcgcag cgacaaggtg ttgacgttgc ccgcctgtgc   2400

cagcatggag ggctctgtgt ggacgcgggc aacacgcacc actgccgctg ccaggcgggc   2460

tacacaggca gctactgtga ggacctggtg gacgagtgct cacccagccc ctgccagaac   2520

ggggccacct gcacggacta cctgggcggc tactcctgca agtgcgtggc cggctaccac   2580

ggggtgaact gctctgagga gatcgacgag tgcctctccc acccctgcca gaacgggggc   2640

acctgcctcg acctccccaa cacctacaag tgctcctgcc cacggggcac tcagggtgtg   2700

cactgtgaga tcaacgtgga cgactgcaat cccccgttg accccgtgtc ccggagcccc   2760

aagtgcttta acaacggcac ctgcgtggac caggtgggcg gctacagctg cacctgcccg   2820

ccgggcttcg tgggtgagcg ctgtgagggg gatgtcaacg agtgcctgtc caatccctgc   2880

gacgcccgtg gcacccagaa ctgcgtgcag cgcgtcaatg acttccactg cgagtgccgt   2940

gctggtcaca ccgggcgccg ctgcgagtcc gtcatcaatg gctgcaaagg caagccctgc   3000

aagaatgggg gcacctgcgc cgtggcctcc aacaccgccc gcgggttcat ctgcaagtgc   3060

cctgcgggct tcgagggcgc cacgtgtgag aatgacgctc gtacctgcgg cagcctgcgc   3120

tgcctcaacg gcggcacatg catctccggc ccgcgcagcc ccacctgcct gtgcctgggc   3180

cccttcacgg gccccgaatg ccagttcccg gccagcagcc cctgcctggg cggcaacccc   3240

tgctacaacc aggggacctg tgagcccaca tccgagagcc ccttctaccg ttgcctgtgc   3300

cccgccaaat tcaacgggct cttgtgccac atcctggact acagcttcgg agatctgggc   3360

ccgggcgagc ccaaatcttg tgacaaaact cacacatgcc caccgtgccc agcacctgaa   3420

ctcctggggg gaccgtcagt cttcctcttc cccccaaaac ccaaggacac cctcatgatc   3480

tcccggaccc ctgaggtcac atgcgtggtg gtggacgtga gccacgaaga ccctgaggtc   3540

aagttcaact ggtacgtgga cggcgtggag gtgcataatg ccaagacaaa gccgcgggag   3600

gagcagtaca acagcacgta ccgtgtggtc agcgtcctca ccgtcctgca ccaggactgg   3660

ctgaatggca aggagtacaa gtgcaaggtc tccaacaaag ccctcccagc ccccatcgag   3720

aaaaccatct ccaaagccaa agggcagccc cgagaaccac aggtgtacac cctgccccca   3780

tcccgggatg agctgaccaa gaaccaggtc agcctgacct gcctggtcaa aggcttctat   3840

cccagcgaca tcgccgtgga gtgggagagc aatgggcagc cggagaacaa ctacaagacc   3900

acgcctcccg tgctggactc cgacggctcc ttcttcctct acagcaagct caccgtggac   3960

aagagcaggt ggcagcaggg gaacgtcttc tcatgctccg tgatgcatga ggctctgcac   4020

aaccactaca cgcagaagag cctctccctg tctccgggta aatga                   4065
```

<210> SEQ ID NO 72
<211> LENGTH: 2148
<212> TYPE: DNA
<213> ORGANISM: Homo sapiens

<400> SEQUENCE: 72

```
atgccgccgc tcctggcgcc cctgctctgc ctggcgctgc tgcccgcgct cgccgcacga     60

ggcccgcgat gtgccagcag cccctgcctg cacaatggcc gctgcctgga caagatcaat    120

gagttccagt gcgagtgccc cacgggcttc actgggcatc tgtgccagta cgatgtggac    180
```

gagtgtgcca gcacccccctg caagaatggt gccaagtgcc tggacggacc caacacttac 240
acctgtgtgt gcacggaagg gtacacgggg acgcactgcg aggtggacat cgatgagtgc 300
gaccccgacc cctgccacta cggctcctgc aaggacggcg tcgccacctt cacctgcctc 360
tgccgcccag gctacacggg ccaccactgc gagaccaaca tcaacgagtg ctccagccag 420
ccctgccgcc acgggggcac ctgccaggac cgcgacaacg cctacctctg cttctgcctg 480
aaggggacca caggacccaa ctgcgagatc aacctggatg actgtgccag cagcccctgc 540
gactcgggca cctgtctgga caagatcgat ggctacgagt gtgcctgtga gccgggctac 600
acagggagca tgtgtaacat caacatcgat gagtgtgcgg gcaacccctg ccacaacggg 660
ggcacctgcg aggacggcat caatggcttc acctgccgct gccccgaggg ctaccacgac 720
cccacctgcc tgtctgaggt caatgagtgc aacagcaacc cctgcgtcca cggggcctgc 780
cgggacagcc tcaacgggta caagtgcgac tgtgaccctg ggtggagtgg gaccaactgt 840
gacatcaaca acaatgagtg tgaatccaac ccttgtgtca acggcggcac ctgcaaagac 900
atgaccagtg gctacgtgtg cacctgccgg gagggcttca gcggtcccaa ctgccagacc 960
aacatcaacg agtgtgcgtc caacccatgt ctgaaccagg gcacgtgtat tgacgacgtt 1020
gccgggtaca agtgcaactg cctgctgccc tacacaggtg ccacgtgtga ggtggtgctg 1080
gccccgtgtg cccccagccc ctgcagaaac ggcggggagt gcaggcaatc cgaggactat 1140
gagagcttct cctgtgtctg ccccacgggc tggcaagggc agacctgtga ggtcgacatc 1200
aacgagtgcg ttctgagccc gtgccggcac ggcgcatcct gccagaacac ccacggcggc 1260
taccgctgcc actgccaggc cggctacagt gggcgcaact gcgagaccga catcgacgac 1320
tgccggccca acccgtgtca caacgggggc tcctgcacag acggcatcaa cacggccttc 1380
tgcgactgcc tgcccggctt ccggggcact ttctgtgagg aggacatcaa cgaggatctg 1440
ggcccgggcg agcccaaatc ttgtgacaaa actcacacat gcccaccgtg cccagcacct 1500
gaactcctgg ggggaccgtc agtcttcctc ttccccccaa aacccaagga caccctcatg 1560
atctcccgga cccctgaggt cacatgcgtg gtggtggacg tgagccacga agaccctgag 1620
gtcaagttca actggtacgt ggacggcgtg gaggtgcata atgccaagac aaagccgcgg 1680
gaggagcagt acaacagcac gtaccgtgtg gtcagcgtcc tcaccgtcct gcaccaggac 1740
tggctgaatg gcaaggagta caagtgcaag gtctccaaca aagccctccc agcccccatc 1800
gagaaaacca tctccaaagc caaagggcag ccccgagaac cacaggtgta caccctgccc 1860
ccatcccggg atgagctgac caagaaccag gtcagcctga cctgcctggt caaaggcttc 1920
tatcccagcg acatcgccgt ggagtgggag agcaatgggc agccggagaa caactacaag 1980
accacgcctc ccgtgctgga ctccgacggc tccttcttcc tctacagcaa gctcaccgtg 2040
gacaagagca ggtggcagca ggggaacgtc ttctcatgct ccgtgatgca tgaggctctg 2100
cacaaccact acacgcagaa gagcctctcc ctgtctccgg gtaaatga 2148

<210> SEQ ID NO 73
<211> LENGTH: 2145
<212> TYPE: DNA
<213> ORGANISM: Homo sapiens

<400> SEQUENCE: 73
atgtggggct ggaagtgcct cctcttctgg gctgtgctgg tcacagccac tctctgcact 60
gccaggtgtg ccagcagccc ctgcctgcac aatggccgct gcctggacaa gatcaatgag 120

-continued

```
ttccagtgcg agtgccccac gggcttcact gggcatctgt gccagtacga tgtggacgag    180

tgtgccagca cccccctgcaa gaatggtgcc aagtgcctgg acggacccaa cacttacacc    240

tgtgtgtgca cggaagggta cacggggacg cactgcgagg tggacatcga tgagtgcgac    300

cccgacccct gccactacgg ctcctgcaag gacggcgtcg ccaccttcac ctgcctctgc    360

cgcccaggct acacgggcca ccactgcgag accaacatca acgagtgctc cagccagccc    420

tgccgccacg gggcacctg ccaggaccgc gacaacgcct acctctgctt ctgcctgaag    480

gggaccacag gacccaactg cgagatcaac ctggatgact gtgccagcag cccctgcgac    540

tcgggcacct gtctggacaa gatcgatggc tacgagtgtg cctgtgagcc gggctacaca    600

gggagcatgt gtaacatcaa catcgatgag tgtgcgggca acccctgcca caacgggggc    660

acctgcgagg acggcatcaa tggcttcacc tgccgctgcc ccgagggcta ccacgacccc    720

acctgcctgt ctgaggtcaa tgagtgcaac agcaacccct gcgtccacgg ggcctgccgg    780

gacagcctca acgggtacaa gtgcgactgt gaccctgggt ggagtgggac caactgtgac    840

atcaacaaca atgagtgtga atccaaccct tgtgtcaacg gcggcacctg caaagacatg    900

accagtggct acgtgtgcac ctgccgggag ggcttcagcg gtcccaactg ccagaccaac    960

atcaacgagt gtgcgtccaa cccatgtctg aaccagggca cgtgtattga cgacgttgcc   1020

gggtacaagt gcaactgcct gctgccctac acaggtgcca cgtgtgaggt ggtgctggcc   1080

ccgtgtgccc ccagcccctg cagaaacggc ggggagtgca ggcaatccga ggactatgag   1140

agcttctcct gtgtctgccc cacgggctgg caagggcaga cctgtgaggt cgacatcaac   1200

gagtgcgttc tgagcccgtg ccggcacggc gcatcctgcc agaacaccca cggcggctac   1260

cgctgccact gccaggccgg ctacagtggg cgcaactgcg agaccgacat cgacgactgc   1320

cggcccaacc cgtgtcacaa cgggggctcc tgcacagacg gcatcaacac ggccttctgc   1380

gactgcctgc ccggcttccg gggcactttc tgtgaggagg acatcaacga ggatctgggc   1440

ccgggcgagc ccaaatcttg tgacaaaact cacacatgcc caccgtgccc agcacctgaa   1500

ctcctggggg gaccgtcagt cttcctcttc cccccaaaac ccaaggacac cctcatgatc   1560

tcccggaccc ctgaggtcac atgcgtggtg gtggacgtga gccacgaaga ccctgaggtc   1620

aagttcaact ggtacgtgga cggcgtggag gtgcataatg ccaagacaaa gccgcgggag   1680

gagcagtaca acagcacgta ccgtgtggtc agcgtcctca ccgtcctgca ccaggactgg   1740

ctgaatggca aggagtacaa gtgcaaggtc tccaacaaag ccctcccagc ccccatcgag   1800

aaaaccatct ccaaagccaa agggcagccc cgagaaccac aggtgtacac cctgccccca   1860

tcccgggatg agctgaccaa gaaccaggtc agcctgacct gcctggtcaa aggcttctat   1920

cccagcgaca tcgccgtgga gtgggagagc aatgggcagc cggagaacaa ctacaagacc   1980

acgcctcccg tgctggactc cgacggctcc ttcttcctct acagcaagct caccgtggac   2040

aagagcaggt ggcagcaggg gaacgtcttc tcatgctccg tgatgcatga ggctctgcac   2100

aaccactaca cgcagaagag cctctccctg tctccgggta aatga                  2145
```

<210> SEQ ID NO 74
<211> LENGTH: 2238
<212> TYPE: DNA
<213> ORGANISM: Homo sapiens

<400> SEQUENCE: 74

```
atgccgccgc tcctggcgcc cctgctctgc ctggcgctgc tgcccgcgct cgccgcacga     60

ggcccgcgat gtgccagtga cccctgccgc aacggggcca actgcacgga ctgcgtggac    120
```

```
agctacacgt gcacctgccc cgcaggcttc agcgggatcc actgtgagaa caacacgcct    180
gactgcacag agagctcctg cttcaacggt ggcacctgcg tggacggcat caactcgttc    240
acctgcctgt gtccacccgg cttcacgggc agctactgcc agcacgatgt caatgagtgc    300
gactcacagc cctgcctgca tggcggcacc tgtcaggacg gctgcggctc ctacaggtgc    360
acctgccccc agggctacac tggccccaac tgccagaacc ttgtgcactg gtgtgactcc    420
tcgccctgca agaacggcgg caaatgctgg cagacccaca cccagtaccg ctgcgagtgc    480
cccagcggct ggaccggcct ttactgcgac gtgcccagcg tgtcctgtga ggtggctgcg    540
cagcgacaag gtgttgacgt tgcccgcctg tgccagcatg gagggctctg tgtggacgcg    600
ggcaacacgc accactgccg ctgccaggcg ggctacacag gcagctactg tgaggacctg    660
gtggacgagt gctcacccag cccctgccag aacggggcca cctgcacgga ctacctgggc    720
ggctactcct gcaagtgcgt ggccggctac cacggggtga actgctctga ggagatcgac    780
gagtgcctct cccacccctg ccagaacggg ggcacctgcc tcgacctccc caacacctac    840
aagtgctcct gcccacgggg cactcagggt gtgcactgtg agatcaacgt ggacgactgc    900
aatccccccg ttgaccccgt gtcccggagc cccaagtgct ttaacaacgg cacctgcgtg    960
gaccaggtgg gcggctacag ctgcacctgc ccgccgggct tcgtgggtga gcgctgtgag   1020
gggatgtca acgagtgcct gtccaatccc tgcgacgccc gtggcaccca gaactgcgtg   1080
cagcgcgtca atgacttcca ctgcgagtgc cgtgctggtc acaccgggcg ccgctgcgag   1140
tccgtcatca atggctgcaa aggcaagccc tgcaagaatg gggcacctg cgccgtggcc    1200
tccaacaccg cccgcgggtt catctgcaag tgccctgcgg gcttcgaggg cgccacgtgt   1260
gagaatgacg ctcgtacctg cggcagcctg cgctgcctca acggcggcac atgcatctcc   1320
ggcccgcgca gccccacctg cctgtgcctg ggccccttca cgggccccga atgccagttc   1380
ccggccagca gcccctgcct gggcggcaac ccctgctaca accaggggac ctgtgagccc   1440
acatccgaga gccccttcta ccgttgcctg tgccccgcca aattcaacgg gctcttgtgc   1500
cacatcctgg actacagctt cggagatctg ggcccgggcg agcccaaatc ttgtgacaaa   1560
actcacacat gcccaccgtg cccagcacct gaactcctgg ggggaccgtc agtcttcctc   1620
ttccccccaa aacccaagga caccctcatg atctcccgga cccctgaggt cacatgcgtg   1680
gtggtggacg tgagccacga agaccctgag gtcaagttca actggtacgt ggacggcgtg   1740
gaggtgcata atgccaagac aaagccgcgg gaggagcagt acaacagcac gtaccgtgtg   1800
gtcagcgtcc tcaccgtcct gcaccaggac tggctgaatg gcaaggagta caagtgcaag   1860
gtctccaaca aagccctccc agcccccatc gagaaaacca tctccaaagc caaagggcag   1920
ccccgagaac cacaggtgta caccctgccc ccatcccggg atgagctgac caagaaccag   1980
gtcagcctga cctgcctggt caaaggcttc tatcccagcg acatcgccgt ggagtgggag   2040
agcaatgggc agccggagaa caactacaag accacgcctc ccgtgctgga ctccgacggc   2100
tccttcttcc tctacagcaa gctcaccgtg gacaagagca ggtggcagca ggggaacgtc   2160
ttctcatgct ccgtgatgca tgaggctctg cacaaccact acacgcagaa gagcctctcc   2220
ctgtctccgg gtaaatga                                                 2238
```

<210> SEQ ID NO 75
<211> LENGTH: 2235
<212> TYPE: DNA
<213> ORGANISM: Homo sapiens

<400> SEQUENCE: 75

```
atgtggggct ggaagtgcct cctcttctgg gctgtgctgg tcacagccac tctctgcact      60
gccaggtgtg ccagtgaccc ctgccgcaac ggggccaact gcacggactg cgtggacagc     120
tacacgtgca cctgccccgc aggcttcagc gggatccact gtgagaacaa cacgcctgac     180
tgcacagaga gctcctgctt caacggtggc acctgcgtgg acggcatcaa ctcgttcacc     240
tgcctgtgtc cacccggctt cacgggcagc tactgccagc acgatgtcaa tgagtgcgac     300
tcacagccct gcctgcatgg cggcacctgt caggacggct gcggctccta caggtgcacc     360
tgcccccagg gctacactgg ccccaactgc cagaaccttg tgcactggtg tgactcctcg     420
ccctgcaaga acggcggcaa atgctggcag acccacaccc agtaccgctg cgagtgcccc     480
agcggctgga ccggccttta ctgcgacgtg cccagcgtgt cctgtgaggt ggctgcgcag     540
cgacaaggtg ttgacgttgc ccgcctgtgc cagcatggag ggctctgtgt ggacgcgggc     600
aacacgcacc actgccgctg ccaggcgggc tacacaggca gctactgtga ggacctggtg     660
gacgagtgct cacccagccc ctgccagaac ggggccacct gcacggacta cctgggcggc     720
tactcctgca agtgcgtggc cggctaccac ggggtgaact gctctgagga gatcgacgag     780
tgcctctccc acccctgcca gaacgggggc acctgcctcg acctccccaa cacctacaag     840
tgctcctgcc cacggggcac tcagggtgtg cactgtgaga tcaacgtgga cgactgcaat     900
ccccccgttg accccgtgtc ccggagcccc aagtgcttta acaacggcac ctgcgtggac     960
caggtgggcg gctacagctg cacctgcccg ccgggcttcg tgggtgagcg ctgtgagggg    1020
gatgtcaacg agtgcctgtc caatccctgc gacgcccgtg gcacccagaa ctgcgtgcag    1080
cgcgtcaatg acttccactg cgagtgccgt gctggtcaca ccgggcgccg ctgcgagtcc    1140
gtcatcaatg gctgcaaagg caagccctgc aagaatgggg gcacctgcgc cgtggcctcc    1200
aacaccgccc gcgggttcat ctgcaagtgc cctgcgggct tcgagggcgc cacgtgtgag    1260
aatgacgctc gtacctgcgg cagcctgcgc tgcctcaacg gcggcacatg catctccggc    1320
ccgcgcagcc ccacctgcct gtgcctgggc cccttcacgg gccccgaatg ccagttcccg    1380
gccagcagcc cctgcctggg cggcaacccc tgctacaacc aggggacctg tgagcccaca    1440
tccgagagcc ccttctaccg ttgcctgtgc cccgccaaat tcaacgggct cttgtgccac    1500
atcctggact acagcttcgg agatctgggc ccgggcgagc ccaaatcttg tgacaaaact    1560
cacacatgcc caccgtgccc agcacctgaa ctcctggggg gaccgtcagt cttcctcttc    1620
cccccaaaac ccaaggacac cctcatgatc tcccggaccc ctgaggtcac atgcgtggtg    1680
gtggacgtga gccacgaaga ccctgaggtc aagttcaact ggtacgtgga cggcgtggag    1740
gtgcataatg ccaagacaaa gccgcgggag gagcagtaca acagcacgta ccgtgtggtc    1800
agcgtcctca ccgtcctgca ccaggactgg ctgaatggca aggagtacaa gtgcaaggtc    1860
tccaacaaag ccctcccagc ccccatcgag aaaaccatct ccaaagccaa agggcagccc    1920
cgagaaccac aggtgtacac cctgccccca tcccgggatg agctgaccaa gaaccaggtc    1980
agcctgacct gcctggtcaa aggcttctat cccagcgaca tcgccgtgga gtgggagagc    2040
aatgggcagc cggagaacaa ctacaagacc acgcctcccg tgctggactc cgacggctcc    2100
ttcttcctct acagcaagct caccgtggac aagagcaggt ggcagcaggg gaacgtcttc    2160
tcatgctccg tgatgcatga ggctctgcac aaccactaca cgcagaagag cctctccctg    2220
tctccgggta aatga                                                     2235
```

<210> SEQ ID NO 76
<211> LENGTH: 2003
<212> TYPE: PRT
<213> ORGANISM: Homo sapiens

<400> SEQUENCE: 76

```
Met Gln Pro Pro Ser Leu Leu Leu Leu Leu Leu Leu Leu Leu Leu Leu
1               5                   10                  15

Cys Val Ser Val Val Arg Pro Arg Gly Leu Leu Cys Gly Ser Phe Pro
            20                  25                  30

Glu Pro Cys Ala Asn Gly Gly Thr Cys Leu Ser Leu Ser Leu Gly Gln
        35                  40                  45

Gly Thr Cys Gln Cys Ala Pro Gly Phe Leu Gly Glu Thr Cys Gln Phe
    50                  55                  60

Pro Asp Pro Cys Gln Asn Ala Gln Leu Cys Gln Asn Gly Gly Ser Cys
65                  70                  75                  80

Gln Ala Leu Leu Pro Ala Pro Leu Gly Leu Pro Ser Ser Pro Ser Pro
                85                  90                  95

Leu Thr Pro Ser Phe Leu Cys Thr Cys Leu Pro Gly Phe Thr Gly Glu
            100                 105                 110

Arg Cys Gln Ala Lys Leu Glu Asp Pro Cys Pro Pro Ser Phe Cys Ser
        115                 120                 125

Lys Arg Gly Arg Cys His Ile Gln Ala Ser Gly Arg Pro Gln Cys Ser
    130                 135                 140

Cys Met Pro Gly Trp Thr Gly Glu Gln Cys Gln Leu Arg Asp Phe Cys
145                 150                 155                 160

Ser Ala Asn Pro Cys Val Asn Gly Gly Val Cys Leu Ala Thr Tyr Pro
                165                 170                 175

Gln Ile Gln Cys His Cys Pro Pro Gly Phe Glu Gly His Ala Cys Glu
            180                 185                 190

Arg Asp Val Asn Glu Cys Phe Gln Asp Pro Gly Pro Cys Pro Lys Gly
        195                 200                 205

Thr Ser Cys His Asn Thr Leu Gly Ser Phe Gln Cys Leu Cys Pro Val
    210                 215                 220

Gly Gln Glu Gly Pro Arg Cys Glu Leu Arg Ala Gly Pro Cys Pro Pro
225                 230                 235                 240

Arg Gly Cys Ser Asn Gly Gly Thr Cys Gln Leu Met Pro Glu Lys Asp
                245                 250                 255

Ser Thr Phe His Leu Cys Leu Cys Pro Pro Gly Phe Ile Gly Pro Asp
            260                 265                 270

Cys Glu Val Asn Pro Asp Asn Cys Val Ser His Gln Cys Gln Asn Gly
        275                 280                 285

Gly Thr Cys Gln Asp Gly Leu Asp Thr Tyr Thr Cys Leu Cys Pro Glu
    290                 295                 300

Thr Trp Thr Gly Trp Asp Cys Ser Glu Asp Val Asp Glu Cys Glu Thr
305                 310                 315                 320

Gln Gly Pro Pro His Cys Arg Asn Gly Gly Thr Cys Gln Asn Ser Ala
                325                 330                 335

Gly Ser Phe His Cys Val Cys Val Ser Gly Trp Gly Gly Thr Ser Cys
            340                 345                 350

Glu Glu Asn Leu Asp Asp Cys Ile Ala Ala Thr Cys Ala Pro Gly Ser
        355                 360                 365

Thr Cys Ile Asp Arg Val Gly Ser Phe Ser Cys Leu Cys Pro Pro Gly
    370                 375                 380
```

-continued

```
Arg Thr Gly Leu Leu Cys His Leu Glu Asp Met Cys Leu Ser Gln Pro
385                 390                 395                 400

Cys His Gly Asp Ala Gln Cys Ser Thr Asn Pro Leu Thr Gly Ser Thr
                405                 410                 415

Leu Cys Leu Cys Gln Pro Gly Tyr Ser Gly Pro Thr Cys His Gln Asp
            420                 425                 430

Leu Asp Glu Cys Leu Met Ala Gln Gln Gly Pro Ser Pro Cys Glu His
        435                 440                 445

Gly Gly Ser Cys Leu Asn Thr Pro Gly Ser Phe Asn Cys Leu Cys Pro
    450                 455                 460

Pro Gly Tyr Thr Gly Ser Arg Cys Glu Ala Asp His Asn Glu Cys Leu
465                 470                 475                 480

Ser Gln Pro Cys His Pro Gly Ser Thr Cys Leu Asp Leu Leu Ala Thr
                485                 490                 495

Phe His Cys Leu Cys Pro Pro Gly Leu Glu Gly Gln Leu Cys Glu Val
            500                 505                 510

Glu Thr Asn Glu Cys Ala Ser Ala Pro Cys Leu Asn His Ala Asp Cys
        515                 520                 525

His Asp Leu Leu Asn Gly Phe Gln Cys Ile Cys Leu Pro Gly Phe Ser
    530                 535                 540

Gly Thr Arg Cys Glu Glu Asp Ile Asp Glu Cys Arg Ser Ser Pro Cys
545                 550                 555                 560

Ala Asn Gly Gly Gln Cys Gln Asp Gln Pro Gly Ala Phe His Cys Lys
                565                 570                 575

Cys Leu Pro Gly Phe Glu Gly Pro Arg Cys Gln Thr Glu Val Asp Glu
            580                 585                 590

Cys Leu Ser Asp Pro Cys Pro Val Gly Ala Ser Cys Leu Asp Leu Pro
        595                 600                 605

Gly Ala Phe Phe Cys Leu Cys Pro Ser Gly Phe Thr Gly Gln Leu Cys
    610                 615                 620

Glu Val Pro Leu Cys Ala Pro Asn Leu Cys Gln Pro Lys Gln Ile Cys
625                 630                 635                 640

Lys Asp Gln Lys Asp Lys Ala Asn Cys Leu Cys Pro Asp Gly Ser Pro
                645                 650                 655

Gly Cys Ala Pro Pro Glu Asp Asn Cys Thr Cys His His Gly His Cys
            660                 665                 670

Gln Arg Ser Ser Cys Val Cys Asp Val Gly Trp Thr Gly Pro Glu Cys
        675                 680                 685

Glu Ala Glu Leu Gly Gly Cys Ile Ser Ala Pro Cys Ala His Gly Gly
    690                 695                 700

Thr Cys Tyr Pro Gln Pro Ser Gly Tyr Asn Cys Thr Cys Pro Thr Gly
705                 710                 715                 720

Tyr Thr Gly Pro Thr Cys Ser Glu Glu Met Thr Ala Cys His Ser Gly
                725                 730                 735

Pro Cys Leu Asn Gly Gly Ser Cys Asn Pro Ser Pro Gly Gly Tyr Tyr
            740                 745                 750

Cys Thr Cys Pro Pro Ser His Thr Gly Pro Gln Cys Gln Thr Ser Thr
        755                 760                 765

Asp Tyr Cys Val Ser Ala Pro Cys Phe Asn Gly Gly Thr Cys Val Asn
    770                 775                 780

Arg Pro Gly Thr Phe Ser Cys Leu Cys Ala Met Gly Phe Gln Gly Pro
785                 790                 795                 800

Arg Cys Glu Gly Lys Leu Arg Pro Ser Cys Ala Asp Ser Pro Cys Arg
```

-continued 805 810 815

Asn Arg Ala Thr Cys Gln Asp Ser Pro Gln Gly Pro Arg Cys Leu Cys
820 825 830

Pro Thr Gly Tyr Thr Gly Gly Ser Cys Gln Thr Leu Met Asp Leu Cys
835 840 845

Ala Gln Lys Pro Cys Pro Arg Asn Ser His Cys Leu Gln Thr Gly Pro
850 855 860

Ser Phe His Cys Leu Cys Leu Gln Gly Trp Thr Gly Pro Leu Cys Asn
865 870 875 880

Leu Pro Leu Ser Ser Cys Gln Lys Ala Ala Leu Ser Gln Gly Ile Asp
885 890 895

Val Ser Ser Leu Cys His Asn Gly Gly Leu Cys Val Asp Ser Gly Pro
900 905 910

Ser Tyr Phe Cys His Cys Pro Pro Gly Phe Gln Gly Ser Leu Cys Gln
915 920 925

Asp His Val Asn Pro Cys Glu Ser Arg Pro Cys Gln Asn Gly Ala Thr
930 935 940

Cys Met Ala Gln Pro Ser Gly Tyr Leu Cys Gln Cys Ala Pro Gly Tyr
945 950 955 960

Asp Gly Gln Asn Cys Ser Lys Glu Leu Asp Ala Cys Gln Ser Gln Pro
965 970 975

Cys His Asn His Gly Thr Cys Thr Pro Lys Pro Gly Gly Phe His Cys
980 985 990

Ala Cys Pro Pro Gly Phe Val Gly Leu Arg Cys Glu Gly Asp Val Asp
995 1000 1005

Glu Cys Leu Asp Gln Pro Cys His Pro Thr Gly Thr Ala Ala Cys
1010 1015 1020

His Ser Leu Ala Asn Ala Phe Tyr Cys Gln Cys Leu Pro Gly His
1025 1030 1035

Thr Gly Gln Trp Cys Glu Val Glu Ile Asp Pro Cys His Ser Gln
1040 1045 1050

Pro Cys Phe His Gly Gly Thr Cys Glu Ala Thr Ala Gly Ser Pro
1055 1060 1065

Leu Gly Phe Ile Cys His Cys Pro Lys Gly Phe Glu Gly Pro Thr
1070 1075 1080

Cys Ser His Arg Ala Pro Ser Cys Gly Phe His His Cys His His
1085 1090 1095

Gly Gly Leu Cys Leu Pro Ser Pro Lys Pro Gly Phe Pro Pro Arg
1100 1105 1110

Cys Ala Cys Leu Ser Gly Tyr Gly Gly Pro Asp Cys Leu Thr Pro
1115 1120 1125

Pro Ala Pro Lys Gly Cys Gly Pro Pro Ser Pro Cys Leu Tyr Asn
1130 1135 1140

Gly Ser Cys Ser Glu Thr Thr Gly Leu Gly Gly Pro Gly Phe Arg
1145 1150 1155

Cys Ser Cys Pro His Ser Ser Pro Gly Pro Arg Cys Gln Lys Pro
1160 1165 1170

Gly Ala Lys Gly Cys Glu Gly Arg Ser Gly Asp Gly Ala Cys Asp
1175 1180 1185

Ala Gly Cys Ser Gly Pro Gly Gly Asn Trp Asp Gly Gly Asp Cys
1190 1195 1200

Ser Leu Gly Val Pro Asp Pro Trp Lys Gly Cys Pro Ser His Ser
1205 1210 1215

```
Arg Cys  Trp Leu Leu Phe Arg  Asp Gly Gln Cys His  Pro Gln Cys
    1220                 1225                 1230

Asp Ser  Glu Glu Cys Leu Phe  Asp Gly Tyr Asp Cys  Glu Thr Pro
    1235                 1240                 1245

Pro Ala  Cys Thr Pro Ala Tyr  Asp Gln Tyr Cys His  Asp His Phe
    1250                 1255                 1260

His Asn  Gly His Cys Glu Lys  Gly Cys Asn Thr Ala  Glu Cys Gly
    1265                 1270                 1275

Trp Asp  Gly Gly Asp Cys Arg  Pro Glu Asp Gly Asp  Pro Glu Trp
    1280                 1285                 1290

Gly Pro  Ser Leu Ala Leu Leu  Val Val Leu Ser Pro  Pro Ala Leu
    1295                 1300                 1305

Asp Gln  Gln Leu Phe Ala Leu  Ala Arg Val Leu Ser  Leu Thr Leu
    1310                 1315                 1320

Arg Val  Gly Leu Trp Val Arg  Lys Asp Arg Asp Gly  Arg Asp Met
    1325                 1330                 1335

Val Tyr  Pro Tyr Pro Gly Ala  Arg Ala Glu Glu Lys  Leu Gly Gly
    1340                 1345                 1350

Thr Arg  Asp Pro Thr Tyr Gln  Glu Arg Ala Ala Pro  Gln Thr Gln
    1355                 1360                 1365

Pro Leu  Gly Lys Glu Thr Asp  Ser Leu Ser Ala Gly  Phe Val Val
    1370                 1375                 1380

Val Met  Gly Val Asp Leu Ser  Arg Cys Gly Pro Asp  His Pro Ala
    1385                 1390                 1395

Ser Arg  Cys Pro Trp Asp Pro  Gly Leu Leu Leu Arg  Phe Leu Ala
    1400                 1405                 1410

Ala Met  Ala Ala Val Gly Ala  Leu Glu Pro Leu Leu  Pro Gly Pro
    1415                 1420                 1425

Leu Leu  Ala Val His Pro His  Ala Gly Thr Ala Pro  Pro Ala Asn
    1430                 1435                 1440

Gln Leu  Pro Trp Pro Val Leu  Cys Ser Pro Val Ala  Gly Val Ile
    1445                 1450                 1455

Leu Leu  Ala Leu Gly Ala Leu  Leu Val Leu Gln Leu  Ile Arg Arg
    1460                 1465                 1470

Arg Arg  Arg Glu His Gly Ala  Leu Trp Leu Pro Pro  Gly Phe Thr
    1475                 1480                 1485

Arg Arg  Pro Arg Thr Gln Ser  Ala Pro His Arg Arg  Arg Pro Pro
    1490                 1495                 1500

Leu Gly  Glu Asp Ser Ile Gly  Leu Lys Ala Leu Lys  Pro Lys Ala
    1505                 1510                 1515

Glu Val  Asp Glu Asp Gly Val  Val Met Cys Ser Gly  Pro Glu Glu
    1520                 1525                 1530

Gly Glu  Glu Val Gly Gln Ala  Glu Glu Thr Gly Pro  Pro Ser Thr
    1535                 1540                 1545

Cys Gln  Leu Trp Ser Leu Ser  Gly Gly Cys Gly Ala  Leu Pro Gln
    1550                 1555                 1560

Ala Ala  Met Leu Thr Pro Pro  Gln Glu Ser Glu Met  Glu Ala Pro
    1565                 1570                 1575

Asp Leu  Asp Thr Arg Gly Pro  Asp Gly Val Thr Pro  Leu Met Ser
    1580                 1585                 1590

Ala Val  Cys Cys Gly Glu Val  Gln Ser Gly Thr Phe  Gln Gly Ala
    1595                 1600                 1605
```

Trp Leu Gly Cys Pro Glu Pro Trp Glu Pro Leu Leu Asp Gly Gly
1610 1615 1620

Ala Cys Pro Gln Ala His Thr Val Gly Thr Gly Glu Thr Pro Leu
1625 1630 1635

His Leu Ala Ala Arg Phe Ser Arg Pro Thr Ala Ala Arg Arg Leu
1640 1645 1650

Leu Glu Ala Gly Ala Asn Pro Asn Gln Pro Asp Arg Ala Gly Arg
1655 1660 1665

Thr Pro Leu His Ala Ala Val Ala Ala Asp Ala Arg Glu Val Cys
1670 1675 1680

Gln Leu Leu Leu Arg Ser Arg Gln Thr Ala Val Asp Ala Arg Thr
1685 1690 1695

Glu Asp Gly Thr Thr Pro Leu Met Leu Ala Ala Arg Leu Ala Val
1700 1705 1710

Glu Asp Leu Val Glu Glu Leu Ile Ala Ala Gln Ala Asp Val Gly
1715 1720 1725

Ala Arg Asp Lys Trp Gly Lys Thr Ala Leu His Trp Ala Ala Ala
1730 1735 1740

Val Asn Asn Ala Arg Ala Ala Arg Ser Leu Leu Gln Ala Gly Ala
1745 1750 1755

Asp Lys Asp Ala Gln Asp Asn Arg Glu Gln Thr Pro Leu Phe Leu
1760 1765 1770

Ala Ala Arg Glu Gly Ala Val Glu Val Ala Gln Leu Leu Leu Gly
1775 1780 1785

Leu Gly Ala Ala Arg Glu Leu Arg Asp Gln Ala Gly Leu Ala Pro
1790 1795 1800

Ala Asp Val Ala His Gln Arg Asn His Trp Asp Leu Leu Thr Leu
1805 1810 1815

Leu Glu Gly Ala Gly Pro Pro Glu Ala Arg His Lys Ala Thr Pro
1820 1825 1830

Gly Arg Glu Ala Gly Pro Phe Pro Arg Ala Arg Thr Val Ser Val
1835 1840 1845

Ser Val Pro Pro His Gly Gly Gly Ala Leu Pro Arg Cys Arg Thr
1850 1855 1860

Leu Ser Ala Gly Ala Gly Pro Arg Gly Gly Gly Ala Cys Leu Gln
1865 1870 1875

Ala Arg Thr Trp Ser Val Asp Leu Ala Ala Arg Gly Gly Gly Ala
1880 1885 1890

Tyr Ser His Cys Arg Ser Leu Ser Gly Val Gly Ala Gly Gly Gly
1895 1900 1905

Pro Thr Pro Arg Gly Arg Arg Phe Ser Ala Gly Met Arg Gly Pro
1910 1915 1920

Arg Pro Asn Pro Ala Ile Met Arg Gly Arg Tyr Gly Val Ala Ala
1925 1930 1935

Gly Arg Gly Gly Arg Val Ser Thr Asp Asp Trp Pro Cys Asp Trp
1940 1945 1950

Val Ala Leu Gly Ala Cys Gly Ser Ala Ser Asn Ile Pro Ile Pro
1955 1960 1965

Pro Pro Cys Leu Thr Pro Ser Pro Glu Arg Gly Ser Pro Gln Leu
1970 1975 1980

Asp Cys Gly Pro Pro Ala Leu Gln Glu Met Pro Ile Asn Gln Gly
1985 1990 1995

Gly Glu Gly Lys Lys

2000

<210> SEQ ID NO 77
<211> LENGTH: 237
<212> TYPE: PRT
<213> ORGANISM: Homo sapiens

<400> SEQUENCE: 77

```
Asp Leu Gly Pro Gly Glu Pro Lys Ser Cys Asp Lys Thr His Thr Cys
1               5                   10                  15

Pro Pro Cys Pro Ala Pro Glu Leu Leu Gly Gly Pro Ser Val Phe Leu
            20                  25                  30

Phe Pro Pro Lys Pro Lys Asp Thr Leu Met Ile Ser Arg Thr Pro Glu
        35                  40                  45

Val Thr Cys Val Val Val Asp Val Ser His Glu Asp Pro Glu Val Lys
    50                  55                  60

Phe Asn Trp Tyr Val Asp Gly Val Glu Val His Asn Ala Lys Thr Lys
65                  70                  75                  80

Pro Arg Glu Glu Gln Tyr Asn Ser Thr Tyr Arg Val Val Ser Val Leu
                85                  90                  95

Thr Val Leu His Gln Asp Trp Leu Asn Gly Lys Glu Tyr Lys Cys Lys
            100                 105                 110

Val Ser Asn Lys Ala Leu Pro Ala Pro Ile Glu Lys Thr Ile Ser Lys
        115                 120                 125

Ala Lys Gly Gln Pro Arg Glu Pro Gln Val Tyr Thr Leu Pro Pro Ser
    130                 135                 140

Arg Asp Glu Leu Thr Lys Asn Gln Val Ser Leu Thr Cys Leu Val Lys
145                 150                 155                 160

Gly Phe Tyr Pro Ser Asp Ile Ala Val Glu Trp Glu Ser Asn Gly Gln
                165                 170                 175

Pro Glu Asn Asn Tyr Lys Thr Thr Pro Pro Val Leu Asp Ser Asp Gly
            180                 185                 190

Ser Phe Phe Leu Tyr Ser Lys Leu Thr Val Asp Lys Ser Arg Trp Gln
        195                 200                 205

Gln Gly Asn Val Phe Ser Cys Ser Val Met His Glu Ala Leu His Asn
    210                 215                 220

His Tyr Thr Gln Lys Ser Leu Ser Leu Ser Pro Gly Lys
225                 230                 235
```

<210> SEQ ID NO 78
<211> LENGTH: 1410
<212> TYPE: PRT
<213> ORGANISM: Homo sapiens

<400> SEQUENCE: 78

```
Gln Pro Pro Ser Leu Leu Leu Leu Leu Leu Leu Leu Leu Leu Leu Cys
1               5                   10                  15

Val Ser Val Val Arg Pro Arg Gly Leu Leu Cys Gly Ser Phe Pro Glu
            20                  25                  30

Pro Cys Ala Asn Gly Gly Thr Cys Leu Ser Leu Ser Leu Gly Gln Gly
        35                  40                  45

Thr Cys Gln Cys Ala Pro Gly Phe Leu Gly Glu Thr Cys Gln Phe Pro
    50                  55                  60

Asp Pro Cys Gln Asn Ala Gln Leu Cys Gln Asn Gly Gly Ser Cys Gln
65                  70                  75                  80

Ala Leu Leu Pro Ala Pro Leu Gly Leu Pro Ser Ser Pro Ser Pro Leu
```

-continued

```
                85                  90                  95

Thr Pro Ser Phe Leu Cys Thr Cys Leu Pro Gly Phe Thr Gly Glu Arg
            100                 105                 110

Cys Gln Ala Lys Leu Glu Asp Pro Cys Pro Pro Ser Phe Cys Ser Lys
        115                 120                 125

Arg Gly Arg Cys His Ile Gln Ala Ser Gly Arg Pro Gln Cys Ser Cys
    130                 135                 140

Met Pro Gly Trp Thr Gly Glu Gln Cys Gln Leu Arg Asp Phe Cys Ser
145                 150                 155                 160

Ala Asn Pro Cys Val Asn Gly Gly Val Cys Leu Ala Thr Tyr Pro Gln
                165                 170                 175

Ile Gln Cys His Cys Pro Pro Gly Phe Glu Gly His Ala Cys Glu Arg
            180                 185                 190

Asp Val Asn Glu Cys Phe Gln Asp Pro Gly Pro Cys Pro Lys Gly Thr
        195                 200                 205

Ser Cys His Asn Thr Leu Gly Ser Phe Gln Cys Leu Cys Pro Val Gly
    210                 215                 220

Gln Glu Gly Pro Arg Cys Glu Leu Arg Ala Gly Pro Cys Pro Pro Arg
225                 230                 235                 240

Gly Cys Ser Asn Gly Gly Thr Cys Gln Leu Met Pro Glu Lys Asp Ser
                245                 250                 255

Thr Phe His Leu Cys Leu Cys Pro Pro Gly Phe Ile Gly Pro Asp Cys
            260                 265                 270

Glu Val Asn Pro Asp Asn Cys Val Ser His Gln Cys Gln Asn Gly Gly
        275                 280                 285

Thr Cys Gln Asp Gly Leu Asp Thr Tyr Thr Cys Leu Cys Pro Glu Thr
    290                 295                 300

Trp Thr Gly Trp Asp Cys Ser Glu Asp Val Asp Glu Cys Glu Thr Gln
305                 310                 315                 320

Gly Pro Pro His Cys Arg Asn Gly Gly Thr Cys Gln Asn Ser Ala Gly
                325                 330                 335

Ser Phe His Cys Val Cys Val Ser Gly Trp Gly Gly Thr Ser Cys Glu
            340                 345                 350

Glu Asn Leu Asp Asp Cys Ile Ala Ala Thr Cys Ala Pro Gly Ser Thr
        355                 360                 365

Cys Ile Asp Arg Val Gly Ser Phe Ser Cys Leu Cys Pro Pro Gly Arg
    370                 375                 380

Thr Gly Leu Leu Cys His Leu Glu Asp Met Cys Leu Ser Gln Pro Cys
385                 390                 395                 400

His Gly Asp Ala Gln Cys Ser Thr Asn Pro Leu Thr Gly Ser Thr Leu
                405                 410                 415

Cys Leu Cys Gln Pro Gly Tyr Ser Gly Pro Thr Cys His Gln Asp Leu
            420                 425                 430

Asp Glu Cys Leu Met Ala Gln Gln Gly Pro Ser Pro Cys Glu His Gly
        435                 440                 445

Gly Ser Cys Leu Asn Thr Pro Gly Ser Phe Asn Cys Leu Cys Pro Pro
    450                 455                 460

Gly Tyr Thr Gly Ser Arg Cys Glu Ala Asp His Asn Glu Cys Leu Ser
465                 470                 475                 480

Gln Pro Cys His Pro Gly Ser Thr Cys Leu Asp Leu Leu Ala Thr Phe
                485                 490                 495

His Cys Leu Cys Pro Pro Gly Leu Glu Gly Gln Leu Cys Glu Val Glu
            500                 505                 510
```

-continued

```
Thr Asn Glu Cys Ala Ser Ala Pro Cys Leu Asn His Ala Asp Cys His
        515                 520                 525

Asp Leu Leu Asn Gly Phe Gln Cys Ile Cys Leu Pro Gly Phe Ser Gly
    530                 535                 540

Thr Arg Cys Glu Glu Asp Ile Asp Glu Cys Arg Ser Ser Pro Cys Ala
545                 550                 555                 560

Asn Gly Gly Gln Cys Gln Asp Gln Pro Gly Ala Phe His Cys Lys Cys
                565                 570                 575

Leu Pro Gly Phe Glu Gly Pro Arg Cys Gln Thr Glu Val Asp Glu Cys
            580                 585                 590

Leu Ser Asp Pro Cys Pro Val Gly Ala Ser Cys Leu Asp Leu Pro Gly
        595                 600                 605

Ala Phe Phe Cys Leu Cys Pro Ser Gly Phe Thr Gly Gln Leu Cys Glu
    610                 615                 620

Val Pro Leu Cys Ala Pro Asn Leu Cys Gln Pro Lys Gln Ile Cys Lys
625                 630                 635                 640

Asp Gln Lys Asp Lys Ala Asn Cys Leu Cys Pro Asp Gly Ser Pro Gly
                645                 650                 655

Cys Ala Pro Pro Glu Asp Asn Cys Thr Cys His His Gly His Cys Gln
            660                 665                 670

Arg Ser Ser Cys Val Cys Asp Val Gly Trp Thr Gly Pro Glu Cys Glu
        675                 680                 685

Ala Glu Leu Gly Gly Cys Ile Ser Ala Pro Cys Ala His Gly Gly Thr
    690                 695                 700

Cys Tyr Pro Gln Pro Ser Gly Tyr Asn Cys Thr Cys Pro Thr Gly Tyr
705                 710                 715                 720

Thr Gly Pro Thr Cys Ser Glu Glu Met Thr Ala Cys His Ser Gly Pro
                725                 730                 735

Cys Leu Asn Gly Gly Ser Cys Asn Pro Ser Pro Gly Gly Tyr Tyr Cys
            740                 745                 750

Thr Cys Pro Pro Ser His Thr Gly Pro Gln Cys Gln Thr Ser Thr Asp
        755                 760                 765

Tyr Cys Val Ser Ala Pro Cys Phe Asn Gly Gly Thr Cys Val Asn Arg
    770                 775                 780

Pro Gly Thr Phe Ser Cys Leu Cys Ala Met Gly Phe Gln Gly Pro Arg
785                 790                 795                 800

Cys Glu Gly Lys Leu Arg Pro Ser Cys Ala Asp Ser Pro Cys Arg Asn
                805                 810                 815

Arg Ala Thr Cys Gln Asp Ser Pro Gln Gly Pro Arg Cys Leu Cys Pro
            820                 825                 830

Thr Gly Tyr Thr Gly Gly Ser Cys Gln Thr Leu Met Asp Leu Cys Ala
        835                 840                 845

Gln Lys Pro Cys Pro Arg Asn Ser His Cys Leu Gln Thr Gly Pro Ser
    850                 855                 860

Phe His Cys Leu Cys Leu Gln Gly Trp Thr Gly Pro Leu Cys Asn Leu
865                 870                 875                 880

Pro Leu Ser Ser Cys Gln Lys Ala Ala Leu Ser Gln Gly Ile Asp Val
                885                 890                 895

Ser Ser Leu Cys His Asn Gly Gly Leu Cys Val Asp Ser Gly Pro Ser
            900                 905                 910

Tyr Phe Cys His Cys Pro Pro Gly Phe Gln Gly Ser Leu Cys Gln Asp
        915                 920                 925
```

```
His Val Asn Pro Cys Glu Ser Arg Pro Cys Gln Asn Gly Ala Thr Cys
    930                 935                 940

Met Ala Gln Pro Ser Gly Tyr Leu Cys Gln Cys Ala Pro Gly Tyr Asp
945                 950                 955                 960

Gly Gln Asn Cys Ser Lys Glu Leu Asp Ala Cys Gln Ser Gln Pro Cys
                965                 970                 975

His Asn His Gly Thr Cys Thr Pro Lys Pro Gly Gly Phe His Cys Ala
            980                 985                 990

Cys Pro Pro Gly Phe Val Gly Leu  Arg Cys Glu Gly Asp  Val Asp Glu
        995                 1000                1005

Cys Leu  Asp Gln Pro Cys His  Pro Thr Gly Thr Ala  Ala Cys His
    1010                 1015                 1020

Ser Leu  Ala Asn Ala Phe Tyr  Cys Gln Cys Leu Pro  Gly His Thr
    1025                 1030                 1035

Gly Gln  Trp Cys Glu Val Glu  Ile Asp Pro Cys His  Ser Gln Pro
    1040                 1045                 1050

Cys Phe  His Gly Gly Thr Cys  Glu Ala Thr Ala Gly  Ser Pro Leu
    1055                 1060                 1065

Gly Phe  Ile Cys His Cys Pro  Lys Gly Phe Glu Gly  Pro Thr Cys
    1070                 1075                 1080

Ser His  Arg Ala Pro Ser Cys  Gly Phe His His Cys  His His Gly
    1085                 1090                 1095

Gly Leu  Cys Leu Pro Ser Pro  Lys Pro Gly Phe Pro  Pro Arg Cys
    1100                 1105                 1110

Ala Cys  Leu Ser Gly Tyr Gly  Gly Pro Asp Cys Leu  Thr Pro Pro
    1115                 1120                 1125

Ala Pro  Lys Gly Cys Gly Pro  Pro Ser Pro Cys Leu  Tyr Asn Gly
    1130                 1135                 1140

Ser Cys  Ser Glu Thr Thr Gly  Leu Gly Gly Pro Gly  Phe Arg Cys
    1145                 1150                 1155

Ser Cys  Pro His Ser Ser Pro  Gly Pro Arg Cys Gln  Lys Pro Gly
    1160                 1165                 1170

Asp Leu  Gly Pro Gly Glu Pro  Lys Ser Cys Asp Lys  Thr His Thr
    1175                 1180                 1185

Cys Pro  Pro Cys Pro Ala Pro  Glu Leu Leu Gly Gly  Pro Ser Val
    1190                 1195                 1200

Phe Leu  Phe Pro Pro Lys Pro  Lys Asp Thr Leu Met  Ile Ser Arg
    1205                 1210                 1215

Thr Pro  Glu Val Thr Cys Val  Val Val Asp Val Ser  His Glu Asp
    1220                 1225                 1230

Pro Glu  Val Lys Phe Asn Trp  Tyr Val Asp Gly Val  Glu Val His
    1235                 1240                 1245

Asn Ala  Lys Thr Lys Pro Arg  Glu Glu Gln Tyr Asn  Ser Thr Tyr
    1250                 1255                 1260

Arg Val  Val Ser Val Leu Thr  Val Leu His Gln Asp  Trp Leu Asn
    1265                 1270                 1275

Gly Lys  Glu Tyr Lys Cys Lys  Val Ser Asn Lys Ala  Leu Pro Ala
    1280                 1285                 1290

Pro Ile  Glu Lys Thr Ile Ser  Lys Ala Lys Gly Gln  Pro Arg Glu
    1295                 1300                 1305

Pro Gln  Val Tyr Thr Leu Pro  Pro Ser Arg Asp Glu  Leu Thr Lys
    1310                 1315                 1320

Asn Gln  Val Ser Leu Thr Cys  Leu Val Lys Gly Phe  Tyr Pro Ser
```

```
    1325                1330                1335

Asp Ile  Ala Val Glu Trp Glu  Ser Asn Gly Gln Pro  Glu Asn Asn
    1340                1345                1350

Tyr Lys  Thr Thr Pro Pro Val  Leu Asp Ser Asp Gly  Ser Phe Phe
    1355                1360                1365

Leu Tyr  Ser Lys Leu Thr Val  Asp Lys Ser Arg Trp  Gln Gln Gly
    1370                1375                1380

Asn Val  Phe Ser Cys Ser Val  Met His Glu Ala Leu  His Asn His
    1385                1390                1395

Tyr Thr  Gln Lys Ser Leu Ser  Leu Ser Pro Gly Lys
    1400                1405                1410


<210> SEQ ID NO 79
<211> LENGTH: 791
<212> TYPE: PRT
<213> ORGANISM: Homo sapiens

<400> SEQUENCE: 79

Met Gln Pro Pro Ser Leu Leu Leu Leu Leu Leu Leu Leu Leu Leu Leu
1               5                   10                  15

Cys Val Ser Val Val Arg Pro Arg Gly Leu Leu Cys Gly Ser Phe Pro
            20                  25                  30

Glu Pro Cys Ala Asn Gly Gly Thr Cys Leu Ser Leu Ser Leu Gly Gln
        35                  40                  45

Gly Thr Cys Gln Cys Ala Pro Gly Phe Leu Gly Glu Thr Cys Gln Phe
    50                  55                  60

Pro Asp Pro Cys Gln Asn Ala Gln Leu Cys Gln Asn Gly Gly Ser Cys
65                  70                  75                  80

Gln Ala Leu Leu Pro Ala Pro Leu Gly Leu Pro Ser Ser Pro Ser Pro
                85                  90                  95

Leu Thr Pro Ser Phe Leu Cys Thr Cys Leu Pro Gly Phe Thr Gly Glu
            100                 105                 110

Arg Cys Gln Ala Lys Leu Glu Asp Pro Cys Pro Pro Ser Phe Cys Ser
        115                 120                 125

Lys Arg Gly Arg Cys His Ile Gln Ala Ser Gly Arg Pro Gln Cys Ser
    130                 135                 140

Cys Met Pro Gly Trp Thr Gly Glu Gln Cys Gln Leu Arg Asp Phe Cys
145                 150                 155                 160

Ser Ala Asn Pro Cys Val Asn Gly Gly Val Cys Leu Ala Thr Tyr Pro
                165                 170                 175

Gln Ile Gln Cys His Cys Pro Pro Gly Phe Glu Gly His Ala Cys Glu
            180                 185                 190

Arg Asp Val Asn Glu Cys Phe Gln Asp Pro Gly Pro Cys Pro Lys Gly
        195                 200                 205

Thr Ser Cys His Asn Thr Leu Gly Ser Phe Gln Cys Leu Cys Pro Val
    210                 215                 220

Gly Gln Glu Gly Pro Arg Cys Glu Leu Arg Ala Gly Pro Cys Pro Pro
225                 230                 235                 240

Arg Gly Cys Ser Asn Gly Gly Thr Cys Gln Leu Met Pro Glu Lys Asp
                245                 250                 255

Ser Thr Phe His Leu Cys Leu Cys Pro Pro Gly Phe Ile Gly Pro Asp
            260                 265                 270

Cys Glu Val Asn Pro Asp Asn Cys Val Ser His Gln Cys Gln Asn Gly
        275                 280                 285
```

-continued

```
Gly Thr Cys Gln Asp Gly Leu Asp Thr Tyr Thr Cys Leu Cys Pro Glu
    290                 295                 300

Thr Trp Thr Gly Trp Asp Cys Ser Glu Asp Val Asp Glu Cys Glu Thr
305                 310                 315                 320

Gln Gly Pro Pro His Cys Arg Asn Gly Gly Thr Cys Gln Asn Ser Ala
                325                 330                 335

Gly Ser Phe His Cys Val Cys Val Ser Gly Trp Gly Gly Thr Ser Cys
            340                 345                 350

Glu Glu Asn Leu Asp Asp Cys Ile Ala Ala Thr Cys Ala Pro Gly Ser
        355                 360                 365

Thr Cys Ile Asp Arg Val Gly Ser Phe Ser Cys Leu Cys Pro Pro Gly
    370                 375                 380

Arg Thr Gly Leu Leu Cys His Leu Glu Asp Met Cys Leu Ser Gln Pro
385                 390                 395                 400

Cys His Gly Asp Ala Gln Cys Ser Thr Asn Pro Leu Thr Gly Ser Thr
                405                 410                 415

Leu Cys Leu Cys Gln Pro Gly Tyr Ser Gly Pro Thr Cys His Gln Asp
            420                 425                 430

Leu Asp Glu Cys Leu Met Ala Gln Gln Gly Pro Ser Pro Cys Glu His
        435                 440                 445

Gly Gly Ser Cys Leu Asn Thr Pro Gly Ser Phe Asn Cys Leu Cys Pro
    450                 455                 460

Pro Gly Tyr Thr Gly Ser Arg Cys Glu Ala Asp His Asn Glu Cys Leu
465                 470                 475                 480

Ser Gln Pro Cys His Pro Gly Ser Thr Cys Leu Asp Leu Leu Ala Thr
                485                 490                 495

Phe His Cys Leu Cys Pro Pro Gly Leu Glu Gly Gln Leu Cys Glu Val
            500                 505                 510

Glu Thr Asn Glu Cys Ala Ser Ala Pro Cys Leu Asn His Ala Asp Cys
        515                 520                 525

His Asp Leu Leu Asn Gly Phe Gln Cys Ile Cys Leu Pro Gly Phe Ser
    530                 535                 540

Gly Thr Arg Cys Glu Glu Asp Ile Asp Glu Asp Leu Gly Pro Gly Glu
545                 550                 555                 560

Pro Lys Ser Cys Asp Lys Thr His Thr Cys Pro Pro Cys Pro Ala Pro
                565                 570                 575

Glu Leu Leu Gly Gly Pro Ser Val Phe Leu Phe Pro Pro Lys Pro Lys
            580                 585                 590

Asp Thr Leu Met Ile Ser Arg Thr Pro Glu Val Thr Cys Val Val Val
        595                 600                 605

Asp Val Ser His Glu Asp Pro Glu Val Lys Phe Asn Trp Tyr Val Asp
    610                 615                 620

Gly Val Glu Val His Asn Ala Lys Thr Lys Pro Arg Glu Glu Gln Tyr
625                 630                 635                 640

Asn Ser Thr Tyr Arg Val Val Ser Val Leu Thr Val Leu His Gln Asp
                645                 650                 655

Trp Leu Asn Gly Lys Glu Tyr Lys Cys Lys Val Ser Asn Lys Ala Leu
            660                 665                 670

Pro Ala Pro Ile Glu Lys Thr Ile Ser Lys Ala Lys Gly Gln Pro Arg
        675                 680                 685

Glu Pro Gln Val Tyr Thr Leu Pro Pro Ser Arg Asp Glu Leu Thr Lys
    690                 695                 700

Asn Gln Val Ser Leu Thr Cys Leu Val Lys Gly Phe Tyr Pro Ser Asp
```

-continued

```
705                 710                 715                 720

Ile Ala Val Glu Trp Glu Ser Asn Gly Gln Pro Glu Asn Asn Tyr Lys
                725                 730                 735

Thr Thr Pro Pro Val Leu Asp Ser Asp Gly Ser Phe Phe Leu Tyr Ser
            740                 745                 750

Lys Leu Thr Val Asp Lys Ser Arg Trp Gln Gln Gly Asn Val Phe Ser
        755                 760                 765

Cys Ser Val Met His Glu Ala Leu His Asn His Tyr Thr Gln Lys Ser
    770                 775                 780

Leu Ser Leu Ser Pro Gly Lys
785                 790


<210> SEQ ID NO 80
<211> LENGTH: 1170
<212> TYPE: PRT
<213> ORGANISM: Homo sapiens

<400> SEQUENCE: 80

Met Gln Pro Pro Ser Leu Leu Leu Leu Leu Leu Leu Leu Leu Leu Leu
1               5                   10                  15

Cys Val Ser Val Val Arg Pro Arg Gly Leu Leu Cys Gly Ser Phe Pro
            20                  25                  30

Glu Pro Cys Ala Asn Gly Gly Thr Cys Leu Ser Leu Ser Leu Gly Gln
        35                  40                  45

Gly Thr Cys Gln Cys Ala Pro Gly Phe Leu Gly Glu Thr Cys Gln Phe
    50                  55                  60

Pro Asp Pro Cys Gln Asn Ala Gln Leu Cys Gln Asn Gly Gly Ser Cys
65                  70                  75                  80

Gln Ala Leu Leu Pro Ala Pro Leu Gly Leu Pro Ser Ser Pro Ser Pro
                85                  90                  95

Leu Thr Pro Ser Phe Leu Cys Thr Cys Leu Pro Gly Phe Thr Gly Glu
            100                 105                 110

Arg Cys Gln Ala Lys Leu Glu Asp Pro Cys Pro Pro Ser Phe Cys Ser
        115                 120                 125

Lys Arg Gly Arg Cys His Ile Gln Ala Ser Gly Arg Pro Gln Cys Ser
    130                 135                 140

Cys Met Pro Gly Trp Thr Gly Glu Gln Cys Gln Leu Arg Asp Phe Cys
145                 150                 155                 160

Ser Ala Asn Pro Cys Val Asn Gly Gly Val Cys Leu Ala Thr Tyr Pro
                165                 170                 175

Gln Ile Gln Cys His Cys Pro Pro Gly Phe Glu Gly His Ala Cys Glu
            180                 185                 190

Arg Asp Val Asn Glu Cys Phe Gln Asp Pro Gly Pro Cys Pro Lys Gly
        195                 200                 205

Thr Ser Cys His Asn Thr Leu Gly Ser Phe Gln Cys Leu Cys Pro Val
    210                 215                 220

Gly Gln Glu Gly Pro Arg Cys Glu Leu Arg Ala Gly Pro Cys Pro Pro
225                 230                 235                 240

Arg Gly Cys Ser Asn Gly Gly Thr Cys Gln Leu Met Pro Glu Lys Asp
                245                 250                 255

Ser Thr Phe His Leu Cys Leu Cys Pro Pro Gly Phe Ile Gly Pro Asp
            260                 265                 270

Cys Glu Val Asn Pro Asp Asn Cys Val Ser His Gln Cys Gln Asn Gly
        275                 280                 285
```

```
Gly Thr Cys Gln Asp Gly Leu Asp Thr Tyr Thr Cys Leu Cys Pro Glu
    290                 295                 300

Thr Trp Thr Gly Trp Asp Cys Ser Glu Asp Val Asp Glu Cys Glu Thr
305                 310                 315                 320

Gln Gly Pro Pro His Cys Arg Asn Gly Gly Thr Cys Gln Asn Ser Ala
                325                 330                 335

Gly Ser Phe His Cys Val Cys Val Ser Gly Trp Gly Gly Thr Ser Cys
            340                 345                 350

Glu Glu Asn Leu Asp Asp Cys Ile Ala Ala Thr Cys Ala Pro Gly Ser
        355                 360                 365

Thr Cys Ile Asp Arg Val Gly Ser Phe Ser Cys Leu Cys Pro Pro Gly
    370                 375                 380

Arg Thr Gly Leu Leu Cys His Leu Glu Asp Met Cys Leu Ser Gln Pro
385                 390                 395                 400

Cys His Gly Asp Ala Gln Cys Ser Thr Asn Pro Leu Thr Gly Ser Thr
                405                 410                 415

Leu Cys Leu Cys Gln Pro Gly Tyr Ser Gly Pro Thr Cys His Gln Asp
            420                 425                 430

Leu Asp Glu Cys Leu Met Ala Gln Gln Gly Pro Ser Pro Cys Glu His
        435                 440                 445

Gly Gly Ser Cys Leu Asn Thr Pro Gly Ser Phe Asn Cys Leu Cys Pro
    450                 455                 460

Pro Gly Tyr Thr Gly Ser Arg Cys Glu Ala Asp His Asn Glu Cys Leu
465                 470                 475                 480

Ser Gln Pro Cys His Pro Gly Ser Thr Cys Leu Asp Leu Leu Ala Thr
                485                 490                 495

Phe His Cys Leu Cys Pro Pro Gly Leu Glu Gly Gln Leu Cys Glu Val
            500                 505                 510

Glu Thr Asn Glu Cys Ala Ser Ala Pro Cys Leu Asn His Ala Asp Cys
        515                 520                 525

His Asp Leu Leu Asn Gly Phe Gln Cys Ile Cys Leu Pro Gly Phe Ser
    530                 535                 540

Gly Thr Arg Cys Glu Glu Asp Ile Asp Glu Cys Arg Ser Ser Pro Cys
545                 550                 555                 560

Ala Asn Gly Gly Gln Cys Gln Asp Gln Pro Gly Ala Phe His Cys Lys
                565                 570                 575

Cys Leu Pro Gly Phe Glu Gly Pro Arg Cys Gln Thr Glu Val Asp Glu
            580                 585                 590

Cys Leu Ser Asp Pro Cys Pro Val Gly Ala Ser Cys Leu Asp Leu Pro
        595                 600                 605

Gly Ala Phe Phe Cys Leu Cys Pro Ser Gly Phe Thr Gly Gln Leu Cys
    610                 615                 620

Glu Val Pro Leu Cys Ala Pro Asn Leu Cys Gln Pro Lys Gln Ile Cys
625                 630                 635                 640

Lys Asp Gln Lys Asp Lys Ala Asn Cys Leu Cys Pro Asp Gly Ser Pro
                645                 650                 655

Gly Cys Ala Pro Pro Glu Asp Asn Cys Thr Cys His His Gly His Cys
            660                 665                 670

Gln Arg Ser Ser Cys Val Cys Asp Val Gly Trp Thr Gly Pro Glu Cys
        675                 680                 685

Glu Ala Glu Leu Gly Gly Cys Ile Ser Ala Pro Cys Ala His Gly Gly
    690                 695                 700

Thr Cys Tyr Pro Gln Pro Ser Gly Tyr Asn Cys Thr Cys Pro Thr Gly
```

705 710 715 720

Tyr Thr Gly Pro Thr Cys Ser Glu Glu Met Thr Ala Cys His Ser Gly
725 730 735

Pro Cys Leu Asn Gly Gly Ser Cys Asn Pro Ser Pro Gly Gly Tyr Tyr
740 745 750

Cys Thr Cys Pro Pro Ser His Thr Gly Pro Gln Cys Gln Thr Ser Thr
755 760 765

Asp Tyr Cys Val Ser Ala Pro Cys Phe Asn Gly Gly Thr Cys Val Asn
770 775 780

Arg Pro Gly Thr Phe Ser Cys Leu Cys Ala Met Gly Phe Gln Gly Pro
785 790 795 800

Arg Cys Glu Gly Lys Leu Arg Pro Ser Cys Ala Asp Ser Pro Cys Arg
805 810 815

Asn Arg Ala Thr Cys Gln Asp Ser Pro Gln Gly Pro Arg Cys Leu Cys
820 825 830

Pro Thr Gly Tyr Thr Gly Gly Ser Cys Gln Thr Leu Met Asp Leu Cys
835 840 845

Ala Gln Lys Pro Cys Pro Arg Asn Ser His Cys Leu Gln Thr Gly Pro
850 855 860

Ser Phe His Cys Leu Cys Leu Gln Gly Trp Thr Gly Pro Leu Cys Asn
865 870 875 880

Leu Pro Leu Ser Ser Cys Gln Lys Ala Ala Leu Ser Gln Gly Ile Asp
885 890 895

Val Ser Ser Leu Cys His Asn Gly Gly Leu Cys Val Asp Ser Gly Pro
900 905 910

Ser Tyr Phe Cys His Cys Pro Pro Gly Phe Gln Gly Ser Leu Cys Gln
915 920 925

Asp His Val Asn Pro Asp Leu Gly Pro Gly Glu Pro Lys Ser Cys Asp
930 935 940

Lys Thr His Thr Cys Pro Pro Cys Pro Ala Pro Glu Leu Leu Gly Gly
945 950 955 960

Pro Ser Val Phe Leu Phe Pro Pro Lys Pro Lys Asp Thr Leu Met Ile
965 970 975

Ser Arg Thr Pro Glu Val Thr Cys Val Val Val Asp Val Ser His Glu
980 985 990

Asp Pro Glu Val Lys Phe Asn Trp Tyr Val Asp Gly Val Glu Val His
995 1000 1005

Asn Ala Lys Thr Lys Pro Arg Glu Glu Gln Tyr Asn Ser Thr Tyr
1010 1015 1020

Arg Val Val Ser Val Leu Thr Val Leu His Gln Asp Trp Leu Asn
1025 1030 1035

Gly Lys Glu Tyr Lys Cys Lys Val Ser Asn Lys Ala Leu Pro Ala
1040 1045 1050

Pro Ile Glu Lys Thr Ile Ser Lys Ala Lys Gly Gln Pro Arg Glu
1055 1060 1065

Pro Gln Val Tyr Thr Leu Pro Pro Ser Arg Asp Glu Leu Thr Lys
1070 1075 1080

Asn Gln Val Ser Leu Thr Cys Leu Val Lys Gly Phe Tyr Pro Ser
1085 1090 1095

Asp Ile Ala Val Glu Trp Glu Ser Asn Gly Gln Pro Glu Asn Asn
1100 1105 1110

Tyr Lys Thr Thr Pro Pro Val Leu Asp Ser Asp Gly Ser Phe Phe
1115 1120 1125

-continued

Leu Tyr Ser Lys Leu Thr Val Asp Lys Ser Arg Trp Gln Gln Gly
    1130                1135                1140

Asn Val Phe Ser Cys Ser Val Met His Glu Ala Leu His Asn His
    1145                1150                1155

Tyr Thr Gln Lys Ser Leu Ser Leu Ser Pro Gly Lys
    1160                1165                1170

<210> SEQ ID NO 81
<211> LENGTH: 839
<212> TYPE: PRT
<213> ORGANISM: Homo sapiens

<400> SEQUENCE: 81

Met Gln Pro Pro Ser Leu Leu Leu Leu Leu Leu Leu Leu Leu Leu Leu
1               5                   10                  15

Cys Val Ser Val Val Arg Pro Arg Gly Leu Leu Cys Ile Ala Ala Thr
            20                  25                  30

Cys Ala Pro Gly Ser Thr Cys Ile Asp Arg Val Gly Ser Phe Ser Cys
        35                  40                  45

Leu Cys Pro Pro Gly Arg Thr Gly Leu Leu Cys His Leu Glu Asp Met
    50                  55                  60

Cys Leu Ser Gln Pro Cys His Gly Asp Ala Gln Cys Ser Thr Asn Pro
65                  70                  75                  80

Leu Thr Gly Ser Thr Leu Cys Leu Cys Gln Pro Gly Tyr Ser Gly Pro
                85                  90                  95

Thr Cys His Gln Asp Leu Asp Glu Cys Leu Met Ala Gln Gln Gly Pro
            100                 105                 110

Ser Pro Cys Glu His Gly Gly Ser Cys Leu Asn Thr Pro Gly Ser Phe
        115                 120                 125

Asn Cys Leu Cys Pro Pro Gly Tyr Thr Gly Ser Arg Cys Glu Ala Asp
    130                 135                 140

His Asn Glu Cys Leu Ser Gln Pro Cys His Pro Gly Ser Thr Cys Leu
145                 150                 155                 160

Asp Leu Leu Ala Thr Phe His Cys Leu Cys Pro Pro Gly Leu Glu Gly
                165                 170                 175

Gln Leu Cys Glu Val Glu Thr Asn Glu Cys Ala Ser Ala Pro Cys Leu
            180                 185                 190

Asn His Ala Asp Cys His Asp Leu Leu Asn Gly Phe Gln Cys Ile Cys
        195                 200                 205

Leu Pro Gly Phe Ser Gly Thr Arg Cys Glu Glu Asp Ile Asp Glu Cys
    210                 215                 220

Arg Ser Ser Pro Cys Ala Asn Gly Gly Gln Cys Gln Asp Gln Pro Gly
225                 230                 235                 240

Ala Phe His Cys Lys Cys Leu Pro Gly Phe Glu Gly Pro Arg Cys Gln
                245                 250                 255

Thr Glu Val Asp Glu Cys Leu Ser Asp Pro Cys Pro Val Gly Ala Ser
            260                 265                 270

Cys Leu Asp Leu Pro Gly Ala Phe Phe Cys Leu Cys Pro Ser Gly Phe
        275                 280                 285

Thr Gly Gln Leu Cys Glu Val Pro Leu Cys Ala Pro Asn Leu Cys Gln
    290                 295                 300

Pro Lys Gln Ile Cys Lys Asp Gln Lys Asp Lys Ala Asn Cys Leu Cys
305                 310                 315                 320

Pro Asp Gly Ser Pro Gly Cys Ala Pro Pro Glu Asp Asn Cys Thr Cys

```
                325                 330                 335

His His Gly His Cys Gln Arg Ser Ser Cys Val Cys Asp Val Gly Trp
            340                 345                 350

Thr Gly Pro Glu Cys Glu Ala Glu Leu Gly Gly Cys Ile Ser Ala Pro
        355                 360                 365

Cys Ala His Gly Gly Thr Cys Tyr Pro Gln Pro Ser Gly Tyr Asn Cys
    370                 375                 380

Thr Cys Pro Thr Gly Tyr Thr Gly Pro Thr Cys Ser Glu Glu Met Thr
385                 390                 395                 400

Ala Cys His Ser Gly Pro Cys Leu Asn Gly Gly Ser Cys Asn Pro Ser
                405                 410                 415

Pro Gly Gly Tyr Tyr Cys Thr Cys Pro Pro Ser His Thr Gly Pro Gln
            420                 425                 430

Cys Gln Thr Ser Thr Asp Tyr Cys Val Ser Ala Pro Cys Phe Asn Gly
        435                 440                 445

Gly Thr Cys Val Asn Arg Pro Gly Thr Phe Ser Cys Leu Cys Ala Met
    450                 455                 460

Gly Phe Gln Gly Pro Arg Cys Glu Gly Lys Leu Arg Pro Ser Cys Ala
465                 470                 475                 480

Asp Ser Pro Cys Arg Asn Arg Ala Thr Cys Gln Asp Ser Pro Gln Gly
                485                 490                 495

Pro Arg Cys Leu Cys Pro Thr Gly Tyr Thr Gly Gly Ser Cys Gln Thr
            500                 505                 510

Leu Met Asp Leu Cys Ala Gln Lys Pro Cys Pro Arg Asn Ser His Cys
        515                 520                 525

Leu Gln Thr Gly Pro Ser Phe His Cys Leu Cys Leu Gln Gly Trp Thr
    530                 535                 540

Gly Pro Leu Cys Asn Leu Pro Leu Ser Ser Cys Gln Lys Ala Ala Leu
545                 550                 555                 560

Ser Gln Gly Ile Asp Val Ser Ser Leu Cys His Asn Gly Gly Leu Cys
                565                 570                 575

Val Asp Ser Gly Pro Ser Tyr Phe Cys His Cys Pro Pro Gly Phe Gln
            580                 585                 590

Gly Ser Leu Cys Gln Asp His Val Asn Pro Asp Leu Gly Pro Gly Glu
        595                 600                 605

Pro Lys Ser Cys Asp Lys Thr His Thr Cys Pro Pro Cys Pro Ala Pro
    610                 615                 620

Glu Leu Leu Gly Gly Pro Ser Val Phe Leu Phe Pro Pro Lys Pro Lys
625                 630                 635                 640

Asp Thr Leu Met Ile Ser Arg Thr Pro Glu Val Thr Cys Val Val Val
                645                 650                 655

Asp Val Ser His Glu Asp Pro Glu Val Lys Phe Asn Trp Tyr Val Asp
            660                 665                 670

Gly Val Glu Val His Asn Ala Lys Thr Lys Pro Arg Glu Glu Gln Tyr
        675                 680                 685

Asn Ser Thr Tyr Arg Val Val Ser Val Leu Thr Val Leu His Gln Asp
    690                 695                 700

Trp Leu Asn Gly Lys Glu Tyr Lys Cys Lys Val Ser Asn Lys Ala Leu
705                 710                 715                 720

Pro Ala Pro Ile Glu Lys Thr Ile Ser Lys Ala Lys Gly Gln Pro Arg
                725                 730                 735

Glu Pro Gln Val Tyr Thr Leu Pro Pro Ser Arg Asp Glu Leu Thr Lys
            740                 745                 750
```

```
Asn Gln Val Ser Leu Thr Cys Leu Val Lys Gly Phe Tyr Pro Ser Asp
        755                 760                 765

Ile Ala Val Glu Trp Glu Ser Asn Gly Gln Pro Glu Asn Asn Tyr Lys
    770                 775                 780

Thr Thr Pro Pro Val Leu Asp Ser Asp Gly Ser Phe Phe Leu Tyr Ser
785                 790                 795                 800

Lys Leu Thr Val Asp Lys Ser Arg Trp Gln Gln Gly Asn Val Phe Ser
                805                 810                 815

Cys Ser Val Met His Glu Ala Leu His Asn His Tyr Thr Gln Lys Ser
            820                 825                 830

Leu Ser Leu Ser Pro Gly Lys
        835


<210> SEQ ID NO 82
<211> LENGTH: 834
<212> TYPE: PRT
<213> ORGANISM: Homo sapiens

<400> SEQUENCE: 82

Met Trp Gly Trp Lys Cys Leu Leu Phe Trp Ala Val Leu Val Thr Ala
1               5                   10                  15

Thr Leu Cys Thr Ala Arg Cys Ile Ala Ala Thr Cys Ala Pro Gly Ser
            20                  25                  30

Thr Cys Ile Asp Arg Val Gly Ser Phe Ser Cys Leu Cys Pro Pro Gly
        35                  40                  45

Arg Thr Gly Leu Leu Cys His Leu Glu Asp Met Cys Leu Ser Gln Pro
    50                  55                  60

Cys His Gly Asp Ala Gln Cys Ser Thr Asn Pro Leu Thr Gly Ser Thr
65                  70                  75                  80

Leu Cys Leu Cys Gln Pro Gly Tyr Ser Gly Pro Thr Cys His Gln Asp
                85                  90                  95

Leu Asp Glu Cys Leu Met Ala Gln Gln Gly Pro Ser Pro Cys Glu His
            100                 105                 110

Gly Gly Ser Cys Leu Asn Thr Pro Gly Ser Phe Asn Cys Leu Cys Pro
        115                 120                 125

Pro Gly Tyr Thr Gly Ser Arg Cys Glu Ala Asp His Asn Glu Cys Leu
    130                 135                 140

Ser Gln Pro Cys His Pro Gly Ser Thr Cys Leu Asp Leu Leu Ala Thr
145                 150                 155                 160

Phe His Cys Leu Cys Pro Pro Gly Leu Glu Gly Gln Leu Cys Glu Val
                165                 170                 175

Glu Thr Asn Glu Cys Ala Ser Ala Pro Cys Leu Asn His Ala Asp Cys
            180                 185                 190

His Asp Leu Leu Asn Gly Phe Gln Cys Ile Cys Leu Pro Gly Phe Ser
        195                 200                 205

Gly Thr Arg Cys Glu Glu Asp Ile Asp Glu Cys Arg Ser Ser Pro Cys
    210                 215                 220

Ala Asn Gly Gly Gln Cys Gln Asp Gln Pro Gly Ala Phe His Cys Lys
225                 230                 235                 240

Cys Leu Pro Gly Phe Glu Gly Pro Arg Cys Gln Thr Glu Val Asp Glu
                245                 250                 255

Cys Leu Ser Asp Pro Cys Pro Val Gly Ala Ser Cys Leu Asp Leu Pro
            260                 265                 270

Gly Ala Phe Phe Cys Leu Cys Pro Ser Gly Phe Thr Gly Gln Leu Cys
```

```
        275                 280                 285

Glu Val Pro Leu Cys Ala Pro Asn Leu Cys Gln Pro Lys Gln Ile Cys
    290                 295                 300

Lys Asp Gln Lys Asp Lys Ala Asn Cys Leu Cys Pro Asp Gly Ser Pro
305                 310                 315                 320

Gly Cys Ala Pro Pro Glu Asp Asn Cys Thr Cys His His Gly His Cys
                325                 330                 335

Gln Arg Ser Ser Cys Val Cys Asp Val Gly Trp Thr Gly Pro Glu Cys
            340                 345                 350

Glu Ala Glu Leu Gly Gly Cys Ile Ser Ala Pro Cys Ala His Gly Gly
        355                 360                 365

Thr Cys Tyr Pro Gln Pro Ser Gly Tyr Asn Cys Thr Cys Pro Thr Gly
    370                 375                 380

Tyr Thr Gly Pro Thr Cys Ser Glu Glu Met Thr Ala Cys His Ser Gly
385                 390                 395                 400

Pro Cys Leu Asn Gly Gly Ser Cys Asn Pro Ser Pro Gly Gly Tyr Tyr
                405                 410                 415

Cys Thr Cys Pro Pro Ser His Thr Gly Pro Gln Cys Gln Thr Ser Thr
            420                 425                 430

Asp Tyr Cys Val Ser Ala Pro Cys Phe Asn Gly Gly Thr Cys Val Asn
        435                 440                 445

Arg Pro Gly Thr Phe Ser Cys Leu Cys Ala Met Gly Phe Gln Gly Pro
    450                 455                 460

Arg Cys Glu Gly Lys Leu Arg Pro Ser Cys Ala Asp Ser Pro Cys Arg
465                 470                 475                 480

Asn Arg Ala Thr Cys Gln Asp Ser Pro Gln Gly Pro Arg Cys Leu Cys
                485                 490                 495

Pro Thr Gly Tyr Thr Gly Gly Ser Cys Gln Thr Leu Met Asp Leu Cys
            500                 505                 510

Ala Gln Lys Pro Cys Pro Arg Asn Ser His Cys Leu Gln Thr Gly Pro
        515                 520                 525

Ser Phe His Cys Leu Cys Leu Gln Gly Trp Thr Gly Pro Leu Cys Asn
    530                 535                 540

Leu Pro Leu Ser Ser Cys Gln Lys Ala Ala Leu Ser Gln Gly Ile Asp
545                 550                 555                 560

Val Ser Ser Leu Cys His Asn Gly Gly Leu Cys Val Asp Ser Gly Pro
                565                 570                 575

Ser Tyr Phe Cys His Cys Pro Pro Gly Phe Gln Gly Ser Leu Cys Gln
            580                 585                 590

Asp His Val Asn Pro Asp Leu Gly Pro Gly Glu Pro Lys Ser Cys Asp
        595                 600                 605

Lys Thr His Thr Cys Pro Pro Cys Pro Ala Pro Glu Leu Leu Gly Gly
    610                 615                 620

Pro Ser Val Phe Leu Phe Pro Pro Lys Pro Lys Asp Thr Leu Met Ile
625                 630                 635                 640

Ser Arg Thr Pro Glu Val Thr Cys Val Val Val Asp Val Ser His Glu
                645                 650                 655

Asp Pro Glu Val Lys Phe Asn Trp Tyr Val Asp Gly Val Glu Val His
            660                 665                 670

Asn Ala Lys Thr Lys Pro Arg Glu Glu Gln Tyr Asn Ser Thr Tyr Arg
        675                 680                 685

Val Val Ser Val Leu Thr Val Leu His Gln Asp Trp Leu Asn Gly Lys
    690                 695                 700
```

```
Glu Tyr Lys Cys Lys Val Ser Asn Lys Ala Leu Pro Ala Pro Ile Glu
705                 710                 715                 720

Lys Thr Ile Ser Lys Ala Lys Gly Gln Pro Arg Glu Pro Gln Val Tyr
                725                 730                 735

Thr Leu Pro Pro Ser Arg Asp Glu Leu Thr Lys Asn Gln Val Ser Leu
            740                 745                 750

Thr Cys Leu Val Lys Gly Phe Tyr Pro Ser Asp Ile Ala Val Glu Trp
        755                 760                 765

Glu Ser Asn Gly Gln Pro Glu Asn Asn Tyr Lys Thr Thr Pro Pro Val
    770                 775                 780

Leu Asp Ser Asp Gly Ser Phe Phe Leu Tyr Ser Lys Leu Thr Val Asp
785                 790                 795                 800

Lys Ser Arg Trp Gln Gln Gly Asn Val Phe Ser Cys Ser Val Met His
                805                 810                 815

Glu Ala Leu His Asn His Tyr Thr Gln Lys Ser Leu Ser Leu Ser Pro
            820                 825                 830

Gly Lys


<210> SEQ ID NO 83
<211> LENGTH: 1080
<212> TYPE: PRT
<213> ORGANISM: Homo sapiens

<400> SEQUENCE: 83

Met Gln Pro Pro Ser Leu Leu Leu Leu Leu Leu Leu Leu Leu Leu Leu
1               5                   10                  15

Cys Val Ser Val Val Arg Pro Arg Gly Leu Leu Cys Ile Ala Ala Thr
            20                  25                  30

Cys Ala Pro Gly Ser Thr Cys Ile Asp Arg Val Gly Ser Phe Ser Cys
        35                  40                  45

Leu Cys Pro Pro Gly Arg Thr Gly Leu Leu Cys His Leu Glu Asp Met
    50                  55                  60

Cys Leu Ser Gln Pro Cys His Gly Asp Ala Gln Cys Ser Thr Asn Pro
65                  70                  75                  80

Leu Thr Gly Ser Thr Leu Cys Leu Cys Gln Pro Gly Tyr Ser Gly Pro
                85                  90                  95

Thr Cys His Gln Asp Leu Asp Glu Cys Leu Met Ala Gln Gln Gly Pro
            100                 105                 110

Ser Pro Cys Glu His Gly Gly Ser Cys Leu Asn Thr Pro Gly Ser Phe
        115                 120                 125

Asn Cys Leu Cys Pro Pro Gly Tyr Thr Gly Ser Arg Cys Glu Ala Asp
    130                 135                 140

His Asn Glu Cys Leu Ser Gln Pro Cys His Pro Gly Ser Thr Cys Leu
145                 150                 155                 160

Asp Leu Leu Ala Thr Phe His Cys Leu Cys Pro Pro Gly Leu Glu Gly
                165                 170                 175

Gln Leu Cys Glu Val Glu Thr Asn Glu Cys Ala Ser Ala Pro Cys Leu
            180                 185                 190

Asn His Ala Asp Cys His Asp Leu Leu Asn Gly Phe Gln Cys Ile Cys
        195                 200                 205

Leu Pro Gly Phe Ser Gly Thr Arg Cys Glu Glu Asp Ile Asp Glu Cys
    210                 215                 220

Arg Ser Ser Pro Cys Ala Asn Gly Gly Gln Cys Gln Asp Gln Pro Gly
225                 230                 235                 240
```

-continued

```
Ala Phe His Cys Lys Cys Leu Pro Gly Phe Glu Gly Pro Arg Cys Gln
                245                 250                 255

Thr Glu Val Asp Glu Cys Leu Ser Asp Pro Cys Pro Val Gly Ala Ser
            260                 265                 270

Cys Leu Asp Leu Pro Gly Ala Phe Phe Cys Leu Cys Pro Ser Gly Phe
        275                 280                 285

Thr Gly Gln Leu Cys Glu Val Pro Leu Cys Ala Pro Asn Leu Cys Gln
    290                 295                 300

Pro Lys Gln Ile Cys Lys Asp Gln Lys Asp Lys Ala Asn Cys Leu Cys
305                 310                 315                 320

Pro Asp Gly Ser Pro Gly Cys Ala Pro Pro Glu Asp Asn Cys Thr Cys
                325                 330                 335

His His Gly His Cys Gln Arg Ser Ser Cys Val Cys Asp Val Gly Trp
            340                 345                 350

Thr Gly Pro Glu Cys Glu Ala Glu Leu Gly Gly Cys Ile Ser Ala Pro
        355                 360                 365

Cys Ala His Gly Gly Thr Cys Tyr Pro Gln Pro Ser Gly Tyr Asn Cys
    370                 375                 380

Thr Cys Pro Thr Gly Tyr Thr Gly Pro Thr Cys Ser Glu Glu Met Thr
385                 390                 395                 400

Ala Cys His Ser Gly Pro Cys Leu Asn Gly Gly Ser Cys Asn Pro Ser
                405                 410                 415

Pro Gly Gly Tyr Tyr Cys Thr Cys Pro Pro Ser His Thr Gly Pro Gln
            420                 425                 430

Cys Gln Thr Ser Thr Asp Tyr Cys Val Ser Ala Pro Cys Phe Asn Gly
        435                 440                 445

Gly Thr Cys Val Asn Arg Pro Gly Thr Phe Ser Cys Leu Cys Ala Met
    450                 455                 460

Gly Phe Gln Gly Pro Arg Cys Glu Gly Lys Leu Arg Pro Ser Cys Ala
465                 470                 475                 480

Asp Ser Pro Cys Arg Asn Arg Ala Thr Cys Gln Asp Ser Pro Gln Gly
                485                 490                 495

Pro Arg Cys Leu Cys Pro Thr Gly Tyr Thr Gly Gly Ser Cys Gln Thr
            500                 505                 510

Leu Met Asp Leu Cys Ala Gln Lys Pro Cys Pro Arg Asn Ser His Cys
        515                 520                 525

Leu Gln Thr Gly Pro Ser Phe His Cys Leu Cys Leu Gln Gly Trp Thr
    530                 535                 540

Gly Pro Leu Cys Asn Leu Pro Leu Ser Ser Cys Gln Lys Ala Ala Leu
545                 550                 555                 560

Ser Gln Gly Ile Asp Val Ser Ser Leu Cys His Asn Gly Gly Leu Cys
                565                 570                 575

Val Asp Ser Gly Pro Ser Tyr Phe Cys His Cys Pro Pro Gly Phe Gln
            580                 585                 590

Gly Ser Leu Cys Gln Asp His Val Asn Pro Cys Glu Ser Arg Pro Cys
        595                 600                 605

Gln Asn Gly Ala Thr Cys Met Ala Gln Pro Ser Gly Tyr Leu Cys Gln
    610                 615                 620

Cys Ala Pro Gly Tyr Asp Gly Gln Asn Cys Ser Lys Glu Leu Asp Ala
625                 630                 635                 640

Cys Gln Ser Gln Pro Cys His Asn His Gly Thr Cys Thr Pro Lys Pro
                645                 650                 655
```

```
Gly Gly Phe His Cys Ala Cys Pro Pro Gly Phe Val Gly Leu Arg Cys
            660                 665                 670

Glu Gly Asp Val Asp Glu Cys Leu Asp Gln Pro Cys His Pro Thr Gly
        675                 680                 685

Thr Ala Ala Cys His Ser Leu Ala Asn Ala Phe Tyr Cys Gln Cys Leu
    690                 695                 700

Pro Gly His Thr Gly Gln Trp Cys Glu Val Glu Ile Asp Pro Cys His
705                 710                 715                 720

Ser Gln Pro Cys Phe His Gly Gly Thr Cys Glu Ala Thr Ala Gly Ser
                725                 730                 735

Pro Leu Gly Phe Ile Cys His Cys Pro Lys Gly Phe Glu Gly Pro Thr
            740                 745                 750

Cys Ser His Arg Ala Pro Ser Cys Gly Phe His His Cys His His Gly
        755                 760                 765

Gly Leu Cys Leu Pro Ser Pro Lys Pro Gly Phe Pro Pro Arg Cys Ala
    770                 775                 780

Cys Leu Ser Gly Tyr Gly Gly Pro Asp Cys Leu Thr Pro Pro Ala Pro
785                 790                 795                 800

Lys Gly Cys Gly Pro Pro Ser Pro Cys Leu Tyr Asn Gly Ser Cys Ser
                805                 810                 815

Glu Thr Thr Gly Leu Gly Gly Pro Gly Phe Arg Cys Ser Cys Pro His
            820                 825                 830

Ser Ser Pro Gly Pro Arg Cys Gln Lys Pro Gly Asp Leu Gly Pro Gly
        835                 840                 845

Glu Pro Lys Ser Cys Asp Lys Thr His Thr Cys Pro Pro Cys Pro Ala
    850                 855                 860

Pro Glu Leu Leu Gly Gly Pro Ser Val Phe Leu Phe Pro Pro Lys Pro
865                 870                 875                 880

Lys Asp Thr Leu Met Ile Ser Arg Thr Pro Glu Val Thr Cys Val Val
                885                 890                 895

Val Asp Val Ser His Glu Asp Pro Glu Val Lys Phe Asn Trp Tyr Val
            900                 905                 910

Asp Gly Val Glu Val His Asn Ala Lys Thr Lys Pro Arg Glu Glu Gln
        915                 920                 925

Tyr Asn Ser Thr Tyr Arg Val Val Ser Val Leu Thr Val Leu His Gln
    930                 935                 940

Asp Trp Leu Asn Gly Lys Glu Tyr Lys Cys Lys Val Ser Asn Lys Ala
945                 950                 955                 960

Leu Pro Ala Pro Ile Glu Lys Thr Ile Ser Lys Ala Lys Gly Gln Pro
                965                 970                 975

Arg Glu Pro Gln Val Tyr Thr Leu Pro Pro Ser Arg Asp Glu Leu Thr
            980                 985                 990

Lys Asn Gln Val Ser Leu Thr Cys  Leu Val Lys Gly Phe  Tyr Pro Ser
        995                 1000                1005

Asp Ile  Ala Val Glu Trp Glu  Ser Asn Gly Gln Pro  Glu Asn Asn
    1010                1015                1020

Tyr Lys  Thr Thr Pro Pro Val  Leu Asp Ser Asp Gly  Ser Phe Phe
    1025                1030                1035

Leu Tyr  Ser Lys Leu Thr Val  Asp Lys Ser Arg Trp  Gln Gln Gly
    1040                1045                1050

Asn Val  Phe Ser Cys Ser Val  Met His Glu Ala Leu  His Asn His
    1055                1060                1065

Tyr Thr  Gln Lys Ser Leu Ser  Leu Ser Pro Gly Lys
```

1070 1075 1080

<210> SEQ ID NO 84
<211> LENGTH: 1075
<212> TYPE: PRT
<213> ORGANISM: Homo sapiens

<400> SEQUENCE: 84

Met Trp Gly Trp Lys Cys Leu Leu Phe Trp Ala Val Leu Val Thr Ala
1 5 10 15

Thr Leu Cys Thr Ala Arg Cys Ile Ala Ala Thr Cys Ala Pro Gly Ser
20 25 30

Thr Cys Ile Asp Arg Val Gly Ser Phe Ser Cys Leu Cys Pro Pro Gly
35 40 45

Arg Thr Gly Leu Leu Cys His Leu Glu Asp Met Cys Leu Ser Gln Pro
50 55 60

Cys His Gly Asp Ala Gln Cys Ser Thr Asn Pro Leu Thr Gly Ser Thr
65 70 75 80

Leu Cys Leu Cys Gln Pro Gly Tyr Ser Gly Pro Thr Cys His Gln Asp
85 90 95

Leu Asp Glu Cys Leu Met Ala Gln Gln Gly Pro Ser Pro Cys Glu His
100 105 110

Gly Gly Ser Cys Leu Asn Thr Pro Gly Ser Phe Asn Cys Leu Cys Pro
115 120 125

Pro Gly Tyr Thr Gly Ser Arg Cys Glu Ala Asp His Asn Glu Cys Leu
130 135 140

Ser Gln Pro Cys His Pro Gly Ser Thr Cys Leu Asp Leu Leu Ala Thr
145 150 155 160

Phe His Cys Leu Cys Pro Pro Gly Leu Glu Gly Gln Leu Cys Glu Val
165 170 175

Glu Thr Asn Glu Cys Ala Ser Ala Pro Cys Leu Asn His Ala Asp Cys
180 185 190

His Asp Leu Leu Asn Gly Phe Gln Cys Ile Cys Leu Pro Gly Phe Ser
195 200 205

Gly Thr Arg Cys Glu Glu Asp Ile Asp Glu Cys Arg Ser Ser Pro Cys
210 215 220

Ala Asn Gly Gly Gln Cys Gln Asp Gln Pro Gly Ala Phe His Cys Lys
225 230 235 240

Cys Leu Pro Gly Phe Glu Gly Pro Arg Cys Gln Thr Glu Val Asp Glu
245 250 255

Cys Leu Ser Asp Pro Cys Pro Val Gly Ala Ser Cys Leu Asp Leu Pro
260 265 270

Gly Ala Phe Phe Cys Leu Cys Pro Ser Gly Phe Thr Gly Gln Leu Cys
275 280 285

Glu Val Pro Leu Cys Ala Pro Asn Leu Cys Gln Pro Lys Gln Ile Cys
290 295 300

Lys Asp Gln Lys Asp Lys Ala Asn Cys Leu Cys Pro Asp Gly Ser Pro
305 310 315 320

Gly Cys Ala Pro Pro Glu Asp Asn Cys Thr Cys His His Gly His Cys
325 330 335

Gln Arg Ser Ser Cys Val Cys Asp Val Gly Trp Thr Gly Pro Glu Cys
340 345 350

Glu Ala Glu Leu Gly Gly Cys Ile Ser Ala Pro Cys Ala His Gly Gly
355 360 365

-continued

```
Thr Cys Tyr Pro Gln Pro Ser Gly Tyr Asn Cys Thr Cys Pro Thr Gly
    370                 375                 380

Tyr Thr Gly Pro Thr Cys Ser Glu Glu Met Thr Ala Cys His Ser Gly
385                 390                 395                 400

Pro Cys Leu Asn Gly Gly Ser Cys Asn Pro Ser Pro Gly Gly Tyr Tyr
                405                 410                 415

Cys Thr Cys Pro Pro Ser His Thr Gly Pro Gln Cys Gln Thr Ser Thr
            420                 425                 430

Asp Tyr Cys Val Ser Ala Pro Cys Phe Asn Gly Gly Thr Cys Val Asn
        435                 440                 445

Arg Pro Gly Thr Phe Ser Cys Leu Cys Ala Met Gly Phe Gln Gly Pro
    450                 455                 460

Arg Cys Glu Gly Lys Leu Arg Pro Ser Cys Ala Asp Ser Pro Cys Arg
465                 470                 475                 480

Asn Arg Ala Thr Cys Gln Asp Ser Pro Gln Gly Pro Arg Cys Leu Cys
                485                 490                 495

Pro Thr Gly Tyr Thr Gly Gly Ser Cys Gln Thr Leu Met Asp Leu Cys
            500                 505                 510

Ala Gln Lys Pro Cys Pro Arg Asn Ser His Cys Leu Gln Thr Gly Pro
        515                 520                 525

Ser Phe His Cys Leu Cys Leu Gln Gly Trp Thr Gly Pro Leu Cys Asn
    530                 535                 540

Leu Pro Leu Ser Ser Cys Gln Lys Ala Ala Leu Ser Gln Gly Ile Asp
545                 550                 555                 560

Val Ser Ser Leu Cys His Asn Gly Gly Leu Cys Val Asp Ser Gly Pro
                565                 570                 575

Ser Tyr Phe Cys His Cys Pro Pro Gly Phe Gln Gly Ser Leu Cys Gln
            580                 585                 590

Asp His Val Asn Pro Cys Glu Ser Arg Pro Cys Gln Asn Gly Ala Thr
        595                 600                 605

Cys Met Ala Gln Pro Ser Gly Tyr Leu Cys Gln Cys Ala Pro Gly Tyr
    610                 615                 620

Asp Gly Gln Asn Cys Ser Lys Glu Leu Asp Ala Cys Gln Ser Gln Pro
625                 630                 635                 640

Cys His Asn His Gly Thr Cys Thr Pro Lys Pro Gly Gly Phe His Cys
                645                 650                 655

Ala Cys Pro Pro Gly Phe Val Gly Leu Arg Cys Glu Gly Asp Val Asp
            660                 665                 670

Glu Cys Leu Asp Gln Pro Cys His Pro Thr Gly Thr Ala Ala Cys His
        675                 680                 685

Ser Leu Ala Asn Ala Phe Tyr Cys Gln Cys Leu Pro Gly His Thr Gly
    690                 695                 700

Gln Trp Cys Glu Val Glu Ile Asp Pro Cys His Ser Gln Pro Cys Phe
705                 710                 715                 720

His Gly Gly Thr Cys Glu Ala Thr Ala Gly Ser Pro Leu Gly Phe Ile
                725                 730                 735

Cys His Cys Pro Lys Gly Phe Glu Gly Pro Thr Cys Ser His Arg Ala
            740                 745                 750

Pro Ser Cys Gly Phe His His Cys His His Gly Gly Leu Cys Leu Pro
        755                 760                 765

Ser Pro Lys Pro Gly Phe Pro Pro Arg Cys Ala Cys Leu Ser Gly Tyr
    770                 775                 780

Gly Gly Pro Asp Cys Leu Thr Pro Pro Ala Pro Lys Gly Cys Gly Pro
```

785 790 795 800

Pro Ser Pro Cys Leu Tyr Asn Gly Ser Cys Ser Glu Thr Thr Gly Leu
805 810 815

Gly Gly Pro Gly Phe Arg Cys Ser Cys Pro His Ser Ser Pro Gly Pro
820 825 830

Arg Cys Gln Lys Pro Gly Asp Leu Gly Pro Gly Glu Pro Lys Ser Cys
835 840 845

Asp Lys Thr His Thr Cys Pro Pro Cys Pro Ala Pro Glu Leu Leu Gly
850 855 860

Gly Pro Ser Val Phe Leu Phe Pro Pro Lys Pro Lys Asp Thr Leu Met
865 870 875 880

Ile Ser Arg Thr Pro Glu Val Thr Cys Val Val Val Asp Val Ser His
885 890 895

Glu Asp Pro Glu Val Lys Phe Asn Trp Tyr Val Asp Gly Val Glu Val
900 905 910

His Asn Ala Lys Thr Lys Pro Arg Glu Glu Gln Tyr Asn Ser Thr Tyr
915 920 925

Arg Val Val Ser Val Leu Thr Val Leu His Gln Asp Trp Leu Asn Gly
930 935 940

Lys Glu Tyr Lys Cys Lys Val Ser Asn Lys Ala Leu Pro Ala Pro Ile
945 950 955 960

Glu Lys Thr Ile Ser Lys Ala Lys Gly Gln Pro Arg Glu Pro Gln Val
965 970 975

Tyr Thr Leu Pro Pro Ser Arg Asp Glu Leu Thr Lys Asn Gln Val Ser
980 985 990

Leu Thr Cys Leu Val Lys Gly Phe Tyr Pro Ser Asp Ile Ala Val Glu
995 1000 1005

Trp Glu Ser Asn Gly Gln Pro Glu Asn Asn Tyr Lys Thr Thr Pro
1010 1015 1020

Pro Val Leu Asp Ser Asp Gly Ser Phe Phe Leu Tyr Ser Lys Leu
1025 1030 1035

Thr Val Asp Lys Ser Arg Trp Gln Gln Gly Asn Val Phe Ser Cys
1040 1045 1050

Ser Val Met His Glu Ala Leu His Asn His Tyr Thr Gln Lys Ser
1055 1060 1065

Leu Ser Leu Ser Pro Gly Lys
1070 1075

<210> SEQ ID NO 85
<211> LENGTH: 681
<212> TYPE: PRT
<213> ORGANISM: Homo sapiens

<400> SEQUENCE: 85

Met Gln Pro Pro Ser Leu Leu Leu Leu Leu Leu Leu Leu Leu Leu Leu
1 5 10 15

Cys Val Ser Val Val Arg Pro Arg Gly Leu Leu Cys Ala Ser Ala Pro
20 25 30

Cys Leu Asn His Ala Asp Cys His Asp Leu Leu Asn Gly Phe Gln Cys
35 40 45

Ile Cys Leu Pro Gly Phe Ser Gly Thr Arg Cys Glu Glu Asp Ile Asp
50 55 60

Glu Cys Arg Ser Ser Pro Cys Ala Asn Gly Gly Gln Cys Gln Asp Gln
65 70 75 80

-continued

```
Pro Gly Ala Phe His Cys Lys Cys Leu Pro Gly Phe Glu Gly Pro Arg
                85                  90                  95

Cys Gln Thr Glu Val Asp Glu Cys Leu Ser Asp Pro Cys Pro Val Gly
            100                 105                 110

Ala Ser Cys Leu Asp Leu Pro Gly Ala Phe Phe Cys Leu Cys Pro Ser
        115                 120                 125

Gly Phe Thr Gly Gln Leu Cys Glu Val Pro Leu Cys Ala Pro Asn Leu
    130                 135                 140

Cys Gln Pro Lys Gln Ile Cys Lys Asp Gln Lys Asp Lys Ala Asn Cys
145                 150                 155                 160

Leu Cys Pro Asp Gly Ser Pro Gly Cys Ala Pro Pro Glu Asp Asn Cys
                165                 170                 175

Thr Cys His His Gly His Cys Gln Arg Ser Ser Cys Val Cys Asp Val
            180                 185                 190

Gly Trp Thr Gly Pro Glu Cys Glu Ala Glu Leu Gly Gly Cys Ile Ser
        195                 200                 205

Ala Pro Cys Ala His Gly Gly Thr Cys Tyr Pro Gln Pro Ser Gly Tyr
    210                 215                 220

Asn Cys Thr Cys Pro Thr Gly Tyr Thr Gly Pro Thr Cys Ser Glu Glu
225                 230                 235                 240

Met Thr Ala Cys His Ser Gly Pro Cys Leu Asn Gly Gly Ser Cys Asn
                245                 250                 255

Pro Ser Pro Gly Gly Tyr Tyr Cys Thr Cys Pro Pro Ser His Thr Gly
            260                 265                 270

Pro Gln Cys Gln Thr Ser Thr Asp Tyr Cys Val Ser Ala Pro Cys Phe
        275                 280                 285

Asn Gly Gly Thr Cys Val Asn Arg Pro Gly Thr Phe Ser Cys Leu Cys
    290                 295                 300

Ala Met Gly Phe Gln Gly Pro Arg Cys Glu Gly Lys Leu Arg Pro Ser
305                 310                 315                 320

Cys Ala Asp Ser Pro Cys Arg Asn Arg Ala Thr Cys Gln Asp Ser Pro
                325                 330                 335

Gln Gly Pro Arg Cys Leu Cys Pro Thr Gly Tyr Thr Gly Gly Ser Cys
            340                 345                 350

Gln Thr Leu Met Asp Leu Cys Ala Gln Lys Pro Cys Pro Arg Asn Ser
        355                 360                 365

His Cys Leu Gln Thr Gly Pro Ser Phe His Cys Leu Cys Leu Gln Gly
    370                 375                 380

Trp Thr Gly Pro Leu Cys Asn Leu Pro Leu Ser Ser Cys Gln Lys Ala
385                 390                 395                 400

Ala Leu Ser Gln Gly Ile Asp Val Ser Ser Leu Cys His Asn Gly Gly
                405                 410                 415

Leu Cys Val Asp Ser Gly Pro Ser Tyr Phe Cys His Cys Pro Pro Gly
            420                 425                 430

Phe Gln Gly Ser Leu Cys Gln Asp His Val Asn Pro Asp Leu Gly Pro
        435                 440                 445

Gly Glu Pro Lys Ser Cys Asp Lys Thr His Thr Cys Pro Pro Cys Pro
    450                 455                 460

Ala Pro Glu Leu Leu Gly Gly Pro Ser Val Phe Leu Phe Pro Pro Lys
465                 470                 475                 480

Pro Lys Asp Thr Leu Met Ile Ser Arg Thr Pro Glu Val Thr Cys Val
                485                 490                 495

Val Val Asp Val Ser His Glu Asp Pro Glu Val Lys Phe Asn Trp Tyr
```

```
            500                 505                 510

Val Asp Gly Val Glu Val His Asn Ala Lys Thr Lys Pro Arg Glu Glu
        515                 520                 525

Gln Tyr Asn Ser Thr Tyr Arg Val Val Ser Val Leu Thr Val Leu His
    530                 535                 540

Gln Asp Trp Leu Asn Gly Lys Glu Tyr Lys Cys Lys Val Ser Asn Lys
545                 550                 555                 560

Ala Leu Pro Ala Pro Ile Glu Lys Thr Ile Ser Lys Ala Lys Gly Gln
                565                 570                 575

Pro Arg Glu Pro Gln Val Tyr Thr Leu Pro Pro Ser Arg Asp Glu Leu
            580                 585                 590

Thr Lys Asn Gln Val Ser Leu Thr Cys Leu Val Lys Gly Phe Tyr Pro
        595                 600                 605

Ser Asp Ile Ala Val Glu Trp Glu Ser Asn Gly Gln Pro Glu Asn Asn
    610                 615                 620

Tyr Lys Thr Thr Pro Pro Val Leu Asp Ser Asp Gly Ser Phe Phe Leu
625                 630                 635                 640

Tyr Ser Lys Leu Thr Val Asp Lys Ser Arg Trp Gln Gln Gly Asn Val
                645                 650                 655

Phe Ser Cys Ser Val Met His Glu Ala Leu His Asn His Tyr Thr Gln
            660                 665                 670

Lys Ser Leu Ser Leu Ser Pro Gly Lys
        675                 680


<210> SEQ ID NO 86
<211> LENGTH: 676
<212> TYPE: PRT
<213> ORGANISM: Homo sapiens

<400> SEQUENCE: 86

Met Trp Gly Trp Lys Cys Leu Leu Phe Trp Ala Val Leu Val Thr Ala
1               5                   10                  15

Thr Leu Cys Thr Ala Arg Cys Ala Ser Ala Pro Cys Leu Asn His Ala
            20                  25                  30

Asp Cys His Asp Leu Leu Asn Gly Phe Gln Cys Ile Cys Leu Pro Gly
        35                  40                  45

Phe Ser Gly Thr Arg Cys Glu Glu Asp Ile Asp Glu Cys Arg Ser Ser
    50                  55                  60

Pro Cys Ala Asn Gly Gly Gln Cys Gln Asp Gln Pro Gly Ala Phe His
65                  70                  75                  80

Cys Lys Cys Leu Pro Gly Phe Glu Gly Pro Arg Cys Gln Thr Glu Val
                85                  90                  95

Asp Glu Cys Leu Ser Asp Pro Cys Pro Val Gly Ala Ser Cys Leu Asp
            100                 105                 110

Leu Pro Gly Ala Phe Phe Cys Leu Cys Pro Ser Gly Phe Thr Gly Gln
        115                 120                 125

Leu Cys Glu Val Pro Leu Cys Ala Pro Asn Leu Cys Gln Pro Lys Gln
    130                 135                 140

Ile Cys Lys Asp Gln Lys Asp Lys Ala Asn Cys Leu Cys Pro Asp Gly
145                 150                 155                 160

Ser Pro Gly Cys Ala Pro Pro Glu Asp Asn Cys Thr Cys His His Gly
                165                 170                 175

His Cys Gln Arg Ser Ser Cys Val Cys Asp Val Gly Trp Thr Gly Pro
            180                 185                 190
```

```
Glu Cys Glu Ala Glu Leu Gly Gly Cys Ile Ser Ala Pro Cys Ala His
        195                 200                 205

Gly Gly Thr Cys Tyr Pro Gln Pro Ser Gly Tyr Asn Cys Thr Cys Pro
    210                 215                 220

Thr Gly Tyr Thr Gly Pro Thr Cys Ser Glu Glu Met Thr Ala Cys His
225                 230                 235                 240

Ser Gly Pro Cys Leu Asn Gly Gly Ser Cys Asn Pro Ser Pro Gly Gly
                245                 250                 255

Tyr Tyr Cys Thr Cys Pro Pro Ser His Thr Gly Pro Gln Cys Gln Thr
            260                 265                 270

Ser Thr Asp Tyr Cys Val Ser Ala Pro Cys Phe Asn Gly Gly Thr Cys
        275                 280                 285

Val Asn Arg Pro Gly Thr Phe Ser Cys Leu Cys Ala Met Gly Phe Gln
    290                 295                 300

Gly Pro Arg Cys Glu Gly Lys Leu Arg Pro Ser Cys Ala Asp Ser Pro
305                 310                 315                 320

Cys Arg Asn Arg Ala Thr Cys Gln Asp Ser Pro Gln Gly Pro Arg Cys
                325                 330                 335

Leu Cys Pro Thr Gly Tyr Thr Gly Gly Ser Cys Gln Thr Leu Met Asp
            340                 345                 350

Leu Cys Ala Gln Lys Pro Cys Pro Arg Asn Ser His Cys Leu Gln Thr
        355                 360                 365

Gly Pro Ser Phe His Cys Leu Cys Leu Gln Gly Trp Thr Gly Pro Leu
    370                 375                 380

Cys Asn Leu Pro Leu Ser Ser Cys Gln Lys Ala Ala Leu Ser Gln Gly
385                 390                 395                 400

Ile Asp Val Ser Ser Leu Cys His Asn Gly Gly Leu Cys Val Asp Ser
                405                 410                 415

Gly Pro Ser Tyr Phe Cys His Cys Pro Pro Gly Phe Gln Gly Ser Leu
            420                 425                 430

Cys Gln Asp His Val Asn Pro Asp Leu Gly Pro Gly Glu Pro Lys Ser
        435                 440                 445

Cys Asp Lys Thr His Thr Cys Pro Pro Cys Pro Ala Pro Glu Leu Leu
    450                 455                 460

Gly Gly Pro Ser Val Phe Leu Phe Pro Pro Lys Pro Lys Asp Thr Leu
465                 470                 475                 480

Met Ile Ser Arg Thr Pro Glu Val Thr Cys Val Val Val Asp Val Ser
                485                 490                 495

His Glu Asp Pro Glu Val Lys Phe Asn Trp Tyr Val Asp Gly Val Glu
            500                 505                 510

Val His Asn Ala Lys Thr Lys Pro Arg Glu Glu Gln Tyr Asn Ser Thr
        515                 520                 525

Tyr Arg Val Val Ser Val Leu Thr Val Leu His Gln Asp Trp Leu Asn
    530                 535                 540

Gly Lys Glu Tyr Lys Cys Lys Val Ser Asn Lys Ala Leu Pro Ala Pro
545                 550                 555                 560

Ile Glu Lys Thr Ile Ser Lys Ala Lys Gly Gln Pro Arg Glu Pro Gln
                565                 570                 575

Val Tyr Thr Leu Pro Pro Ser Arg Asp Glu Leu Thr Lys Asn Gln Val
            580                 585                 590

Ser Leu Thr Cys Leu Val Lys Gly Phe Tyr Pro Ser Asp Ile Ala Val
        595                 600                 605

Glu Trp Glu Ser Asn Gly Gln Pro Glu Asn Asn Tyr Lys Thr Thr Pro
```

```
    610                 615                 620

Pro Val Leu Asp Ser Asp Gly Ser Phe Phe Leu Tyr Ser Lys Leu Thr
625                 630                 635                 640

Val Asp Lys Ser Arg Trp Gln Gln Gly Asn Val Phe Ser Cys Ser Val
                645                 650                 655

Met His Glu Ala Leu His Asn His Tyr Thr Gln Lys Ser Leu Ser Leu
            660                 665                 670

Ser Pro Gly Lys
        675


<210> SEQ ID NO 87
<211> LENGTH: 629
<212> TYPE: PRT
<213> ORGANISM: Homo sapiens

<400> SEQUENCE: 87

Met Gln Pro Pro Ser Leu Leu Leu Leu Leu Leu Leu Leu Leu Leu Leu
1               5                   10                  15

Cys Val Ser Val Val Arg Pro Arg Gly Leu Leu Cys Ala Asp Ser Pro
            20                  25                  30

Cys Arg Asn Arg Ala Thr Cys Gln Asp Ser Pro Gln Gly Pro Arg Cys
        35                  40                  45

Leu Cys Pro Thr Gly Tyr Thr Gly Gly Ser Cys Gln Thr Leu Met Asp
    50                  55                  60

Leu Cys Ala Gln Lys Pro Cys Pro Arg Asn Ser His Cys Leu Gln Thr
65                  70                  75                  80

Gly Pro Ser Phe His Cys Leu Cys Leu Gln Gly Trp Thr Gly Pro Leu
                85                  90                  95

Cys Asn Leu Pro Leu Ser Ser Cys Gln Lys Ala Ala Leu Ser Gln Gly
            100                 105                 110

Ile Asp Val Ser Ser Leu Cys His Asn Gly Gly Leu Cys Val Asp Ser
        115                 120                 125

Gly Pro Ser Tyr Phe Cys His Cys Pro Pro Gly Phe Gln Gly Ser Leu
    130                 135                 140

Cys Gln Asp His Val Asn Pro Cys Glu Ser Arg Pro Cys Gln Asn Gly
145                 150                 155                 160

Ala Thr Cys Met Ala Gln Pro Ser Gly Tyr Leu Cys Gln Cys Ala Pro
                165                 170                 175

Gly Tyr Asp Gly Gln Asn Cys Ser Lys Glu Leu Asp Ala Cys Gln Ser
            180                 185                 190

Gln Pro Cys His Asn His Gly Thr Cys Thr Pro Lys Pro Gly Gly Phe
        195                 200                 205

His Cys Ala Cys Pro Pro Gly Phe Val Gly Leu Arg Cys Glu Gly Asp
    210                 215                 220

Val Asp Glu Cys Leu Asp Gln Pro Cys His Pro Thr Gly Thr Ala Ala
225                 230                 235                 240

Cys His Ser Leu Ala Asn Ala Phe Tyr Cys Gln Cys Leu Pro Gly His
                245                 250                 255

Thr Gly Gln Trp Cys Glu Val Glu Ile Asp Pro Cys His Ser Gln Pro
            260                 265                 270

Cys Phe His Gly Gly Thr Cys Glu Ala Thr Ala Gly Ser Pro Leu Gly
        275                 280                 285

Phe Ile Cys His Cys Pro Lys Gly Phe Glu Gly Pro Thr Cys Ser His
    290                 295                 300
```

```
Arg Ala Pro Ser Cys Gly Phe His His Cys His His Gly Gly Leu Cys
305                 310                 315                 320

Leu Pro Ser Pro Lys Pro Gly Phe Pro Pro Arg Cys Ala Cys Leu Ser
                325                 330                 335

Gly Tyr Gly Gly Pro Asp Cys Leu Thr Pro Pro Ala Pro Lys Gly Cys
            340                 345                 350

Gly Pro Pro Ser Pro Cys Leu Tyr Asn Gly Ser Cys Ser Glu Thr Thr
        355                 360                 365

Gly Leu Gly Gly Pro Gly Phe Arg Cys Ser Cys Pro His Ser Ser Pro
    370                 375                 380

Gly Pro Arg Cys Gln Lys Pro Gly Asp Leu Gly Pro Gly Glu Pro Lys
385                 390                 395                 400

Ser Cys Asp Lys Thr His Thr Cys Pro Pro Cys Pro Ala Pro Glu Leu
                405                 410                 415

Leu Gly Gly Pro Ser Val Phe Leu Phe Pro Pro Lys Pro Lys Asp Thr
            420                 425                 430

Leu Met Ile Ser Arg Thr Pro Glu Val Thr Cys Val Val Val Asp Val
        435                 440                 445

Ser His Glu Asp Pro Glu Val Lys Phe Asn Trp Tyr Val Asp Gly Val
    450                 455                 460

Glu Val His Asn Ala Lys Thr Lys Pro Arg Glu Glu Gln Tyr Asn Ser
465                 470                 475                 480

Thr Tyr Arg Val Val Ser Val Leu Thr Val Leu His Gln Asp Trp Leu
                485                 490                 495

Asn Gly Lys Glu Tyr Lys Cys Lys Val Ser Asn Lys Ala Leu Pro Ala
            500                 505                 510

Pro Ile Glu Lys Thr Ile Ser Lys Ala Lys Gly Gln Pro Arg Glu Pro
        515                 520                 525

Gln Val Tyr Thr Leu Pro Pro Ser Arg Asp Glu Leu Thr Lys Asn Gln
    530                 535                 540

Val Ser Leu Thr Cys Leu Val Lys Gly Phe Tyr Pro Ser Asp Ile Ala
545                 550                 555                 560

Val Glu Trp Glu Ser Asn Gly Gln Pro Glu Asn Asn Tyr Lys Thr Thr
                565                 570                 575

Pro Pro Val Leu Asp Ser Asp Gly Ser Phe Phe Leu Tyr Ser Lys Leu
            580                 585                 590

Thr Val Asp Lys Ser Arg Trp Gln Gln Gly Asn Val Phe Ser Cys Ser
        595                 600                 605

Val Met His Glu Ala Leu His Asn His Tyr Thr Gln Lys Ser Leu Ser
    610                 615                 620

Leu Ser Pro Gly Lys
625


<210> SEQ ID NO 88
<211> LENGTH: 624
<212> TYPE: PRT
<213> ORGANISM: Homo sapiens

<400> SEQUENCE: 88

Met Trp Gly Trp Lys Cys Leu Leu Phe Trp Ala Val Leu Val Thr Ala
1               5                   10                  15

Thr Leu Cys Thr Ala Arg Cys Ala Asp Ser Pro Cys Arg Asn Arg Ala
            20                  25                  30

Thr Cys Gln Asp Ser Pro Gln Gly Pro Arg Cys Leu Cys Pro Thr Gly
        35                  40                  45
```

```
Tyr Thr Gly Gly Ser Cys Gln Thr Leu Met Asp Leu Cys Ala Gln Lys
    50                  55                  60

Pro Cys Pro Arg Asn Ser His Cys Leu Gln Thr Gly Pro Ser Phe His
65                  70                  75                  80

Cys Leu Cys Leu Gln Gly Trp Thr Gly Pro Leu Cys Asn Leu Pro Leu
                85                  90                  95

Ser Ser Cys Gln Lys Ala Ala Leu Ser Gln Gly Ile Asp Val Ser Ser
            100                 105                 110

Leu Cys His Asn Gly Gly Leu Cys Val Asp Ser Gly Pro Ser Tyr Phe
        115                 120                 125

Cys His Cys Pro Pro Gly Phe Gln Gly Ser Leu Cys Gln Asp His Val
    130                 135                 140

Asn Pro Cys Glu Ser Arg Pro Cys Gln Asn Gly Ala Thr Cys Met Ala
145                 150                 155                 160

Gln Pro Ser Gly Tyr Leu Cys Gln Cys Ala Pro Gly Tyr Asp Gly Gln
                165                 170                 175

Asn Cys Ser Lys Glu Leu Asp Ala Cys Gln Ser Gln Pro Cys His Asn
            180                 185                 190

His Gly Thr Cys Thr Pro Lys Pro Gly Gly Phe His Cys Ala Cys Pro
        195                 200                 205

Pro Gly Phe Val Gly Leu Arg Cys Glu Gly Asp Val Asp Glu Cys Leu
    210                 215                 220

Asp Gln Pro Cys His Pro Thr Gly Thr Ala Ala Cys His Ser Leu Ala
225                 230                 235                 240

Asn Ala Phe Tyr Cys Gln Cys Leu Pro Gly His Thr Gly Gln Trp Cys
                245                 250                 255

Glu Val Glu Ile Asp Pro Cys His Ser Gln Pro Cys Phe His Gly Gly
            260                 265                 270

Thr Cys Glu Ala Thr Ala Gly Ser Pro Leu Gly Phe Ile Cys His Cys
        275                 280                 285

Pro Lys Gly Phe Glu Gly Pro Thr Cys Ser His Arg Ala Pro Ser Cys
    290                 295                 300

Gly Phe His His Cys His His Gly Gly Leu Cys Leu Pro Ser Pro Lys
305                 310                 315                 320

Pro Gly Phe Pro Pro Arg Cys Ala Cys Leu Ser Gly Tyr Gly Gly Pro
                325                 330                 335

Asp Cys Leu Thr Pro Pro Ala Pro Lys Gly Cys Gly Pro Pro Ser Pro
            340                 345                 350

Cys Leu Tyr Asn Gly Ser Cys Ser Glu Thr Thr Gly Leu Gly Gly Pro
        355                 360                 365

Gly Phe Arg Cys Ser Cys Pro His Ser Ser Pro Gly Pro Arg Cys Gln
    370                 375                 380

Lys Pro Gly Asp Leu Gly Pro Gly Glu Pro Lys Ser Cys Asp Lys Thr
385                 390                 395                 400

His Thr Cys Pro Pro Cys Pro Ala Pro Glu Leu Leu Gly Gly Pro Ser
                405                 410                 415

Val Phe Leu Phe Pro Pro Lys Pro Lys Asp Thr Leu Met Ile Ser Arg
            420                 425                 430

Thr Pro Glu Val Thr Cys Val Val Val Asp Val Ser His Glu Asp Pro
        435                 440                 445

Glu Val Lys Phe Asn Trp Tyr Val Asp Gly Val Glu Val His Asn Ala
    450                 455                 460
```

Lys Thr Lys Pro Arg Glu Glu Gln Tyr Asn Ser Thr Tyr Arg Val Val
465 470 475 480

Ser Val Leu Thr Val Leu His Gln Asp Trp Leu Asn Gly Lys Glu Tyr
485 490 495

Lys Cys Lys Val Ser Asn Lys Ala Leu Pro Ala Pro Ile Glu Lys Thr
500 505 510

Ile Ser Lys Ala Lys Gly Gln Pro Arg Glu Pro Gln Val Tyr Thr Leu
515 520 525

Pro Pro Ser Arg Asp Glu Leu Thr Lys Asn Gln Val Ser Leu Thr Cys
530 535 540

Leu Val Lys Gly Phe Tyr Pro Ser Asp Ile Ala Val Glu Trp Glu Ser
545 550 555 560

Asn Gly Gln Pro Glu Asn Asn Tyr Lys Thr Thr Pro Pro Val Leu Asp
565 570 575

Ser Asp Gly Ser Phe Phe Leu Tyr Ser Lys Leu Thr Val Asp Lys Ser
580 585 590

Arg Trp Gln Gln Gly Asn Val Phe Ser Cys Ser Val Met His Glu Ala
595 600 605

Leu His Asn His Tyr Thr Gln Lys Ser Leu Ser Leu Ser Pro Gly Lys
610 615 620

<210> SEQ ID NO 89
<211> LENGTH: 6012
<212> TYPE: DNA
<213> ORGANISM: Homo sapiens

<400> SEQUENCE: 89
atgcagcccc cttcactgct gctgctgctg ctgctgctgc tgctgctatg tgtctcagtg 60
gtcagaccca gagggctgct gtgtgggagt ttcccagaac cctgtgccaa tggaggcacc 120
tgcctgagcc tgtctctggg acaagggacc tgccagtgtg cccctggctt cctgggtgag 180
acgtgccagt ttcctgaccc ctgccagaac gcccagctct gccaaaatgg aggcagctgc 240
caagccctgc ttcccgctcc cctagggctc cccagctctc cctctccatt gacacccagc 300
ttcttgtgca cttgcctccc tggcttcact ggtgagagat gccaggccaa gcttgaagac 360
ccttgtcctc cctccttctg ttccaaaagg ggccgctgcc acatccaggc ctcgggccgc 420
ccacagtgct cctgcatgcc tggatggaca ggtgagcagt gccagcttcg ggacttctgt 480
tcagccaacc catgtgttaa tggaggggtg tgtctggcca catacccccca gatccagtgc 540 cactgcccac cgggcttcga gggccatgcc tgtgaacgtg atgtcaacga gtgcttccag 600
gacccaggac cctgccccaa aggcacctcc tgccataaca ccctgggctc cttccagtgc 660
ctctgccctg tggggcagga gggtccacgt tgtgagctgc gggcaggacc ctgccctcct 720
aggggctgtt cgaatggggg cacctgccag ctgatgccag agaaagactc cacctttcac 780
ctctgcctct gtcccccagg tttcataggc ccagactgtg aggtgaatcc agacaactgt 840
gtcagccacc agtgtcagaa tgggggcact tgccaggatg ggctggacac ctacacctgc 900
ctctgcccag aaacctggac aggctgggac tgctccgaag atgtggatga gtgtgagacc 960
cagggtcccc ctcactgcag aaacgggggc acctgccaga actctgctgg tagctttcac 1020
tgcgtgtgtg tgagtggctg gggcggcaca agctgtgagg agaacctgga tgactgtatt 1080
gctgccacct gtgccccggg atccacctgc attgaccggg tgggctcttt ctcctgcctc 1140
tgcccacctg gacgcacagg actcctgtgc cacttggaag acatgtgtct gagccagccg 1200
tgccatgggg atgcccaatg cagcaccaac cccctcacag gctccacact ctgcctgtgt 1260

-continued cagcctggct attcggggcc cacctgccac caggacctgg acgagtgtct gatggcccag 1320
caaggcccaa gtccctgtga acatggcggt tcctgcctca acactcctgg ctccttcaac 1380
tgcctctgtc cacctggcta cacaggctcc cgttgtgagg ctgatcacaa tgagtgcctc 1440
tcccagccct gccacccagg aagcacctgt ctggacctac ttgccacctt ccactgcctc 1500
tgcccgccag gcttagaagg gcagctctgt gaggtggaga ccaacgagtg tgcctcagct 1560
ccctgcctga accacgcgga ttgccatgac ctgctcaacg gcttccagtg catctgcctg 1620
cctggattct ccggcacccg atgtgaggag gatatcgatg agtgcagaag ctctccctgt 1680
gccaatggtg ggcagtgcca ggaccagcct ggagccttcc actgcaagtg tctcccaggc 1740
tttgaagggc cacgctgtca aacagaggtg gatgagtgcc tgagtgaccc atgtcccgtt 1800
ggagccagct gccttgatct tccaggagcc ttcttttgcc tctgcccctc tggtttcaca 1860
ggccagctct gtgaggttcc cctgtgtgct cccaacctgt gccagcccaa gcagatatgt 1920
aaggaccaga aagacaaggc caactgcctc tgtcctgatg gaagccctgg ctgtgcccca 1980
cctgaggaca actgcacctg ccaccacggg cactgccaga gatcctcatg tgtgtgtgac 2040
gtgggttgga cggggccaga gtgtgaggca gagctagggg gctgcatctc tgcaccctgt 2100
gcccatgggg ggacctgcta cccccagccc tctggctaca actgcacctg ccctacaggc 2160
tacacaggac ccacctgtag tgaggagatg acagcttgtc actcagggcc atgtctcaat 2220
ggcggctcct gcaaccctag ccctggaggc tactactgca cctgccctcc aagccacaca 2280
gggccccagt gccaaaccag cactgactac tgtgtgtctg ccccgtgctt caatgggggt 2340
acctgtgtga acaggcctgg caccttctcc tgcctctgtg ccatgggctt ccagggcccg 2400
cgctgtgagg gaaagctccg ccccagctgt gcagacagcc cctgtaggaa tagggcaacc 2460
tgccaggaca gccctcaggg tccccgctgc ctctgcccca ctggctacac cggaggcagc 2520
tgccagactc tgatggactt atgtgcccag aagccctgcc cacgcaattc ccactgcctc 2580
cagactgggc cctccttcca ctgcttgtgc ctccagggat ggaccgggcc tctctgcaac 2640
cttccactgt cctcctgcca gaaggctgca ctgagccaag gcatagacgt ctcttccctt 2700
tgccacaatg gaggcctctg tgtcgacagc ggcccctcct atttctgcca ctgcccccct 2760
ggattccaag gcagcctgtg ccaggatcac gtgaacccat gtgagtccag gccttgccag 2820
aacggggcca cctgcatggc ccagcccagt gggtatctct gccagtgtgc cccaggctac 2880
gatggacaga actgctcaaa ggaactcgat gcttgtcagt cccaaccctg tcacaaccat 2940
ggaacctgta ctcccaaacc tggaggattc cactgtgcct gccctccagg ctttgtgggg 3000
ctacgctgtg agggagacgt ggacgagtgt ctggaccagc cctgccaccc cacaggcact 3060
gcagcctgcc actctctggc caatgccttc tactgccagt gtctgcctgg acacacaggc 3120
cagtggtgtg aggtggagat agacccctgc cacagccaac cctgctttca tggagggacc 3180
tgtgaggcca cagcaggatc acccctgggt ttcatctgcc actgccccaa gggttttgaa 3240
ggccccacct gcagccacag ggccccttcc tgcggcttcc atcactgcca ccacggaggc 3300
ctgtgtctgc cctcccctaa gccaggcttc ccaccacgct gtgcctgcct cagtggctat 3360
gggggtcctg actgcctgac ccccaccagct cctaaaggct gtggccctcc ctccccatgc 3420
ctatacaatg gcagctgctc agagaccacg ggcttggggg gcccaggctt tcgatgctcc 3480
tgccctcaca gctctccagg gccccggtgt cagaaacccg gagccaaggg gtgtgagggc 3540
agaagtggag atggggcctg cgatgctggc tgcagtggcc cgggaggaaa ctgggatgga 3600

-continued

```
ggggactgct ctctgggagt cccagacccc tggaagggct gcccctccca ctctcggtgc   3660
tggcttctct tccgggacgg gcagtgccac ccacagtgtg actctgaaga gtgtctgttt   3720
gatggctacg actgtgagac ccctccagcc tgcactccag cctatgacca gtactgccat   3780
gatcacttcc acaacgggca ctgtgagaaa ggctgcaaca ctgcagagtg tggctgggat   3840
ggaggtgact gcaggcctga agatggggac ccagagtggg ggccctccct ggccctgctg   3900
gtggtactga gcccccccagc cctagaccag cagctgtttg ccctggcccg ggtgctgtcc   3960
ctgactctga gggtaggact ctgggtaagg aaggatcgtg atggcaggga catggtgtac   4020
ccctatcctg ggcccgggc tgaagaaaag ctaggaggaa ctcgggaccc cacctatcag   4080
gagagagcag cccctcaaac gcagcccctg ggcaaggaga ccgactccct cagtgctggg   4140
tttgtggtgg tcatgggtgt ggatttgtcc cgctgtggcc ctgaccaccc ggcatcccgc   4200
tgtccctggg accctgggct tctactccgc ttccttgctg cgatggctgc agtgggagcc   4260
ctggagcccc tgctgcctgg accactgctg gctgtccacc ctcatgcagg gaccgcaccc   4320
cctgccaacc agcttccctg gcctgtgctg tgctccccag tggccggggt gattctcctg   4380
gccctagggg ctcttctcgt cctccagctc atccggcgtc gacgccgaga gcatggagct   4440
ctctggctgc cccctggttt cactcgacgg cctcggactc agtcagctcc ccaccgacgc   4500
cggcccccac taggcgagga cagcattggt ctcaaggcac tgaagccaaa ggcagaagtt   4560
gatgaggatg gagttgtgat gtgctcaggc cctgaggagg gagaggaggt gggccaggct   4620
gaagaaacag gcccaccctc cacgtgccag ctctggtctc tgagtggtgg ctgtggggcg   4680
ctccctcagg cagccatgct aactcctccc caggaatctg agatggaagc ccctgacctg   4740
gacacccgtg gacctgatgg ggtgacaccc ctgatgtcag cagtttgctg tggggaagta   4800
cagtccggga ccttccaagg ggcatggttg ggatgtcctg agccctggga acctctgctg   4860
gatggagggg cctgtcccca ggctcacacc gtgggcactg gggagacccc cctgcacctg   4920
gctgcccgat tctcccggcc aaccgctgcc cgccgcctcc ttgaggctgg agccaacccc   4980
aaccagccag accgggcagg gcgcacaccc cttcatgctg ctgtggctgc tgatgctcgg   5040
gaggtctgcc agcttctgct ccgtagcaga caaactgcag tggacgctcg cacagaggac   5100
gggaccacac ccttgatgct ggctgccagg ctggcggtgg aagacctggt tgaagaactg   5160
attgcagccc aagcagacgt gggggccaga gataaatggg ggaaaactgc gctgcactgg   5220
gctgctgccg tgaacaacgc ccgagccgcc cgctcgcttc tccaggccgg agccgataaa   5280
gatgcccagg acaacaggga gcagacgccg ctattcctgg cggcgcggga aggagcggtg   5340
gaagtagccc agctactgct ggggctgggg gcagcccgag agctgcggga ccaggctggg   5400
ctagcgccgg cggacgtcgc tcaccaacgt aaccactggg atctgctgac gctgctggaa   5460
ggggctgggc caccagaggc ccgtcacaaa gccacgccgg gccgcgaggc tgggcccttc   5520
ccgcgcgcac ggacggtgtc agtaagcgtg cccccgcatg gggcggggc tctgccgcgc   5580
tgccggacgc tgtcagccgg agcaggccct cgtgggggcg gagcttgtct gcaggctcgg   5640
acttggtccg tagacttggc tgcgcggggg ggcggggcct attctcattg ccggagcctc   5700
tcgggagtag gagcaggagg aggcccgacc cctcgcggcc gtaggttttc tgcaggcatg   5760
cgcgggcctc ggcccaaccc tgcgataatg cgaggaagat acggagtggc tgccgggcgc   5820
ggaggcaggg tctcaacgga tgactggccc tgtgattggg tggccctggg agcttgcggt   5880
tctgcctcca acattccgat cccgcctcct tgccttactc cgtccccgga gcggggatca   5940
cctcaacttg actgtggtcc cccagccctc caagaaatgc ccataaacca aggaggagag   6000
```

ggtaaaaaat ag 6012

<210> SEQ ID NO 90
<211> LENGTH: 81
<212> TYPE: DNA
<213> ORGANISM: Homo sapiens

<400> SEQUENCE: 90
atgcagcccc cttcactgct gctgctgctg ctgctgctgc tgctgctatg tgtctcagtg 60
gtcagaccca gagggctgct g 81

<210> SEQ ID NO 91
<211> LENGTH: 66
<212> TYPE: DNA
<213> ORGANISM: Homo sapiens

<400> SEQUENCE: 91
atgtggggct ggaagtgcct cctcttctgg gctgtgctgg tcacagccac tctctgcact 60
gccagg 66

<210> SEQ ID NO 92
<211> LENGTH: 714
<212> TYPE: DNA
<213> ORGANISM: Homo sapiens

<400> SEQUENCE: 92
gatctgggcc cgggcgagcc caaatcttgt gacaaaactc acacatgccc accgtgccca 60
gcacctgaac tcctgggggg accgtcagtc ttcctcttcc ccccaaaacc caaggacacc 120
ctcatgatct cccggacccc tgaggtcaca tgcgtggtgg tggacgtgag ccacgaagac 180
cctgaggtca agttcaactg gtacgtggac ggcgtggagg tgcataatgc caagacaaag 240
ccgcgggagg agcagtacaa cagcacgtac cgtgtggtca gcgtcctcac cgtcctgcac 300
caggactggc tgaatggcaa ggagtacaag tgcaaggtct ccaacaaagc cctcccagcc 360
cccatcgaga aaaccatctc caaagccaaa gggcagcccc gagaaccaca ggtgtacacc 420
ctgcccccat cccgggatga gctgaccaag aaccaggtca gcctgacctg cctggtcaaa 480
ggcttctatc ccagcgacat cgccgtggag tgggagagca atgggcagcc ggagaacaac 540
tacaagacca cgcctcccgt gctggactcc gacggctcct tcttcctcta cagcaagctc 600
accgtggaca agagcaggtg gcagcagggg aacgtcttct catgctccgt gatgcatgag 660
gctctgcaca accactacac gcagaagagc ctctccctgt ctccgggtaa atga 714

<210> SEQ ID NO 93
<211> LENGTH: 4236
<212> TYPE: DNA
<213> ORGANISM: Homo sapiens

<400> SEQUENCE: 93
atgcagcccc cttcactgct gctgctgctg ctgctgctgc tgctgctatg tgtctcagtg 60
gtcagaccca gagggctgct gtgtgggagt ttcccagaac cctgtgccaa tggaggcacc 120
tgcctgagcc tgtctctggg acaagggacc tgccagtgtg cccctggctt cctgggtgag 180
acgtgccagt ttcctgaccc ctgccagaac gcccagctct gccaaaatgg aggcagctgc 240
caagccctgc ttcccgctcc cctagggctc cccagctctc cctctccatt gacacccagc 300
ttcttgtgca cttgcctccc tggcttcact ggtgagagat gccaggccaa gcttgaagac 360

-continued

```
ccttgtcctc cctccttctg ttccaaaagg ggccgctgcc acatccaggc ctcgggccgc    420
ccacagtgct cctgcatgcc tggatggaca ggtgagcagt gccagcttcg ggacttctgt    480
tcagccaacc catgtgttaa tggaggggtg tgtctggcca catacccca gatccagtgc     540
cactgcccac cgggcttcga gggccatgcc tgtgaacgtg atgtcaacga gtgcttccag    600
gacccaggac cctgccccaa aggcacctcc tgccataaca ccctgggctc cttccagtgc    660
ctctgccctg tggggcagga gggtccacgt tgtgagctgc gggcaggacc ctgccctcct    720
aggggctgtt cgaatggggg cacctgccag ctgatgccag agaaagactc cacctttcac    780
ctctgcctct gtcccccagg tttcataggc ccagactgtg aggtgaatcc agacaactgt    840
gtcagccacc agtgtcagaa tgggggcact tgccaggatg ggctggacac ctacacctgc    900
ctctgcccag aaacctggac aggctgggac tgctccgaag atgtggatga gtgtgagacc    960
cagggtcccc ctcactgcag aaacgggggc acctgccaga actctgctgg tagctttcac   1020
tgcgtgtgtg tgagtggctg ggcggcaca agctgtgagg agaacctgga tgactgtatt    1080
gctgccacct gtgccccggg atccacctgc attgaccggg tgggctcttt ctcctgcctc   1140
tgcccacctg gacgcacagg actcctgtgc cacttggaag acatgtgtct gagccagccg   1200
tgccatgggg atgcccaatg cagcaccaac cccctcacag gctccacact ctgcctgtgt   1260
cagcctggct attcggggcc cacctgccac caggacctgg acgagtgtct gatggcccag   1320
caaggcccaa gtccctgtga acatggcggt tcctgcctca acactcctgg ctccttcaac   1380
tgcctctgtc cacctggcta cacaggctcc cgttgtgagg ctgatcacaa tgagtgcctc   1440
tcccagccct gccacccagg aagcacctgt ctggacctac ttgccacctt ccactgcctc   1500
tgcccgccag gcttagaagg gcagctctgt gaggtggaga ccaacgagtg tgcctcagct   1560
ccctgcctga accacgcgga ttgccatgac ctgctcaacg gcttccagtg catctgcctg   1620
cctggattct ccggcacccg atgtgaggag gatatcgatg agtgcagaag ctctccctgt   1680
gccaatggtg ggcagtgcca ggaccagcct ggagccttcc actgcaagtg tctcccaggc   1740
tttgaagggc cacgctgtca aacagaggtg gatgagtgcc tgagtgaccc atgtcccgtt   1800
ggagccagct gccttgatct tccaggagcc ttcttttgcc tctgcccctc tggtttcaca   1860
ggccagctct gtgaggttcc cctgtgtgct cccaacctgt gccagcccaa gcagatatgt   1920
aaggaccaga aagacaaggc caactgcctc tgtcctgatg gaagccctgg ctgtgcccca   1980
cctgaggaca actgcacctg ccaccacggg cactgccaga gatcctcatg tgtgtgtgac   2040
gtgggttgga cggggccaga gtgtgaggca gagctagggg gctgcatctc tgcaccctgt   2100
gcccatgggg ggacctgcta cccccagccc tctggctaca actgcacctg ccctacaggc   2160
tacacaggac ccacctgtag tgaggagatg acagcttgtc actcagggcc atgtctcaat   2220
ggcggctcct gcaaccctag ccctggaggc tactactgca cctgccctcc aagccacaca   2280
gggccccagt gccaaaccag cactgactac tgtgtgtctg ccccgtgctt caatgggggt   2340
acctgtgtga acaggcctgg caccttctcc tgcctctgtg ccatgggctt ccagggcccg   2400
cgctgtgagg gaaagctccg ccccagctgt gcagacagcc cctgtaggaa tagggcaacc   2460
tgccaggaca gccctcaggg tccccgctgc ctctgcccca ctggctacac cggaggcagc   2520
tgccagactc tgatggactt atgtgcccag aagccctgcc cacgcaattc ccactgcctc   2580
cagactgggc cctccttcca ctgcttgtgc ctccagggat ggaccgggcc tctctgcaac   2640
cttccactgt cctcctgcca gaaggctgca ctgagccaag gcatagacgt ctcttccctt   2700
tgccacaatg gaggcctctg tgtcgacagc ggcccctcct atttctgcca ctgcccccct   2760
```

ggattccaag gcagcctgtg ccaggatcac gtgaacccat gtgagtccag gccttgccag 2820
aacggggcca cctgcatggc ccagcccagt gggtatctct gccagtgtgc cccaggctac 2880
gatggacaga actgctcaaa ggaactcgat gcttgtcagt cccaaccctg tcacaaccat 2940
ggaacctgta ctcccaaacc tggaggattc cactgtgcct gccctccagg ctttgtgggg 3000
ctacgctgtg agggagacgt ggacgagtgt ctggaccagc cctgccaccc cacaggcact 3060
gcagcctgcc actctctggc caatgccttc tactgccagt gtctgcctgg acacacaggc 3120
cagtggtgtg aggtggagat agacccctgc cacagccaac cctgctttca tggagggacc 3180
tgtgaggcca cagcaggatc acccctgggt ttcatctgcc actgccccaa gggttttgaa 3240
ggccccacct gcagccacag ggccccttcc tgcggcttcc atcactgcca ccacggaggc 3300
ctgtgtctgc cctcccctaa gccaggcttc ccaccacgct gtgcctgcct cagtggctat 3360
gggggtcctg actgcctgac cccaccagct cctaaaggct gtggccctcc ctccccatgc 3420
ctatacaatg gcagctgctc agagaccacg ggcttggggg gcccaggctt tcgatgctcc 3480
tgccctcaca gctctccagg gccccggtgt cagaaacccg gagatctggg cccgggcgag 3540
cccaaatctt gtgacaaaac tcacacatgc ccaccgtgcc cagcacctga actcctgggg 3600
ggaccgtcag tcttcctctt ccccccaaaa cccaaggaca ccctcatgat ctcccggacc 3660
cctgaggtca catgcgtggt ggtggacgtg agccacgaag accctgaggt caagttcaac 3720
tggtacgtgg acggcgtgga ggtgcataat gccaagacaa agccgcggga ggagcagtac 3780
aacagcacgt accgtgtggt cagcgtcctc accgtcctgc accaggactg gctgaatggc 3840
aaggagtaca agtgcaaggt ctccaacaaa gccctcccag cccccatcga gaaaaccatc 3900
tccaaagcca aagggcagcc ccgagaacca caggtgtaca ccctgccccc atcccgggat 3960
gagctgacca agaaccaggt cagcctgacc tgcctggtca aaggcttcta tcccagcgac 4020
atcgccgtgg agtgggagag caatgggcag ccggagaaca actacaagac cacgcctccc 4080
gtgctggact ccgacggctc cttcttcctc tacagcaagc tcaccgtgga caagagcagg 4140
tggcagcagg ggaacgtctt ctcatgctcc gtgatgcatg aggctctgca caaccactac 4200
acgcagaaga gcctctccct gtctccgggt aaatga 4236

<210> SEQ ID NO 94
<211> LENGTH: 2376
<212> TYPE: DNA
<213> ORGANISM: Homo sapiens

<400> SEQUENCE: 94
atgcagcccc cttcactgct gctgctgctg ctgctgctgc tgctgctatg tgtctcagtg 60
gtcagaccca gagggctgct gtgtgggagt ttcccagaac cctgtgccaa tggaggcacc 120
tgcctgagcc tgtctctggg acaagggacc tgccagtgtg cccctggctt cctgggtgag 180
acgtgccagt ttcctgaccc ctgccagaac gcccagctct gccaaaatgg aggcagctgc 240
caagccctgc ttcccgctcc cctagggctc cccagctctc cctctccatt gacacccagc 300
ttcttgtgca cttgcctccc tggcttcact ggtgagagat gccaggccaa gcttgaagac 360
ccttgtcctc cctccttctg ttccaaaagg ggccgctgcc acatccaggc ctcgggccgc 420
ccacagtgct cctgcatgcc tggatggaca ggtgagcagt gccagcttcg ggacttctgt 480
tcagccaacc catgtgttaa tggaggggtg tgtctggcca catacccccca gatccagtgc 540 cactgcccac cgggcttcga gggccatgcc tgtgaacgtg atgtcaacga gtgcttccag 600

```
gacccaggac cctgccccaa aggcacctcc tgccataaca ccctgggctc cttccagtgc    660

ctctgccctg tggggcagga gggtccacgt tgtgagctgc gggcaggacc ctgccctcct    720

aggggctgtt cgaatggggg cacctgccag ctgatgccag agaaagactc cacctttcac    780

ctctgcctct gtcccccagg tttcataggc ccagactgtg aggtgaatcc agacaactgt    840

gtcagccacc agtgtcagaa tgggggcact tgccaggatg ggctggacac ctacacctgc    900

ctctgcccag aaacctggac aggctgggac tgctccgaag atgtggatga gtgtgagacc    960

cagggtcccc ctcactgcag aaacgggggc acctgccaga actctgctgg tagctttcac   1020

tgcgtgtgtg tgagtggctg ggcggcaca agctgtgagg agaacctgga tgactgtatt   1080

gctgccacct gtgccccggg atccacctgc attgaccggg tgggctcttt ctcctgcctc   1140

tgcccacctg gacgcacagg actcctgtgc cacttggaag acatgtgtct gagccagccg   1200

tgccatgggg atgcccaatg cagcaccaac cccctcacag gctccacact ctgcctgtgt   1260

cagcctggct attcggggcc cacctgccac caggacctgg acgagtgtct gatggcccag   1320

caaggcccaa gtccctgtga acatggcggt tcctgcctca acactcctgg ctccttcaac   1380

tgcctctgtc cacctggcta cacaggctcc cgttgtgagg ctgatcacaa tgagtgcctc   1440

tcccagccct gccacccagg aagcacctgt ctggacctac ttgccacctt ccactgcctc   1500

tgcccgccag gcttagaagg gcagctctgt gaggtggaga ccaacgagtg tgcctcagct   1560

ccctgcctga accacgcgga ttgccatgac ctgctcaacg gcttccagtg catctgcctg   1620

cctggattct ccggcacccg atgtgaggag gatatcgatg aggatctggg cccgggcgag   1680

cccaaatctt gtgacaaaac tcacacatgc ccaccgtgcc cagcacctga actcctgggg   1740

ggaccgtcag tcttcctctt ccccccaaaa cccaaggaca ccctcatgat ctcccggacc   1800

cctgaggtca catgcgtggt ggtggacgtg agccacgaag accctgaggt caagttcaac   1860

tggtacgtgg acggcgtgga ggtgcataat gccaagacaa agccgcggga ggagcagtac   1920

aacagcacgt accgtgtggt cagcgtcctc accgtcctgc accaggactg gctgaatggc   1980

aaggagtaca agtgcaaggt ctccaacaaa gccctcccag cccccatcga gaaaaccatc   2040

tccaaagcca aagggcagcc ccgagaacca caggtgtaca ccctgccccc atcccgggat   2100

gagctgacca agaaccaggt cagcctgacc tgcctggtca aaggcttcta tcccagcgac   2160

atcgccgtgg agtgggagag caatgggcag ccggagaaca actacaagac cacgcctccc   2220

gtgctggact ccgacggctc cttcttcctc tacagcaagc tcaccgtgga caagagcagg   2280

tggcagcagg ggaacgtctt ctcatgctcc gtgatgcatg aggctctgca caaccactac   2340

acgcagaaga gcctctccct gtctccgggt aaatga                             2376
```

<210> SEQ ID NO 95
<211> LENGTH: 3513
<212> TYPE: DNA
<213> ORGANISM: Homo sapiens

<400> SEQUENCE: 95

```
atgcagcccc cttcactgct gctgctgctg ctgctgctgc tgctgctatg tgtctcagtg     60

gtcagaccca gagggctgct gtgtgggagt ttcccagaac cctgtgccaa tggaggcacc    120

tgcctgagcc tgtctctggg acaagggacc tgccagtgtg cccctggctt cctgggtgag    180

acgtgccagt ttcctgaccc ctgccagaac gcccagctct gccaaaatgg aggcagctgc    240

caagccctgc ttcccgctcc cctagggctc cccagctctc cctctccatt gacacccagc    300

ttcttgtgca cttgcctccc tggcttcact ggtgagagat gccaggccaa gcttgaagac    360
```

-continued

```
ccttgtcctc cctccttctg ttccaaaagg ggccgctgcc acatccaggc ctcgggccgc    420
ccacagtgct cctgcatgcc tggatggaca ggtgagcagt gccagcttcg ggacttctgt    480
tcagccaacc catgtgttaa tggaggggtg tgtctggcca cataccccca gatccagtgc    540
cactgcccac cgggcttcga gggccatgcc tgtgaacgtg atgtcaacga gtgcttccag    600
gacccaggac cctgccccaa aggcacctcc tgccataaca ccctgggctc cttccagtgc    660
ctctgccctg tggggcagga gggtccacgt tgtgagctgc gggcaggacc ctgccctcct    720
aggggctgtt cgaatggggg cacctgccag ctgatgccag agaaagactc cacctttcac    780
ctctgcctct gtcccccagg tttcataggc ccagactgtg aggtgaatcc agacaactgt    840
gtcagccacc agtgtcagaa tgggggcact tgccaggatg ggctggacac ctacacctgc    900
ctctgcccag aaacctggac aggctgggac tgctccgaag atgtggatga gtgtgagacc    960
cagggtcccc ctcactgcag aaacgggggc acctgccaga actctgctgg tagctttcac   1020
tgcgtgtgtg tgagtggctg gggcggcaca agctgtgagg agaacctgga tgactgtatt   1080
gctgccacct gtgccccggg atccacctgc attgaccggg tgggctcttt ctcctgcctc   1140
tgcccacctg gacgcacagg actcctgtgc cacttggaag acatgtgtct gagccagccg   1200
tgccatgggg atgcccaatg cagcaccaac cccctcacag gctccacact ctgcctgtgt   1260
cagcctggct attcggggcc cacctgccac caggacctgg acgagtgtct gatggcccag   1320
caaggcccaa gtccctgtga acatggcggt tcctgcctca acactcctgg ctccttcaac   1380
tgcctctgtc cacctggcta cacaggctcc cgttgtgagg ctgatcacaa tgagtgcctc   1440
tcccagccct gccacccagg aagcacctgt ctggacctac ttgccacctt ccactgcctc   1500
tgcccgccag gcttagaagg gcagctctgt gaggtggaga ccaacgagtg tgcctcagct   1560
ccctgcctga accacgcgga ttgccatgac ctgctcaacg gcttccagtg catctgcctg   1620
cctggattct ccggcacccg atgtgaggag gatatcgatg agtgcagaag ctctccctgt   1680
gccaatggtg ggcagtgcca ggaccagcct ggagccttcc actgcaagtg tctcccaggc   1740
tttgaagggc cacgctgtca aacagaggtg gatgagtgcc tgagtgaccc atgtcccgtt   1800
ggagccagct gccttgatct tccaggagcc ttcttttgcc tctgcccctc tggtttcaca   1860
ggccagctct gtgaggttcc cctgtgtgct cccaacctgt gccagcccaa gcagatatgt   1920
aaggaccaga aagacaaggc caactgcctc tgtcctgatg gaagccctgg ctgtgcccca   1980
cctgaggaca actgcacctg ccaccacggg cactgccaga gatcctcatg tgtgtgtgac   2040
gtgggttgga cggggccaga gtgtgaggca gagctagggg gctgcatctc tgcaccctgt   2100
gcccatgggg ggacctgcta cccccagccc tctggctaca actgcacctg ccctacaggc   2160
tacacaggac ccacctgtag tgaggagatg acagcttgtc actcagggcc atgtctcaat   2220
ggcggctcct gcaaccctag ccctggaggc tactactgca cctgccctcc aagccacaca   2280
gggccccagt gccaaaccag cactgactac tgtgtgtctg ccccgtgctt caatgggggt   2340
acctgtgtga acaggcctgg caccttctcc tgcctctgtg ccatgggctt ccagggcccg   2400
cgctgtgagg gaaagctccg ccccagctgt gcagacagcc cctgtaggaa tagggcaacc   2460
tgccaggaca gccctcaggg tccccgctgc ctctgcccca ctggctacac cggaggcagc   2520
tgccagactc tgatggactt atgtgcccag aagccctgcc cacgcaattc ccactgcctc   2580
cagactgggc cctccttcca ctgcttgtgc ctccagggat ggaccgggcc tctctgcaac   2640
cttccactgt cctcctgcca gaaggctgca ctgagccaag gcatagacgt ctcttccctt   2700
```

-continued

```
tgccacaatg gaggcctctg tgtcgacagc ggcccctcct atttctgcca ctgcccccct   2760
ggattccaag gcagcctgtg ccaggatcac gtgaacccag atctgggccc gggcgagccc   2820
aaatcttgtg acaaaactca cacatgccca ccgtgcccag cacctgaact cctgggggga   2880
ccgtcagtct tcctcttccc cccaaaaccc aaggacaccc tcatgatctc ccggacccct   2940
gaggtcacat gcgtggtggt ggacgtgagc cacgaagacc ctgaggtcaa gttcaactgg   3000
tacgtggacg gcgtggaggt gcataatgcc aagacaaagc cgcgggagga gcagtacaac   3060
agcacgtacc gtgtggtcag cgtcctcacc gtcctgcacc aggactggct gaatggcaag   3120
gagtacaagt gcaaggtctc caacaaagcc ctcccagccc ccatcgagaa aaccatctcc   3180
aaagccaaag ggcagccccg agaaccacag gtgtacaccc tgcccccatc ccgggatgag   3240
ctgaccaaga accaggtcag cctgacctgc ctggtcaaag gcttctatcc cagcgacatc   3300
gccgtggagt gggagagcaa tgggcagccg gagaacaact acaagaccac gcctcccgtg   3360
ctggactccg acggctcctt cttcctctac agcaagctca ccgtggacaa gagcaggtgg   3420
cagcagggga acgtcttctc atgctccgtg atgcatgagg ctctgcacaa ccactacacg   3480
cagaagagcc tctccctgtc tccgggtaaa tga                                3513
```

<210> SEQ ID NO 96
<211> LENGTH: 3243
<212> TYPE: DNA
<213> ORGANISM: Homo sapiens

<400> SEQUENCE: 96

```
atgcagcccc cttcactgct gctgctgctg ctgctgctgc tgctgctatg tgtctcagtg     60
gtcagaccca gagggctgct gtgtattgct gccacctgtg ccccgggatc cacctgcatt    120
gaccgggtgg gctctttctc ctgcctctgc ccacctggac gcacaggact cctgtgccac    180
ttggaagaca tgtgtctgag ccagccgtgc catggggatg cccaatgcag caccaacccc    240
ctcacaggct ccacactctg cctgtgtcag cctggctatt cggggcccac ctgccaccag    300
gacctggacg agtgtctgat ggcccagcaa ggcccaagtc cctgtgaaca tggcggttcc    360
tgcctcaaca ctcctggctc ctttcaactgc ctctgtccac ctggctacac aggctcccgt    420
tgtgaggctg atcacaatga gtgcctctcc cagccctgcc acccaggaag cacctgtctg    480
gacctacttg ccaccttcca ctgcctctgc ccgccaggct tagaagggca gctctgtgag    540
gtggagacca acgagtgtgc ctcagctccc tgcctgaacc acgcggattg ccatgacctg    600
ctcaacggct tccagtgcat ctgcctgcct ggattctccg gcacccgatg tgaggaggat    660
atcgatgagt gcagaagctc tccctgtgcc aatggtgggc agtgccagga ccagcctgga    720
gccttccact gcaagtgtct cccaggcttt gaagggccac gctgtcaaac agaggtggat    780
gagtgcctga gtgacccatg tcccgttgga gccagctgcc ttgatcttcc aggagccttc    840
ttttgcctct gcccctctgg tttcacaggc cagctctgtg aggttcccct gtgtgctccc    900
aacctgtgcc agcccaagca gatatgtaag gaccagaaag acaaggccaa ctgcctctgt    960
cctgatggaa gccctggctg tgccccacct gaggacaact gcacctgcca ccacgggcac   1020
tgccagagat cctcatgtgt gtgtgacgtg ggttggacgg ggccagagtg tgaggcagag   1080
ctagggggct gcatctctgc accctgtgcc catgggggga cctgctaccc ccagccctct   1140
ggctacaact gcacctgccc tacaggctac acaggaccca cctgtagtga ggagatgaca   1200
gcttgtcact cagggccatg tctcaatggc ggctcctgca accctagccc tggaggctac   1260
tactgcacct gccctccaag ccacacaggg ccccagtgcc aaaccagcac tgactactgt   1320
```

```
gtgtctgccc cgtgcttcaa tgggggtacc tgtgtgaaca ggcctggcac cttctcctgc   1380
ctctgtgcca tgggcttcca gggcccgcgc tgtgagggaa agctccgccc cagctgtgca   1440
gacagcccct gtaggaatag ggcaacctgc caggacagcc ctcagggtcc ccgctgcctc   1500
tgccccactg gctacaccgg aggcagctgc cagactctga tggacttatg tgcccagaag   1560
ccctgcccac gcaattccca ctgcctccag actgggccct ccttccactg cttgtgcctc   1620
cagggatgga ccgggcctct ctgcaacctt ccactgtcct cctgccagaa ggctgcactg   1680
agccaaggca tagacgtctc ttccctttgc cacaatggag gcctctgtgt cgacagcggc   1740
ccctcctatt tctgccactg ccccccctgga ttccaaggca gcctgtgcca ggatcacgtg   1800
aacccatgtg agtccaggcc ttgccagaac ggggccacct gcatggccca gcccagtggg   1860
tatctctgcc agtgtgcccc aggctacgat ggacagaact gctcaaagga actcgatgct   1920
tgtcagtccc aaccctgtca caaccatgga acctgtactc ccaaacctgg aggattccac   1980
tgtgcctgcc ctccaggctt tgtggggcta cgctgtgagg gagacgtgga cgagtgtctg   2040
gaccagccct gccaccccac aggcactgca gcctgccact ctctggccaa tgccttctac   2100
tgccagtgtc tgcctggaca cacaggccag tggtgtgagg tggagataga cccctgccac   2160
agccaaccct gctttcatgg agggacctgt gaggccacag caggatcacc cctgggtttc   2220
atctgccact gccccaaggg ttttgaaggc cccacctgca gccacagggc cccttcctgc   2280
ggcttccatc actgccacca cggaggcctg tgtctgccct cccctaagcc aggcttccca   2340
ccacgctgtg cctgcctcag tggctatggg ggtcctgact gcctgacccc accagctcct   2400
aaaggctgtg gccctccctc cccatgccta tacaatggca gctgctcaga gaccacgggc   2460
ttgggggggcc caggctttcg atgctcctgc cctcacagct ctccagggcc ccggtgtcag   2520
aaacccggag atctgggccc gggcgagccc aaatcttgtg acaaaactca cacatgccca   2580
ccgtgcccag cacctgaact cctgggggga ccgtcagtct tcctcttccc cccaaaaccc   2640
aaggacaccc tcatgatctc ccggacccct gaggtcacat gcgtggtggt ggacgtgagc   2700
cacgaagacc ctgaggtcaa gttcaactgg tacgtggacg gcgtggaggt gcataatgcc   2760
aagacaaagc cgcgggagga gcagtacaac agcacgtacc gtgtggtcag cgtcctcacc   2820
gtcctgcacc aggactggct gaatggcaag gagtacaagt gcaaggtctc caacaaagcc   2880
ctcccagccc ccatcgagaa aaccatctcc aaagccaaag ggcagccccg agaaccacag   2940
gtgtacaccc tgcccccatc ccgggatgag ctgaccaaga accaggtcag cctgacctgc   3000
ctggtcaaag gcttctatcc cagcgacatc gccgtggagt gggagagcaa tgggcagccg   3060
gagaacaact acaagaccac gcctcccgtg ctggactccg acggctcctt cttcctctac   3120
agcaagctca ccgtggacaa gagcaggtgg cagcagggga acgtcttctc atgctccgtg   3180
ttgcatgagg ctctgcacaa ccactacacg cagaagagcc tctccctgtc tccgggtaaa   3240
tga                                                                 3243
```

<210> SEQ ID NO 97
<211> LENGTH: 3228
<212> TYPE: DNA
<213> ORGANISM: Homo sapiens

<400> SEQUENCE: 97

```
atgtggggct ggaagtgcct cctcttctgg gctgtgctgg tcacagccac tctctgcact     60
gccaggtgta ttgctgccac ctgtgccccg ggatccacct gcattgaccg ggtgggctct    120
```

-continued

```
ttctcctgcc tctgcccacc tggacgcaca ggactcctgt gccacttgga agacatgtgt    180
ctgagccagc cgtgccatgg ggatgcccaa tgcagcacca accccctcac aggctccaca    240
ctctgcctgt gtcagcctgg ctattcgggg cccacctgcc accaggacct ggacgagtgt    300
ctgatggccc agcaaggccc aagtccctgt gaacatggcg gttcctgcct caacactcct    360
ggctccttca actgcctctg tccacctggc tacacaggct cccgttgtga ggctgatcac    420
aatgagtgcc tctcccagcc ctgccaccca ggaagcacct gtctggacct acttgccacc    480
ttccactgcc tctgcccgcc aggcttagaa gggcagctct gtgaggtgga gaccaacgag    540
tgtgcctcag ctccctgcct gaaccacgcg gattgccatg acctgctcaa cggcttccag    600
tgcatctgcc tgcctggatt ctccggcacc cgatgtgagg aggatatcga tgagtgcaga    660
agctctccct gtgccaatgg tgggcagtgc caggaccagc ctggagcctt ccactgcaag    720
tgtctcccag gctttgaagg gccacgctgt caaacagagg tggatgagtg cctgagtgac    780
ccatgtcccg ttggagccag ctgccttgat cttccaggag ccttcttttg cctctgcccc    840
tctggtttca caggccagct ctgtgaggtt cccctgtgtg ctcccaacct gtgccagccc    900
aagcagatat gtaaggacca gaaagacaag gccaactgcc tctgtcctga tggaagccct    960
ggctgtgccc cacctgagga caactgcacc tgccaccacg ggcactgcca gagatcctca   1020
tgtgtgtgtg acgtgggttg gacggggcca gagtgtgagg cagagctagg gggctgcatc   1080
tctgcaccct gtgcccatgg ggggacctgc taccccccagc cctctggcta caactgcacc  1140
tgccctacag gctacacagg acccacctgt agtgaggaga tgacagcttg tcactcaggg   1200
ccatgtctca atggcggctc ctgcaaccct agccctggag gctactactg cacctgccct   1260
ccaagccaca cagggcccca gtgccaaacc agcactgact actgtgtgtc tgccccgtgc   1320
ttcaatgggg gtacctgtgt gaacaggcct ggcaccttct cctgcctctg tgccatgggc   1380
ttccagggcc cgcgctgtga gggaaagctc cgcccccagct gtgcagacag cccctgtagg  1440
aatagggcaa cctgccagga cagccctcag ggtccccgct gcctctgccc cactggctac   1500
accggaggca gctgccagac tctgatggac ttatgtgccc agaagccctg cccacgcaat   1560
tcccactgcc tccagactgg gccctccttc cactgcttgt gcctccaggg atggaccggg   1620
cctctctgca accttccact gtcctcctgc cagaaggctg cactgagcca aggcatagac   1680
gtctcttccc tttgccacaa tggaggcctc tgtgtcgaca gcggcccctc ctatttctgc   1740
cactgccccc ctggattcca aggcagcctg tgccaggatc acgtgaaccc atgtgagtcc   1800
aggccttgcc agaacggggc cacctgcatg gcccagccca gtgggtatct ctgccagtgt   1860
gccccaggct acgatggaca gaactgctca aaggaactcg atgcttgtca gtcccaaccc   1920
tgtcacaacc atggaacctg tactcccaaa cctggaggat tccactgtgc ctgccctcca   1980
ggctttgtgg ggctacgctg tgagggagac gtggacgagt gtctggacca gccctgccac   2040
cccacaggca ctgcagcctg ccactctctg gccaatgcct tctactgcca gtgtctgcct   2100
ggacacacag gccagtggtg tgaggtggag atagacccct gccacagcca accctgcttt   2160
catggaggga cctgtgaggc cacagcagga tcacccctgg gtttcatctg ccactgcccc   2220
aagggttttg aaggccccac ctgcagccac agggcccctt cctgcggctt ccatcactgc   2280
caccacggag gcctgtgtct gccctcccct aagccaggct tcccaccacg ctgtgcctgc   2340
ctcagtggct atgggggtcc tgactgcctg accccaccag ctcctaaagg ctgtggccct   2400
ccctccccat gcctatacaa tggcagctgc tcagagacca cgggcttggg gggcccaggc   2460
tttcgatgct cctgccctca cagctctcca gggccccggt gtcagaaacc cggagatctg   2520
```

ggcccgggcg agcccaaatc ttgtgacaaa actcacacat gcccaccgtg cccagcacct 2580
gaactcctgg ggggaccgtc agtcttcctc ttccccccaa aacccaagga caccctcatg 2640
atctcccgga cccctgaggt cacatgcgtg gtggtggacg tgagccacga agaccctgag 2700
gtcaagttca actggtacgt ggacggcgtg gaggtgcata atgccaagac aaagccgcgg 2760
gaggagcagt acaacagcac gtaccgtgtg gtcagcgtcc tcaccgtcct gcaccaggac 2820
tggctgaatg gcaaggagta caagtgcaag gtctccaaca aagccctccc agcccccatc 2880
gagaaaacca tctccaaagc caaagggcag ccccgagaac cacaggtgta caccctgccc 2940
ccatcccggg atgagctgac caagaaccag gtcagcctga cctgcctggt caaaggcttc 3000
tatcccagcg acatcgccgt ggagtgggag agcaatgggc agccggagaa caactacaag 3060
accacgcctc ccgtgctgga ctccgacggc tccttcttcc tctacagcaa gctcaccgtg 3120
gacaagagca ggtggcagca ggggaacgtc ttctcatgct ccgtgatgca tgaggctctg 3180
cacaaccact acacgcagaa gagcctctcc ctgtctccgg gtaaatga 3228

<210> SEQ ID NO 98
<211> LENGTH: 2520
<212> TYPE: DNA
<213> ORGANISM: Homo sapiens

<400> SEQUENCE: 98
atgcagcccc cttcactgct gctgctgctg ctgctgctgc tgctgctatg tgtctcagtg 60
gtcagaccca gagggctgct gtgtattgct gccacctgtg ccccgggatc cacctgcatt 120
gaccgggtgg gctctttctc ctgcctctgc ccacctggac gcacaggact cctgtgccac 180
ttggaagaca tgtgtctgag ccagccgtgc catggggatg cccaatgcag caccaacccc 240
ctcacaggct ccacactctg cctgtgtcag cctggctatt cggggcccac ctgccaccag 300
gacctggacg agtgtctgat ggcccagcaa ggcccaagtc cctgtgaaca tggcggttcc 360
tgcctcaaca ctcctggctc cttcaactgc ctctgtccac ctggctacac aggctcccgt 420
tgtgaggctg atcacaatga gtgcctctcc cagccctgcc acccaggaag cacctgtctg 480
gacctacttg ccaccttcca ctgcctctgc ccgccaggct tagaagggca gctctgtgag 540
gtggagacca acgagtgtgc ctcagctccc tgcctgaacc acgcggattg ccatgacctg 600
ctcaacggct tccagtgcat ctgcctgcct ggattctccg gcacccgatg tgaggaggat 660
atcgatgagt gcagaagctc tccctgtgcc aatggtgggc agtgccagga ccagcctgga 720
gccttccact gcaagtgtct cccaggcttt gaagggccac gctgtcaaac agaggtggat 780
gagtgcctga gtgacccatg tcccgttgga gccagctgcc ttgatcttcc aggagccttc 840
ttttgcctct gcccctctgg tttcacaggc cagctctgtg aggttcccct gtgtgctccc 900
aacctgtgcc agcccaagca gatatgtaag gaccagaaag acaaggccaa ctgcctctgt 960
cctgatggaa gccctggctg tgccccacct gaggacaact gcacctgcca ccacgggcac 1020
tgccagagat cctcatgtgt gtgtgacgtg ggttggacgg ggccagagtg tgaggcagag 1080
ctagggggct gcatctctgc accctgtgcc catgggggga cctgctaccc ccagccctct 1140
ggctacaact gcacctgccc tacaggctac acaggaccca cctgtagtga ggagatgaca 1200
gcttgtcact cagggccatg tctcaatggc ggctcctgca accctagccc tggaggctac 1260
tactgcacct gccctccaag ccacacaggg ccccagtgcc aaaccagcac tgactactgt 1320
gtgtctgccc cgtgcttcaa tgggggtacc tgtgtgaaca ggcctggcac cttctcctgc 1380
ctctgtgcca tgggcttcca gggcccgcgc tgtgagggaa agctccgccc cagctgtgca 1440
gacagcccct gtaggaatag ggcaacctgc caggacagcc ctcagggtcc ccgctgcctc 1500
tgccccactg gctacaccgg aggcagctgc cagactctga tggacttatg tgcccagaag 1560
ccctgcccac gcaattccca ctgcctccag actgggccct ccttccactg cttgtgcctc 1620
cagggatgga ccgggcctct ctgcaacctt ccactgtcct cctgccagaa ggctgcactg 1680
agccaaggca tagacgtctc ttccctttgc cacaatggag gcctctgtgt cgacagcggc 1740
ccctcctatt tctgccactg ccccccctgga ttccaaggca gcctgtgcca ggatcacgtg 1800
aacccagatc tgggcccggg cgagcccaaa tcttgtgaca aaactcacac atgcccaccg 1860
tgcccagcac ctgaactcct ggggggaccg tcagtcttcc tcttcccccc aaaacccaag 1920
gacaccctca tgatctcccg gacccctgag gtcacatgcg tggtggtgga cgtgagccac 1980
gaagaccctg aggtcaagtt caactggtac gtggacggcg tggaggtgca taatgccaag 2040
acaaagccgc gggaggagca gtacaacagc acgtaccgtg tggtcagcgt cctcaccgtc 2100
ctgcaccagg actggctgaa tggcaaggag tacaagtgca aggtctccaa caaagccctc 2160
ccagccccca tcgagaaaac catctccaaa gccaaagggc agccccgaga accacaggtg 2220
tacaccctgc ccccatcccg ggatgagctg accaagaacc aggtcagcct gacctgcctg 2280
gtcaaaggct tctatcccag cgacatcgcc gtggagtggg agagcaatgg gcagccggag 2340
aacaactaca agaccacgcc tcccgtgctg gactccgacg gctccttctt cctctacagc 2400
aagctcaccg tggacaagag caggtggcag caggggaacg tcttctcatg ctccgtgatg 2460
catgaggctc tgcacaacca ctacacgcag aagagcctct ccctgtctcc gggtaaatga 2520

<210> SEQ ID NO 99
<211> LENGTH: 2505
<212> TYPE: DNA
<213> ORGANISM: Homo sapiens

<400> SEQUENCE: 99
atgtggggct ggaagtgcct cctcttctgg gctgtgctgg tcacagccac tctctgcact 60
gccaggtgta ttgctgccac ctgtgccccg ggatccacct gcattgaccg ggtgggctct 120
ttctcctgcc tctgcccacc tggacgcaca ggactcctgt gccacttgga agacatgtgt 180
ctgagccagc cgtgccatgg ggatgcccaa tgcagcacca acccccctcac aggctccaca 240 ctctgcctgt gtcagcctgg ctattcgggg cccacctgcc accaggacct ggacgagtgt 300
ctgatggccc agcaaggccc aagtccctgt gaacatggcg gttcctgcct caacactcct 360
ggctccttca actgcctctg tccacctggc tacacaggct cccgttgtga ggctgatcac 420
aatgagtgcc tctcccagcc ctgccaccca ggaagcacct gtctggacct acttgccacc 480
ttccactgcc tctgcccgcc aggcttagaa gggcagctct gtgaggtgga gaccaacgag 540
tgtgcctcag ctccctgcct gaaccacgcg gattgccatg acctgctcaa cggcttccag 600
tgcatctgcc tgcctggatt ctccggcacc cgatgtgagg aggatatcga tgagtgcaga 660
agctctccct gtgccaatgg tgggcagtgc caggaccagc ctggagcctt ccactgcaag 720
tgtctcccag gctttgaagg gccacgctgt caaacagagg tggatgagtg cctgagtgac 780
ccatgtcccg ttggagccag ctgccttgat cttccaggag ccttcttttg cctctgcccc 840
tctggtttca caggccagct ctgtgaggtt cccctgtgtg ctcccaacct gtgccagccc 900
aagcagatat gtaaggacca gaaagacaag gccaactgcc tctgtcctga tggaagccct 960
ggctgtgccc cacctgagga caactgcacc tgccaccacg ggcactgcca gagatcctca 1020
tgtgtgtgtg acgtgggttg gacggggcca gagtgtgagg cagagctagg gggctgcatc 1080
tctgcaccct gtgcccatgg ggggacctgc tacccccagc cctctggcta caactgcacc 1140
tgccctacag gctacacagg acccacctgt agtgaggaga tgacagcttg tcactcaggg 1200
ccatgtctca atggcggctc ctgcaaccct agccctggag gctactactg cacctgccct 1260
ccaagccaca cagggcccca gtgccaaacc agcactgact actgtgtgtc tgccccgtgc 1320
ttcaatgggg gtacctgtgt gaacaggcct ggcaccttct cctgcctctg tgccatgggc 1380
ttccagggcc cgcgctgtga gggaaagctc cgccccagct gtgcagacag cccctgtagg 1440
aatagggcaa cctgccagga cagccctcag ggtccccgct gcctctgccc cactggctac 1500
accggaggca gctgccagac tctgatggac ttatgtgccc agaagccctg cccacgcaat 1560
tcccactgcc tccagactgg gccctccttc cactgcttgt gcctccaggg atggaccggg 1620
cctctctgca accttccact gtcctcctgc cagaaggctg cactgagcca aggcatagac 1680
gtctcttccc tttgccacaa tggaggcctc tgtgtcgaca gcggcccctc ctatttctgc 1740
cactgccccc ctggattcca aggcagcctg tgccaggatc acgtgaaccc agatctgggc 1800
ccgggcgagc ccaaatcttg tgacaaaact cacacatgcc caccgtgccc agcacctgaa 1860
ctcctggggg gaccgtcagt cttcctcttc cccccaaaac ccaaggacac cctcatgatc 1920
tcccggaccc ctgaggtcac atgcgtggtg gtggacgtga gccacgaaga ccctgaggtc 1980
aagttcaact ggtacgtgga cggcgtggag gtgcataatg ccaagacaaa gccgcgggag 2040
gagcagtaca acagcacgta ccgtgtggtc agcgtcctca ccgtcctgca ccaggactgg 2100
ctgaatggca aggagtacaa gtgcaaggtc tccaacaaag ccctcccagc ccccatcgag 2160
aaaaccatct ccaaagccaa agggcagccc cgagaaccac aggtgtacac cctgccccca 2220
tcccgggatg agctgaccaa gaaccaggtc agcctgacct gcctggtcaa aggcttctat 2280
cccagcgaca tcgccgtgga gtgggagagc aatgggcagc cggagaacaa ctacaagacc 2340
acgcctcccg tgctggactc cgacggctcc ttcttcctct acagcaagct caccgtggac 2400
aagagcaggt ggcagcaggg gaacgtcttc tcatgctccg tgatgcatga ggctctgcac 2460
aaccactaca cgcagaagag cctctccctg tctccgggta aatga 2505

<210> SEQ ID NO 100
<211> LENGTH: 2046
<212> TYPE: DNA
<213> ORGANISM: Homo sapiens

<400> SEQUENCE: 100
atgcagcccc cttcactgct gctgctgctg ctgctgctgc tgctgctatg tgtctcagtg 60
gtcagaccca gagggctgct gtgtgcctca gctccctgcc tgaaccacgc ggattgccat 120
gacctgctca acggcttcca gtgcatctgc ctgcctggat tctccggcac ccgatgtgag 180
gaggatatcg atgagtgcag aagctctccc tgtgccaatg gtgggcagtg ccaggaccag 240
cctggagcct tccactgcaa gtgtctccca ggctttgaag ggccacgctg tcaaacagag 300
gtggatgagt gcctgagtga cccatgtccc gttggagcca gctgccttga tcttccagga 360
gccttctttt gcctctgccc ctctggtttc acaggccagc tctgtgaggt tcccctgtgt 420
gctcccaacc tgtgccagcc caagcagata tgtaaggacc agaaagacaa ggccaactgc 480
ctctgtcctg atggaagccc tggctgtgcc ccacctgagg acaactgcac ctgccaccac 540
gggcactgcc agagatcctc atgtgtgtgt gacgtgggtt ggacggggcc agagtgtgag 600
gcagagctag ggggctgcat ctctgcaccc tgtgcccatg gggggacctg ctaccccccag 660 ccctctggct acaactgcac ctgccctaca ggctacacag gacccacctg tagtgaggag 720
atgacagctt gtcactcagg gccatgtctc aatggcggct cctgcaaccc tagccctgga 780
ggctactact gcacctgccc tccaagccac acagggcccc agtgccaaac cagcactgac 840
tactgtgtgt ctgccccgtg cttcaatggg ggtacctgtg tgaacaggcc tggcaccttc 900
tcctgcctct gtgccatggg cttccagggc ccgcgctgtg agggaaagct ccgccccagc 960
tgtgcagaca gcccctgtag gaatagggca acctgccagg acagccctca gggtccccgc 1020
tgcctctgcc ccactggcta caccggaggc agctgccaga ctctgatgga cttatgtgcc 1080
cagaagccct gcccacgcaa ttcccactgc ctccagactg ggccctcctt ccactgcttg 1140
tgcctccagg gatggaccgg gcctctctgc aaccttccac tgtcctcctg ccagaaggct 1200
gcactgagcc aaggcataga cgtctcttcc ctttgccaca atggaggcct ctgtgtcgac 1260
agcggcccct cctatttctg ccactgcccc cctggattcc aaggcagcct gtgccaggat 1320
cacgtgaacc cagatctggg cccgggcgag cccaaatctt gtgacaaaac tcacacatgc 1380
ccaccgtgcc cagcacctga actcctgggg ggaccgtcag tcttcctctt ccccccaaaa 1440
cccaaggaca ccctcatgat ctcccggacc cctgaggtca catgcgtggt ggtggacgtg 1500
agccacgaag accctgaggt caagttcaac tggtacgtgg acggcgtgga ggtgcataat 1560
gccaagacaa agccgcggga ggagcagtac aacagcacgt accgtgtggt cagcgtcctc 1620
accgtcctgc accaggactg gctgaatggc aaggagtaca agtgcaaggt ctccaacaaa 1680
gccctcccag cccccatcga gaaaaccatc tccaaagcca aagggcagcc ccgagaacca 1740
caggtgtaca ccctgccccc atcccgggat gagctgacca agaaccaggt cagcctgacc 1800
tgcctggtca aaggcttcta tcccagcgac atcgccgtgg agtgggagag caatgggcag 1860
ccggagaaca actacaagac cacgcctccc gtgctggact ccgacggctc cttcttcctc 1920
tacagcaagc tcaccgtgga caagagcagg tggcagcagg ggaacgtctt ctcatgctcc 1980
gtgatgcatg aggctctgca caaccactac acgcagaaga gcctctccct gtctccgggt 2040
aaatga 2046

<210> SEQ ID NO 101
<211> LENGTH: 2031
<212> TYPE: DNA
<213> ORGANISM: Homo sapiens

<400> SEQUENCE: 101
atgtggggct ggaagtgcct cctcttctgg gctgtgctgg tcacagccac tctctgcact 60
gccaggtgtg cctcagctcc ctgcctgaac cacgcggatt gccatgacct gctcaacggc 120
ttccagtgca tctgcctgcc tggattctcc ggcacccgat gtgaggagga tatcgatgag 180
tgcagaagct ctccctgtgc caatggtggg cagtgccagg accagcctgg agccttccac 240
tgcaagtgtc tcccaggctt tgaagggcca cgctgtcaaa cagaggtgga tgagtgcctg 300
agtgacccat gtcccgttgg agccagctgc cttgatcttc caggagcctt cttttgcctc 360
tgcccctctg gtttcacagg ccagctctgt gaggttcccc tgtgtgctcc caacctgtgc 420
cagcccaagc agatatgtaa ggaccagaaa gacaaggcca actgcctctg tcctgatgga 480
agccctggct gtgccccacc tgaggacaac tgcacctgcc accacgggca ctgccagaga 540
tcctcatgtg tgtgtgacgt gggttggacg gggccagagt gtgaggcaga gctagggggc 600
tgcatctctg caccctgtgc ccatgggggg acctgctacc cccagccctc tggctacaac 660

```
tgcacctgcc ctacaggcta cacaggaccc acctgtagtg aggagatgac agcttgtcac    720

tcagggccat gtctcaatgg cggctcctgc aaccctagcc ctggaggcta ctactgcacc    780

tgccctccaa gccacacagg gccccagtgc caaaccagca ctgactactg tgtgtctgcc    840

ccgtgcttca atgggggtac ctgtgtgaac aggcctggca ccttctcctg cctctgtgcc    900

atgggcttcc agggcccgcg ctgtgaggga aagctccgcc ccagctgtgc agacagcccc    960

tgtaggaata gggcaacctg ccaggacagc cctcagggtc cccgctgcct ctgccccact   1020

ggctacaccg gaggcagctg ccagactctg atggacttat gtgcccagaa gccctgccca   1080

cgcaattccc actgcctcca gactgggccc tccttccact gcttgtgcct ccagggatgg   1140

accgggcctc tctgcaacct tccactgtcc tcctgccaga aggctgcact gagccaaggc   1200

atagacgtct cttccctttg ccacaatgga ggcctctgtg tcgacagcgg cccctcctat   1260

ttctgccact gcccccctgg attccaaggc agcctgtgcc aggatcacgt gaacccagat   1320

ctgggcccgg gcgagcccaa atcttgtgac aaaactcaca catgcccacc gtgcccagca   1380

cctgaactcc tggggggacc gtcagtcttc ctcttccccc caaaacccaa ggacaccctc   1440

atgatctccc ggacccctga ggtcacatgc gtggtggtgg acgtgagcca cgaagaccct   1500

gaggtcaagt tcaactggta cgtggacggc gtggaggtgc ataatgccaa gacaaagccg   1560

cgggaggagc agtacaacag cacgtaccgt gtggtcagcg tcctcaccgt cctgcaccag   1620

gactggctga atggcaagga gtacaagtgc aaggtctcca acaaagccct cccagccccc   1680

atcgagaaaa ccatctccaa agccaaaggg cagccccgag aaccacaggt gtacaccctg   1740

cccccatccc gggatgagct gaccaagaac caggtcagcc tgacctgcct ggtcaaaggc   1800

ttctatccca gcgacatcgc cgtggagtgg gagagcaatg ggcagccgga gaacaactac   1860

aagaccacgc ctcccgtgct ggactccgac ggctccttct tcctctacag caagctcacc   1920

gtggacaaga gcaggtggca gcaggggaac gtcttctcat gctccgtgat gcatgaggct   1980

ctgcacaacc actacacgca gaagagcctc tccctgtctc cgggtaaatg a            2031
```

<210> SEQ ID NO 102
<211> LENGTH: 1890
<212> TYPE: DNA
<213> ORGANISM: Homo sapiens

<400> SEQUENCE: 102

```
atgcagcccc cttcactgct gctgctgctg ctgctgctgc tgctgctatg tgtctcagtg     60

gtcagaccca gagggctgct gtgtgcagac agcccctgta ggaatagggc aacctgccag    120

gacagccctc agggtccccg ctgcctctgc cccactggct acaccggagg cagctgccag    180

actctgatgg acttatgtgc ccagaagccc tgcccacgca attcccactg cctccagact    240

gggccctcct tccactgctt gtgcctccag ggatggaccg ggcctctctg caaccttcca    300

ctgtcctcct gccagaaggc tgcactgagc caaggcatag acgtctcttc cctttgccac    360

aatggaggcc tctgtgtcga cagcggcccc tcctatttct gccactgccc ccctggattc    420

caaggcagcc tgtgccagga tcacgtgaac ccatgtgagt ccaggccttg ccagaacggg    480

gccacctgca tggcccagcc cagtgggtat ctctgccagt gtgccccagg ctacgatgga    540

cagaactgct caaaggaact cgatgcttgt cagtcccaac cctgtcacaa ccatggaacc    600

tgtactccca aacctggagg attccactgt gcctgccctc caggctttgt ggggctacgc    660

tgtgagggag acgtggacga gtgtctggac cagccctgcc accccacagg cactgcagcc    720
```

```
tgccactctc tggccaatgc cttctactgc cagtgtctgc ctggacacac aggccagtgg    780
tgtgaggtgg agatagaccc ctgccacagc caaccctgct ttcatggagg gacctgtgag    840
gccacagcag gatcacccct gggtttcatc tgccactgcc ccaagggttt tgaaggcccc    900
acctgcagcc acagggcccc ttcctgcggc ttccatcact gccaccacgg aggcctgtgt    960
ctgccctccc ctaagccagg cttcccacca cgctgtgcct gcctcagtgg ctatgggggt   1020
cctgactgcc tgaccccacc agctcctaaa ggctgtggcc ctccctcccc atgcctatac   1080
aatggcagct gctcagagac cacgggcttg gggggcccag gctttcgatg ctcctgccct   1140
cacagctctc cagggccccg gtgtcagaaa cccggagatc tgggcccggg cgagcccaaa   1200
tcttgtgaca aaactcacac atgcccaccg tgcccagcac ctgaactcct ggggggaccg   1260
tcagtcttcc tcttcccccc aaaacccaag gacaccctca tgatctcccg gacccctgag   1320
gtcacatgcg tggtggtgga cgtgagccac gaagaccctg aggtcaagtt caactggtac   1380
gtggacggcg tggaggtgca taatgccaag acaaagccgc gggaggagca gtacaacagc   1440
acgtaccgtg tggtcagcgt cctcaccgtc ctgcaccagg actggctgaa tggcaaggag   1500
tacaagtgca aggtctccaa caaagccctc ccagccccca tcgagaaaac catctccaaa   1560
gccaaagggc agccccgaga accacaggtg tacaccctgc ccccatcccg ggatgagctg   1620
accaagaacc aggtcagcct gacctgcctg gtcaaaggct tctatcccag cgacatcgcc   1680
gtggagtggg agagcaatgg gcagccggag aacaactaca agaccacgcc tcccgtgctg   1740
gactccgacg gctccttctt cctctacagc aagctcaccg tggacaagag caggtggcag   1800
caggggaacg tcttctcatg ctccgtgatg catgaggctc tgcacaacca ctacacgcag   1860
aagagcctct ccctgtctcc gggtaaatga                                    1890
```

<210> SEQ ID NO 103
<211> LENGTH: 1875
<212> TYPE: DNA
<213> ORGANISM: Homo sapiens

<400> SEQUENCE: 103

```
atgtggggct ggaagtgcct cctcttctgg gctgtgctgg tcacagccac tctctgcact     60
gccaggtgtg cagacagccc ctgtaggaat agggcaacct gccaggacag ccctcagggt    120
ccccgctgcc tctgccccac tggctacacc ggaggcagct gccagactct gatggactta    180
tgtgcccaga agccctgccc acgcaattcc cactgcctcc agactgggcc ctccttccac    240
tgcttgtgcc tccagggatg gaccgggcct ctctgcaacc ttccactgtc ctcctgccag    300
aaggctgcac tgagccaagg catagacgtc tcttcccttt gccacaatgg aggcctctgt    360
gtcgacagcg gcccctccta tttctgccac tgcccccctg gattccaagg cagcctgtgc    420
caggatcacg tgaacccatg tgagtccagg ccttgccaga acggggccac ctgcatggcc    480
cagcccagtg ggtatctctg ccagtgtgcc ccaggctacg atggacagaa ctgctcaaag    540
gaactcgatg cttgtcagtc ccaaccctgt cacaaccatg gaacctgtac tcccaaacct    600
ggaggattcc actgtgcctg ccctccaggc tttgtggggc tacgctgtga gggagacgtg    660
gacgagtgtc tggaccagcc ctgccacccc acaggcactg cagcctgcca ctctctggcc    720
aatgccttct actgccagtg tctgcctgga cacacaggcc agtggtgtga ggtggagata    780
gacccctgcc acagccaacc ctgctttcat ggagggacct gtgaggccac agcaggatca    840
cccctgggtt tcatctgcca ctgccccaag ggttttgaag gccccacctg cagccacagg    900
gccccttcct gcggcttcca tcactgccac cacggaggcc tgtgtctgcc ctcccctaag    960
```

```
ccaggcttcc caccacgctg tgcctgcctc agtggctatg ggggtcctga ctgcctgacc     1020

ccaccagctc ctaaaggctg tggccctccc tccccatgcc tatacaatgg cagctgctca     1080

gagaccacgg gcttgggggg cccaggcttt cgatgctcct gccctcacag ctctccaggg     1140

ccccggtgtc agaaacccgg agatctgggc ccgggcgagc ccaaatcttg tgacaaaact     1200

cacacatgcc caccgtgccc agcacctgaa ctcctggggg gaccgtcagt cttcctcttc     1260

cccccaaaac ccaaggacac cctcatgatc tcccggaccc ctgaggtcac atgcgtggtg     1320

gtggacgtga gccacgaaga ccctgaggtc aagttcaact ggtacgtgga cggcgtggag     1380

gtgcataatg ccaagacaaa gccgcgggag gagcagtaca acagcacgta ccgtgtggtc     1440

agcgtcctca ccgtcctgca ccaggactgg ctgaatggca aggagtacaa gtgcaaggtc     1500

tccaacaaag ccctcccagc ccccatcgag aaaaccatct ccaaagccaa agggcagccc     1560

cgagaaccac aggtgtacac cctgccccca tcccgggatg agctgaccaa gaaccaggtc     1620

agcctgacct gcctggtcaa aggcttctat cccagcgaca tcgccgtgga gtgggagagc     1680

aatgggcagc cggagaacaa ctacaagacc acgcctcccg tgctggactc cgacggctcc     1740

ttcttcctct acagcaagct caccgtggac aagagcaggt ggcagcaggg gaacgtcttc     1800

tcatgctccg tgatgcatga ggctctgcac aaccactaca cgcagaagag cctctccctg     1860

tctccgggta aatga                                                      1875
```

<210> SEQ ID NO 104
<211> LENGTH: 24
<212> TYPE: PRT
<213> ORGANISM: Homo sapiens

<400> SEQUENCE: 104

```
Met Gln Pro Pro Ser Leu Leu Leu Leu Leu Leu Leu Leu Leu Leu Leu
1               5                   10                  15

Cys Val Ser Val Val Arg Pro Arg
            20
```

<210> SEQ ID NO 105
<211> LENGTH: 69
<212> TYPE: DNA
<213> ORGANISM: Homo sapiens

<400> SEQUENCE: 105

```
atgcagcccc cttcactgct gctgctgctg ctgctgctgc tgctgctatg tgtctcagtg     60

gtcagaccc                                                             69
```

<210> SEQ ID NO 106
<211> LENGTH: 12
<212> TYPE: DNA
<213> ORGANISM: Homo sapiens

<400> SEQUENCE: 106

```
cagaaacccg ga                                                         12
```

<210> SEQ ID NO 107
<211> LENGTH: 12
<212> TYPE: DNA
<213> ORGANISM: Homo sapiens

<400> SEQUENCE: 107

```
tccgggtttc tg                                                         12
```

<210> SEQ ID NO 108
<211> LENGTH: 4
<212> TYPE: PRT
<213> ORGANISM: Homo sapiens

<400> SEQUENCE: 108

Gln Lys Pro Gly
1

<210> SEQ ID NO 109
<211> LENGTH: 17
<212> TYPE: DNA
<213> ORGANISM: Homo sapiens

<400> SEQUENCE: 109
cagaaacccg gagatct 17

<210> SEQ ID NO 110
<211> LENGTH: 17
<212> TYPE: DNA
<213> ORGANISM: Homo sapiens

<400> SEQUENCE: 110
agatctccgg gtttctg 17

<210> SEQ ID NO 111
<211> LENGTH: 24
<212> TYPE: DNA
<213> ORGANISM: Homo sapiens

<400> SEQUENCE: 111
cagaaacccg gagatctggg cccg 24

<210> SEQ ID NO 112
<211> LENGTH: 24
<212> TYPE: DNA
<213> ORGANISM: Homo sapiens

<400> SEQUENCE: 112
cgggcccaga tctccgggtt tctg 24

<210> SEQ ID NO 113
<211> LENGTH: 8
<212> TYPE: PRT
<213> ORGANISM: Homo sapiens

<400> SEQUENCE: 113

Gln Lys Pro Gly Asp Leu Gly Pro
1 5

<210> SEQ ID NO 114
<211> LENGTH: 12
<212> TYPE: DNA
<213> ORGANISM: Homo sapiens

<400> SEQUENCE: 114
gatatcgatg ag 12

<210> SEQ ID NO 115
<211> LENGTH: 12
<212> TYPE: DNA
<213> ORGANISM: Homo sapiens

<400> SEQUENCE: 115
ctcatcgata tc 12

<210> SEQ ID NO 116
<211> LENGTH: 4
<212> TYPE: PRT
<213> ORGANISM: Homo sapiens

<400> SEQUENCE: 116

Asp Ile Asp Glu
1

<210> SEQ ID NO 117
<211> LENGTH: 17
<212> TYPE: DNA
<213> ORGANISM: Homo sapiens

<400> SEQUENCE: 117
gatatcgatg aggatcc 17

<210> SEQ ID NO 118
<211> LENGTH: 17
<212> TYPE: DNA
<213> ORGANISM: Homo sapiens

<400> SEQUENCE: 118
ggatcctcat cgatatc 17

<210> SEQ ID NO 119
<211> LENGTH: 24
<212> TYPE: DNA
<213> ORGANISM: Homo sapiens

<400> SEQUENCE: 119
gatatcgatg aggatctggg cccg 24

<210> SEQ ID NO 120
<211> LENGTH: 24
<212> TYPE: DNA
<213> ORGANISM: Homo sapiens

<400> SEQUENCE: 120
cgggcccaga tcctcatcga tatc 24

<210> SEQ ID NO 121
<211> LENGTH: 8
<212> TYPE: PRT
<213> ORGANISM: Homo sapiens

<400> SEQUENCE: 121

Asp Ile Asp Glu Asp Leu Gly Pro
1               5

<210> SEQ ID NO 122
<211> LENGTH: 12
<212> TYPE: DNA
<213> ORGANISM: Homo sapiens

<400> SEQUENCE: 122
cacgtgaacc ca 12

<210> SEQ ID NO 123
<211> LENGTH: 12
<212> TYPE: DNA

<213> ORGANISM: Homo sapiens

<400> SEQUENCE: 123
tgggttcacg tg 12

<210> SEQ ID NO 124
<211> LENGTH: 4
<212> TYPE: PRT
<213> ORGANISM: Homo sapiens

<400> SEQUENCE: 124

His Val Asn Pro
1

<210> SEQ ID NO 125
<211> LENGTH: 17
<212> TYPE: DNA
<213> ORGANISM: Homo sapiens

<400> SEQUENCE: 125
cacgtgaacc cagatct 17

<210> SEQ ID NO 126
<211> LENGTH: 17
<212> TYPE: DNA
<213> ORGANISM: Homo sapiens

<400> SEQUENCE: 126
agatctgggt tcacgtg 17

<210> SEQ ID NO 127
<211> LENGTH: 24
<212> TYPE: DNA
<213> ORGANISM: Homo sapiens

<400> SEQUENCE: 127
cacgtgaacc cagatctggg cccg 24

<210> SEQ ID NO 128
<211> LENGTH: 24
<212> TYPE: DNA
<213> ORGANISM: Homo sapiens

<400> SEQUENCE: 128
cgggcccaga tctgggttca cgtg 24

<210> SEQ ID NO 129
<211> LENGTH: 8
<212> TYPE: PRT
<213> ORGANISM: Homo sapiens

<400> SEQUENCE: 129

His Val Asn Pro Asp Leu Gly Pro
1 5

<210> SEQ ID NO 130
<211> LENGTH: 23
<212> TYPE: PRT
<213> ORGANISM: Homo sapiens

<400> SEQUENCE: 130

Met Pro Pro Leu Leu Ala Pro Leu Leu Cys Leu Ala Leu Leu Pro Ala
1 5 10 15

-continued

```
Leu Ala Ala Arg Gly Pro Arg
            20


<210> SEQ ID NO 131
<211> LENGTH: 27
<212> TYPE: PRT
<213> ORGANISM: Homo sapiens

<400> SEQUENCE: 131

Met Gln Pro Pro Ser Leu Leu Leu Leu Leu Leu Leu Leu Leu Leu Leu
1               5                   10                  15

Cys Val Ser Val Val Arg Pro Arg Gly Leu Leu
            20                  25
```

COMPOSITIONS OF HUMANIZED NOTCH FUSION PROTEINS AND METHODS OF TREATMENT

This application is a §371 national stage of PCT International Application No. PCT/US2008/010045, filed Aug. 22, 2008, and claims the benefit of U.S. Provisional Application No. 60/966,052, filed Aug. 23, 2007, the contents of all of which are hereby incorporated by reference into this application.

This invention was made with government support under grant number HL62454 awarded by the National Institutes of Health, grant number DAMRDCW81XWH-04-1-054 awarded by the Department of Defense, and grant number DAMD17-03-1-0218 awarded by the Department of Defense. The government has certain rights in the invention.

Throughout this application, various publications are referenced by arabic numbers within parentheses or by author and publication date within parentheses. Full citations for these publications may be found at the end of the specification. The disclosures of these publications are hereby incorporated by reference into this application to describe more fully the art to which this invention pertains.

BACKGROUND OF THE INVENTION

Vascular Development

During mammalian embryogenesis, formation of the vascular system is an early and essential process. In the embryo, vascular development initiates with the pluripotent hemangioblast derived from the paraxial and lateral plate mesoderm. The hemangioblast has the potential to differentiate into either a hematopoietic progenitor or an endothelial cell progenitor, known as the angioblast.

Vascular development begins with a process known as vasculogenesis whereby angioblasts differentiate into endothelial cells and migrate together to form the primitive vascular plexus. This initial vascular network consists of vessels that are homogenous in size and made up wholly of endothelial cells. The vascular plexus is then remodeled via angiogenesis.

Angiogenesis involves the sprouting of new vessels, the migration of these vessels into avascular regions, and the recruitment of accessory cells, pericytes and smooth muscle cells (Gale and Yancopoulos, 1999). The smooth muscle cells that differentiate and form the contractile vessel walls originate from multiple progenitors including neural crest cells, mesenchymal cells and even endothelial cells (Owens, 1995). In adults, angiogenesis is involved in follicular development, wound healing, and pathological processes such as tumor angiogenesis and heart disease.

The Notch Family and Notch Ligands

Studies of *Drosophila, C. Elegans*, zebrafish and mammals have demonstrated that the Notch pathway is an evolutionarily conserved signaling mechanism that functions to modulate numerous cell-fate decisions. Notch signaling is required for the proper patterning of cells originating from all three germ layers. Depending on the cellular context, Notch signaling may both inhibit and induce differentiation, induce proliferation, and promote cell survival (Artavanis-Tsakonas et al., 1995; Lewis, 1998; Weinmaster, 1997). In *Drosophila*, a single Notch protein is activated by two ligands, Serrate and Delta. In mammals these families have been expanded to four Notch genes (Notch1, Notch2, Notch3 and Notch4) and five ligands, 2 Serrate-like (Jagged1-2) and 3 Delta (Dl1, 3, 4) (Bettenhausen et al., 1995; Dunwoodie et al., 1997; Gallahan and Callahan, 1997; Lardelli et al., 1994; Lindsell et al., 1995; Shawber et al., 1996a; Shutter et al., 2000a; Uyttendaele et al., 1996; Weinmaster et al., 1992; Weinmaster et al., 1991). During embryogenesis, Notch receptors and ligands are expressed in dynamic spatial and temporal patterns. However, it is not known if all ligands activate all receptors.

Notch Signaling and Function

Notch signaling influences many different types of cell-fate decisions by providing inhibitory, inductive or proliferative signals depending on the environmental context (reviewed in Artavanis-Tsakonas et al., 1995; Greenwald, 1998; Robey, 1997; Vervoort et al., 1997). This pleiotropic function suggests that Notch modulates multiple signaling pathways in a spatio-temporal manner.

Consistent with Notch regulating cell-fate decisions, both the receptors and ligands are cell surface proteins with single transmembrane domains (FIG. 1). The regulatory extracellular domain of Notch proteins consists largely of tandemly arranged EGF-like repeats that are required for ligand binding (Artavanis-Tsakonas et al., 1995; Weinmaster, 1998). C-terminal to the EGF-like repeats are an additional three cysteine-rich repeats, designated the LIN12/Notch repeats (LNR) (Greenwald, 1994). Downstream of the LNR lies the proteolytic cleavage sequence (RXRR) that is recognized by a furin-like convertase. For Notch1, cleavage at this site yields a 180 kilodalton extracellular peptide and a 120 kilodalton intracellular peptide that are held together to generate a heterodimeric receptor at the cell surface (Blaumueller et al., 1997; Kopan et al., 1996; Logeat et al., 1998).

The intracellular domain of Notch (NotchICD, FIG. 1) rescues loss-of-function Notch phenotypes indicating that this form of Notch signals constitutively (Fortini and Artavanis-Tsakonas, 1993; Lyman and Young, 1993; Rebay et al., 1993; Struhl et al., 1993).

The cytoplasmic domain of Notch contains three identifiable domains: the RAM domain, the ankyrin repeat domain and the C-terminal PEST domain (FIG. 1). Upon ligand-activation Notch undergoes two additional proteolytic cleavages which results in the release of the cytoplasmic domain (Weinmaster, 1998). This Notch peptide translocates to the nucleus and interacts with transcriptional repressors known as CSL (CBF, Su (H), Lag-2) and converts it to transcriptional activator. The CSL/Notch interaction is dependent on the presence of the RAM domain of Notch; while, transcriptional activity also requires the presence of the ankyrin repeats (Hsieh et al., 1996; Hsieh et al., 1997; Roehl et al., 1996; Tamura et al., 1995; Wettstein et al., 1997). Both in vivo and in vitro studies indicate that the HES and Hey genes are the direct targets of Notch/CSL-dependent signaling (Bailey and Posakony, 1995; Eastman et al., 1997; Henderson et al., 2001; Jarriault et al., 1995; Nakagawa et al., 2000; Wettstein et al., 1997). The HES and Hey genes are bHLH transcriptional repressor that bind DNA at N-boxes (Nakagawa et al., 2000; Sasai et al., 1992; Tietze et al., 1992). Notch has also been proposed to signal by a CSL-independent pathway. In fact, expression of just the ankyrin repeat domain is necessary and sufficient for some forms of Notch signaling (Lieber et al., 1993; Matsuno et al., 1997; Shawber et al., 1996b).

Finally, the PEST domain has been implicated in protein turnover by a SEL-10/ubiquitin-dependent pathway (Greenwald, 1994; Oberg et al., 2001; Rogers et al., 1986; Wu et al., 1998; Wu et al., 2001). Similar to the receptors, the extracellular domain of the Notch ligands also consist mostly of tandemly arranged EGF-like repeats (FIG. 1). Upstream of these repeats is a divergent EGF-like repeat known as the DSL (Delta, Serrate, Lag-2) that is required for ligand binding and activation of the receptors (Artavanis-Tsakonas et al., 1995).

Notch Signaling and Vascular Development

Although many of the genes that function to induce vasculogenesis and angiogenesis have been identified, little is known about how cell-fate decisions are specified during vascular development. A number of observations suggest that the Notch signaling pathway may play a role in cell fate determination and patterning of the vascular system.

Notch1, Notch4, Jagged1 and Dll4 are all expressed in the developing vasculature, while Notch3 is expressed in the accessory smooth muscle cells (Krebs et al., 2000; Shutter et al., 2000b; Uyttendaele et al., 1996; Villa et al., 2001; Xue et al., 1999). Mice lacking Jagged1 are embryonic lethal and have severe vascular defects (Xue et al., 1999). Mice nullizygous for Notch1 are embryonic lethal and die of severe neuronal defects, but also have defects in angiogenesis (Krebs et al., 2000; Swiatek et al., 1994). Mice lacking Notch4 are born and appear to be normal, but embryos that have lost both Notch1 and Notch4 die at E9.5 of severe hemorrhaging and vascular patterning defects indicating Notch1 and Notch4 may be functionally redundant during vascular development (Krebs et al., 2000). Exogenous expression of an activated form of Notch4 in endothelium also resulted in vascular defects similar to those seen for the double Notch1/Notch4 nullizygous mice, suggesting that appropriate levels of Notch signaling is critical for proper development of the embryonic vasculature (Uyttendaele et al., 2001).

Taken together, the data from mice mutant for Notch/Notch signaling components uncover several processes dependent on Notch including vascular remodeling, arterial venous specification, vascular smooth muscle cell recruitment and heart/heart outflow vessel development.

Recent experiments have implicated Notch signaling in arterial/venous endothelial cell specification. In situ analysis of E13.5 embryos found that Notch1, Notch3, Notch4, Dl4, Jagged1 and Jagged2 expression was restricted to the arteries and absent in the veins (Villa et al., 2001). Consistent with expression data, disruption of Notch signaling in Zebrafish was associated with loss of the arterial marker ephrinB2; while, ectopic expression of an activated form of Notch lead to a loss in the venous cell marker EphB4 within the dorsal aorta (Lawson et al., 2001). These data suggest that Notch signaling may help to specify arterial and venous cell fates during angiogenesis.

Taken together, the data from mice mutant for Notch/Notch signaling components uncover several processes dependent on Notch including vascular remodeling, arterial venous specification, vascular smooth muscle cell recruitment and heart/heart outflow vessel development.

Notch signaling has also been suggested to function in the adult vascular system. In humans, missense mutations in the extracellular domain of Notch3 correlate with the development of the degenerative vascular disease, CADASIL (Caronti et al., 1998; Desmond et al., 1998; Joutel et al., 2000; Joutel et al., 1996). In a wound healing model, an increase in Jagged1 expression was observed at the regenerating endothelial wound edge, suggesting Notch signaling may function during processes of adult angiogenesis (Lindner et al., 2001). Taken together these data support Notch signaling functions at a number of critical steps during vascular development: vasculogenesis, vascular patterning/angiogenesis, and arterial/venous specification. However, the molecular mechanism(s) by which the Notch signaling pathways influence these different steps has yet to be elucidated.

Significance

Shimizu et al. (*J. Biol. Chem.* 274(46): 32961-32969 (1999)) describe the use of Notch1ECD/Fc, Notch2ECD/Fc and Notch3ECD/Fc in binding studies. However, Shimizu et al. do not mention the use of such proteins for inhibiting angiogenesis.

U.S. Pat. No. 6,379,925 issued Apr. 30, 2002 to Kitajewski et al. describes murine Notch4. However, it does not describe Notch-based fusion proteins as set forth in the subject application.

Notch proteins play key roles in developmental decisions involving the vasculature, the hematopoietic system, and the nervous system. As such, an understanding of their function is key to understanding how cell-fate decisions and commitment are controlled during development and in adult tissues. To date, several reports on Notch or Notch ligand gene disruptions have described vascular phenotypes providing emphasis that this pathway is a fundamental part of the machinery that guides vascular development. Aberrant Notch activity has been linked to human pathologies; including both cancer and vascular disorders (CADASIL). The analysis of Notch in tumor angiogenesis has only recently begun; however, our discovery of potential downstream targets of Notch suggests a role in pathological processes associated with angiogenesis. For instance, VEGFR-3 has been linked to both tumor angiogenesis and tumor lymphangiogenesis. The expression or function of several other potential Notch targets has also been linked to tumor angiogenesis; including ephrinB2, Id3, Angiopoietin 1, and PDGF-B. Insights on the role of these targets in Notch gene function will clearly facilitate future analysis of Notch in human pathologies.

SUMMARY OF THE INVENTION

This invention provides a fusion protein comprising a signal peptide, an extracellular domain of human Notch receptor protein and an Fc portion of an antibody bound thereto.

This invention provides a method for treating a subject having a tumor comprising administering to the subject an amount of the above fusion protein effective to treat the subject, thereby treating the subject having a tumor.

This invention provides a method for inhibiting angiogenesis in a subject comprising administering to the subject an amount of the above fusion protein effective to inhibit angiogenesis in the subject, thereby inhibiting angiogenesis in the subject.

This invention provides a method for treating a subject having ovarian cancer comprising administering to the subject an amount of the above fusion protein effective to treat the subject, thereby treating the subject having ovarian cancer.

This invention provides a method for treating a subject having a metabolic disorder comprising administering to the subject an amount of the above fusion protein effective to treat the subject, thereby treating the subject having a metabolic disorder.

This invention provides use of the above fusion protein for the preparation of a pharmaceutical composition for the treatment of a subject having a tumor.

This invention provides use of the above fusion protein for the preparation of a pharmaceutical composition for inhibiting angiogenesis in a subject.

This invention provides use of the above fusion protein for the preparation of a pharmaceutical composition for treating a subject having ovarian cancer.

This invention provides use of the above fusion protein for the preparation of a pharmaceutical composition for for treating a subject having a metabolic disorder.

This invention provides a method for inhibiting physiological lymphangiogenesis or pathological lymphangionesis in a subject comprising administering to the subject an amount of the above fusion protein effective to inhibit physiological lymphangiogenesis or pathological lymphangionesis in the subject.

This invention provides a method of inhibiting tumor metastasis in a subject comprising administering to the subject an amount of the above fusion protein effective to inhibit tumor metastasis in the subject.

This invention provides a method of inhibiting growth of a secondary tumor in a subject comprising administering to the subject an amount of the above fusion protein of effective to inhibit growth of the secondary tumor in the subject.

This invention provides a method of inhibiting blood vessel cooption by a tumor in subject comprising administering to the subject an amount of the above fusion protein effective to inhibit blood vessel cooption by a tumor in the subject.

This invention provides a method of treating cancer in a subject comprising administering to the subject the above fusion protein and an inhibitor of Vascular Endothelial Growth Factor (VEGF), VEGF-A, P1GF, VEGF-B, VEGF-C, or VEGF-D, each in an amount effective to treat the cancer in the subject.

This invention provides a method of treating cancer in a subject comprising administering to the subject the above fusion protein and a VEGF receptor antagonist, a VEGFR-1 antagonist, a VEGFR-2 antagonist or a VEGFR-3 antagonist, each in an amount effective to treat the cancer in the subject.

This invention provides a method of treating cancer in a subject comprising administering to the subject the above fusion protein and an inhibitor of Platelet Derived Growth Factor (PDGF), PDGF-A or PDGF-B, each in an amount effective to treat the cancer in the subject.

This invention provides a method of treating cancer in a subject comprising administering to the subject the above fusion protein and a PDGF receptor antagonist, each in an amount effective to treat the cancer in the subject.

This invention provides a method of treating cancer in a subject comprising administering to the subject the above fusion protein and an inhibitor of HER2/neu, each in an amount effective to treat the cancer in the subject.

This invention provides a method of treating vascular proliferative retinopathy comprising administering to the subject the above fusion protein in an amount effective to treat the vascular proliferative retinopathy.

BRIEF DESCRIPTION OF THE FIGURES

FIG. 10 This Figure shows the amino acid sequence of the extracellular domain of the rat Notch1 protein (SEQ ID NO:1) and a linker sequence (SEQ ID NO:2).

FIG. 11 This Figure shows the amino acid sequence of the extracellular domain of the rat Notch2 protein (SEQ ID NO:3) and a linker sequence (SEQ ID NO:2).

FIG. 12 This Figure shows the amino acid sequence of the extracellular domain of the mouse Notch3 protein (SEQ ID NO:4).

FIG. 13 This Figure shows the amino acid sequence of the extracellular domain of the mouse Notch4 protein (SEQ ID NO:5) and a linker sequence (SEQ ID NO:2).

FIGS. 14A and 14B This Figure shows the nucleic acid sequence of the extracellular domain of the rat Notch1 gene (SEQ ID NO:6).

FIGS. 15A and 15B This Figure shows the nucleic acid sequence of the extracellular domain of the rat Notch2 gene (SEQ ID NO:7).

FIGS. 16A and 16B This Figure shows the nucleic acid sequence of the extracellular domain of the mouse Notch3 gene (SEQ ID NO:8).

FIGS. 17A and 17B This Figure shows the nucleic acid sequence of the extracellular domain of the mouse Notch4 gene (SEQ ID NO:9) and the nucleic acid sequence (SEQ ID NO:10) and the amino acid sequence (SEQ ID NO:2) of a linker sequence.

FIGS. 18A and 18B This Figure shows the nucleic acid sequence of the extracellular domain of the human Notch1 gene (SEQ ID NO:11).

FIGS. 19A and 19B This Figure shows the nucleic acid sequence of the extracellular domain of the human Notch2 gene (SEQ ID NO:12).

FIGS. 20A and 20B This Figure shows the nucleic acid sequence of the extracellular domain of the human Notch3 gene (SEQ ID NO:13).

FIGS. 21A and 21B This Figure shows the nucleic acid sequence of the extracellular domain of the human Notch4 gene (SEQ ID NO:14).

FIG. 22A shows RT-PCR analysis of Notch and Notch ligand expression. Numbers show PCR cycles. FIG. 22B shows the effect of transduced VEGF on CSL reporter activity. FIG. 22C shows the effect of SU5416 on CSL reporter activity transactivated by Ad-VEGF. FIG. 22D shows the construct of Notch decoy (N1ECDFc). FIG. 22E shows secretion of N1ECDFc from HUVEC transduced with Ad-N1ECDFc. FIG. 22F shows the effect of N1ECDFc against ligand-induced CSL reporter activity in a co-culture assay (□: (–); ■: 0.33 ng pHyTC-N1ECDFc; ■: 0.67 ng pHyTC-N1ECDFc). FIGS. 22G-I show the effect of N1ECDFc against Ad-VEGF-transduced HUVEC. Notch signaling was activated with transduction of Ad-VEGF in HUVEC in the absence or presence of co-transduction of Ad-N1ECDFc at indicated dosage. FIG. 22G shows the effect of N1ECDFc on CSL reporter activity transactivated by Ad-VEGF. FIG. 22H shows inhibition of budding of Ad-VEGF-transduced HUVEC with co-transduction of Ad-N1ECDFc at 40 MOI. FIG. 22I shows quantification of the effect of N1ECDFc on budding of Ad-VEGF-transduced HUVEC (□: bud; ■: cell number).

FIGS. 23A-23C show the effect of inhibitors for receptor tyrosine kinases on Notch-induced HUVEC budding. FIG. 23A is a photograph of budding of Ad-N1IC-transduced HUVEC treated with PD166866, ZD1893 at 1 μM and SU5416 at 0.5 μM. FIG. 23B shows quantification of the effect of inhibitors at 1 μM (□: bud; ■: cell number). FIG. 23C shows dose-dependency of the effect of SU5416 (□: bud; ■: cell number). FIGS. 23D-E show induction of Flt-1 expression in Ad-N1IC-transduced HUVEC. FIG. 23D shows RT-PCR analysis of Flt-1 mRNA expression. FIG. 23E shows W.B. analysis of Flt-1 protein expression. FIGS. 23F-G show promotion of Notch-induced HUVEC budding with PlGF stimulation. Ad-N1IC-transduced HUVEC were cultured on collagen gel with SFM, instead of complete medium, in the absence or presence of 50 ng/ml PlGF. FIG. 23F shows PlGF-induced budding of Ad-N1IC-transduced HUVEC (arrow head: buds with single filopodia; arrow: buds with multiple filopodia). FIG. 23G shows the quantification of the effect of PlGF on budding of Ad-N1IC-transduced HUVEC (□: multi; ■: total). FIGS. 23H-I show the effect of Flt-1 siRNA transfection on Flt1 expression. Ad-N1IC-transduced HUVEC were transfected with 200 pmol of either control (CT) or Flt-1 siRNA. FIG. 23H shows the reduction of Flt-1 mRNA expression. FIG. 23I shows the reduction of Flt-1 protein expression. FIG. 23J shows the effect of Flt-1 siRNA transfection on Notch-induced HUVEC budding. Ad-N1IC-transduced HUVEC were transfected with either 100 or 200 pmol of siRNA and cultured on collagen gel for 2 days.

FIGS. 24A-B show gelatin zymography analysis of MMP-9 and MMP-2 activity stimulated by VEGF in HUVEC. FIG. 24A shows the effect of N1ECDFc on MMP-9 activity. Transduced HUVEC were cultured on fibrin gel on the indicated day (i.e. D2, D4, D6, D8). Similar results were also obtained by using collagen gel, although induction of MMP-9 was stronger on fibrin gel than collagen gel (data not shown). FIG. 24B shows the effect of N1ECDFc on MMP-2 activity. HUVEC were transduced with Ad-N1ECDFc at the indicated doses and condition medium was collected from HUVEC cultured on collagen gel at day 4. FIGS. 24C-D show up-regulation of MMP-9 and MT1-MMP with Notch signaling. HUVEC were transduced with either Ad-LacZ or Ad-N1IC at 40 MOI. Numbers show PCR cycles. FIG. 24C shows RT-PCR analysis of the effect of Notch signaling on expression of MMP-9 and MMP-2. FIG. 24D shows the induction of MT1-MMP expression of both transcript and protein with Notch signaling. FIG. 24E shows RT-PCR analysis of MMP-9 and MT1-MMP expression in Ad-VEGF-HUVEC with co-transduction of Ad-N1ECDFc. HUVEC were transduced with Ad-VEGF in the absence or presence of co-transduction of Ad-N1ECDFc at 40 MOI each. Ad-LacZ was co-transduced to make the same total amount of adenovirus at 80 MOI.

FIGS. 25A-25D show inhibition of VEGF-induced angiogenesis with N1ECDFc in mouse DAS assay. Representative photographs are shown. FIG. 25A show subcutaneous induced angiogenesis with 293/VEGF transfectant versus 293/VEGF also expressing Notch decoy (Notch-based fusion protein) N1ECDFc. FIG. 25B shows the quantitation of degree of vascularization induced by 293/VEGF in control versus 293 expressing Notch decoy (Notch-based fusion protein)—N1ECDFc. FIG. 25C shows subcutaneous induced angiogenesis with Ad-LacZ infected MDA-MB-231 cells versus Ad-N1ECDFc (Notch-based fusion protein) infected MDA-MB-231 cells. MDA-MB-231 breast cancer cells produce VEGF (data not shown). FIG. 25D shows quantitation of degree of vascularization induced by Ad-LacZ infected MDA-MB-231 cells versus Ad-N1ECDFc (Notch-based fusion protein) infected MDA-MB-231 cells.

FIG. 26A shows the effect of transduced VEGF on proliferation. FIG. 26B shows the inhibitory effect of SU5416. Ad-VEGF-transduced HUVEC were treated with SU5416 at the indicated dosages.

FIG. 28A shows the effect of transduced N1IC and Notch fusion protein on the proliferation of HUVEC. Transduced HUVEC were suspended in complete medium and then plated at $1\times10^4$ cells/well in 24-well multiwell plates with 0.4 ml of indicated medium (□: Ad-N1IC; ■: Ad-N1ECDFc). FIG. 28B shows the effect of Notch fusion protein on proliferation of KP1/VEGF transfectants. Transduced KP1/VEGF transfectants were suspended in RPMI1640 medium and then plated at $2\times10^4$ cells/well in 24-well multiwell plates with 0.5 ml of medium.

FIG. 30A shows reduction of Flk-1 mRNA and protein expression in Ad-VEGF-HUVEC with transfection of 200 pmol Flk-1 siRNA. Ad-VEGF-HUVEC at a MOI of 40 pfu/cell were transfected with 200 pmol of either control (CT) or Flk-1 siRNA. Total RNA was isolated 48 hours after transfection. Total cell lysate was collected from serum starved cells with SFM for 48 hours after transfection. FIGS. 30B and 30C show the inhibitory effect of Flk-1 siRNA transfection on either VEGF or Notch-induced HUVEC buds. Either Ad-N1IC- or Ad-VEGF-HUVEC at a MOI of 40 pfu/cell were transfected with 200 pmol of siRNA as indicated and cultured on collagen gel for 5 days. FIG. 30B shows the effect of Flk-1 siRNA transfection on HUVEC buds (□: Ad-VEGF; ■: Ad-N1IC). FIG. 30C shows quantification of the inhibitory effect of Flk-1 siRNA transfection.

FIG. 31A shows the effect of GM6001 on Notch-induced HUVEC buds. FIG. 31B shows quantification of the inhibitory effect of GM6001.

FIG. 32A shows a schematic of Notch1 decoy (N1ECDFc) and Western blotting to detect secreted Notch1 decoy in conditioned medium. HUVECs transduced with adenovirus coding Notch1 decoy (Ad-N1ECDFc) at indicated m.o.i. FIG. 32B shows that Notch1 decoy inhibits ligand-induced CSL reporter activity in co-culture signaling assay. Activation of Notch signaling was measured in HeLa cells expressing Notch1 co-cultured with 293 cells expressing Notch ligands. Data is shown as mean±SD. FIG. 32C shows ectopic expression of Notch4 induces the morphogenesis of HUVECs cultured on fibrin gel. HUVECs were transduced with adenovirus encoding Notch4 (Ad-Notch4) at 30 m.o.i. and Ad-GFP at 10 m.o.i, to mark infected cells. Two days later, HUVECs were co-cultured with stable HUVEC transfectants on fibrin gel and morphological changes were documented using fluorescence microscopy. Notch 4 induces cell extensions (upper left, white arrows) and treatment with 200 nM compound E blocks Notch4-induced extensions (upper right). Notch1 decoy expression blocks Notch4-induced cell extensions. Adenovirus-transduced HUVECs were co-cultured on fibrin gels with stable HUVEC transfectants expressing either Fc (lower left) or Notch1 decoy (lower right) and photographed two days later. Bar=200 μm. FIG. 32D shows quantification of effect of Notch signal inhibition on Notch4-induced extensions. Reduction in sprouting was statistically significant after treatment with compound E and transduction of N1ECDFc ($p<0.0001$, both; data is shown as mean±SD).

FIG. 33A shows quantitative RT-PCR analysis of the expression of Notch ligands showing induction of Jagged1 and Dll1 in Mm5MT transfectants expressing FGF4 (Mm5MT-FGF4), compared to mock transfectants (Mm5MT-X). FIG. 33B shows Jagged1 protein is elevated in Mm5MT-FGF4 versus Mm5MT-X, as determined by western blotting. FIG. 33C shows reduction of Notch ligand expression in Mm5MT-FGF4 cells with PD166866, an inhibitor of FGF receptor kinase. FIG. 33DB shows immunohistochemical analysis of Jagged1 staining in Mm5MT transfectants. Bar=50 μm.

FIG. 34A shows tumor volumes of Mm5MT-FGF4-X and Mm5MT-FGF4-Fc differ significantly from Mm5MT-FGF4-N1ECDFc transfectants in mice (day 21, $P=0.037$ and $P=0.008$, Mm5MT-FGF4-X and Mm5MT-FGF4-Fc versus Mm5MT-FGF4-N1ECDFc respectively; data is shown as mean±SD). FIG. 34B shows immunohistochemical analysis of neovessels with CD31 staining within tumors of Mm5MT-FGF4 transfectants. Upper panels, Bar=100 μm, Lower panels, Bar=50 μm. FIG. 34C shows quantitative analysis demonstrated a reduction in CD31(+) neovessels in Mm5MT-FGF4-N1ECDFc transfectants as compared to Fc or mock-transfected tumors ($P<0.001$ for both Mm5MT-FGF4-X and Mm5MT-FGF4-Fc versus Mm5MT-FGF4-N1ECDFc; data is shown as mean±SD). Xenografts were harvested 22 days after inoculation and stained with anti-CD31 antibody.

FIG. 38A shows Western blotting analysis of myosin expression in C2C12 cells. FIG. 38B shows morphometric analysis of Myosin-positive cells. Results from differentiation experiments were analyzed by scoring the number of Myosin-immunostained cells as percentage of all DAPI-positive cells. FIG. 38C shows DBD-Foxo1ADA reporter gene assays. We carried out reporter gene assays using the canonical Foxo1-responsive Igfbp1 promoter (left panel) and the Hes1 promoter (right panel) in cells co-transfected with Foxo1-ADA or DBD-Foxo1ADA. Western blot (inset) demonstrates that expression levels of the two proteins are similar. An asterisk indicates P<0.01 by ANOVA.

FIG. 55 This Figure shows the human Notch1/Fc fusion sequence for all constructs that end after EGF Repeat 36 of human Notch1.

FIG. 56 This Figure shows the human Notch1/Fc fusion sequence for all constructs that end after EGF Repeat 13 of human Notch1.

FIG. 57 This Figure shows the human Notch1/Fc fusion sequence for all constructs that end after EGF Repeat 23 of human Notch1.

FIG. 58 This Figure shows the human Notch1/Fc fusion sequence for all constructs that end after EGF Repeat 24 of human Notch1.

FIGS. 59A and 59B This Figure shows the full-length amino acid (aa) sequence of human Notch1, consisting of aa residue 1 (M=methionine) to aa residue 2555 (K=lysine) (SEQ ID NO: 52). The signal peptide and first 36 EGF-like repeat domains are present in aa 1-1433 of this sequence. Amino acids 1-1433, or a subset of these aa, were utilized for the design of the human Notch1 decoy proteins, described in the ensuing sections. The amino acids encompassing EGF-repeats 1-36 are underlined.

FIG. 60 This Figure shows the human Fc amino acid sequence utilized to generate the Fc tag on Notch1 decoy proteins (SEQ ID NO: 53). The 237 amino acids of human Fc were fused at the C-terminus of all Notch1 decoy constructs, just downstream of Notch1EGF-like repeats. This region of human Fc allows for detection and purification of the Notch decoys and serves to stabilize the secreted human Notch1-human Fc fusion proteins.

FIG. 61 This Figure shows the amino acid sequence of h-Notch1$^{(1-36)}$ decoy protein (SEQ ID NO: 54). h-Notch1$^{(1-36)}$ decoy protein consists of the following three components: (1) human Notch1 signal sequence consisting of amino acids 1-23 of human Notch1, followed by (2) amino acids encoding the EGF-like repeats 1-36 of human Notch1 consisting of amino acids 24-1433 followed by (3) amino acids 1434-1670 that contain the human HC tag. The predicted signal peptide sequence is underlined and the human Fc tag is underlined and italicized. This formulation contains 1670 amino acids.

FIG. 62 This Figure shows the amino acid sequence of h-Notch1$^{(1-13)}$ decoy protein (SEQ ID NO: 55). h-Notch1$^{(1-13)}$ decoy protein consists of the following three components: (1) human Notch1 signal sequence consisting of amino acids 1-23 of human Notch1, followed by (2) amino acids encoding the EGF-like repeats 1-13 of human Notch1 consisting of amino acids 24-531 followed by (3) amino acids 532-768 that contain the human Fc tag. The predicted signal peptide sequence is underlined and the human Fc tag is underlined and italicized. This formulation contains 768 amino acids.

FIG. 63 This Figure shows the amino acid sequence of h-Notch1$^{(1-24)}$ decoy protein (SEQ ID NO: 56). h-Notch1$^{(1-24)}$ decoy protein consists of the following three components: (1) human Notch1 signal sequence consisting of amino acids 1-23 of human Notch1, followed by (2) amino acids encoding the EGF-like repeats 1-24 of human Notch1 consisting of amino acids 24-948 followed by (3) amino acids 949-1185 that contain the human Fc tag. The predicted signal peptide sequence is underlined and the human Fc tag is underlined and italicized. This formulation contains 1185 amino acids.

FIG. 64 This Figure shows the amino acid sequence of h-sp$^{N}$Notch1$^{(9-23)}$ decoy protein (SEQ ID NO: 57). h-sp$^{N}$-Notch1$^{(9-23)}$ decoy protein consists of the following three components: (1) human Notch1 signal sequence consisting of amino acids 1-23 of human Notch1, followed by (2) amino acids encoding the EGF-like repeats 9-23 of human Notch1 consisting of amino acids 24-594 followed by (3) amino acids 595-831 that contain the human Fc tag. The predicted signal peptide sequence is underlined and the human Fc tag is underlined and italicized. This formulation contains 829 amino acids.

FIG. 65 This Figure shows the amino acid sequence of h-sp$^{HC}$Notch1$^{(9-23)}$ decoy protein (SEQ ID NO: 58). h-sp$^{HC}$-Notch1$^{(9-23)}$ decoy protein consists of the following three components: (1) human HC signal sequence consisting of amino acids 1-22 of human HC, followed by (2) amino acids encoding the EGF-like repeats 9-23 of human Notch1 consisting of amino acids 23-593 followed by (3) amino acids 594-830 that contain the human HC tag. The predicted signal peptide sequence is underlined and the human Fc tag is underlined and italicized. This formulation contains 829 amino acids.

FIG. 66 This Figure shows the amino acid sequence of h-sp$^{N}$Notch1$^{(9-36)}$ decoy protein (SEQ ID NO: 59). The abbreviation sp$^{N}$ denotes that the human Notch1 signal peptide is used in this formulation. h-sp$^{N}$Notch1$^{(9-36)}$ decoy protein consists of the following three components: (1) human Notch1 signal sequence consisting of amino acids 1-23 of human Notch1, followed by (2) amino acids encoding the EGF-like repeats 9-36 of human Notch1 consisting of amino acids 24-1118 followed by (3) amino acids 1119-1355 that contain the human Fc tag. The predicted signal peptide sequence is underlined and the human Fc tag is underlined and italicized. This formulation contains 1355 amino acids.

FIG. 67 This Figure shows the amino acid sequence of h-sp$^{HC}$Notch1$^{(9-36)}$ decoy protein (SEQ ID NO: 60). The abbreviation $sp^{HC}$ denotes that the human HC signal peptide is used in this formulation. h-$sp^{HC}$Notch1$^{(9-36)}$ decoy protein consists of the following three components: (1) human HC signal sequence consisting of amino acids 1-22 of human HC, followed by (2) amino acids encoding the EGF-like repeats 9-36 of human Notch1 consisting of amino acids 23-1117 followed by (3) amino acids 1118-1354 that contain the human HC tag. The predicted signal peptide sequence is underlined and the human Fc tag is underlined and italicized. This formulation contains 1354 amino acids.

FIG. 68 This Figure shows the amino acid sequence of h-$sp^{N}$Notch1$^{(13-24)}$ decoy protein (SEQ ID NO: 61). The abbreviation $sp^{N}$ denotes that the human Notch1 signal peptide is used in this formulation. h-$sp^{N}$Notch1$^{(13-24)}$ decoy protein consists of the following three components: (1) human Notch1 signal sequence consisting of amino acids 1-23 of human Notch1, followed by (2) amino acids encoding the EGF-like repeats 13-24 of human Notch1 consisting of amino acids 24-478 followed by (3) amino acids 479-715 that contain the human Fc tag. The predicted signal peptide sequence is underlined and the human Fc tag is underlined and italicized. This formulation contains 715 amino acids.

FIG. 69 This Figure shows the amino acid sequence of h-$sp^{HC}$Notch1$^{(13-24)}$ decoy protein (SEQ ID NO: 62). The abbreviation $sp^{HC}$ denotes that the human HC signal peptide is used in this formulation. h-$sp^{HC}$Notch1$^{(13-24)}$ decoy protein consists of the following three components: (1) human HC signal sequence consisting of amino acids 1-22 of human HC, followed by (2) amino acids encoding the EGF-like repeats 13-24 of human Notch1 consisting of amino acids 23-477 followed by (3) amino acids 478-714 that contain the human Fc tag. The predicted signal peptide sequence is underlined and the human Fc tag is underlined and italicized. This formulation contains 714 amino acids.

FIG. 70 This Figure shows the amino acid sequence of h-$sp^{N}$Notch1$^{(25-36)}$ decoy protein (SEQ ID NO: 63). The abbreviation $sp^{N}$ denotes that the human Notch1 signal peptide is used in this formulation. h-$sp^{N}$Notch1$^{(25-36)}$ decoy protein consists of the following three components: (1) human Notch1 signal sequence consisting of amino acids 1-23 of human Notch1, followed by (2) amino acids encoding the EGF-like repeats 25-36 of human Notch1 consisting of amino acids 24-508 followed by (3) amino acids 509-745 that contain the human Fc tag. The predicted signal peptide sequence is underlined and the human Fc tag is underlined and italicized. This formulation contains 745 amino acids.

FIG. 71 This Figure shows the amino acid sequence of h-$sp^{HC}$Notch1$^{(25-36)}$ decoy protein (SEQ ID NO: 64). The abbreviation $sp^{HC}$ denotes that the human HC signal peptide is used in this formulation. h-$sp^{HC}$Notch1$^{(25-36)}$ decoy protein consists of the following three components: (1) human HC signal sequence consisting of amino acids 1-22 of human HC, followed by (2) amino acids encoding the EGF-like repeats 25-36 of human Notch1 consisting of amino acids 23-507 followed by (3) amino acids 508-744 that contain the human HC tag. The predicted signal peptide sequence is underlined and the human Fc tag is underlined and italicized. This formulation contains 744 amino acids.

FIGS. 72A and 72B This Figure shows the nucleic acid sequence which encodes h-Notch1$^{(1-36)}$ decoy protein set forth in FIG. 61 (SEQ ID NO: 65).

FIG. 73 This Figure shows the nucleic acid sequence which encodes h-Notch1$^{(1-13)}$ decoy protein set forth in FIG. 62 (SEQ ID NO: 66).

FIGS. 74A and 74B This Figure shows the nucleic acid sequence which encodes h-Notch1$^{(1-24)}$ decoy protein set forth in FIG. 63 (SEQ ID NO: 67).

FIG. 75 This Figure shows the nucleic acid sequence which encodes h-$sp^{N}$Notch1$^{(9-23)}$ decoy protein set forth in FIG. 64 (SEQ ID NO: 68).

FIG. 76 This Figure shows the nucleic acid sequence which encodes h-$sp^{HC}$Notch1$^{(9-23)}$ decoy protein set forth in FIG. 65 (SEQ ID NO: 69).

FIGS. 77A and 77B This Figure shows the nucleic acid sequence which encodes h-$sp^{N}$Notch1$^{(9-36)}$ decoy protein set forth in FIG. 66 (SEQ ID NO: 70).

FIGS. 78A and 78B This Figure shows the nucleic acid sequence which encodes h-$sp^{Hc}$Notch1$^{(9-36)}$ decoy protein set forth in FIG. 67 (SEQ ID NO: 71).

FIG. 79 This Figure shows the nucleic acid sequence which encodes h-$sp^{N}$Notch1$^{(13-24)}$ decoy protein set forth in FIG. 68 (SEQ ID NO: 72).

FIG. 80 This Figure shows the nucleic acid sequence which encodes h-$sp^{Hc}$Notch1$^{(13-24)}$ decoy protein set forth in FIG. 69 (SEQ ID NO: 73).

FIG. 81 This Figure shows the nucleic acid sequence which encodes h-$sp^{N}$Notch1$^{(25-36)}$ decoy protein set forth in FIG. 70 (SEQ ID NO: 74).

FIG. 82 This Figure shows the nucleic acid sequence which encodes h-$sp^{Hc}$Notch1$^{(25-36)}$ decoy protein set forth in FIG. 71 (SEQ ID NO: 75).

FIG. 83 This Figure shows the full-length amino acid (aa) sequence of human Notch4, consisting of aa 1 (M=methionine) to aa 2003 (K=lysine) (SEQ ID NO: 76). The signal peptide and first 29 EGF-like repeat domains are present in aa 1-1174 of this sequence. Amino acids 1-1174, or a subset of these aa, were utilized for the design of the human Notch4 decoy proteins, described in the ensuing sections. The amino acids encompassing EGF-repeats 1-29 are underlined.

FIG. 84 This Figure shows the Human Fc sequence utilized to generate the Fc tag on Notch4 decoy proteins (SEQ ID NO: 77). The 237 amino acids of human Fc, shown here, were fused at the C-terminus of all Notch4 decoy constructs, just downstream of Notch4 EGF-like repeats. This region of human Fc allows for detection and purification of the Notch decoys and serves to stabilize the secreted human Notch4-human Fc fusion proteins.

FIG. 85 This Figure shows the amino acid sequence of h-Notch4$^{(1-29)}$ decoy protein (SEQ ID NO: 78). h-Notch4$^{1-29)}$ decoy protein consists of the following three components: (1) human Notch4 signal sequence consisting of amino acids 1-27 of human Notch4, followed by (2) amino acids encoding the EGF-like repeats 1-29 of human Notch4 consisting of amino acids 28-1173 followed by (3) amino acids 1174-1410 that contain the human HC tag. The predicted signal peptide sequence is underlined and the human Fc tag is underlined and italicized. This formulation contains 1410 amino acids.

FIG. 86 This Figure shows the amino acid sequence of h-Notch4$^{(1-13)}$ decoy protein (SEQ ID NO: 79). h-Notch4$^{(1-13)}$ decoy protein consists of the following three components: (1) human Notch4 signal sequence consisting of amino acids 1-27 of human Notch4, followed by (2) amino acids encoding the EGF-like repeats 1-13 of human Notch4 consisting of amino acids 28-554 followed by (3) amino acids 555-791 that contain the human Fc tag. The predicted signal peptide sequence is underlined and the human Fc tag is underlined and italicized. This formulation contains 791 amino acids.

FIG. 87 This Figure shows the amino acid sequence of h-Notch4$^{(1-23)}$ decoy protein (SEQ ID NO: 80). h-Notch4$^{(1-23)}$ decoy protein consists of the following three components: (1) human Notch4 signal sequence consisting of amino acids 1-27 of human Notch4, followed by (2) amino acids encoding the EGF-like repeats 1-23 of human Notch4 consisting of amino acids 28-933 followed by (3) amino acids 934-1170 that contain the human Fc tag. The predicted signal peptide sequence is underlined and the human Fc tag is underlined and italicized. This formulation contains 1170 amino acids.

Figure 1:
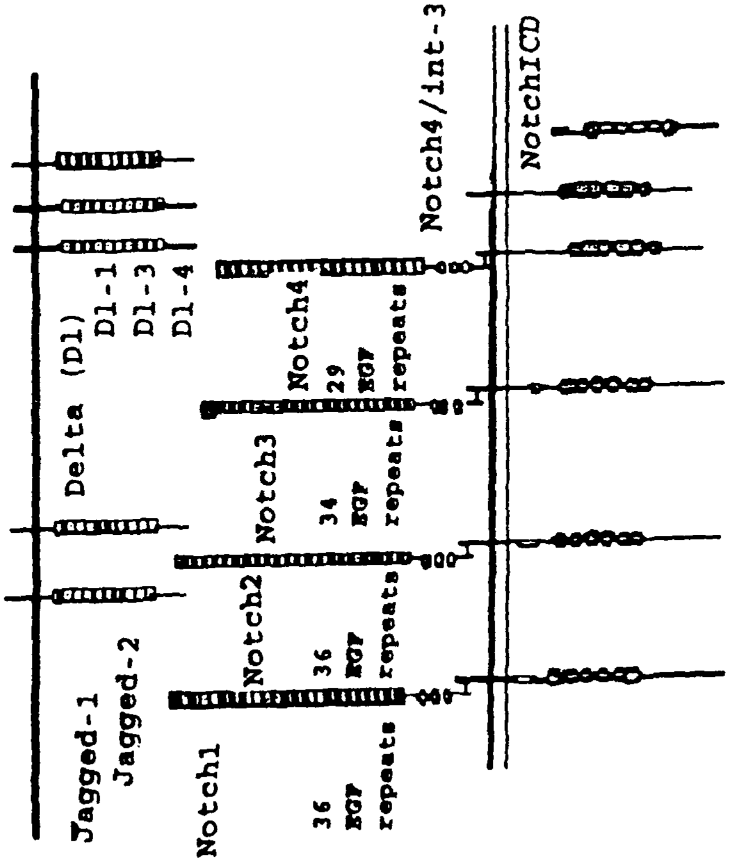
FIG. 1 This Figure shows the schematic structure of Notch and Notch ligands: Notch1, Notch2, Notch3, Notch4, Jagged-1, Jagged-2, Delta-like 1, Delta-like 3, Delta-like 4.

FIG. 88 This Figure shows the amino acid sequence of h-sp$^N$Notch4$^{(9-23)}$ decoy protein (SEQ ID NO: 81). The abbreviation sp$^N$ denotes that the human Notch4 signal peptide is used in this formulation. h-sp$^N$Notch4$^{(9-23)}$ decoy protein consists of the following three components: (1) human Notch4 signal sequence consisting of amino acids 1-27 of human Notch4, followed by (2) amino acids encoding the EGF-like repeats 9-23 of human Notch4 consisting of amino acids 28-602 followed by (3) amino acids 603-839 that contain the human Fc tag. The predicted signal peptide sequence is underlined and the human Fc tag is underlined and italicized. This formulation contains 839 amino acids.

FIG. 89 This Figure shows the amino acid sequence of h-sp$^{HC}$Notch4$^{(9-23)}$ decoy protein (SEQ ID NO: 82). The abbreviation sp$^{HC}$ denotes that the human HC signal peptide is used in this formulation. h-sp$^{HC}$Notch4$^{(9-23)}$ decoy protein consists of the following three components: (1) human HC signal sequence consisting of amino acids 1-22 of human HC, followed by (2) amino acids encoding the EGF-like repeats 9-23 of human Notch4 consisting of amino acids 23-597 followed by (3) amino acids 598-834 that contain the human Fc tag. The predicted signal peptide sequence is underlined and the human Fc tag is underlined and italicized. This formulation contains 834 amino acids.

FIG. 90 This Figure shows the amino acid sequence of h-sp$^N$Notch4$^{(9-29)}$ decoy protein (SEQ ID NO: 83). The abbreviation sp$^N$ denotes that the human Notch4 signal peptide is used in this formulation. h-sp$^N$Notch4$^{(9-29)}$ decoy protein consists of the following three components: (1) human Notch4 signal sequence consisting of amino acids 1-27 of human Notch4, followed by (2) amino acids encoding the EGF-like repeats 9-29 of human Notch4 consisting of amino acids 28-843 followed by (3) amino acids 844-1080 that contain the human Fc tag. The predicted signal peptide sequence is underlined and the human Fc tag is underlined and italicized. This formulation contains 1080 amino acids.

FIG. 91 This Figure shows the amino acid sequence of h-sp$^{HC}$Notch4$^{(9-29)}$ decoy protein (SEQ ID NO: 84). The abbreviation sp$^{HC}$ denotes that the human HC signal peptide is used in this formulation. h-sp$^{HC}$Notch4$^{(9-29)}$ decoy protein consists of the following three components: (1) human HC signal sequence consisting of amino acids 1-22 of human HC, followed by (2) amino acids encoding the EGF-like repeats 9-29 of human Notch4 consisting of amino acids 23-838 followed by (3) amino acids 839-1075 that contain the human Fc tag. The predicted signal peptide sequence is underlined and the human Fc tag is underlined and italicized. This formulation contains 1075 amino acids.

FIG. 92 This Figure shows the amino acid sequence of h-sp$^N$Notch4$^{(13-23)}$ decoy protein (SEQ ID NO: 85). The abbreviation sp$^N$ denotes that the human Notch4 signal peptide is used in this formulation. h-sp$^N$Notch4$^{(13-23)}$ decoy protein consists of the following three components: (1) human Notch4 signal sequence consisting of amino acids 1-27 of human Notch4, followed by (2) amino acids encoding the EGF-like repeats 13-23 of human Notch4 consisting of amino acids 28-444 followed by (3) amino acids 445-681 that contain the human Fc tag. The predicted signal peptide sequence is underlined and the human Fc tag is underlined and italicized. This formulation contains 681 amino acids.

FIG. 93 This Figure shows the amino acid sequence of h-sp$^{HC}$Notch4$^{(13-23)}$ decoy protein (SEQ ID NO: 86). The abbreviation sp$^{HC}$ denotes that the human HC signal peptide is used in this formulation. h-sp$^{HC}$Notch4$^{(13-23)}$ decoy protein consists of the following three components: (1) human HC signal sequence consisting of amino acids 1-22 of human HC, followed by (2) amino acids encoding the EGF-like repeats 13-23 of human Notch4 consisting of amino acids 23-439 followed by (3) amino acids 440-676 that contain the human Fc tag. The predicted signal peptide sequence is underlined and the human Fc tag is underlined and italicized. This formulation contains 676 amino acids.

FIG. 94 This Figure shows the amino acid sequence of h-sp$^N$Notch4$^{(21-29)}$ decoy protein (SEQ ID NO: 87). The abbreviation sp$^N$ denotes that the human Notch4 signal peptide is used in this formulation. h-sp$^N$Notch4$^{(21-29)}$ decoy protein consists of the following three components: (1) human Notch4 signal sequence consisting of amino acids 1-27 of human Notch4, followed by (2) amino acids encoding the EGF-like repeats 21-29 of human Notch4 consisting of amino acids 28-392 followed by (3) amino acids 393-629 that contain the human Fc tag. The predicted signal peptide sequence is underlined and the human Fc tag is underlined and italicized. This formulation contains 629 amino acids.

FIG. 95 This Figure shows the amino acid sequence of h-sp$^{HC}$Notch4$^{(21-29)}$ decoy protein (SEQ ID NO: 88). The abbreviation sp$^{HC}$ denotes that the human HC signal peptide is used in this formulation. h-sp$^{HC}$Notch4$^{(21-29)}$ decoy protein consists of the following three components: (1) human HC signal sequence consisting of amino acids 1-22 of human HC, followed by (2) amino acids encoding the EGF-like repeats 21-29 of human Notch4 consisting of amino acids 23-387 followed by (3) amino acids 388-624 that contain the human Fc tag. The predicted signal peptide sequence is underlined and the human Fc tag is underlined and italicized. This formulation contains 624 amino acids.

FIGS. 96A and 96B This Figure shows the nucleic acid sequence of human Notch4 (SEQ ID NO: 89).

FIG. 97 This Figure shows human Notch4 signal peptide sequence (SEQ ID NO: 90). The underlined sequence encodes Signal Peptide.

FIG. 98 This Figure shows the nucleic acid sequence of human HC signal peptide (nt 1-66) (SEQ ID NO: 91).

FIG. 99 This Figure shows the nucleic acid sequence of the human FC Tag (SEQ ID NO: 92).

FIG. 100 This Figure shows the nucleic acid sequence which encodes h-Notch4$^{(1-29)}$ decoy protein (SEQ ID NO: 93). Human Notch4 decoy (EGF like repeats 1-29) [nt 1-3522].

FIG. 101 This Figure shows the nucleic acid sequence which encodes h-Notch4$^{(1-13)}$ decoy protein (SEQ ID NO: 94). Human Notch4 decoy (EGF like repeats 1-13) [nt 1-1662].

FIG. 102 This Figure shows the nucleic acid sequence which encodes h-Notch4$^{(1-23)}$ decoy protein (SEQ ID NO: 95). Human Notch4 decoy (EGF like repeats 1-23) [nt1-2799].

FIG. 103 This Figure shows the nucleic acid sequence which encodes h-sp$^N$Notch4$^{(9-29)}$ decoy protein (SEQ ID NO: 96). Human Notch4 decoy (EGF like repeats 9-29) [nt 1-81, 1075-3522].

FIG. 104 This Figure shows the nucleic acid sequence which encodes h-sp$^{HC}$Notch4$^{(9-29)}$ decoy protein (SEQ ID NO: 97). Human Notch4 decoy (EGF like repeats 9-29) [nt 1075-3522] & HC Signal Peptide [nt 1-66].

FIG. 105 This Figure shows the nucleic acid sequence which encodes h-sp$^N$Notch4$^{(9-23)}$ decoy protein (SEQ ID NO: 98). Human Notch4 decoy (EGF like repeats 9-23) [nt 1-81, 1075-2799].

FIG. 106 This Figure shows the nucleic acid sequence which encodes h-sp$^{HC}$Notch4$^{(9-23)}$ decoy protein (SEQ ID NO: 99). Human Notch4 decoy (EGF like repeats 9-23) [nt 1075-2799] & HC Signal Peptide [nt 1-66].

FIG. 107 This Figure shows the nucleic acid sequence which encodes h-sp$^{N}$Notch4$^{(13-23)}$ decoy protein (SEQ ID NO: 100). Human Notch4 decoy (EGF like repeats 13-23) [nt 1-81, 1549-2799].

FIG. 108 This Figure shows the nucleic acid sequence which encodes h-sp$^{HC}$Notch4$^{(13-23)}$ decoy protein (SEQ ID NO: 101). Human Notch4 decoy (EGF like repeats 13-23) [nt 1549-2799] & HC Signal Peptide [nt 1-66].

FIG. 109 This Figure shows the nucleic acid sequence which encodes h-sp$^{N}$Notch4$^{(21-29)}$ decoy protein (SEQ ID NO: 102). Human Notch4 decoy (EGF like repeats 21-29) [nt 1-81, 2428-3522].

FIG. 110 This Figure shows the nucleic acid sequence which encodes h-sp$^{HC}$Notch4$^{(21-29)}$ decoy protein (SEQ ID NO: 103). Human Notch4 decoy (EGF like repeats 21-29) [nt 2428-3522] & HC Signal Peptide [nt 1-66].

Figure 111:
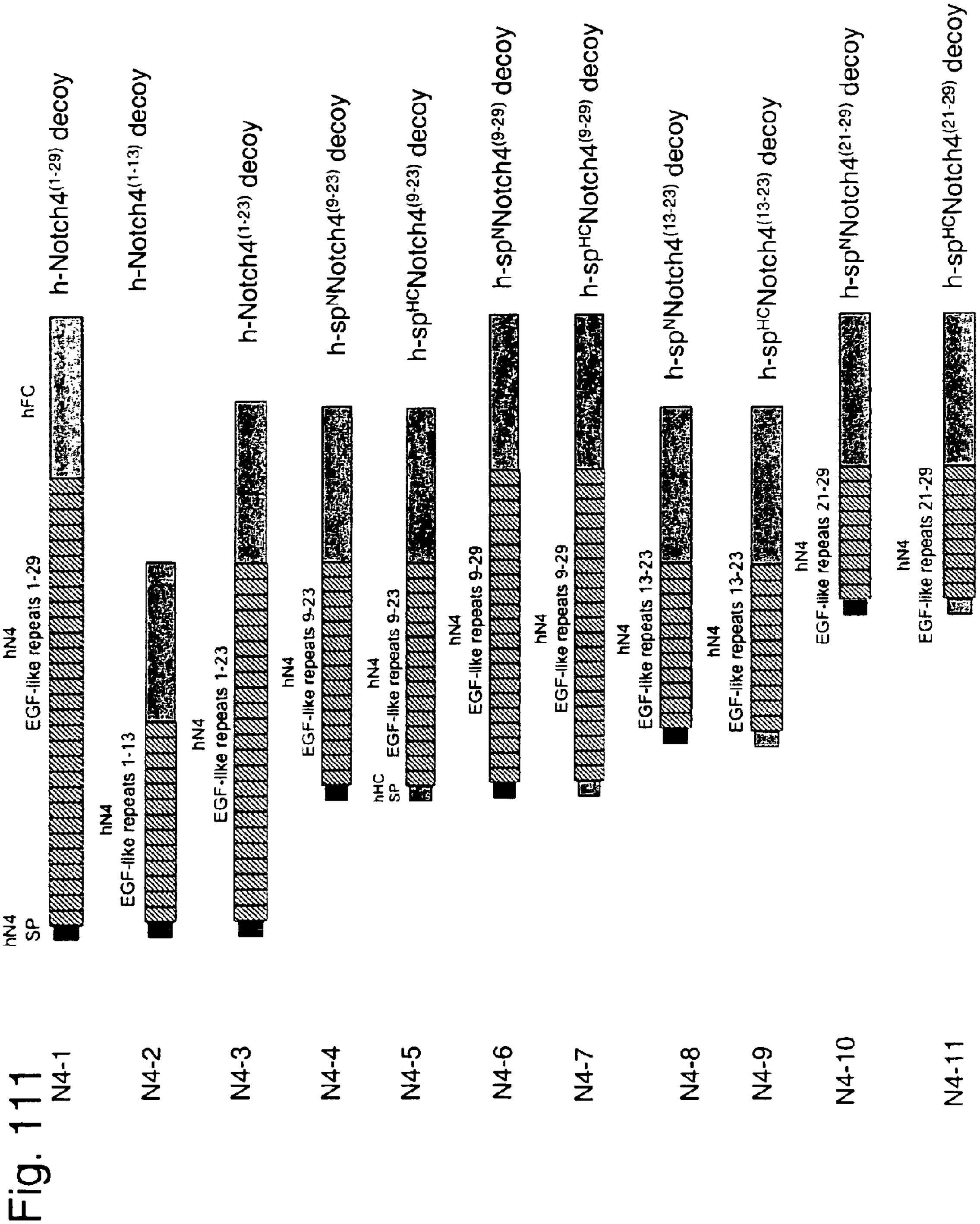

FIG. 111 This Figure shows a schematization of eleven formulations of human Notch4 decoys.

Figure 112:
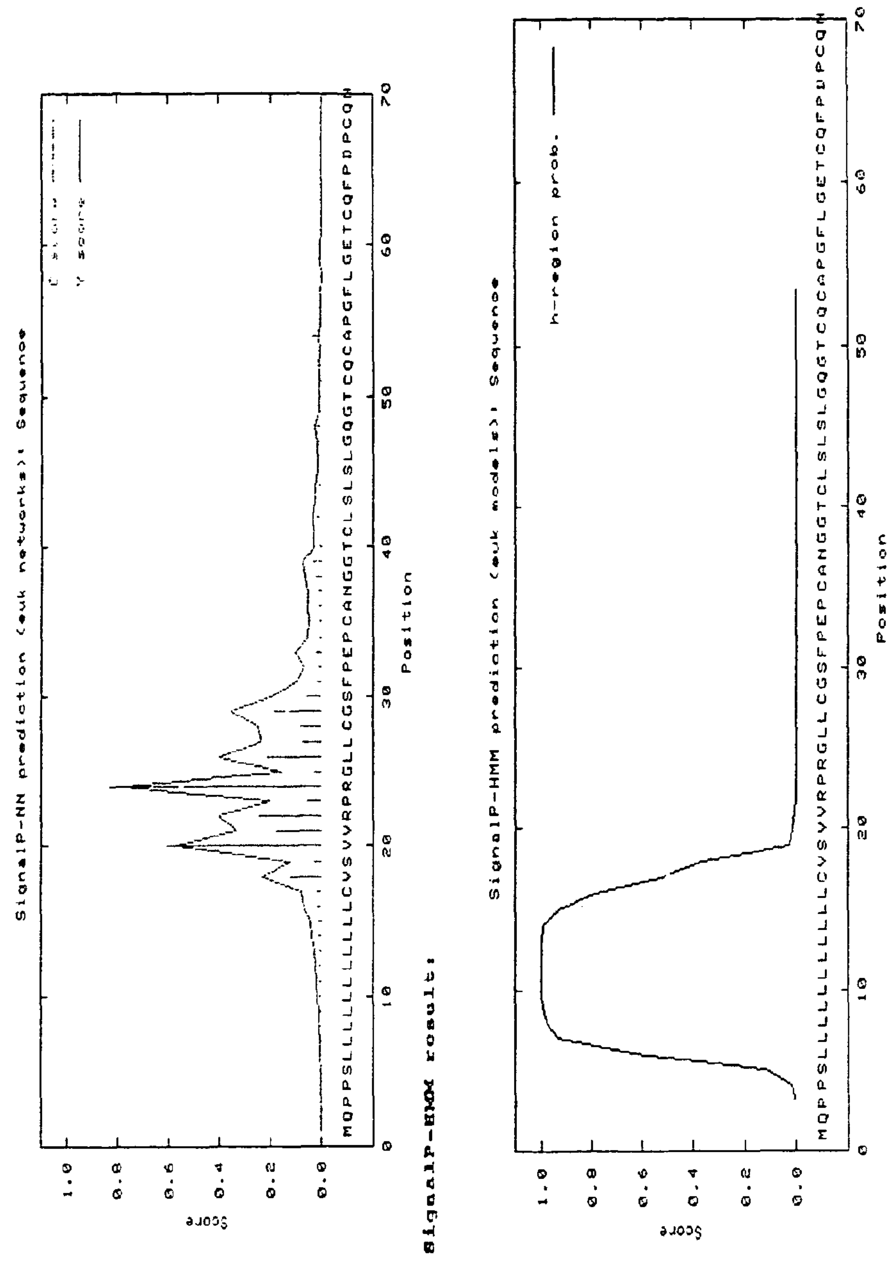

FIG. 112 This Figure shows signal sequence analysis of Notch 4 to determine where Notch4 signal peptide ends.

FIG. 113 This Figure shows the human Notch4/Fc fusion sequence for all constructs that end after EGF Repeat 29 of human Notch4.

FIG. 114 This Figure shows the human Notch4/Fc fusion sequence for all constructs that end after EGF Repeat 13 of human Notch4.

FIG. 115 This Figure shows the human Notch4/Fc fusion sequence for all constructs that end after EGF Repeat 23 of human Notch4.

Figure 116:
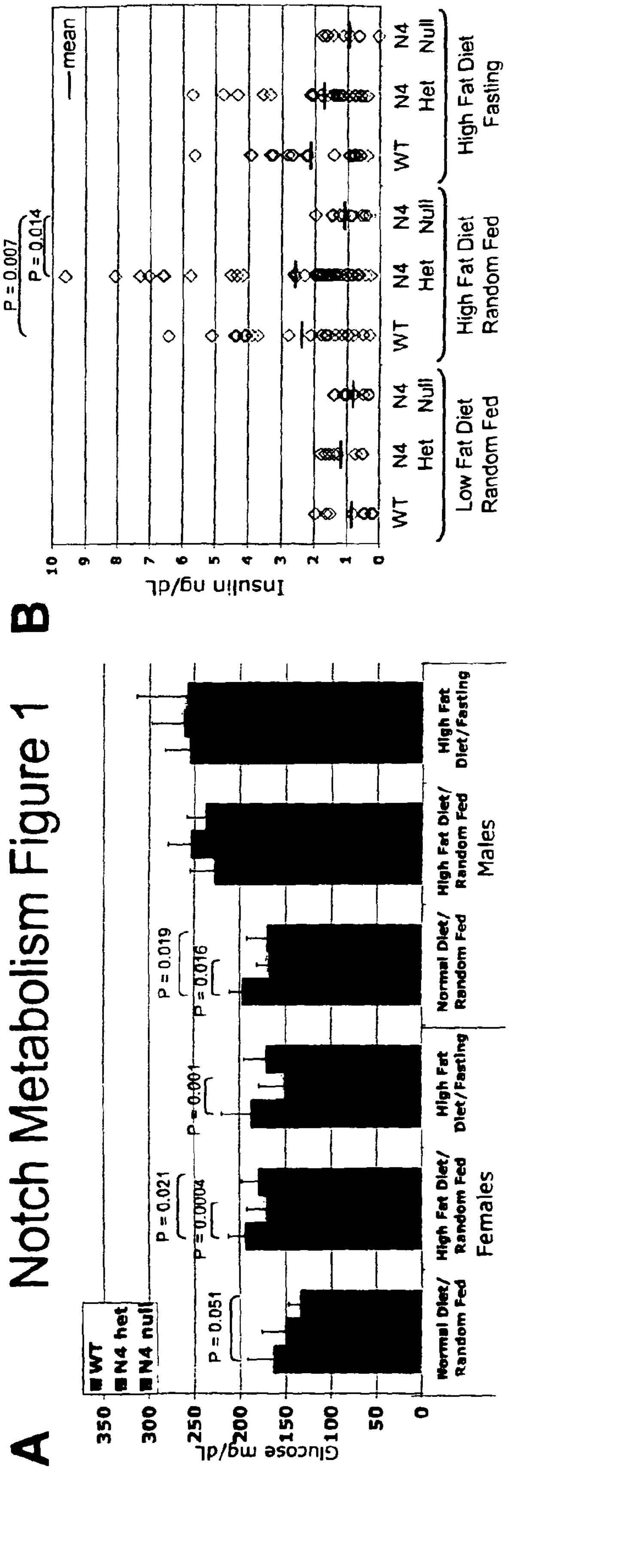
Figure 117:
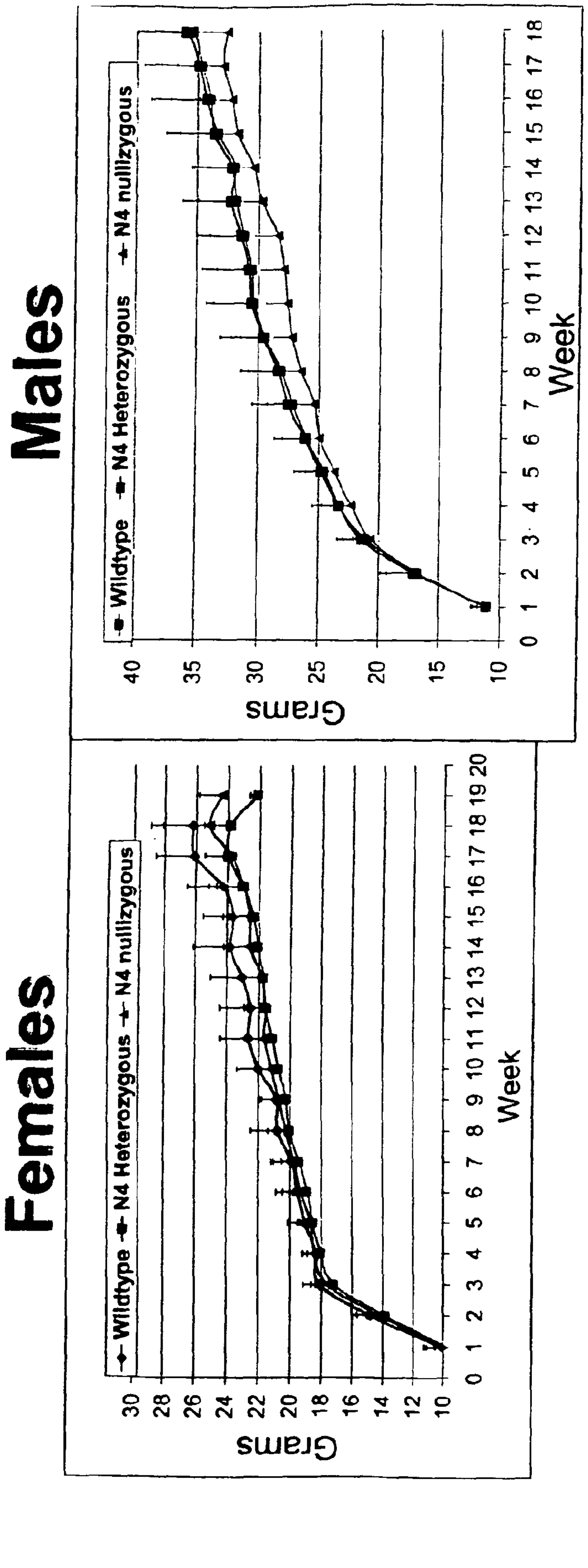

FIG. 116 This Figure shows Notch4 insufficiency reduces circulating glucose and insulin levels. We are currently analyzing the blood glucose and insulin levels of Notch4 (N4) mutant mice. At weaning (P21), multiple litters generated from N4+/− matings have either been fed a normal diet or a high fat diet consisting of 45% of calories from fat. At 5 months of age, blood was draw and glucose and insulin levels determined from random fed mice or mice after 6 hours of fasting. In females, reduction in N4 alleles correlated with a significant decrease in circulating glucose levels independent of the diet. In contrast, N4 insufficiency was associated with a decrease in glucose levels in only males fed a normal diet. Insulin levels of all females were unaffected (data not shown). This may due to female mice being genetically protected against insulin resistance, and thus the metabolic abnormalities are exquisitely mild. On the normal diet, there were no differences in the insulin levels of the male mice. However, ablation of N4 correlated with a significant decrease in the random fed insulin levels of male mice fed a high fat diet. A similar trend was observed for N4 knockout males that had been fasted 6 hours. Thus, loss of N4 correlated with a significant decrease in blood glucose levels in both males and females fed a normal diet. In females, this reduction of glucose levels, but not insulin levels was observed in N4 mutant females fed a high fat diet. In contrast, glucose levels were unchanged in N4 knockout males, whereas insulin levels were reduced. These results are consistent with Notch4 insufficiency protecting against genetic and environmental forms of hyperglycemia due to disrupted insulin signaling FIG. 117 This Figure shows loss of Notch4 expression suppressed weight gain in mice fed a high fat diet.

Figure 118:

FIG. 118 This Figure shows Rat Notch1 decoy is present in murine serum. The stability of the rat Notch1 decoy formulation in the mammalian blood stream was tested. Western blot analysis demonstrates that the full-length protein can be expressed in mice and is present at detectable levels with little evidence of degradation.

Figure 119:
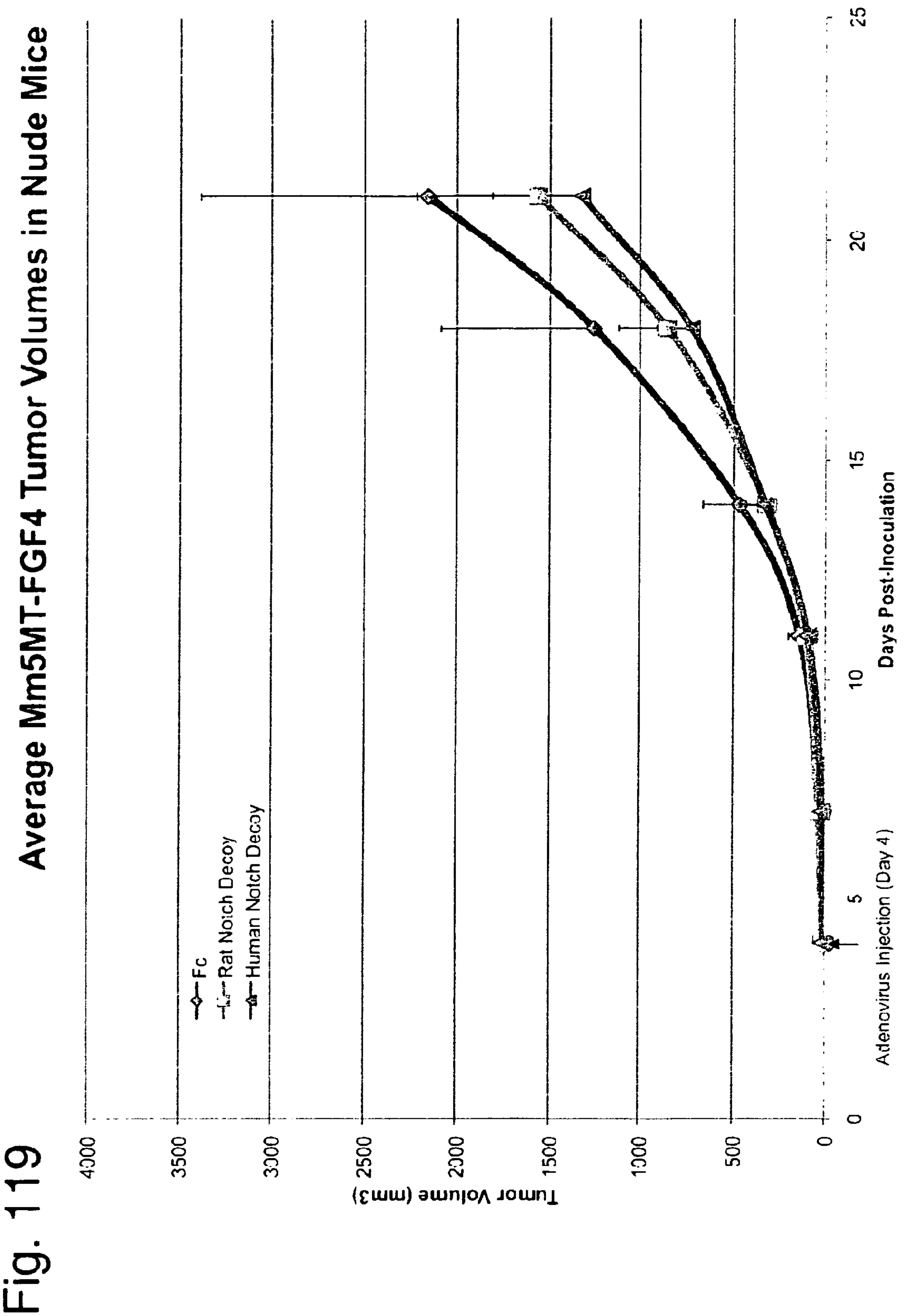

FIG. 119 This Figure shows Human Notch 1 decoy (n-Notch(1-36)decoy) and rat Notch1 decoy block mouse mammary tumor growth. The growth curve presented here demonstrates that either Rat Notch1 decoy or human Notch1 decoy reduced the growth of tumor xenografts in nude mice.

Figure 120:
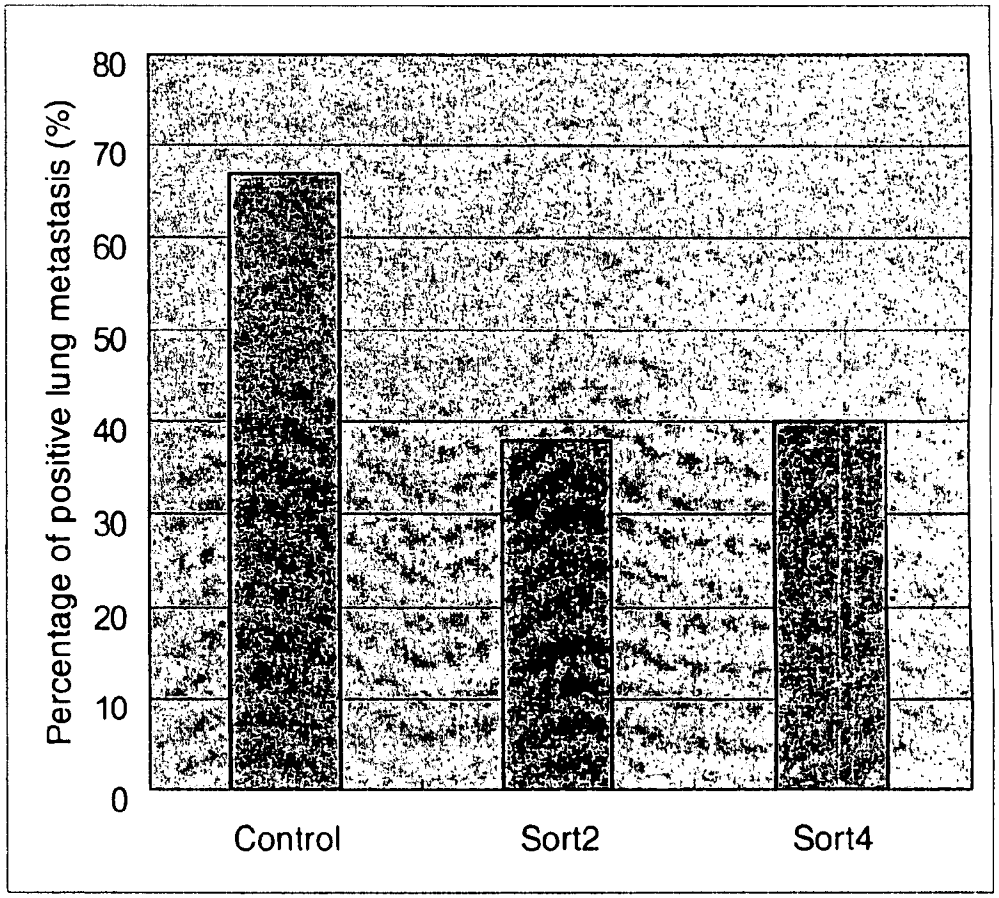

FIG. 120 This Figure shows rat Notch1 decoy inhibits SKNEP1 metastasis to lung tissue. SKNEP1 Ewings Sarcoma cells were programmed to express control Fc protein or rat Notch1 decoy s1 (sort 2) or rat Notch1 decoy s4 (sort 4). These SKNEP1 cell lines were orthotopically implanted into kidney of nude mice. After 6 weeks of tumor growth, metastasis to lung was assessed histologically. SKNEP1 cells expressing Rat Notch1 decoy showed fewer lungs that were positive for metastasis. We conclude that expression of the rat Notch1 decoy in nude mice diminishes the capacity of SKNEP1 cells to metastasize to lung.

Figure 121:
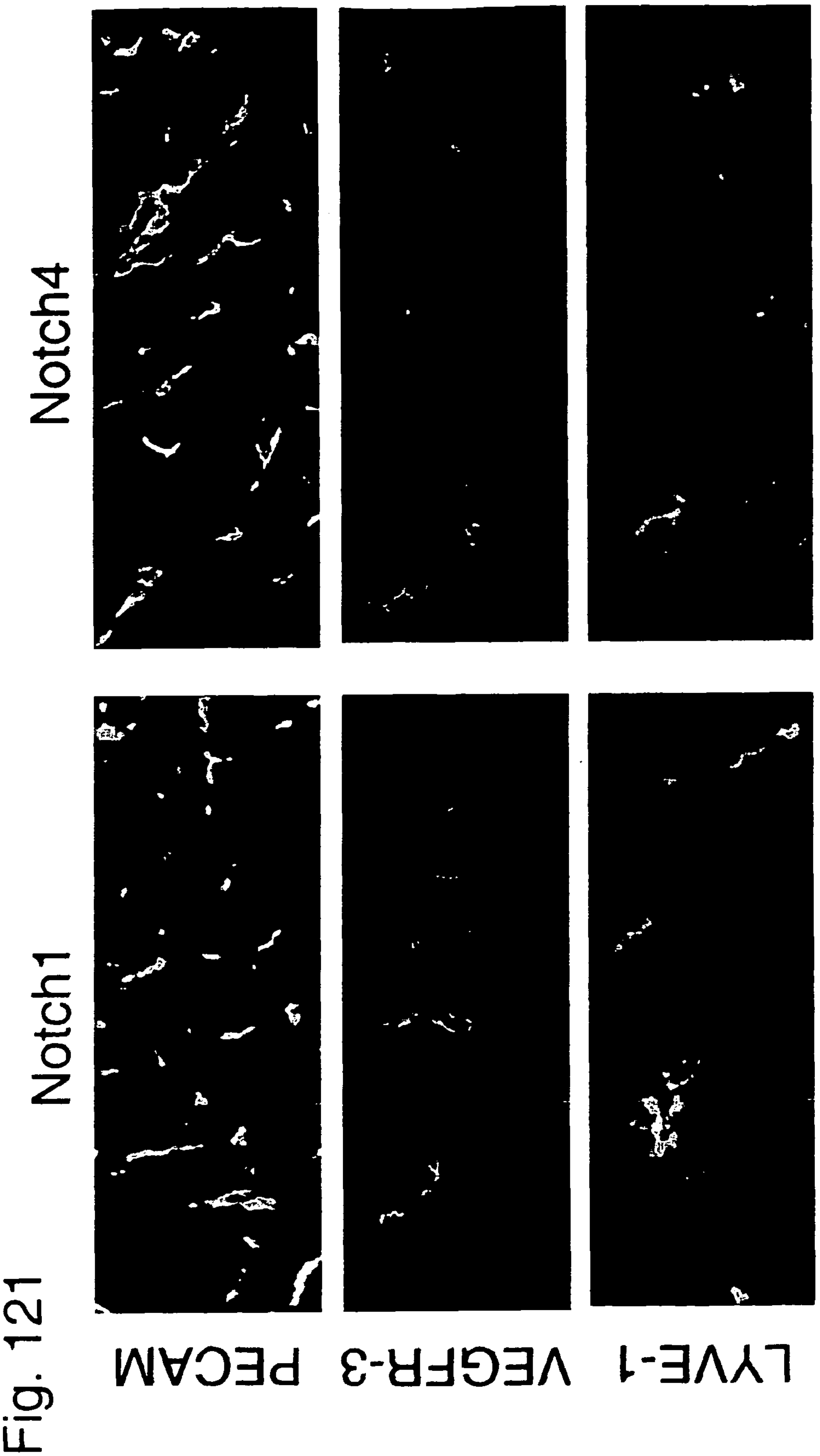

FIG. 121: This figure shoes Notch1 and Notch4 are co-expressed with VEGFR-3 and LYVE-1 in lymphatics of mouse skin. The expression of Notch1 and Notch4 was analyzed in the vasculature of mouse P4 dorsal skin. At this time point, the dermal lymphatics are actively remodeling into the lymphatic capillaries near the surface and collecting ducts in the lower dermal layers. 5 μm cross-sections of skin were co-stained with antibodies against Notch1 or Notch4 (red), and PECAM, VEGFR-3 or LYVE-1 (green). Notch1 and Notch4 share an overlapping pattern of expression with the blood and lymphatic endothelial cell marker, PECAM (upper panels). Notch1 and Notch4 were co-expressed with both VEGFR-3 (middle panels) and LYVE-1 in the dermal vasculature (lower panels). This expression pattern demonstrates that Notch1 and Notch4 are expressed and may function in the lymphatic vessels of the neonatal dermis.

Figure 122:
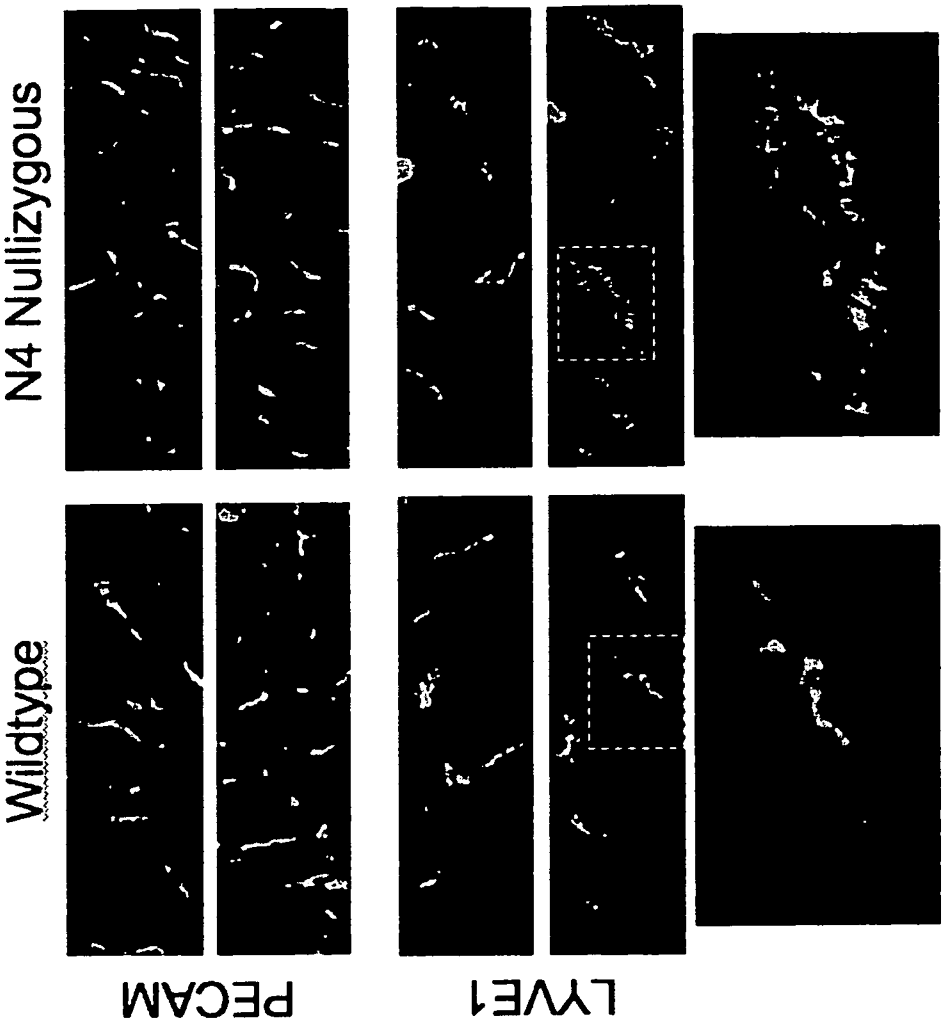

FIG. 122 This Figure shows dermal lymphatic capillaries are altered in Notch4 homozygous knockout mice. We examined the dermal lymphatics of P4 mice. Sections of wildtype and Notch4 nullizygous were immunostained with antibodies against PECAM and LYVE-1 (green). Analysis of PECAM staining appeared similar between mutant and wildtype skin (upper panels). In contrast, LYVE-1-positive vessels in the dermis of Notch4 mutants had a different morphology than that of wildtype (middle panels). Notch4 mutant LYVE-1 vessels were often dilated and LYVE-1 staining was discontinuous (lower panels). These results suggest that Notch4 signaling may be involved in remodeling of the lymphatic vascular plexus.

Figure 123:
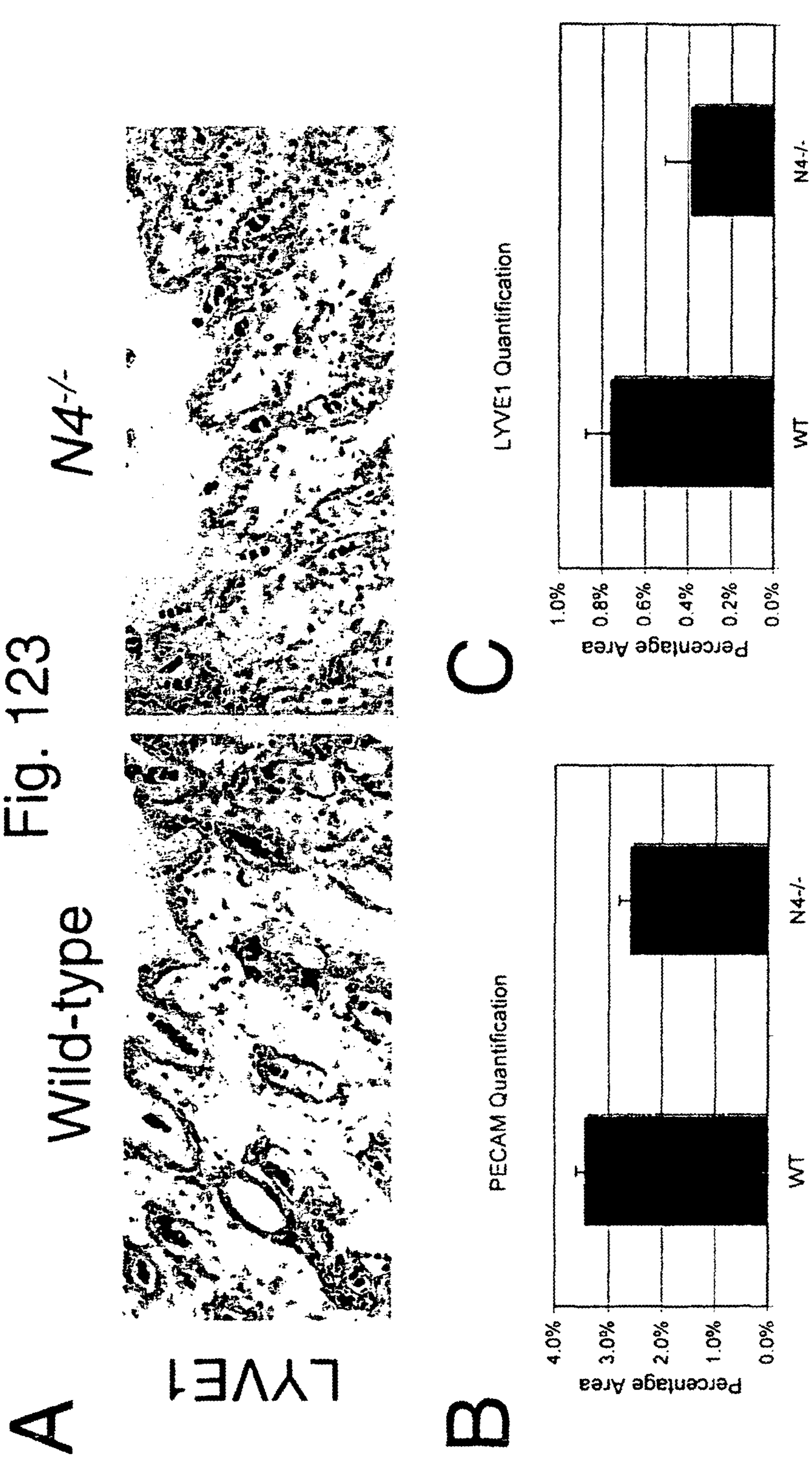

FIG. 123 This Figure shows loss of Notch4 correlates with reduced LYVE1 expression in murine dermal lymphatics. Notch4 heterozygous (N4+/−) mice were mated and the dorsal skin of the resulting pups removed and embedded 14 days postnatally. Cross-sections of skin were immunostained for the endothelial cell marker, PECAM (data not shown), or the lymphatic endothelial cell marker, LYVE1 (A). Five areas for each were captured by microscopy and PECAM and LYVE1 staining quantitated using imaging software (B, C). PECAM expression was reduced approximately 25% in the N4−/− dermis compared to wild-type (WT) dermis (B). LYVE-1 staining was more affected than the PECAM with LYVE1 staining decreased nearly 50% in N4−/− relative to WT mice (C). There was also a reduction in the intensity of the LYVE1 staining in the N4−/− lymphatics relative to the WT (A).

Figure 124:
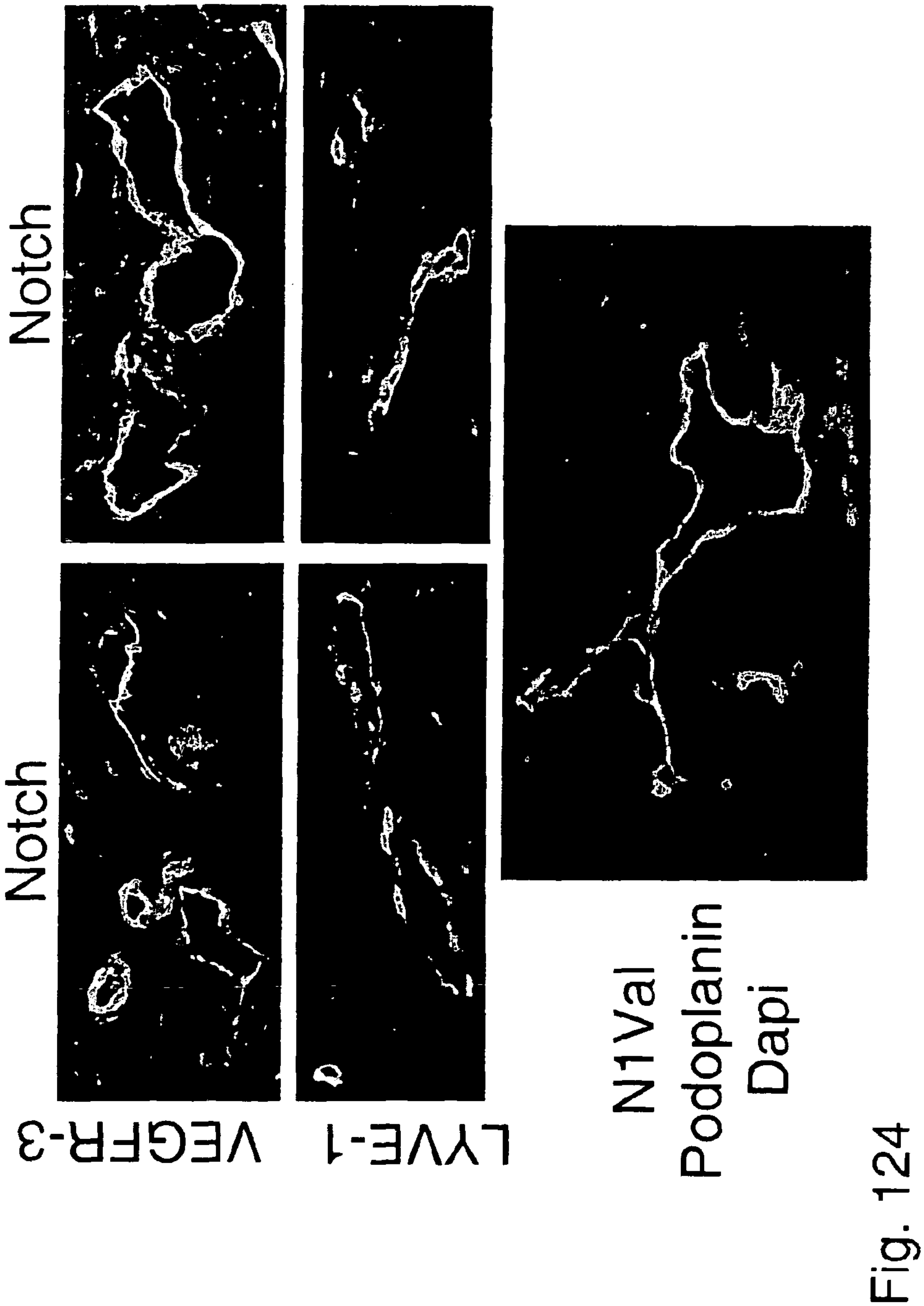

FIG. 124 This Figure shows Notch1 and Notch4 are expressed in human breast cancer lymphatic vessels. We performed double immunohistochemistry with antibodies against VEGFR-3 or LYVE-1 (green) and Notch1 or Notch4

(red) of human breast cancers. Notch1 and Notch4 were expressed in the extratumoral blood and lymphatic endothelium of human micropapillary breast carcinomas. To determine if Notch1 signaling was activated within the tumoral lymphatic endothelium, we double stained with an antibody against podoplanin (green) and N1Val (red; Cell Signaling), an antibody that specifically detects the activated Notch1 peptide. Expression of the activated Notch1 peptide was observed in most (white arrows) but not all (yellow arrows) of the lymphatic endothelial nuclei (lower panel). These results demonstrate that Notch1 was actively signaling in the pathological lymphatic vessels.

DETAILED DESCRIPTION OF THE INVENTION

Terms

As used in this application, except as otherwise expressly provided herein, each of the following terms shall have the meaning set forth below.

"Administering" may be effected or performed using any of the methods known to one skilled in the art. The methods comprise, for example, intralesional, intramuscular, subcutaneous, intravenous, intraperitoneal, liposome-mediated, transmucosal, intestinal, topical, nasal, oral, anal, ocular or otic means of delivery.

"Affixed" shall mean attached by any means. In one embodiment, affixed means attached by a covalent bond. In another embodiment, affixed means attached non-covalently.

"Amino acid," "amino acid residue" and "residue" are used interchangeably herein to refer to an amino acid that is incorporated into a protein, polypeptide or peptide. The amino acid can be, for example, a naturally occurring amino acid or an analog of a natural amino acid that can function in a manner similar to that of the naturally occurring amino acid.

"Antibody" shall include, without limitation, (a) an immunoglobulin molecule comprising two heavy chains and two light chains and which recognizes an antigen; (b) a polyclonal or monoclonal immunoglobulin molecule; and (c) a monovalent or divalent fragment thereof. Immunoglobulin molecules may derive from any of the commonly known classes, including but not limited to IgA, secretory IgA, IgG, IgE and IgM. IgG subclasses are well known to those in the art and include, but are not limited to, human IgG1, IgG2, IgG3 and IgG4. Antibodies can be both naturally occurring and non-naturally occurring. Furthermore, antibodies include chimeric antibodies, wholly synthetic antibodies, single chain antibodies, and fragments thereof. Antibodies may be human or nonhuman. Nonhuman antibodies may be humanized by recombinant methods to reduce their immunogenicity in humans. Antibody fragments include, without limitation, Fab and $F_c$ fragments. The "Fc portion of an antibody", in one embodiment, is a crystallizable fragment obtained by papain digestion of immunoglobulin that consists of the C-terminal half of two heavy chains linked by disulfide bonds and known as the "effector region" of the immunoglobulin. In another embodiment, "Fc portion of an antibody" means all, or substantially all, of one C-terminal half of a heavy chain.

"Humanized", with respect to an antibody, means an antibody wherein some, most or all of the amino acids outside the CDR region are replaced with corresponding amino acids derived from a human immunoglobulin molecule. Small additions, deletions, insertions, substitutions or modifications of amino acids are permissible as long as they do not abrogate the ability of the antibody to bind a given antigen. Suitable human immunoglobulin molecules include, without limitation, IgG1, IgG2, IgG3, IgG4, IgA and IgM molecules. Various publications describe how to make humanized antibodies, e.g., U.S. Pat. Nos. 4,816,567, 5,225,539, 5,585,089 and 5,693,761, and PCT International Publication No. WO 90/07861.

As used herein, the term "composition", as in pharmaceutical composition, is intended to encompass a product comprising the active ingredient(s) and the inert ingredient(s) that make up the carrier, as well as any product which results, directly or indirectly from combination, complexation, or aggregation of any two or more of the ingredients, or from dissociation of one or more of the ingredients, or from other types of reactions or interactions of one or more of the ingredients.

As used herein, "effective amount" refers to an amount which is capable of treating a subject having a tumor, a disease or a disorder. Accordingly, the effective amount will vary with the subject being treated, as well as the condition to be treated. A person of ordinary skill in the art can perform routine titration experiments to determine such sufficient amount. The effective amount of a compound will vary depending on the subject and upon the particular route of administration used. Based upon the compound, the amount can be delivered continuously, such as by continuous pump, or at periodic intervals (for example, on one or more separate occasions). Desired time intervals of multiple amounts of a particular compound can be determined without undue experimentation by one skilled in the art. In one embodiment, the effective amount is between about 1 μg/kg-10 mg/kg. In another embodiment, the effective amount is between about 10 μg/kg-1 mg/kg. In a further embodiment, the effective amount is 100 μg/kg.

"Extracellular domain" as used in connection with Notch receptor protein means all or a portion of Notch which (i) exists extracellularly (i.e. exists neither as a transmembrane portion or an intracellular portion) and (ii) binds to extracellular ligands to which intact Notch receptor protein binds. The extracellular domain of Notch may optionally include a signal peptide. "Extracellular domain", "ECD" and "Ectodomain" are synonymous.

"Half-life-increasing moiety" means a moiety which, when operably affixed to a second moiety, increases the in vivo half-life of the second moiety. Half-life-increasing moieties include, for example, Fc portions of antibodies, glycosylation tags (i.e. glycosylated polypeptides), polyethylene glycol (PEG), polypeptides having PEG affixed thereto, and lipid-modified polypeptides.

"Inhibiting" the onset of a disorder or undesirable biological process shall mean either lessening the likelihood of the disorder's or process' onset, or preventing the onset of the disorder or process entirely.

In the preferred embodiment, inhibiting the onset of a disorder or process means preventing its onset entirely.

"Notch", "Notch protein", and "Notch receptor protein" are synonymous. In addition, the terms "Notch-based fusion protein" and "Notch decoy" are synonymous. The following Notch amino acid sequences are known and hereby incorporated by reference: Notch1(Genbank accession no. S18188 (rat)); Notch2 (Genbank accession no. NP_077334 (rat)); Notch3 (Genbank accession no. Q61982 (mouse)); and Notch4 (Genbank accession no. T09059 (mouse)). The following Notch nucleic acid sequences are known and hereby incorporated by reference: Notch1(Genbank accession no. XM_342392 (rat) and NM_017617 (human)); Notch2 (Genbank accession no. NM_024358 (rat), M99437 (human and AF308601 (human)); Notch3 (Genbank accession no.

NM_008716 (mouse) and XM_009303 (human)); and Notch4 (Genbank accession no. NM_010929 (mouse) and NM_004557 (human)).

The terms "nucleic acid", "polynucleotide" and "nucleic acid sequence" are used interchangeably herein, and each refers to a polymer of deoxyribonucleotides and/or ribonucleotides. The deoxyribonucleotides and ribonucleotides can be naturally occurring or synthetic analogues thereof. "Nucleic acid" shall mean any nucleic acid, including, without limitation, DNA, RNA and hybrids thereof. The nucleic acid bases that form nucleic acid molecules can be the bases A, C, G, T and U, as well as derivatives thereof. Derivatives of these bases are well known in the art, and are exemplified in PCR Systems, Reagents and Consumables (Perkin Elmer Catalogue 1996-1997, Roche Molecular Systems, Inc., Branchburg, N.J., USA). Nucleic acids include, without limitation, anti-sense molecules and catalytic nucleic acid molecules such as ribozymes and DNAzymes. Nucleic acids also include nucleic acids coding for peptide analogs, fragments or derivatives which differ from the naturally-occurring forms in terms of the identity of one or more amino acid residues (deletion analogs containing less than all of the specified residues; substitution analogs wherein one or more residues are replaced by one or more residues; and addition analogs, wherein one or more resides are added to a terminal or medial portion of the peptide) which share some or all of the properties of the naturally-occurring forms.

"Operably affixed" means, with respect to a first moiety affixed to a second moiety, affixed in a manner permitting the first moiety to function (e.g. binding properties) as it would were it not so affixed.

The terms "polypeptide," "peptide" and "protein" are used interchangeably herein, and each means a polymer of amino acid residues. The amino acid residues can be naturally occurring or chemical analogues thereof. Polypeptides, peptides and proteins can also include modifications such as glycosylation, lipid attachment, sulfation, hydroxylation, and ADP-ribosylation.

As used herein, "pharmaceutically acceptable carrier" means that the carrier is compatible with the other ingredients of the formulation and is not deleterious to the recipient thereof, and encompasses any of the standard pharmaceutically accepted carriers. Such carriers include, for example, 0.01-0.1 M and preferably 0.05 M phosphate buffer or 0.8% saline. Additionally, such pharmaceutically acceptable carriers can be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions and suspensions, including saline and buffered media. Parenteral vehicles include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, chelating agents, inert gases, and the like.

"Subject" shall mean any organism including, without limitation, a mammal such as a mouse, a rat, a dog, a guinea pig, a ferret, a rabbit and a primate. In the preferred embodiment, the subject is a human being.

"Treating" means either slowing, stopping or reversing the progression of a disease or disorder. As used herein, "treating" also means the amelioration of symptoms associated with the disease or disorder. Diseases include, but are not limited to, Tumor Angiogenesis, Atherosclerosis, Wound Healing, Macular degeneration, Retinopathy of Prematurity, Pre-eclampsia, Diabetic retinopathy, Ischemia, Stroke, Cardiovascular Disease, Psoriasis, lymphedema, tumorigenesis and tumor lymphangiogenesis.

Angiogenesis is encountered during wound healing processes, the female menstrual cycle and endometrial remodeling, as well as during embryonic development and organ growth. In the pathological setting, angiogenesis plays an important role in different diseases like rheumatoid arthritis, psoriasis, macular degeneration, diabetic retinopathy, and tumor growth.

There has been considerable evidence in vivo, including clinical observations, that abnormal angiogenesis is implicated in a number of disease conditions, which include rheumatoid arthritis, inflammation, cancer, psoriasis, degenerative eye conditions and others.

Other diseases for use of Notch fusion proteins are metabolic disorders such as, but not limited to, Diabetes, Obesity, Prediabetic state, Atherosclerosis, Ischemia, Stroke, Cardiovascular Disease, Regulating expression of Insulin, and Regulating the function of Insulin.

The use of Notch fusion proteins is also indicated for Metabolic Syndrome refers to a combination of medical disorders that increases the risk to a person for cardiovascular disease and diabetes. Other known names referring to such syndrome is syndrome X, insulin resistance syndrome, Reaven's syndrome. Several features of the syndromes include: fasting hyperglycemia, high blood pressure, central obesity (also known as visceral obesity), decreased High Density Lipoprotein (LDL), elevated triglycerides, elevated uric acid levels. Fasting hyperglycemia, listed above, includes diabetes mellitus type 2 or impaired fasting glucose and impaired glucose tolerance or insulin resistance. In addition to metabolic syndrome, the Notch decoy may have indications for pre-diabetic states.

Units, prefixes and symbols may be denoted in their SI accepted form. Unless otherwise indicated, nucleic acid sequences are written left to right in 5' to 3' orientation and amino acid sequences are written left to right in amino- to carboxy-terminal orientation. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The following abbreviations are used herein: ECD: extracellular domain; IC: intracellular domain; NECD/Fc: Notch-based fusion protein; N1: Notch1; N2: Notch2; N3: Notch3; N4: Notch4; Dll: Delta-like; EC: endothelial cells; FGF: fibroblast growth factor; FGFR: fibroblast growth factor receptor; HUVEC: human umbilical vein endothelial cell; m.o.i.: multiplicity of infection; VMC: vascular mural cells; VEGF: vascular endothelial cell growth factor; VEGFR: vascular endothelial cell growth factor receptor; sp: signal peptide; PDGF: platelet derived growth factor; PDGFR: platelet derived growth factor receptor; P1GF: placental growth factor.

Embodiments of the Invention

This invention provides a fusion protein comprising a signal peptide, an extracellular domain of human Notch receptor protein and an Fc portion of an antibody bound thereto.

In a first embodiment of the fusion protein, the Notch receptor protein is Notch1 receptor protein. In one embodiment, the extracellular domain of Notch1 receptor protein comprises EGF-like repeats 1-36. In another embodiment, the extracellular domain of Notch1 receptor protein comprises EGF-like repeats 1-13. In another embodiment, the extracellular domain of Notch1 receptor protein comprises EGF-like repeats 1-24. In another embodiment, the extracellular domain of Notch1 receptor protein comprises EGF-like repeats 9-23. In another embodiment, the extracellular domain of Notch1 receptor protein comprises EGF-like repeats 9-36. In another embodiment, the extracellular domain of Notch1 receptor protein comprises EGF-like repeats 13-24. In a further embodiment, the extracellular domain of Notch1 receptor protein comprises EGF-like repeats 25-36.

In a second embodiment of the fusion protein, the Notch receptor protein is Notch2 receptor protein.

In a third embodiment of the fusion protein, the Notch receptor protein is Notch3 receptor protein.

In a fourth embodiment of the fusion protein, the Notch receptor protein is Notch4 receptor protein. In one embodiment, the extracellular domain of Notch4 receptor protein comprises EGF-like repeats 1-29. In another embodiment, the extracellular domain of Notch4 receptor protein comprises EGF-like repeats 1-13. In another embodiment, the extracellular domain of Notch4 receptor protein comprises EGF-like repeats 1-23. In another embodiment, the extracellular domain of Notch4 receptor protein comprises EGF-like repeats 9-23. In another embodiment, the extracellular domain of Notch4 receptor protein comprises EGF-like repeats 9-29. In another embodiment, the extracellular domain of Notch4 receptor protein comprises EGF-like repeats 13-23. In a further embodiment, the extracellular domain of Notch4 receptor protein comprises EGF-like repeats 21-29.

In one embodiment of the fusion protein, the Fc portion of the antibody is the Fc portion of a human antibody.

In one embodiment of the fusion protein, the signal peptide is the signal peptide of Notch1, Notch2, Notch3, Notch4, or the Hc (HC; Heavy Chain) portion of an antibody.

In one embodiment, the fusion protein comprises consecutive amino acids, the sequence of which is set forth in SEQ ID NO: 54. In another embodiment, the fusion protein comprises consecutive amino acids, the sequence of which is set forth in SEQ ID NO: 55. In another embodiment, the fusion protein comprises consecutive amino acids, the sequence of which is set forth in SEQ ID NO: 56. In another embodiment, the fusion protein comprises consecutive amino acids, the sequence of which is set forth in SEQ ID NO: 57. In another embodiment, the fusion protein comprises consecutive amino acids, the sequence of which is set forth in SEQ ID NO: 58. In another embodiment, the fusion protein comprises consecutive amino acids, the sequence of which is set forth in SEQ ID NO: 59. In another embodiment, the fusion protein comprises consecutive amino acids, the sequence of which is set forth in SEQ ID NO: 60. In another embodiment, the fusion protein comprises consecutive amino acids, the sequence of which is set forth in SEQ ID NO: 61. In another embodiment, the fusion protein comprises consecutive amino acids, the sequence of which is set forth in SEQ ID NO: 62. In another embodiment, the fusion protein comprises consecutive amino acids, the sequence of which is set forth in SEQ ID NO: 63. In a further embodiment, the fusion protein comprises consecutive amino acids, the sequence of which is set forth in SEQ ID NO: 64.

In one embodiment, the fusion protein is encoded by consecutive nucleotides, the sequence of which is set forth in SEQ ID NO: 65. In another embodiment, the fusion protein is encoded by consecutive nucleotides, the sequence of which is set forth in SEQ ID NO: 66. In another embodiment, the fusion protein is encoded by consecutive nucleotides, the sequence of which is set forth in SEQ ID NO: 67. In another embodiment, the fusion protein is encoded by consecutive nucleotides, the sequence of which is set forth in SEQ ID NO: 68. In another embodiment, the fusion protein is encoded by consecutive nucleotides, the sequence of which is set forth in SEQ ID NO: 69. In another embodiment, the fusion protein is encoded by consecutive nucleotides, the sequence of which is set forth in SEQ ID NO: 70. In another embodiment, the fusion protein is encoded by consecutive nucleotides, the sequence of which is set forth in SEQ ID NO: 71. In another embodiment, the fusion protein is encoded by consecutive nucleotides, the sequence of which is set forth in SEQ ID NO: 72. In another embodiment, the fusion protein is encoded by consecutive nucleotides, the sequence of which is set forth in SEQ ID NO: 73. In another embodiment, the fusion protein is encoded by consecutive nucleotides, the sequence of which is set forth in SEQ ID NO: 74. In a further embodiment, the fusion protein is encoded by consecutive nucleotides, the sequence of which is set forth in SEQ ID NO: 75.

In one embodiment, the fusion protein comprises consecutive amino acids, the sequence of which is set forth in SEQ ID NO: 78. In another embodiment, the fusion protein comprises consecutive amino acids, the sequence of which is set forth in SEQ ID NO: 79. In another embodiment, the fusion protein comprises consecutive amino acids, the sequence of which is set forth in SEQ ID NO: 80. In another embodiment, the fusion protein comprises consecutive amino acids, the sequence of which is set forth in SEQ ID NO: 81. In another embodiment, the fusion protein comprises consecutive amino acids, the sequence of which is set forth in SEQ ID NO: 82. In another embodiment, the fusion protein comprises consecutive amino acids, the sequence of which is set forth in SEQ ID NO: 83. In another embodiment, the fusion protein comprises consecutive amino acids, the sequence of which is set forth in SEQ ID NO: 84. In another embodiment, the fusion protein comprises consecutive amino acids, the sequence of which is set forth in SEQ ID NO: 85. In another embodiment, the fusion protein comprises consecutive amino acids, the sequence of which is set forth in SEQ ID NO: 86. In another embodiment, the fusion protein comprises consecutive amino acids, the sequence of which is set forth in SEQ ID NO: 87. In another embodiment, the fusion protein comprises consecutive amino acids, the sequence of which is set forth in SEQ ID NO: 88.

In one embodiment, the fusion protein is encoded by consecutive nucleotides, the sequence of which is set forth in SEQ ID NO: 89. In another embodiment, the fusion protein is encoded by consecutive nucleotides, the sequence of which is set forth in SEQ ID NO: 90. In another embodiment, the fusion protein is encoded by consecutive nucleotides, the sequence of which is set forth in SEQ ID NO: 91. In another embodiment, the fusion protein is encoded by consecutive nucleotides, the sequence of which is set forth in SEQ ID NO: 92. In another embodiment, the fusion protein is encoded by consecutive nucleotides, the sequence of which is set forth in SEQ ID NO: 93. In another embodiment, the fusion protein is encoded by consecutive nucleotides, the sequence of which is set forth in SEQ ID NO: 94. In another embodiment, the fusion protein is encoded by consecutive nucleotides, the sequence of which is set forth in SEQ ID NO: 95. In another embodiment, the fusion protein is encoded by consecutive nucleotides, the sequence of which is set forth in SEQ ID NO: 96. In another embodiment, the fusion protein is encoded by consecutive nucleotides, the sequence of which is set forth in SEQ ID NO: 97. In another embodiment, the fusion protein is encoded by consecutive nucleotides, the sequence of which is set forth in SEQ ID NO: 98. In another embodiment, the fusion protein is encoded by consecutive nucleotides, the sequence of which is set forth in SEQ ID NO: 99. In another embodiment, the fusion protein is encoded by consecutive nucleotides, the sequence of which is set forth in SEQ ID NO: 100. In another embodiment, the fusion protein is encoded by consecutive nucleotides, the sequence of which is set forth in SEQ ID NO: 101. In another embodiment, the fusion protein is encoded by consecutive nucleotides, the sequence of which is set forth in SEQ ID NO: 102. In another embodiment, the fusion protein is encoded by consecutive nucleotides, the sequence of which is set forth in SEQ ID NO: 103.

This invention provides a method for treating a subject having a tumor comprising administering to the subject an amount of the above fusion protein effective to treat the subject, thereby treating the subject having a tumor.

This invention provides a method for inhibiting angiogenesis in a subject comprising administering to the subject an amount of the above fusion protein effective to inhibit angiogenesis in the subject, thereby inhibiting angiogenesis in the subject.

This invention provides a method for treating a subject having ovarian cancer comprising administering to the subject an amount of the above fusion protein effective to treat the subject, thereby treating the subject having ovarian cancer.

This invention provides a method for treating a subject having a metabolic disorder comprising administering to the subject an amount of the above fusion protein effective to treat the subject, thereby treating the subject having a metabolic disorder. In one embodiment, the metabolic disorder is diabetes, obesity, atherosclerosis, ischemia, stroke, or cardiovascular disease.

This invention provides use of the above fusion protein for the preparation of a pharmaceutical composition for the treatment of a subject having a tumor.

This invention provides use of the above fusion protein for the preparation of a pharmaceutical composition for inhibiting angiogenesis in a subject.

This invention provides use of the above fusion protein for the preparation of a pharmaceutical composition for treating a subject having ovarian cancer.

This invention provides use of the above fusion protein for the preparation of a pharmaceutical composition for for treating a subject having a metabolic disorder. In one embodiment, the metabolic disorder is diabetes, obesity, atherosclerosis, ischemia, stroke, or cardiovascular disease.

This invention provides a method for inhibiting physiological lymphangiogenesis or pathological lymphangionesis in a subject comprising administering to the subject an amount of the above fusion protein effective to inhibit physiological lymphangiogenesis or pathological lymphangionesis in the subject. In one embodiment the pathological lymphangiogenesis is tumor lymphangiogenesis or lymph node metastasis that may be dependent on tumor lymphangiogenesis.

This invention provides method of inhibiting tumor metastasis in a subject comprising administering to the subject an amount of the above fusion effective to inhibit tumor metastasis in the subject. In on embodiment, the metastasis occurs via a blood vessel, the lymphatic vasculature or a lymph node. Tumor metastasis is the spread of cancer from one organ to another non-adjacent organ.

This invention provides a method of inhibiting growth of a secondary tumor in a subject comprising administering to the subject an amount of the above fusion protein effective to inhibit growth of the secondary tumor in the subject. Inhibition may also be of the tumor angiogenesis associated with the secondary or metastatic tumor. In one embodiment the secondary tumor growth is inhibited by inhibition of angiogenesis associated with the secondary tumor.

This invention provides a method of inhibiting blood vessel cooption by a tumor in subject comprising administering to the subject an amount of the above fusion protein effective to inhibit blood vessel cooption by a tumor in the subject. The process of vessel cooption is a process whereby tumor cells associate with pre-existing vessels and growth with assistance of coopted vessels. This growth of tumors on coopted vessels may be in the absence of, precede, or be in conjunction with tumor angiogenesis.

This invention provides a method of treating cancer in a subject comprising administering to the subject the above fusion protein and an inhibitor of Vascular Endothelial Growth Factor (VEGF), each in an amount effective to treat the cancer in the subject. In one embodiment the inhibitor of VEGF is an inhibitor of VEGF-A, an inhibitor of P1GF, an inhibitor of VEGF-B, an inhibitor of VEGF-C, or an inhibitor of VEGF-D. Examples of VEGF-inhibitors include, but are not limited to, bevacizumab, PTK787, Bay43-9006, SU11248, AG013676, ZD6474, VEGF-trap and Anti-VEGFR2. Examples of such inhibitors are more fully described in Ferrara et al., (2004) *Nature Reviews Drug Discovery*, Vol. 3:391-400 and Ellis et al. (2008) *Nature Reviews Cancer Vol* 8:579-591, the contents of each of which are hereby incorporated by reference.

This invention provides a method of treating cancer in a subject comprising administering to the subject the above fusion protein and an inhibitor of VEGFR-1, VEGFR-2 or VEGFR-3, each in an amount effective to treat the cancer in the subject. In one embodiment, the inhibitor targets one or more of the VEGFR.

This invention provides a method of treating cancer in a subject comprising administering to the subject the above fusion protein and an inhibitor of Platelet Derived Growth Factor (PDGF), each in an amount effective to treat the cancer in the subject. In on embodiment the inhibitor of Platelet Derived Growth Factors is an inhibitor of PDGF-A or an inhibitor of PDGF-B This invention provides a method of treating cancer in a subject comprising administering to the subject the above fusion protein and a PDGF receptor antagonist, each in an amount effective to treat the cancer in the subject. In one embodiment the PDGF receptor antagonist is a PDGF Receptor-B antagonist.

This invention provides a method of treating cancer in a subject comprising administering to the subject the above fusion protein and an inhibitor of HER2/neu, each in an amount effective to treat the cancer in the subject.

This invention provides a method of treating vascular proliferative retinopathy comprising administering to the subject the above fusion protein in an amount effective to treat the vascular proliferative retinopathy.

101. The method of claim 100, wherein the vascular proliferative retinopathy is diabetic retinopathy, macular defernation or retinopathy of prematurity This invention also provides a first method for treating a subject having a tumor comprising administering to the subject an effective amount of a composition of matter comprising the extracellular domain of a Notch receptor protein operably affixed to a half-life-increasing moiety, so as to thereby treat the subject.

This invention also provides a second method for inhibiting angiogenesis in a subject comprising administering to the subject an effective amount of a composition of matter comprising the extracellular domain of a Notch receptor protein operably affixed to a half-life-increasing moiety, so as to thereby inhibit angiogenesis in the subject.

In a first embodiment of the above methods, the Notch receptor protein is Notch1 receptor protein. In one embodiment, the Notch1 receptor protein is human Notch1 receptor protein. In another embodiment, the half-life-increasing moiety is an Fc portion of an antibody. In another embodiment, the Fc portion of the antibody is the Fc portion of a human antibody. In a further embodiment, the extracellular domain and the half-life-increasing moiety are within the same polypeptide chain.

In a second embodiment of the above methods, the Notch receptor protein is Notch2 receptor protein. In one embodiment, the Notch2 receptor protein is human Notch2 receptor protein. In another embodiment, the half-life-increasing moiety is an Fc portion of an antibody. In another embodiment, the Fc portion of the antibody is the Fc portion of a human antibody. In a further embodiment, the extracellular domain and the half-life-increasing moiety are within the same polypeptide chain.

In a third embodiment of the above methods, the Notch receptor protein is Notch3 receptor protein. In one embodiment, the Notch3 receptor protein is human Notch3 receptor protein. In another embodiment, the half-life-increasing moiety is an Fc portion of an antibody. In another embodiment, the Fc portion of the antibody is the Fc portion of a human antibody. In a further embodiment, the extracellular domain and the half-life-increasing moiety are within the same polypeptide chain.

In a fourth embodiment of the above methods, the Notch receptor protein is Notch4 receptor protein. In one embodiment, the Notch4 receptor protein is human Notch4 receptor protein. In another embodiment, the half-life-increasing moiety is an Fc portion of an antibody. In another embodiment, the Fc portion of the antibody is the Fc portion of a human antibody. In a further embodiment, the extracellular domain and the half-life-increasing moiety are within the same polypeptide chain.

In a fifth embodiment of the above methods, the subject is a mammal. In one embodiment, the mammal is a human.

In a sixth embodiment of the above methods, the angiogenesis is tumor angiogenesis.

In a further embodiment of the second method, the subject has a tumor. In another embodiment, the subject is afflicted with a pathologic vascular hyperplasia. In one embodiment, the pathologic vascular hyperplasia is a benign hemagioma. In a further embodiment, the subject is afflicted with a lymphatic vascular proliferative disease.

This invention provides a first composition of matter comprising the extracellular domain of Notch4 receptor protein operably affixed to a half-life-increasing moiety. In one embodiment, the extracellular domain is covalently bound to the half-life-increasing moiety. In another embodiment, the extracellular domain and the half-life-increasing moiety are within the same polypeptide chain.

This invention also provides a second composition of matter comprising the extracellular domain of Notch4 receptor protein operably affixed to a half-life-increasing moiety and a pharmaceutically acceptable carrier.

This invention further provides an article of manufacture comprising (i) a packaging material having therein a composition of matter comprising the extracellular domain of a Notch receptor protein operably affixed to a half-life-increasing moiety and (ii) a label indicating that the composition is intended for use in treating a subject having a tumor or other disorder treatable by inhibiting angiogenesis in the subject.

In a first embodiment of the above article, the Notch receptor protein is Notch1 receptor protein. In one embodiment, the Notch1 receptor protein is human Notch1 receptor protein. In another embodiment, the half-life-increasing moiety is an Fc portion of an antibody. In another embodiment, the Fc portion of the antibody is the Fc portion of a human antibody. In a further embodiment, the extracellular domain and the Half-life-increasing moiety are within the same polypeptide chain.

In a second embodiment of the above article, the Notch receptor protein is Notch2 receptor protein. In one embodiment, the Notch2 receptor protein is human Notch2 receptor protein. In another embodiment, the half-life-increasing moiety is an Fc portion of an antibody. In another embodiment, the Fc portion of the antibody is the Fc portion of a human antibody. In a further embodiment, the extracellular domain and the Half-life-increasing moiety are within the same polypeptide chain.

In a third embodiment of the above article, the Notch receptor protein is Notch3 receptor protein. In one embodiment, the Notch3 receptor protein is human Notch3 receptor protein. In another embodiment, the half-life-increasing moiety is an Fc portion of an antibody. In another embodiment, the Fc portion of the antibody is the Fc portion of a human antibody. In a further embodiment, the extracellular domain and the Half-life-increasing moiety are within the same polypeptide chain.

In a fourth embodiment of the above article, the Notch receptor protein is Notch4 receptor protein. In one embodiment, the Notch4 receptor protein is human Notch4 receptor protein. In another embodiment, the half-life-increasing moiety is an Fc portion of an antibody. In another embodiment, the Fc portion of the antibody is the Fc portion of a human antibody. In a further embodiment, the extracellular domain and the Half-life-increasing moiety are within the same polypeptide chain.

In another embodiment of the above article, the composition is admixed with a pharmaceutical carrier. In a final embodiment, the subject is a human.

This invention provides a replicable vector which encodes a polypeptide comprising the extracellular domain of a Notch4 receptor protein operably affixed to a half-life-increasing moiety. In one embodiment, the half-life-increasing moiety is an Fc portion of an antibody. In another embodiment, the vector includes, without limitation, a plasmid, a cosmid, a retrovirus, an adenovirus, a lambda phage or a YAC.

This invention also provides a host vector system which comprises a replicable vector which encodes a polypeptide comprising the extracellular domain of a Notch receptor protein operably affixed to a half-life-increasing moiety and a suitable host cell. In one embodiment, the host cell is a eukaryotic cell. In another embodiment, the eukaryotic cell is a CHO cell. In a another embodiment, the eukaryotic cell is a HeLa cell. In a further embodiment, the host cell is a bacterial cell.

Finally, this invention provides a third method of producing a polypeptide which comprises growing a host vector system which comprises a replicable vector which encodes a polypeptide comprising the extracellular domain of a Notch receptor protein operably affixed to a half-life-increasing moiety and a suitable host cell under conditions permitting production of the polypeptide, and recovering the polypeptide so produced.

This invention is illustrated in the Experimental Details section which follows. This section is set forth to aid in an understanding of the invention but is not intended to, and should not be construed to, limit in any way the invention as set forth in the claims which follow thereafter.

EXPERIMENTAL DETAILS

First Series of Experiments

Human Notch1 Fusion Proteins (Notch Decoys)

The Notch1 decoys are assembled using sequences encoding a signal peptide, a portion of the Notch1 extracellular domain encompassing all or a subset of the EGF-like repeat domains, and a portion of the human Fc protein (amino acids 1-237). The complete full-length sequence of human Notch1 is provided in FIG. 59.

The signal peptides utilized are either the native Notch1 signal peptide or the human Hc signal peptide, each fused to a region of Notch1. The signal peptide allows for secretion of the Notch decoy proteins.

The Notch1 extracellular domains used are designed to bind to Notch ligands and consist of all or a subset of the 36 EGF-like repeat domains of the human Notch1 protein.

The Fc tag is fused to the C-terminus of a given EGF-like repeat of human Notch1 and serves to allow for purification, detection, and stabilization of the Notch1 decoy proteins.

The overall design of the human Notch1 decoys, eleven formulations, is to encode for; (1) a signal peptide to allow for secretion of Notch1 decoy proteins into the extracellular media of eukaryotic cells that are used to produce the proteins, (2) a portion of the extracellular domain of all or a portion of the EGF-like repeats of human Notch1 to allow for association with Notch ligands, and (3) a portion of the human Fc protein to allow for detection.

The following eleven formulations of human Notch1 decoys will be described and are schematized in FIG. 52.

Figure 52:
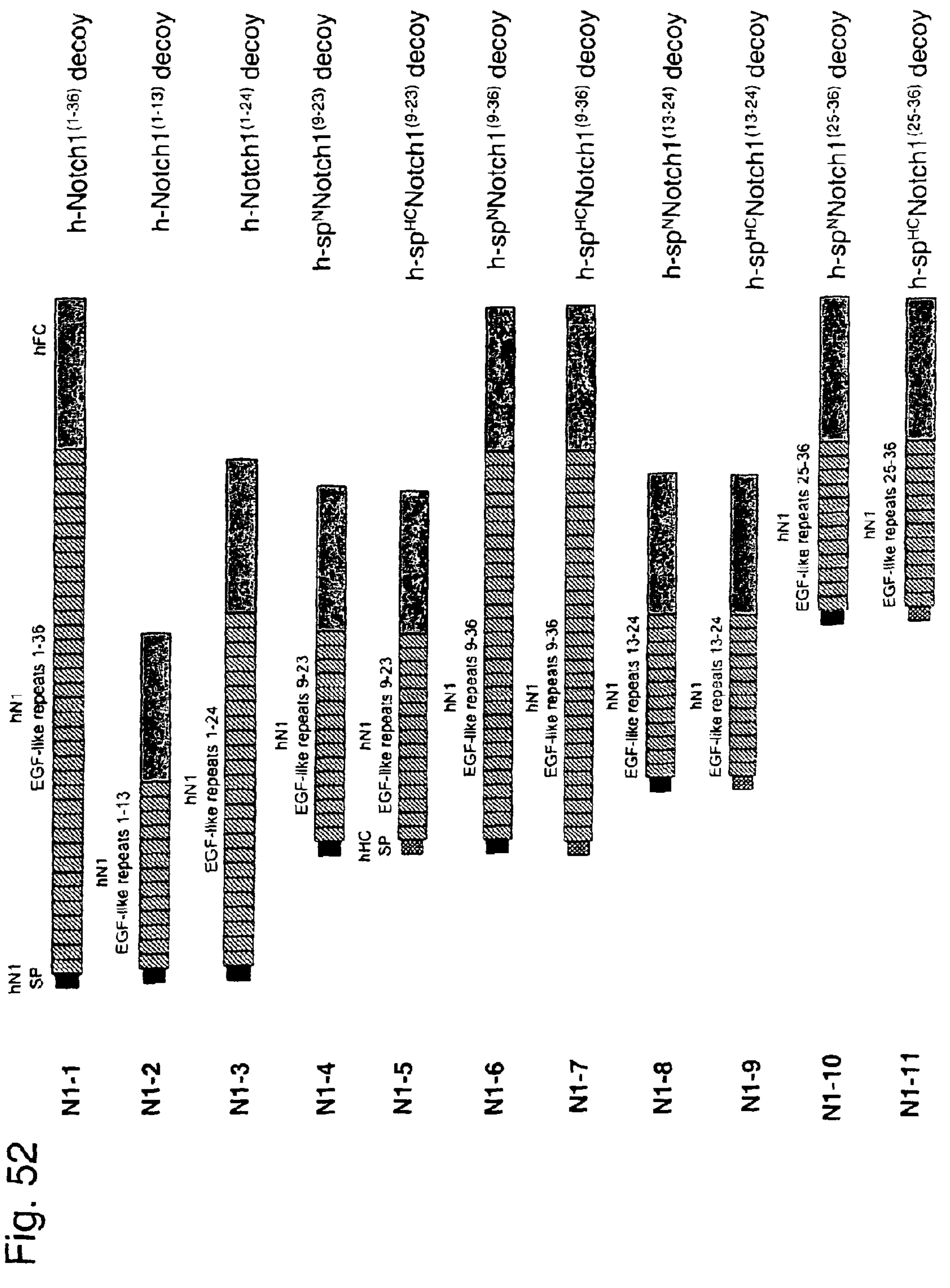
FIG. 52 This Figure shows a schematization of eleven formulations of human Notch1 decoys.

1) h-Notch1$^{(1-36)}$ decoy (N1-1 of FIG. 52)
2) h-Notch1$^{(1-43)}$ decoy (N1-2 of FIG. 52)
3) h-Notch1$^{(1-24)}$ decoy (N1-3 of FIG. 52)
4) h-sp$^{N}$Notch1$^{(9-23)}$ decoy (N1-4 of FIG. 52)
5) h-sp$^{HC}$Notch1$^{(9-23)}$ decoy (N1-5 of FIG. 52)
6) h-sp$^{N}$Notch1$^{(9-36)}$ decoy (N1-6 of FIG. 52)
7) h-sp$^{HC}$Notch1$^{(9-36)}$ decoy (N1-7 of FIG. 52)
8) h-sp$^{N}$Notch1$^{(13-24)}$ decoy (N1-8 of FIG. 52)
9) h-sp$^{HC}$Notch1$^{(13-24)}$ decoy (N1-9 of FIG. 52)
10) h-sp$^{N}$Notch1$^{(25-36)}$ decoy (N1-10 of FIG. 52)
11) h-sp$^{HC}$Notch1$^{(25-36)}$ decoy (N1-11 of FIG. 52)

Human Notch1 Sequence

The full-length amino acid (aa) sequence of human Notch1, consisting of aa residue 1 (M=methionine) to aa residue 2555 (K=lysine) is set forth in FIG. 59. The signal peptide and first 36 EGF-like repeat domains are present in aa 1-1433 of this sequence. Amino acids 1-1433, or a subset of these aa, were utilized for the design of the human Notch1 decoy proteins, described in the ensuing sections. The amino acids encompassing EGF-repeats 1-36 are underlined.

Human Fc Sequence Utilized to Generate the Fc Tag on Notch1 Decoy Proteins

The 237 amino acids of human Fc, shown in FIG. 60, were fused at the C-terminus of all Notch1 decoy constructs, just downstream of Notch1EGF-like repeats. This region of human Fc allows for detection and purification of the Notch decoys and serves to stabilize the secreted human Notch1-human Fc fusion proteins.

Signal Peptides Utilized in Notch1 Decoy Proteins

Two distinct signal peptide sequences were incorporated into the design of the human Notch1 decoy proteins. The first is the human Notch1 signal peptide that is predicted to encompass amino acids 1-20 of human Notch1.

This determination was made using the Signal IP 3.0 Server program provided by the Technical University of Denmark. The second is the human Hc signal peptide that is predicted to encompass amino acids 1-22 of human IgG heavy chain (HC) signal peptide.

1. Human Notch1 signal peptide (aa 1-20)

```
MPPLLAPLLCLALLPALA/A/R     (SEQ ID NO: 16)
```

Figure 53:
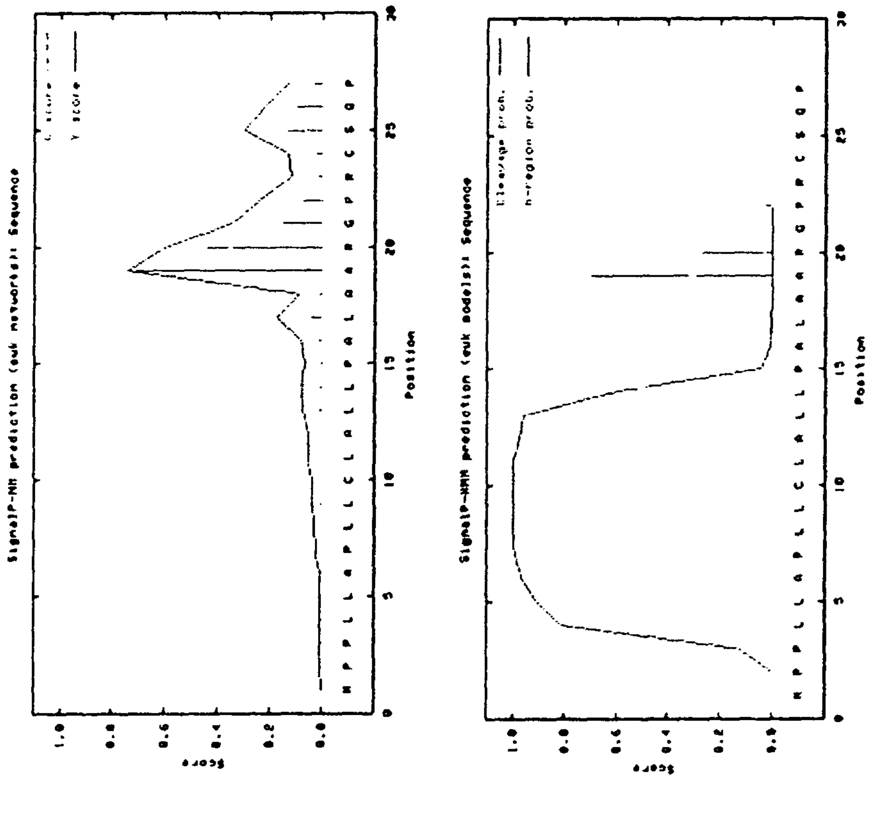
FIG. 53 This Figure shows signal sequence analysis of Notch 1 to determine where Notch1 signal peptide ends. The prediction results of analysis utilizing the SignalI 3.0 Server provided online by the Technical University of Denmark are shown. The results predict a major site of cleavage located between alanine 18 (A19) and A19 and a minor site of cleavage between A19 and Arginine 20 (R20). These two cleavage sites are indicated by the "/" in amino acid sequence 1-20 of human Notch 1: MPPLLAPLLCLALLPALA/A/R (SEQ ID NO:15) The nucleotide sequence encoding amino acids 1-23 of human Notch1 is atgccgccgc tcctggcgcc cctgctctgc ctggcgctgc tgcccgcgct cgccgcacga ggcccgcga (SEQ ID NO:16).
Figure 54:
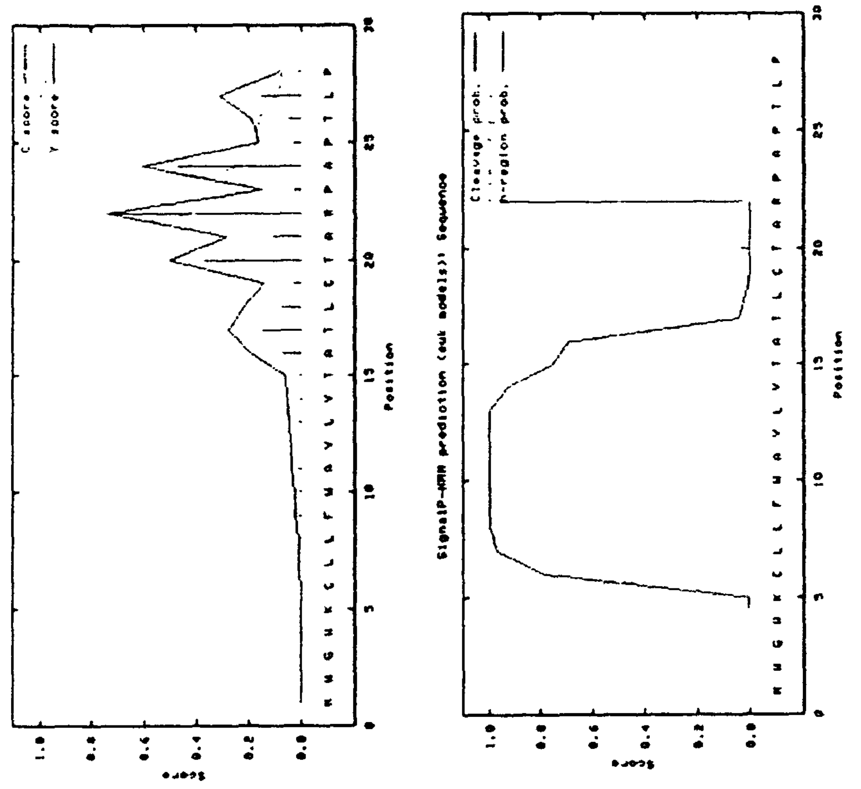
FIG. 54 This Figure shows signal sequence analysis of human Hc to determine where human Hc signal peptide ends. MWGWKCLLFWAVLVTATLCTA/R (SEQ ID NO: 17). The prediction results of analysis utilizing the SignalIP 3.0 Server provided online by the Technical University of Denmark are shown above. These results predict a major site of cleavage located between alanine 21 (A21) and arginine 22 (R22). This cleavage site is indicated by the "/" in amino acid sequence 1-22 of human Hc (SEQ ID NO:17) provided above. The nucleotide sequence encoding amino acids 1-22 of human Hc is atgtggggct ggaagtgcct cctcttctgg gctgtgctgg tcacagccac tctctgcact gccagg (SEQ ID NO:18).

Amino acid sequence of the predicted human Notch1 signal peptide is schematized in FIG. 53. The prediction results of analysis utilizing the SignalIP 3.0 Server provided online by the Technical University of Denmark are shown in FIG. 53. These results predict a major site of cleavage located between alanine 18 (A18) and alanine 19 (A19) and a minor site of cleavage between A19 and Arginine 20 (R20). These two cleavage sites are indicated by the "/" in amino acid sequence 1-20 of human Notch1, provided above.

2. Human Notch1 Signal Peptide Fusion Peptide (aa 1-23) Utilized in Notch1 Decoys that Utilize this Signal Sequence.

In order to make sure that the Notch1 signal peptide is utilized efficiently three additional amino acids beyond the predicted minor site of cleavage are provided in the human Notch1 decoys. Thus the amino acid sequence utilized in the human Notch1 decoy formulation, that incorporate a Notch1 signal peptide, contains glycine-proline-arginine (GPR—bold/underlined) between the sites of predicted signal peptide cleavage and the Notch1EGF-like repeats as shown below.

MPPLLAPLLCLALLPALAAR<u>GPR</u>     (SEQ ID NO: 130)

3. Human Hc Signal Peptide (aa 1-22)

The amino acid sequence of the predicted human Hc signal peptide is

```
MWGWKCLLFWAVLVTATLCTA/R     (SEQ ID NO: 18)
```

The prediction results of analysis utilizing the SignalIP 3.0 Server provided online by the Technical University of Denmark are shown above. These results predict a major site of cleavage located between alanine 21 (A21) and arginine 22 (22). This cleavage site is indicated by the "/" in amino acid sequence 1-22 of human Hc provided above.

h-Notch1$^{(1-36)}$ Decoy h-Notch1$^{(1-36)}$ decoy denotes the human Notch1 decoy that encompass EGF-like repeats 1-36 of Notch1(N1-1 of FIG. 52).

h-Notch1$^{(1-36)}$ decoy protein which is set forth in FIG. 61 consists of the following three components: (1) human Notch1 signal sequence consisting of amino acids 1-23 of human Notch1, followed by (2) amino acids encoding the EGF-like repeats 1-36 of human Notch1 consisting of amino acids 24-1433 followed by (3) amino acids 1434-1670 that contain the human Fc tag. The predicted signal peptide sequence is underlined and the human Fc tag is underlined and italicized. This formulation contains 1670 amino acids.

h-Notch1$^{(1-13)}$ Decoy h-Notch1$^{(1-13)}$ decoy denotes the human Notch1 decoy that encompass EGF-like repeats 1-13 of Notch1(N1-2 of FIG. 52).

h-Notch1$^{(1-13)}$ decoy protein which is set forth in FIG. 62 consists of the following three components:

(1) human Notch1 signal sequence consisting of amino acids 1-23 of human Notch1, followed by (2) amino acids encoding the EGF-like repeats 1-13 of human Notch1 consisting of amino acids 24-531 followed by (3) amino acids 532-768 that contain the human Fc tag. The predicted signal peptide sequence is underlined and the human Fc tag is underlined and italicized. This formulation contains 768 amino acids.

h-Notch1$^{(1-24)}$ Decoy h-Notch1$^{(1-24)}$ decoy denotes the human Notch1 decoy that encompass EGF-like repeats 1-24 of Notch1(N1-3 of FIG. 52).

h-Notch1$^{(1-24)}$ decoy protein which is set forth in FIG. 63 consists of the following three components:

(1) human Notch1 signal sequence consisting of amino acids 1-23 of human Notch1, followed by (2) amino acids encoding the EGF-like repeats 1-24 of human Notch1 consisting of amino acids 24-948 followed by (3) amino acids 949-1185 that contain the human Fc tag. The predicted signal peptide sequence is underlined and the human Fc tag is underlined and italicized. This formulation contains 1185 amino acids.

h-sp$^{N}$Notch1$^{(9-23)}$ Decoy h-sp$^{N}$Notch1$^{(9-23)}$ decoy denotes the human Notch1 decoy that encompass EGF-like repeats 9-23 of Notch1(N1-4 of FIG. 52). The abbreviation sp$^{N}$ denotes that the human Notch1 signal peptide is used in this formulation.

h-sp$^{N}$Notch1$^{(9-23)}$ decoy protein which is set forth in FIG. 64 consists of the following three components:

(1) human Notch1 signal sequence consisting of amino acids 1-23 of human Notch1, followed by (2) amino acids encoding the EGF-like repeats 9-23 of human Notch1 consisting of amino acids 24-593 followed by (3) amino acids 594-830 that contain the human Fc tag. The predicted signal peptide sequence is underlined and the human Fc tag is underlined and italicized. This formulation contains 830 amino acids.

h-sp$^{HC}$Notch1$^{(9-23)}$ Decoy h-sp$^{HC}$Notch1$^{(9-23)}$ decoy denotes the human Notch1 decoy that encompass EGF-like repeats 9-23 of Notch1 (N1-5 of FIG. 52). The abbreviation sp$^{HC}$ denotes that the human Hc signal peptide is used in this formulation.

h-sp$^{HC}$Notch1$^{(9-23)}$ decoy protein which is set forth in FIG. 65 consists of the following three components:

(1) human Hc signal sequence consisting of amino acids 1-22 of human Hc, followed by (2) amino acids encoding the EGF-like repeats 9-23 of human Notch1 consisting of amino acids 23-592 followed by (3) amino acids 593-829 that contain the human Fc tag. The predicted signal peptide sequence is underlined and the human Fc tag is underlined and italicized. This formulation contains 829 amino acids.

h-sp$^{N}$Notch1$^{(9-36)}$ Decoy h-sp$^{N}$Notch1$^{(9-36)}$ decoy denotes the human Notch1 decoy that encompass EGF-like repeats 9-36 of Notch1(N1-6 of FIG. 52). The abbreviation sp$^{N}$ denotes that the human Notch1 signal peptide is used in this formulation.

h-sp$^{N}$Notch1$^{(9-36)}$ decoy protein which is set forth in FIG. 66 consists of the following three components:

(1) human Notch1 signal sequence consisting of amino acids 1-23 of human Notch1, followed by (2) amino acids encoding the EGF-like repeats 9-36 of human Notch1 consisting of amino acids 24-1118 followed by (3) amino acids 1119-1355 that contain the human Fc tag. The predicted signal peptide sequence is underlined and the human Fc tag is underlined and italicized. This formulation contains 1355 amino acids.

h-sp$^{HC}$Notch1$^{(9-36)}$ Decoy h-sp$^{HC}$Notch1$^{(9-36)}$ decoy denotes the human Notch1 decoy that encompass EGF-like repeats 9-36 of Notch1 (N1-7 of FIG. 52). The abbreviation sp$^{HC}$ denotes that the human Hc signal peptide is used in this formulation.

h-sp$^{HC}$Notch1$^{(9-36)}$ decoy protein which is set forth in FIG. 67 consists of the following three components:

(1) human Hc signal sequence consisting of amino acids 1-22 of human Hc, followed by (2) amino acids encoding the EGF-like repeats 9-36 of human Notch1 consisting of amino acids 23-1117 followed by (3) amino acids 1118-1354 that contain the human Fc tag. The predicted signal peptide sequence is underlined and the human Fc tag is underlined and italicized. This formulation contains 1354 amino acids.

h-sp$^{N}$Notch1$^{(13-24)}$Decoy h-sp$^{N}$Notch1$^{(13-24)}$ decoy denotes the human Notch1 decoy that encompass EGF-like repeats 13-24 of Notch1 (N1-8 of FIG. 52). The abbreviation sp$^{N}$ denotes that the human Notch1 signal peptide is used in this formulation.

h-sp$^{N}$Notch1$^{(13-24)}$ decoy protein which is set forth in FIG. 68 consists of the following three components:

(1) human Notch1 signal sequence consisting of amino acids 1-23 of human Notch1, followed by (2) amino acids encoding the EGF-like repeats 13-24 of human Notch1 consisting of amino acids 24-478 followed by (3) amino acids 479-715 that contain the human Fc tag. The predicted signal peptide sequence is underlined and the human Fc tag is underlined and italicized. This formulation contains 715 amino acids.

h-sp$^{HC}$Notch1$^{(13-24)}$Decoy h-sp$^{HC}$Notch1$^{(13-24)}$ decoy denotes the human Notch1 decoy that encompass EGF-like repeats 13-24 of Notch1 (N1-9 of FIG. 52). The abbreviation sp$^{HC}$ denotes that the human Hc signal peptide is used in this formulation.

h-sp$^{HC}$Notch1$^{(13-24)}$ decoy protein which is set forth in FIG. 69 consists of the following three components:

(1) human Hc signal sequence consisting of amino acids 1-22 of human Hc, followed by (2) amino acids encoding the EGF-like repeats 13-24 of human Notch1 consisting of amino acids 23-477 followed by (3) amino acids 478-714 that contain the human Fc tag. The predicted signal peptide sequence is underlined and the human Fc tag is underlined and italicized. This formulation contains 714 amino acids.

h-sp$^{N}$Notch1$^{(25-36)}$ Decoy h-sp$^{N}$Notch1$^{(25-36)}$ decoy denotes the human Notch1 decoy that encompass EGF-like repeats 25-36 of Notch1 (N1-10 of FIG. 52). The abbreviation sp$^{N}$ denotes that the human Notch1 signal peptide is used in this formulation.

h-sp$^{N}$Notch1$^{(25-36)}$ decoy protein which is set forth in FIG. 70 consists of the following three components:

(1) human Notch1 signal sequence consisting of amino acids 1-23 of human Notch1, followed by (2) amino acids encoding the EGF-like repeats 25-36 of human Notch1 consisting of amino acids 24-508 followed by (3) amino acids 509-745 that contain the human Fc tag. The predicted signal peptide sequence is underlined and the human Fc tag is underlined and italicized. This formulation contains 745 amino acids.

h-sp$^{HC}$Notch1$^{25-36)}$ decoy h-sp$^{HC}$Notch1$^{(25-36)}$ decoy denotes the human Notch1 decoy that encompass EGF-like repeats 25-36 of Notch1 (N1-11 of FIG. 52). The abbreviation sp$^{HC}$ denotes that the human Hc signal peptide is used in this formulation.

h-sp$^{HC}$Notch1$^{(25-36)}$ decoy protein which is set forth in FIG. 71 consists of the following three components:

(1) human Hc signal sequence consisting of amino acids 1-22 of human Hc, followed by (2) amino acids encoding the EGF-like repeats 25-36 of human Notch1 consisting of amino acids 23-507 followed by (3) amino acids 508-744 that contain the human Fc tag. The predicted signal peptide sequence is underlined and the human Fc tag is underlined and italicized. This formulation contains 744 amino acids.

Methods

Construction of Human Notch1 Decoys

Total RNA from human umbilical venous endothelial cells (HUVEC) was used to generate the human Notch1 decoy variants. Total RNA was reverse transcribed with M-MLV reverse transcriptase and either random hexamer primers or a Notch1 decoy specific primer. The synthesized cDNA was then amplified with Notch1 decoy specific upstream (sense) and downstream (antisense) primers.

The downstream primer encodes either BamHI or BglII restriction site at the 5' end that will ligate with the BglII site in the Fc sequence to generate an in frame human Notch1/Fc chimera.

Figure 4:
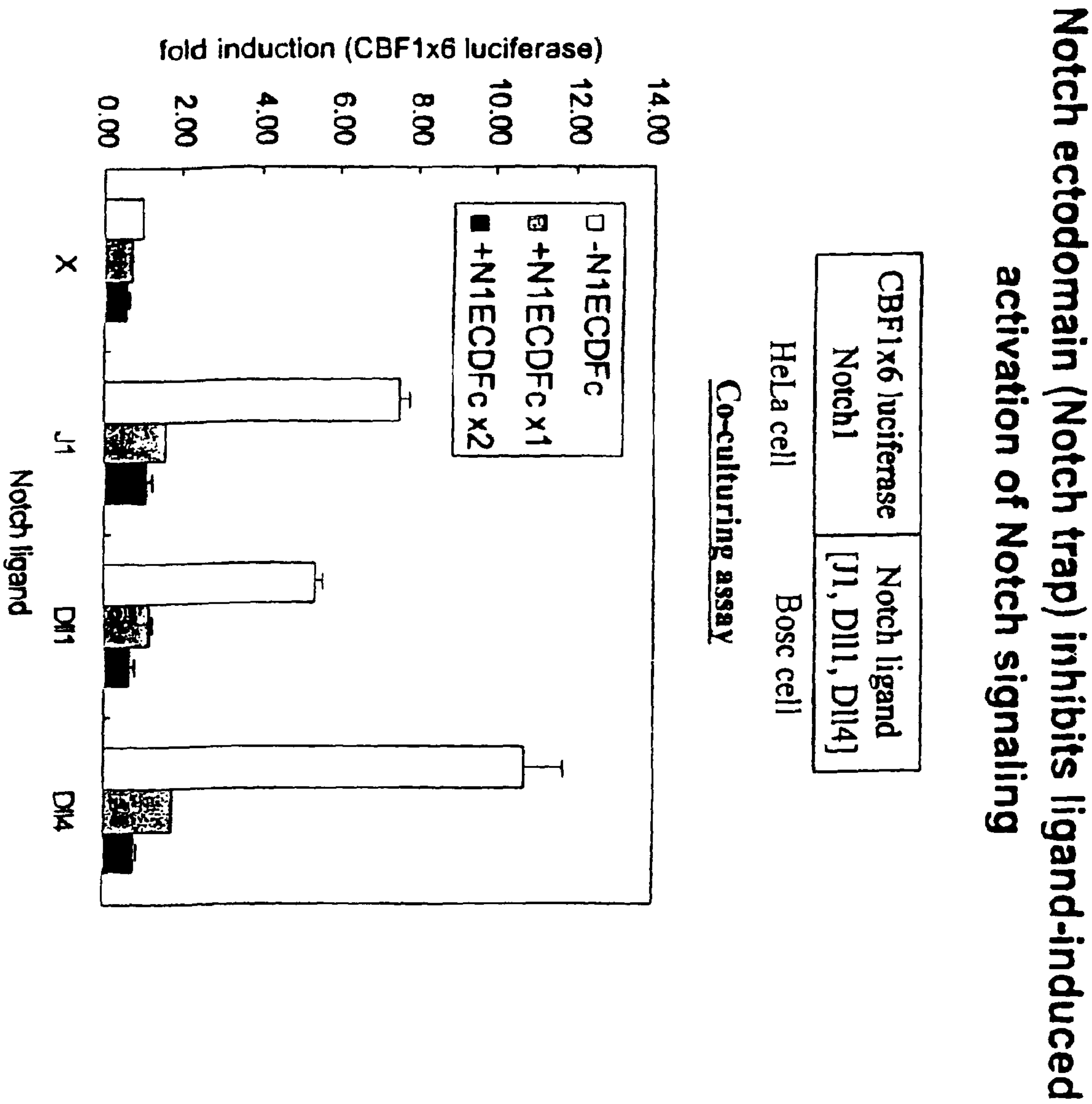
FIG. 4 This Figure shows the inhibitory activity of Notch-based fusion protein against activation of Notch signaling by interaction between Notch and Notch ligand. Induction of Notch signaling was detected by co-cultivating both Notch1- and 3 types of Notch ligand-expressing cells and these inductions were inhibited by co-transfection of Notch-based fusion protein-expressing vector into Notch1-expressing cells. Therefore, Notch-based fusion proteins can be used as Notch inhibitor based on inhibition of interaction between Notch and Notch ligand.

In the case of Notch1 decoys that generate the fusion after nucleotide sequence encoding EGF-like repeat 36, a BglII site will be generated to create the fusion site and this fusion sequence is provided (Notch1, FIG. 4). This applies to formulations; h-Notch1$^{(1-36)}$ decoy, h-sp$^{N}$Notch1$^{(9-36)}$ decoy, h-sp$^{HC}$Notch1$^{(9-36)}$ decoy, h-sp$^{N}$Notch1$^{(25-36)}$ decoy, h-sp$^{HC}$Notch1$^{25-36)}$ decoy.

Figure 5:
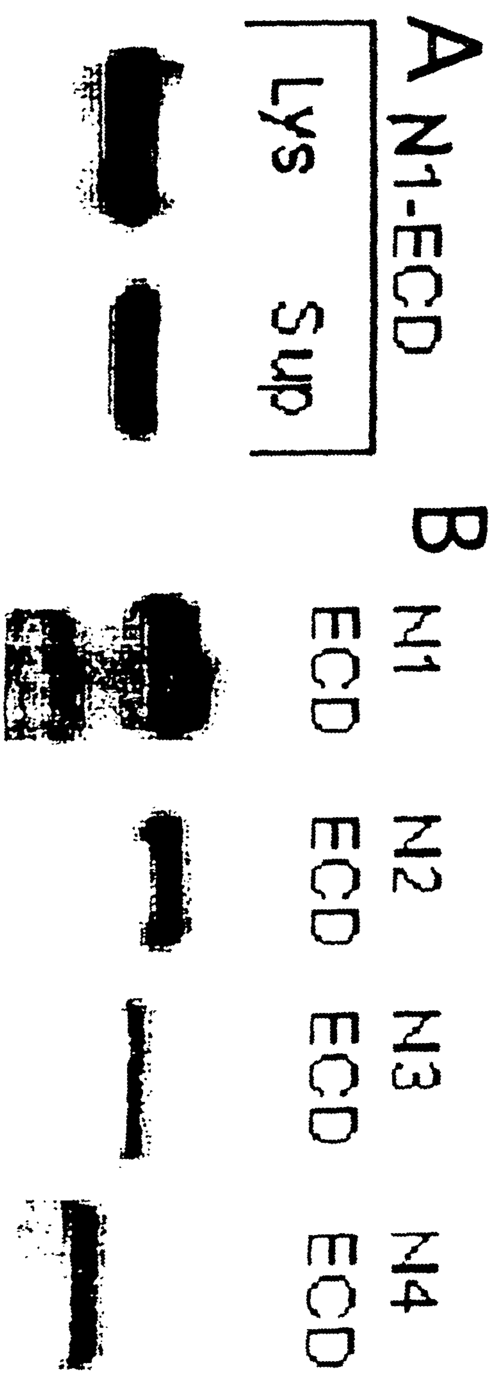
FIG. 5 This Figure shows the expression of Notch1-based fusion protein (Notch1ECD/Fc) in 293. Panel A: expression in cell lystates (lys) or secreted into media (sup). Panel B: expression in 293 lysates of NECD/Fcs, as listed.

In the case of Notch1 decoys that generate the fusion after nucleotide sequence encoding EGF-like repeat 13, a BamHI site will be generated to create the fusion site and this fusion sequence is provided (Notch1, FIG. 5). This applies to formulation h-Notch1$^{(1-13)}$ decoy.

Figure 6:
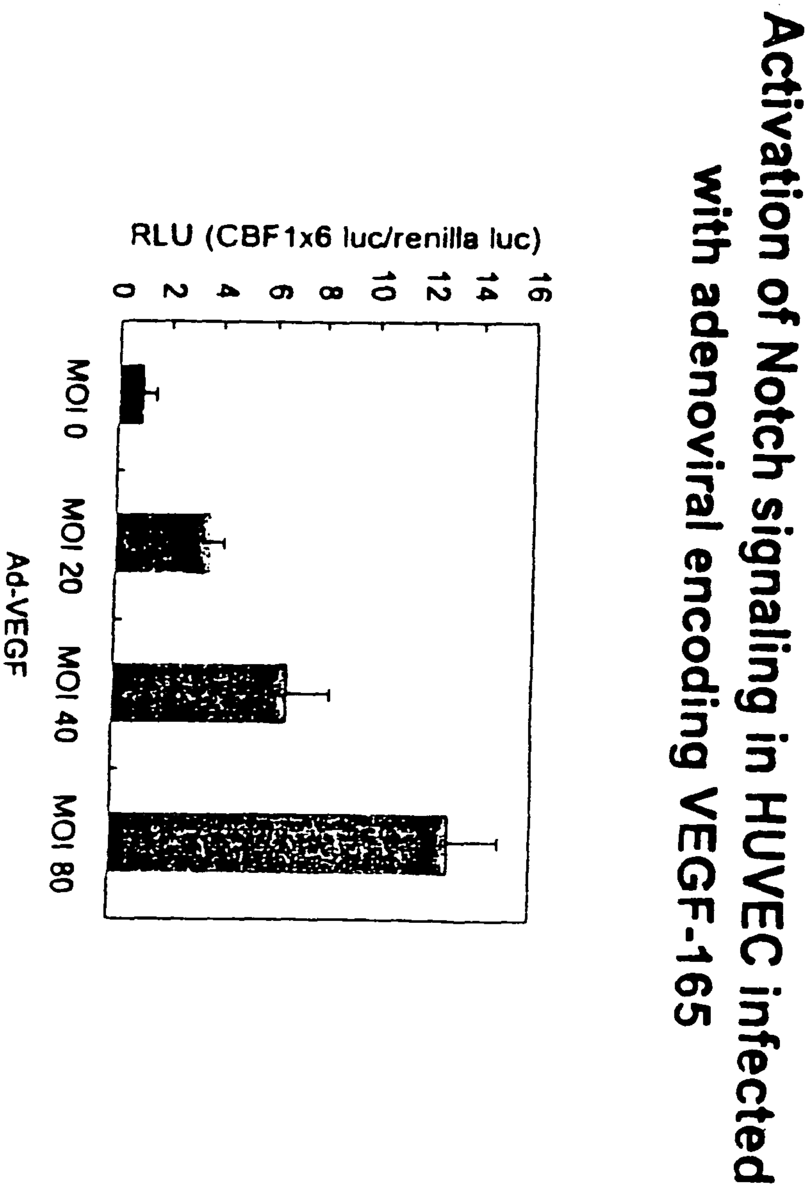
FIG. 6 This Figure shows activation of Notch signaling in HUVEC infected with adenoviral-encoding VEGF-165. Activation of Notch signaling can be detected by using CBF1 promoter activity. Transcriptional activity of CBF1 promoter is activated by binding of Notch-IC to CBF1. We measured CBF1 promoter activity in HUVEC which was infected with adenovirus-encoding VEGF-165 at different MOI. Induction of CBF1 promoter was clearly detected in Ad-VEGF-infected HUVEC, compared to Ad-LacZ-infected cells in the MOI dependent manner. This data showed overexpression of VEGF could activate Notch signaling in HUVEC.

In the case of Notch1 decoys that generate the fusion after nucleotide sequence encoding EGF-like repeat 23, a BglII site will be generated to create the fusion site and this fusion sequence is provided (Notch1, FIG. 6). This applies to formulations h-sp$^{N}$Notch1$^{(9-23)}$ decoy, h-sp$^{HC}$Notch1$^{(9-23)}$ decoy.

Figure 7:
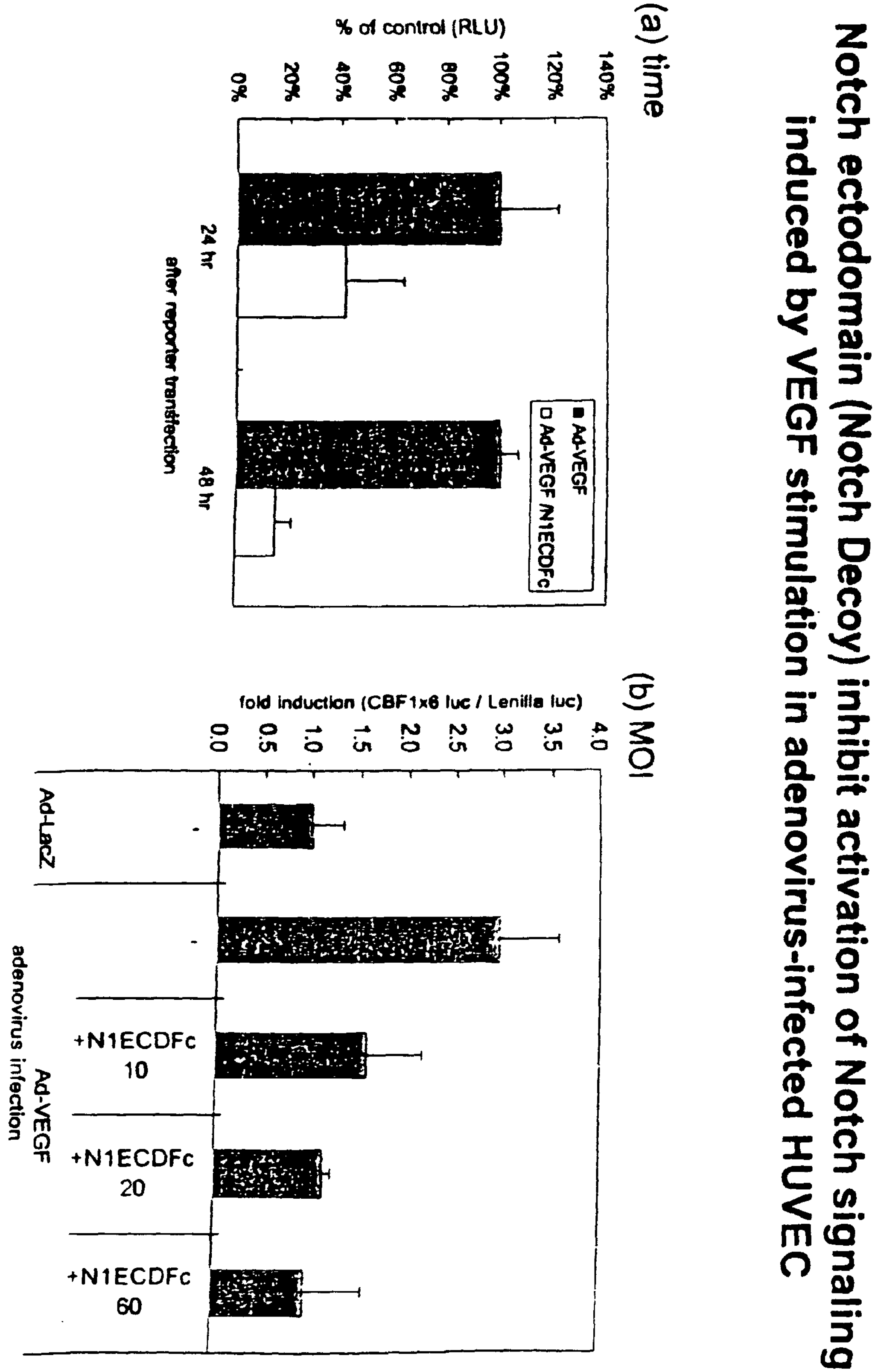
FIG. 7 This Figure shows the effect of Notch-based fusion proteins on VEGF-induced activation of Notch signaling. Co-infection of Ad-Notch-based fusion protein with Ad-VEGF clearly reduced activation of CBF1 promoter activity induced by Ad-VEGF infection alone. In the case of infection at 40 MOI for each adenovirus in panel A, 60% inhibition at 24 hour and 90% inhibition at 48 hour after reporter gene transfection was detected. This inhibitory activity of Notch trap was dependent on MOI of Ad-Notch-based fusion protein.

In the case of Notch1 decoys that generate the fusion after nucleotide sequence encoding EGF-like repeat 24, a BglII site will be generated to create the fusion site and this fusion sequence is provided (Notch1, FIG. 7). This applies to formulations h-Notch1$^{(1-24)}$ decoy, h-sp$^{N}$Notch1$^{(13-24)}$ decoy, h-sp$^{HC}$Notch1$^{(13-24)}$ decoy.

The amplified PCR product is subcloned into pBluescript SK II Fc to generate the different human Notch1/Fc chimeras. The human Notch1/Fc decoy sequences are then shuttled into mammalian expression vectors (pAd-lox, pCCL, pcDNA3) for expression and purification of human Notch1 decoy proteins.

Human Notch4 Fusion Proteins (Notch Decoys)

The Notch4 decoys are assembled using sequences encoding a signal peptide, a portion of the Notch4 extracellular domain encompassing all or a subset of the EGF-like repeat domains, and a portion of the human Fc protein (amino acids 1-237). The complete full-length sequence of human Notch4 is provided in FIG. 83.

The signal peptides utilized are either the native Notch4 signal peptide or the human Hc signal peptide, each fused to a region of Notch4. The signal peptide allows for secretion of the Notch decoy proteins.

The Notch4 extracellular domains used are designed to bind to Notch ligands and consist of all or a subset of the 29 EGF-like repeat domains of the human Notch4 protein The Fc tag is fused to the C-terminus of a given EGF-like repeat of human Notch4 and serves to allow for purification, detection, and stabilization of the Notch4 decoy proteins.

The overall design of the human Notch4 decoys, eleven formulations, is to encode for; (1) a signal peptide to allow for secretion of Notch4 decoy proteins into the extracellular media of eukaryotic cells that are used to produce the proteins, (2) a portion of the extracellular domain of all or a portion of the EGF-like repeats of human Notch4 to allow for association with Notch ligands, and (3) a portion of the human Fc protein to allow for detection.

The following eleven formulations of human Notch4 decoys will be described and are schematized in FIG. 111.

1) h-Notch4$^{(1-29)}$ decoy (N4-1 of FIG. 111)

2) h-Notch4$^{(1-13)}$ decoy (N4-2 of FIG. 111)

3) h-Notch4$^{(1-23)}$ decoy (N4-3 of FIG. 111)

4) h-sp$^{N}$Notch4$^{(9-23)}$ decoy (N4-4 of FIG. 111)

5) h-sp$^{HC}$Notch4$^{(9-23)}$ decoy (N4-5 of FIG. 111)

6) h-sp$^{N}$Notch4$^{(9-29)}$ decoy (N4-6 of FIG. 111)

7) h-sp$^{HC}$Notch4$^{(9-29)}$ decoy (N4-7 of FIG. 111)

8) h-sp$^{N}$Notch4$^{(13-23)}$ decoy (N4-8 of FIG. 111)

9) h-sp$^{HC}$Notch4$^{(13-23)}$ decoy (N4-9 of FIG. 111)

10) h-sp$^{N}$Notch4$^{(21-29)}$ decoy (N4-10 of FIG. 111)

11) h-sp$^{HC}$Notch4$^{(21-29)}$ decoy (N4-11 of FIG. 111)

Human Notch4 Sequence

The full-length amino acid (aa) sequence of human Notch4, consisting of aa residue 1 (M=methionine) to aa residue 2003 (K=lysine) is set forth in FIG. 83. The signal peptide and first 29 EGF-like repeat domains are present in aa 1-1174 of this sequence. Amino acids 1-1174, or a subset of these aa, were utilized for the design of the human Notch4 decoy proteins, described in the ensuing sections. The amino acids encompassing EGF-repeats 1-29 are underlined.

Human Fc Sequence Utilized to Generate the Fc Tag on Notch4 Decoy Proteins

The 237 amino acids of human Fc, shown in FIG. 84, were fused at the C-terminus of all Notch4 decoy constructs, just downstream of Notch4 EGF-like repeats. This region of human Fc allows for detection and purification of the Notch decoys and serves to stabilize the secreted human Notch4-human Fc fusion proteins.

Signal Peptides Utilized in Notch4 Decoy Proteins

Two distinct signal peptide sequences were incorporated into the design of the human Notch4 decoy proteins. The first is the human Notch4 signal peptide that is predicted to encompass amino acids 1-24 of human Notch4.

This determination was made using the Signal IP 3.0 Server program provided by the Technical University of Denmark. The second is the human Hc signal peptide that is predicted to encompass amino acids 1-22 of human Hc.

1. Human Notch4 Signal Peptide (aa 1-24)

```
MQPPSLLLLLLLLLLLCVSVVRP/R    (SEQ ID NO: 104)
```

Amino acid sequence of the predicted human Notch4 signal peptide is schematized in FIG. 112. The prediction results of analysis utilizing the SignalIP 3.0 Server provided online by the Technical University of Denmark are shown in FIG. 112. These results predict a site of cleavage located between proline 23 (A23) and Arginine 24 (R24). The cleavage site is indicated by the "/" in amino acid sequence 1-24 of human Notch4, provided above.

2. Human Notch4 Signal Peptide Fusion Peptide (aa 1-27) utilized in Notch4 Decoys that Utilize this Signal Sequence In order to make sure that the Notch4 signal peptide is utilized efficiently three additional amino acids beyond the predicted minor site of cleavage are provided in the human Notch4 decoys. Thus the amino acid sequence utilized in the human Notch4 decoy formulation, that incorporate a Notch4 signal peptide, contains glycine-proline-arginine (GLL— bold/underlined) between the sites of predicted signal peptide cleavage and the Notch4 EGF-like repeats.

MQPPSLLLLLLLLLLLCVSVVRPRGLL (SEQ ID NO: 131)

3. Human HC Signal Peptide (aa 1-22)

The amino acid sequence of the predicted human Hc signal peptide is

MWGWKCLLFWAVLVTATLCTA/R (SEQ ID NO: 17)

The prediction results of analysis utilizing the SignalIP 3.0 Server provided online by the Technical University of Denmark are shown above. These results predict a major site of cleavage located between alanine 21 (A21) and arginine 22 (22). This cleavage sites is indicated by the "/" in amino acid sequence 1-22 of human Hc provided above.

h-Notch4$^{(1-29)}$ Decoy h-Notch4$^{(1-29)}$ decoy denotes the human Notch4 decoy that encompasses EGF-like repeats 1-29 of Notch4 (N4-1 of FIG. 111).

h-Notch4$^{(1-29)}$ decoy protein consists of the following three components:

(1) human Notch4 signal sequence consisting of amino acids 1-27 of human Notch4, followed by (2) amino acids encoding the EGF-like repeats 1-29 of human Notch4 consisting of amino acids 28-1173 followed by (3) amino acids 1174-1410 that contain the human Fc tag. The predicted signal peptide sequence is underlined and the human Fc tag is underlined and italicized. This formulation contains 1410 amino acids.

h-Notch4$^{(1-13)}$ Decoy h-Notch4$^{(1-13)}$ decoy denotes the human Notch4 decoy that encompasses EGF-like repeats 1-13 of Notch4 (N4-2 of FIG. 111).

h-Notch4$^{(1-13)}$ decoy protein consists of the following three components:

(1) human Notch4 signal sequence consisting of amino acids 1-27 of human Notch4, followed by (2) amino acids encoding the EGF-like repeats 1-13 of human Notch4 consisting of amino acids 28-554 followed by (3) amino acids 555-791 that contain the human Fc tag. The predicted signal peptide sequence is underlined and the human Fc tag is underlined and italicized. This formulation contains 791 amino acids.

h-Notch4$^{(1-23)}$ Decoy h-Notch4$^{(1-23)}$ decoy denotes the human Notch4 decoy that encompasses EGF-like repeats 1-23 of Notch4 (N4-3 of FIG. 111).

h-Notch4$^{(1-23)}$ decoy protein consists of the following three components:

(1) human Notch4 signal sequence consisting of amino acids 1-27 of human Notch4, followed by (2) amino acids encoding the EGF-like repeats 1-23 of human Notch4 consisting of amino acids 28-933 followed by (3) amino acids 934-1170 that contain the human Fc tag. The predicted signal peptide sequence is underlined and the human Fc tag is underlined and italicized. This formulation contains 1170 amino acids.

h-sp$^{N}$Notch4$^{(9-23)}$ Decoy h-sp$^{N}$Notch4$^{(9-23)}$ decoy denotes the human Notch4 decoy that encompasses EGF-like repeats 9-23 of Notch4 (N4-4 of FIG. 111). The abbreviation sp$^{N}$ denotes that the human Notch4 signal peptide is used in this formulation.

h-sp$^{N}$Notch4$^{(9-23)}$ decoy protein consists of the following three components:

(1) human Notch4 signal sequence consisting of amino acids 1-27 of human Notch4, followed by (2) amino acids encoding the EGF-like repeats 9-23 of human Notch4 consisting of amino acids 28-602 followed by (3) amino acids 603-839 that contain the human Fc tag. The predicted signal peptide sequence is underlined and the human Fc tag is underlined and italicized. This formulation contains 839 amino acids.

h-sp$^{HC}$Notch4$^{9-23)}$ decoy h-sp$^{HC}$Notch4$^{(9-23)}$ decoy denotes the human Notch4 decoy that encompasses EGF-like repeats 9-23 of Notch4 (N4-5 of FIG. 111). The abbreviation sp$^{HC}$ denotes that the human Hc signal peptide is used in this formulation.

h-sp$^{HC}$Notch4$^{(9-23)}$ decoy protein consists of the following three components:

(1) human Hc signal sequence consisting of amino acids 1-22 of human Hc, followed by (2) amino acids encoding the EGF-like repeats 9-23 of human Notch4 consisting of amino acids 23-597 followed by (3) amino acids 598-834 that contain the human Fc tag. The predicted signal peptide sequence is underlined and the human Fc tag is underlined and italicized. This formulation contains 834 amino acids.

h-sp$^{N}$Notch4$^{(9-29)}$ Decoy h-sp$^{N}$Notch4$^{(9-29)}$ decoy denotes the human Notch4 decoy that encompasses EGF-like repeats 9-29 of Notch4 (N4-6 of FIG. 111). The abbreviation sp$^{N}$ denotes that the human Notch4 signal peptide is used in this formulation.

h-sp$^{N}$Notch4$^{(9-29)}$ decoy protein consists of the following three components:

(1) human Notch4 signal sequence consisting of amino acids 1-27 of human Notch4, followed by (2) amino acids encoding the EGF-like repeats 9-29 of human Notch4 consisting of amino acids 28-843 followed by (3) amino acids 844-1080 that contain the human Fc tag. The predicted signal peptide sequence is underlined and the human Fc tag is underlined and italicized. This formulation contains 1080 amino acids.

h-sp$^{HC}$Notch4$^{9-29)}$ Decoy h-sp$^{HC}$Notch4$^{(9-29)}$ decoy denotes the human Notch4 decoy that encompasses EGF-like repeats 9-29 of Notch4 (N4-7 of FIG. 111). The abbreviation sp$^{HC}$ denotes that the human Hc signal peptide is used in this formulation.

h-sp$^{HC}$Notch4$^{(9-29)}$ decoy protein consists of the following three components:

(1) human Hc signal sequence consisting of amino acids 1-22 of human Hc, followed by (2) amino acids encoding the EGF-like repeats 9-29 of human Notch4 consisting of amino acids 23-838 followed by (3) amino acids 839-1075 that contain the human Fc tag. The predicted signal peptide sequence is underlined and the human Fc tag is underlined and italicized. This formulation contains 1075 amino acids.

h-sp$^{N}$Notch4$^{(13-23)}$ Decoy h-sp$^{N}$Notch4$^{(13-23)}$ decoy denotes the human Notch4 decoy that encompasses EGF-like repeats 13-23 of Notch4 (N4-8 of FIG. 111). The abbreviation sp$^{N}$ denotes that the human Notch4 signal peptide is used in this formulation.

h-sp$^{N}$Notch4$^{(13-23)}$ decoy protein consists of the following three components:

(1) human Notch4 signal sequence consisting of amino acids 1-27 of human Notch4, followed by (2) amino acids encoding the EGF-like repeats 13-23 of human Notch4 consisting of amino acids 28-444 followed by (3) amino acids 445-681 that contain the human Fc tag. The predicted signal peptide sequence is underlined and the human Fc tag is underlined and italicized. This formulation contains 681 amino acids.

h-sp$^{HC}$Notch4$^{(13-23)}$ Decoy h-sp$^{HC}$Notch4$^{(13-23)}$ decoy denotes the human Notch4 decoy that encompasses EGF-like repeats 13-23 of Notch4 (N4-9 of FIG. 111). The abbreviation sp$^{HC}$ denotes that the human Hc signal peptide is used in this formulation.

h-sp$^{HC}$Notch4$^{(13-23)}$ decoy protein consists of the following three components:

(1) human Hc signal sequence consisting of amino acids 1-22 of human Hc, followed by (2) amino acids encoding the EGF-like repeats 13-23 of human Notch4 consisting of amino acids 23-439 followed by (3) amino acids 440-676 that contain the human Fc tag. The predicted signal peptide sequence is underlined and the human Fc tag is underlined and italicized. This formulation contains 676 amino acids.

h-$sp^{N}$Notch4$^{(21-29)}$ Decoy h-$sp^{N}$Notch4$^{(21-29)}$ decoy denotes the human Notch4 decoy that encompasses EGF-like repeats 21-29 of Notch4 (N4-10 of FIG. 111). The abbreviation $sp^{N}$ denotes that the human Notch4 signal peptide is used in this formulation.

h-$sp^{N}$Notch4$^{(21-29)}$ decoy protein consists of the following three components:

(1) human Notch4 signal sequence consisting of amino acids 1-27 of human Notch4, followed by (2) amino acids encoding the EGF-like repeats 21-29 of human Notch4 consisting of amino acids 28-392 followed by (3) amino acids 393-629 that contain the human Fc tag. The predicted signal peptide sequence is underlined and the human Fc tag is underlined and italicized. This formulation contains 629 amino acids.

h-$sp^{HC}$Notch4$^{(21-29)}$ Decoy h-$sp^{HC}$Notch4$^{(21-29)}$ decoy denotes the human Notch4 decoy that encompass EGF-like repeats 21-29 of Notch4 (N4-11 of FIG. 111). The abbreviation $sp^{HC}$ denotes that the human Hc signal peptide is used in this formulation.

h-$sp^{HC}$Notch4$^{(21-29)}$ decoy protein consists of the following three components:

(1) human Hc signal sequence consisting of amino acids 1-22 of human Hc, followed by (2) amino acids encoding the EGF-like repeats 21-29 of human Notch4 consisting of amino acids 23-387 followed by (3) amino acids 388-624 that contain the human Fc tag. The predicted signal peptide sequence is underlined and the human Fc tag is underlined and italicized. This formulation contains 624 amino acids.

Methods

Construction of Human Notch4 Decoys

Total RNA from human umbilical venous endothelial cells (HUVEC) was used to generate the human Notch4 decoy variants. Total RNA was reverse transcribed with M-MLV reverse transcriptase and either random hexamer primers or a Notch4 decoy specific primer. The synthesized cDNA was then amplified with Notch4 decoy specific upstream (sense) and downstream (antisense) primers.

The downstream primer encodes either BamHI or BglII restriction site at the 5' end that will ligate with the BglII site in the Fc sequence to generate an in frame human Notch4/Fc chimera.

In the case of Notch4 decoys that generate the fusion after nucleotide sequence encoding EGF-like repeat 29, a BglII site will be generated to create the fusion site and this fusion sequence is provided (Notch4, FIG. 113). This applies to formulations; h-Notch4$^{(1-29)}$ decoy, h-$sp^{N}$Notch4$^{(9-29)}$ decoy, h-$sp^{HC}$Notch4$^{(9-29)}$ decoy, h-$sp^{N}$Notch4$^{(21-29)}$ decoy, h-$sp^{H}$-$_{C}$Notch4$^{(21-29)}$ decoy.

In the case of Notch4 decoys that generate the fusion after nucleotide sequence encoding EGF-like repeat 13, a BamHI site will be generated to create the fusion site and this fusion sequence is provided (Notch4, FIG. 114). This applies to formulation h-Notch4$^{(1-13)}$ decoy.

In the case of Notch4 decoys that generate the fusion after nucleotide sequence encoding EGF-like repeat 23, a BglII site will be generated to create the fusion site and this fusion sequence is provided (Notch4, FIG. 115). This applies to formulations h-Notch4$^{(1-23)}$ decoy, h-$sp^{N}$Notch4$^{(9-23)}$ decoy, h-$sp^{HC}$Notch4$^{(9-23)}$ decoy, h-$sp^{N}$Notch4$^{(13-23)}$ decoy, h-$sp^{H}$-$_{C}$Notch4$^{(13-23)}$ decoy.

The amplified PCR product is subcloned into pBluescript SK II Fc to generate the different human Notch4/Fc chimeras. The human Notch4/Fc decoy sequences are then shuttled into mammalian expression vectors (pAd-lox, pCCL) for expression and purification of human Notch4 decoy proteins.

Second Series of Experiments

Materials & Methods

Plasmid Constructs

Adenovirus constructs encoding LacZ, full-length Notch4, or the activated form of Notch4/int3 have been previously described (Shawber et al., 2003). An activated form of Notch1 cDNA fused in frame with 6 myc tags (Kopan et al., 1994) was cloned into the adenovirus expression vector, pAd-lox. Both VEGF165 and N1ECDFc was also cloned into the pAd-lox. Adenoviral stocks were generated and titered as previously described (Hardy et al., 1997). The retroviral expression vector pHyTc encoding either LacZ, the activated form of Notch4/int3, J1, Dll1 and Dll4 have been previously described (Uyttendaele et al., 2000, Shawber et al., 2003, Das et al., 2004 in print). Plasmids encoding the intracellular domain of Notch1(bp 5479-7833, Genbank accession# X57405) and the extracellular domain of Dll4 (bp 1-1545, Genbank accession# AF253468, provided by Chiron) fused in frame with a myc/His tag, were engineered into pHyTC.

Notch1ECD, Notch2ECD, Notch3ECD and Notch4ECD are engineered using the Fc sequences contained in the plasmid pCMX-sFR1-IgG using the methods set forth in *Clin. Exp. Immunol.* (1992) 87(1):105-110 to create the Notch-based fusion proteins, i.e. Notch1ECD/Fc, Notch2ECD/Fc, Notch3ECD/Fc and Notch4ECD/Fc.

Adenoviral Gene Transfer $7.5\times10^5$ cells of HUVEC at passage 3 were seeded into type I collagen-coated 6 well plates on the day before adenoviral infection. Adenoviral infection with Ad-lacZ, Ad-VEGF165 or Ad-N1ECDFc was performed at indicated m.o.i., and incubated at 37° C. for 1 hr with occasional swirling of plates.

Luciferase Reporter Assays

To determine ligand-induced Notch signaling, co-culture assays were performed using HeLa and 293-derived Bosc cells. Transient transfections were performed by calcium phosphate precipitation. Hela cells plated 1-day prior in 10-cm plates at $1.5\times10^6$ were transfected with 333 ng of pBOS Notch1, 333 ng pGA981-6, and 83 ng pLNC lacZ with either 666 ng pCMV-Fc or pHyTC-N1ECDFc (333 ng for x1, 666 ng for x2). Bosc cells plated 1-day prior in 10-cm plates at $4\times10^6$ were transfected with either 680 ng pHyTc-Jagged1, pHyTc-Dll1, pHyTc-Dll4, or pHyTc-x (empty vector). One day after transfection, the cells were co-cultured in triplicate (HeLa:Bosc, 1:2) on 12-well plates for 24 hours. Cells were harvested and luciferase activity was determined 2-days post-transfection using the Enhanced Luciferase assay kit (BD PharMingen), and β-galactosidase activity was determined using the Galacto-Light Plus kit (PE Biosystems). All assays were performed in a Berthold dual-injection luminometer.

To determine VEGF-induced Notch signaling, HUVEC which were infected with adenovirus were used. HUVEC plated 1-day prior in 6 well plates at $8.0\times10^5$ were infected with either Ad-LacZ as control or Ad-VEGF at indicated m.o.i. in the presence or absence of Ad-N1ECD/Fc. Two days after infection, infected HUVEC were re-seeded into 24-well plate at $1.5\times10^5$ cell in triplicate and cultured for 24 hours, and then transfected with 12.5 ng pRL-SV40 (Promega) and 137.5 ng pGA981-6 using Effectene transfection reagent (Qiagen). Cells were harvested either 1 or 2 days post-transfection and luciferase activity was determined by using the Dual-Luciferase® Reporter Assay System (Promega).

Sprouting Assay

For making collagen gels, an ice-cold solution of porcine type I collagen (Nitta gelatin, Tokyo, Japan) was mixed with 10×RPMI1640 medium and neutralization buffer at the ratio of 8:1:1. 400 μl aliquots of collagen gel were then added to 24-well plates and allowed to gel for at least 1 hour at 37° C. Following adenoviral infection (above), HUVEC was harvested and plated at $1.3\times10^5$ cells per well onto the top of the collagen gel in 24-well plates in 0.8 ml of EGM2 medium. HUVEC became nearly confluent 48 hours after plating. After seeding, medium was changed every 2 days for 1 week. Sprouting was observed and photographs taken after 8 days with an Olympus digital camera mounted to a microscope. For quantification of the number of sprouts, 5 fields per each well were randomly selected and sprouting was counted under microscopy in a blind manner by two investigators.

Results and Discussion

NOTCHECD/Fc Fusion Proteins

Function as Antagonists of Notch

Notch Antagonists-NotchECD/Fc Fusion Proteins

Figure 2:
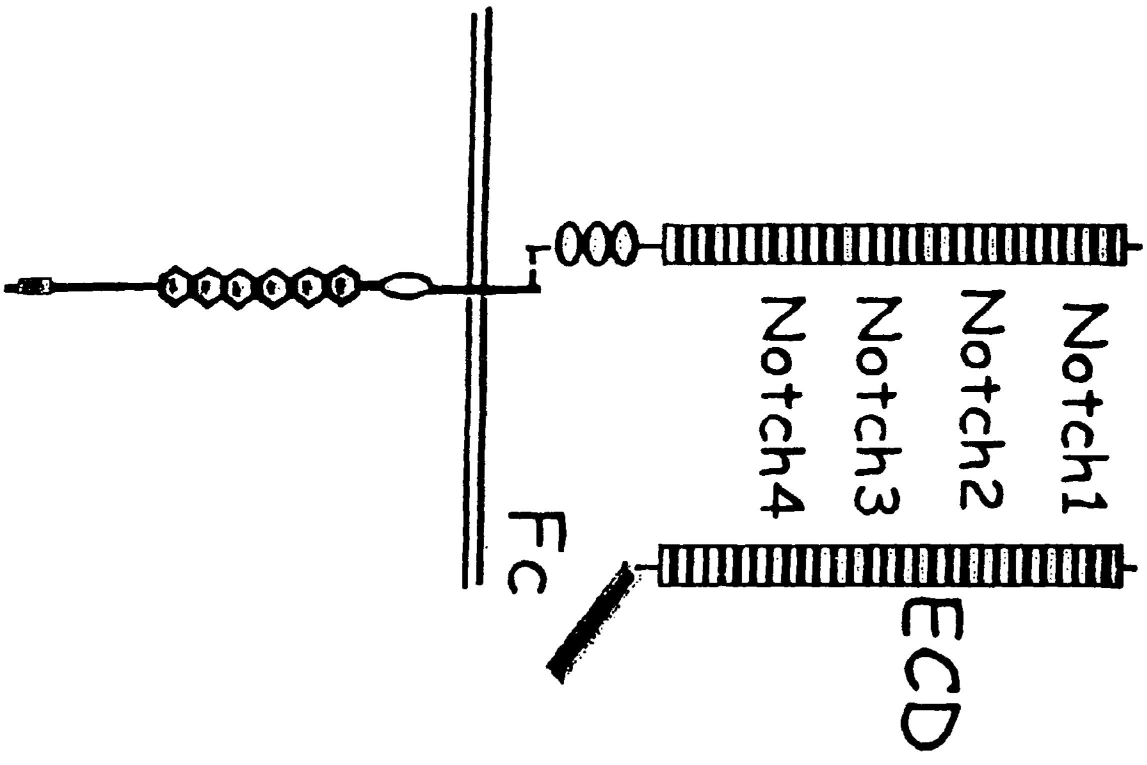
FIG. 2 This Figure shows the schematic design of Notch-based fusion proteins (NotchECD/Fc). The extracellular domain of Notch1, Notch2, Notch3, or Notch4 containing the EGF-repeats is fused to the Fc portion of an antibody.

We have made several Notch antagonists (FIG. 2). Our strategy was to fuse the coding sequence of Notch EGF repeats in the Extracellular Domain (ECD) to the human or mouse Fc domain. This design makes a secreted protein without signaling function but which retains the ligand-binding domain and thus should bind to and inhibit ligand function. We refer to these proteins as “NotchECD/Fc” and all four Notch1-4ECD/Fcs have been made. The Fc domain facilitates affinity purification and protein detection by immunoblotting or immunohistochemistry.

Testing Notch Antagonists

Figure 3:
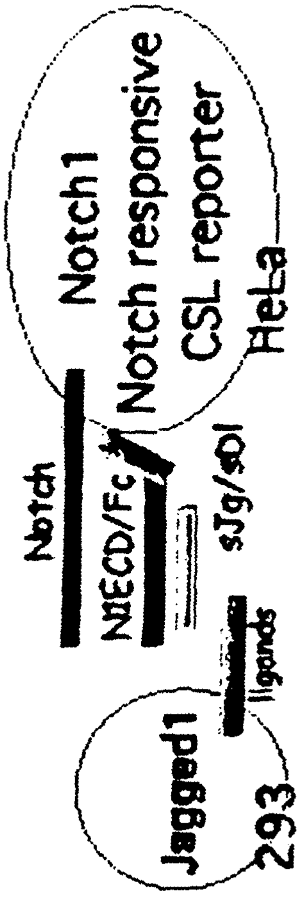
FIG. 3 This Figure shows a co-culture assay for testing the activity of Notch-based fusion proteins. Notch and Notch responsive transcriptional reporters are expressed in a "Notch-responsive" cell, HeLa. Notch ligands, Jagged-1, Delta-like 1, or Delta-like 4 are expressed in a "ligand-presenting" cell, 293. Expression is mediated by transfection of individual cell populations, cells are co-cultured, and then assayed for Notch-dependent reporter activity.

An in vitro co-culture system (FIG. 3) with ligands expressed on one cell and Notch receptor activation scored in another cell was used to measure transcriptional activation of the Notch pathway. We used this co-culture assay to show that Notch1ECD/Fc functions to block ligand-dependent Notch signaling (FIG. 4). The N1ECD/Fc expression vector was co-transfected at different ratios with full-length Notch1 and the CSL-luciferase reporter in HeLa cells, followed by co-culture with ligand expressing 293 cells. We observed that activation of Notch1 signaling by Notch ligands was reduced by N1ECD/Fc expression. This effect displayed concentration-dependency; a 2:1 ratio of N1ECD/Fc to Notch1 was more effective in inhibiting signaling than a 1:1 ratio. Notch1ECD/Fc could block signaling mediated by Jagged1, Delta-like 1 or Delta-like 4.

Expressing and Purifying Notch Antagonists

We have made CHO and HeLa cell lines expressing NotchECD/FCs using retroviral vectors for the purpose of protein purification. N1ECD/Fc proteins are secreted (FIG. 5); as shown in conditioned media collected from HeLa-NotchECD/Fc lines and purified with Protein-A (pA) agarose. The pA purified sample (Sup) and whole cell lysates (Lys) were immunoblotted with α-Fc antibody (FIG. 5, panel A) demonstrating that N1ECD/Fc is secreted into the media. Adenovirus vectors for NotchECD/Fc were used to infect HeLa cells and lysates from these cells were immunoblotted with α-Fc antibodies demonstrating that they express NotchECD/Fc(1, 2, 3, 4) proteins (FIG. 5, panel B). We are currently purifying N1ECD/Fc from CHO cell conditioned media using pA-affinity chromatography.

Defining Angiogenic Inhibition Using Notch Fusion Proteins

Activation of Notch Signaling can be Detected by Using CBF1 Promoter Activity

One can measure Notch signaling function by measuring transcriptional activity of CBF1 promoter, which is activated by binding of Notch-IC to CBF1. We measured CBF1 promoter activity in HUVEC which was infected with adenovirus encoding VEGF-165 at different MOI (FIG. 6). Induction of CBF1 promoter was clearly detected in Ad-VEGF-infected HUVEC, compared to Ad-LacZ-infected cells in the MOI dependent manner. This data showed overexpression of VEGF could activate Notch signaling in HUVEC. Thus VEGF induced Notch signaling activity.

We asked whether Notch fusion proteins could block VEGF-induced activation of Notch signaling. Co-infection of Ad-Notch fusion protein with Ad-VEGF clearly reduced activation of CBF1 promoter activity induced by Ad-VEGF infection alone (FIG. 7). In the case of infection at 40 MOI for each adenovirus in FIG. 7 (panel A), 60% inhibition at 24 hr and 90% inhibition at 48 hr after reporter gene transfection were detected also the inhibitory activity of Notch decoy was dependent on MOI of Ad-Notch fusion protein.

Notch Fusion Proteins Block Initiation of Angiogenic Sprouting Induced by VEGF

Figure 8:
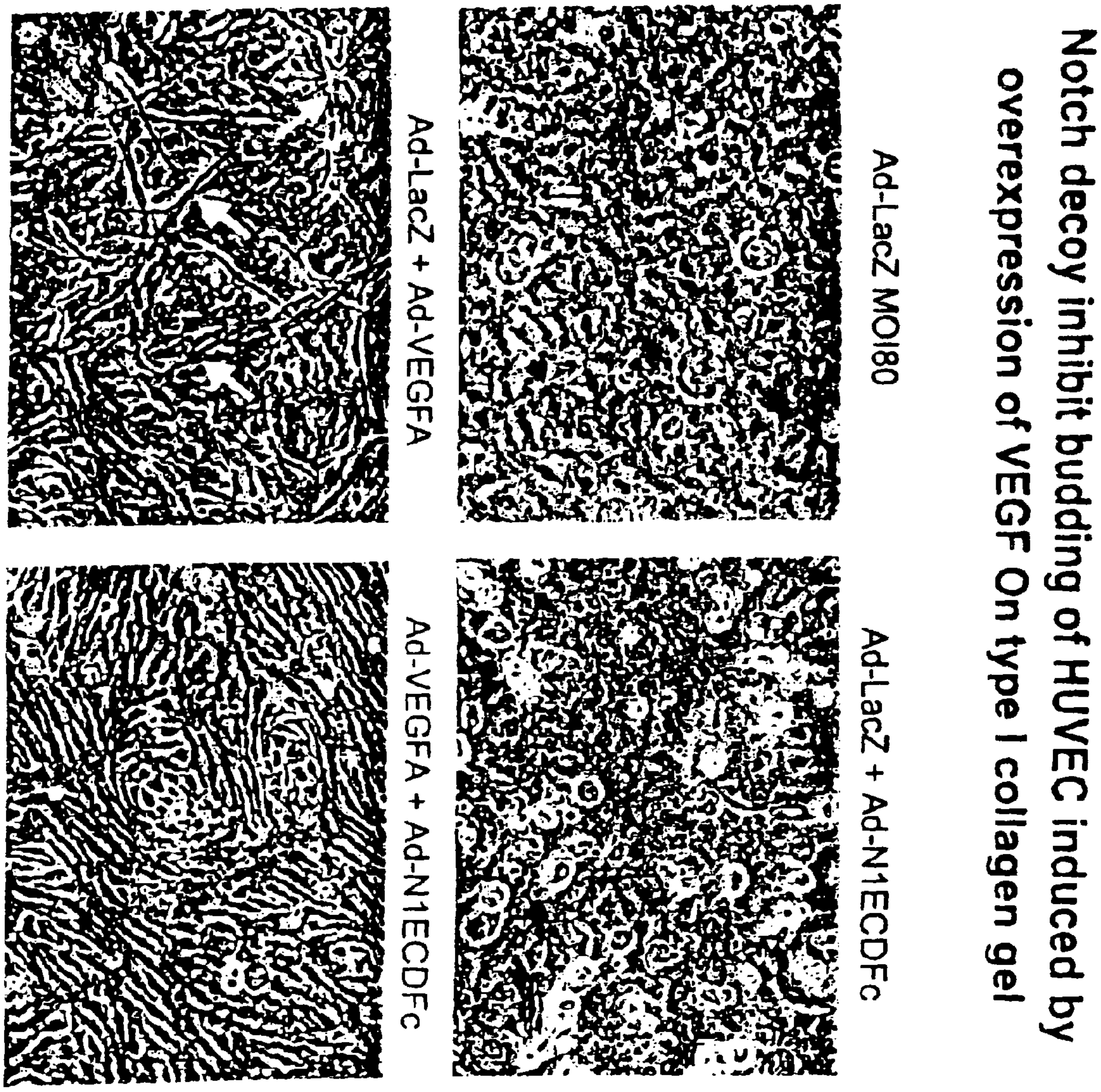
FIG. 8 This Figure shows an experiment in which we evaluated the effect of Notch-based fusion proteins on induction of budding by overexpressed VEGF-165 in HUVEC. When Ad-VEGF-infected HUVEC were cultured on type collagen gel for 8 days, budding was induced into collagen gel. This induction of budding by overexpressed VEGF was clearly inhibited by coinfection of adenoviral-encoding Notch-based fusion proteins. Ad-Notch-based fusion protein itself had less effect on morphology.

In this experiment, we evaluated the effect of Notch decoy on induction of budding (initiation of sprouting) by overexpressed VEGF-165 in HUVEC. When Ad-VEGF-infected HUVEC were cultured on type collagen gel for 8 days, budding was induced into collagen gel. This induction of budding by overexpressed VEGF was clearly inhibited by coinfection of adenoviral encoding Notch fusion protein (FIG. 8). Ad-Notch fusion protein itself had less effect on morphology.

Figure 9:
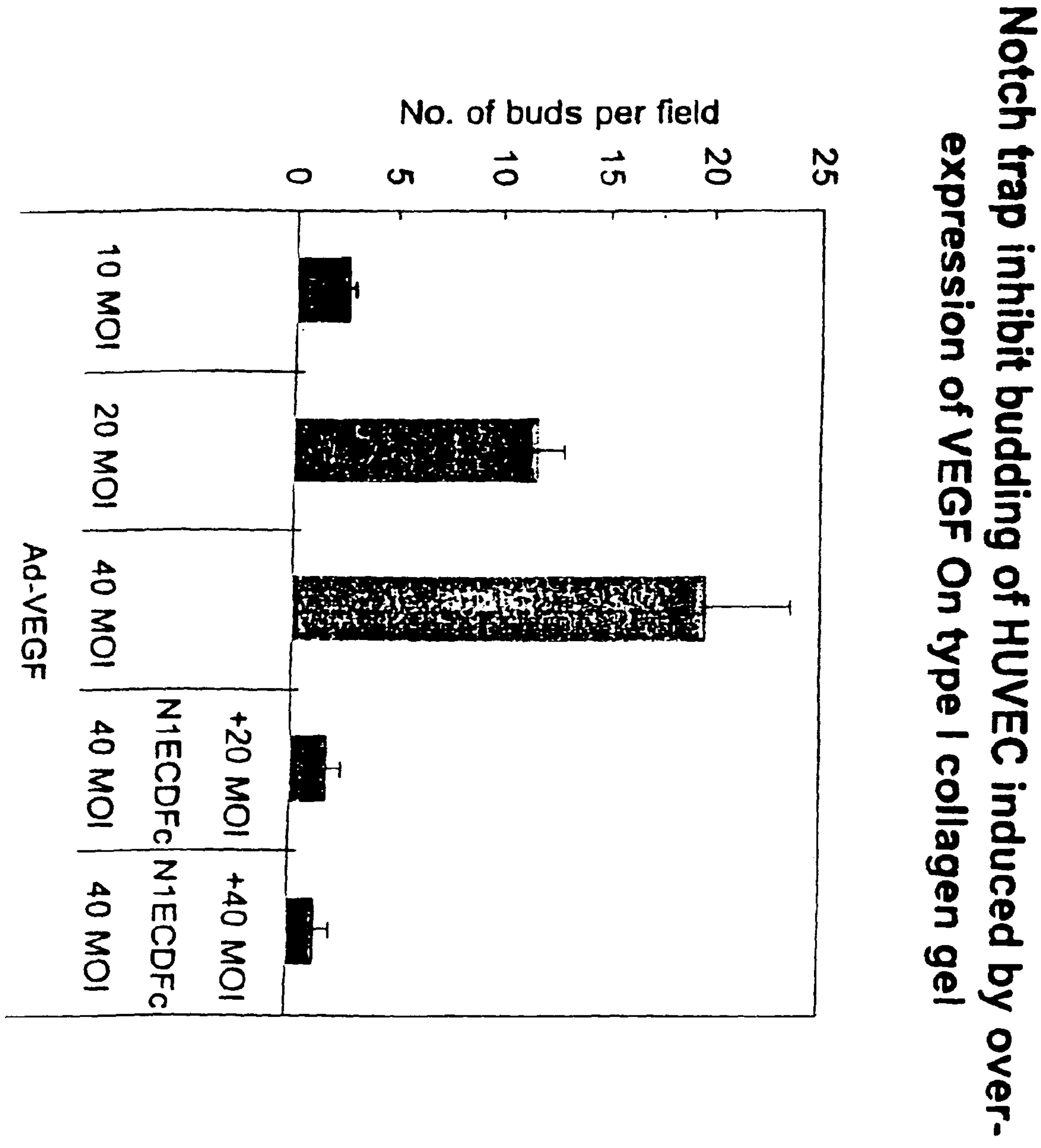
FIG. 9 This Figure shows the result of counting buds per field under microscope. Ad-VEGF-infection into HUVEC increased the number of buds depending on used MOI. Even though a half MOI of Notch-based fusion protein was used, compared to Ad-VEGF, Ad-VEGF-induced budding was clearly inhibited. These data suggested that VEGF induced budding of HUVEC through activation of Notch signaling and Notch-based fusion protein could inhibit VEGF-induced budding.

In FIG. 9 we counted buds per field using the microscope. Ad-VEGF-infection into HUVEC increased the number of buds depending on the MOI used. Ad-VEGF-induced budding was clearly inhibited. These data suggest that VEGF induced budding of HUVEC through activation of Notch signaling and that the Notch fusion protein could inhibit VEGF-induced budding.

REFERENCES CITED IN SECOND SERIES OF EXPERIMENTS

1. Artavanis-Tsakonas, S., K. Matsuno, and M. E. Fortini. 1995. Notch signaling. *Science* 268:225-232.
2. Bailey, A. M., and J. W. Posakony. 1995. Suppressor of hairless directly activates transcription of enhancer of split complex genes in response to Notch receptor activity. *Genes & Development* 9:2609-22.
3. Bettenhausen, B., M. Hrabe de Angelis, D. Simon, J. L. Guenet, and A. Gossler. 1995. Transient and restricted expression during mouse embryogenesis of Dll, a murine gene closely related to *Drosophila Delta*. *Development* 121:2407-18.
4. Blaumueller, C. M., H. Qi, P. Zagouras, and S. Artavanis-Tsakonas. 1997. Intracellular cleavage of Notch leads to a heterodimeric receptor on the plasma membrane. *Cell* 90:281-91.
5. Caronti, B., L. Calandriello, A. Francia, L. Scorretti, M. Manfredi, T. Sansolini, E. M. Pennisi, C. Calderaro, and G. Palladini. 1998. Cerebral autosomal dominant arteriopathy with subcortical infarcts and leucoencephalopathy (CA- DASIL). Neuropathological and in vitro studies of abnormal elastogenesis. *Acta Neurol Scand.* 98:259-67.
6. Desmond, D. W., J. T. Moroney, T. Lynch, S. Chan, S. S. Chin, D. C. Shungu, A. B. Naini, and J. P. Mohr. 1998. CADASIL in a North American family: clinical, pathologic, and radiologic findings [see comments]. *Neurology* 51:844-9.
7. Dunwoodie, S. L., D. Henrique, S. M. Harrison, and R. S. Beddington. 1997. Mouse Dll3: a novel divergent Delta gene which may complement the function of other Delta homologues during early pattern formation in the mouse embryo. *Development* 124:3065-76.
8. Eastman, D. S., R. Slee, E. Skoufos, L. Bangalore, S. Bray, and C. Delidakis. 1997. Synergy between suppressor of Hairless and Notch in regulation of Enhancer of split m gamma and m delta expression. *Mol Cell Biol.* 17:5620-5634.
9. Fortini, M. E., and S. Artavanis-Tsakonas. 1993. Notch: neurogenesis is only part of the picture. *Cell* 75:1245-7.
10. Gale, N. W., and G. D. Yancopoulos. 1999. Growth factors acting via endothelial cell-specific receptor tyrosine kinases: VEGFs, Angiopoietins, and ephrins in vascular development. *Genes and Development* 13:1055-1066.
11. Gallahan, D., and R. Callahan. 1997. The mouse mammary tumor associated gene INT3 is a unique member of the NOTCH gene family (NOTCH4). *Oncogene* 14:1883-90.
12. Greenwald, I. 1994. Structure/function studies of lin-12/Notch proteins. *Current Opinion in Genetics & Development* 4:556-62.
13. Greenwald, I. 1998. LIN-12/Notch signaling: lessons from worms and flies. *Genes Dev.* 12:1751-62.
14. Henderson, A. M., S. J. Wang, A. C. Taylor, M. Aitkenhead, and C. C. W. Hughes. 2001. The basic helix-loop-helix transcription factor HESR1 regulates endothelial cell tube formation. *J Biol Chem.* 276:6169-6176.
15. Hicks, C., S. H. Johnston, G. diSibio, A. Collazo, T. F. Vogt, and G. Weinmaster. 2000. Fringe differentially modulates Jagged1 and Delta1 signalling through Notch1 and Notch2. *Nature Cell Biology* 2:515-520.
16. Hsieh, J. J., T. Henkel, P. Salmon, E. Robey, M. G. Peterson, and S. D. Hayward. 1996. Truncated mammalian Notch1 activates CBF1/RBPJk-repressed genes by a mechanism resembling that of Epstein-Barr virus EBNA2. *Molecular & Cellular Biology* 16:952-9.
17. Hsieh, J. J., D. E. Nofziger, G. Weinmaster, and S. D. Hayward. 1997. Epstein-Barr virus immortalization: Notch2 interacts with CBF1 and blocks differentiation. *J Virol.* 71:1938-45.
18. Jarriault, S., C. Brou, F. Logeat, E. H. Schroeter, R. Kopan, and A. Israel. 1995. Signaling downstream of activated mammalian Notch. *Nature* 377:355-358.
19. Joutel, A., F. Andreux, S. Gaulis, V. Domenga, M. Cecillon, N. Battail, N. Piga, F. Chapon, C. Godfrain, and E. Tournier-Lasserve. 2000. The ectodomain of the Notch3 receptor accumulates within the cerebrovasculature of CADASIL patients [see comments]. *J Clin Invest.* 105:597-605.
20. Joutel, A., C. Corpechot, A. Ducros, K. Vahedi, H. Chabriat, P. Mouton, S. Alamowitch, V. Domenga, M. Cecillion, E. Marechal, J. Maciazek, C. Vayssiere, C. Cruaud, E. A. Cabanis, M. M. Ruchoux, J. Weissenbach, J. F. Bach, M. G. Bousser, and E. Tournier-Lasserve. 1996. Notch3 mutations in CADASIL, a hereditary adult-onset condition causing stroke and dementia. *Nature* 383:707-10.
21. Kopan, R., E. H. Schroeter, H. Weintraub, and J. S. Nye. 1996. Signal transduction by activated mNotch: importance of proteolytic processing and its regulation by the extracellular domain. *Proc Natl Acad Sci USA* 93:1683-8.
22. Krebs, L. T., Y. Xue, C. R. Norton, J. R. Shutter, M. Maguire, J. P. Sundberg, D. Gallahan, V. Closson, J. Kitajewski, R. Callahan, G. H. Smith, K. L. Stark, and T. Gridley. 2000. Notch signaling is essential for vascular morphogenesis in mice. *Genes and Development* 14:1343-1352.
23. Lardelli, M., J. Dahlstrand, and U. Lendahl. 1994. The novel Notch homologue mouse Notch3 lacks specific epidermal growth factor-repeats and is expressed in proliferating neuroepithelium. *Mechanism of Development* 46:123-136.
24. Lawson, N. D., N. Scheer, V. N. Pham, C. Kim, A. B. Chitnis, J. A. Campos-Ortega, and B. M. Weinstein. 2001. Notch signaling is required for arterial-venous differentiation during embryonic vascular development. *Development* 128:3675-3683.
25. Lewis, J. 1998. Notch signaling and the control of cell fate choices in vertebrates. *Semin Cell Dev Biol.* 9:583-589.
26. Lieber, T., S. Kidd, E. Alcomo, V. Corbin, and M. W. Young. 1993. Antineurogenic phenotypes induced by truncated Notch proteins indicate a role in signal transduction and may point to a novel function for Notch in nuclei. *Genes Dev.* 7:1949-1965.
27. Lindner, V., C. Booth, I. Prudovsky, D. Small, T. Maciag, and L. Liaw. 2001. Members of the Jagged/Notch gene families are expressed in injured arteries and regulate cell phenotype via alteration in cell matrix and cell-cell interations. *Pathology* 159:875-883.
28. Lindsell, C. E., C. J. Shawber, J. Boulter, and G. Weinmaster. 1995. Jagged: A mammalian ligand that activates Notch1. *Cell* 80:909-917.
29. Logeat, F., C. Bessia, C. Brou, O. LeBail, S. Jarriault, N. G. Seidah, and A. Israel. 1998. The Notch1 receptor is cleaved constitutively by a furin-like convertase. *Proc Natl Acad Sci USA* 95:8108-12.
30. Lyman, D., and M. W. Young. 1993. Further evidence for function of the *Drosophila* Notch protein as a transmembrane receptor. *Proc Natl Acad Sci USA* 90:10395-10399.
31. Matsuno, K., M. J. Go, X. Sun, D. S. Eastman, and S. Artavanis-Tsakonas. 1997. Suppressor of Hairless-independent events in Notch signaling imply novel pathway elements. *Development* 124:4265-4273.
32. Nakagawa, O., D. G. McFadden, M. Nakagawa, H. Yanagisawa, T. Hu, D. Srivastava, and E. N. Olson. 2000. Members of the HRT family of basic helix-loop-helix proteins act as transcriptional repressors downstream of Notch signaling. *Proc Natl Acad Sci USA* 97:13655-13660.
33. Oberg, C., J. Li, A. Pauley, E. Wolf, M. Gurney, and U. Lendahl. 2001. The Notch intracellular domain is ubiquitinated and negatively regulated by the mammalian Sel-10 homolog. *J Biol Chem.* 276:35847-35853.
34. Owens, G. K. 1995. Regulation of differentiation of vascular smooth muscle cells. *Physiol Rev.* 75:487-527.
35. Rebay, I., R. G. Fehon, and S. Artavanis-Tsakonas. 1993. Specific truncations of *Drosophila* Notch define dominant activated and dominant negative forms of the receptor. *Cell* 74:319-29.
36. Robey, E. 1997. Notch in vertebrates. *Curr Opin Genet Dev.* 7:551-7.
37. Roehl, H., M. Bosenberg, R. Blelloch, and J. Kimble. 1996. Roles of the RAM and ANK domains in signaling by the *C. elegans* GLP-1 receptor. *Embo J.* 15:7002-7012.

38. Rogers, S., R. Wells, and M. Rechsteiner. 1986. Amino acid sequences common to rapidly degrade proteins: The PEST hypothesis. *Science* 234:364-368.

39. Sasai, Y., R. Kageyama, Y. Tagawa, R. Shigemoto, and S. Nakanishi. 1992. Two mammalian helix-loop-helix factors structurally related to *Drosophila* hairy and Enhancer of split. *Genes & Dev.* 6:2620-2634.

40. Shawber, C., J. Boulter, C. E. Lindsell, and G. Weinmaster. 1996a. Jagged2: a serrate-like gene expressed during rat embryogenesis. *Dev Biol.* 180:370-6.

41. Shawber, C., D. Nofziger, J. J. Hsieh, C. Lindsell, O. Bogler, D. Hayward, and G. Weinmaster. 1996b. Notch signaling inhibits muscle cell differentiation through a CBF1-independent pathway. *Development* 122:3765-73.

42. Shimizu, K., S. Chiba, T. Saito, T. Takahashi, K. Kumano, H. Hamada, and H. Hirai. 2002. Integrity of intracellular domain of Notch ligand is indespensable for cleavage required for the release of the Notch2 intracellular domain. *Embo J.* 21:294-302.

43. Shutter, J. R., S. Scully, W. Fan, W. G. Richards, J. Kitajewski, G. A. Deblandre, C. R. Kintner, and K. L. Stark. 2000a. Dll4, a novel Notch ligand expressed in arterial endothelium. *Genes Dev.* 14:1313-1318.

44. Shutter, J. R., S. Scully, W. Fan, W. G. Richards, J. Kitajewski, G. A. Deblandre, C. R. Kitner, and K. L. Stark. 2000b. Dll4, a novel Notch ligand expressed in arterial endothelium. *Genes and Development* 14:1313-1318.

45. Struhl, G., K. Fitzgerald, and I. Greenwald. 1993. Intrinsic activity of the Lin-12 and Notch intracellular domains in vivo. *Cell* 74:331-45.

46. Swiatek, P. J., C. E. Lindsell, F. Franco del Amo, G. Weinmaster, and T. Gridley. 1994. Notch 1 is essential for postimplantation development in mice. *Genes & Development* 8:707-719.

47. Tamura, K., Y. Taniguchi, S. Minoguchi, T. Sakai, T. Tun, T. Furukawa, and T. Honjo. 1995. Physical interaction between a novel domain of the receptor Notch and the transcription factor RBP-J kappa/Su(H). *Curr Biol.* 5:1416-1423.

48. Tietze, K., N. Oellers, and E. Knust. 1992. Enhancer of splitD, a dominant mutation of *Drosophila*, and its use in the study of functional domains of a helix-loop-helix protein. *Proc Natl Acad Sci USA* 89:6152-6156.

49. Uyttendaele, H., J. Ho, J. Rossant, and J. Kitajewski. 2001. Vascular patterning defects associated with expression of activated Notch4 in embryonic endothelium. *PNAS.* 98:5643-5648.

50. Uyttendaele, H., G. Marazzi, G. Wu, Q. Yan, D. Sassoon, and J. Kitajewski. 1996. Notch4/int-3, a mammary protooncogene, is an endothelial cell-specific mammalian Notch gene. *Development* 122:2251-9.

51. Vervoort, M., C. Dambly-Chaudiere, and A. Ghysen. 1997. Cell fate determination in *Drosophila. Curr Opin Neurobiol.* 7:21-28.

52. Villa, N., L. Walker, C. E. Lindsell, J. Gasson, M. L. Iruela-Arispe, and G. Weinmaster. 2001. Vascular expression of Notch pathway receptors and ligands is restricted to arterial vessels. *Mechanisms of Development* 108:161-164.

53. Weinmaster, G. 1997. The Ins and Outs of Notch Signaling. *Mol Cel Neurosci.* 9:91-102.

54. Weinmaster, G. 1998. Notch signaling: direct or what? *Curr Opin Genet Dev.* 8:436-42.

55. Weinmaster, G., V. J. Roberts, and G. Lemke. 1992. Notch 2: a second mammalian Notch gene. *Development* 116: 931-941.

56. Weinmaster, G., V. J. Roberts, and G. A. Lemke. 1991. A homolog of *Drosophila* Notch expressed during mammalian development. *Development* 113:199-205.

57. Wettstein, D. A., D. L. Turner, and C. Kintner. 1997. The Xenopus homolog of *Drosophila* Suppressor of Hairless mediates Notch signaling during primary neurogenesis. *Development* 124:693-702.

58. Wu, G., E. J. Hubbard, J. K. Kitajewski, and I. Greenwald. 1998. Evidence for functional and physical association between Caenorhabditis elegans SEL-10, a Cdc4p-related protein, and SEL-12 presenilin. *Proc Natl Acad Sci USA* 95:15787-91.

59. Wu, G., S. A. Lyapina, I. Das, J. Li, M. Gurney, A. Pauley, I. Chui, R. J. Deshaies, and J. Kitajewski. 2001. SEL-10 is an inhibitor of notch signaling that targets notch for ubiquitin-mediated protein degradation. *Mol Cell Biol.* 21:7403-7015.

60. Xue, Y., X. Gao, C. E. Lindsell, C. R. Norton, B. Chang, C. Hicks, M. Gendron-Maguire, E. B. Rand, G. Weinmaster, and T. Gridley. 1999. Embryonic lethality and vascular defects in mice lacking the Notch ligand Jagged1. *Hum Mol Genet.* 8:723-30.

Third Series of Experiments

VEGF Initiates Angiogenesis Via an Activation of Notch Signaling

Both the VEGF and Notch signaling pathways are critical for vascular development. Here we show that VEGF activates Notch signaling to initiate angiogenesis. VEGF increased the expression of Delta4 and Notch4 causing Notch signal activation and inducing filopodia in cultured primary endothelial cells. Studies using VEGF Receptor inhibitors show that Notch signal activation in turn enhances VEGF action by inducing VEGFR-1 (Flt-1) expression. Other elements of VEGF action, including the induction of MMP-9 and MT1-MMP, are mediated by Notch. Using in vivo assays to model VEGF-induced skin neovascularization, we found that a secreted Notch inhibitor (Notch-based fusion protein) blocks VEGF-induced neo-vascularization and induction of VEGFR-1 expression. Thus, Notch signaling is requisite for angiogenesis regulated by VEGF, likely at the level of initiation.

VEGF is a key regulator of angiogenesis progression consisting of multiple processes, such as degradation of ECM, budding (filopodia formation), proliferation, survival, and migration of endothelial cells. Although most of the steps might be co-operated with downstream molecules of VEGF signaling, it is not known how these steps are coordinately regulated to result in more complex morphogenetic events, such as angiogenic sprouting. Notch signaling is an evolutionarily conserved signaling mechanism that functions to regulate cell fate decisions (1). Upon binding by a ligand, such as Jagged and Delta-like, the cytoplasmic domain of Notch (NotchIC) is released by presenilin/γ-secretase, translocates to the nucleus, interacts with the transcriptional repressor CSL (CBF1/Su(H)/lag2), and converts it to a transcriptional activator (1). Roles of Notch signaling in vascular development were suggested by studies of mice with targeted mutation (2). Since Notch activation within the endothelium also disrupts vascular remodeling, proper Notch signaling is essential for vascular development (3). Although relevance of Notch to VEGF signaling is suggested (4-6), it is still unclear how Notch signaling has a role in VEGF-regulated angiogenesis and whether Notch signaling participates in physiological and pathological angiogenesis in the adult vasculature.

Figure 22A:
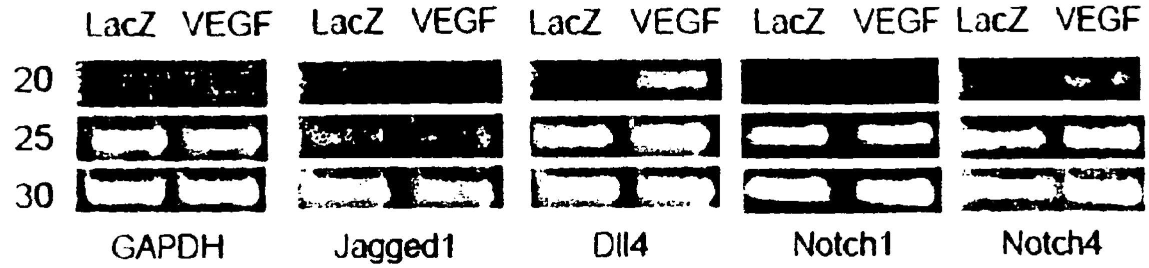
FIGS. 22A-22I These Figures show that VEGF activates Notch signaling to induce HUVEC budding. HUVEC were transduced with Ad-VEGF at 40 MOI (FIGS. 22A, 22H, 22I) or 20 MOI (FIGS. 22C, 22G). Ad-LacZ was co-transduced to HUVEC to make the same total amount of adenovirus 60 MOI (FIG. 22G), 80 MOI (FIG. 22A) and 100 MOI (FIGS. 22H, 22I).
Figure 22B:
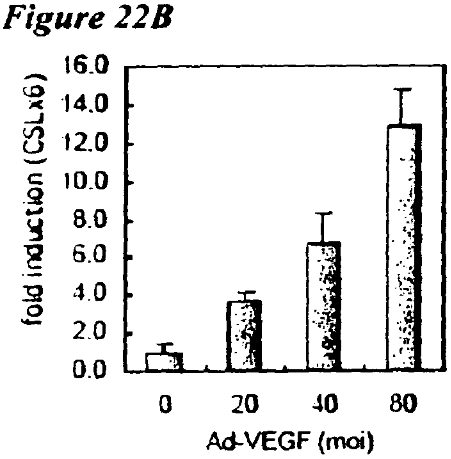
Figure 22C:
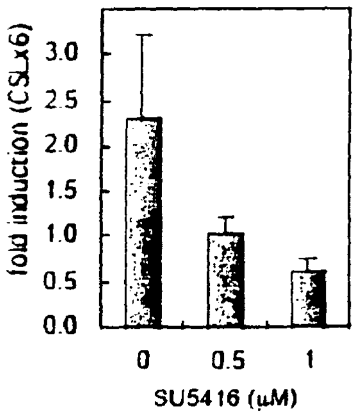
Figure 22D:
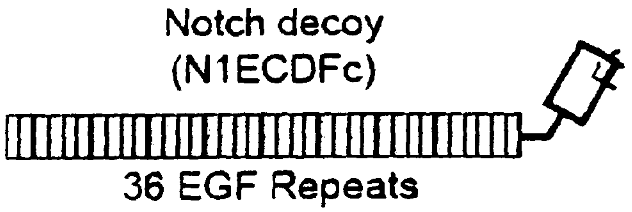
Figure 22E:
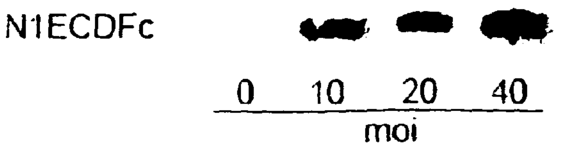
Figure 22F:
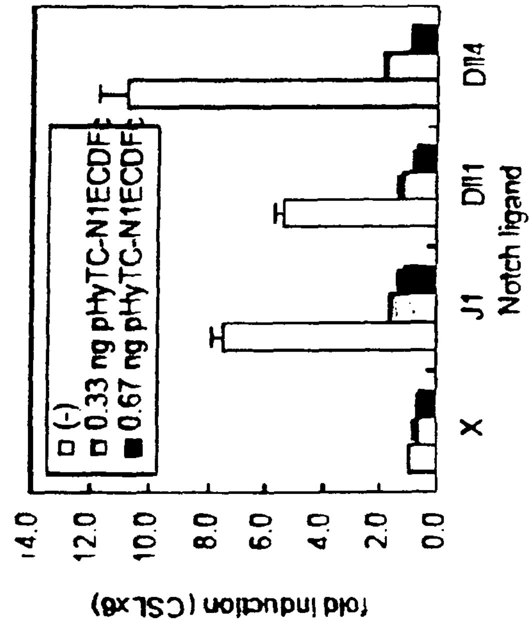
Figure 22G:
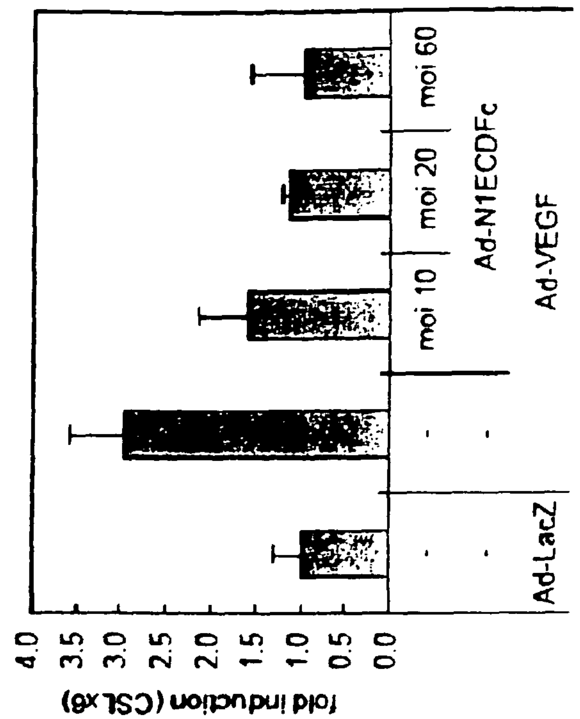
Figure 22I:
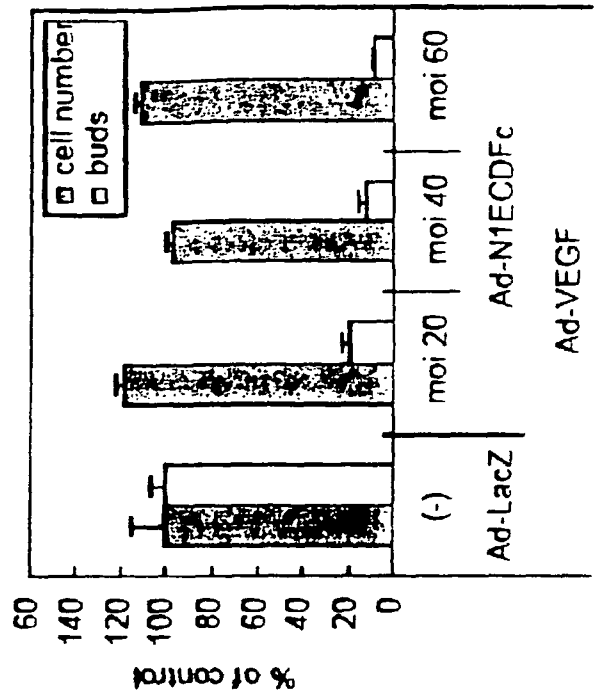
Figure 22H:
Figure 23A:
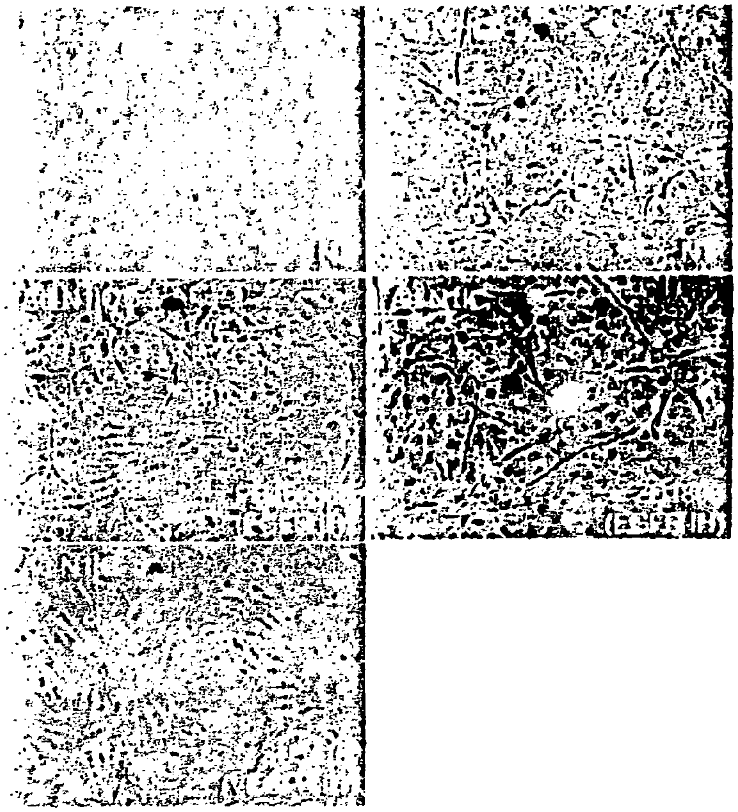
FIGS. 23A-23J These Figures show that Notch signaling up-regulates Flt1 expression to induce HUVEC budding. HUVEC were transduced with either Ad-LacZ or Ad-N1IC at 40 MOI.
Figure 26A:
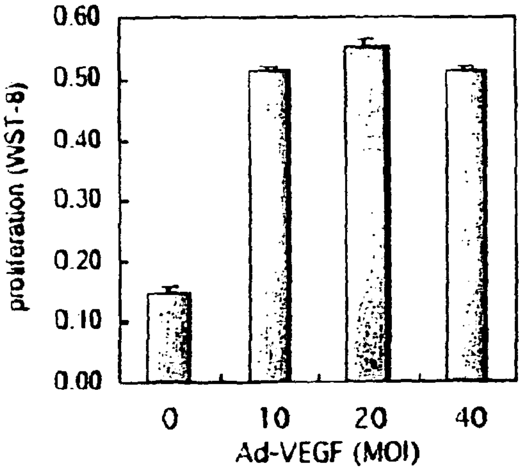
FIGS. 26A and 26B These Figures show proliferation of Ad-VEGF165-transduced HUVEC. HUVEC were transduced with Ad-VEGF165 at the indicated dosages. Ad-LacZ was also co-infected to make the same total amount of adenovirus at a MOI of 40 pfu/cell. HUVEC were suspended in SFM supplemented with 1% FBS and then plated at $1\times10^4$ cells/well in 24-well multi-well plates with 0.4 ml of medium. After 4 days, cell numbers were determined using the CCK-8 kit and the results are indicated as the ratio of cell numbers determined to the number of control cells, which were transduced with Ad-GFP at a MOI of 40 pfu/cell.
Figure 26B:
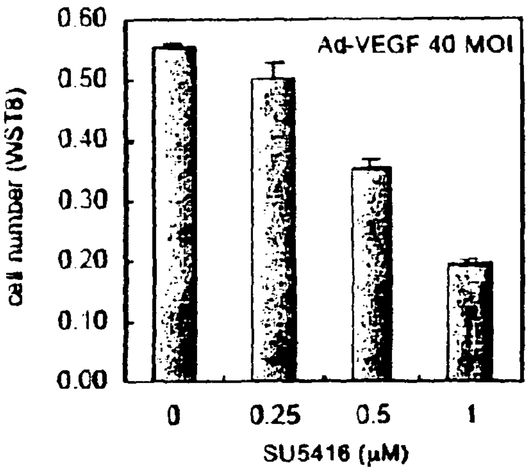
Figure 27A:
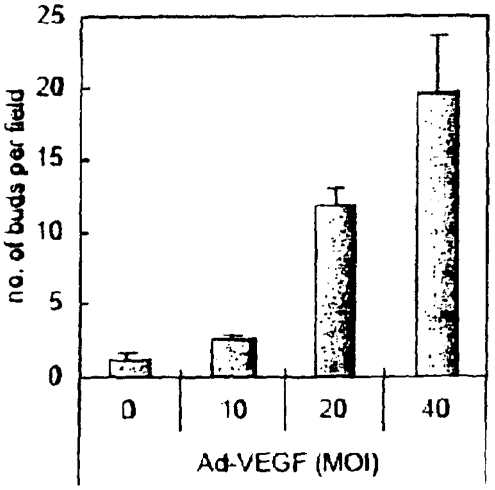
FIGS. 27A and 27B These Figures show the induction of HUVEC buds on type I collagen gel. HUVEC were transduced with either Ad-VEGF165 or AD-N1IC at the indicated dosages. Ad-LacZ was also co-infected to make the same total amount of adenovirus at a MOI of 40 pfu/cell. Transduced HUVEC were cultured on collagen gel with complete medium. The amount of budding was evaluated under microscopy at day 7.
Figure 27B:
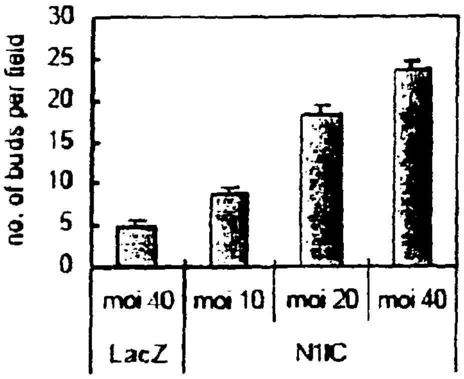
Figure 28A:
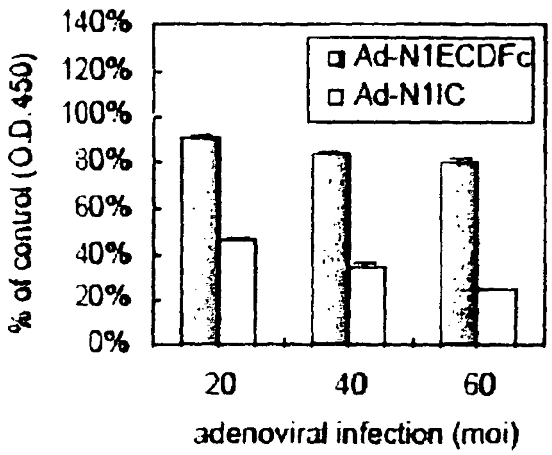
FIGS. 28A and 28B These Figures show the effect of alteration of Notch signaling on cell proliferation. The cells were transduced with the indicated adenoviruses. Ad-GFP was also co-infected to make the same total amount of adenovirus at a MOI of 60 pfu/cell. After 4 days, cell numbers were determined using the CCK-8 kit and results are indicated as the ratio of cell numbers determined to the number of control cells, which were transduced with AD-GFP at MOI of 60 pfu/cell.
Figure 28B:
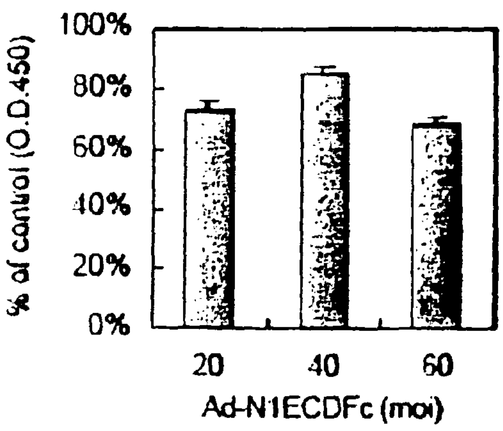

HUVEC (Human Umbilical Vein Endothelial cells) growth are dependent on VEGF (FIGS. 26A and 26B) and differentiation-related biological responses, such as sprouting, and can be evaluated at an early stage (7). At first, we examined whether adenovirally transduced VEGF induced both Notch and Notch ligand expression in HUVEC cultured with complete medium containing bFGF (FIG. 22A), as reported (5). RT-PCR analysis showed that both Dl4 and Notch4 mRNA was up-regulated in adenovirally-transduced VEGF HUVEC (Ad-VEGF-HUVEC), compared to adenovirally-transduced LacZ HUVEC (Ad-LacZ-HUVEC) (FIG. 22A). Transduced VEGF did not appear to induce Jagged1 and Notch1 expression. Transduced-VEGF also activated Notch signaling in a dose-dependent manner by measuring CSL-luciferase reporter activity (FIG. 22B), which was transactivated with Notch signaling (8). Notch signaling was activated at a higher dosage of Ad-VEGF, compared to proliferation (FIG. 26A). Since SU5416, which is an inhibitor of VEGFR kinases, decreased VEGF-induced CSL-luciferase reporter activity (FIG. 22C), VEGF induced Notch signaling through activation of receptor kinase. Since Notch mutants lacking both transmembrane and cytoplasmic domains functioned as dominant negative inhibitors against Notch signaling (9), we made a Notch-based fusion protein or decoy (N1ECDFc) to inhibit Notch signaling (FIG. 22D). Western blotting analysis of conditioned medium of Ad-N1ECDFc-transduced HUVEC (Ad-N1ECDFc-HUVEC) demonstrated that N1ECDFc was expressed and secreted well (FIG. 22E). By using a co-culture assay, in which Bosc cells expressing Notch ligands (either J1, Dll or Dl4) activated Notch signaling in HeLa cells expressing Notch1 compared to control Bosc cells, we determined inhibition of Notch signaling with transfection of a N1ECDFc-expression plasmid (FIG. 22F). Then, we examined whether N1ECDFc inhibited activation of Notch signaling by transduced VEGF in HUVEC (FIG. 22G). Co-transduction of Ad-N1ECDFc with Ad-VEGF into HUVEC clearly decreased CSL luciferase activity induced by VEGF. Gerhardt et al. reported that VEGF controlled angiogenesis in the early postnatal retina by guiding filopodia extension at the tips of the vascular sprouts (10). During angiogenic sprouting, the formation of a specialized endothelial cell making filopodia projections among quiescent endothelial cells, might be one of the early events. Here we mean formation of a single endothelial cell making filopodia protrusions as budding. Budding of the primary endothelial cells is induced by cultivating them 3-dimensionally on either fibrin or collagen gel (11). In the case where Ad-VEGF-HUVEC were cultured on collagen gel with complete medium, transduced-HUVEC made filopodia extensions into the collagen gel for 5 days (FIG. 22H) and the number of buds was increased in a dose-dependent manner (FIG. 27A). Activation of Notch signaling by adenovirus encoding the activated form of Notch4 (Ad-Notch4/int3) induced HUVEC budding (12) and that of Notch1(Ad-N1IC) also induced HUVEC budding (FIGS. 23A & 27B). Since both VEGF and Notch signaling induce HUVEC budding, we examined whether N1ECDFc inhibited VEGF-induced HUVEC budding (FIG. 22H-I). Budding of Ad-VEGF-HUVEC was clearly inhibited by co-transduction of Ad-N1ECDFc. Neither Ad-LacZ or Ad-N1ECDFc-transduced HUVEC formed buds (FIG. 22H). N1ECDFc inhibited VEGF-induced HUVEC budding without affecting cell number (FIG. 22I). Transduced-N1ECDFc did not clearly alter proliferation of HUVEC, while that of Ad-N1IC-transduced HUVEC was inhibited in a dose-dependent manner (FIG. 28A), consistent with the inhibitory efficacy of Notch signaling against endothelial proliferation (13).

Figure 23B:
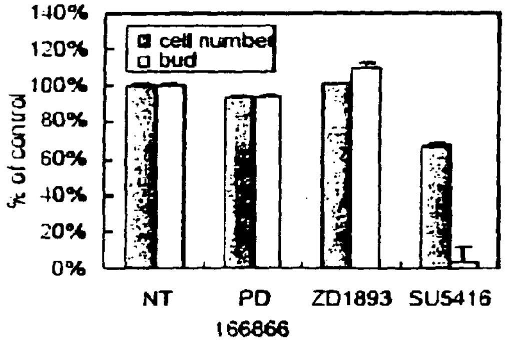
Figure 23C:
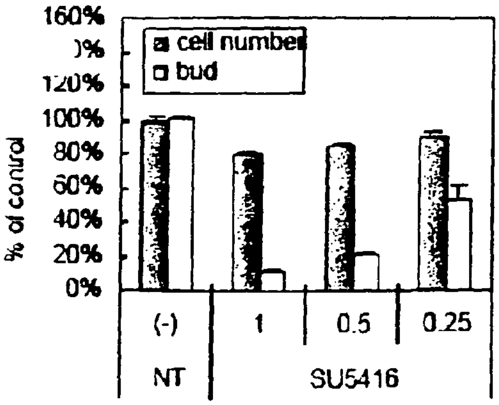
Figure 23D:
Figure 23E:
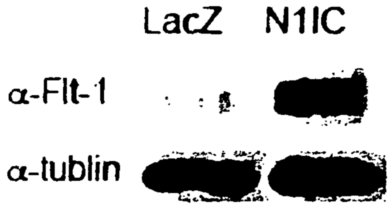
Figure 23F:
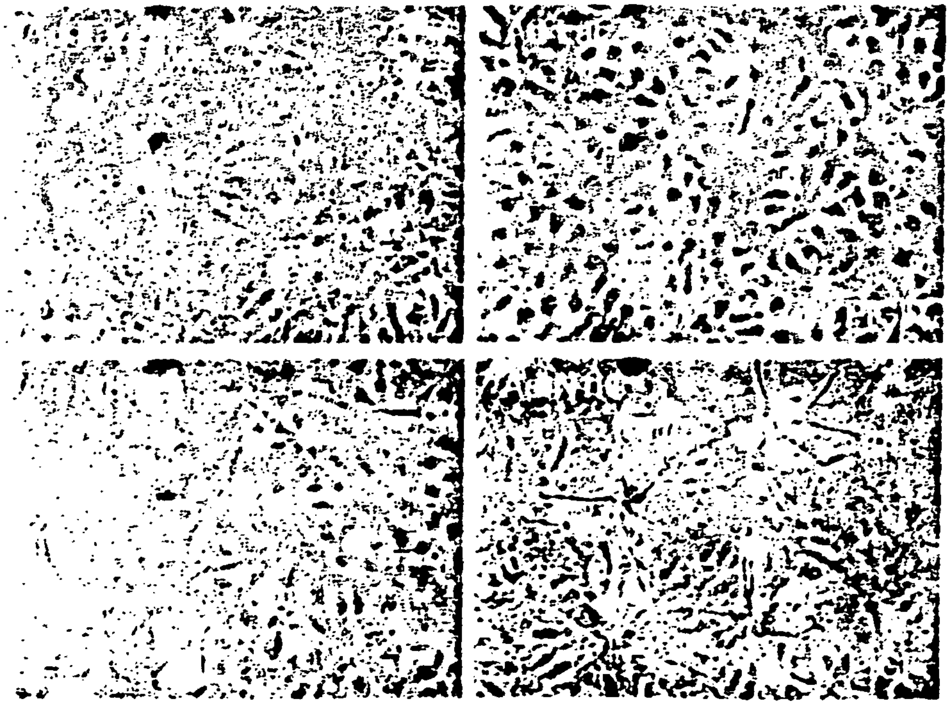
Figure 23G:
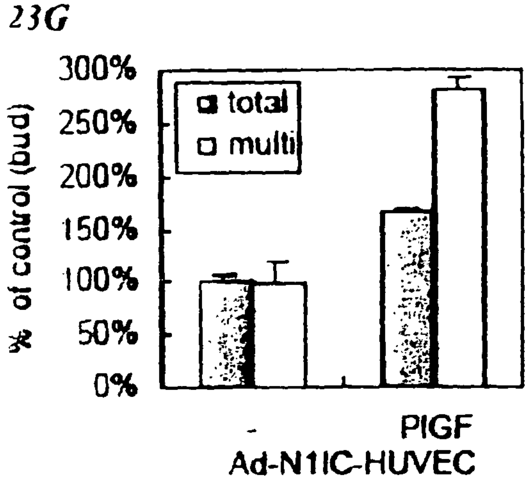
Figure 23H:
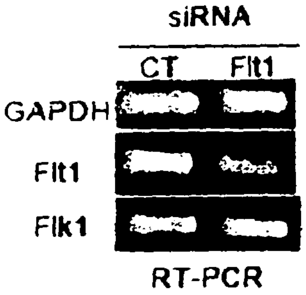
Figure 23I:
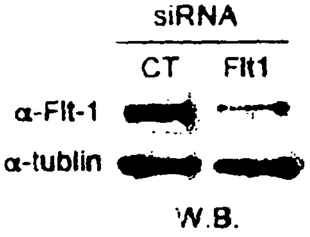
Figure 23J:
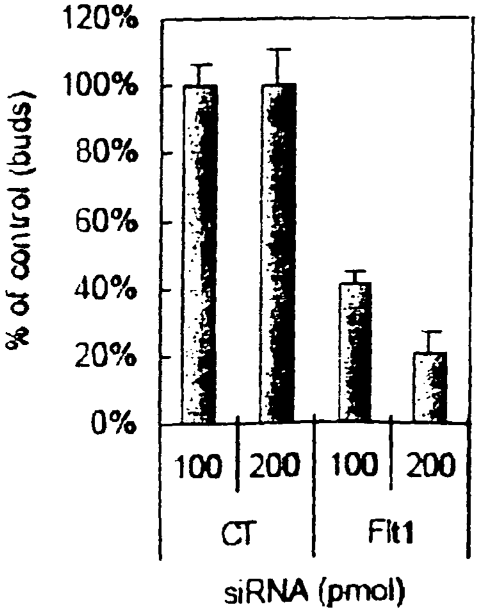
Figure 30A:
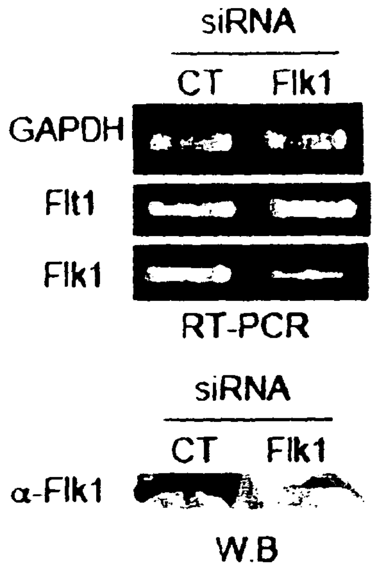
FIGS. 30A-30C These Figures show inhibition of budding of either Ad-N1IC- or Ad-VEGF-transduced HUVEC with Flk-1 siRNA transfection.
Figure 30B:
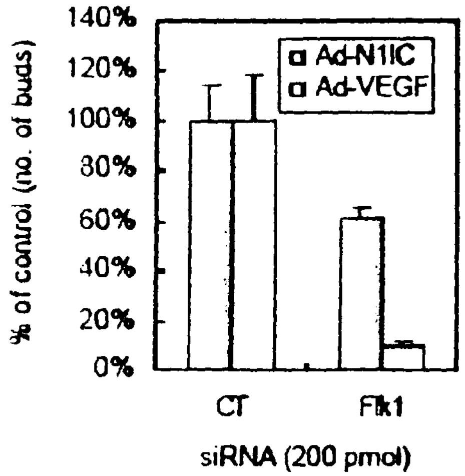
Figure 30C:
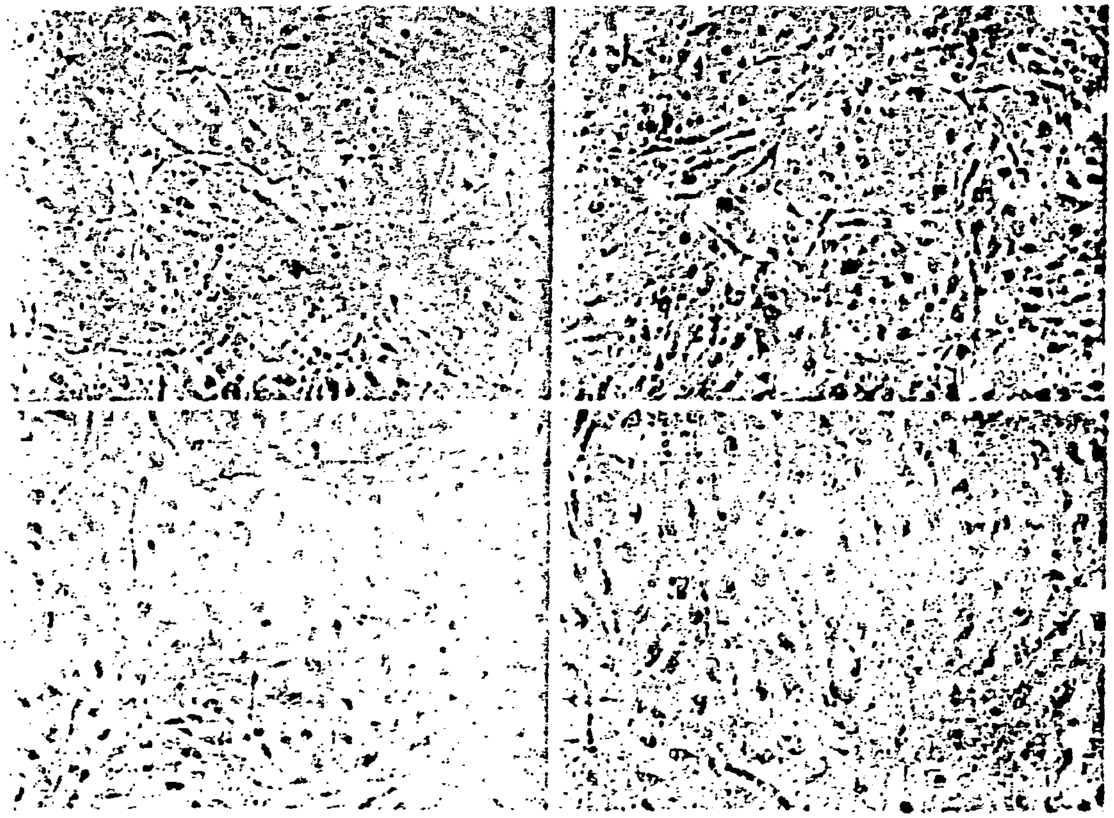

To test whether Notch signaling is down-stream of VEGF, we evaluated three distinct inhibitors for receptor tyrosine kinases, including VEGFR on N1IC-induced HUVEC budding, because three growth factors existed in complete medium (FIG. 23A-C). At a concentration of 1 μm, each compound showed selective inhibition against each kinase (data not shown). Neither PD166866 or ZD1893 affected budding of Ad-N1IC-HUVEC, while SU5416 clearly inhibited it (FIG. 23A-B). SU5416 selectively inhibited budding of Ad-N1IC-HUVEC with less reduction of viability at lower concentrations (FIG. 23C). Since Taylor et al. reported that Notch down-regulated Flk1/KDR/VEGFR2 expression (14), it was unlikely that Notch co-operated with Flk1 to promote budding. Thus, we examined whether activation of Notch signaling affected Flt1/VEGFR1 expression in HUVEC, because SU5416 inhibits both Flt1 and Flk1 kinase activity (15). RT-PCR analysis demonstrated that expression of Flt1 mRNA was up-regulated in Ad-N1IC-HUVEC, while expression of endothelial cell maker, CD31 mRNA, was not compared to that in Ad-LacZ-HUVEC (FIG. 23D). Western blotting analysis also showed that expression of Flt1 protein was up-regulated in Ad-N1IC-HUVEC (FIG. 23E). Thus, we examined whether PlGF, which is a selective ligand for Flt1, promoted budding of HUVEC in which Flt1 was up-regulated via activation of Notch signaling (FIG. 23F-G). PlGF increased the number of Ad-N1IC-HUVEC buds by 150%, compared to the absence of PlGF (FIG. 23F). Moreover, PlGF increased HUVEC buds containing multiple filopodia by 250% (FIG. 23G). While reduction of Flt1 expression using small interfering RNA (siRNA) for Flt1 inhibited budding of Ad-N1IC-HUVEC (FIG. 23J), transfection of which selectively decreased expression of Flt1 mRNA (FIG. 23H) and that of Flt1 protein (FIG. 23I). Although reduction of Flk1 expression with Flk1 siRNA also inhibited budding of Ad-N1IC-HUVEC (FIG. 30B), the inhibitory efficacy of Flk1 siRNA was less than that of Flt1 siRNA (FIG. 23J). Effects of Flk1 siRNA were more effective on budding of Ad-VEGF-HUVEC than that of Ad-N1IC-HUVEC (FIG. 30B-C). Transfection with Flt1 siRNA inhibited budding of both Ad-N1IC- and Ad-VEGF-HUVEC to a similar extent (data not shown).

Several studies demonstrated that VEGF regulated gelatinase activities in endothelial cells and the significance of gelatinase activity like MMP-2 and MMP-9 has been firmly established to induce angiogenic sprouting (16). We examined whether VEGF regulated gelatinase activity via Notch signaling in HUVEC.

Figures 24A, 24B, 24C, 24D, 24E:
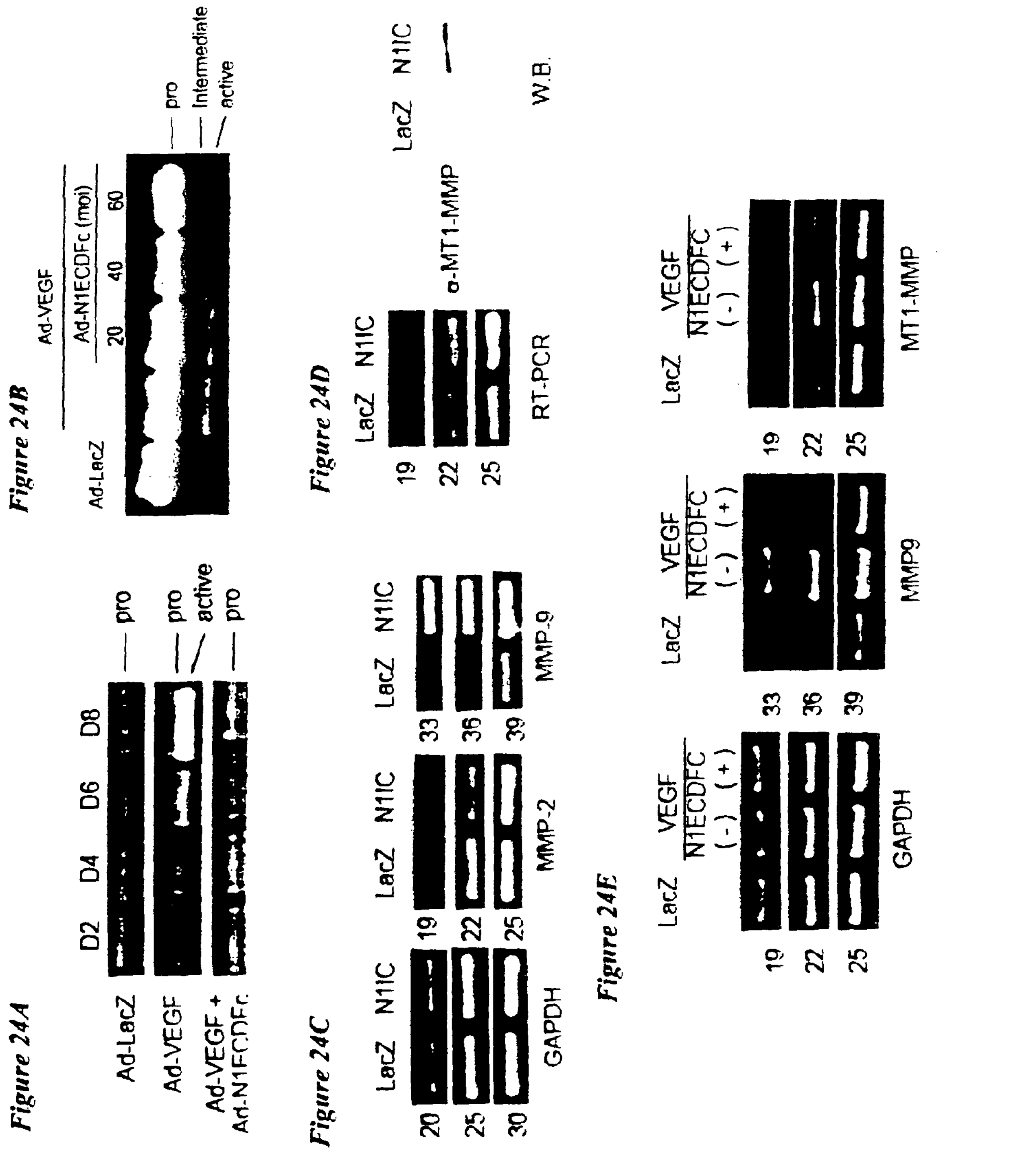
FIGS. 24A-24E These Figures show that VEGF regulates gelatinase activity via Notch signaling by up-regulation of both MMP-9 and MT1-MMP.
Figure 31A:
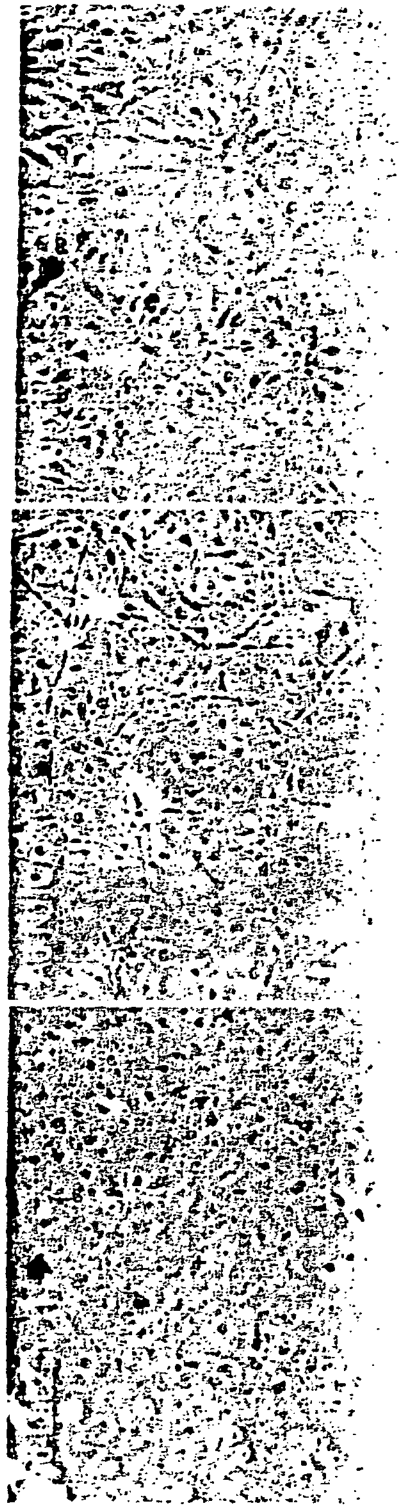
FIGS. 31A and 31B These Figures show inhibition of budding of Ad-N1IC-transduced HUVEC with treatment of matrix metalloproteinase inhibitor GM6001. Either Ad-LacZ or Ad-N1IC-HUVEC at a MOI of 40 pfu/cell were cultured on collagen gel for 5 days in the absence or presence of GM6001 at 50 μm.
Figure 31B:
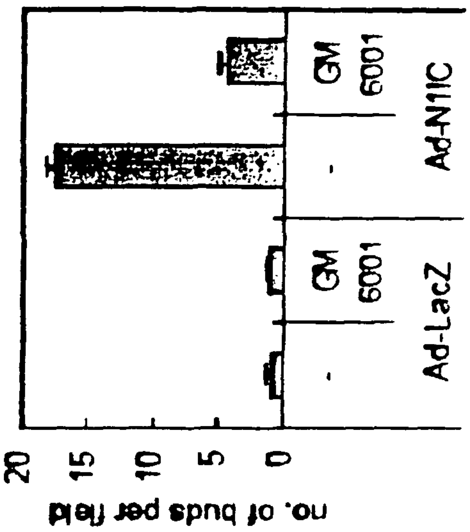

In Gelatin zymography, conditioned medium of Ad-VEGF-HUVEC showed both induction and activation of MMP9, which started to be detected at day 6 (FIG. 24A) and activation of MMP2, which was detected at day 4 (FIG. 24B), compared to those of Ad-LacZ-HUVEC. Co-transduction of Ad-N1ECDFc with Ad-VEGF showed inhibition of both induction and activation of MMP9 (FIG. 24A) and an activation of MMP2 (FIG. 24B). RT-PCR analysis demonstrated that expression of MMP9 mRNA was up-regulated in Ad-N1IC-HUVEC, but expression of MMP2 mRNA was decreased in Ad-N1IC-HUVEC (FIG. 24C). Since induction of MMP2 activity was not detected in gelatin zymography (FIG. 24B), this result was a likely consequence. While expression of MT1-MMP, which is able to activate MMP2 at the cell surface (17), was up-regulated at both the transcript and protein levels in Ad-N1IC-HUVEC (FIG. 24D). As VEGF can regulate both gelatinase and MT1-MMP expression (16), RT-PCR analysis demonstrated that both MMP9 and MT1-MMP were up-regulated in Ad-VEGF-HUVEC, compared to Ad-LacZ-HUVEC and this induction was inhibited with co-transduction of Ad-N1ECDFc (FIG. 24E). Ad-N1ECDFc infection alone did not affect expression of either MMP9 or MT1-MMP in Ad-LacZ infected HUVEC (data not shown). Requisition of MMPs for angiogenic sprouting has been established by synthetic MMP inhibitors (16). GM6001 is one broad inhibitor against MMPs including MMP2, MMP9 and MT1-MMP (18). GM6001 clearly decreased budding of Ad-N1IC-HUVEC on both collagen (FIGS. 31A-B) and fibrin gel (data not shown).

Figure 25A:
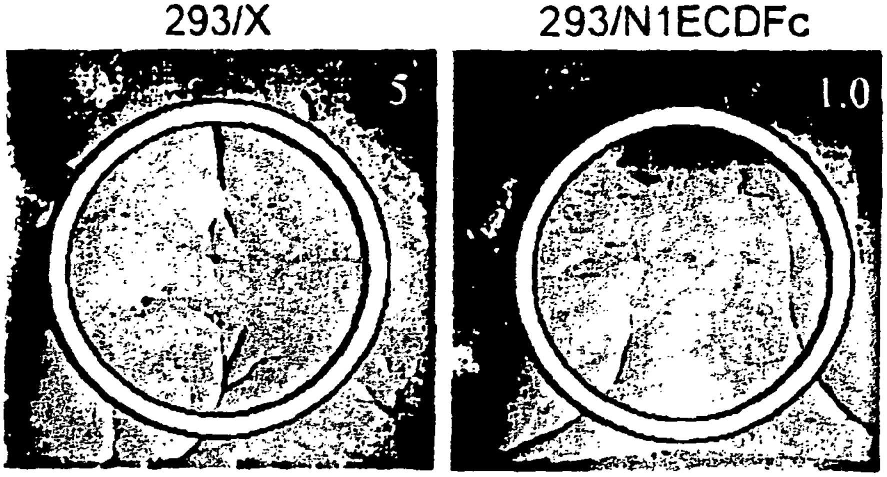
FIGS. 25A-25D These Figures show the role of Notch signaling in VEGF-dependent in vivo angiogenesis.
Figure 25:
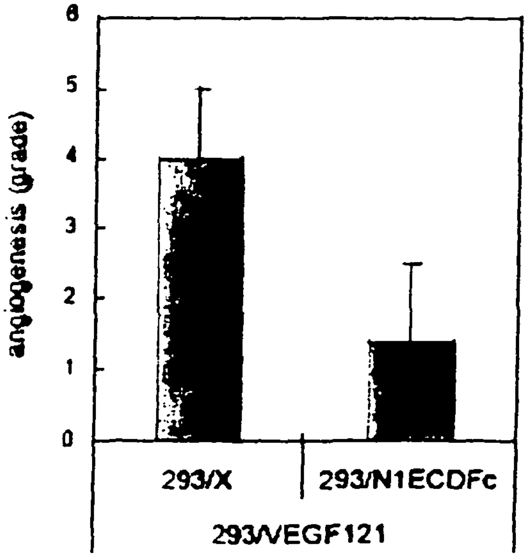

In the mouse Dorsa Air Sac (DAS) assay (19), stable transfectant of 293 cells over-expressing VEGF121 (293/VEGF) significantly induced in vivo angiogenesis (FIG. 25A, left panel). This VEGF-induced angiogenesis was clearly inhibited by coexpression of N1ECDFc, compared to 293/VEGF alone (FIG. 25A). Vessel density was measured and an index of angiogenesis given in FIG. 25B, demonstrating the 293/VEGF induced angiogenesis is inhibited by co-expression of 293/N1ECDFc (FIG. 25B).

Figure 25C:
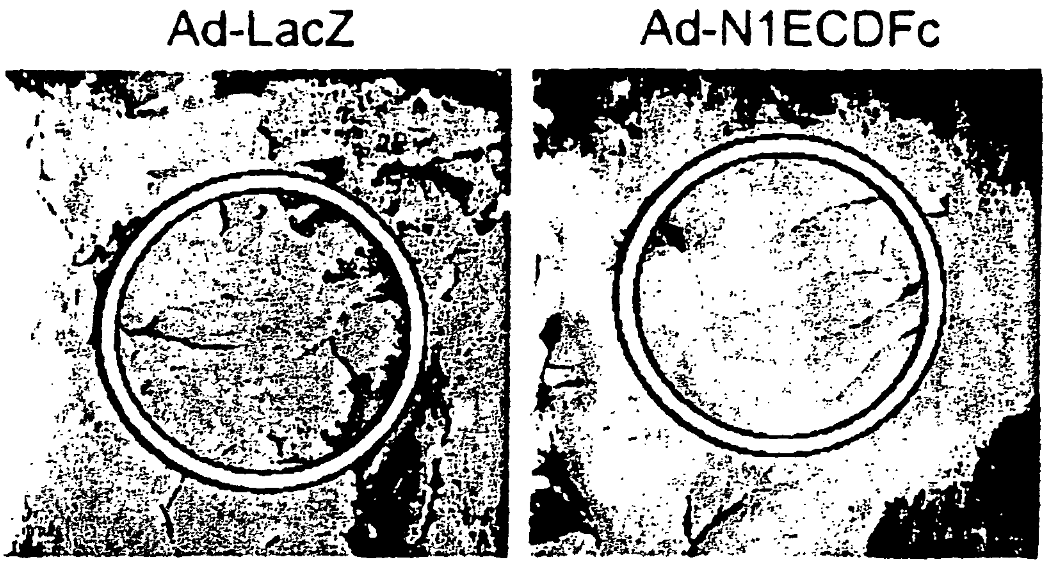
Figure 25D:
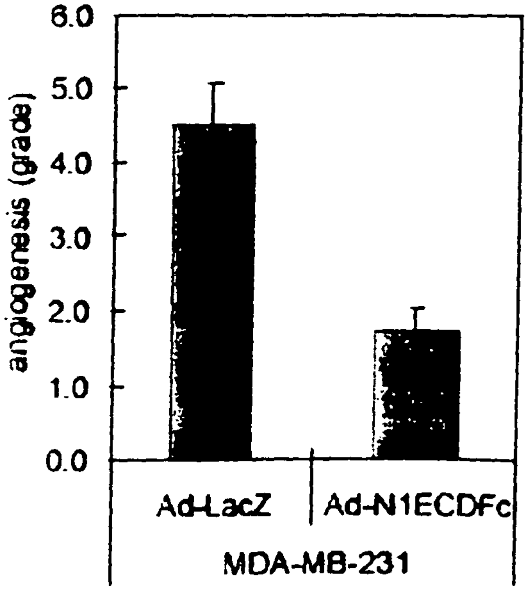

Also, in the mouse Dorsa Air Sac (DAS) assay (19), the human breast cancer cell line, MDA-MB-231 significantly induced in vivo angiogenesis, presumably via the secretion of VEGF (FIG. 25C, left panel). This VEGF-induced angiogenesis was clearly inhibited by adenovirus mediated expression of N1ECDFc, compared to adenovirus expressing LacZ. (FIG. 25C). Vessel density was measured and an index of angiogenesis given in FIG. 25D, demonstrating the MDA-MB-231 induced angiogenesis is inhibited by expression of N1ECDFc.

Figure 29:
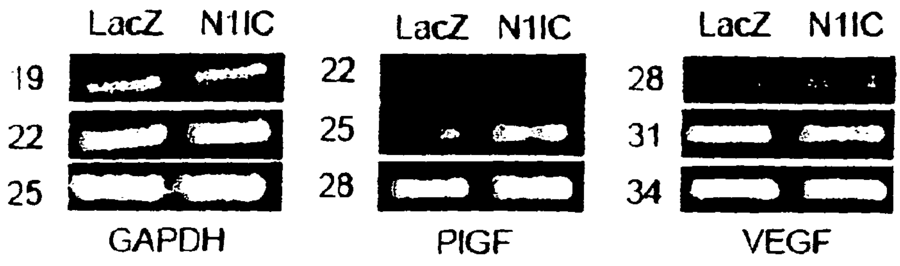
FIG. 29 This Figure shows the RT-PCR analysis of induction of PIGF expression in Ad-N1IC-transduced HUVEC. HUVEC were infected with either Ad-LacZ or Ad-N1IC at a MOI of 40 pfu/cell. Total RNA was isolated from transduced HUVEC cultured on collagen gel for 5 days with complete medium.

Flk1 is a major positive signal transducer for angiogenesis through its strong tyrosine kinase activity in the embryo, while Flt1 is thought to be a negative signal transducer for angiogenesis. However, a positive role for Flt-1 was demonstrated in adult mice, as in vivo growth of LLC over-expressing PlGF2 was severely compromised in mice lacking the cytoplasmic Flt-1 kinase domain (20). Notch might function to alter VEGF signaling by inducing Flt-1 signaling and moderate Flk-1 signaling either to induce filopodia extension or potentiate angiogenic sprouting, since PlGF/Flt-1 signaling altered the phospholyration site of Flk-1 and potentiated ischemic myocardial angiogenesis (21). Interestingly, Notch signaling also up-regulated PlGF expression (FIG. 29). However, continuous activation of Notch signaling inhibits formation of multi-cellular lumen-containing angiogenic sprouts, as previously reported (22). Notch signaling should be turned off after budding/filopodia formation and transient activation of the Notch pathway might be required. In a transgenic mouse model of pancreatic beta-cell carcinogenesis (Rip1Tag2 mice) in which tumor angiogenesis is VEGF dependent, the level of VEGF expression is not increased, but mobilization of extracellular VEGF stored in the matrix to VEGF receptors occurs. MMP-9 is responsible for this mobilization and tumor progression was inhibited in Rip1Tag23MMP-9-null double-transgenic mice (23). Notch up-regulated MMP-9 expression and might increase local VEGF level at the site for angiogenic sprouting. While Notch also up-regulates MT1-MMP expression, extracellular MMP-2 might be targeted to the cell membrane of Notch-activated endothelial cells. Notch might determine the site for angiogenic sprouting by regulating gelatinase activity and VEGF concentration. Since endothelial MMP-9 was regulated by Flt-1 in lung specific metastasis (20), Flt-1 might participate in induction of MMP-9 indirectly.

REFERENCES CITED IN THIRD SERIES OF EXPERIMENTS

1. Artavanis-Tsakonas S, Rand M D, Lake R J. Notch Signaling: Cell Fate Control and Signal Integration in Development. Science 1999; 284(5415):770-776.
2. Shawber C J, J. K. Notch function in the vasculature: insights from zebrafish, mouse and man. Bioessays. 2004; 26(3):225-34.
3. Uyttendaele H, Ho J, Rossant J, J. K. Vascular patterning defects associated with expression of activated Notch4 in embryonic endothelium. Proc Natl Acad Sci USA. 2001; 98(10):5643-8.
4. Lawson N D, Vogel A M, B M. W. sonic hedgehog and vascular endothelial growth factor act upstream of the Notch pathway during arterial endothelial differentiation. Dev Cell 2002; 3(1):127-36.
5. Liu Z J, Shirakawa T, Li Y, Soma A, Oka M, Dotto G P, et al. Regulation of Notch1 and Dll4 by vascular endothelial growth factor in arterial endothelial cells: implications for modulating arteriogenesis and angiogenesis. Mol Cell Biol. 2003; 23(1):14-25.
6. Gale N W, Dominguez M G, Noguera I, Pan L, Hughes V, Valenzuela D M, et al. Haploinsufficiency of delta-like 4 ligand results in embryonic lethality due to major defects in arterial and vascular development. Proc Natl Acad Sci USA. 2004; 101(45):5949-54.
7. Montesano R, L. O. Phorbol esters induce angiogenesis in vitro from large-vessel endothelial cells. J Cell Physiol. 1987; 130(2):284-91.
8. Jarriault S, Brou C, Logeat F, Schroeter E H, Kopan R, A. I. Signalling downstream of activated mammalian Notch. Nature. 1995; 377(6547):355-8.
9. Small D, Kovalenko D, Kacer D, Liaw L, Landriscina M, Di Serio C, et al. Soluble Jagged 1 represses the function of its transmembrane form to induce the formation of the Src-dependent chord-like phenotype. J Biol Chem 2001; 276(34):32022-30.
10. Gerhardt H, Golding M, Fruttiger M, Ruhrberg C, Lundkvist A, Abramsson A, et al. VEGF guides angiogenic sprouting utilizing endothelial tip cell filopodia. J Cell Biol 2003; 161(6):1163-77.
11. Koolwijk P, van Erck M G, de Vree W J, Vermeer M A, Weich H A, Hanemaaijer R, et al. Cooperative effect of TNFalpha, bFGF, and VEGF on the formation of tubular structures of human microvascular endothelial cells in a fibrin matrix. Role of urokinase activity. J Cell Biol 1996; 132(6):1177-88.
12. Das I, Craig C, Funahashi Y, Jung K M, Kim T W, Byers R, et al. Notch oncoproteins depend on gamma-secretase/presenilin activity for processing and function. J Biol Chem 2004; 279(29):30771-80.
13. Noseda M, Chang L, McLean G, Grim J E, Clurman B E, Smith L L, et al. Notch activation induces endothelial cell cycle arrest and participates in contact inhibition: role of p21Cip1 repression. Mol Cell Biol 2004; 24(20):8813-22.
14. Taylor K L, Henderson A M, C C. H. Notch activation during endothelial cell network formation in vitro targets the basic HLH transcription factor HESR-1 and downregulates VEGFR-2/KDR expression. Microvasc Res 2002; 64(3):372-83.
15. Itokawa T, Nokihara H, Nishioka Y, Sone S, Iwamoto Y, Yamada Y, et al. Antiangiogenic effect by SU5416 is partly attributable to inhibition of Flt-1 receptor signaling. Mol Cancer Ther 2002; 1(5):295-302.
16. Pepper M S. Role of the matrix metalloproteinase and plasminogen activator-plasmin systems in angiogenesis. Arterioscler Thromb Vasc Biol 2001; 21(7):1104-17.
17. Seiki M, Koshikawa N, I. Y. Role of pericellular proteolysis by membrane-type 1 matrix metalloproteinase in cancer invasion and angiogenesis. Cancer Metastasis Rev 2003; 22(2-3):129-43.

18. Yamamoto M, Tsujishita H, Hori N, Ohishi Y, Inoue S, Ikeda S, et al. Inhibition of membrane-type 1 matrix metalloproteinase by hydroxamate inhibitors: an examination of the subsite pocket. J Med Chem 1998; 41(8):1209-17.
19. Funahashi Y, Wakabayashi T, Semba T, Sonoda J, Kitoh K, K. Y. Establishment of a quantitative mouse dorsal air sac model and its application to evaluate a new angiogenesis inhibitor. Oncol Res. 1999; 11(7):319-29.
20. Hiratsuka S, Nakamura K, Iwai S, Murakami M, Itoh T, Kijima H, et al. MMP9 induction by vascular endothelial growth factor receptor-1 is involved in lung-specific metastasis. Cancer Cell 2002; 2(4):289-300.
21. Autiero M, Waltenberger J, Communi D, Kranz A, Moons L, Lambrechts D, et al. Role of PlGF in the intra- and intermolecular cross talk between the VEGF receptors Flt1 and Flk1. Nat Med 2003; 9(7):936-43.
22. Leong K G, Hu X L L, Noseda M, Larrivee B, Hull C, Hood L, et al. Activated Notch4 inhibits angiogenesis: role of beta 1-integrin activation. Mol Cell Biol 2002; 22(8): 2830-41.
23. Bergers G, Brekken R, McMahon G, Vu T H, Itoh T, Tamaki K, et al. Matrix metalloproteinase-9 triggers the angiogenic switch during carcinogenesis. Nat Cell Biol 2000; 2(10):737-44.

FOURTH SERIES OF EXPERIMENTS

A Novel Construct Derived From The Notch1 Ectodomain Inhibits Notch Signaling, Endothelial Morphogenesis, and Tumor Angiogenesis Notch signaling is required for vascular development, but also functions in tumor angiogenesis. Inhibition of vascular endothelial growth factor (VEGF) is a validated anti-angiogenic therapy, and VEGF can induce both Notch and Notch ligand Delta-like 4 (Dll4) expression in endothelial cells (EC). Although Dll4 inhibition can restrict tumor growth and disrupt neovasculature, the effect of inhibiting Notch receptor function on tumor angiogenesis has yet to be defined. In this study, we generated a soluble fusion protein of the Notch1 receptor (N1ECDFc, or Notch1 decoy) to block this pathway, and assessed its effect on angiogenesis in vitro and in vivo. Notch1 decoy expression reduced signaling stimulated by the binding of three distinct Notch ligands to Notch1, and also inhibited morphogenesis of EC overexpressing Notch4. We tested the effects of Notch1 decoy expression on tumor angiogenesis using two models: mouse mammary tumor Mm5MT cells overexpressing fibroblast growth factor 4 (Mm5MT-FGF4), and NGP human neuroblastoma cells. Exogenously expressed FGF4 induced the expression of Notch ligands Jagged1 and Delta-like 1 (Dll1) in Mm5MT-FGF4 cells, and Jagged1 was expressed in Mm5MT-FGF4 xenografts. Overexpression of Notch1 decoy did not affect tumorigenicity of Mm5MT-FGF4 cells in vitro, but restricted Mm5MT-FGF4 xenograft growth in mice, while markedly impairing neoangiogenesis. Similarly, Notch1 decoy expression did not affect NGP cells in vitro but disrupted vessels and decreased tumor viability in NGP xenografts. These results strongly suggest that Notch receptor signaling is required for tumor neoangiogenesis, and provides a new target for tumor therapy.

Angiogenesis is exquisitely regulated by multiple signal pathways, including VEGFs, fibroblast growth factors (FGFs), and hepatocyte growth factor (HGF). Among these, VEGF critically influences almost all steps of angiogenesis, including endothelial proliferation, survival, and tube formation (1). Consistent with this protean role, VEGF inhibitors reduce angiogenesis in preclinical models, and have been clinically validated as cancer therapy (2). Despite this established efficacy, different tumor types exhibit widely varying susceptibility to VEGF blockade (2). The underlying reasons for this variability are not clear. One possibility is that alternative signals rescue tumor vasculature, allowing for perfusion despite VEGF inhibition. Identification of such pathways is therefore of clear therapeutic importance.

The highly conserved Notch gene family encodes transmembrane receptors (Notch1, -2, -3, -4) and ligands (Jagged1, -2; Delta-like or Dll1, -3, -4), also transmembrane proteins. Upon ligand binding, the Notch cytoplasmic domain (NotchIC) is released by presenilin/γ-secretase (3). Notch signaling defects produce severe vascular defects in embryos (4), with haploinsufficiency of Dll4 causing lethality. The potential role of Notch signaling in tumor angiogenesis has thus excited much recent interest. Mice transgenic for a Dll4-reporter construct demonstrate expression in tumor endothelial cells (EC) (5), and increased Dll4 expression has been detected in human cancers (6, 7). Two recent reports confirm that this role is critical by demonstrating that Dll4 blockade suppresses growth and perfusion in experimental tumors (8, 9). Intriguingly, in these studies Dll4 inhibition disorganized tumor vasculature rather than simply preventing vessel proliferation, suggesting that Dll4 is required for functional vessel assembly.

Recent data indicate that Notch receptors also function in tumor vasculature. For example, in head and neck squamous cell carcinoma (HNSCC) HGF was recently shown to up-regulate expression of Jagged1 on tumor cells, but not on endothelium. Increased Jagged1 expression activated Notch signaling in neighboring EC, stimulating tumor angiogenesis and growth in mice (10). Thus, these data suggest that there are at least two distinct mechanisms for activating Notch signaling in tumor EC.

In these studies, we evaluated the role of Notch receptor activation in angiogenesis using a novel soluble construct based on the extracellular domain of Notch1 (N1ECDFc, or Notch1 decoy). In vitro, Notch1 decoy inhibited both ligand-induced activation of Notch signaling and morphogenesis of EC adenovirally over-expressing Notch4. In vivo, Notch1 decoy expression delayed growth of murine Mm5MT xenografts in which Jagged1 expression was up-regulated by transduction of FGF4, and disrupted vasculature and tumor viability in NGP neuroblastoma tumors. These data support a requirement for Notch receptor function during tumor neoangiogenesis, and suggest that inhibition of this pathway may provide an effective new anti-tumor strategy.

Materials and Methods

Reagents and Expression Vectors

Compound E was purchased from Calbiochem (San Diego, Calif.), and PD166866 from Eisai (Tokyo, Japan). Notch1 decoy (N1ECDFc) encodes the rat Notch1 ectodomain (bp 241-4229, Genbank accession #X57405) fused in frame to human IgG Fc. Retroviral pHyTC-Jagged1, -Dll1, -Dll4, and pBos-Notch1 have been described (11). Notch1 decoy and Fc were engineered into retroviral vector pHyTCX, and mouse FGF4 engineered into pQNCX. Adenoviral constructs encoding LacZ and mouse Notch4 and pAdlox-GFP have been described (12)(13).

HUVECs, Adenoviral, and Retroviral Infections

HUVECs were isolated as described (14) and mouse mammary carcinoma Mm5MT obtained (ATCC, Manassas, Va.). We used adenovirus at indicated multiplicity of infection (m.o.i.) and retroviral supernatants from GP2-293 cells (BD Biosciences, Bedford, Mass.) for infection. HUVECs were selected using 300 μg/ml hygromycinB (Invitrogen, Carlsbad, Calif.) and Mm5MT-FGF4 selected in 1 mg/ml G418

(Gibco-Invitrogen, Grand Island, N.Y.), with double transfectants in 300 μg/ml hygromycinB.

Western Blotting

Ad-N1ECDFc-transduced HUVEC were cultured in endothelium serum-free medium (GIBCO-Invitrogen) 48 h, and Mm5MT-FGF4 transfectants in DMEM. Western blots were performed using anti-human Fc (Pierce, Rockford, Ill.).

Quantitative RT-PCR

Mm5MT transfectants were cultured 7 days with vehicle or 1 μm PD166866 (inhibitor of FGF receptor-kinase), total RNA isolated (RNeasy mini-kit, Qiagen, Valencia, Calif.), and first-strand cDNA synthesized (SuperScript™ First-Strand Synthesis System, Invitrogen). Quantitative RT-PCR for β-actin, FGF4, Jagged1, Dll1, and Dll4 (SYBER Green PCR Master Mix, 7300 Real Time PCR; Applied Biosystems, Foster City, Calif.) was performed in triplicate and values normalized for β-actin. Values are shown for fold induction compared to controls (primer sequences available on request).

Co-Culture Signaling Assay

Notch1 decoy inhibition of ligand-induced signaling was performed as described (11). HeLa cells were transfected with 333 ng pBOS-Notch1, 333 ng pGA981-6, and 83 ng pLNC-LacZ with either 666 ng pCMV-Fc or pHyTC-N1ECDFc (333 ng for x1, 666 ng for x2). 293 cells were transfected with 680 ng pHyTc-Jagged1, pHyTc-Dll1, pHyTc-Dll4, or pHyTc-X (empty vector). Cells were harvested, luciferase activity determined 48 h post-transfection (Enhanced Luciferase assay kit, BD PharMingen, San Diego, Calif.), and β-galactosidase activity determined (Galacto-Light Plus kit, Applied Biosystems). Assays were performed in triplicate.

Endothelial Co-Culture Morphogenesis Assay

HUVEC morphogenesis was assessed as described (11), modified by adding co-culturing of Ad-Notch4 transduced HUVEC with Notch1 decoy- or Fc-HUVEC transfectants. Ad-GFP at 10 m.o.i. was co-transduced in HUVECs with Ad-LacZ or Ad-Notch4 at 30 m.o.i and 48 h later seeded on fibrin gels (24-well plates, $1.5\times10^4$ cells/well). Stable HUVEC-mock (HUVEC-X), HUVEC-Fc, or HUVEC-N1ECDFc transfectants were seeded at $1.35\times10^5$ cells/well, and vehicle or 200 nM compound E added 3 h later. Seven days later, HUVEC morphogenesis was calculated as the number of GFP-positive cells with processes compared to total GFP-positive cells/field.

Mm5MT Tumor Model 6-8 week-old female C3H mice (Taconic, Hudson, N.Y.) underwent subcutaneous implantation of $10^6$ Mm5MT transfectants (N=10 each). Tumor diameters were measured with calipers, and volume calculated (length (mm)×width $(mm)^2\times$ ½). Tumors were harvested at day 22 and analyzed. Experiments were performed thrice.

Immunohistochemistry

5 μm fresh-frozen Mm5MT tissue sections were immunostained (15) (see supplemental data for antibody list). CD31 quantitation was performed using an Eclipse E800 microscope and ImagePro Plus v. 4.01 (Silver Spring, Md.). 20 different fields/slide were measured, and density ratios calculated as (area of specific staining)/(total area, each field). Data is shown as the ratio of the mean of average density ratios of each Mm5MT transfectant to Mm5MT mock-transfectant.

NGP Tumor Model

The NGP tumor model has previously been described in detail (16). NGP cells were transfected with LacZ or N1ECDFc, as above, and $10^6$ NGP-LacZ or NGP-N1ECDFc cells implanted intrarenally in 4-6 week old NCR nude mice (Taconic, Germantown, N.Y.; NGP-LacZ n=11, NGP-N1ECDFc n=13). At 6 weeks, tumors were harvested for analysis. 5 uM paraffin-embedded sections were immunostained for CD-31/PECAM and α-smooth muscle actin (αSMA). To detect apoptosis (TUNEL assay) we used the Apoptag Red in situ Kit (Chemicon). Signal was quantified by photographing 20-23 randomly selected fields of each tissue, excluding areas of normal kidney. Each frame was photographed in both red (TUNEL signal) and green channels. Using Adobe Photoshop, green channel signals were subtracted, in order to eliminate erythrocyte autofluorescence. A uniform red-channel threshold was arbitrarily selected, and total signal area measured in 4 NGP-N1ECDFc and 3 NGP-LacZ tumors. Erythrocyte quantification was performed similarly.

Statistical Analysis

Significance in quantitative studies was assessed using Tukey-Kramer tests (CD31 quantitation) and Kruskal-Wallis analysis (all others).

Results

Notch1 Decoy Inhibits Ligand-Induced Notch Signaling in Cells Expressing Notch1

Figure 32:
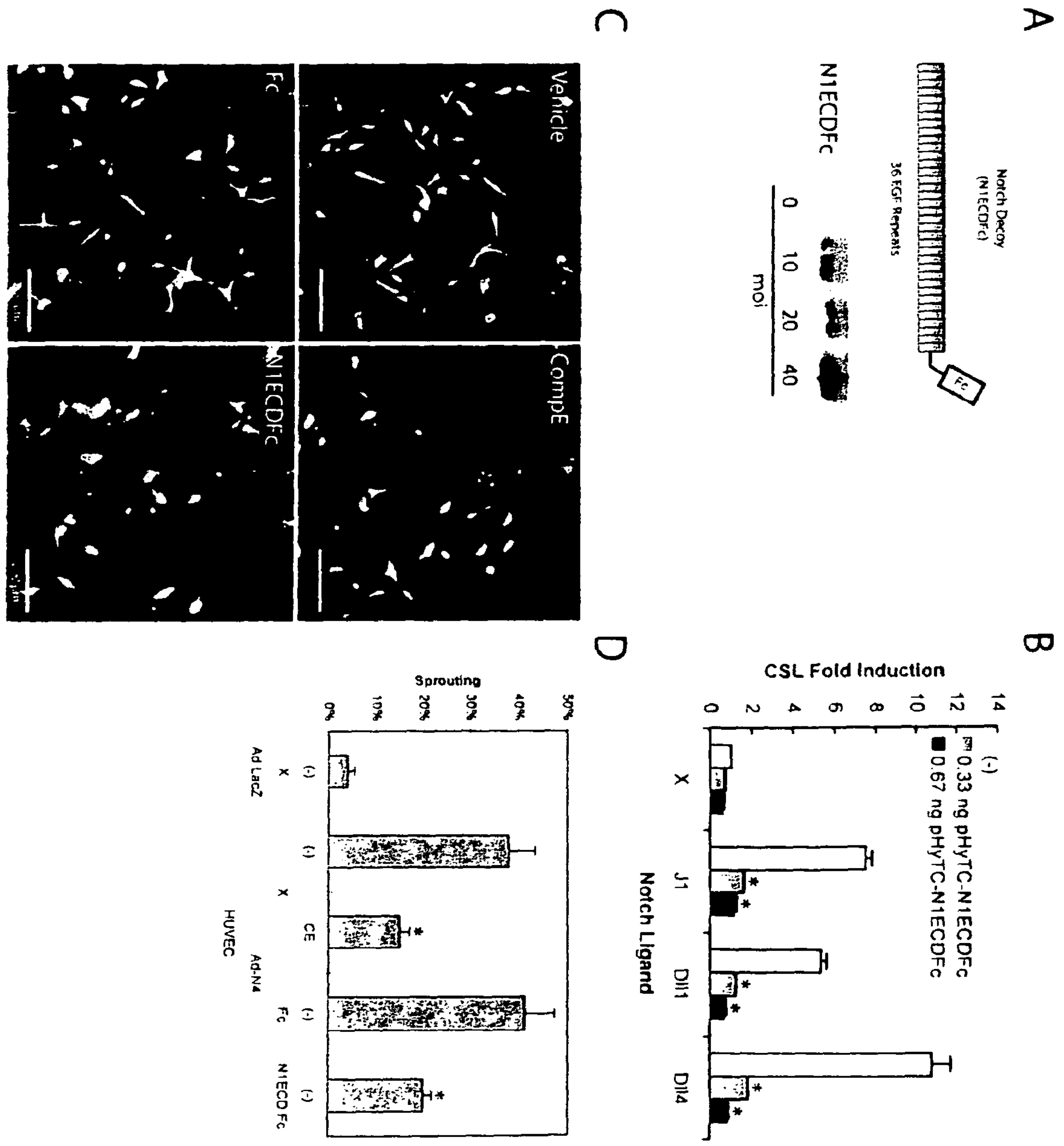
FIGS. 32A-32D These Figures show that Notch1 decoy inhibits activation of Notch signaling stimulated by Notch ligands.

Notch1 decoy is based on the ectodomain of Notch1 fused to human IgG Fc and is secreted, as determined by blotting of media conditioned by adenovirus Notch1 decoy (Ad-N1ECDFc)-infected HUVEC (FIG. 32A). We assessed Notch1 decoy activity using co-culture signaling assays (11). 293 cells expressing Notch ligands (Jagged1, Dll1, Dll4) activated Notch signaling when cultured with HeLa cells expressing Notch1, measured by CSL-luciferase reporter activity (FIG. 32B). Expression of Notch1 decoy in either HeLa (FIG. 32B) or 293 cells (data not shown) blocked Notch1 signaling in co-culture assays, indicating that Notch1 decoy prevented activation by Jagged1, Dll1, or Dll4.

Notch1 Decoy Blocks Morphogenesis of HUVEC Induced by Notch4

Notch4 expression induced cellular extensions from HUVECs cultured on fibrin gels (FIG. 32C), resembling morphologic changes induced by VEGF and FGF2 (17, 18). Fibrin can induce Jagged1 in EC (19). We tested the hypothesis that such extensions reflect endogenous Notch ligand activation of Notch4 transduced in HUVECs using either Compound E (CE), a (-secretase inhibitor (GSI), or Notch1 decoy. Compared to vehicle, treatment with 200 nM CE clearly inhibited extensions in Notch4-HUVECs, (FIG. 32C upper panels, 32D). Reduction in sprouting was significant (FIG. 32D, $p<0.0001$ for both compound E treatment and N1ECDFc transduction; data shown as mean±SD). Notch4+ Notch1 decoy co-expression in HUVECs similarly blocked endothelial extensions relative to Notch4+Fc control (FIG. 32C, lower panels; 32D). Collectively, these data indicate that Notch receptor activation is both necessary and sufficient to induce HUVEC extensions in this assay, and that the Notch1 decoy functions similarly to GSI, further validating its activity as a Notch receptor inhibitor.

Figure 33:
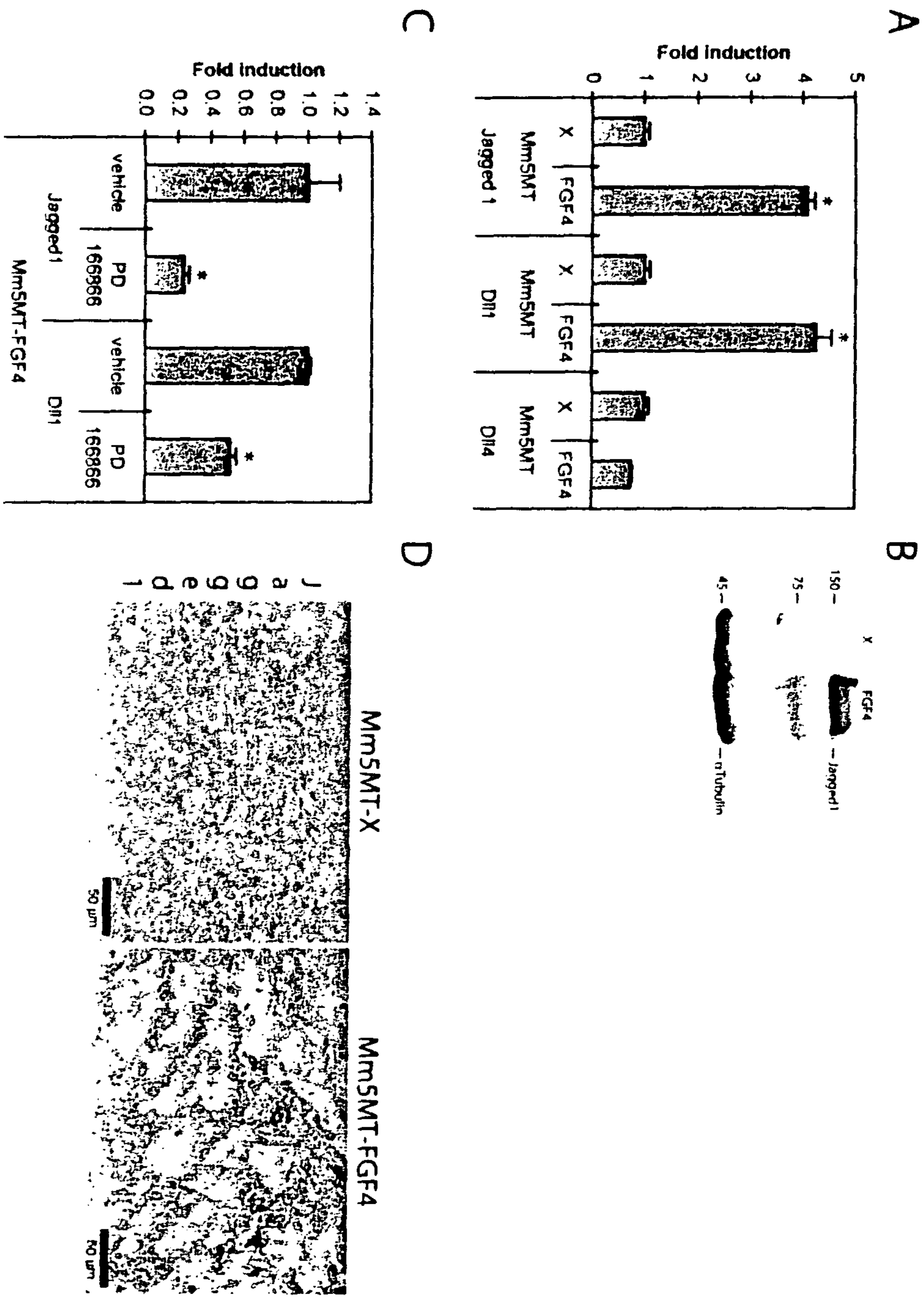
FIGS. 33A-33D These Figures show that FGF4 induces the expression of Notch ligands in murine mammary carcinoma Mm5MT cells. Stable Mm5MT transfectants generated by retroviral gene transfer.

FGF4 Induced the Expression of Notch Ligands, Jagged1 and Dll1, in Mouse Mammary Tumor Mm5MT Cells Overexpression of FGF4 in Mm5MT cells promoted tumorigenicity in clonogenic and xenograft assays (data not shown). Since HGF/MAPK signaling induced Jagged1 expression in HNSCC (10), we asked whether FGF4 would stimulate expression of Notch ligands in Mm5MT cells. We detected up-regulation of Jagged1 and Dll1 in Mm5MT-FGF4 transfectants using quantitative PCR (Dll4 expression was unaltered) (FIG. 33A). The FGFR-kinase inhibitor PD166866 suppressed induction of both Jagged1 and Dll1 in Mm5MT-FGF4 transfectants (FIG. 33C) indicating that FGF4-induced Jagged1 and Dll1 expression requires FGFR signaling. Immunoblotting confirmed up-regulation of Jagged1 protein in Mm5MT-FGF4 cells (FIG. 33B), and immunostaining demonstrated strikingly increased Jagged1 in Mm5MT-FGF4 tumors (FIG. 33D). In addition, Notch4 was detected in Mm5MT-FGF4 tumor endothelium (not shown).

Figure 34:
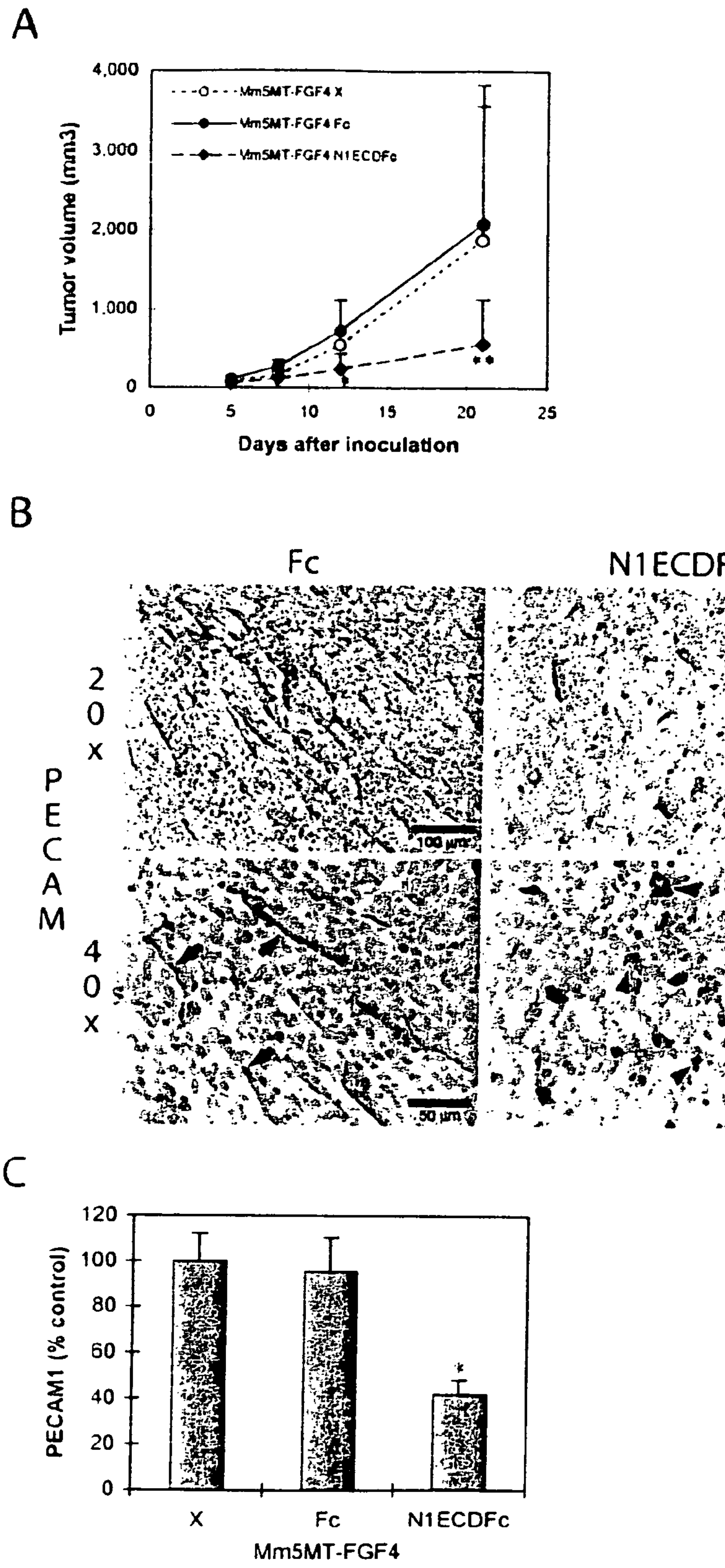
FIGS. 34A-34C These Figures show that Notch1 decoy inhibits angiogenesis and subcutaneous tumor growth of Mm5MT-FGF4 tumors in mice.

Notch1 Decoy Expression Inhibited Angiogenesis and Growth of Mm5MT-FGF4 Tumors in Mice We hypothesized that Mm5MT-FGF4 tumors expressing Jagged1 promote angiogenesis by signaling via endothelial Notch receptors. Thus, we evaluated the effect of Notch1 decoy expression on Mm5MT-FGF4 xenograft growth in mice. Tumorigenicity of Mm5MT-FGF4 stably overexpressing either Fc or Notch1 decoy was unaltered by clonogenic assay (data not shown). However, Mm5MT-FGF4-N1ECDFc xenograft growth was significantly delayed as compared to both Mm5MT-FGF4 mock- and Fc-transfectants, suggesting that Notch inhibition had impaired a critical element in tumorigenesis (FIG. 34A). Immunostaining for the endothelial marker CD31/PECAN demonstrated marked inhibition of angiogenesis in Mm5MT-FGF4-N1ECDFc tumors (FIG. 34B). Consistent with a requirement for Notch in vessel assembly, EC appeared as detached solitary cells or small clusters, with few organized vessels detected. Quantitative analysis of anti-CD31 staining demonstrated a 58% decrease in microvessel density in Notch1 decoy-expressing tumors ($P<0.001$ for both Mm5MT-FGF4-X and Mm5MT-FGF4-Fc versus Mm5MT-FGF4-N1ECDFc; data shown as mean±SD; FIG. 34C).

Figure 35:
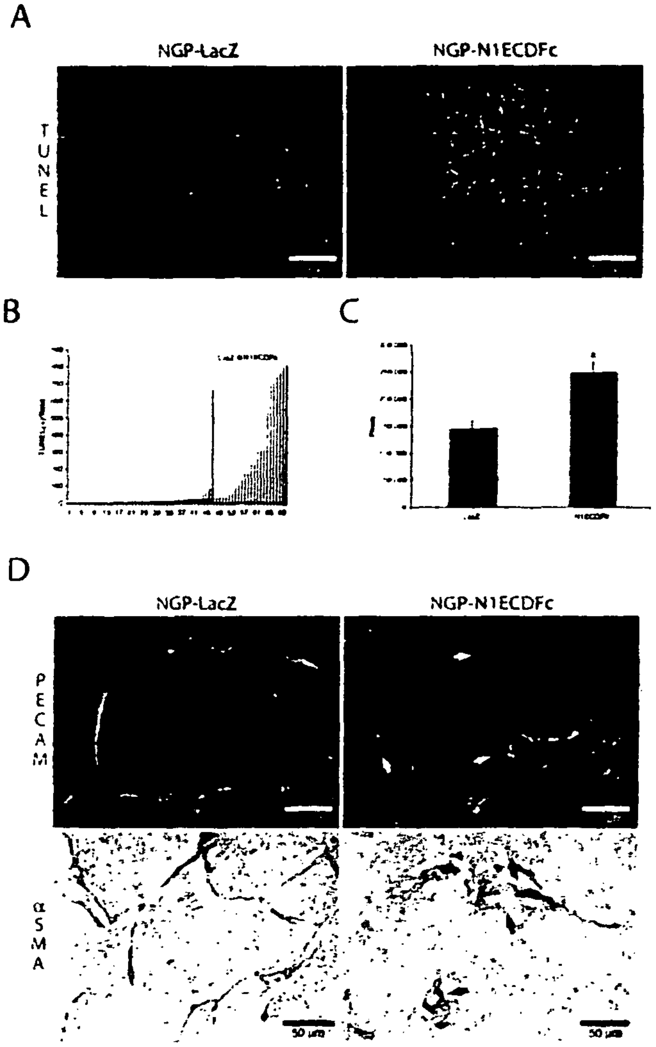
FIGS. 35A-35D These Figures show Notch1 decoy expression disrupts angiogenesis and impairs tumor viability in human NGP xenografts. We have previously reported that these human neuroblastoma xenografts in mice have a mature, hierarchical vasculature that is relatively resistant to VEGF blockade (16). To determine whether Notch receptor activation contributed to NGP angiogenesis, we transfected NGP cells with the Notch1 decoy construct, which did not affect their ability to grow in culture (data not shown). There was, however, a marked decrease in tumor viability in vivo (FIG. 35A) TUNEL=red fluorescence, erythrocytes=green fluorescence, Bar=100 μm), with (FIG. 35B) significantly increased tumor cell apoptosis (P=0.0002, TUNEL-positive cells in NGP-N1ECDFc vs. NGP-LacZ tumors), and (FIG. 35C) increased intratumoral hemorrhage (p<0.0001, quantitation of parenchymal erythrocyte signal). In addition, the tumor vessel networks in NGP-N1ECDFc xenografts appeared to have been physically disrupted as compared to NGP-LacZ controls, with (FIG. 35D) immunostaining for ECs and VMCs (using anti-CD31 and αSMA antibodies, respectively) demonstrating lack of continuity of these vascular cell layers, (Bar=50 μm). Individual vascular cells appeared detached from one another. Taken together, these results suggest that Notch1 decoy expression disrupted the ability of ECs and VMCs to form stable vascular conduits, causing vessel breakdown, hemorrhage, and ischemia of tumor tissues.

Notch1 Decoy Expression Disrupted Angiogenesis in Human NGP Neuroblastoma Xenografts NGP xenografts in mice form a mature hierarchical vasculature that is comparatively resistant to VEGF blockade (16). To determine whether Notch receptor activation contributed to NGP angiogenesis, we transfected NGP cells with N1ECDFc, as above. Similar to results observed with Mm5MT-FGF4-N1ECDFc cells, growth of NGP-N1ECDFc cells in culture was unaffected by transfection (not shown). However, xenograft viability was strikingly impaired (FIG. 35A), with significantly increased tumor cell apoptosis ($P=0.0002$, TUNEL-positive cells in NGP-N1ECDFc vs. NGP-LacZ tumors, FIG. 35B). Intratumoral hemorrhage was significantly increased in NGP-N1ECDFc tumors, suggesting that vessels were physically disrupted ($P<0.0001$, FIG. 36C). Immunostaining for the vascular basement membrane component collagen IV indicated an overall decrease in vasculature, with diminished branching, although remaining collagen sleeves appeared smooth and intact (not shown). However, immunostaining for EC and vascular mural cells (VMC) (using anti-CD31 and anti-αSMA antibodies, respectively) demonstrated disorder of these normally contiguous cell layers. Individual vascular cells appeared irregular, and were erratically detached from one another, with loss of vessel continuity (FIG. 35D). Taken together, these results suggest that Notch1 decoy expression disrupted endothelial and VMC interactions in tumor vasculature, leading to instability, hemorrhage, and defective perfusion of tumor tissues.

Discussion

Recent reports confirm the critical role of the Notch ligand Dll4 in angiogenesis, and demonstrate that Dll4 blockade can effectively repress tumor growth by disrupting vasculature (8, 9). In this study, we show that blockade of Notch receptor function using a novel construct derived from the Notch1 ectodomain also effectively reduces tumor perfusion, although its effects on vasculature are distinct. The Notch1 decoy inhibited signaling induced by the binding of ligands Jagged1, Dll1 and Dll4 to Notch1. Consistent with a role for Notch receptor activation in neoangiogenesis, overexpression of Notch4 induced endothelial cell extensions, which could be prevented by blocking Notch signaling with either Notch1 decoy or GSI. Although Notch1 decoy did not inhibit tumor cell growth in vitro, expression of Notch1 decoy inhibited growth and angiogenesis of Mm5MT-FGF4 xenografts, in which Jagged1 expression is up-regulated. Similarly, Notch1 decoy expression had no effect on NGP tumor cell proliferation in vitro, but disrupted tumor vessels and viability in vivo.

Notch4 overexpression in HUVECs was sufficient to induce endothelial extensions on fibrin gel without exogenous expression of Notch ligands. Since fibrin is known to induce Jagged1 expression in EC, and thus may have functioned to promote HUVEC expression of Jagged1 in this assay, we speculate that this caused activation of Notch4. In HeLa co-culture signaling assays, the Notch1 decoy inhibited signaling via ligand-Notch1 receptor interaction. We were unable to similarly evaluate Notch4 activity as Notch4 was poorly processed and presented in HeLa cells (not shown). However, processed Notch4 is found on HUVECs after adenoviral Notch4 transduction (not shown), indicating that Notch1 decoy can block ligand-induced Notch4 activation.

The multiple roles recently demonstrated for Notch signaling in tumorigenesis increase the attractiveness of this pathway as a potential target for cancer therapy. While Notch activation is likely to function directly in malignant transformation in human cancers (20, 21), it may also be required for angiogenesis (8, 9). Interestingly, Notch ligand induction can be regulated by growth factor signals. For example, Jagged1 is induced in tumor cells by HGF (10), and Dll4 induced in EC by VEGF (22). Here we show that FGF4 can similarly stimulate Jagged1 and Dll1 expression in murine Mm5MT cells. Notch1 decoy reduced Mm5MT-FGF4 tumor growth and angiogenesis in vivo but did not affect tumorigenicity in vitro. Thus, these results suggest that Notch receptor activation in Mm5MT vasculature rather than tumor cells is required for neoplastic growth in this system.

While both Mm5MT-FGF4 and NGP xenografts displayed striking disorder of tumor vasculature after Notch1 decoy expression, the differences in vascular phenotype observed in these models suggest that tumor-specific patterns of Notch function may fine-tune vessel assembly. Mm5MT-FGF4 tumors proliferate rapidly, and develop dense, erratic endothelial networks relatively devoid of recruited VMC. These immature vascular beds express Dll4 (data not shown) and are extensively ablated by Notch1 decoy expression, leaving small clusters or individual EC isolated in tumor parenchyma. Consistent with this initial failure to form vessel networks, decoy-expressing tumor remnants are not necrotic and are significantly smaller than controls. In contrast, NGP tumors develop a mature vascular plexus, with near-uniform coverage of endothelium by VMC. NGP vessels express Notch1 and relatively little Dll4 (not shown). Notch1 decoy expression in NGP tumors causes intratumoral hemorrhage and necrosis, with loss of vessel continuity, suggesting that perfused vessels become unstable after some degree of tumor growth has occurred.

Collectively, these data provide support for a model in which Notch signaling controls multiple aspects of tumor angiogenesis. While Notch activation is broadly required for neoangiogenesis, individual Notch proteins may differentially regulate vascular remodeling. Our results confirm the importance of Notch ligand-receptor interactions in tumor vasculature, and suggest that perturbing Notch receptor function may provide a novel and effective means of disrupting tumor angiogenesis.

REFERENCES FOR FOURTH SERIES OF EXPERIMENTS

1. Ferrara, N. Vascular Endothelial Growth Factor: Basic Science and Clinical Progress. Endocr. Rev., 25: 581-611, 2004.
2. Jain, R., Duda, D., Clark, J., and Loeffler, J. Lessons from phase III clinical trials on anti-VEGF therapy for cancer. Nat Clin Pract Oncol. 2006 January; 3(1):24-40., 3: 24-40, 2006.
3. Kopan, R. Notch: a membrane-bound transcription factor. J Cell Sci., 115: 1095-1097, 2002.
4. Shawber, C. and Kitajewski, J. Notch function in the vasculature: insights from zebrafish, mouse and man. Bioessays., 26: 225-234, 2004.
5. Gale, N. W., Dominguez, M. G., Noguera, I., Pan, L., Hughes, V., Valenzuela, D. M., Murphy, A. J., Adams, N. C., Lin, H. C., Holash, J., Thurston, G., and Yancopoulos, G. D. Haploinsufficiency of delta-like 4 ligand results in embryonic lethality due to major defects in arterial and vascular development. Proc Natl Acad Sci 101: 15949-15954, 2004.
6. Patel, N. S., Li, J.-L., Generali, D., Poulsom, R., Cranston, D. W., and Harris, A. L. Up-regulation of Delta-like 4 Ligand in Human Tumor Vasculature and the Role of Basal Expression in Endothelial Cell Function. Cancer Res., 65: 8690-8697, 2005.
7. Patel, N. S., Dobbie, M. S., Rochester, M., Steers, G., Poulsom, R., Le Monnier, K., Cranston, D. W., Li, J.-L., and Harris, A. L. Up-Regulation of Endothelial Delta-like 4 Expression Correlates with Vessel Maturation in Bladder Cancer. Clin Cancer Res, 12: 4836-4844, 2006.
8. Ridgway, J., Zhang, G., Wu, Y., Stawicki, S., Liang, W. C., Chanthery, Y., Kowalski, J., Watts, R. J., Callahan, C., Kasman, I., Singh, M., Chien, M., Tan, C., Hongo, J. A., de Sauvage, F., Plowman, G., and Yan, M. Inhibition of Dll4 signalling inhibits tumour growth by deregulating angiogenesis. Nature, 444: 1083-1087, 2006.
9. Noguera-Troise, I., Daly, C., Papadopoulos, N. J., Coetzee, S., Boland, P., Gale, N. W., Lin, H. C., Yancopoulos, G. D., and Thurston, G. Blockade of Dll4 inhibits tumour growth by promoting non-productive angiogenesis. Nature, 444: 1032-1037, 2006.
10. Zeng, Q., Li, S., Chepeha, D. B., Giordano, T. J., Li, J., Zhang, H., Polverini, P. J., Nor, J., Kitajewski, J., and Wang, C.-Y. Crosstalk between tumor and endothelial cells promotes tumor angiogenesis by MAPK activation of Notch signaling. Cancer Cell, 8: 13-23, 2005.
11. Das, I., Craig, C., Funahashi, Y., Jung, K.-M., Kim, T.-W., Byers, R., Weng, A. P., Kutok, J. L., Aster, J. C., and Kitajewski, J. Notch Oncoproteins Depend on {gamma}-Secretase/Presenilin Activity for Processing and Function. J Biol Chem., 279: 30771-30780, 2004.
12. Shawber, C. J., Das, I., Francisco, E., and Kitajewski, J. A. N. Notch Signaling in Primary Endothelial Cells. Ann NY Acad Sci, 995: 162-170, 2003.
13. Hardy, S., Kitamura, M., Harris-Stansil, T., Dai, Y., and Phipps, M. L. Construction of adenovirus vectors through Cre-lox recombination. J Virol., 71: 1842-1849, 1997.
14. Jaffe, E., Nachman, R., Becker, C., and Minick, C. Culture of human endothelial cells derived from umbilical veins. Identification by morphologic and immunologic criteria. J Clin Invest., 52: 2745-2756, 1973.
15. Vorontchikhina, M. A., Zimmermann, R. C., Shawber, C. J., Tang, H., and Kitajewski, J. Unique patterns of Notch1, Notch4 and Jagged1 expression in ovarian vessels during folliculogenesis and corpus luteum formation. Gene Expression Patterns, 5: 701-709, 2005.
16. Kim, E. S., Serur, A., Huang, J., Manley, C. A., McCrudden, K. W., Frischer, J. S., Soffer, S. Z., Ring, L., New, T., Zabski, S., Rudge, J. S., Holash, J., Yancopoulos, G. D., Kandel, J. J., and Yamashiro, D. J. Potent VEGF blockade causes regression of coopted vessels in a model of neuroblastoma. Proc Natl Acad Sci USA, 99: 11399-11404, 2002.
17. Montesano R and L., O. Phorbol esters induce angiogenesis in vitro from large-vessel endothelial cells. J Cell Physiol., 130: 284-291., 1987.
18. Koolwijk P, van Erck M G, de Vree W J, Vermeer M A, Weich H A, Hanemaaijer R, and V W., v. H. Cooperative effect of TNFalpha, bFGF, and VEGF on the formation of tubular structures of human microvascular endothelial cells in a fibrin matrix. Role of urokinase activity. J Cell Biol, 132: 1177-1188, 1996.
19. Zimrin, A. B., Pepper, M. S., McMahon, G. A., Nguyen, F., Montesano, R., and Maciag, T. An Antisense Oligonucleotide to the Notch Ligand Jagged Enhances Fibroblast Growth Factor-induced Angiogenesis in Vitro. J Biol Chem, 271: 32499-32502, 1996.
20. Nickoloff, B., Osborne, B., and L., M. Notch signaling as a therapeutic target in cancer: a new approach to the development of cell fate modifying agents. Oncogene, 22: 6598-6608, 2003.
21. Radtke, F. and Raj, K. THE ROLE OF NOTCH IN TUMORIGENESIS: ONCOGENE OR TUMOUR SUPPRESSOR? Nature Reviews Cancer, 3: 756-767, 2003.
22. Liu, Z.-J., Shirakawa, T., Li, Y., Soma, A., Oka, M., Dotto, G. P., Fairman, R. M., Velazquez, O. C., and Herlyn, M. Regulation of Notch1 and Dll4 by Vascular Endothelial Growth Factor in Arterial Endothelial Cells Implications for Modulating Arteriogenesis and Angiogenesis. Mol Cell Biol 23: 14-25, 2003.

FIFTH SERIES OF EXPERIMENTS

Notch as a Therapeutic Target in Ovarian Cancer

Figure 36:
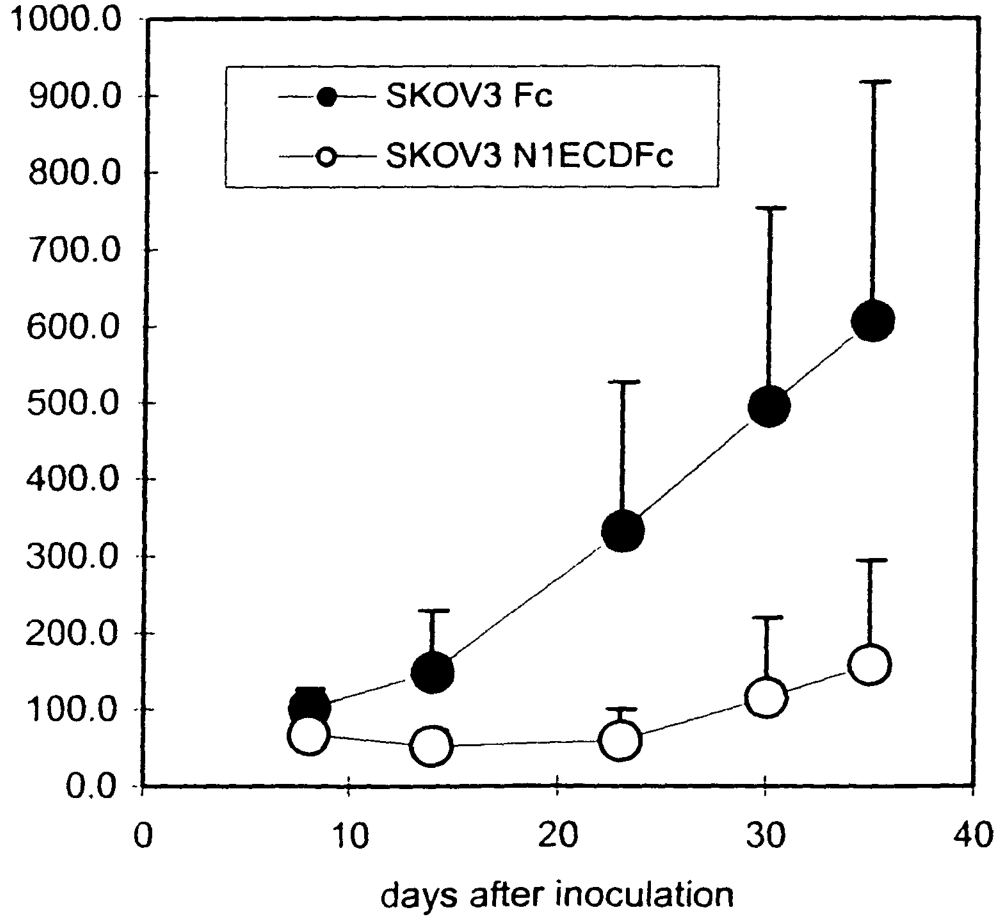
FIG. 36 This Figure shows that SKOV3 tumor cells programmed expressing the Notch1 decoy block the growth of ovarian cancer xenografts.

Epithelial ovarian carcinoma is the leading cause of death from gynecological cancer in the U.S. Patients suffer as a result of our inability to diagnose the disease at an early stage, and from the lack of novel therapeutics directed against this tumor. Vascular endothelial growth factor (VEGF) is produced by malignant epithelial ovarian cancer cells, which, in turn, promotes tumor angiogenesis that nourishes the tumor [1]. Recent clinical trials demonstrate that targeting VEGF for therapeutic intervention can improve outcome, in some cases [2]. Thus, anti-angiogenic therapeutics have been validated as an approach to treat ovarian cancer, but more work needs to be done to build on these gains. We have identified the Notch signaling pathway as a novel angiogenic pathway in both physiological and pathological angiogenesis [3, 4]. Notch is a cell surface receptor (FIG. 1-Notch1) that promotes cell fate determination, cell survival and proliferation. Our lab has developed a Notch inhibitor, called the Notch decoy (schematized in FIG. 1), which is a fusion protein comprising the Notch1 extra-cellular domain fused to an Fc tag (N1ECDFc) which can inhibit ligand-dependent Notch signaling (data not shown). We have demonstrated that the Notch decoy can block VEGF-induced angiogenesis and tumor angiogenesis in a Wilms Tumor mouse model (data not shown). We generated human ovarian cancer cells SKOV3 that over-express the Notch decoy, SKOV3-N1ECDFc. We found that expression of Notch decoy in SKOV3 cell significantly inhibited the growth of tumor when xenografted into mice (FIG. 36). Thus, the Notch decoy blocks ovarian cancer growth. We hypothesize that this inhibition is targeting tumor angiogenesis. Further, we have surveyed human ovarian cancer samples and have found that several Notch ligands and Notch receptors are highly expressed in tumor vessels associated with ovarian cancers, thus supporting the hypothesis that one can target Notch in human ovarian tumor vessels and ultimately block their growth.

This study will test the hypothesis that Notch signaling promotes tumor angiogenesis in ovarian cancer. In addition, we hypothesize that inhibition of Notch, utilizing a "Notch decoy," will block tumor growth. We will determine if Notch decoy action is against tumor vessels or growth of tumor cells or both. The overall goal is to establish Notch decoy as a therapeutic for treatment of ovarian cancer.

Specific Aims:

Specific Aim 1: Determine if Notch decoy expression blocks tumor xenograft growth of SKOV3 or OVCAR3 cells and define whether Notch decoy is targeting tumor angiogenesis.

Specific Aim 2: Modify the Notch decoy design to make versions with increased efficacy/stability.

Specific Aim 3: Use purified Notch decoys to block ovarian cancer tumor xenografts in mice, also in combination with standard chemotherapeutic agents.

Research Strategy:

Specific Aim 1: Determine if Notch decoy blocks tumor xenograft growth of SKOV3 or OVCAR3 cells and define whether Notch decoy is targeting tumor angiogenesis.

Our preliminary results demonstrate that SKOV3 tumor cells programmed expressing the Notch1 decoy block the growth of ovarian cancer xenografts (FIG. 36). This finding will be replicated in another ovarian cancer cell line, OVCAR3. The Notch decoy may inhibit growth of tumor cells, tumor vessels or both. To determine if Notch decoy targets tumor cells, we will determine if ovarian cancer lines expressing Notch decoy grow more poorly in soft-agar assays. To determine if the decoy is targeting tumor angiogenesis, we will evaluate xenografted tumors for evidence of such inhibition. Measures of tumor angiogenesis for control xenografts will include microvessel density assessment, proliferative index of tumor endothelial cells, and imaging tumor vasculature via lectin perfusion. Measures of inhibition of tumor angiogenesis in Notch decoy expressing xenografts will include assessment of apoptotic endothelial cells, reduction of tumor microvasculature and reduced ascites accumulation.

Specific Aim 2: Modify the Notch decoy design to make versions with increased efficacy/stability.

The current Notch1 decoy, although effective as a Notch blocking agent, may not be readily amenable to purification, as it is a relatively large protein. We propose to develop variants of Notch1 decoy that encompass smaller parts of the extracellular domain. These variants will be screened as inhibitors of Notch signaling in cell culture-based assays. Inhibitory variants will also be screened for: their efficiency of secretion from producing cells, their stability once secreted, their solubility, and the ease of purification via the Fc affinity tag. Purified variants will be injected into mice to evaluate potential toxicity.

Specific Aim 3: Use purified Notch decoys to block ovarian cancer tumor xenografts in mice, also in combination with standard chemotherapeutic agents.

The purified decoys, from Specific Aim 2, will be employed, either as single agents, or in combination with chemotherapy, to evaluate their efficacy against ovarian cancer xenografts (SKOV3/OVCAR3). Using the purified Notch decoy as a single agent, we will attempt to replicate the block to tumor xenograft growth seen in experiments of Specific Aim 1 and determine the optimal concentration for inhibition. To accomplish this end, we will determine the optimal dose, dosing schedule, and duration of treatment needed to block SKOV3/OVCAR3 xenograft growth in mice. Next, we will use the Notch decoy in combination with paclitaxol. An optimal dose of Notch decoy will be used with or without paclitaxol to determine efficacy in blocking xenograft growth.

Impact: This study is aimed at directly advancing the treatment of ovarian cancer. Clinical studies have recently established the success of treating ovarian cancers with VEGF blocking agents. Few new therapeutic agents have been developed to supplement chemotherapeutic treatment. Despite this success, targeting of VEGF to block tumor growth may only limit tumor growth to an extent. It may also lead to new tumor vessels growing that are resistant to VEGF blockade. We propose to target an alternative tumor angiogenic pathway implicated in ovarian cancer, the Notch signaling pathway. This study will advance treatment by developing a novel therapeutic entity, the Notch decoy. Our preliminary studies already establish that Notch decoy can block ovarian cancer growth in a mouse model. Thus, the impact of development of the Notch decoy as a therapeutic entity may be highly significant.

Innovation: Our recent development of the Notch decoy presents a novel and previously untested paradigm to treat ovarian cancer. No other published study has yet implicated this pathway in the treatment of ovarian cancer, yet our preliminary evidence defines this as a key area for exploration. In addition, despite the recent success of VEGF-blockade as a new therapeutic approach for treatment of ovarian cancer, we feel that this approach may need to be supplemented by inhibition of other angiogenic pathways, such as Notch.

REFERENCES FOR FIFTH SERIES OF EXPERIMENTS

1. Abu-Jawdeh, G. M., et al., *Strong expression of vascular permeability factor (vascular endothelial growth factor) and its receptors in ovarian borderline and malignant neoplasms*. Lab Invest, 1996. 74(6): p. 1105-15.
2. Monk, B. J., et al., *Activity of bevacizumab (rhuMAB VEGF) in advanced refractory epithelial ovarian cancer*. Gynecol Oncol, 2005. 96(3): p. 902-5.
3. Shawber, C., J. J. Kandel, and J. Kitajewski, *Notch: cell fate determination from vascular development to human vasculopathy*. Drug Discovery Today: Disease Models, 2004. 1(3): p. 351-8.
4. Zeng, Q., et al., *Crosstalk between tumor and endothelial cells promotes tumor angiogenesis by MAPK activation of Notch signaling*. Cancer Cell, 2005. 8(1): p. 13-23.

SIXTH SERIES OF EXPERIMENTS

A Foxo/Notch Pathway Controls Myogenic Differentiation and Fiber Type Specification Foxo transcription factors govern metabolism and cellular differentiation. Unlike Foxo-dependent metabolic pathways and target genes, the mechanisms by which these proteins regulate differentiation have not been explored. Activation of Notch signaling mimics the effects of Foxo gain-of-function on cellular differentiation. Using muscle differentiation as a model system, we show that Foxo physically and functionally interacts with Notch by promoting co-repressor clearance from the Notch effector Csl, leading to activation of Notch target genes. Inhibition of myoblast differentiation by constitutively active Foxo1 is partly rescued by inhibition of Notch signaling, while Foxo1 loss-of-function precludes Notch inhibition of myogenesis and increases MyoD expression. Accordingly, conditional Foxo1 ablation in skeletal muscle results in increased formation of MyoD-containing (fast-twitch) muscle fibers and altered fiber type distribution at the expense of Myogenin-containing (slow-twitch) fibers. Notch/Foxo1 cooperation may integrate environmental cues through Notch with metabolic cues through Foxo1 to regulate progenitor cell maintenance and differentiation.

A central question in regenerative medicine is to understand how highly specialized cell types arise from undifferentiated stem or progenitor cells (1). Germane to this issue is how biochemical signals engendered by microenvironmental and endocrine/nutritional cues are transcriptionally integrated to activate cellular differentiation processes.

The O subfamily of forkhead (Fox) proteins regulates hormonal, nutrient and stress responses to promote cell survival and metabolism. The ability to fine-tune Foxo transcription is essential to control these cellular functions, and is largely dependent on post-transcriptional modifications, including phosphorylation and acetylation (2). In addition to their role in terminally differentiated cells, Foxo proteins have also been implicated in myoblast (3), pre-adipocyte (4) and endothelial cell differentiation (5). Moreover, Foxo4 regulates vascular smooth muscle cells differentiation through interactions with Myocardin (6). Foxo3 knockout mice display premature ovarian failure, consistent with a role for this gene in ovarian follicle maturation (7). The mechanisms by which Foxo proteins control cellular differentiation remain unclear, and recent conditional ablation studies are consistent with a significant degree of functional overlap amongst the three Foxo isoforms in the hematopoietic lineage (8, 9).

The Notch pathway plays an important role in neural, vascular, muscular and endocrine differentiation during embryogenesis (10). Upon ligand-induced cleavage, the intracellular domain of the Notch receptor translocates to the nucleus, where it interacts with the DNA binding protein Csl, changing its transcriptional properties from a suppressor to an activator of transcription (11). Csl targets include the Hairy and Enhancer of Split (Hes, Hey) genes. Hes1 controls gut endoderm (12), pre-adipocyte (13) and neurogenic differentiation (14). Active Notch signaling, or gain of Notch1 receptor function, inhibits differentiation of C2C12 and 10T/2 myoblasts by suppressing MyoD transcription (15-21).

It is noteworthy that Foxo1 gain-of-function (3-5) phenocopies Notch1 activation (13, 17, 22, 23) in every cellular differentiation context. Moreover, Foxo1 ablation (24) phenocopies Notch1 ablation (25) in mice. Despite these intriguing similarities, Foxo and Notch signal through two seemingly distinct mechanisms, the phosphatidylinositol-3-kinase pathway (Foxo), and the Hes/Hey pathway (Notch). In this study, we show that Foxo physically and functionally interacts with Notch by promoting co-repressor clearance from Csl, thus controlling the myogenic program.

Myogenic precursors arise from mesodermal stem cells (26) and are converted into myotubes by a multi-step process culminating in the expression of myogenic transcription factors of the MRF family (MyoD, Myogenin, MRF4 and Myf5) (27). Myogenic transcription factors heterodimerize with E proteins and promote expression of muscle-specific genes, acting in close coordination with myocyte-specific MEF2 enhancer factors (28).

Adult muscle is a heterogeneous tissue, primarily defined by its myofiber content (29). Different myosin heavy chain (MyHC) sub-types characterize different myofibers. Type I fibers express primarily slow-twitch MyHC, whereas type II fibers express fast-twitch MyHC (29). The process of fiber-type specification is controlled at multiple steps. First, there appears to be heterogeneity among myogenic precursor cells, and evidence from avian embryo cross-transplantation experiments indicates that early precursors contribute primarily to slow muscle fibers, and later precursors to fast fibers (29). Post-natally, fiber type specification is also affected by cell autonomous factors, including innervation and endocrine/nutritional cues (28). The Foxo co-activator Pgc1α plays a critical role in promoting the formation of slow-twitch fibers (30), and recent data have also implicated the Foxo deacetylase Sirt1 in this process (31). Using conditional mutagenesis in mice, we show that Foxo1's role in suppressing MyoD-dependent myogenesis in C2C12 cells is mirrored by an increase of MyoD-containing myofibers in Foxo1-deficient skeletal muscle, consistent with a key function in myoblast lineage specification.

Results

Interaction of Foxo1 and Notch Signaling in C2C12 Differentiation

Figure 37:
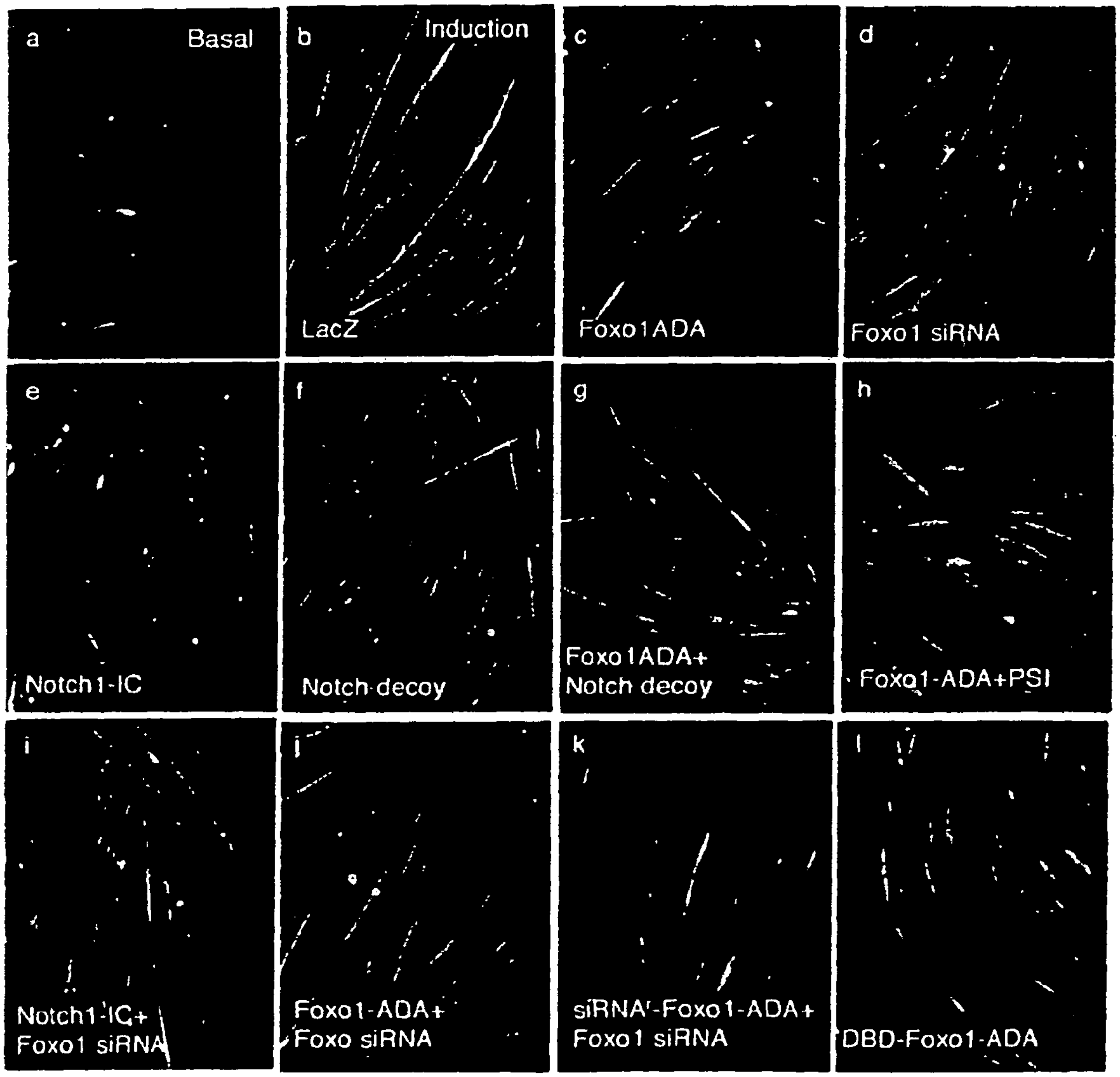
FIG. 37 This Figure shows regulation of myoblast differentiation by Foxo and Notch. C2C12 cells were immunostained with anti-Myosin antibody (green) and DAPI (blue). See text for panel description. Each experiment was repeated ≥six times.
Figure 44:
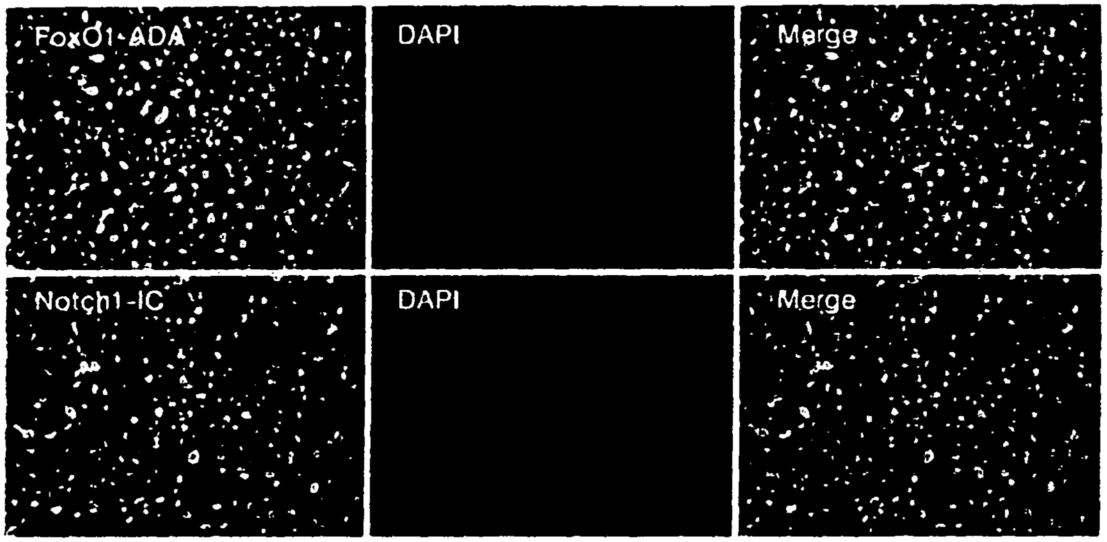
FIG. 44 This Figure shows the efficiency of adenoviral transduction in C2C12 cells. We transduced cells with HA-Foxo1-ADA or HA-Notch1-IC adenovirus and performed immunohistochemistry with anti-HA antibody (red) and DAPI (blue).
Figure 45:
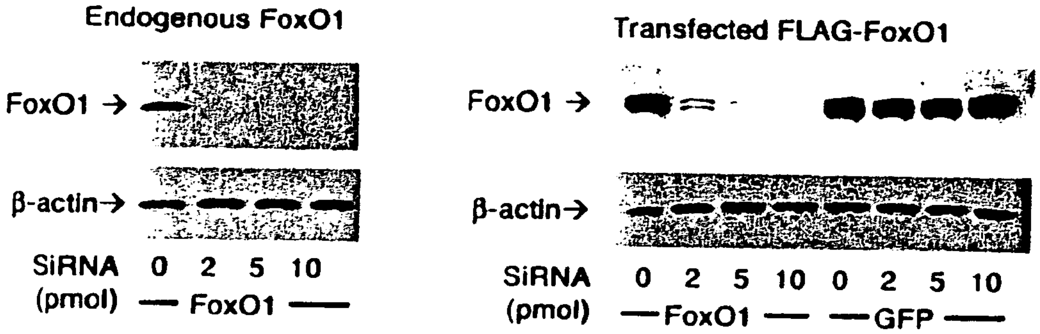
FIG. 45 This Figure shows inhibition of transfected Foxo1 expression. We tested the ability of Foxo1 siRNA to inhibit expression of endogenous (left panel) and transfected (right panel) Foxo1 following adenoviral transduction.
Figure 46:
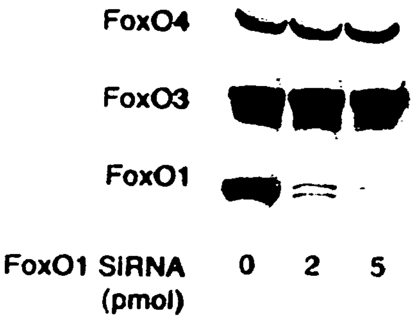
FIG. 46 This Figure shows the specificity of Foxo1 siRNA. Western blot analysis of Foxo1, Foxo3 and Foxo4 expression in C2C12 cells transfected with Foxo1 siRNA.
Figure 47:
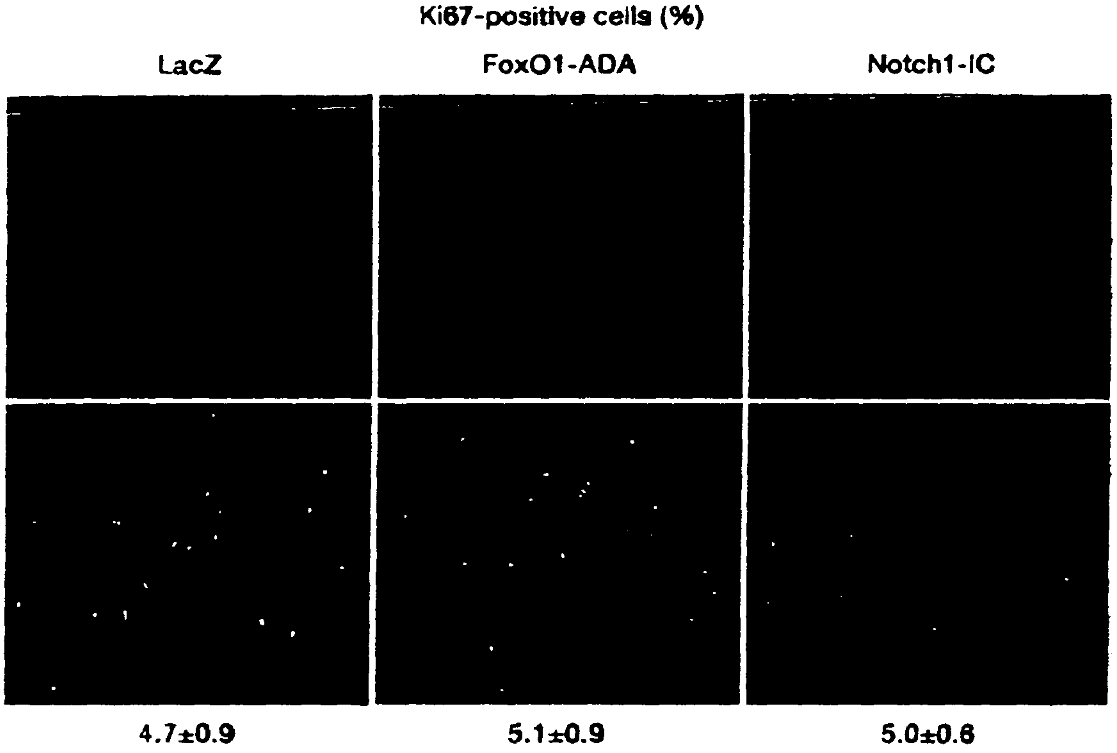
FIG. 47 This Figure shows that Foxo1-ADA and Notch1-IC do not affect cell proliferation. We transduced C2C12 cells with LacZ, Foxo1-ADA or Notch1-IC adenovirus, performed immunohistochemistry with anti-Ki67 antibody and DAPI and quantitated the Ki67 labeling index as percentage of Ki67-positive cells by counting at least 1,000 cells.

To understand whether Notch and Foxo interact to control muscle development, we used a cellular differentiation model. C2C12 cells undergo myogenic conversion and myotube fusion upon growth factor withdrawal, a process associated with Foxo1 nuclear translocation (3). Accordingly, transduction of adenovirus encoding a constitutively active Foxo1 mutant (Foxo1-ADA)(4) blocked the effect of serum withdrawal to induce C2C12 differentiation, as reflected by inhibition of myoblast fusion (FIG. 37*a-c*). Conversely, Foxo1 inhibition by siRNA did not affect these processes (FIG. 37*d*). Similarly, constitutively active Notch (Notch1-IC) phenocopied Foxo1-ADA in blocking myoblast differentiation (FIG. 37*e*). Virtually all cells became transduced with the adenoviruses (FIG. 44). Foxo1 siRNA effectively suppressed expression of both endogenous Foxo1 and transfected FLAG-Foxo1 (FIG. 45) in a dose-dependent manner, without affecting control proteins or other Foxo isoforms (FIG. 46). Neither Foxo1-ADA nor Notch1-IC affected C2C12 proliferation (FIG. 47).

We asked whether we could preempt the effect of Foxo1-ADA by inhibition of endogenous Notch signaling. To this end, we used a truncated Notch1 receptor lacking the transmembrane anchor and intracellular domain, which acts as a decoy receptor by binding Notch ligands (32, 33) (Y.F. and J.K., unpublished observation). The decoy did not affect C2C12's ability to undergo differentiation in response to growth factor withdrawal (FIG. 37*f*), but partly rescued Foxo1-ADA inhibition of myoblast differentiation (FIG. 37*g*). As an alternative probe to block Notch signaling, the presenilin inhibitor (PSI) Compound E (34) also rescued Foxo1-ADA inhibition of myoblast differentiation (FIG. 37*h*).

Figure 38:
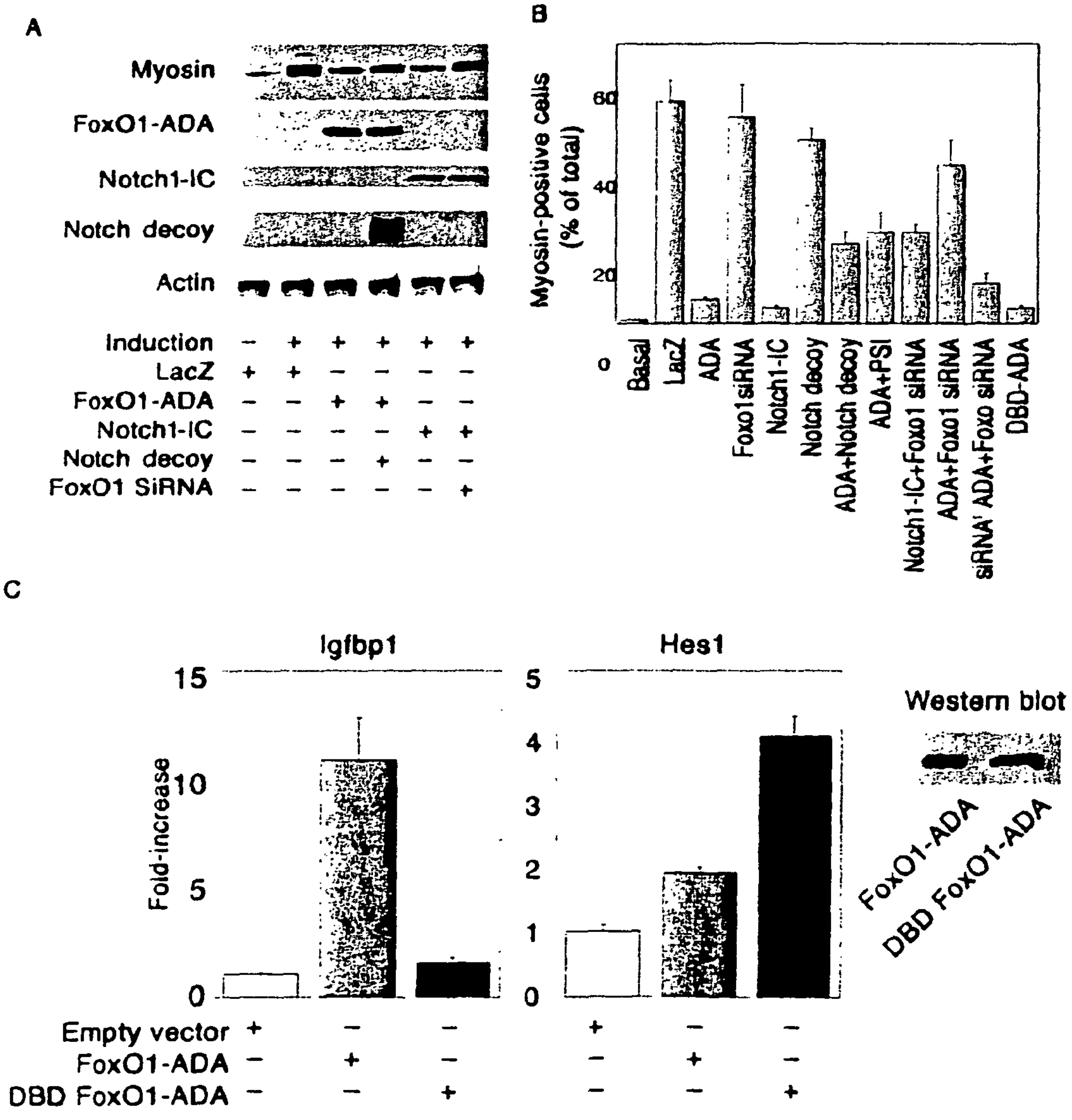
FIGS. 38A-38C These Figures show the quantitative analysis of C2C12 differentiation.
Figure 48:
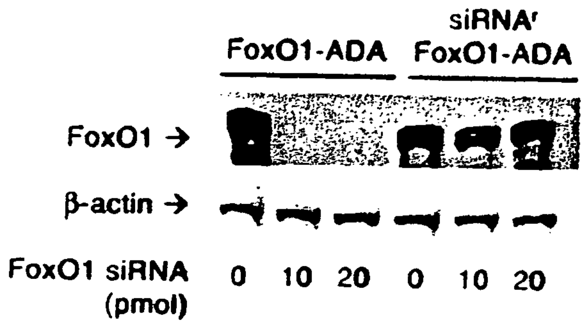
FIG. 48 This Figure shows siRNA-resistant Foxo1-ADA. Western blot of Foxo1-ADA and siRNA-resistant Foxo1-ADA in cells transfected with Foxo1 siRNA.
Figure 49:
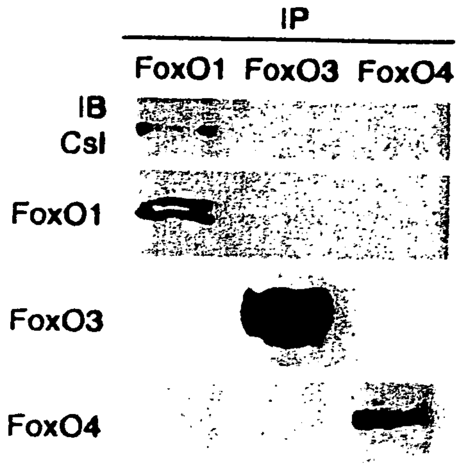
FIG. 49 This Figure shows the specificity of Foxo1-Csl co-immunoprecipitation. Following co-transfection with Foxo3 or Foxo4 expression vectors, we performed co-immunoprecipitation experiments with Csl.

To examine the effect of Foxo1 on Notch signaling, we co-transfected Foxo1 siRNA and Notch-IC. Foxo1 siRNA rescued inhibition of myoblast differentiation and Myosin expression by Notch1-IC (FIG. 37*i*), while control siRNA had no effect (data not shown). To rule out non-specific effects of Foxo1 siRNA on myoblast differentiation, we generated a siRNA-resistant Foxo1-ADA (FIG. 48). Foxo1 siRNA reversed the effects of Foxo1-ADA (FIG. 37*j*), but failed to rescue inhibition of C2C12 differentiation caused by siRNA-resistant Foxo1-ADA (FIG. 37*k*). We present a quantitative analysis of these data in FIG. 38*a*, showing that Foxo1 and Notch1-IC decreased myosin levels by >80%, while Notch decoy and Foxo1 siRNA restored them to ~70% of fully differentiated cells. We obtained similar data by performing a morphometric analysis of Myosin-positive cells (FIG. 38*b*). These data indicate that Foxo1 is required for the effect of Notch on myoblast differentiation.

We next tested whether Foxo1 affects differentiation via its transcriptional function. To this end, we generated a DNA Binding Deficient mutant in the backbone of the ADA mutant, by replacement of N208A and H212R (DBD-Foxo1ADA) (6, 35). We confirmed that this mutant is unable to bind DNA by measuring Igfbp1 promoter activity, a canonical Foxo1 target. Foxo1-ADA increased Igfbp1 promoter activity by 10-fold, whereas DBD-Foxo1ADA was unable to do so (FIG. 38*c*, left panel). Surprisingly, this mutant was as effective as the DNA binding-competent Foxo1-ADA at inhibiting differentiation (FIG. 37*l*). These data indicate that Foxo1 controls differentiation independently of its ability to bind DNA in a sequence-specific manner.

Foxo1 Binds to Csl and is Recruited to the Hes1 Promoter

Figure 39:
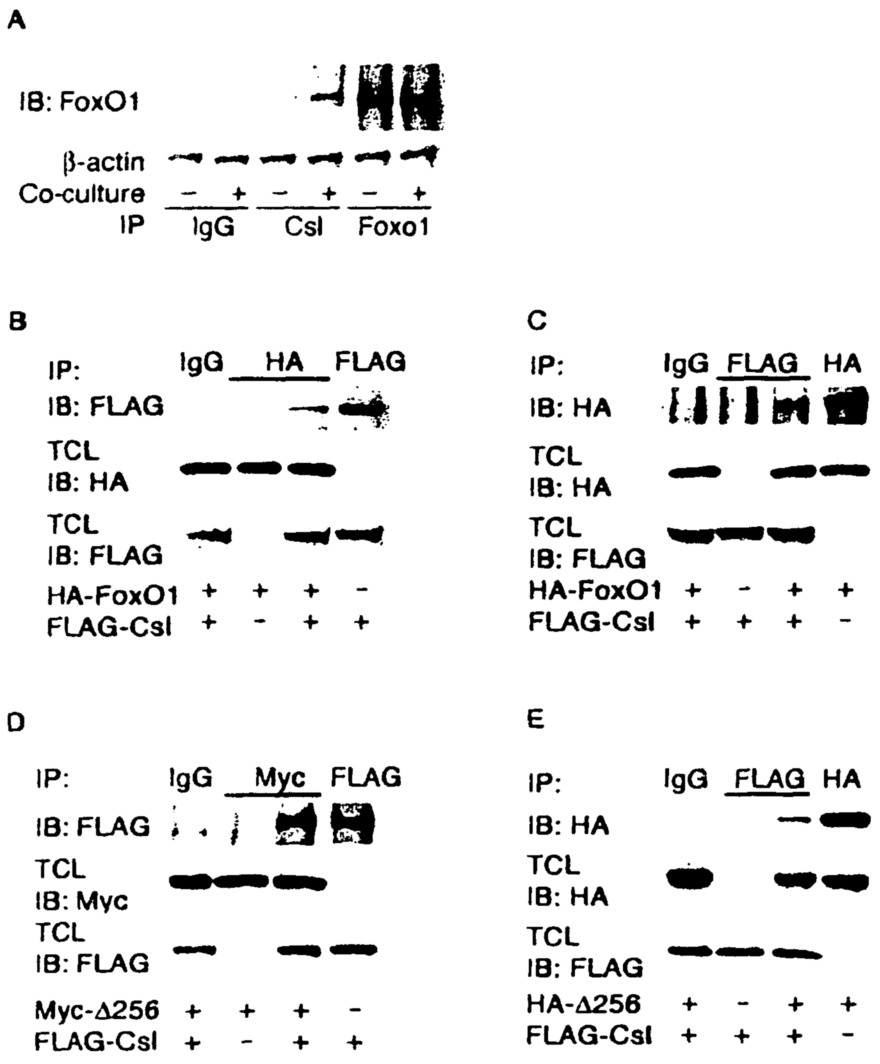
FIG. 39A-39E These Figures show Foxo1 co-immunoprecipitates with Csl. a, Co-immunoprecipitation of endogenous Foxo1 and Csl in C2C12 cells co-cultured with LacZ- (denoted by the "−" sign) or Jagged1-expressing HEK293 cells (denoted by the "+" sign). b-c, Co-immunoprecipitation experiments in C2C12 cells co-transfected with FLAG-Csl and HA-Foxo1. d-e, Co-immunoprecipitation experiments in C2C12 cells co-transfected with FLAG-Csl and the truncated mutant Myc- or HA-tagged Δ256 Foxo1.
Figure 42:
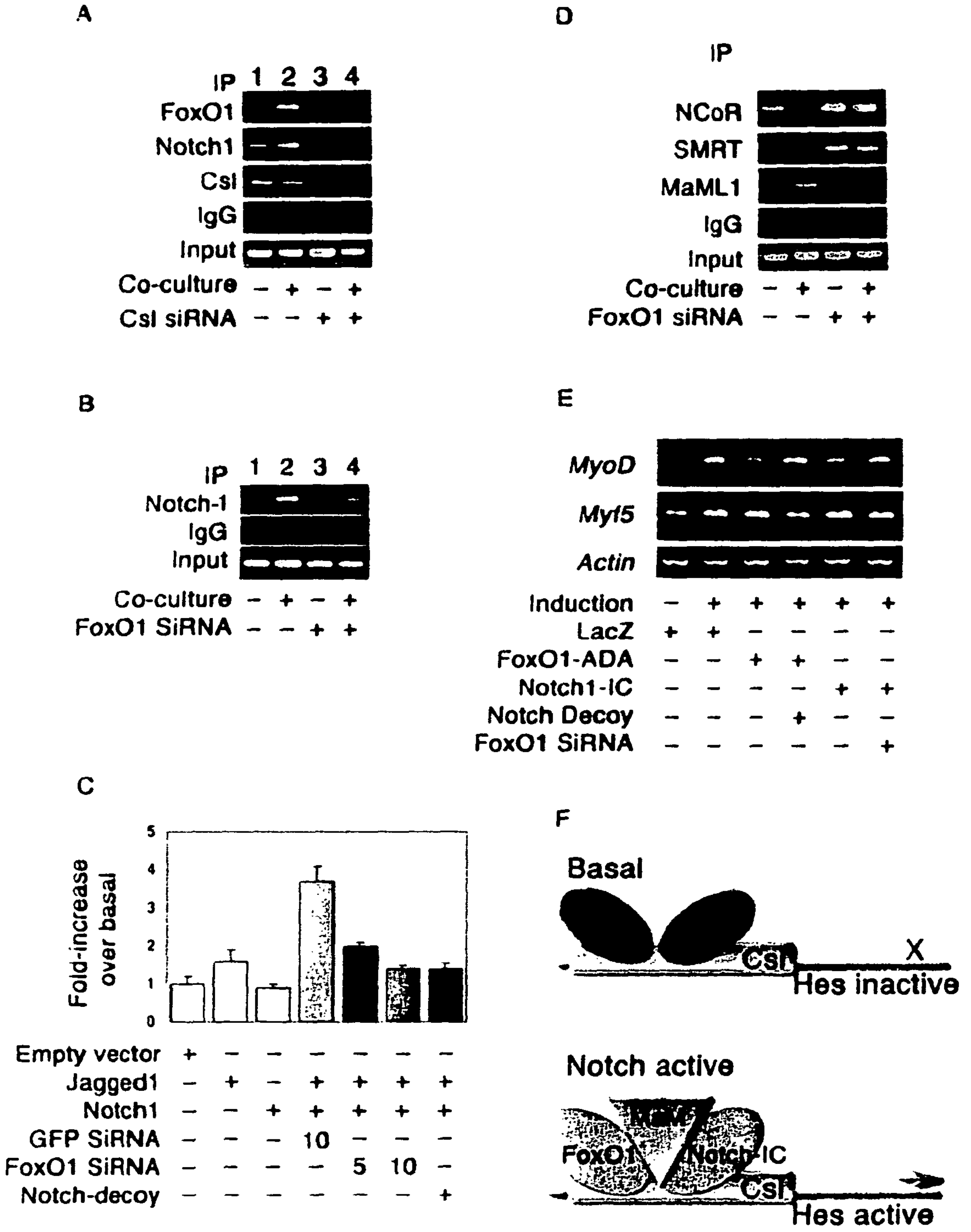
FIGS. 42A-42F These Figures show that Foxo1 is required for Notch binding to the Hes1 promoter and activation of Hes1 target genes.
a, ChIP assays of endogenous Foxo1 and Notch1 in C2C12 cells co-cultured with LacZ- (denoted by a "−" sign) or or Jagged1-expressing HEK293 cells (denoted by a "+" sign) in the absence (lanes 1-2) and presence (lanes 3-4) of Csl siRNA. b, ChIP assays of endogenous Notch1 in co-culture system in the absence (lanes 1-2) and presence (lanes 3-4) of Foxo1 siRNA. c, Hes1 promoter assays following co-culture in the absence and presence of Foxo1 or Gfp siRNA. d, ChIP assays of Ncor and Smrt and Maml1 binding to Hes1 in the co-culture system in the absence (lanes 1-2) and presence (lanes 3-4) of Foxo1 siRNA. e, Expression of MyoD, Myf5 and β-actin in C2C12 cells by semiquantitative RT-PCR. f, Model of Foxo1 and Notch regulation of Hes1 promoter.

Notch1-IC binds to and co-activates Csl to promote Hes and Hey expression (11). Based on the results with the DBD-Foxo1ADA mutant, we tested whether Foxo1 interacts with Csl in a Notch-dependent manner using co-culture of C2C12 cells expressing Notch1 receptor with HEK293 cells expressing the Notch ligand Jagged1 (denoted by the "+" sign), or LacZ as a negative control (denoted by the "−" sign). We provide several lines of evidence that Foxo1 and Csl interact in cultured cells. We detected endogenous Foxo1 in endogenous Csl immunoprecipitates, and the co-immunoprecipitation was significantly enhanced by activation of Notch signaling (FIG. 39*a*). To confirm the specificity of the interaction, we expressed HA-tagged Foxo1 and FLAG-tagged Csl in C2C12 cells. Following immunoprecipitation with anti-HA (Foxo1) antiserum, we detected FLAG-Csl in immunoblots (FIG. 39*b*). Conversely, following immunoprecipitation with anti-FLAG (Csl) antiserum, we detected HA-Foxo1 in immunoblots (FIG. 39*c*). The ability to co-immunoprecipitate with Csl appears to be specific to Foxo1, as we failed to detect other Foxo isoforms in Csl immunoprecipitates (FIG. 42). A truncated Foxo1 mutant (Δ256, encoding amino acids 1-256)(36) retained the ability to interact with Csl. We detected FLAG-Csl in Myc-Δ256 immunoprecipitates (FIG. 39*d*), and HA-Δ256 in FLAG-Csl immunoprecipitates (FIG. 39*e*), indicating that Csl interacts with the Foxo1 N-terminal domain.

Figure 40:
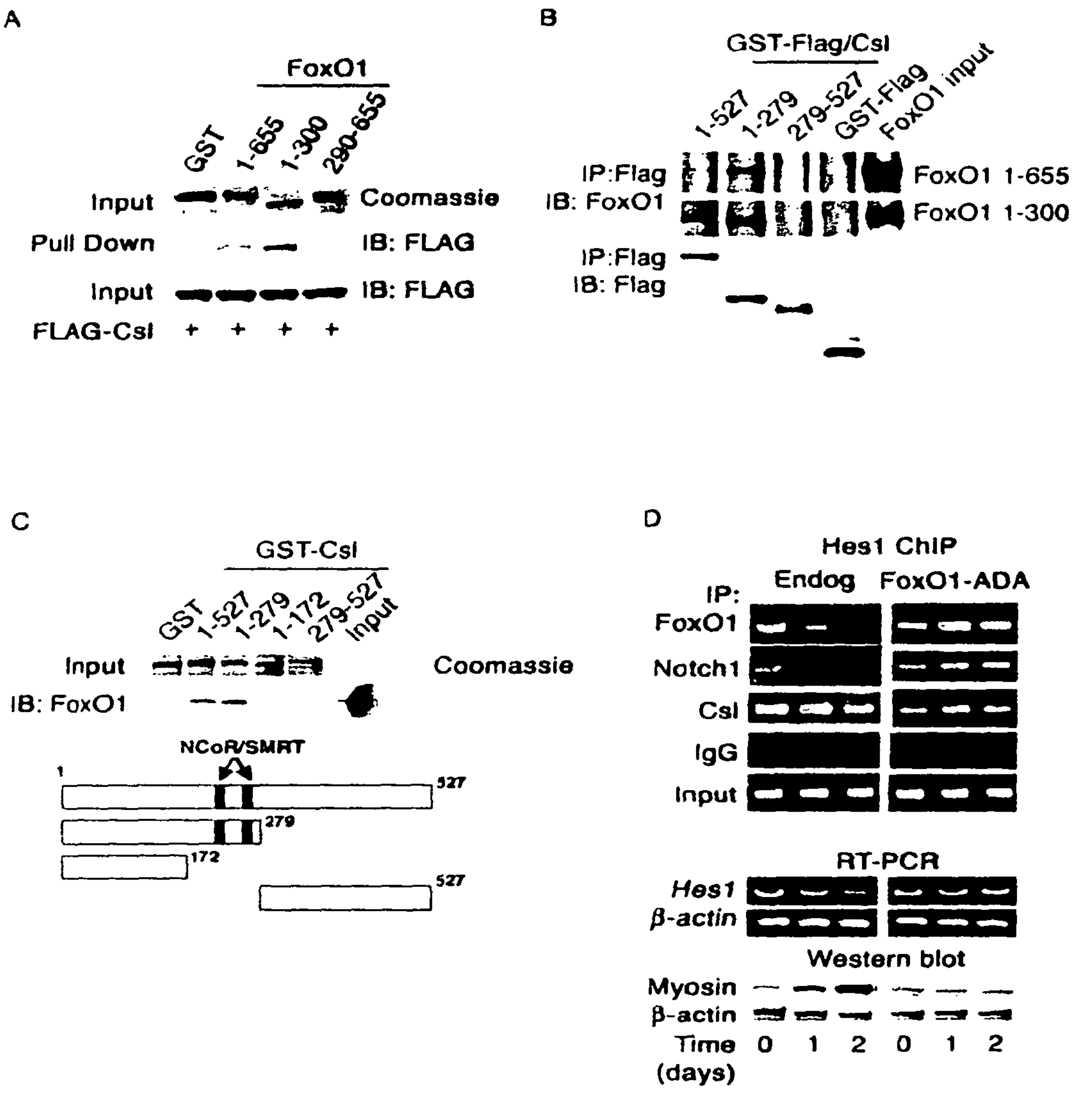
FIGS. 40A-40D These Figures show that Foxo1 binds directly to Csl.
a, GST pull-down assays of GST-Foxo1 fusion protein with Csl immunoprecipitated from HEK293 cells. b-c, Binding of GST-Foxo1 and GST-FLAG-Csl in a cell-free system and mapping of the Csl interaction domain. Full-length and truncated fragments of GST-Foxo1 and GST-FLAG/Csl were purified from bacteria and co-incubated. Thereafter, Csl was isolated using anti-FLAG antibody, and the immunoprecipitate was analyzed by immunoblotting with anti-Foxo1 or anti-FLAG antibodies. d, Hes1 promoter ChIP spanning the Csl binding site in C2C12 cells to detect endogenous Foxo1, Csl and Notch1(Endog) or following transduction with Foxo1-ADA (Foxo1-ADA) during myoblast differentiation. Input represents DNA extracted from chromatin prior to immunoprecipitation. Hes1 (semiquantitative RT-PCR) and Myosin (Western blot) expression corresponding to each time point are shown. Day 0 is defined as the time when cells are serum-deprived to induce myoblast fusion. Abbreviations: IP: immunoprecipitation; IB: immunoblotting; TCL: total cellular lysate.

To determine whether this is a direct protein-protein interaction and map the interaction domain(s), we first carried out pull-down assays with affinity-purified GST-Foxo1 produced in bacteria and FLAG-Csl expressed in HEK293 cells. We detected Csl association with full-length and N-terminal Foxo1 (amino acids 1-300), but not with C-terminal Foxo1 (aa. 290-655) or GST (FIG. 40*a*). We next mapped the Csl domain that interacts with Foxo1 using a cell-free system with GST-Foxo1 and GST-Flag/Csl purified from bacterial cultures. Again, we recovered full-length (1-655) and N-terminal (1-300), but not C-terminal (290-655) Foxo1 in Csl immunoprecipitates. Conversely, N-terminal Foxo1 interacts with N-terminal Csl (FIG. 40*b*).

We used Csl deletion mutants to map the Foxo1-binding domain in Csl. These studies indicate that Foxo1 binds to a domain encompassing amino acids 172-279 (FIG. 40*c*), which is contained within the Csl NTD domain (37) (FIG. 40*c*, diagram). Interestingly, this domain is required for DNA and corepressor binding, but does not contribute to Notch binding (38, 39).

Csl binds to a consensus sequence in the Hes1 promoter (40), which thus provides a useful readout assay of the Foxo/Csl interaction. If the latter were required to regulate C2C12 differentiation, three predictions should be met: (a) Foxo1 should be detected in chromatin immunoprecipitation assays (ChIP) spanning the Csl element in the Hes1 promoter, (b) the interaction should be differentiation-dependent and (c) inhibition of differentiation by Foxo1-ADA should be accompanied by constitutive binding to the Csl element in the Hes1 promoter. FIG. 40*d* demonstrates that all predictions are fulfilled. First, we performed ChIPs using primers spanning the Csl binding site of Hes1 in differentiating C2C12 cells. We detected endogenous Foxo1, Notch1 and Csl in immunoprecipitates from undifferentiated cells (FIG. 40*d* Endog lanes, Day 0). As the PCR-amplified sequence contains no forkhead binding sites, we conclude that Foxo1 binds to this DNA fragment via Csl. Moreover, binding of both Foxo1 and Notch1 decreased as cells became differentiated (day 1 and 2). When we transduced cells with constitutively nuclear Foxo1-ADA, differentiation was inhibited (FIG. 37*c*) and the mutant Foxo1 was persistently bound to the Hes1 promoter, as were Csl and Notch1(FIG. 40*d*, Foxo1-ADA lanes).

We next analyzed Hes1 expression. The prediction was that Hes1 levels should correlate with occupancy of the Hes1 promoter by Foxo1 and Notch1. Indeed, Hes1 mRNA expression declined as Foxo1 and Notch1 binding to Csl decreased, while Myosin protein levels increased (FIG. 40*d*). To rule out a direct effect of Foxo1 on Csl transcription, we carried out reporter gene assays with the Csl promoter. Foxo1 failed to activate expression of a Csl reporter gene, despite the presence of ten repeats of a forkhead binding site in the Csl promoter (41) (Data not shown). Moreover, Csl expression was unaffected in C2C12 cells expressing Foxo1-ADA (not shown). These data indicate that Foxo1 regulates Notch-dependent differentiation via protein/protein interactions with Csl.

Foxo1 is Required for Notch Induction of Hes and Hey Genes Via Csl

Figure 41:
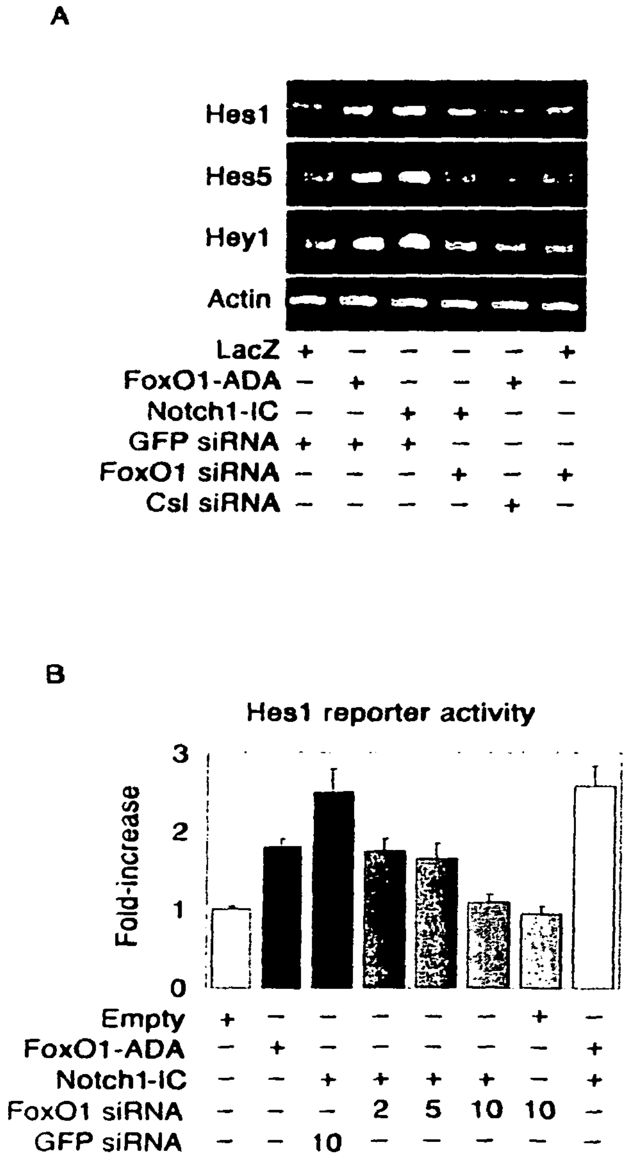
FIGS. 41A-41B These Figures show that Foxo1 regulates Notch-induced Hes1, Hes5 and Hey1 expression. a, Hes1, Hes5 and Hey1 expression measured by semiquantitative RT-PCR in C2C12 cells transduced with Foxo1-ADA or Notch1-IC following transfection of Gfp, Foxo1 or Csl siRNA as indicated. b, Hes1 reporter gene assays in HEK293 cells transduced with Foxo1-ADA, Notch1-IC, Foxo1 siRNA, GFP siRNA or control plasmid. We measured luciferase activity and normalized it by β-galactosidase activity. The data represent arbitrary units relative to control empty vector.

We examined the ability of Foxo1-ADA to promote expression of endogenous Hes1, Hes5 and Hey1 in C2C12 cells. Both Foxo1-ADA and Notch1-IC increased the expression of the three genes, while Foxo1 siRNA inhibited Hes1, Hes5 and Hey1 expression induced by Notch1-IC (FIG. 41*a*). Foxo1 siRNA had no effect on Hes1, Hes5 and Hey1 expression in growth factor-deprived cells (FIG. 41*a*).

Figure 50:
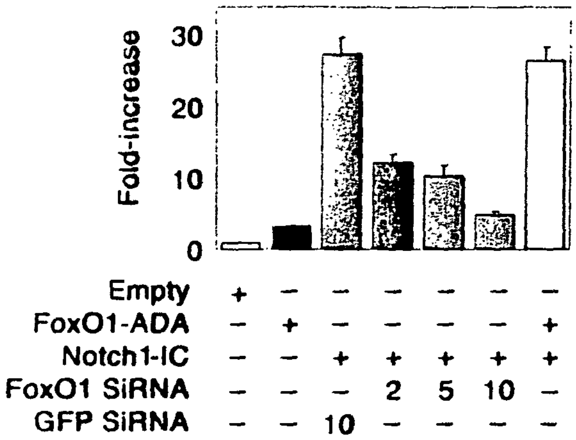
FIG. 50 This Figure shows Hes1 promoter assays. We used a synthetic Hes1 reporter gene containing four tandem repeats of the Csl binding site in promoter assays with Foxo1 and Notch1-IC in C2C12 cells.

We focused the next set of experiments on Hes1, as a prototypical Notch target gene. We tested Foxo1's ability to regulate Hes1 transcription using reporter assays with the Hes1 promoter, as well as measurements of Hes1 expression. Foxo1-ADA and Notch1-IC induced Hes1 promoter activity by 1.8- and 2.5-fold, respectively. Co-transfection of Foxo1-ADA with Notch1-IC caused a 2.5-fold increase (FIG. 41*b*). Co-transfection of Foxo1 siRNA suppressed Notch-induced Hes1 activity in a dose-dependent manner, while control siRNA had no effect (FIG. 41*b*). We obtained similar results with a synthetic Hes1 reporter containing four tandem repeats of the Csl binding motif (FIG. 50). Moreover, the DBD-Foxo1ADA was able to induce Hes1 reporter gene activity to an even greater extent than Foxo1-ADA, confirming that direct DNA binding is not required for Foxo1 activation of Hes1 (FIG. 38*c*, right panel).

Figure 51:
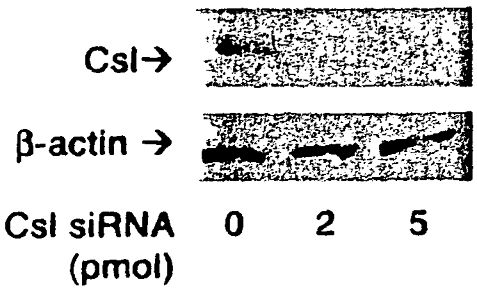
FIG. 51 This Figure shows inhibition of Csl expression by siRNA. We measured Csl levels by western blot following transfection of C2C12 cells with Csl siRNA at different concentrations.

The failure of Notch1-IC to induce Hes1 expression in cells expressing Foxo1 siRNA suggests that Foxo1 is required for Csl/Notch interaction. Thus, we investigated the binding of Foxo1 and Notch1 to the Hes1 promoter in a co-culture system. We co-cultured C2C12 cells expressing Notch1 with HEK293 cells expressing the Notch ligand Jagged1 to induce activation of endogenous Notch signaling. Co-culture in the presence of Jagged1-expressing cells increased endogenous Foxo1 (FIG. 42*a*, lanes 1-2) and Notch1 binding to the Hes1 promoter in ChIP assays (FIG. 42*a, b*, lanes 1-2) (42). These data are consistent with the observation that Foxo1 co-immunoprecipitation with Csl increased upon co-culture (FIG. 39*a*). To test whether Foxo1 binding to the Hes1 promoter is Csl-dependent, we inhibited Csl expression with siRNA (FIG. 51). Transfection of Csl siRNA inhibited both Foxo1 and Notch1 binding to Hes1 promoter (FIG. 42*a*, lanes 3-4), indicating that they are Csl-dependent. Moreover, Foxo1-ADA failed to induce Hes1 expression in the presence of Csl siRNA (FIG. 41*a*, lane 5). The results of ChIP experiments were corroborated by Hes1 promoter assays. Expression of Jagged1 or Notch1 alone had no effect on Hes1 activity, but co-culturing yielded a 3.7-fold increase in Hes1 reporter gene activity (FIG. 42*c*). Foxo1 siRNA abolished Notch binding to the Hes1 promoter in ChIP assays (FIG. 42*b*, lanes 3-4) and induction of Hes1 promoter activity (FIG. 42*c*). These results suggest that Foxo1 is required for binding of Notch1 to the Hes1 promoter, and provide a mechanism whereby inhibition of Foxo1 expression restores differentiation of myoblasts expressing Notch1-IC. The ability of Foxo1 siRNA to inhibit Notch induction of Hes1 in a co-culture system rules out the possibility that the effects observed in differentiation experiments with Notch1-IC are due to non-physiologic activation of Notch signaling by the truncated intracellular Notch1 mutant (15).

Foxo1 Promotes Corepressor Clearance and Maml1 Binding to Csl

To clarify the molecular mechanism of Foxo1-dependent activation of Hes1 expression, we investigated corepressor/coactivator exchange at the Hes1 promoter. Activation of Notch cleared the corepressors Ncor and Smrt (43) and recruited the coactivator Maml1 (42) to the Hes1 promoter. Foxo1 siRNA prevented Notch-induced corepressor exchange (FIG. 42*d*). These data are consistent with the observation that Foxo1 binds to the region 172-279 of Csl (FIG. 40*c*), which has been shown to contain the Ncor/Smrt binding sites (38, 39).

To demonstrate that the observed changes in the transcriptional complex result in changes in Hes1 activity, we investigated expression of Hes1 target genes involved in myogenesis. Hes1 has been proposed to suppress myoblast differentiation by inhibiting the bHLH transcription factor MyoD, without affecting Myf5 (16, 17). Expression analyses revealed that Notch1-IC or Foxo1-ADA suppressed MyoD, while Myf5 was unaffected. Notch decoy or Foxo1 siRNA partly restored MyoD expression (FIG. 42*e*).

Altered Fiber Type Composition in Skeletal Muscle Lacking Foxo1

Based on the cellular data, we undertook to probe Foxo1 function in muscle differentiation in vivo using conditional gene inactivation. The predicted outcome of this experiment is accelerated differentiation of MyoD-containing, but not Myf5-containing myoblasts. Because MyoD is the predominant myogenic factor in fast fibers, while Myogenin is predominant factor in slow fibers (44), the removal of Foxo/Notch inhibition on MyoD expression should result in increased formation of fast fibers, potentially at the expense of slow fibers.

Figure 43:
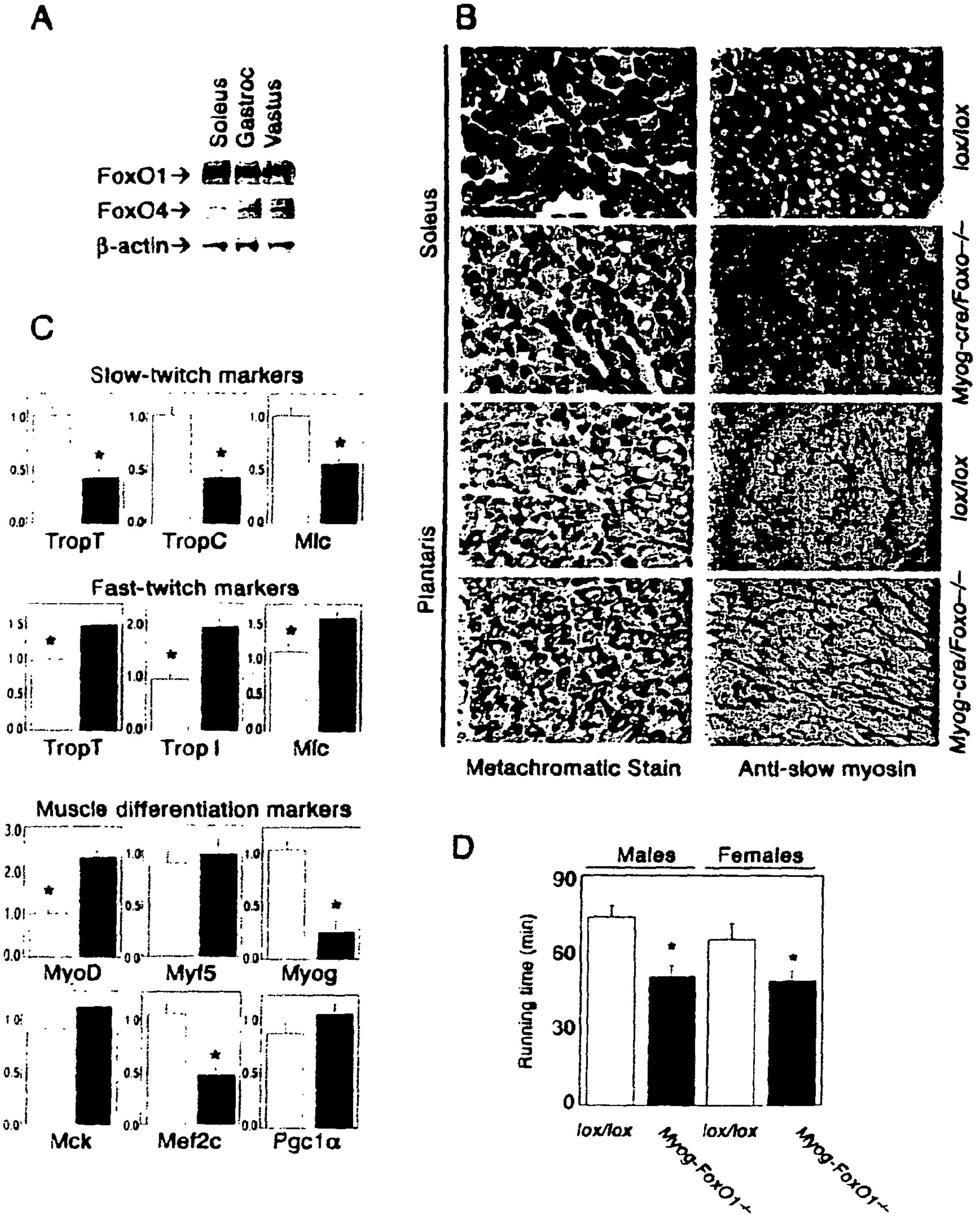
FIGS. 43A-43D These Figures show conditional ablation of Foxo1 in skeletal muscle.
a, Western blot analysis of Foxo1 and Foxo4 expression levels in various muscle types. b, Metachromatic and immunohistochemical analysis of soleus and plantaris muscle from Myog-Foxo1 mice and control (lox/lox) littermates. c, Gene expression analysis of Myog-Foxo1 (sold bars) and control mice (empty bars); TropC: troponin-C; TropT: troponin-T; Mlc: myosin light chain; Myog: Myogenin; Mck: muscle-type creatine kinase. Data are means±SEM of three independent measurements (n=6 for each genotype). An asterisk indicates P<0.05 by ANOVA. d, Treadmill performance test in 8 week-old Myog-Foxo1 mice and lox/lox littermates (n=6 for each genotype). An asterisk indicates P<0.05 by ANOVA.

There are three Foxo isoforms in mice: Foxo1, 3, and 4 (8, 9). The latter is predominant in most muscle types (45) except soleus, where Foxo1 is the most abundant (FIG. 43*a*). Coincidentally, soleus is also physiologically enriched in slow-twitch fibers, and thus allowed us to readily test our hypothesis. We inactivated Foxo1 expression in skeletal muscle by crossing mice homozygous for a floxed Foxo1 allele with Myogenin-cre transgenics. mRNA analysis indicated that the knockout occurred as planned (data not shown). Histological analyses revealed a reduction of type I (slow-twitch) fibers in soleus of Myog-Foxo1 mice, while type II fiber-enriched muscles were unaffected (FIG. 43*b*). Consistent with the histological findings, expression of type I fiber markers decreased, while type II fiber markers increased in Myog-Foxo1 mice (FIG. 43*c*). We then analyzed expression of the myogenic transcription factors MyoD, Myf5 and Myogenin. MyoD is the predominant factor in fast fibers, and Myogenin in slow fibers (44). Consistent with the histopathology, we found a twofold increase in MyoD expression and ~80% decrease in Myogenin, while Myf5 expression was unchanged (FIG. 43*c*). Moreover, expression the Foxo1 coactivator Pgc1α, which regulates type I fiber determination (30) was unchanged, indicating that the phenotype of Myog-Foxo1 mice cannot be accounted for by decreased Foxo1-dependent Pgc1α transcription (FIG. 43*c*) (46). As a functional correlate of the observed fiber type switch, we examined running performance on a treadmill. Indeed, Myog-Foxo1 mice displayed reduced running capacity, as predicted from the reduction in type I (endurance) fibers (FIG. 43*d*).

Finally, to determine whether these changes reflected developmental alterations in fiber-type specification, as opposed to adaptive or cell-nonautonomous factors, we determined MyoD expression in Foxo1 (24) and Notch1 knockout (25) embryos at E9.5. In Foxo1$^{-/-}$ embryos, MyoD levels increased 3.1±1.1 fold, and in Notch1$^{-/-}$ embryos 7.3±2.9 fold compared to controls (P<0.05 in both mutants vs. wild-type, n=4). The increase in MyoD expression observed in vivo is consistent with the physical and functional interactions between Foxo1 and Notch at this key signaling nexus in myoblast differentiation. Thus, we propose that the fiber-type switch in Myog-Foxo1 mice is the result of accelerated differentiation of MyoD-containing myoblasts during embryonic development.

Discussion

This study provides biochemical, cellular and genetic evidence that Foxo and Notch pathways cooperate in the regulation of muscle differentiation. The data reveal a novel mode of Foxo1 action to promote corepressor exchange at the Hes1 promoter via direct binding to the Csl NTD region (FIG. 42*f*). We propose that Foxo1 binding to this domain stabilizes the Notch/Csl complex and promotes corepressor clearance and Maml1 recruitment, consistent with the proposed role of NTD from structural studies (37). The findings also provide a mechanism by which two major biochemical pathways, the phosphoinositol-3-kinase/Akt pathway and the Notch/Hes pathway, converge in a synergistic manner to control cellular differentiation in vivo.

The proposed role for Foxo1 is independent of its transcriptional function, and involves a direct interaction with Csl. While our studies have focused on Hes-1 as a prototypical effector of Notch1 signaling, our data should not be construed to indicate that Hes-1 is the sole mediator of the Notch/Foxo interaction. For example, we have observed a similar Foxo/Notch epistasis in the differentiation of pre-adipocytes, PC-12, and HUVECs, suggesting that Foxo interacts with Notch in multiple cell contexts (data not shown). We propose that Notch/Foxo cooperation integrates environmental cues through Notch with metabolic cues through Foxo1 to regulate progenitor cell maintenance and differentiation. This twotiered mechanism allows committed progenitor cells in various tissues to avoid differentiation in response to developmental cues (Notch) when Foxo1 is active, i.e., in the absence of growth factors. These cells would then persist in a dormant state in adult tissues, where they can terminally differentiate in response to a combination of Notch ligand and hormonal/nutritional cues leading to Foxo1 inhibition. This interpretation is consistent with the fiber-type switch observed in Foxo1-deficient muscle, an observation that appears to position Foxo1 as a fate decider within the myogenic lineage, as opposed to an inducer of the myogenic program. It remains to be seen whether other Foxo and Notch isoforms also interact and how they contribute to this process.

The demonstration that Foxo1 is a coregulator of gene expression provides a potential explanation for the protean functions of this transcription factor. An interesting question emerging from our studies is how the switch from one function to the other is effected, and how the complex post-translational modifications of Foxo1 in response to growth factors, hormones and nutrients impinge on this process. The findings have broad implications for the pathophysiology of disease processes that involve Foxo1 signaling. A potential implication of our observation is the ability to explore the use of agents that inhibit Notch signaling (47) as a treatment of metabolic disorders characterized by excessive Foxo function (48).

Materials and Methods

Animal Generation and Analysis

Myogenin-cre (49) and Foxo1$^{flox}$ mice have been described (9). The wild-type, null and Foxo1$^{flox}$ alleles were detected using PCR with primers 5'-GCT TAG AGC AGA GAT GTT CTC ACA TT-3', 5'-CCA GAG TCT TTG TAT CAG GCA AAT AA-3' and 5'-CAA GTC CAT TAA TTC AGC ACA TTG A-3'. Prior to the treadmill performance test, mice were trained for 2 days (Columbus Instruments). The test was performed at 15 m/min for the first 30 min, followed by 1 m/min increases at 10 min intervals until exhaustion. Skeletal muscle samples were quickly frozen in OCT matrix, and 7 μm serial sections were obtained. Muscle fibers were typed using metachromatic ATPase (50) or immunostaining with anti-skeletal slow myosin (Sigma). For embryonic studies, we set up timed matings of heterozygous Foxo1 (24) or Notch1(25) mice and recovered embryos at E9.5. mRNA was isolated from whole embryos and real-time RT-PCR was performed as described below.

Viral Expression Studies

C2C12 cells were differentiated as described (3, 4). Foxo1-ADA, Notch1-IC, Jagged1, Csl and Notch decoy adenoviral and mammalian expression vectors have been described (36, 51). We generated retroviruses expressing Foxo1-ADA and Notch1-IC using the pQCXIH vector. To generate Notch decoy (pAdlox Notch1ECD-Fc), the extracellular domain of Notch1(bp 241-4229, GenBank accession# X57405) was fused in frame with human IgG Fc tag and cloned into pAdlox. Retroviral supernatant was produced from cells transiently co-transfected with pVSV-G vector and designated pQCXIH vector into GP2-293 cells (BD Bioscience). To generate the DNA binding-deficient Foxo1, we replaced N208 and H212 with alanine and arginine, respectively, using QuikChange Mutagenesis Kit (Stratagene). The mutations were then cloned in the backbone of the Foxo1-ADA mutant.

Luciferase Assay and Co-Culture Assay

We transfected HEK293 cells with Hes1-luciferase (−194 to 160 from transcription start site) (Hes1/pGL2 basic), Synthetic Hes1-luciferase (containing a 4× Csl binding site, 4× Csl/pGL2 basic) or Csl-luciferase (−1536 to 22, Csl/pGL2 basic) reporter genes along with pCMV5, pCMV5-Foxo1-ADA, pQNC-Notch1-IC, pHyTc Notch decoy or Foxo1 siRNA. We used plasmid pRSV-β-galactosidase as a control of transfection efficiency (51). For co-culture assay, we expressed Notch1 in C2C12 cells and Jagged1 or LacZ in HEK293 cells by transfection. We then harvested HEK293 cells and seeded them on C2C12 cells. After 1 hr incubation, we used the co-cultured cells for experiments.

Western Blotting and Immunoprecipitation

We performed these assays according to standard techniques using anti-Myosin (MF-20), anti-HA (12CA5, Boehringer Mannheim), anti-FLAG (M2, Sigma), anti-Foxo1 (H128 and N20, Santa Cruz), anti-Notch1 (C-20, Santa-Cruz), anti-Csl (Chemicon and Santa-Cruz), anti-NcoR (Santa-Cruz), anti-SMRT (Santa-Cruz) or anti-MAML1 (Chemicon) antibodies. For Foxo/Csl co-immunoprecipitation, we used purified nuclear fractions (52). Because Csl migrates close to IgG heavy chain on SDS-PAGE, we used dimethylpyrimilidate (DMP from Pierce) to cross-link antibodies to Protein A beads and avoid IgG contamination of eluted protein complexes (52).

Chromatin Immunoprecipitation Assays

We performed ChIP assay in C2C12 cells as described previously (4) and in co-cultured cells as described by Fryer (42). The primer pairs employed to amplify the Csl binding site of the Hes1 promoter are: 5'-GCAAAGCCCAGAGGAAAGAGTTAG-3' and 5'-AGGAGAGAGGTAGACAGGGGATTC-3'.

siRNA Transfection and siRNA-Resistant Foxo1

The Foxo1-specific siRNA sequence is 5'-ACGGAGGATTGAACCAGTATA-3'. The Csl specific siRNA sequence is 5'-TAGGGAAGCTATGCGAAATTA-3'. siRNA was transfected using lipofectamine-plus reagent (Invitrogen). We generated siRNA-resistant Foxo1 by replacing three residues (underlined) in the sequence 5'-ACGGCGG TCTGAACCAGTATA-3'. Primer sequences employed for real-time RT-PCR studies are available on request.

Recombinant Proteins and Interaction Assays

We generated GST-FLAG-Csl encompassing amino acids 1-527, 1-279, 1-172 and 279-527 fragments by cloning into pGEX6P-1. GST-Foxo1 constructs have been described (53). Following bacterial culture and IPTG induction, we purified GST fusion proteins and incubated them together. Thereafter, we isolated GST-FLAG/Csl by immunoprecipitation with anti-FLAG antibody, washed the immune pellets extensively and performed immunoblot with anti-Foxo1 antiserum.

REFERENCES FOR SIXTH SERIES OF EXPERIMENTS

1. Singec, I., Jandial, R., Crain, A., Nikkhah, G., and Snyder, E. Y. 2007. The leading edge of stem cell therapeutics. *Annu Rev Med* 58:313-328.
2. Accili, D., and Arden, K. C. 2004. FoxOs at the Crossroads of Cellular Metabolism, Differentiation, and Transformation. *Cell* 117:421-426.
3. Hribal, M. L., Nakae, J., Kitamura, T., Shutter, J. R., and Accili, D. 2003. Regulation of insulin-like growth factor-dependent myoblast differentiation by Foxo forkhead transcription factors. *J Cell Biol* 162:535-541.
4. Nakae, J., Kitamura, T., Kitamura, Y., Biggs, W. H., Arden, K. C., and Accili, D. 2003. The forkhead transcription factor foxo1 regulates adipocyte differentiation. *Dev Cell* 4:119-129.
5. Potente, M., Urbich, C., Sasaki, K. I., Hofmann, W. K., Heeschen, C., Aicher, A., Kollipara, R., Depinho, R. A., Zeiher, A. M., and Dimmeler, S. 2005. Involvement of Foxo transcription factors in angiogenesis and postnatal neovascularization. *J Clin Invest* 115:2382-2392.
6. Liu, Z. P., Wang, Z., Yanagisawa, H., and Olson, E. N. 2005. Phenotypic modulation of smooth muscle cells through interaction of Foxo4 and myocardin. *Dev Cell* 9:261-270.
7. Castrillon, D. H., Miao, L., Kollipara, R., Horner, J. W., and DePinho, R. A. 2003. Suppression of ovarian follicle activation in mice by the transcription factor Foxo3a. *Science* 301:215-218.
8. Tothova, Z., Kollipara, R., Huntly, B. J., Lee, B. H., Castrillon, D. H., Cullen, D. E., McDowell, E. P., Lazo-Kallanian, S., Williams, I. R., Sears, C., et al. 2007. FoxOs Are Critical Mediators of Hematopoietic Stem Cell Resistance to Physiologic Oxidative Stress. *Cell* 128:325-339.
9. Paik, J. H., Kollipara, R., Chu, G., Ji, H., Xiao, Y., Ding, Z., Miao, L., Tothova, Z., Horner, J. W., Carrasco, D. R., et al. 2007. FoxOs Are Lineage-Restricted Redundant Tumor Suppressors and Regulate Endothelial Cell Homeostasis. *Cell* 128:309-323.
10. Shawber, C. J., and Kitajewski, J. 2004. Notch function in the vasculature: insights from zebrafish, mouse and man. *Bioessays* 26:225-234.
11. Lai, E. C. 2002. Keeping a good pathway down: transcriptional repression of Notch pathway target genes by CSL proteins. *EMBO Rep* 3:840-845.
12. Jensen, J., Pedersen, E. E., Galante, P., Hald, J., Heller, R. S., Ishibashi, M., Kageyama, R., Guillemot, F., Serup, P., and Madsen, O. D. 2000. Control of endodermal endocrine development by Hes-1. *Nat Genet* 24:36-44.
13. Ross, D. A., Rao, P. K., and Kadesch, T. 2004. Dual roles for the Notch target gene Hes-1 in the differentiation of 3T3-L1 preadipocytes. *Mol Cell Biol* 24:3505-3513.
14. Ohtsuka, T., Ishibashi, M., Gradwohl, G., Nakanishi, S., Guillemot, F., and Kageyama, R. 1999. Hes1 and Hes5 as notch effectors in mammalian neuronal differentiation. *Embo J* 18:2196-2207.
15. Shawber, C., Nofziger, D., Hsieh, J. J., Lindsell, C., Bogler, O., Hayward, D., and Weinmaster, G. 1996. Notch signaling inhibits muscle cell differentiation through a CBF1-independent pathway. *Development* 122:3765-3773.
16. Sasai, Y., Kageyama, R., Tagawa, Y., Shigemoto, R., and Nakanishi, S. 1992. Two mammalian helix-loop-helix factors structurally related to *Drosophila* hairy and Enhancer of split. *Genes Dev* 6:2620-2634.
17. Kuroda, K., Tani, S., Tamura, K., Minoguchi, S., Kurooka, H., and Honjo, T. 1999. Delta-induced Notch signaling mediated by RBP-J inhibits MyoD expression and myogenesis. *J Biol Chem* 274:7238-7244.
18. Nofziger, D., Miyamoto, A., Lyons, K. M., and Weinmaster, G. 1999. Notch signaling imposes two distinct blocks in the differentiation of C2C12 myoblasts. *Development* 126:1689-1702.
19. Wilson-Rawls, J., Molkentin, J. D., Black, B. L., and Olson, E. N. 1999. Activated notch inhibits myogenic activity of the MADS-Box transcription factor myocyte enhancer factor 2C. *Mol Cell Biol* 19:2853-2862.
20. Hirsinger, E., Malapert, P., Dubrulle, J., Delfini, M. C., Duprez, D., Henrique, D., Ish-Horowicz, D., and Pourquie, O. 2001. Notch signalling acts in postmitotic avian myogenic cells to control MyoD activation. *Development* 128:107-116.
21. Conboy, I. M., and Rando, T. A. 2002. The regulation of Notch signaling controls satellite cell activation and cell fate determination in postnatal myogenesis. *Dev Cell* 3:397-409.
22. Shawber, C. J., Das, I., Francisco, E., and Kitajewski, J. 2003. Notch signaling in primary endothelial cells. *Ann N Y Acad Sci* 995:162-170.
23. Limbourg, F. P., Takeshita, K., Radtke, F., Bronson, R. T., Chin, M. T., and Liao, J. K. 2005. Essential role of endothelial Notch1 in angiogenesis. *Circulation* 111:1826-1832.
24. Hosaka, T., Biggs, W. H., 3rd, Tieu, D., Boyer, A. D., Varki, N. M., Cavenee, W. K., and Arden, K. C. 2004. Disruption of forkhead transcription factor (FOXO) family members in mice reveals their functional diversification. *Proc Natl Acad Sci USA* 101:2975-2980.
25. Krebs, L. T., Xue, Y., Norton, C. R., Shutter, J. R., Maguire, M., Sundberg, J. P., Gallahan, D., Closson, V., Kitajewski, J., Callahan, R., et al. 2000. Notch signaling is essential for vascular morphogenesis in mice. *Genes Dev* 14:1343-1352.
26. McKinsey, T. A., Zhang, C. L., and Olson, E. N. 2001. Control of muscle development by dueling HATs and HDACs. *Curr Opin Genet Dev* 11:497-504.
27. Rudnicki, M. A., and Jaenisch, R. 1995. The MyoD family of transcription factors and skeletal myogenesis. *Bioessays* 17:203-209.
28. Bassel-Duby, R., and Olson, E. N. 2006. Signaling pathways in skeletal muscle remodeling. *Annu Rev Biochem* 75:19-37.
29. Schiaffino, S., and Reggiani, C. 1996. Molecular diversity of myofibrillar proteins: gene regulation and functional significance. *Physiol Rev* 76:371-423.
30. Lin, J., Wu, H., Tarr, P. T., Zhang, C. Y., Wu, Z., Boss, O., Michael, L. F., Puigserver, P., Isotani, E., Olson, E. N., et al. 2002. Transcriptional co-activator PGC-1 alpha drives the formation of slow-twitch muscle fibres. *Nature* 418:797-801.
31. Lagouge, M., Argmann, C., Gerhart-Hines, Z., Meziane, H., Lerin, C., Daussin, F., Messadeq, N., Milne, J., Lambert, P., Elliott, P., et al. 2006. Resveratrol improves mitochondrial function and protects against metabolic disease by activating SIRT1 and PGC-1alpha. *Cell* 127:1109-1122.
32. Nickoloff, B. J., Osborne, B. A., and Miele, L. 2003. Notch signaling as a therapeutic target in cancer: a new approach to the development of cell fate modifying agents. *Oncogene* 22:6598-6608.
33. Nickoloff, B. J., Qin, J. Z., Chaturvedi, V., Denning, M. F., Bonish, B., and Miele, L. 2002. Jagged-1 mediated activation of notch signaling induces complete maturation of human keratinocytes through NF-kappaB and PPAR-gamma. *Cell Death Differ* 9:842-855.
34. Pan, Y., Lin, M. H., Tian, X., Cheng, H. T., Gridley, T., Shen, J., and Kopan, R. 2004. gamma-secretase functions through Notch signaling to maintain skin appendages but is not required for their patterning or initial morphogenesis. *Dev Cell* 7:731-743.
35. Dowell, P., Otto, T. C., Adi, S., and Lane, M. D. 2003. Convergence of peroxisome proliferator-activated receptor gamma and Foxo1 signaling pathways. *J Biol Chem* 278:45485-45491.
36. Nakae, J., Kitamura, T., Silver, D. L., and Accili, D. 2001. The forkhead transcription factor Foxo1 (Fkhr) confers insulin sensitivity onto glucose-6-phosphatase expression. *J Clin Invest* 108:1359-1367.
37. Kovall, R. A., and Hendrickson, W. A. 2004. Crystal structure of the nuclear effector of Notch signaling, CSL, bound to DNA. *Embo J* 23:3441-3451.

38. Hsieh, J. J., and Hayward, S. D. 1995. Masking of the CBF1/RBPJ kappa transcriptional repression domain by Epstein-Barr virus EBNA2. *Science* 268:560-563.

39. Kao, H. Y., Ordentlich, P., Koyano-Nakagawa, N., Tang, Z., Downes, M., Kintner, C. R., Evans, R. M., and Kadesch, T. 1998. A histone deacetylase corepressor complex regulates the Notch signal transduction pathway. *Genes Dev* 12:2269-2277.

40. Tun, T., Hamaguchi, Y., Matsunami, N., Furukawa, T., Honjo, T., and Kawaichi, M. 1994. Recognition sequence of a highly conserved DNA binding protein RBP-J kappa. *Nucleic Acids Res* 22:965-971.

41. Kawaichi, M., Oka, C., Shibayama, S., Koromilas, A. E., Matsunami, N., Hamaguchi, Y., and Honjo, T. 1992. Genomic organization of mouse J kappa recombination signal binding protein (RBP-J kappa) gene. *J Biol Chem* 267:4016-4022.

42. Fryer, C. J., White, J. B., and Jones, K. A. 2004. Mastermind recruits CycC:CDK8 to phosphorylate the Notch ICD and coordinate activation with turnover. *Mol Cell* 16:509-520.

43. Liang, Y., Chang, J., Lynch, S. J., Lukac, D. M., and Ganem, D. 2002. The lytic switch protein of KSHV activates gene expression via functional interaction with RBP-Jkappa (CSL), the target of the Notch signaling pathway. *Genes Dev* 16:1977-1989.

44. Hughes, S. M., Taylor, J. M., Tapscott, S. J., Gurley, C. M., Carter, W. J., and Peterson, C. A. 1993. Selective accumulation of MyoD and myogenin mRNAs in fast and slow adult skeletal muscle is controlled by innervation and hormones. *Development* 118:1137-1147.

45. Kitamura, T., Nakae, J., Kitamura, Y., Kido, Y., Biggs, W. H., 3rd, Wright, C. V., White, M. F., Arden, K. C., and Accili, D. 2002. The forkhead transcription factor Foxo1 links insulin signaling to Pdx1 regulation of pancreatic beta cell growth. *J Clin Invest* 110:1839-1847.

46. Daitoku, H., Yamagata, K., Matsuzaki, H., Hatta, M., and Fukamizu, A. 2003. Regulation of PGC-1 promoter activity by protein kinase B and the forkhead transcription factor FKHR. *Diabetes* 52:642-649.

47. Miele, L., Miao, H., and Nickoloff, B. J. 2006. NOTCH signaling as a novel cancer therapeutic target. *Curr Cancer Drug Targets* 6:313-323.

48. Accili, D. 2004. Lilly lecture 2003: the struggle for mastery in insulin action: from triumvirate to republic. *Diabetes* 53:1633-1642.

49. Knapp, J. R., Davie, J. K., Myer, A., Meadows, E., Olson, E. N., and Klein, W. H. 2006. Loss of myogenin in postnatal life leads to normal skeletal muscle but reduced body size. *Development* 133:601-610.

50. Ogilvie, R. W., and Feeback, D. L. 1990. A metachromatic dye-ATPase method for the simultaneous identification of skeletal muscle fiber types I, IIA, IIB and IIC. *Stain Technol* 65:231-241.

51. Das, I., Craig, C., Funahashi, Y., Jung, K. M., Kim, T. W., Byers, R., Weng, A. P., Kutok, J. L., Aster, J. C., and Kitajewski, J. 2004. Notch oncoproteins depend on gamma-secretase/presenilin activity for processing and function. *J Biol Chem* 279:30771-30780.

52. Chi, T., Yan, Z., Xue, Y., and Wang, W. 2004. Purification and functional analysis of the mammalian SWI/SNF-family of chromatin-remodeling complexes. *Methods Enzymol* 377:299-316.

53. Puigserver, P., Rhee, J., Donovan, J., Walkey, C. J., Yoon, J. C., Oriente, F., Kitamura, Y., Altomonte, J., Dong, H., Accili, D., et al. 2003. Insulin-regulated hepatic gluconeogenesis through FOXO1-PGC-1alpha interaction. *Nature* 423:550-555.

SEVENTH SERIES OF EXPERIMENTS

Diabetic patients often develop obesity and vascular pathologies. The molecular mechanisms that contribute to diabetic complications remain to be elucidated. In the past two years, I have been evaluating Notch4 knockout mice for postnatal defects. These analyses revealed that Notch4 mutant mice develop hallmarks of diabetes: 1) early onset obesity as seen by a dramatic increase in subcutaneous fat, and 2) reduced pericyte content in retinal vasculature reminiscent of diabetic retinopathy. We have found that Notch and Foxo1, a transcriptional regulator of insulin signaling, cooperate to regulate adipogenesis and angiogenesis. Mice deficient for Notch1, Notch1/Notch4, or Foxo1 die in utero with angiogenic defects. These data lead us to hypothesize that dysregulated Notch signaling contributes to diabetic obesity and vasculopathologies. The proposal objective is to examine this hypothesis and define the roles of Notch and insulin signaling interactions in adipogenesis and angiogenesis. Mouse models will be used to alter Notch, Foxo1, and insulin receptor activity via genetic manipulation. Adipogenesis and metabolic dysfunction will be evaluated in Notch4 and insulin receptor knockout mice and embryonic fibroblasts derived from these mice. Embryonic and retinal angiogenesis will be evaluated in mice haploinsufficient for Notch1, Notch4 and/or Foxo1. Finally, the function of Notch and Foxo1 signaling in proliferative retinopathy will be evaluated in a hypoxia-driven retinal angiogenesis mouse model. My career goals are to become an independent scientific investigator in the field of diabetic research.

Evaluation of Notch Function in Metabolism.

We have found that Notch and Foxo1, a transcriptional regulator of Insulin signaling, form a transcriptional complex with CSL to regulate cell fate decision. Loss of one allele of Foxo1 rescues hyperglycemia and hyperinsulinemia in insulin receptor haploinsufficient mice. Similarly, loss of Notch4 in mice correlated with lower blood glucose levels as compared to wildtype littermates. Foxo1 and Notch4 share an overlapping expression pattern in the β-cells of the adult murine pancreas, while Notch1 is expressed in both the α- and β-cells. In this aim, we will further characterize the metabolism of Notch mutant mice. We will also determine if defects are present in the pancreases of Notch and Notch/Foxo1 mutant mice.

Evaluation of Notch4 Function in Adipogenesis.

We have found that Notch4 knockout mice have larger adipose tissue depots. In the skin, Notch4 is expressed in both the adipocytes and vessels. Notch4 may regulate adipogenesis by either a cell autonomous or cell nonautonomous mechanism. In the cell autonomous model, Notch functions in the adipocyte to regulate differentiation from committed preadipocytes in the stromavascular fraction. Alternatively, Notch may regulate angiogenesis within adipose tissue, which then affects adipogenesis. We have established that Notch and Foxo1, cooperate to inhibit hormone-induced adipogenesis of cultured fibroblasts. In insulin receptor mutant mice, adipogenesis was perturbed and differentiation was partially rescued by inhibiting Foxo1. However, it is unknown whether abnormalities of Notch function can affect insulin-dependent adipocyte differentiation and function in vivo. To begin to address this question, we will further characterize the adipose phenotype in Notch mutant mice with a focus on the subcutaneous and visceral adipose depots. We will then determine if Notch4 insufficiency rescues the subcutaneous adipose phenotype in Insr mutant mice. Finally, we will evaluate Notch function in adipocyte differentiation of embryonic fibroblasts derived from Notch4 and Insr deficient mice. Our goal is to determine the role of Notch and Insulin signaling interactions in adipocyte differentiation.

Diabetes and Obesity

Obesity is a primary risk factor for insulin resistance, hyperglycemia and the development of type 2 diabetes {Eckel, 2005 #769}. It is also associated with cardiovascular dysfunction. Adipose tissue has an important metabolic function in storing triacylglycerol in times of energy excess and releasing free fatty acids and glycerol in times of energy deprivation. In addition, adipocytes regulate metabolic homeostasis by producing a number of bioactive substances, termed adipokines. Adipokines consist of hormone cytokines, growth factors, and other bioactive compounds. Theses include leptin, tumor necrosis factor alpha, angiotensin II, interleukin-6, interleukin-1, adiponectin, resistin, and prostaglandins. These secreted factors play a major role in regulating both metabolic and vascular biology and as such have been proposed to be the connection between insulin resistance and cardiovascular disease.

The development of obesity appears to be regulated by insulin signaling and dependent on angiogenesis. In adipocytes, insulin signaling induces Vascular Endothelial Growth Factor (VEGF) {Mick, 2002 #767}. VEGF is a potent inducer of angiogenesis that can promote endothelial cell proliferation, migration, and differentiation as well as vessel wall leakiness {Yancopoulos, 2000 #65}. In mouse models of obesity, antagonists of VEGF disrupt not only angiogenesis, but prevent adipogenesis {Rupnick, 2002 #766; Fukumura, 2003 #768}. Thus in adipose tissue, there is a reciprocal paracrine regulation of adipocyte differentiation and angiogenesis.

Notch Function in Adipogenesis

A role for Notch in adipocyte differentiation is just beginning to be elucidated. Using in vitro assays, Notch signaling has been shown to both promote and inhibit hormone-induced adipogenesis of fibroblasts. In stromal cell lines, Notch perturbed osteoblast differentiation that then led to an increase in adipocyte differentiation {Sciaudone, 2003 #772}. In contrast, both ligand-mediated Notch signaling, or ectopic expression of a constitutively active Notch1 inhibited adipogenesis of 3T3-L1 fibroblasts {Garces, 1997 #177; Ross, 2004 #773}. Similarly, overexpression of the Notch target gene, HES1 inhibited adipocyte differentiation of fibroblasts {Ross, 2004 #773}. Disrupting HES1 expression with siRNA also blocked fibroblast adipocyte differentiation. Thus, both inhibition and activation of Notch perturbs adipogenesis suggesting adipogenesis is dosage sensitive to Notch signaling.

Notch-mediated inhibition of fibroblast adipogenesis correlated with loss of the adipocyte-specific genes C/EBPα and PPARγ. Adipocyte differentiation of fibroblasts in which Notch signaling was activated was rescued by the expression either C/EBPα or PPARγ□, suggesting that Notch inhibits adipogenesis by suppressing the expression of these two genes. Consistent with the fibroblast data, retinoic acid induced adipogenesis was slightly enhanced in Notch1 knockout embryoid bodies {Nichols, 2004 #770}. Finally, Notch1 expression was found to be reduced in adipose tissues isolated from insulin-resistant patients relative to insulin-sensitive subjects suggesting a role for Notch in diabetes related adipocyte differentiation {Yang, 2003 #777}.

Vascular Complications in Diabetes

Diabetic patients display multiple vascular complications, including arterial hypertension, strokes, ischemia, retinopathy, atherosclerosis and heart attacks. However, little is known as to the molecular mechanisms contributing to diabetic vascular complications. Blindness is one of such complications that has a vascular origin but is poorly understood. Within 20 years of diagnosis, a quarter of diabetics develop proliferative retinopathy leading to blindness. Diabetic retinopathy initiates with an increase in vascular permeability, thickening of the basement membrane, and loss of pericytes in the retinal microvasculature followed by a proliferative phase of neovascularization {Cukiernik, 2004 #749}. Vascular growth factor (VEGF) has been implicated in the development of diabetic proliferative retinopathy. VEGF signaling can promote endothelial cell proliferation, migration, differentiation and vessel wall leakiness {Yancopoulos, 2000 #65}. In mouse models of type I and type II diabetes, the hypoxia sensing transcription factor, HIF-1α, and VEGF are found to be increased within the eyes {Kondo, 2004 #744} suggesting that hypoxia is an initiating event in the development of diabetic retinopathy. The induction of VEGF is likely mediated by HIF-1α, as VEGF is a direct transcriptional target of HIF-1α {Yancopoulos, 2000 #65}. Supporting the role for VEGF in diabetic retinopathy, ectopic expression of VEGF in primate eyes leads to rapid development of proliferative retinopathy and macular edema {Lebherz, 2005 #748}. In a diabetic rat model, subcutaneous injection of the VEGF receptor signaling inhibitor SU5416 suppresses VEGF induced retinal microvascular permeability and vasoconstriction {Cukiernik, 2004 #749}. Finally, an intravitreal injection of an inhibitor of all three VEGFRs, PTK/ZK, reduces retinal neovascularization in a hypoxic mouse model {Maier, 2005 #750}. Thus, dysregulation of VEGF signaling plays a critical role in the development of proliferative retinopathy and may also contribute to other diabetic vascular complications.

Evaluation of Notch Function in Metabolism.

We have found that Notch and Foxo1, a transcriptional regulator of Insulin signaling, form a transcriptional complex with CSL to regulate cell fate decisions. Loss of one allele of Foxo1 rescues hyperglycemia and hyperinsulinemia in insulin signaling deficient mice (Nakae 2002 ng). In mice, loss of N4 correlated with a significant decrease in blood glucose levels compare to wildtype littermates. Like Foxo1, Notch4 may oppose insulin signaling in regulating the metabolism. Circulating glucose and insulin levels are regulated by both the glucose producing tissues, such as liver and the insulin producing islet β-cells of the pancreas. Increased Foxo1 signaling in the β-cells of Foxo1 transgenic leads to □-cell failure and the development of diabetes (Nakea 2002 ng). Foxo1 and Notch4 share an overlapping expression pattern in the β-cells of the adult murine pancreata, while Notch1 is expressed in both the α- and β-cells. Thus, Notch4 and/or Notch1 may have a function in the endocrine cells of the pancreatic islets. In this aim, we will further characterize the metabolism and pancreata of Notch mutant mice. Notch mutant mice will be crossed with L2 Ttr-Insr$^{-/-}$ mice (FIG. 21), and used to determine if N4 and/or N1 insufficiency suppresses the diabetic and pancreatic defects observed in this Insr deficient background.

Evaluation of Notch Function in Adipogenesis.

We have found that N4 knockout mice have dermal adipose hypertrophy. This adipose tissue phenotype in N4 mutant mice may arise from a cell autonomous defect in the adipocytes or from a non-cell autonomous angiogenic defect. In contrast to N4 nullizygous mice, Insr deficient mice display adipose tissue hypotrophy {Cinti, 1998 #774; Kitamura, 2004 #745} (Okamoto JCI 2004). Ectopic expression of dominant negative Foxo1 restores adipogenesis of $Insr^{-/-}$ embryonic fibroblasts {Nakae, 2003 #765}. We found that Notch and Foxo1 cooperate to inhibit hormone-induced adipogenesis of fibroblasts. Since Foxo1 functions in epistasis with insulin signaling (FIG. 3), Notch may also have an opposing function to insulin signaling in adipogenesis. Consistent with adipose cell autonomous function for Notch4, Notch4 is expressed within the subcutaneous adipocytes. Thus, we will evaluate Notch function adipogenesis of embryonic fibroblasts derived from Notch and Notch; Insr deficient mice. We will further characterize the subcutaneous fat defect and evaluate the visceral fat depot in Notch mutant mice. Finally, we will determine if Notch4 insufficiency rescues the dermal adipose tissue defect in Insr mutant mice.

In mouse models of obesity, antagonists of VEGF block both angiogenesis and adipogenesis {Rupnick, 2002 #766; Fukumura, 2003 #768}, indicating that there is reciprocal regulation of adipogenesis and angiogenesis. Since N4 nullizygous mice also display defects in retinal angiogenesis, the observed increase in subcutaneous adipose tissue may arise from endothelial cell dysfunction. Therefore, we will also determine if there are differences in the adipose tissue vasculature of Notch mutant mice.

EIGHTH SERIES OF EXPERIMENTS

Rat Notch1 Decoy Present in Murine Serum

The stability of rat Notch1 decoy formulation in the mammalian blood stream was tested. As shown in FIG. 118, Notch decoys are stable in the mammalian circulatory system.

Nude mice were injected with control adenovirus or adenovirus expressing rat Notch1 decoy (rN1 decoy). 2 weeks after injection, serum was collected and 4 microliters were evaluated by Western blot analysis. This analysis demonstrates that the full-length rat Notch1 decoy protein (see arrow in FIG. 118) can be expressed in mice and is present at detectable levels with little evidence of degradation.

NINTH SERIES OF EXPERIMENTS

Human Notch1 Decoy (h-Notch (1-36) Decoy) and Rat Notch 1 Decoy Block Mouse Mammary Tumor Growth The activity of the human Notch1 decoy and the Rat Notch 1 decoy was compared against the growth of the mammary tumor cell line, Mm5MT-FGF4. As shown in FIG. 119, both hNotch1 decoy and rNaotch1 decoy reduce the growth rate of Mm5Mt-FGF4.

We developed a tumor model which utilized Mm5MT-FGF4 cells grown in nude mice. In this experiment, $2\times10^5$ Mm5MT-FGF4 cells were implanted into nude mice and four days later adenovirus encoding Fc control, rat Notch1 decoy or human Notch1 decoy was injected into ocular vein. Notch decoys are produced by adenovirus infected liver of mice and secreted into the bloodstream (example in FIG. 118). The growth curve presented in FIG. 119 demonstrates that either Rat Notch1 decoy or human Notch1 decoy reduced the growth of tumor xenografts in nude mice.

Rat Notch1 Decoy Inhibits SKNEP1 Metastasis to Lung Tissue

Notch1 decoys can block metastasis in mouse model. We have tested the activity of the rat Notch1 decoy against tumor growth and metastasis of Ewing's Sarcoma cell line, SKNEP. In this tumor model, SKNEP tumor cells are orthotopically implanted into the kidney where the tumor grows and then metastasized to the lung. Expression of rat Notch1 decoy in SKNEP tumor cells reduced tumor growth and metastasis to lung, as shown in FIG. 120.

SKNEP1 Ewings Sarcoma cells were programmed to express control Fc protein or rat Notch1 decoy s1 (sort 2) or rat Notch1 decoy s4 (sort 4). These SKNEP1 cell lines were orthotopically implanted into kidney of nude mice. After 6 weeks of tumor growth, metastasis to lung was assessed histologically. SKNEP1 cells expressing Rat Notch1 decoy showed fewer lungs that were positive for metastasis. We conclude that expression of the rat Notch1 decoy in nude mice diminishes the capacity of SKNEP1 cells to metastasize to lung.

TENTH SERIES OF EXPERIMENTS

Notch1 and Notch4 are Co-Expressed with VEGFR-3 and LYVE-1 in Lumphatics of Mouse Skin Notch1 and Notch4 are Expressed in Lymphatics of Mouse Skin We analyzed the expression of Notch1 and Notch4 in the vasculature of mouse P4 dorsal skin. At this time point, the dermal lymphatics are actively remodeling into the lymphatic capillaries near the surface and collecting ducts in the lower dermal layers. 5 μm cross-sections of skin were co-stained with antibodies against Notch1 or Notch4 (red), and PECAM, VEGFR-3 or LYVE-1 (green). Notch1 and Notch4 share an overlapping pattern of expression with the blood and lymphatic endothelial cell marker, PECAM (upper panels, FIG. 121). Notch1 and Notch4 were co-expressed with both VEGFR-3 (middle panels, FIG. 121) and LYVE-1 in the dermal vasculature (lower panels, FIG. 121). This expression pattern demonstrates that Notch1 and Notch4 are expressed and may function in the lymphatic vessels of the neonatal dermis.

Dermal Lymphatic Capillaries are Altered in Notch4 Mutant Mice

We examined the dermal lymphatics of P4 mice. Sections of wildtype and Notch4 nullizygous were immunostained with antibodies against PECAM and LYVE-1 (green). Analysis of PECAM staining appeared similar between mutant and wildtype skin (upper panels, FIG. 122). In contrast, LYVE-1-positive vessels in the dermis of Notch4 mutants had a different morphology than that of wildtype (middle panels, FIG. 122). Notch4 mutant LYVE-1 vessels were often dilated and LYVE-1 staining was discontinuous (lower panels, FIG. 122). These results suggest that Notch4 signaling may be involved in remodeling of the lymphatic vascular plexus.

Loss of Notch4 Results in Reduced LYVE-1 Positive Vessels

Notch4 heterozygous ($N4^{+/-}$) mice were mated and the dorsal skin of the resulting pups removed and embedded 14 days postnatally. The results are set forth in FIG. 123. Cross-sections of skin were immunostained for the endothelial cell marker, PECAM (data not shown), or the lymphatic endothelial cell marker, LYVE1 (A). Five areas for each were captured by microscopy and PECAM and LYVE1 staining quantitated using imaging software (B, C). PECAM expression was reduced approximately 25% in the $N4^{-/-}$ dermis compared to wild-type (WT) dermis (B). LYVE-1 staining was more affected than the PECAM with LYVE1 staining decreased nearly 50% in $N4^{-/-}$ relative to WT mice (C). There was also a reduction in the intensity of the LYVE1 staining in the $N4^{-/-}$ lymphatics relative to the WT (A).

Loss of Notch4 function in mice disrupts development of dermal lymphatic's suggesting a role in lymphangiogenesis.

Notch1 and Notch4 Expressed in Human Breast Cancer

We performed double immunohistochemistry with antibodies against VEGFR-3 or LYVE-1 (green) and Notch1 or Notch4 (red) of human breast cancers. The results are set forth in FIG. 124. Notch1 and Notch4 were expressed in the extratumoral blood and lymphatic endothelium of human micropapillary breast carcinomas. To determine if Notch1 signaling was activated within the tumoral lymphatic endothelium, we double stained with an antibody against podoplanin (green) and N1Val (red; Cell Signaling), an antibody that specifically detects the activated Notch1 peptide. Expression of the activated Notch1 peptide was observed in most (white arrows) but not all (yellow arrows) of the lymphatic endothelial nuclei (lower panel). These results demonstrate that Notch1 was actively signaling in the pathological lymphatic vessels. These results also demonstrate that Notch1 and Notch4 may function in tumor lymphangiogenesis.

What is claimed is:

1. A fusion protein the sequence of which (a) is identical to the sequence of a portion of the extracellular domain of a human Notch1 receptor followed by (b) a sequence identical to the sequence of an Pc portion of an antibody, wherein the portion of the extracellular domain of the human Notch1 receptor is selected from the group consisting of EGF-like repeats 1-13, EGF-like repeats 1-24, EGF-like repeats 9-23, EGF-like repeats 9-16, EGF-like repeats 13-24 and EGF-like repeats 25-36, wherein (b) is located to the carboxy terminal side of (a), and wherein (b) is attached to (a) either directly or by means of a linker sequence.

2. A fusion protein the sequence of which (a) is identical to the sequence of a signal peptide followed by a sequence identical to the sequence of a portion of the extracellular domain of a human Notch1 receptor followed by (b) a sequence identical to the sequence of an Fc portion of an antibody, wherein the portion of the extracellular domain of the human Notch1 receptor is selected from the group consisting of EGF-like repeats 1-13, EGF-like repeats 1-24, EGF-like repeats 9-23, EGF-like repeats 9-36, EGF-like repeats 13-24 and EGF-like repeats 25-36, wherein (b) is located to the carboxy terminal side of (a), and wherein (b) is attached to (a) either directly or by means of a linker sequence.

3. The fusion protein of claim 1, wherein the Fc portion of the antibody is the Fc portion of a human antibody.

4. The fusion protein of claim 2, wherein the signal peptide is the signal peptide of human Notch1 receptor protein, human Notch2 receptor protein, human Notch3 receptor protein, human Notch4 receptor protein, or an IgG Heavy Chain.

5. The fusion protein of claim 2, the sequence of which is set forth in any of SEQ ID NOs: 55-64.

6. The fusion protein of claim 1, wherein the portion of the extracellular domain of the human Notch1 receptor protein is EGF-like repeats 1-13.

7. The fusion protein of claim 1, wherein the portion of the extracellular domain of the human Notch1 receptor protein is EGF-like repeats 1-24.

8. The fusion protein of claim 1, wherein the portion of the extracellular domain of the human Notch1 receptor protein is EGF-like repeats 9-23.

9. The fusion protein of claim 1, wherein the portion of the extracellular domain of the human Notch1 receptor protein is EGF-like repeats 9-36.

10. The fusion protein of claim 1, wherein the portion of the extracellular domain of the human Notch1 receptor protein is EGF-like repeats 13-24.

11. The fusion protein of claim 1, wherein the portion of the extracellular domain of the human Notch1 receptor protein is EGF-like repeats 25-36.

12. The fusion protein of claim 5, the sequence of which is set forth in SEQ ID NO: 56.

13. The fusion protein of claim 2, wherein the fusion protein is encoded by consecutive nucleotides, the sequence of which is set forth in any of SEQ ID NOs: 66-75.

14. The fusion protein of claim 13, wherein the fusion protein is encoded by consecutive nucleotides, the sequence of which is set forth in SEQ ID NO: 67.

15. The fusion protein of claim 5, the sequence of which is set forth in SEQ ID NO: 55.

16. The fusion protein of claim 13, wherein the fusion protein is encoded by consecutive nucleotides, the sequence of which is set forth in SEQ ID NO: 66.

17. The fusion protein of claim 1, wherein (b) is attached to (a) by means of a linker sequence.

18. The fusion protein of claim 2, wherein (b) is attached to (a) by means of a linker sequence between.

19. The fusion protein of claim 1, wherein (b) is attached directly to (a).

20. The fusion protein of claim 2, wherein (b) is attached directly to (a).

21. The fusion protein of claim 1, wherein the portion of the extracellular domain of the human Notch1 receptor is selected from the group consisting of EGF-like repeats 1-13, and EGF-like repeats 1-24.

22. The fusion protein of claim 2, wherein the portion of the extracellular domain of the human Notch1 receptor is selected from the group consisting of EGF-like repeats 1-13, and EGF-like repeats 1-24.

* * * * *